(12) United States Patent
Kim et al.

(10) Patent No.: US 12,077,532 B2
(45) Date of Patent: Sep. 3, 2024

(54) HETEROCYCLIC COMPOUND AND ORGANIC LIGHT EMITTING DIODE COMPRISING SAME

(71) Applicant: LT MATERIALS CO., LTD., Yongin (KR)

(72) Inventors: Ji-Young Kim, Yangsan-si (KR); Han-Kook Oh, Osan-si (KR); Won-Jang Jeong, Hwaseong-si (KR)

(73) Assignee: LT MATERIALS CO., LTD., Yongin (KR)

( * ) Notice: Subject to any disclaimer, the term of this patent is extended or adjusted under 35 U.S.C. 154(b) by 692 days.

(21) Appl. No.: 17/288,647

(22) PCT Filed: Nov. 8, 2019

(86) PCT No.: PCT/KR2019/015184
§ 371 (c)(1),
(2) Date: Apr. 26, 2021

(87) PCT Pub. No.: WO2020/096419
PCT Pub. Date: May 14, 2020

(65) Prior Publication Data
US 2023/0013934 A1    Jan. 19, 2023

(30) Foreign Application Priority Data

Nov. 8, 2018   (KR) .......................... 10-2018-0136887

(51) Int. Cl.
*C07D 519/00*   (2006.01)
*C07D 471/04*   (2006.01)
*H10K 30/30*   (2023.01)
*H10K 50/16*   (2023.01)
*H10K 85/60*   (2023.01)

(52) U.S. Cl.
CPC ......... *C07D 471/04* (2013.01); *C07D 519/00* (2013.01); *H10K 30/353* (2023.02); *H10K 50/16* (2023.02); *H10K 85/622* (2023.02); *H10K 85/654* (2023.02); *H10K 85/6572* (2023.02); *H10K 85/6574* (2023.02)

(58) Field of Classification Search
None
See application file for complete search history.

(56) References Cited

U.S. PATENT DOCUMENTS

| 4,356,429 A | 10/1982 | Tang |
| 10,446,765 B2 | 10/2019 | Lee et al. |
| 2017/0133601 A1 | 6/2017 | Sim et al. |

FOREIGN PATENT DOCUMENTS

| KR | 10-2010-0108924 A | 10/2010 |
| KR | 10-1579289 B1 | 12/2015 |

(Continued)

OTHER PUBLICATIONS

Machine translation of KR-20180023626-A, translation generated Jan. 2024, 15 pages. (Year: 2024).*

(Continued)

*Primary Examiner* — Robert S Loewe
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

14 Claims, 3 Drawing Sheets

(56) References Cited

FOREIGN PATENT DOCUMENTS

| KR | 10-2016-0046703 A | 4/2016 | | |
|----|-------------------|--------|---|---|
| KR | 10-2017-0053759 A | 5/2017 | | |
| KR | 10-2017-0142950 A | 12/2017 | | |
| KR | 10-2018-0023626 A | 3/2018 | | |
| KR | 20180023626 A | * 3/2018 | ............. | C09K 11/06 |

OTHER PUBLICATIONS

International Search Report (PCT/ISA/210) issued in PCT/KR2019/015184 mailed on Feb. 21, 2020.
Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials", Advanced Materials, vol. 6, No. 9, 1994, pp. 677-679.

* cited by examiner

[FIG. 1]
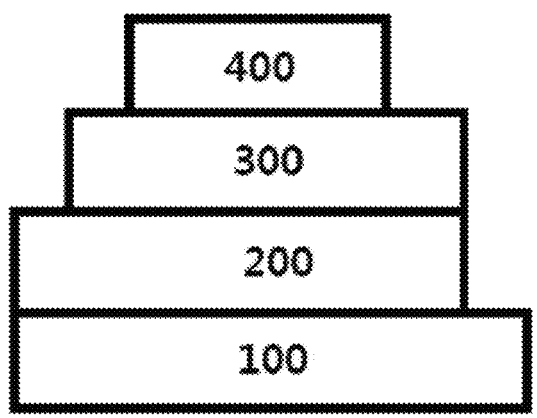
[FIG. 2]
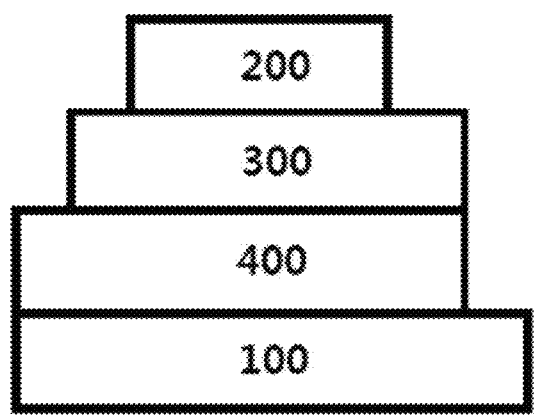

[FIG. 3]
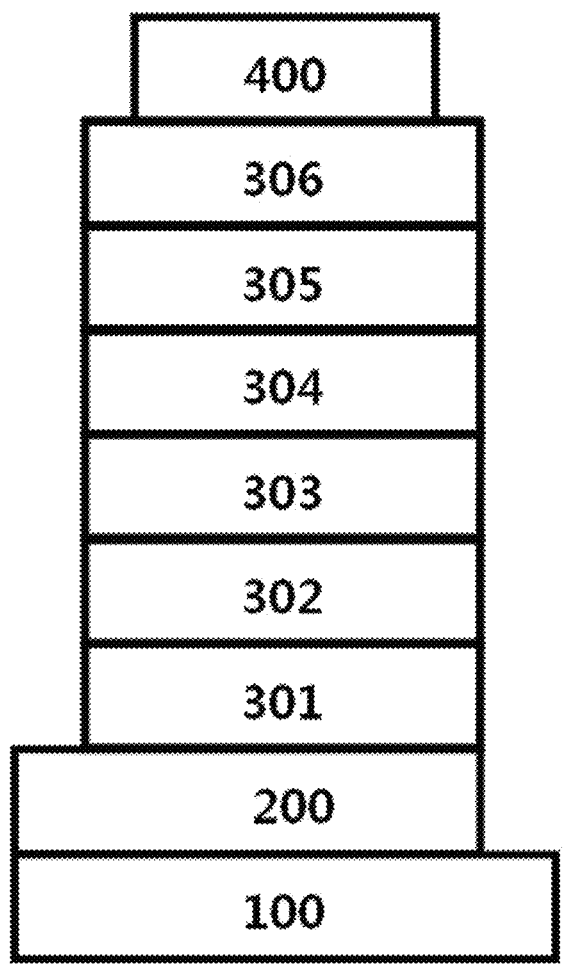

[FIG 4]

| CATHODE |
| --- |
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT EMITTING DIODE COMPRISING SAME

TECHNICAL FIELD

This application claims priority to and the benefits of Korean Patent Application No. 10-2018-0136887, filed with the Korean Intellectual Property Office on Nov. 8, 2018, the entire contents of which are incorporated herein by reference.

The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present disclosure is directed to providing a heterocyclic compound, and an organic light emitting device comprising the same.

Technical Solution

One embodiment of the present application provides a heterocyclic compound represented by the following Chemical Formula 1.

[Chemical Formula 1]

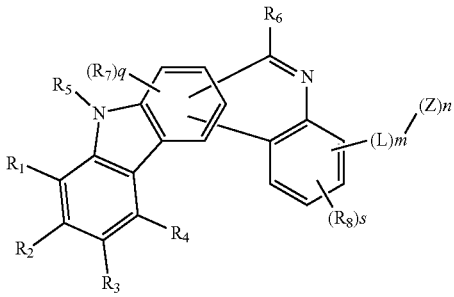

In Chemical Formula 1, $R_1$ to $R_4$, $R_7$ and $R_8$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aromatic hydrocarbon ring or a substituted or unsubstituted heteroring, $R_5$ and $R_6$ are the same as or different from each other, and each independently selected from the group consisting of a substituted or unsubstituted alkyl group; a substituted or unsubstituted aryl group; a substituted or unsubstituted heteroaryl group; and an amine group unsubstituted or substituted with a substituted or unsubstituted alkyl group, a substituted or unsubstituted aryl group, or a substituted or unsubstituted heteroaryl group, L is a direct bond; a substituted or unsubstituted arylene group; or a substituted or unsubstituted heteroarylene group, Z is selected from the group consisting of deuterium; —CN; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, R, R' and R" are the same as or different from each other, and each independently hydrogen; a substituted or unsubstituted alkyl group; a substituted or unsubstituted aryl group; or a substituted or unsubstituted heteroaryl group, m is an integer of 0 to 5, n is an integer of 1 to 6, q is an integer of 0 to 2, and s is an integer of 0 to 3.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material, a charge generation material and the like in an organic light emitting device. Particularly, the compound can be used as a charge generation layer material or an electron transfer layer material of an organic light emitting device.

When using the compound represented by Chemical Formula 1 in an organic material layer, a device driving voltage can be lowered, light efficiency can be enhanced, and device lifetime properties can be enhanced by thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by $-P(=O)R_{101}R_{102}$, and $R_{101}$ and $R_{102}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide group may comprise a diphenylphosphine oxide group, a dinaphthylphosphine oxide group and the like, but are not limited thereto.

In the present specification, the silyl group is a substituent comprising Si, having the Si atom directly linked as a radical, and is represented by $-SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

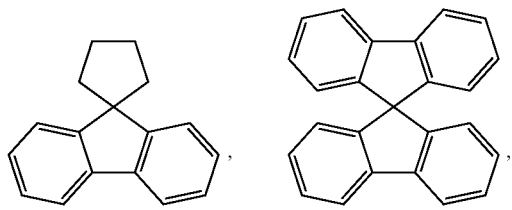

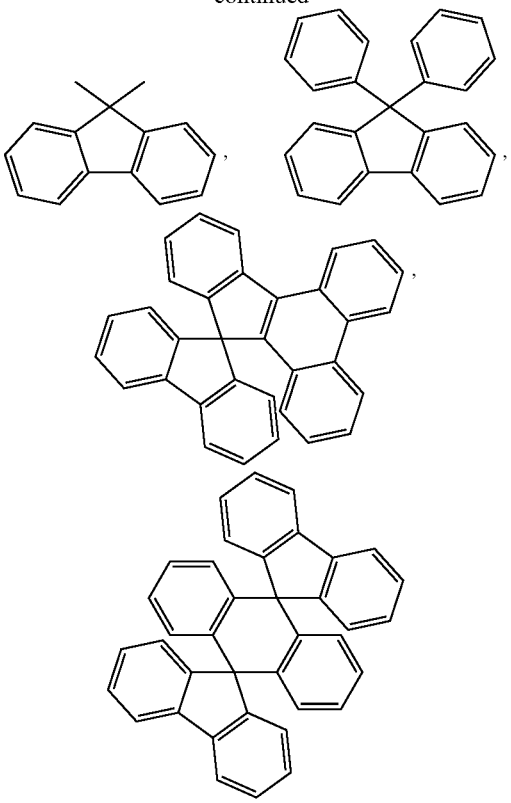

and the like may be included, however, the structure is not limited thereto.

In the present specification, the heteroaryl group comprises O, S, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25.

Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for those that are each a divalent. In addition, the heteroarylene group means the heteroaryl group having two bonding sites, that is, a divalent group. Descriptions on the heteroaryl group provided above may be applied thereto except for those that are each a divalent.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

One embodiment of the present application provides a compound represented by Chemical Formula 1.

In one embodiment of the present application, Chemical Formula 1 may be represented by any one of the following Chemical Formula 2 to Chemical Formula 7.

[Chemical Formula 2]

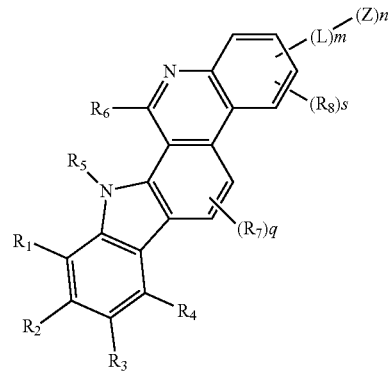

[Chemical Formula 3]

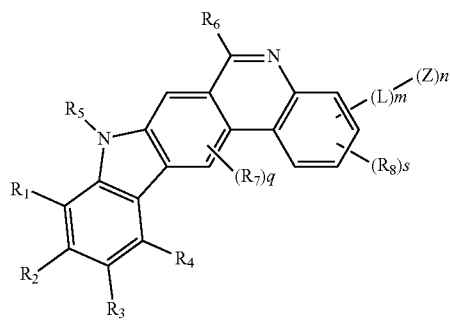

[Chemical Formula 4]

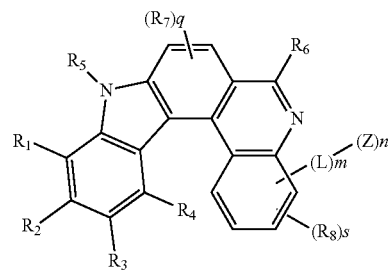

[Chemical Formula 5]

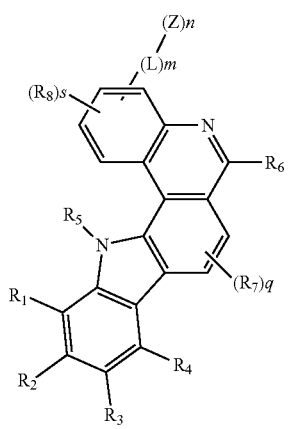

[Chemical Formula 6]

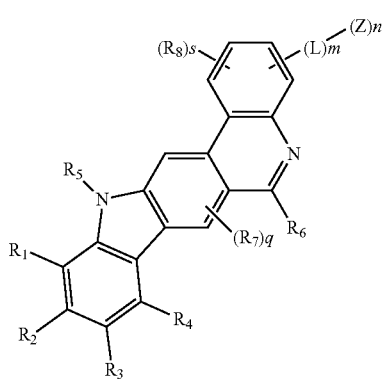

[Chemical Formula 7]

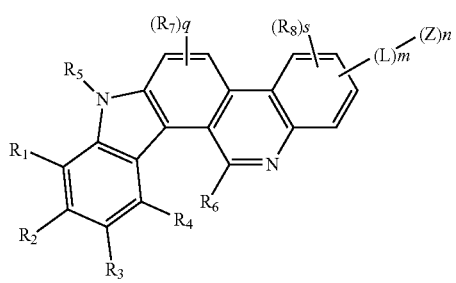

In Chemical Formulae 2 to 7, $R_1$ to $R_8$, L, Z, m, n, s and q have the same definitions as in Chemical Formula 1.

In one embodiment of the present application, Chemical Formula 1 may be represented by any one of the following Chemical Formulae 8 to 11.

[Chemical Formula 8]

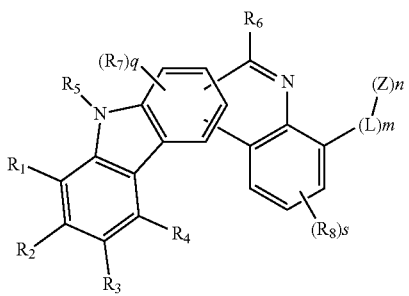

[Chemical Formula 9]

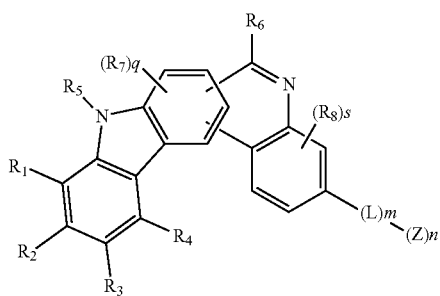

[Chemical Formula 10]

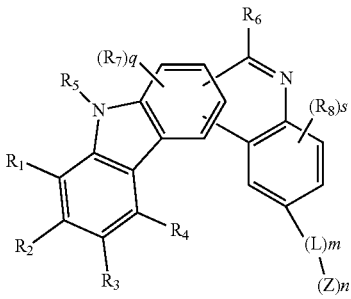

[Chemical Formula 11]

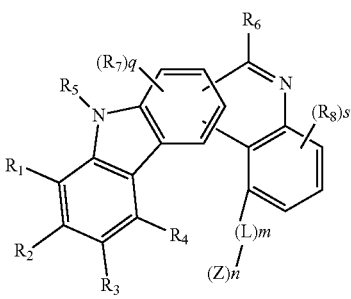

In Chemical Formulae 8 to 11, $R_1$ to $R_8$, L, Z, m, n, s and q have the same definitions as in Chemical Formula 1.

In one embodiment of the present application, $R_1$ to $R_4$, $R_7$ and $R_8$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R''; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aromatic hydrocarbon ring or a substituted or unsubstituted heteroring.

In another embodiment, $R_1$ to $R_4$, $R_7$ and $R_8$ are the same as or different from each other, and may be each independently hydrogen; a substituted or unsubstituted alkyl group; a substituted or unsubstituted aryl group; or a substituted or unsubstituted heteroaryl group.

In another embodiment, $R_1$ to $R_4$, $R_7$ and $R_8$ are the same as or different from each other, and may be each independently hydrogen; a substituted or unsubstituted C1 to C60 alkyl group; a substituted or unsubstituted C6 to C60 aryl group; or a substituted or unsubstituted C2 to C60 heteroaryl group.

In another embodiment, $R_1$ to $R_4$, $R_7$ and $R_8$ are the same as or different from each other, and may be each independently hydrogen; a substituted or unsubstituted C1 to C40 alkyl group; a substituted or unsubstituted C6 to C40 aryl group; or a substituted or unsubstituted C2 to C40 heteroaryl group.

In another embodiment, $R_1$ to $R_4$, $R_7$ and $R_8$ are the same as or different from each other, and may be each independently hydrogen; a C1 to C40 alkyl group; a C6 to C40 aryl group; or a C2 to C40 heteroaryl group.

In another embodiment, $R_1$ to $R_4$, $R_7$ and $R_8$ may be hydrogen.

In one embodiment of the present application, $R_5$ and $R_6$ are the same as or different from each other, and may be each independently selected from the group consisting of a substituted or unsubstituted alkyl group; a substituted or unsubstituted aryl group; a substituted or unsubstituted heteroaryl group; and an amine group unsubstituted or substituted with a substituted or unsubstituted alkyl group, a substituted or unsubstituted aryl group, or a substituted or unsubstituted heteroaryl group.

In another embodiment, $R_5$ and $R_6$ are the same as or different from each other, and may be each independently selected from the group consisting of a substituted or unsubstituted C1 to C60 alkyl group; a substituted or unsubstituted C6 to C60 aryl group; a substituted or unsubstituted C2 to C60 heteroaryl group; and an amine group unsubstituted or substituted with a substituted or unsubstituted C1 to C60 alkyl group, a substituted or unsubstituted C6 to C60 aryl group, or a substituted or unsubstituted C2 to C60 heteroaryl group.

In another embodiment, $R_5$ and $R_6$ are the same as or different from each other, and may be each independently selected from the group consisting of a substituted or unsubstituted C1 to C40 alkyl group; a substituted or unsubstituted C6 to C40 aryl group; a substituted or unsubstituted C2 to C40 heteroaryl group; and an amine group unsubstituted or substituted with a substituted or unsubstituted C1 to C40 alkyl group, a substituted or unsubstituted C6 to C40 aryl group, or a substituted or unsubstituted C2 to C40 heteroaryl group.

In another embodiment, $R_5$ and $R_6$ are the same as or different from each other, and may be each independently a substituted or unsubstituted C6 to C40 aryl group.

In another embodiment, $R_5$ and $R_6$ are the same as or different from each other, and may be each independently a monocyclic or polycyclic C6 to C40 aryl group.

In another embodiment, $R_5$ and $R_6$ are the same as or different from each other, and may be each independently a phenyl group; or a naphthyl group.

Particularly, when $R_5$ and $R_6$ are a substituted or unsubstituted aryl group, excellent thermal stability and strength are obtained compared to unsubstituted compounds due to an increase in the overall molecular weight of the compound.

In addition, the compound has increase planarity compared to compounds in which $R_5$ and $R_6$ are substituted with a heteroaryl group further enhancing an electron transfer ability, and as a result, driving and light emission efficiency may increase when used in an organic light emitting device.

In one embodiment of the present application, L may be a direct bond; a substituted or unsubstituted arylene group; or a substituted or unsubstituted heteroarylene group.

In another embodiment, L may be a direct bond; a substituted or unsubstituted C6 to C60 arylene group; or a substituted or unsubstituted C2 to C60 heteroarylene group.

In another embodiment, L may be a direct bond; a substituted or unsubstituted C6 to C40 arylene group; or a substituted or unsubstituted C2 to C40 heteroarylene group.

In another embodiment, L may be a direct bond; a C6 to C40 arylene group; or a C2 to C40 heteroarylene group unsubstituted or substituted with a C6 to C40 aryl group.

In another embodiment, L may be a direct bond; a phenylene group; a biphenylene group; a naphthylene group; an anthracenylene group; a divalent pyrimidine group unsubstituted or substituted with a phenyl group; or a divalent triazine group unsubstituted or substituted with a phenyl group.

In one embodiment of the present application, Z may be selected from the group consisting of deuterium; —CN; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group.

In another embodiment, Z may be selected from the group consisting of deuterium; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group, or a substituted or unsubstituted C2 to C60 heteroaryl group.

In another embodiment, Z may be selected from the group consisting of deuterium; —CN; a substituted or unsubstituted C1 to C40 alkyl group; a substituted or unsubstituted C6 to C40 aryl group; a substituted or unsubstituted C2 to C40 heteroaryl group; —SiRR'R"; —P(=O)RR'; and an amine group unsubstituted or substituted with a substituted or unsubstituted C1 to C40 alkyl group, a substituted or unsubstituted C6 to C40 aryl group, or a substituted or unsubstituted C2 to C40 heteroaryl group.

In another embodiment, Z may be selected from the group consisting of —CN; a C6 to C40 aryl group unsubstituted or substituted with one or more substituents selected from the group consisting of a C1 to C40 alkyl group, a C6 to C40 aryl group, a C2 to C40 heteroaryl group and —P(=O)RR'; a C2 to C40 heteroaryl group unsubstituted or substituted with one or more substituents selected from the group consisting of a C1 to C40 alkyl group, a C6 to C40 aryl group and a C2 to C40 heteroaryl group; and —P(=O)RR'.

In another embodiment, Z may be selected from the group consisting of —CN; a substituted or unsubstituted phenyl group; a substituted or unsubstituted naphthyl group; a substituted or unsubstituted anthracenyl group; a substituted or unsubstituted spirobifluorenyl group; a substituted or unsubstituted diphenylfluorenyl group; a substituted or unsubstituted triphenylenyl group; a substituted or unsubstituted pyridine group; a substituted or unsubstituted pyrimidine group; a substituted or unsubstituted triazine group; a substituted or unsubstituted phenanthroline group; a substituted or unsubstituted quinazoline group; a substituted or unsubstituted benzimidazole group; a substituted or unsubstituted benzothiazole group; a substituted or unsubstituted benzoxazole group; a substituted or unsubstituted carbazole group; a substituted or unsubstituted dibenzofuran group; a substituted or unsubstituted spiro[fluorene-9,9'-xanthene group]; and —P(=O)RR'.

In another embodiment, Z may be selected from the group consisting of —CN; a phenyl group unsubstituted or substituted with one or more substituents selected from the group consisting of —P(=O)RR', a pyridine group and a dibenzofuran group; a naphthyl group; an anthracenyl group unsubstituted or substituted with a phenyl group or a naphthyl group; a spirobifluorenyl group; a diphenylfluorenyl group; a triphenylenyl group; a pyridine group unsubstituted or substituted with a pyridine group; a pyrimidine group unsubstituted or substituted with one or more substituents selected from the group consisting of a phenyl group, a biphenyl group, a terphenyl group, a dimethylfluorenyl group, a dibenzofuran group, a phenanthrene group and a naphthyl group; a triazine group unsubstituted or substituted with one or more substituents selected from the group consisting of a phenyl group, a biphenyl group, a terphenyl group, a dimethylfluorenyl group, a dibenzofuran group, a phenanthrene group and a naphthyl group; a phenanthroline group unsubstituted or substituted with a phenyl group; a quinazoline group unsubstituted or substituted with a phenyl group; a benzimidazole group unsubstituted or substituted with an ethyl group or a phenyl group; a benzothiazole group; a benzoxazole group; a carbazole group; a dibenzofuran group; a spiro[fluorene-9,9'-xanthene group]; and —P(=O)RR'.

In one embodiment of the present application, Z may be substituted again with one or more substituents selected from the group consisting of —CN; a C1 to C40 alkyl group; a C6 to C40 aryl group; a C2 to C40 heteroaryl group and —P(=O)RR'.

In another embodiment, Z may be substituted again with one or more substituents selected from the group consisting of —CN; a methyl group; a phenyl group; a pyridine group; a carbazole group; a dibenzofuran group; and —P(=O)RR'.

Particularly, when having a substituent of -(L)m-(Z)n in the benzene ring of the fused quinoline group in the core structure of Chemical Formula 1, an electron transfer ability is enhanced due to planarity and an increase in the conjugation range of the compound. In other words, the excited hetero skeleton site is stabilized efficiently transferring electrons without being decomposed or destroyed, and as a result, excellent driving and light emission efficiency are obtained when using the compound of Chemical Formula 1 in an organic light emitting device.

In addition, by having a substituent in the benzene ring of the fused quinoline group as in Chemical Formula 1, properties of increased bipolar with obvious p-type and n-type may be obtained, and efficient electron migration is induced by having uniform molecular arrangement, and excitons are effectively locked in a light emitting layer by blocking hole leakage, and as a result, results of improved light emission efficiency and lifetime are obtained.

In one embodiment of the present application, R, R' and R" are the same as or different from each other, and may be each independently hydrogen; a substituted or unsubstituted alkyl group; a substituted or unsubstituted aryl group; or a substituted or unsubstituted heteroaryl group.

In another embodiment, R, R' and R" are the same as or different from each other, and may be each independently a substituted or unsubstituted C1 to C60 alkyl group; or a substituted or unsubstituted C6 to C60 aryl group.

In another embodiment, R, R' and R" are the same as or different from each other, and may be each independently a substituted or unsubstituted C1 to C40 alkyl group; or a substituted or unsubstituted C6 to C40 aryl group.

In another embodiment, R, R' and R" are the same as or different from each other, and may be each independently a C1 to C40 alkyl group; or a C6 to C40 aryl group.

In another embodiment, R, R' and R" are the same as or different from each other, and may be each independently a methyl group; or a phenyl group.

In one embodiment of the present application, -(L)m-(Z)n of the substituent

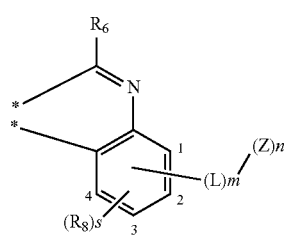

of Chemical Formula 3 may bond to the number 1 position.

In one embodiment of the present application, -(L)m-(Z)n of the substituent

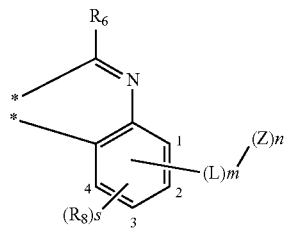

of Chemical Formula 3 may bond to the number 2 position.

In one embodiment of the present application, -(L)m-(Z)n of the substituent

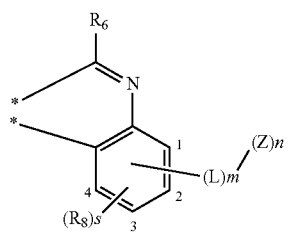

of Chemical Formula 3 may bond to the number 3 position.

In one embodiment of the present application, -(L)m-(Z)n of the substituent

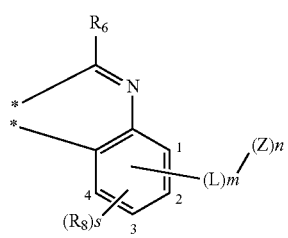

of Chemical Formula 3 may bond to the number 4 position.

In one embodiment of the present application, -(L)m-(Z)n of the substituent

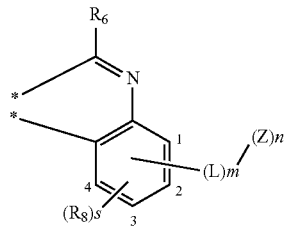

of Chemical Formula 4 may bond to the number 1 position.

In one embodiment of the present application, -(L)m-(Z)n of the substituent

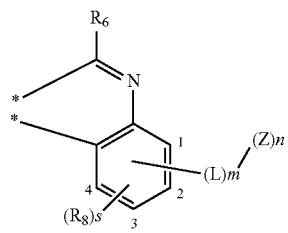

of Chemical Formula 4 may bond to the number 2 position.

In one embodiment of the present application, -(L)m-(Z)n of the substituent

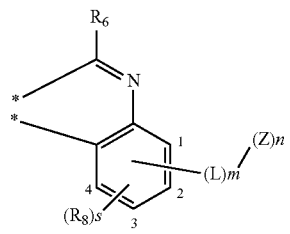

of Chemical Formula 4 may bond to the number 3 position.

In one embodiment of the present application, -(L)m-(Z)n of the substituent

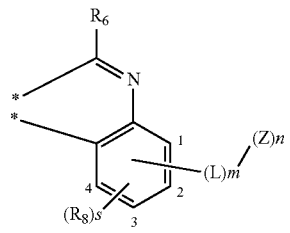

of Chemical Formula 5 may bond to the number 1 position.

In one embodiment of the present application, -(L)m-(Z)n of the substituent

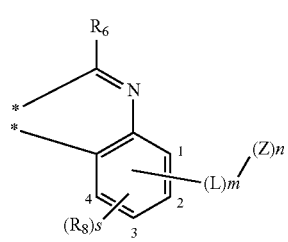

of Chemical Formula 5 may bond to the number 2 position.

In one embodiment of the present application, -(L)m-(Z)n of the substituent

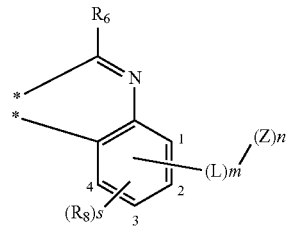

of Chemical Formula 6 may bond to the number 1 position.

In one embodiment of the present application, -(L)m-(Z)n of the substituent

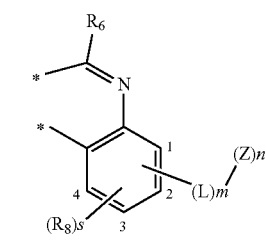

of Chemical Formula 6 may bond to the number 2 position.

In one embodiment of the present application, -(L)m-(Z)n of the substituent

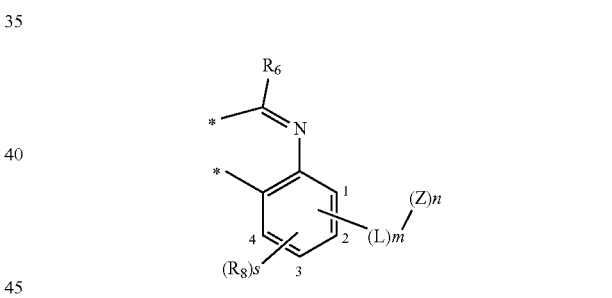

of Chemical Formula 6 may bond to the number 3 position.

In one embodiment of the present application, -(L)m-(Z)n of the substituent

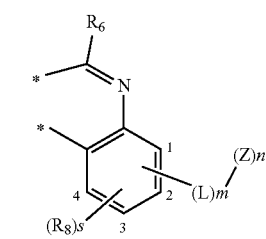

of Chemical Formula 7 may bond to the number 1 position.

In one embodiment of the present application, -(L)m-(Z)n of the substituent

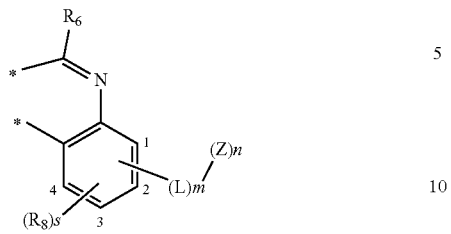

of Chemical Formula 7 may bond to the number 2 position.

In one embodiment of the present application, -(L)m-(Z)n of the substituent


of Chemical Formula 7 may bond to the number 3 position.

In one embodiment of the present application, -(L)m-(Z)n of the substituent

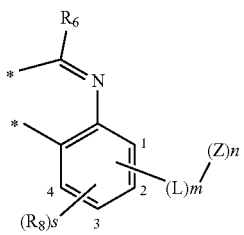

of Chemical Formula 7 may bond to the number 4 position.

•— means a site bonding to the chemical formula.

In the heterocyclic compound provided in one embodiment of the present application, Chemical Formula 1 is represented by any one of the following compounds.

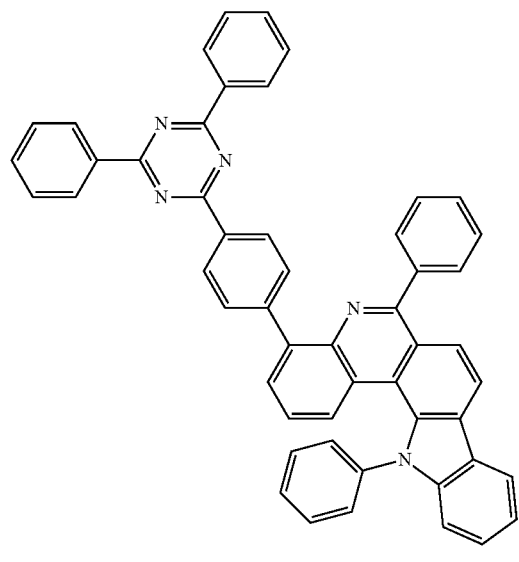

1

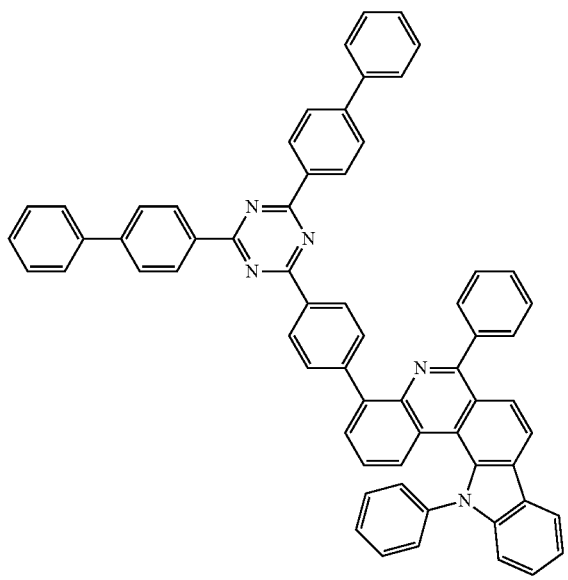 [SMILES: c1ccc(-c2ccc(-c3nc(-c4ccc(-c5ccccc5)cc4)nc(-c4ccc(-c5cccc6c5nc(-c5ccccc5)c5ccc7c8ccccc8n(-c8ccccc8)c7c56)cc4)n3)cc2)cc1]

1-1

-continued
1-2
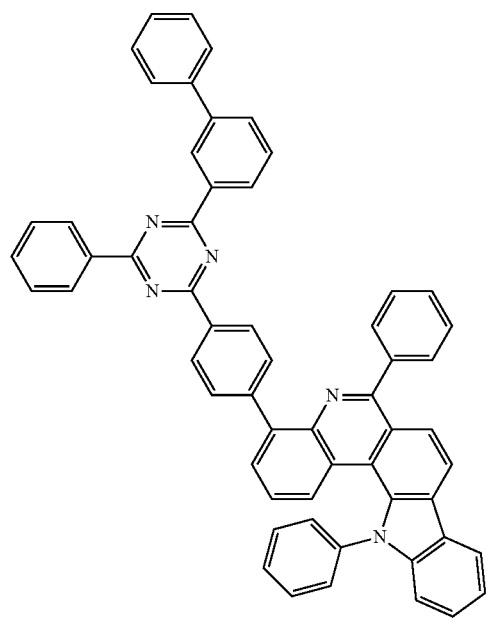
1-3
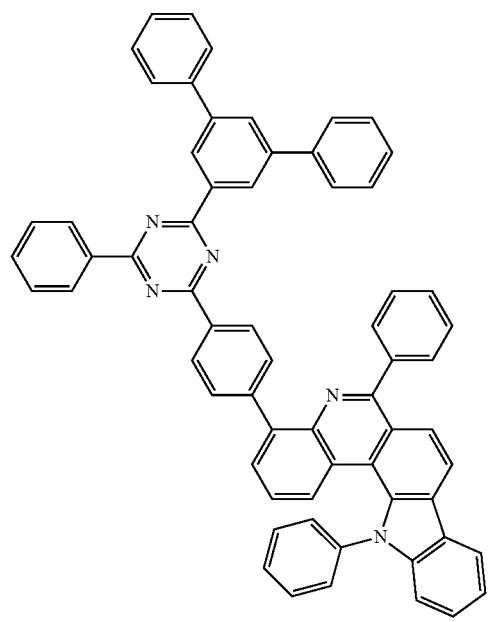
1-4
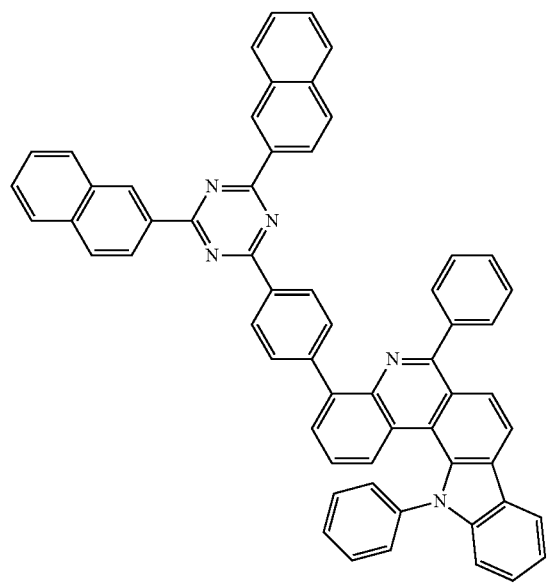
1-5
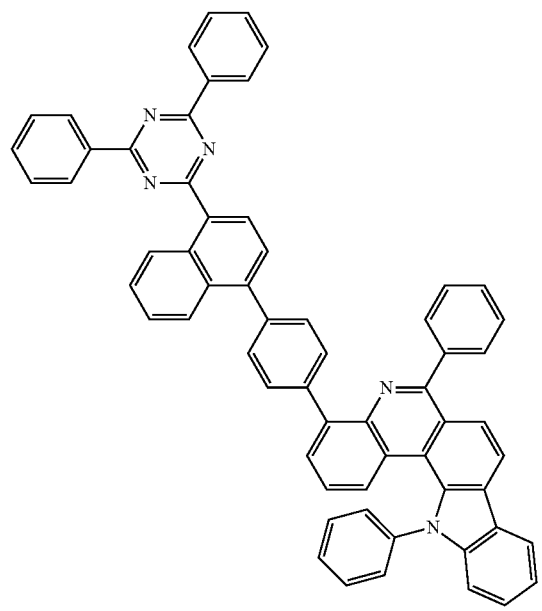

1-6
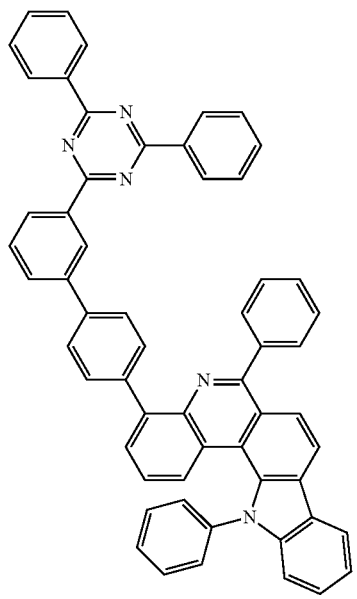
1-7
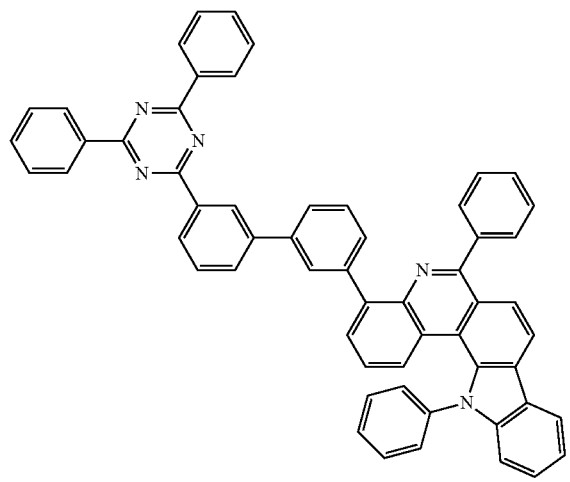
1-8
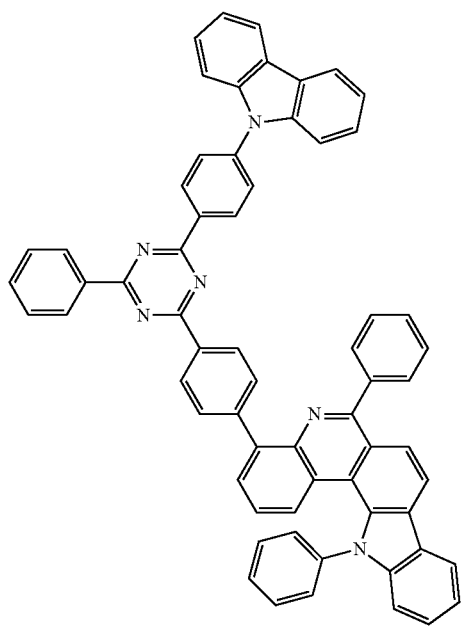
1-9
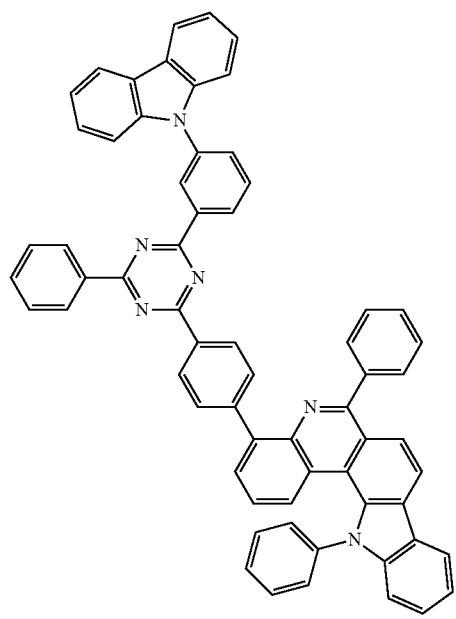

-continued
1-10
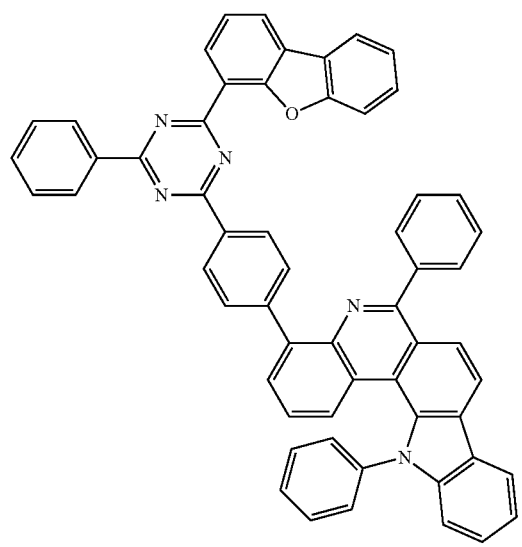
1-11
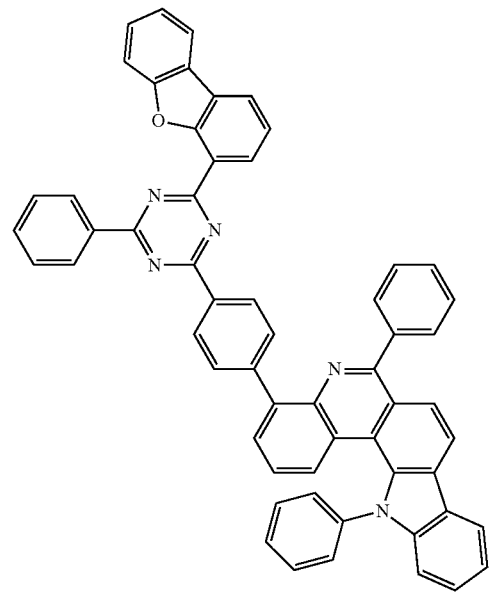
1-12
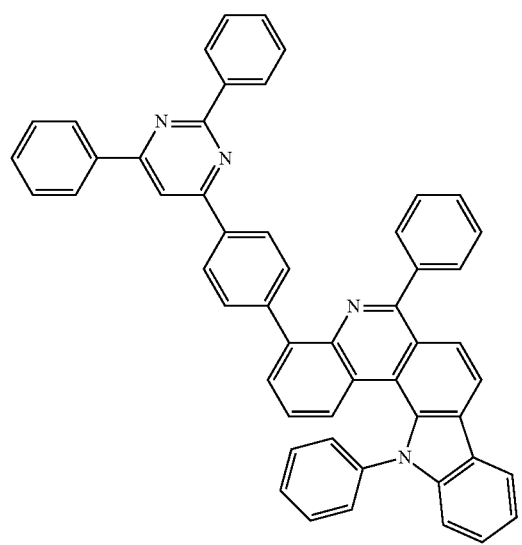
1-13
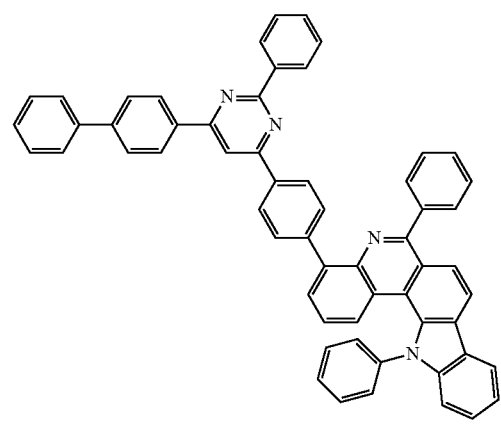

1-14
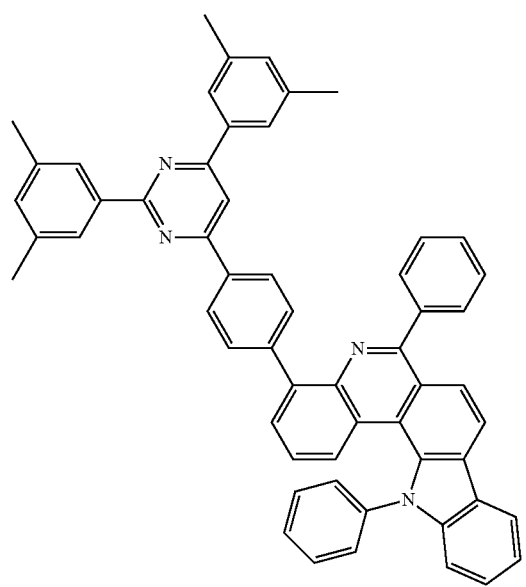
1-15
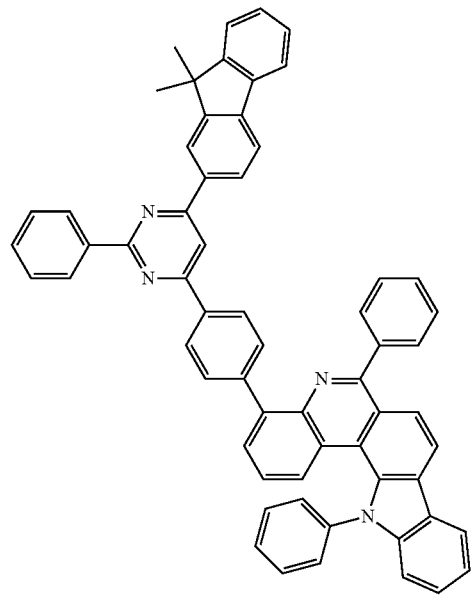
1-16
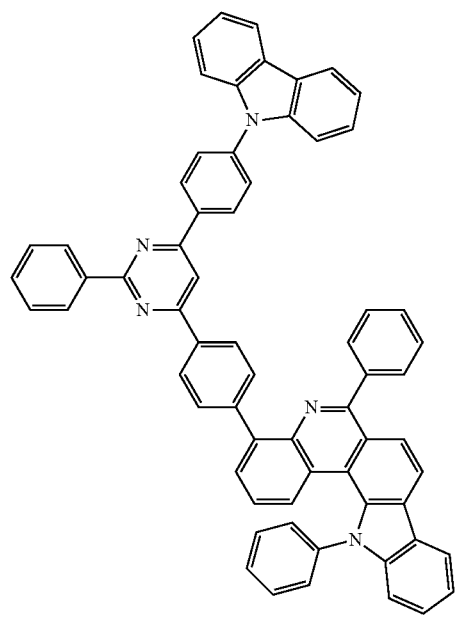
1-17
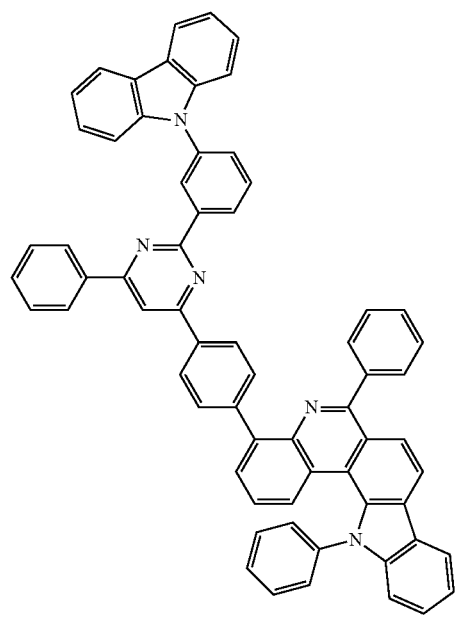

-continued
1-18
1-19
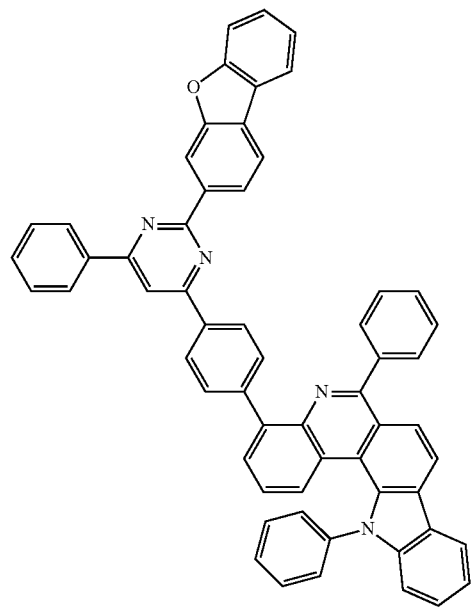
1-20
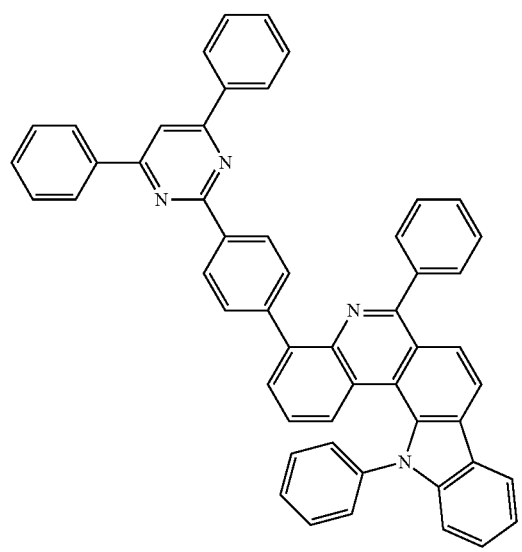 [SMILES: c1ccc(-c2cc(-c3ccccc3)nc(-c3ccc(-c4cccc5c4nc(-c4ccccc4)c4ccc6c7ccccc7n(-c7ccccc7)c6c45)cc3)n2)cc1]
1-21
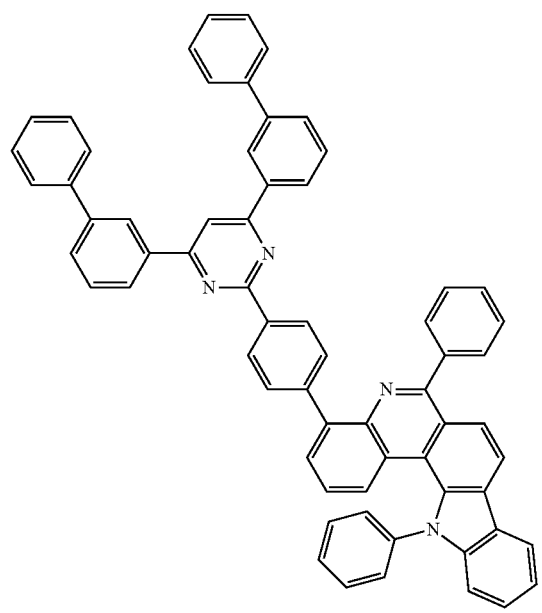

1-22
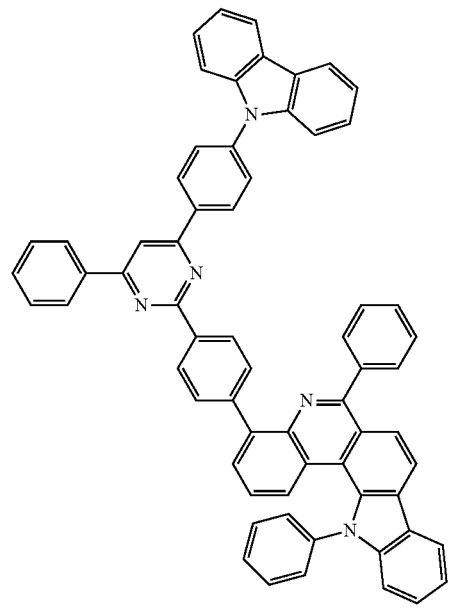
1-23
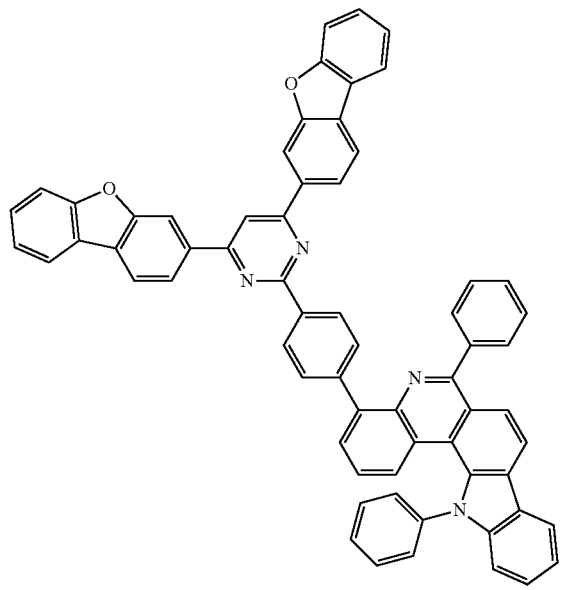
1-24
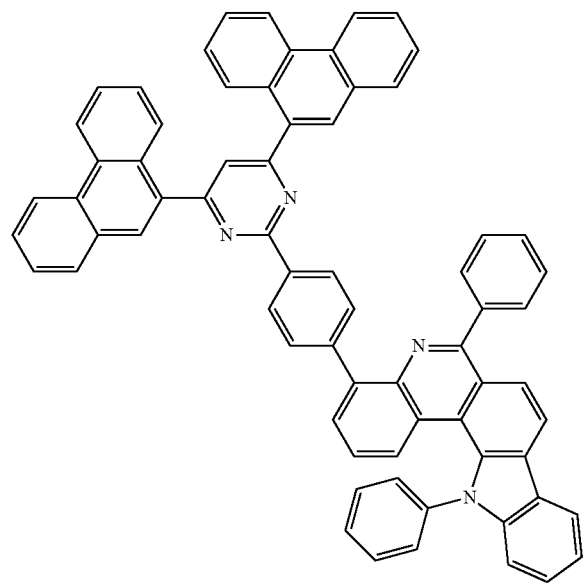
1-25
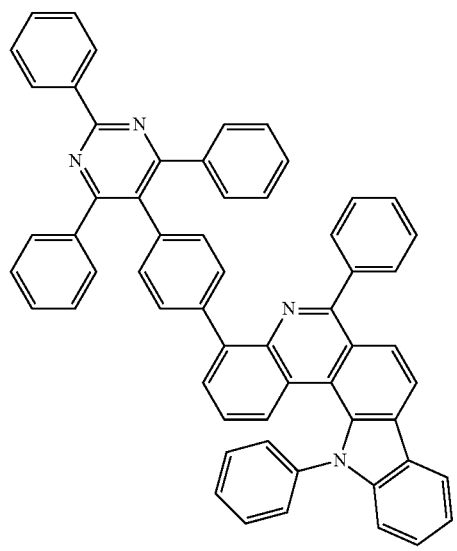

-continued
1-26
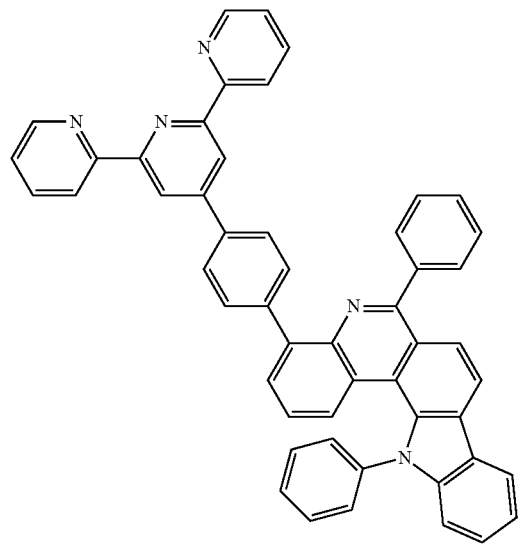 [SMILES: c1ccc(-c2nc3c(-c4ccc(-c5cc(-c6ccccn6)nc(-c6ccccn6)c5)cc4)cccc3c3c2ccc2c4ccccc4n(-c4ccccc4)c23)cc1]
1-27
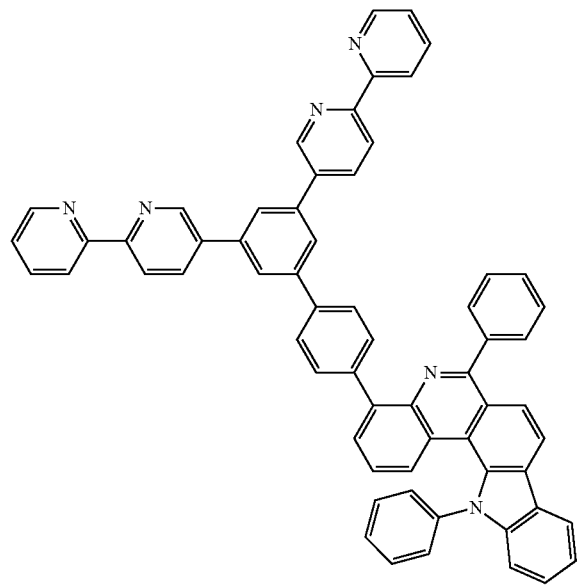
1-28
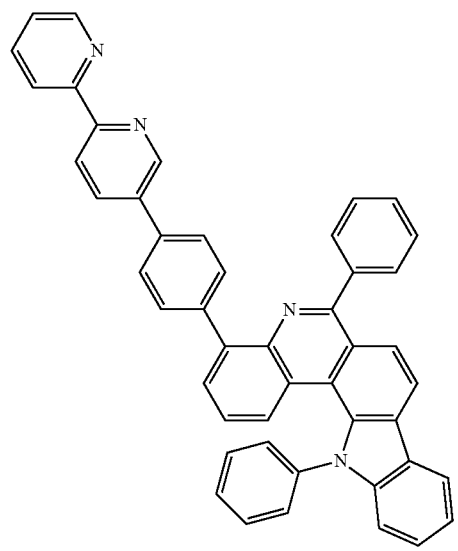
1-29
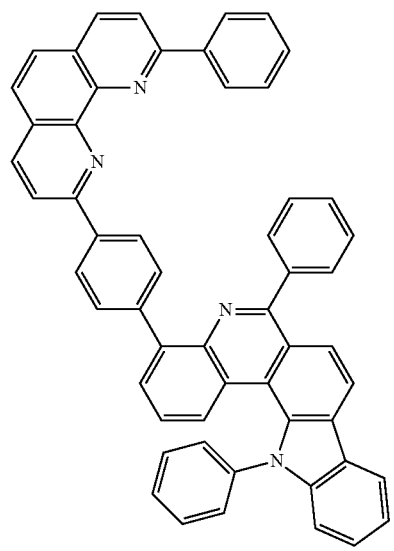 [SMILES: c1ccc(-c2ccc3ccc4ccc(-c5ccc(-c6cccc7c6nc(-c6ccccc6)c6ccc8c9ccccc9n(-c9ccccc9)c8c67)cc5)nc4c3n2)cc1]

-continued
1-30
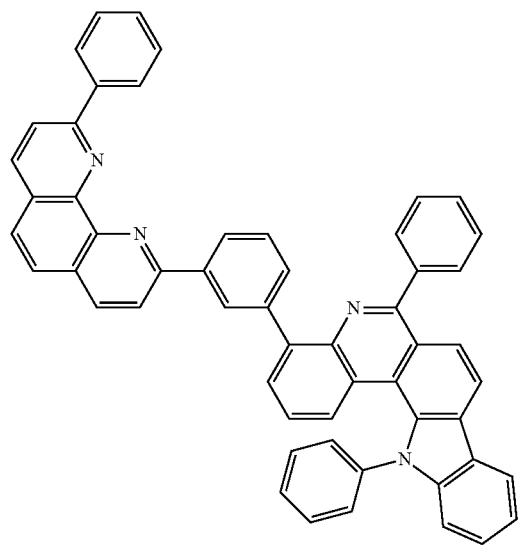
1-31
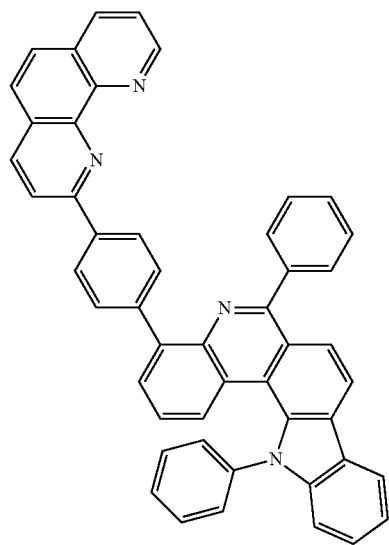
1-32
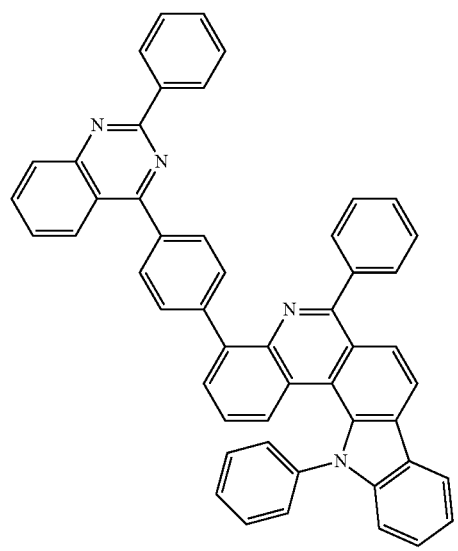 [SMILES: c1ccc(-c2nc(-c3ccc(-c4cccc5c4nc(-c4ccccc4)c4ccc6c7ccccc7n(-c7ccccc7)c6c45)cc3)c3ccccc3n2)cc1]
1-33
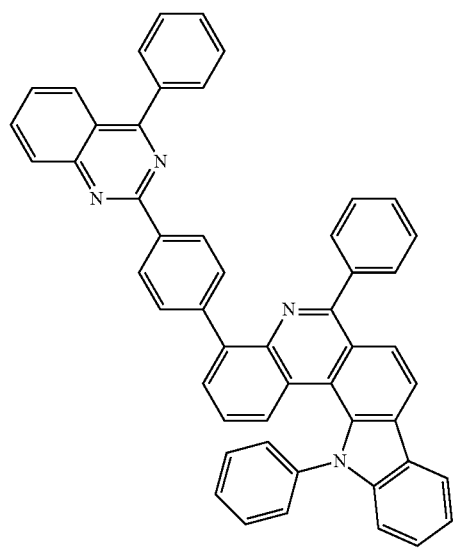

-continued
1-34
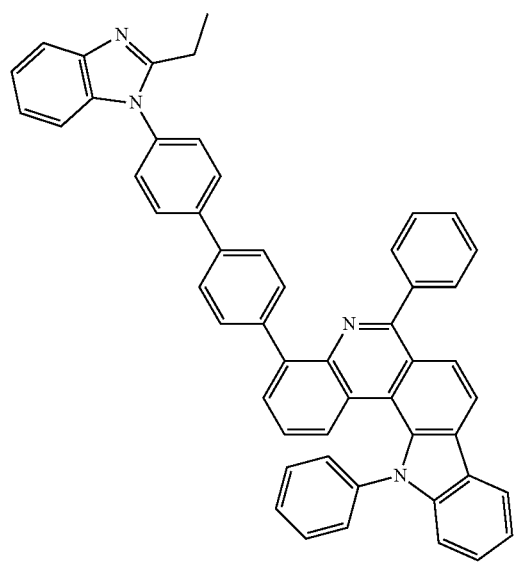
1-35
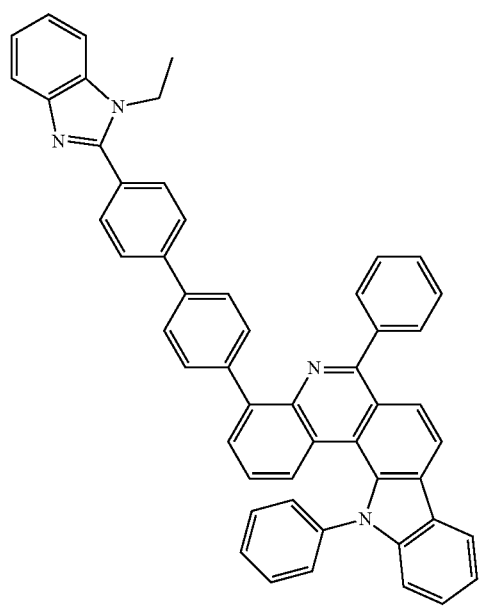
1-36
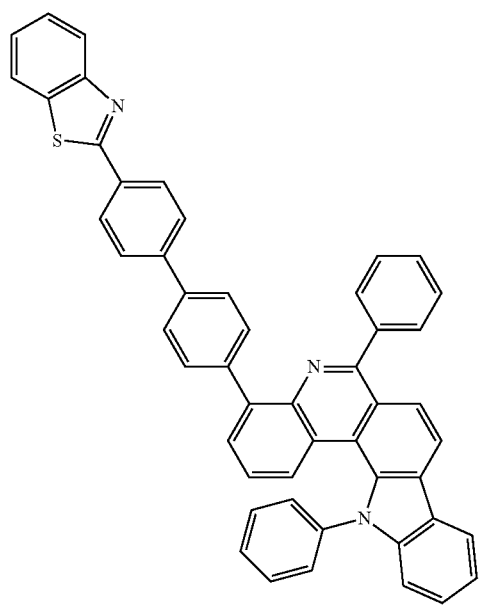
1-37
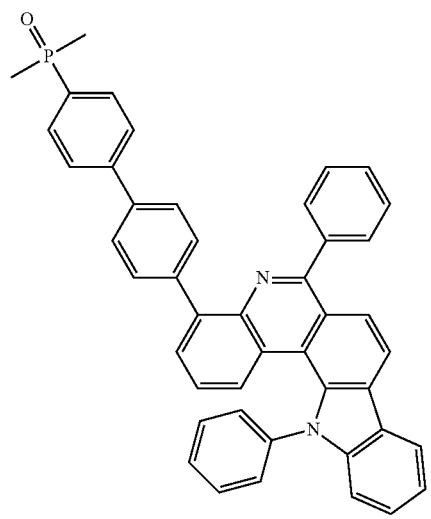

1-38
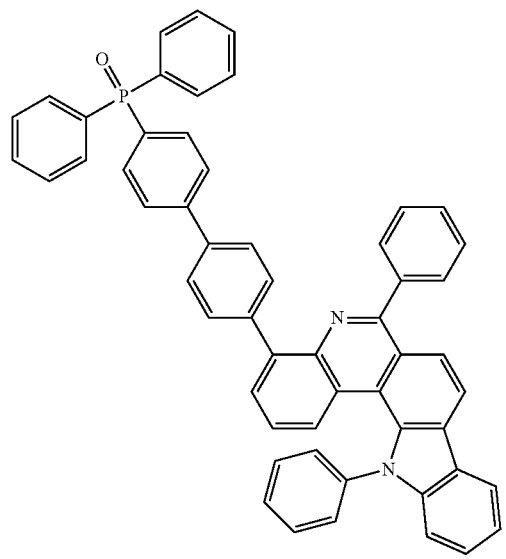
1-39
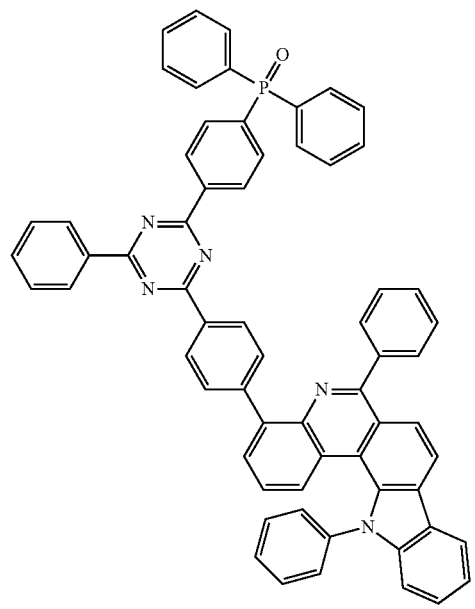
1-40
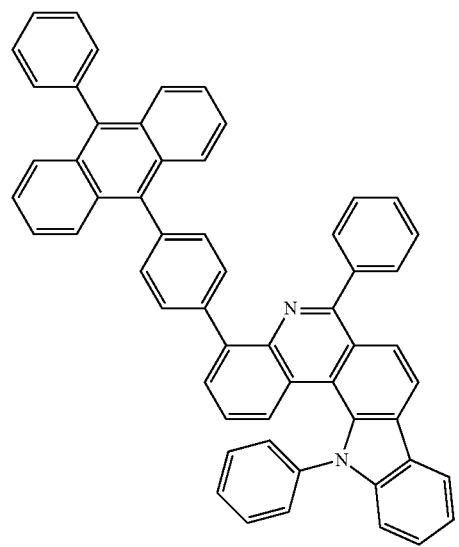 [SMILES: c1ccc(-c2c3ccccc3c(-c3ccc(-c4cccc5c4nc(-c4ccccc4)c4ccc6c7ccccc7n(-c7ccccc7)c6c45)cc3)c3ccccc23)cc1]
1-41
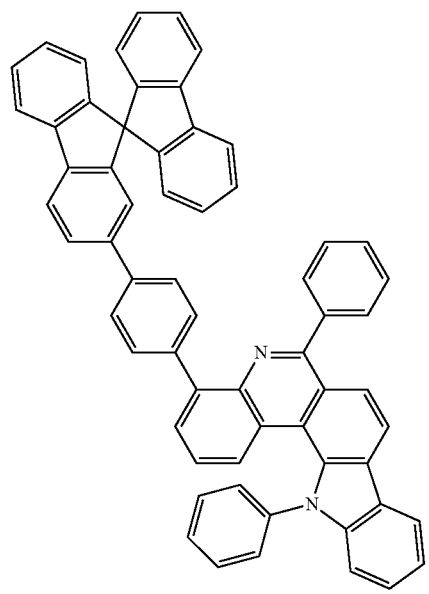

-continued
1-42
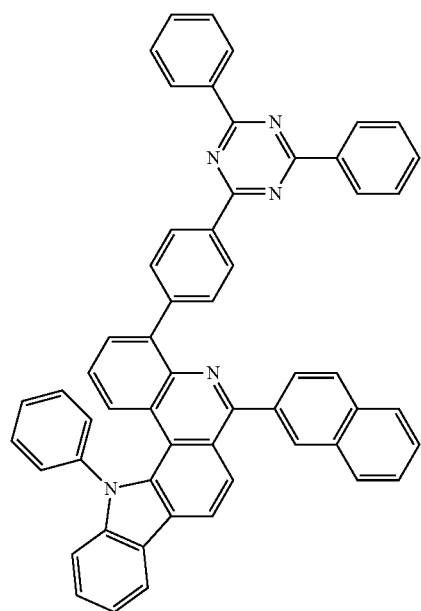
1-43
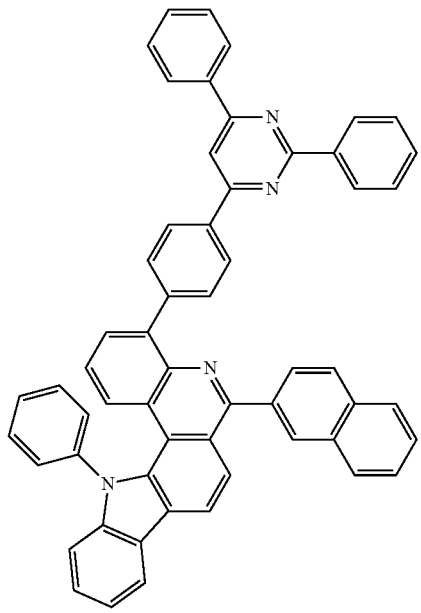 [SMILES: c1ccc(-c2cc(-c3ccc(-c4cccc5c4nc(-c4ccc6ccccc6c4)c4ccc6c7ccccc7n(-c7ccccc7)c6c45)cc3)nc(-c3ccccc3)n2)cc1]
2
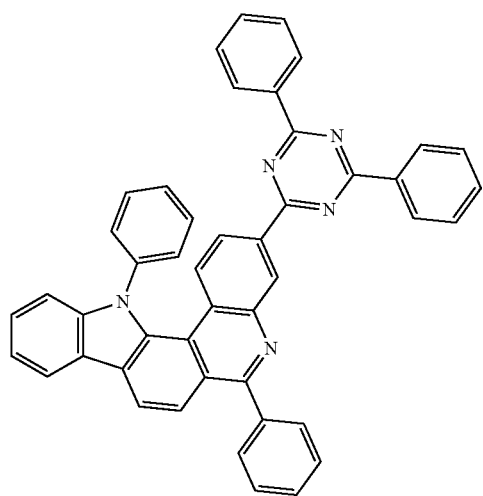
2-1
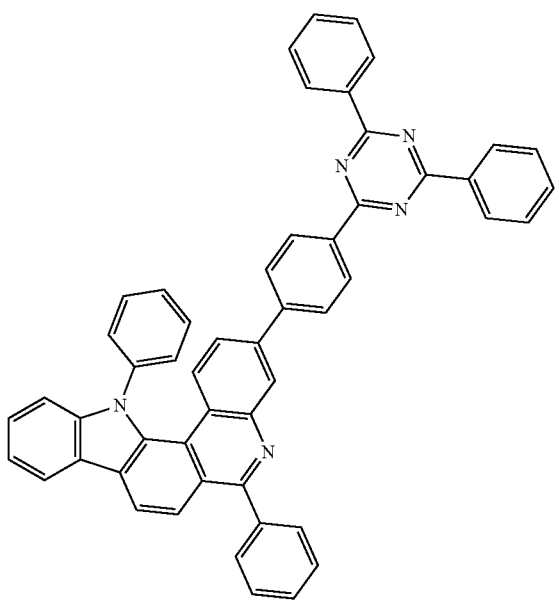

-continued
2-2
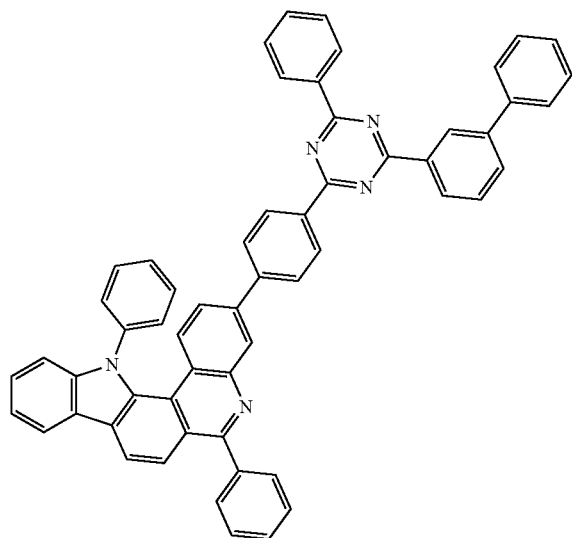
2-3
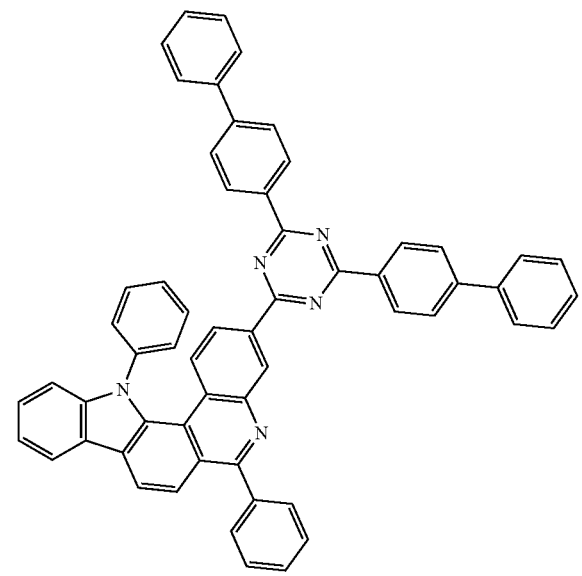
2-4
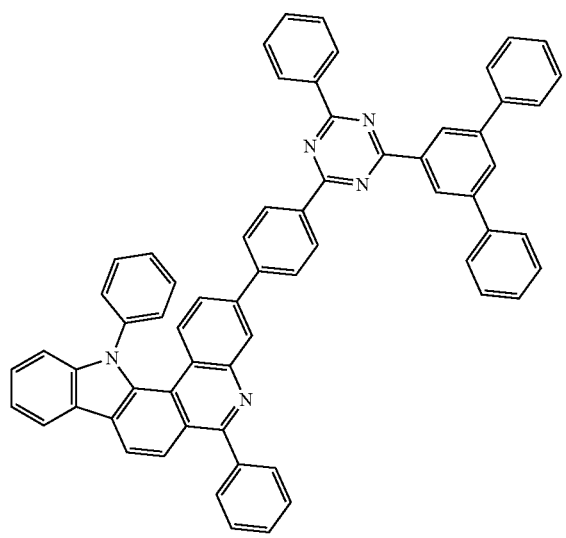
2-5
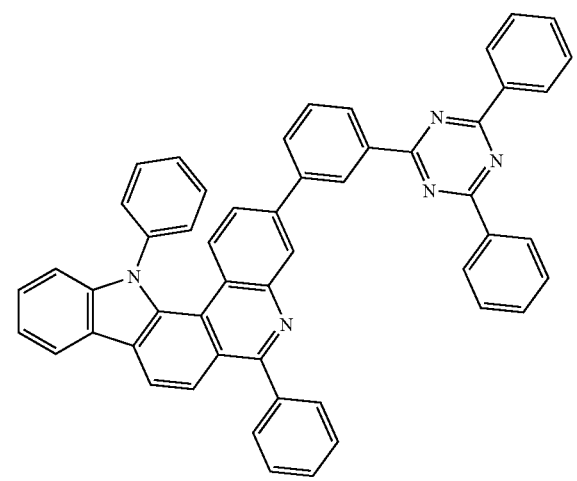
2-6
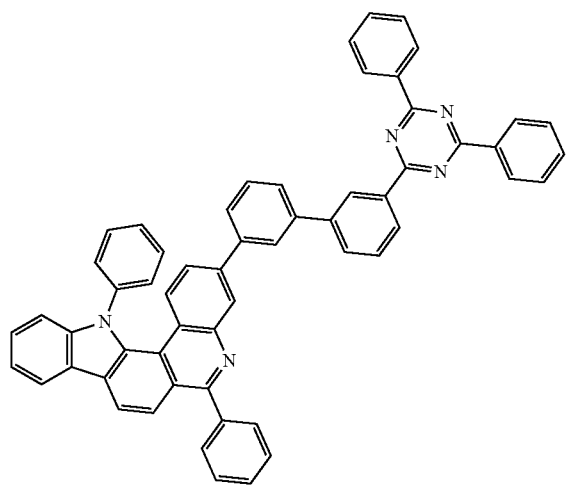
2-7
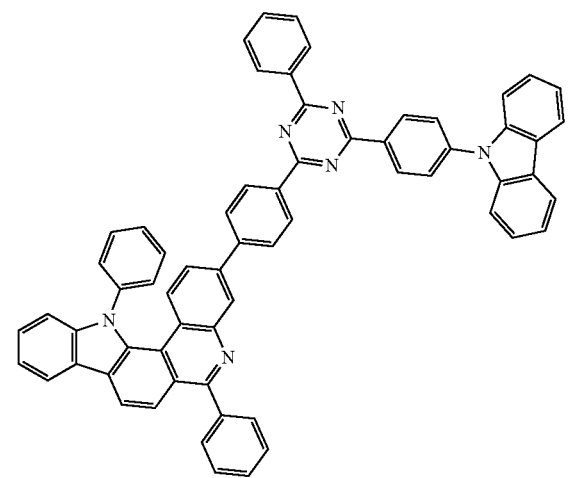

2-8
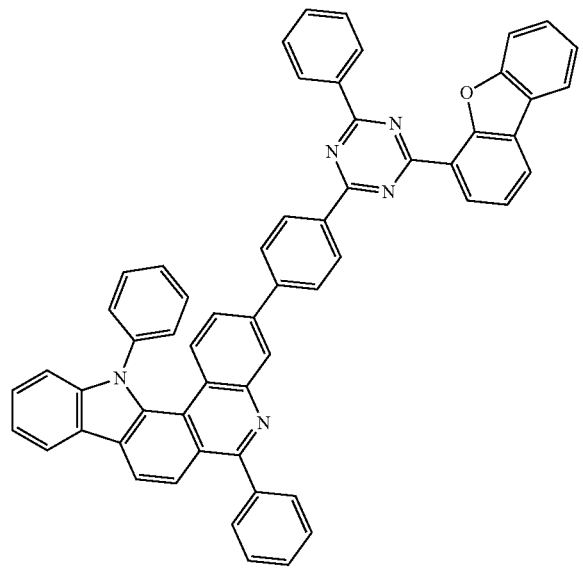
2-9
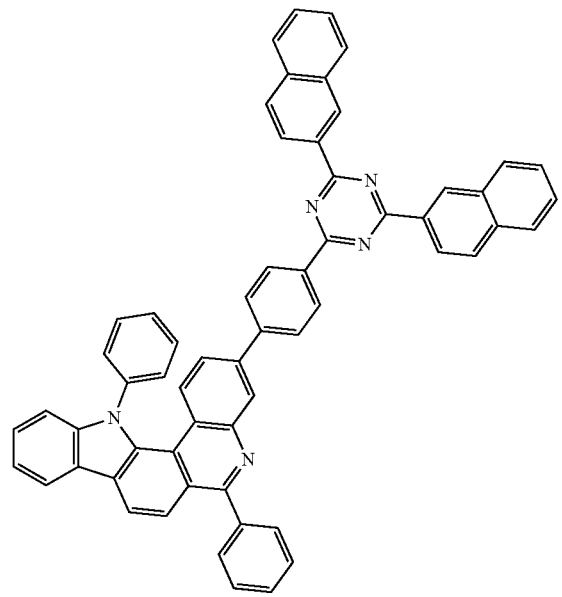
2-10
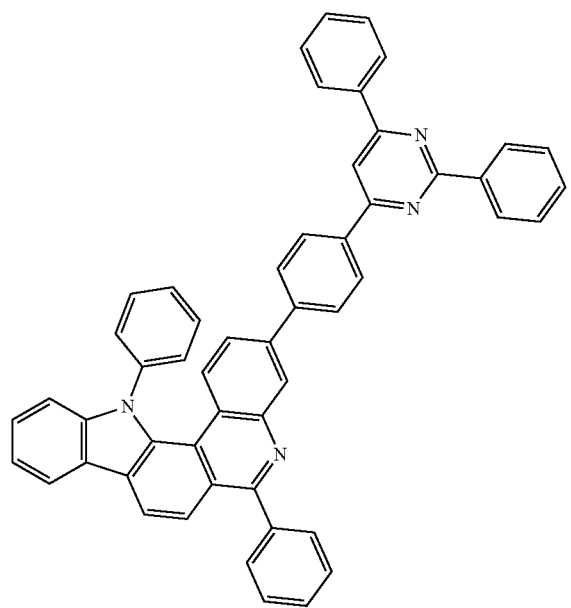
2-11
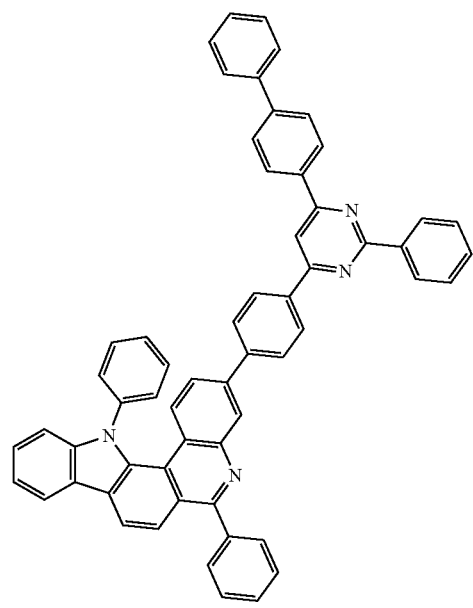

2-12
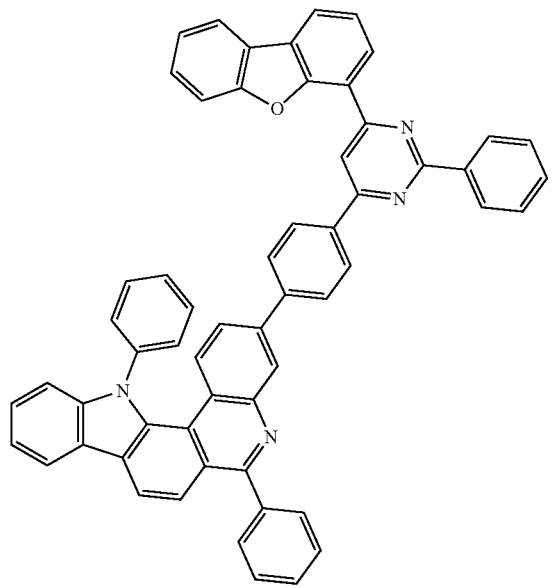
2-13
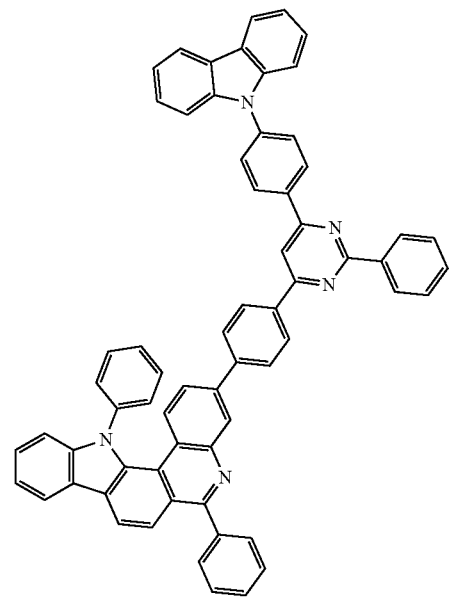
2-14
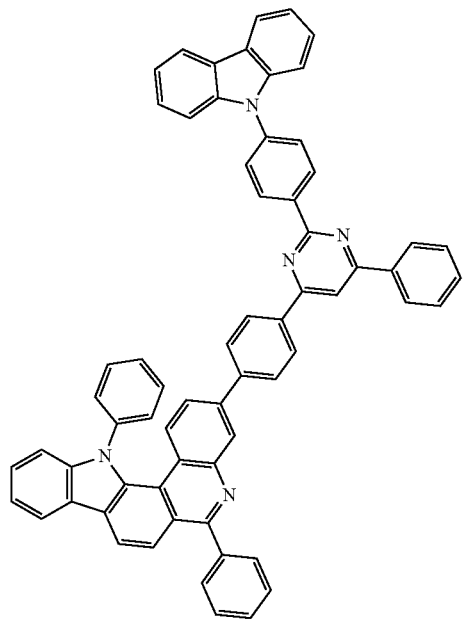
2-16
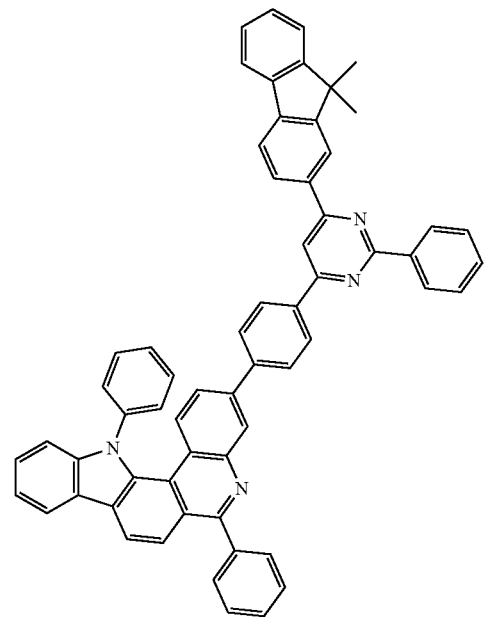

-continued
2-17
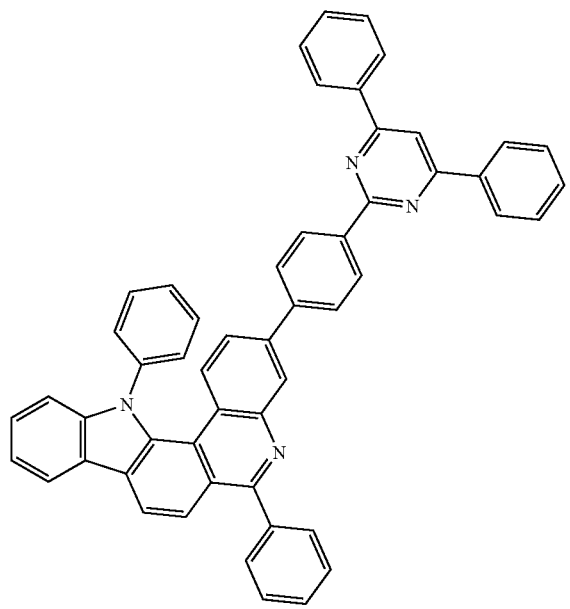
2-18
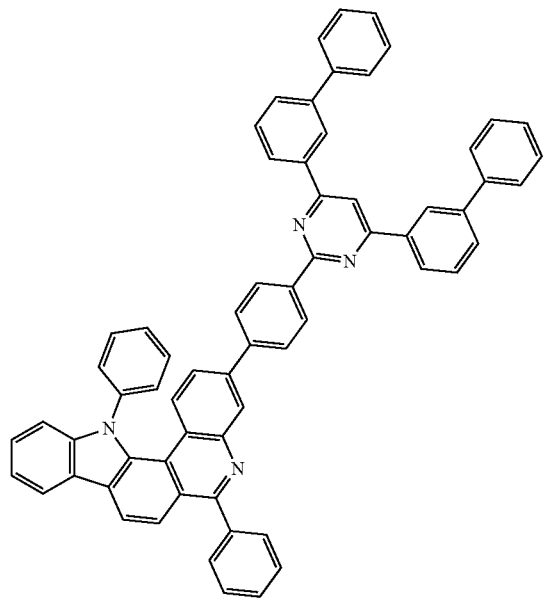
2-19
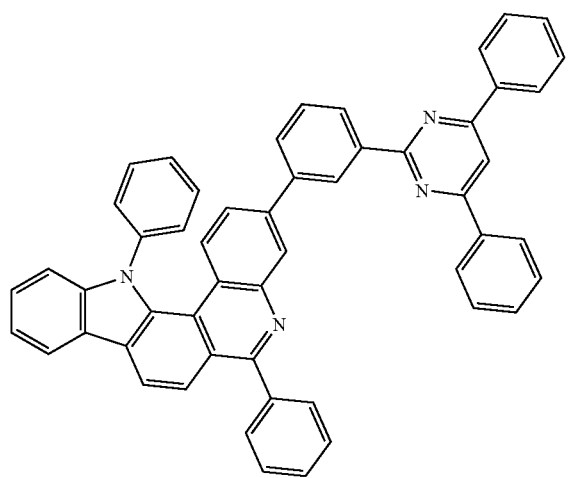
2-20
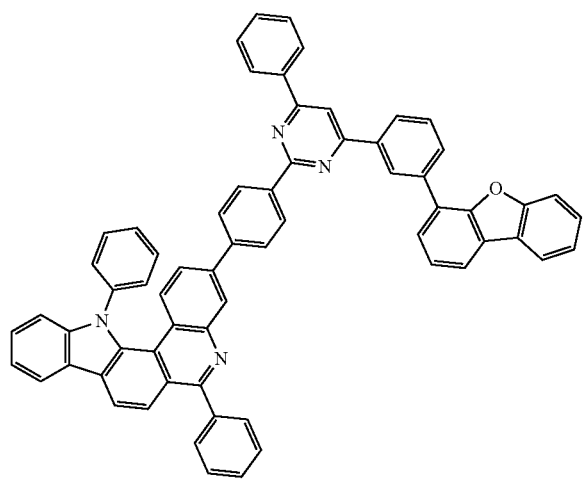

-continued
2-21
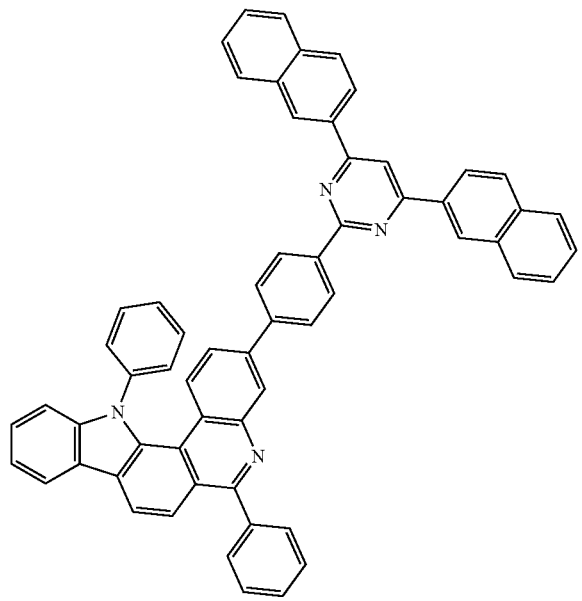
2-22
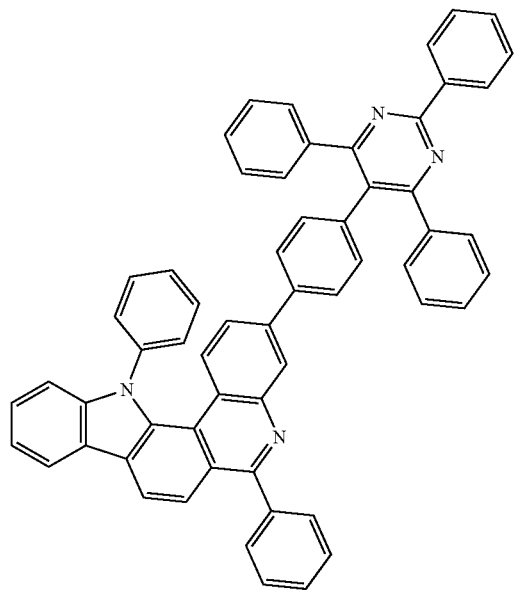
2-23
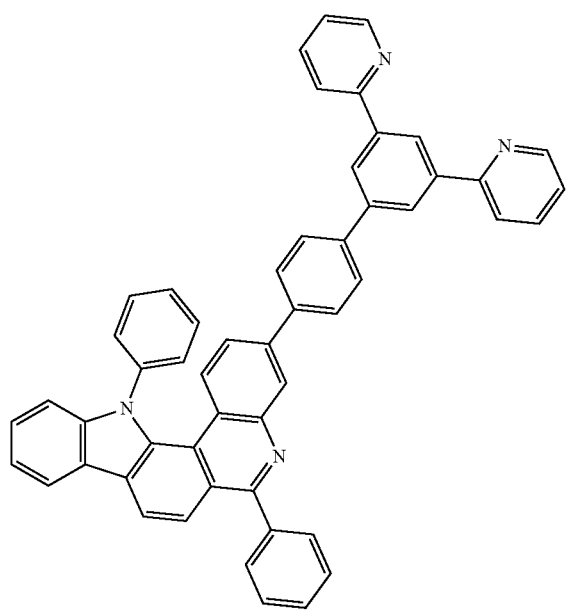
2-24
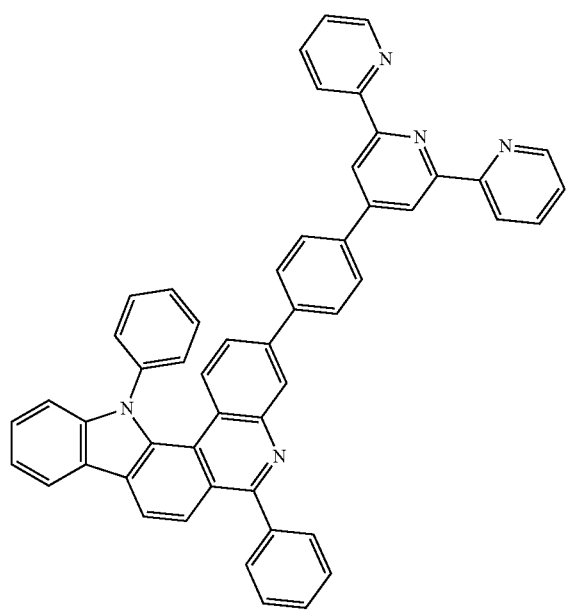

-continued
2-25
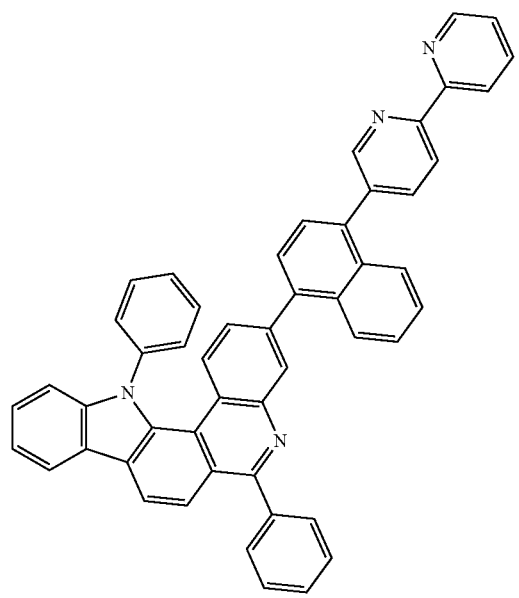
2-26
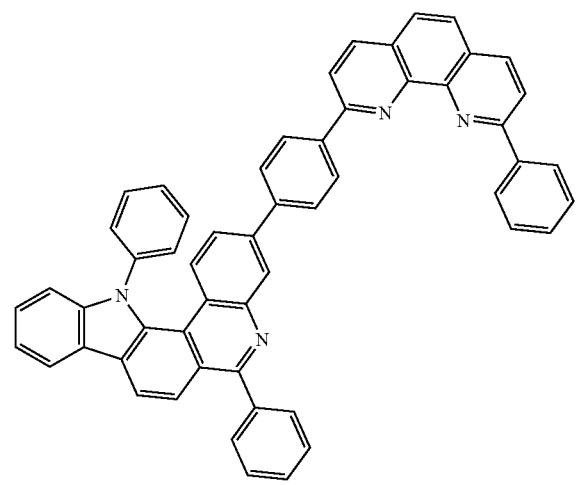
2-27
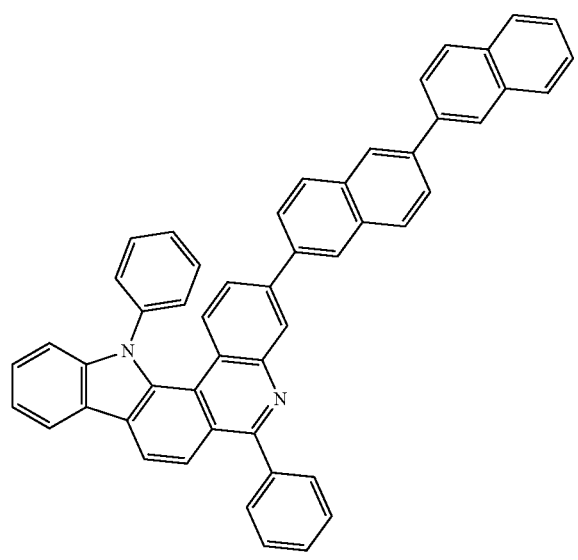
2-28
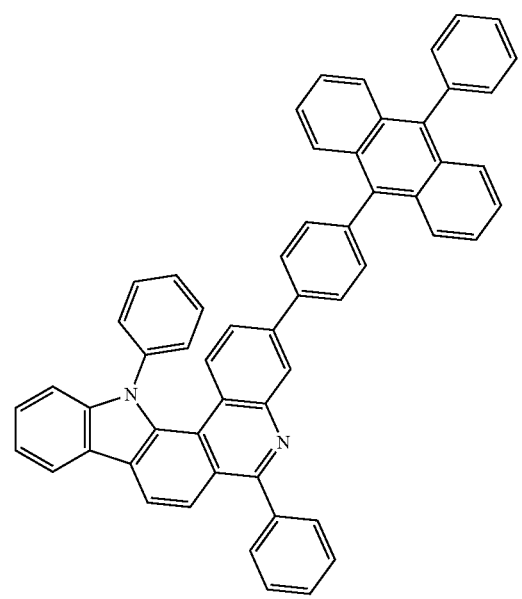

2-29
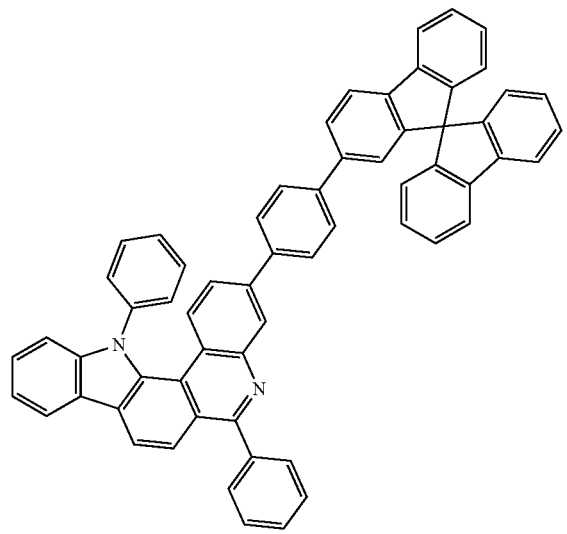
2-30
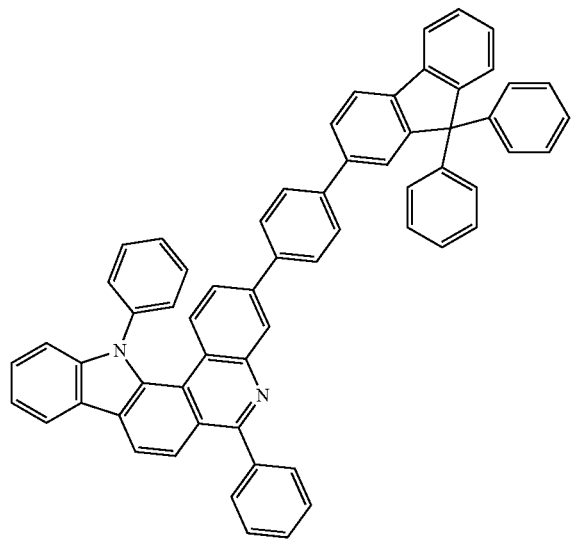
2-31
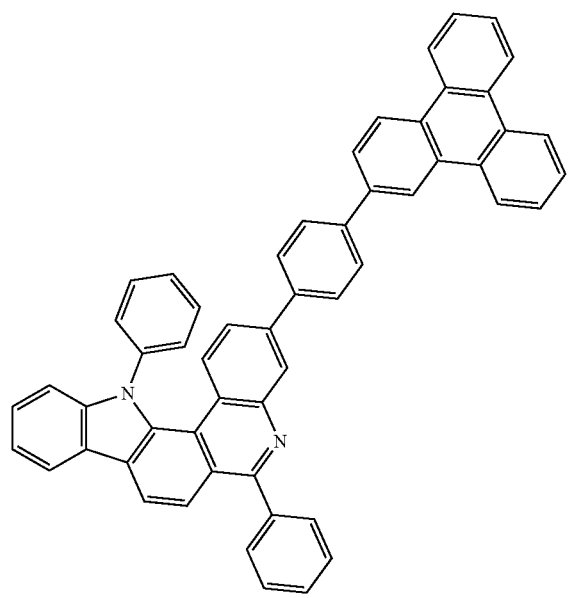
2-32
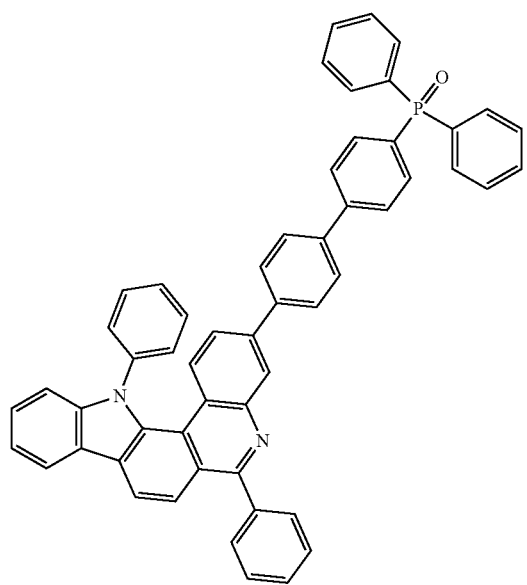

2-33
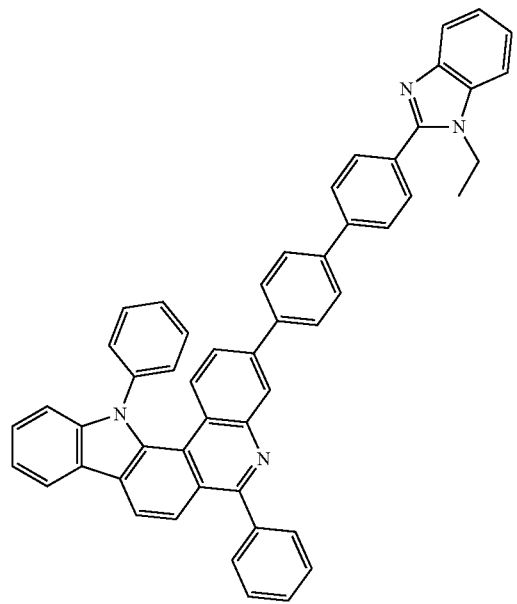
2-34
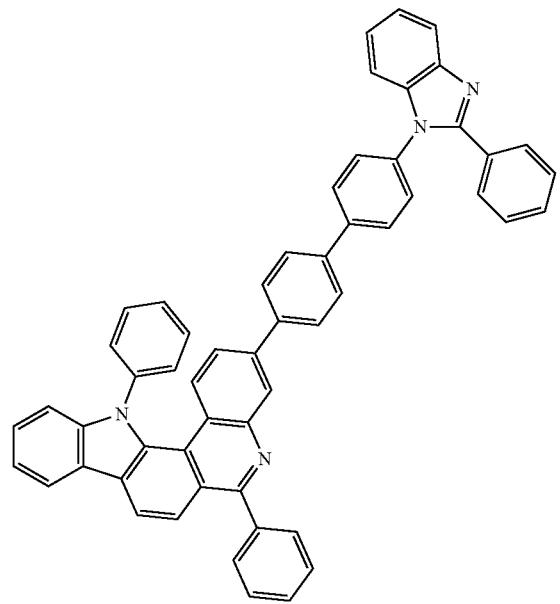
2-35
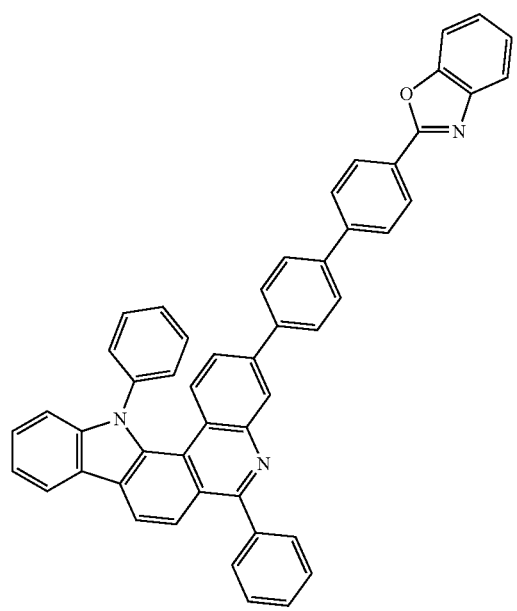
2-36
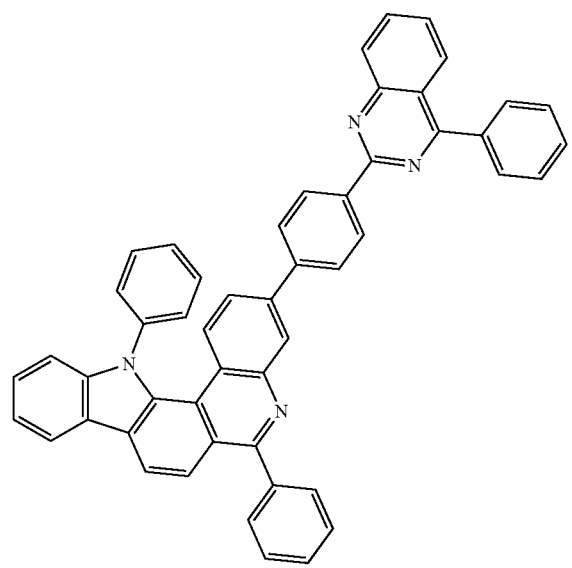

-continued
2-37
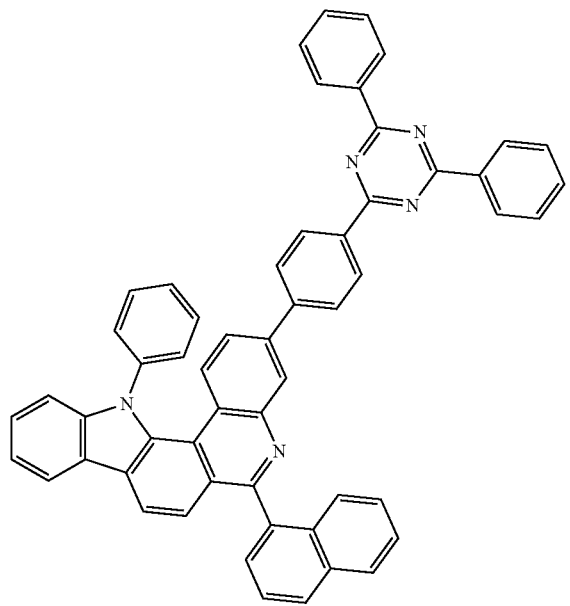
2-38
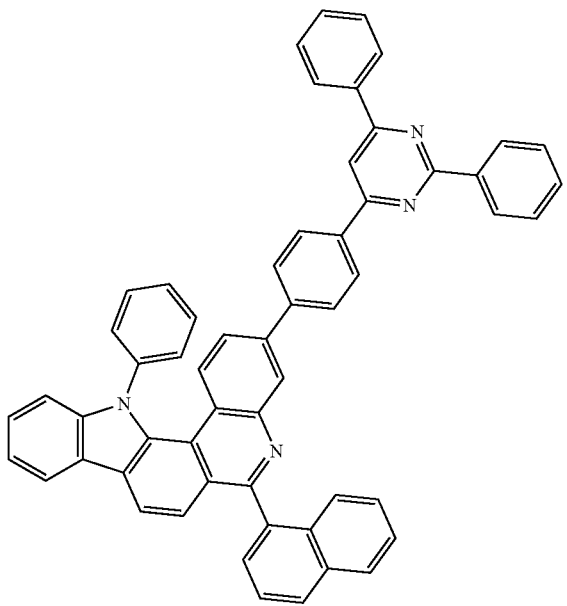
3
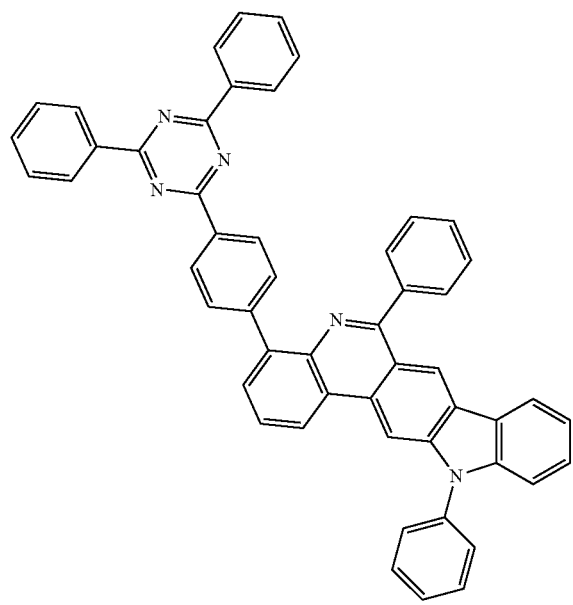
3-1
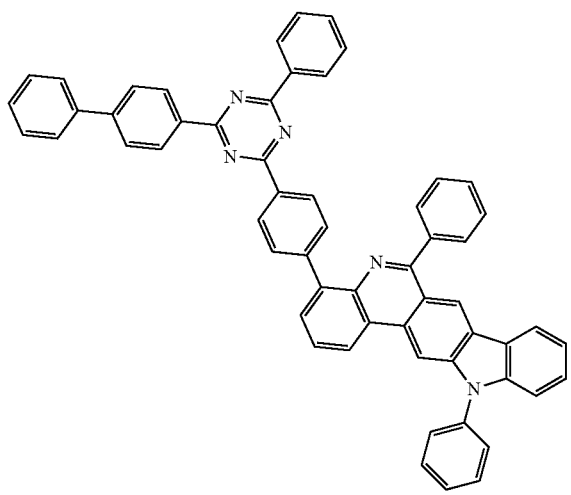

-continued
3-2
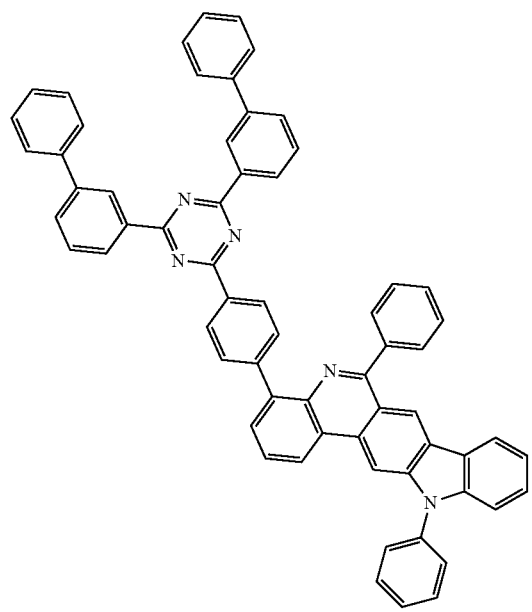
3-3
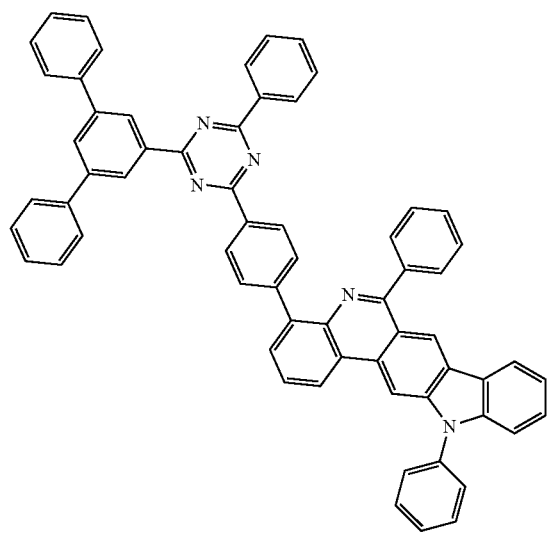
3-4
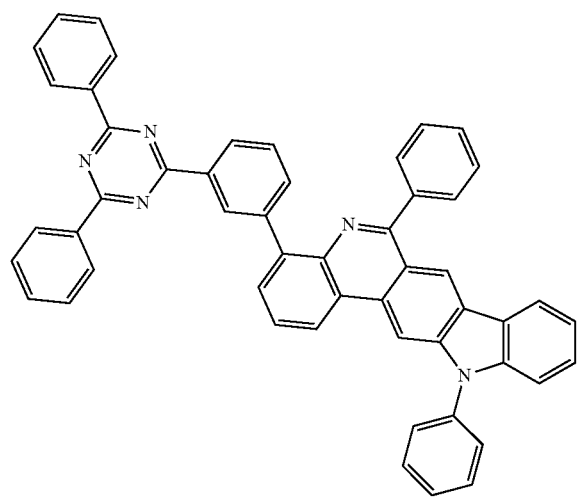
3-5
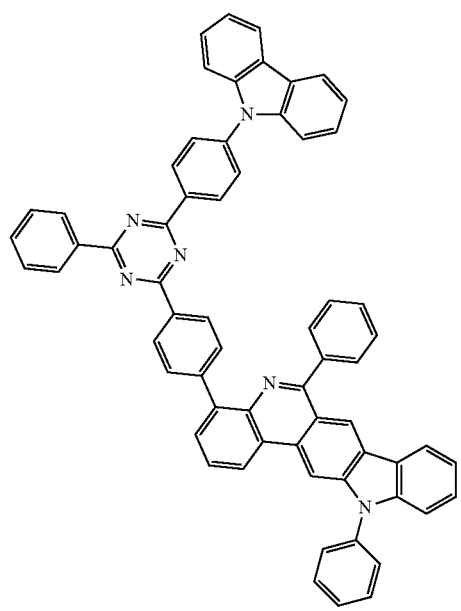

3-6
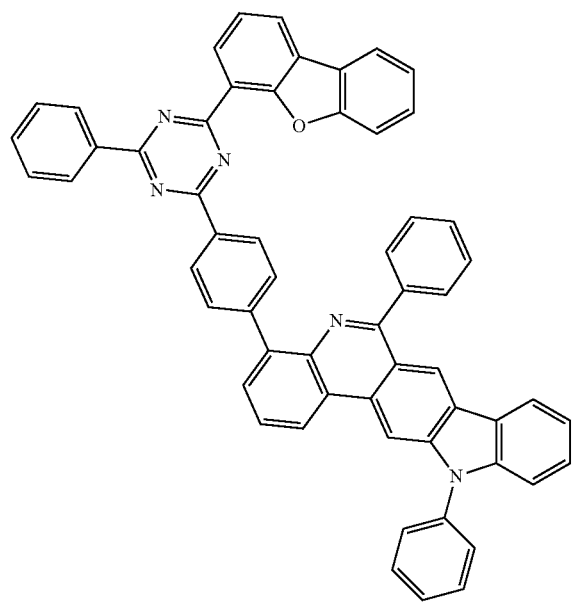
3-7
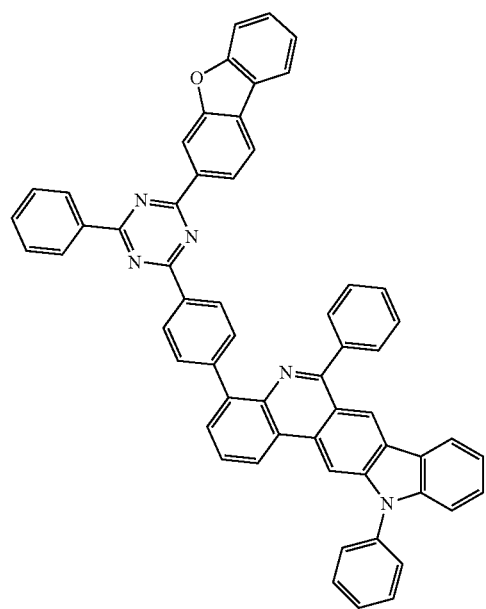
3-8
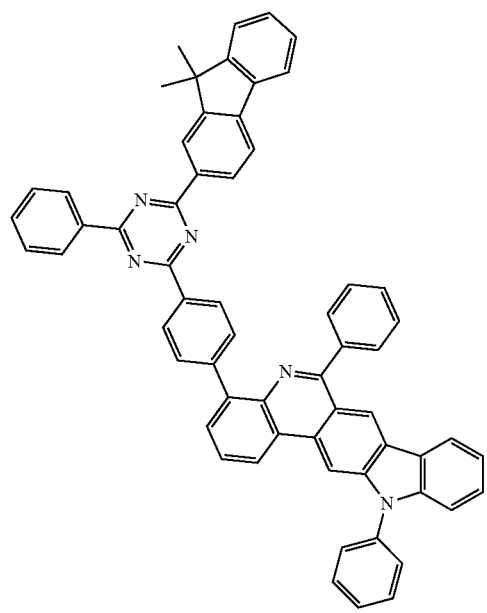
3-9
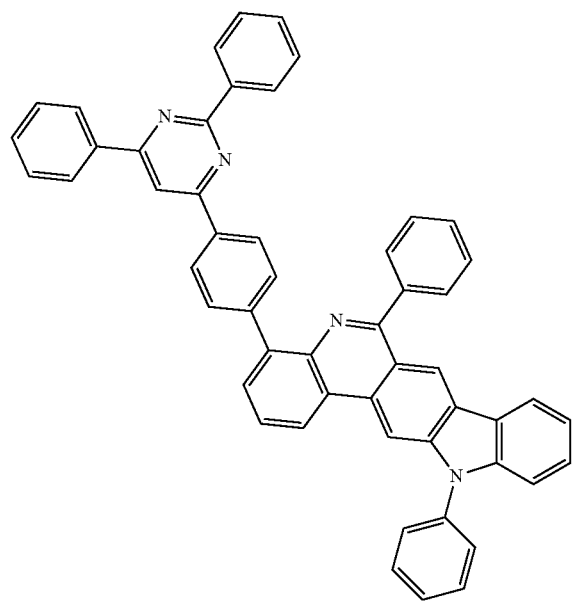

-continued
3-10
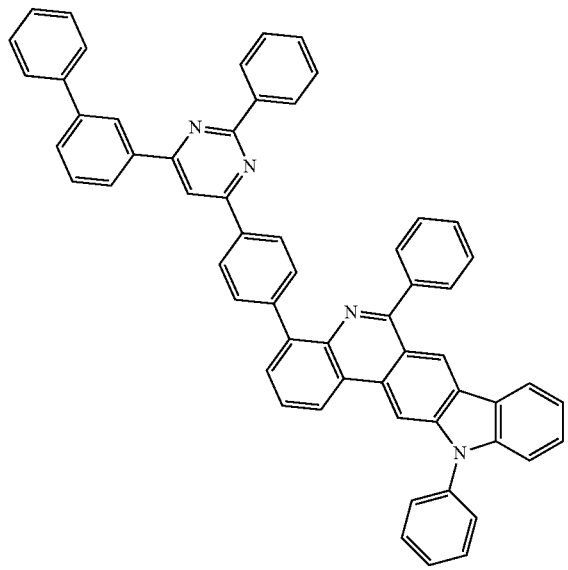
3-11
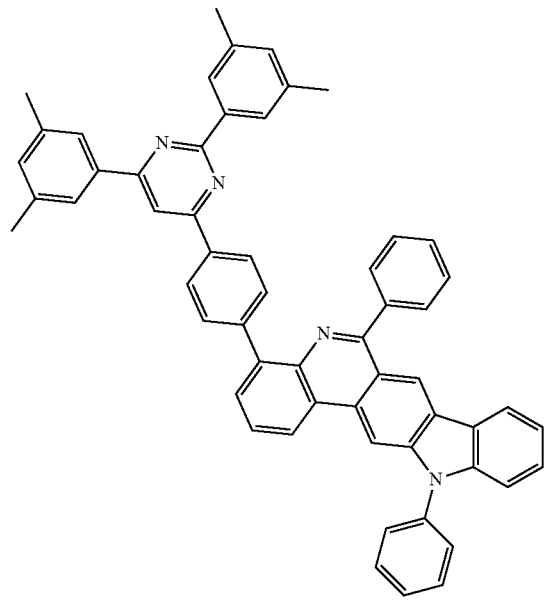
3-12
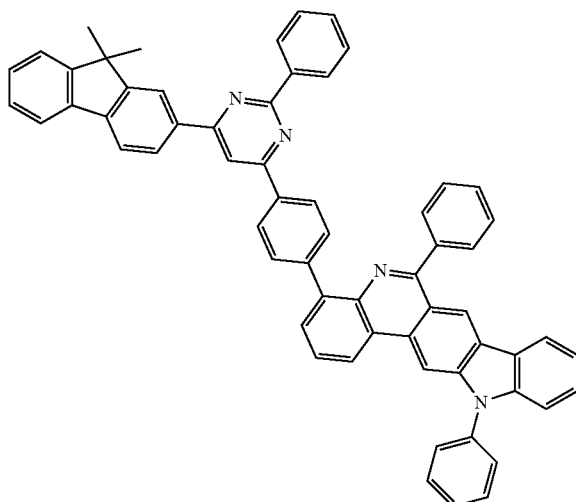
3-13
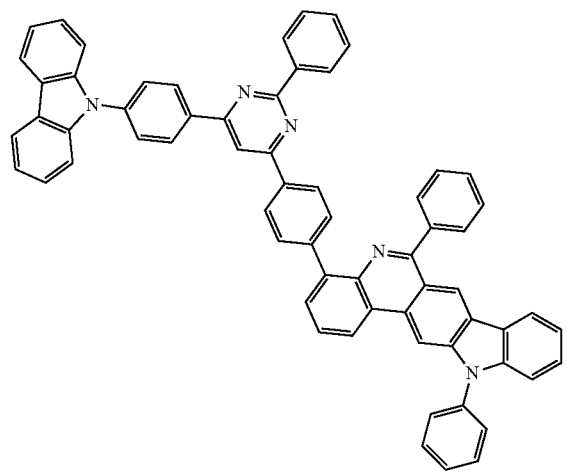
3-14
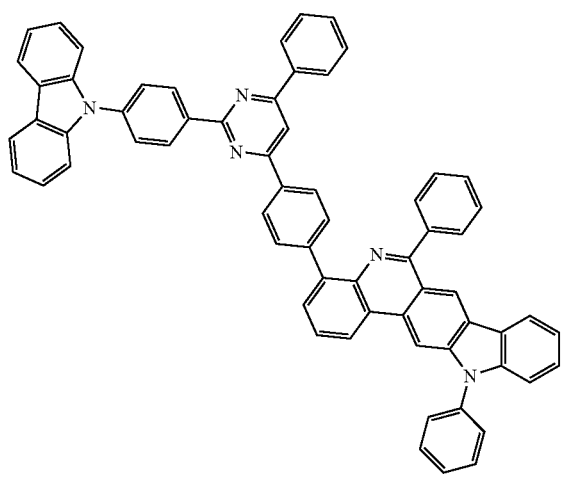
3-15
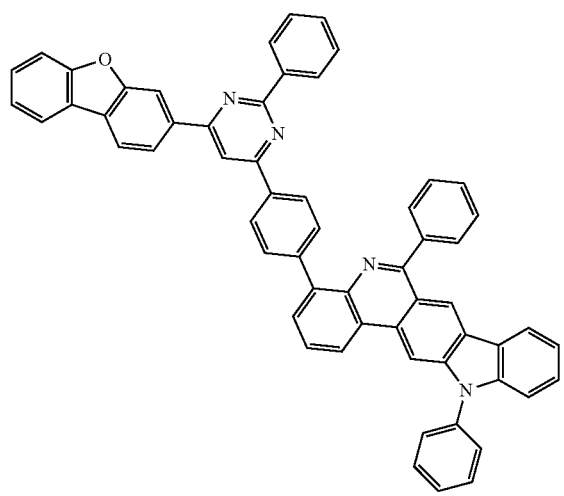

3-16
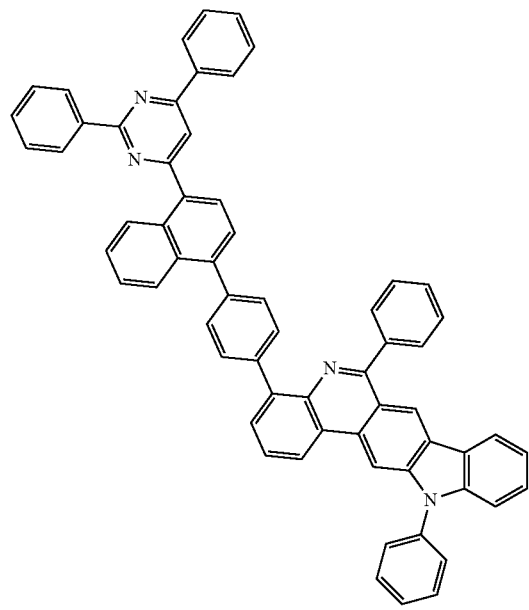
3-17
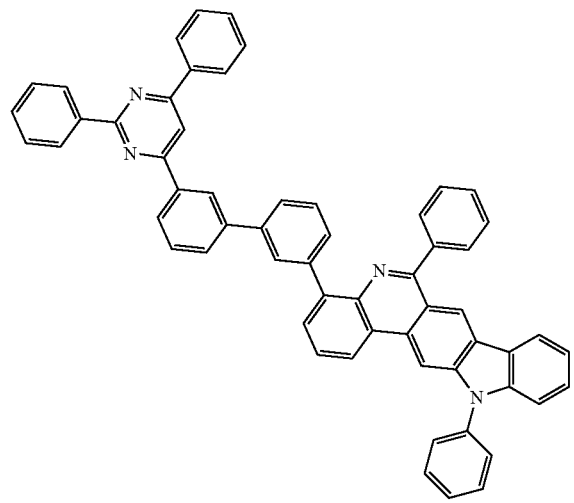
3-18
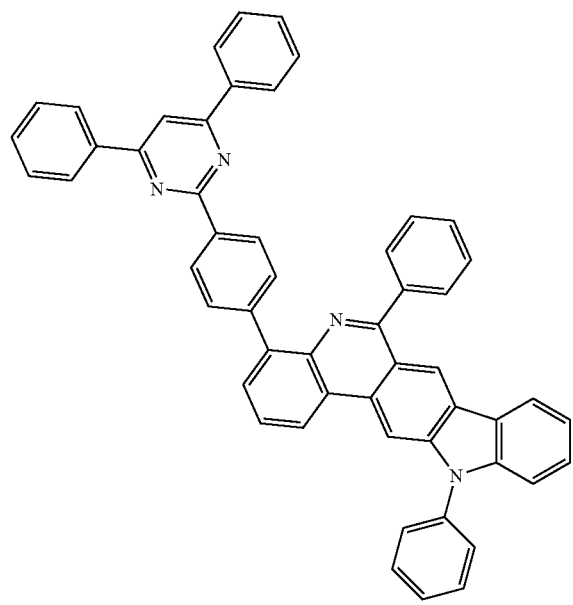
3-19
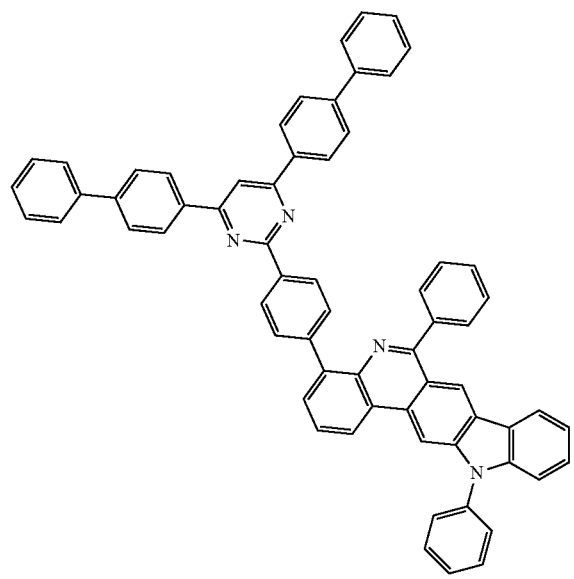

3-20
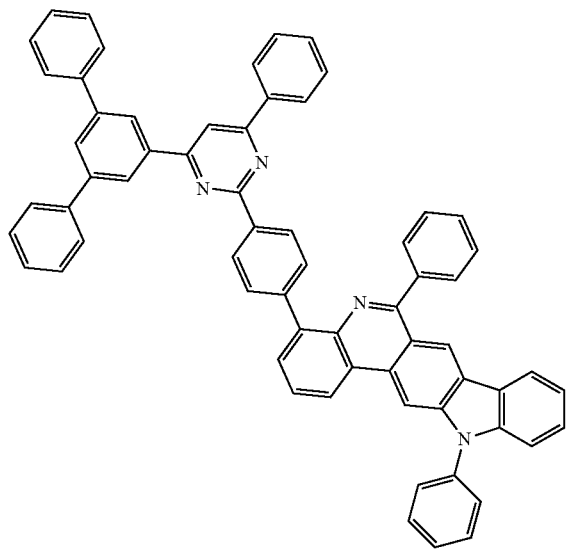
3-21
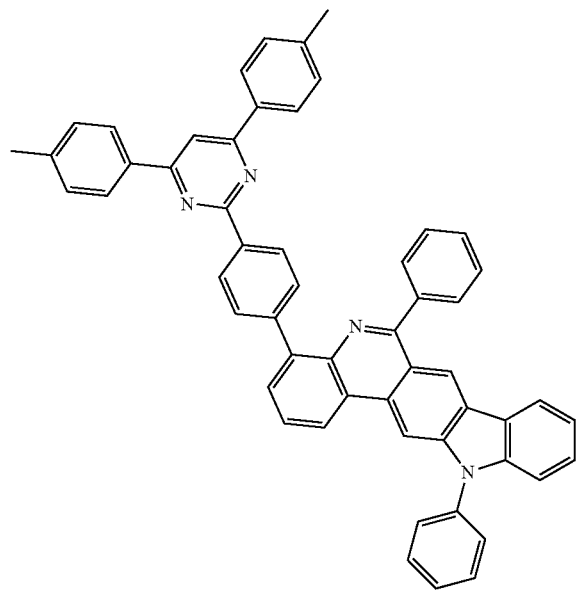
3-22
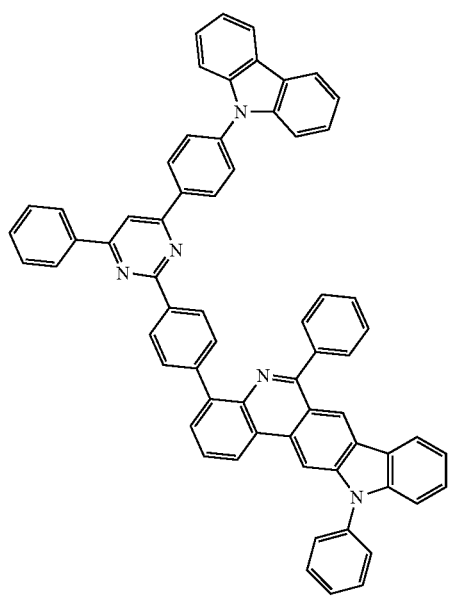
3-23
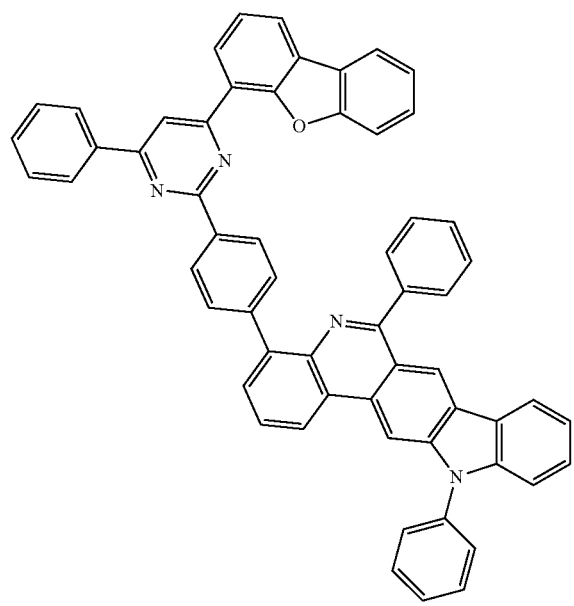

-continued
3-24
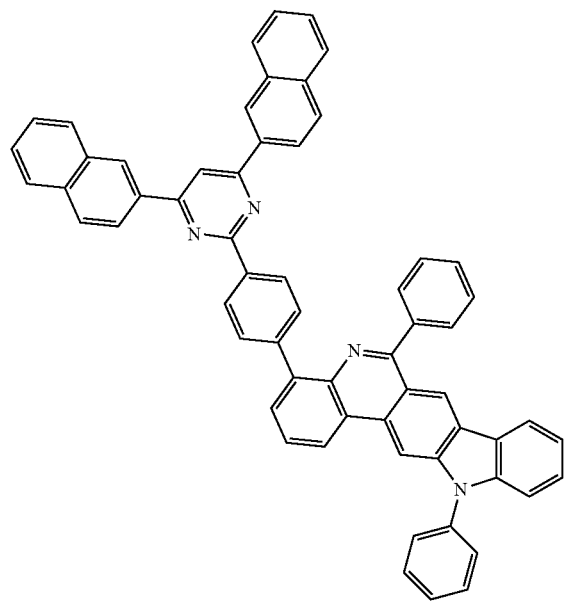
3-25
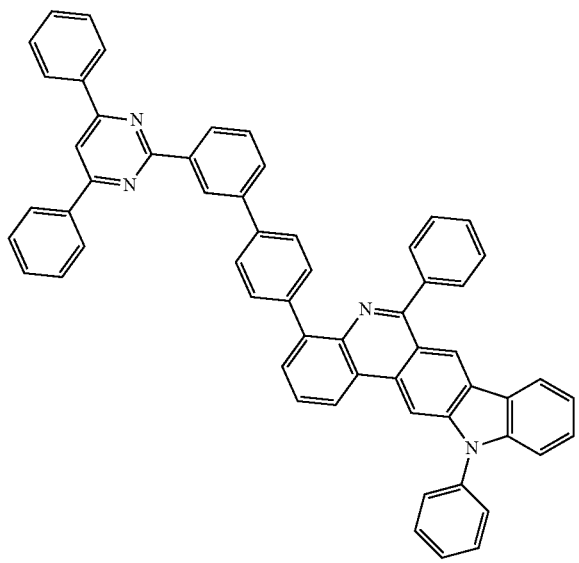
3-26
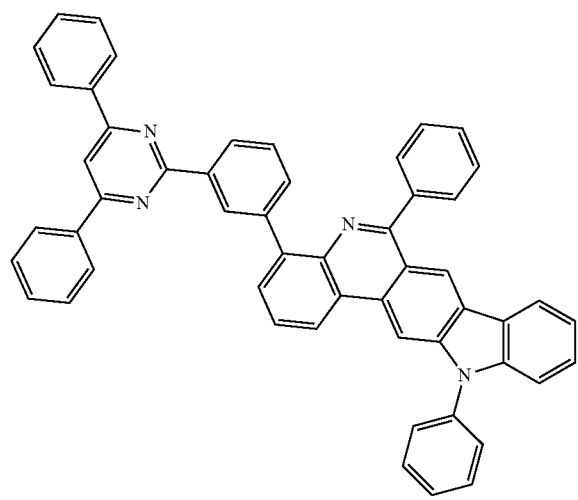
3-27
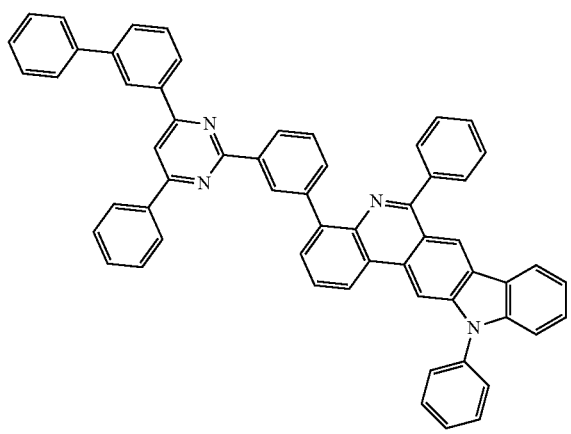

-continued
3-28
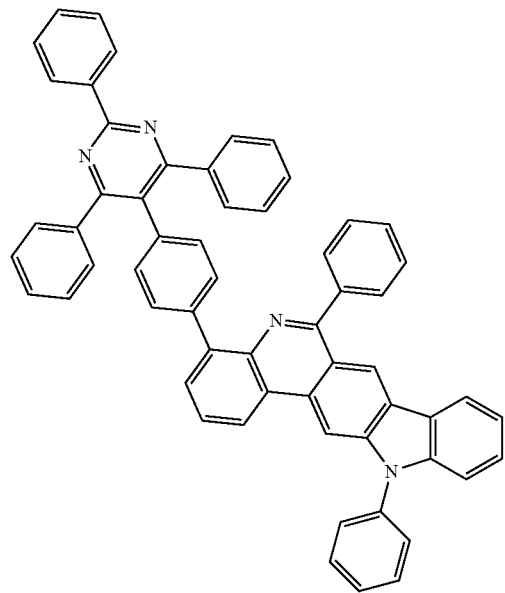
3-29
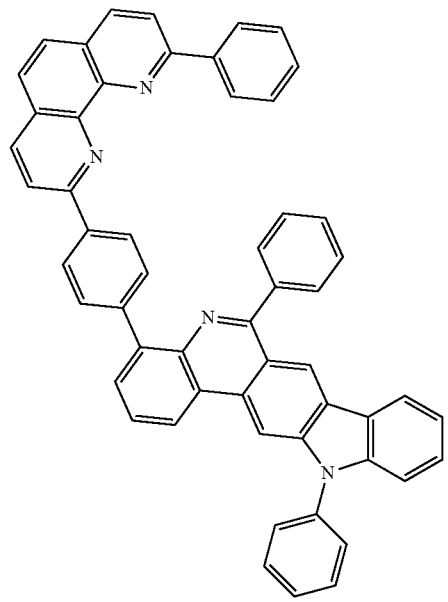
3-30
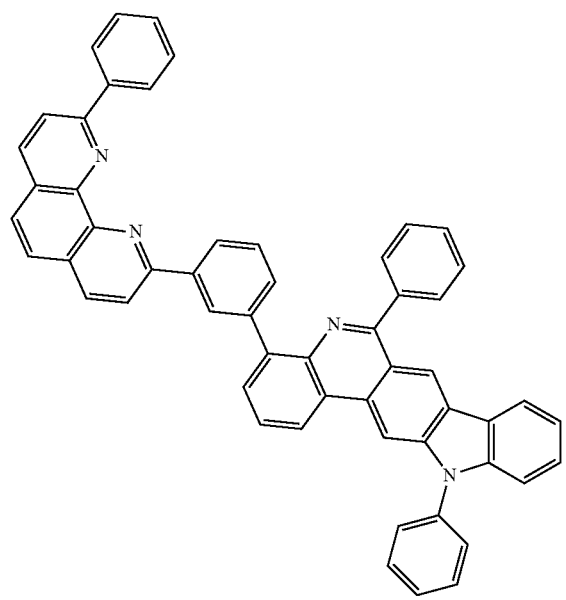
3-31
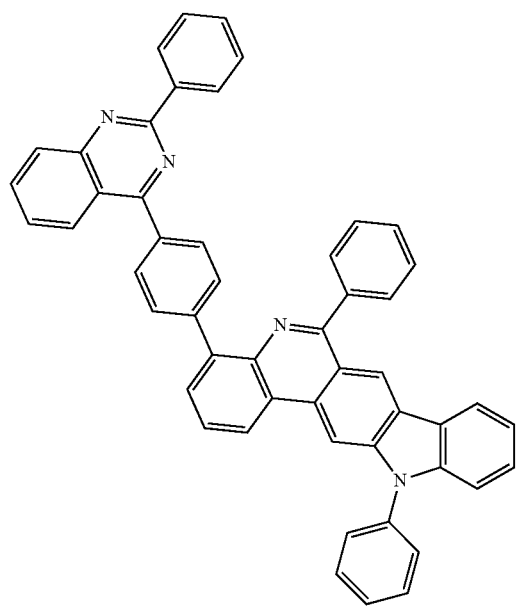

3-32
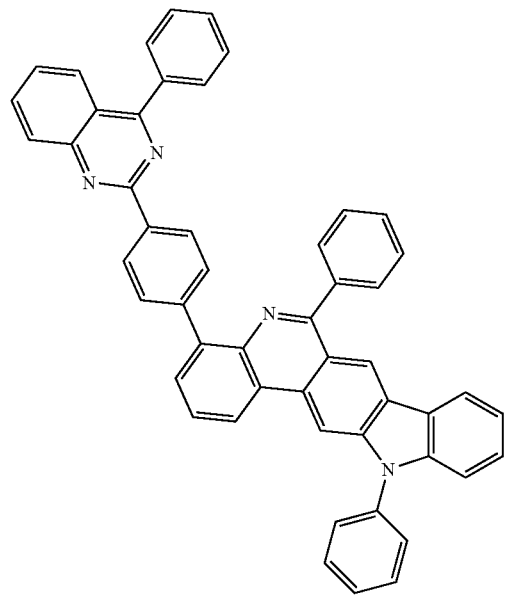
3-33
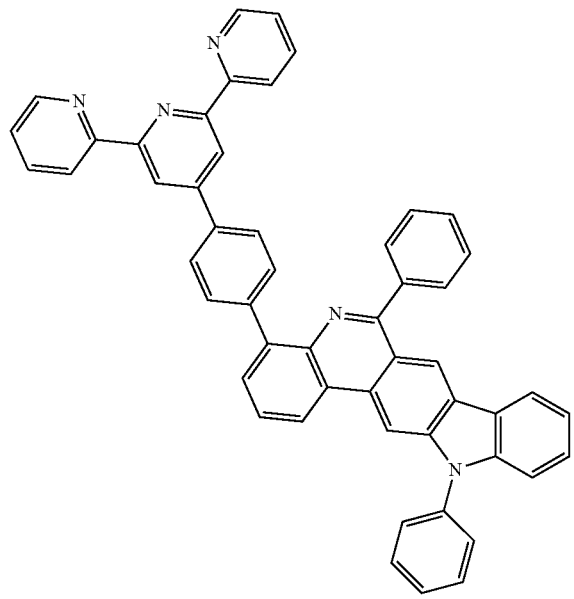
3-34
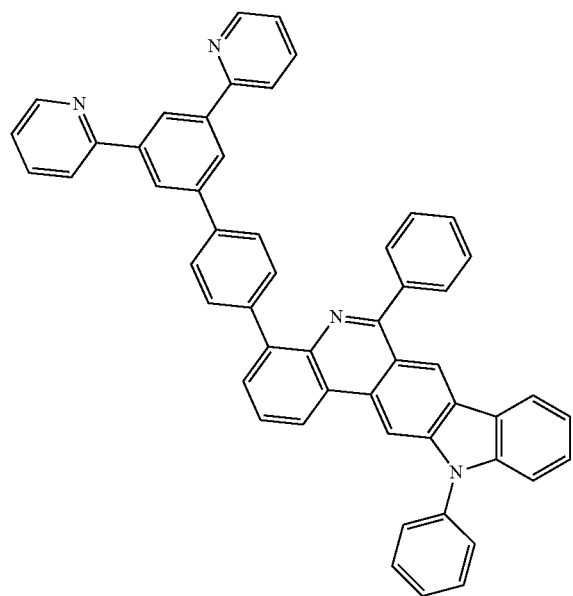
3-35
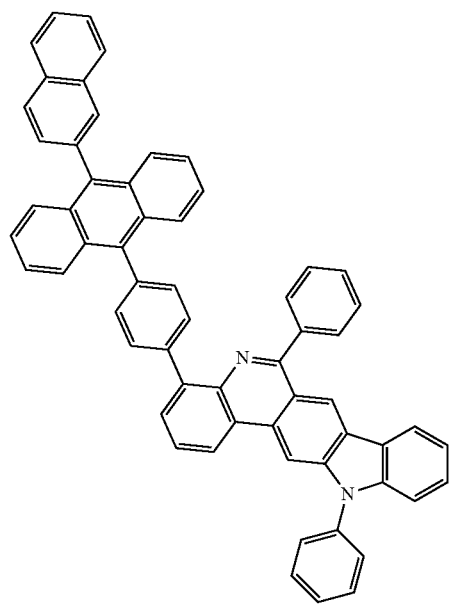

-continued
3-36
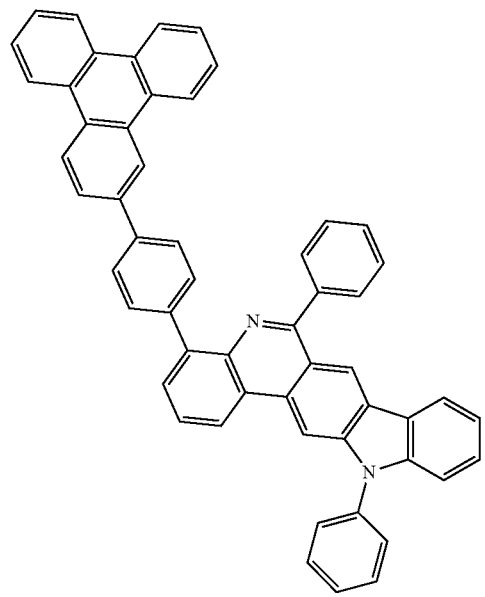
3-37
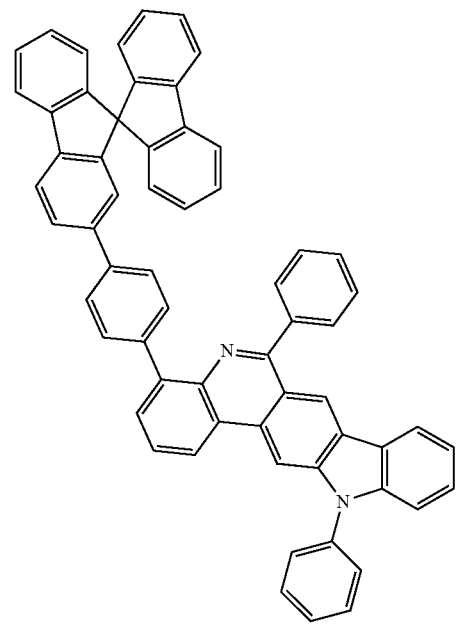
3-38
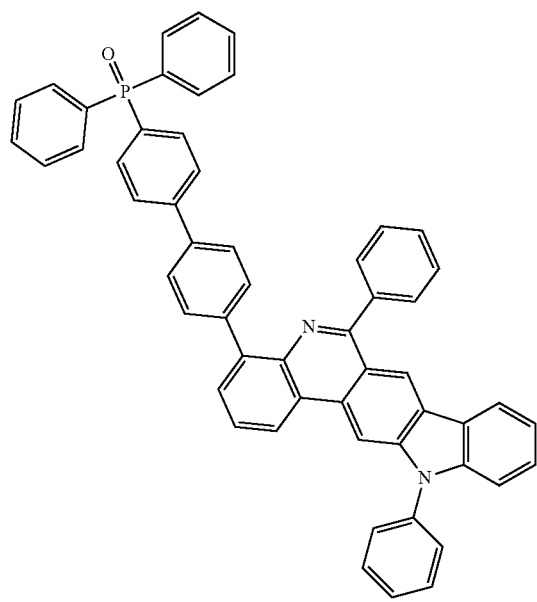
3-39
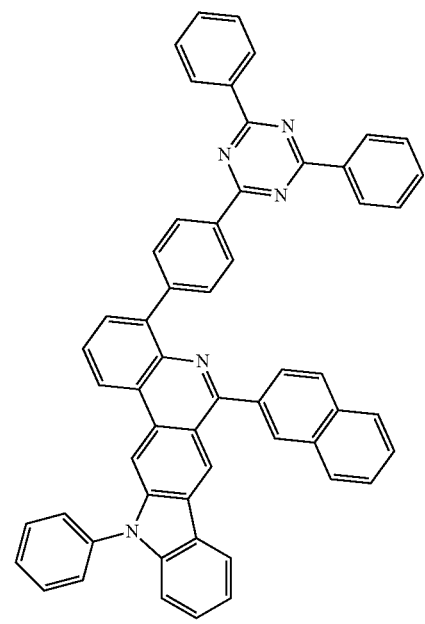

3-40
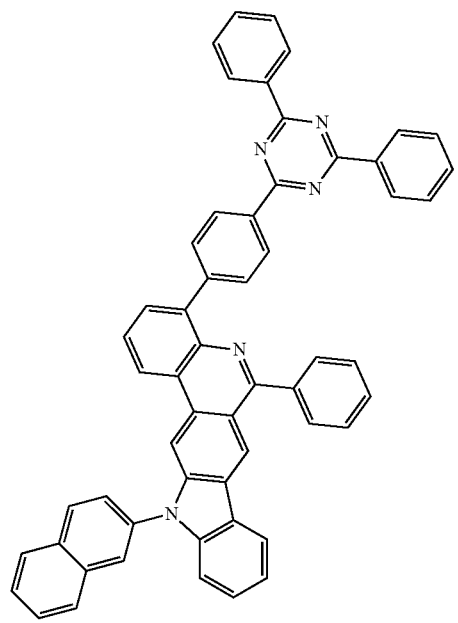
3-41
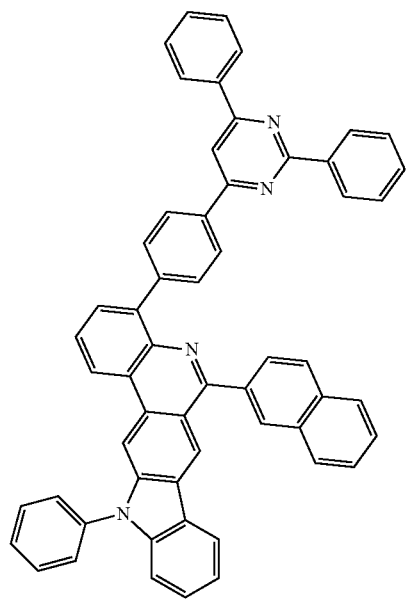
3-42
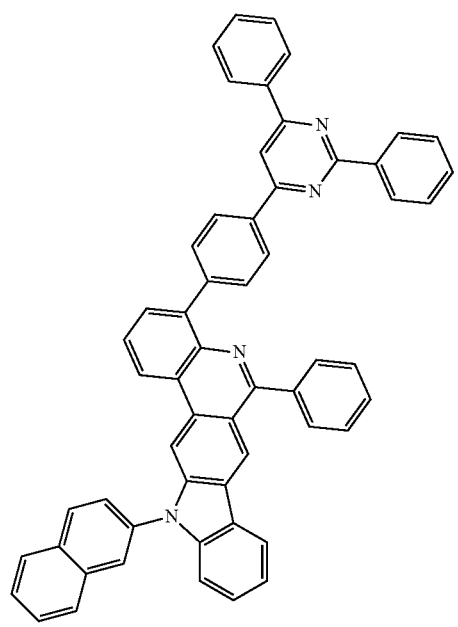
4
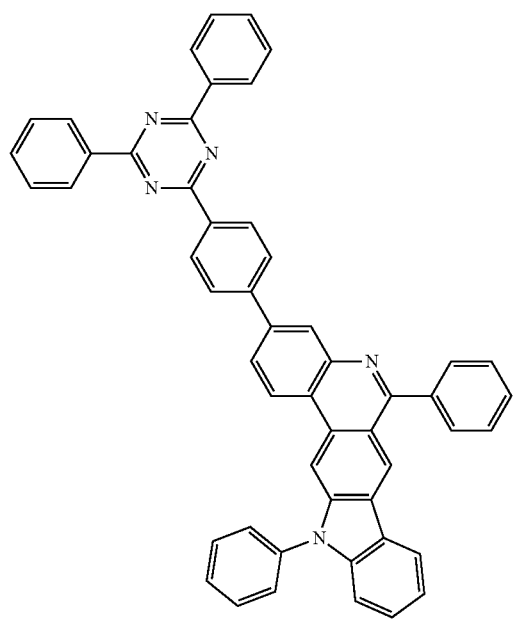

-continued
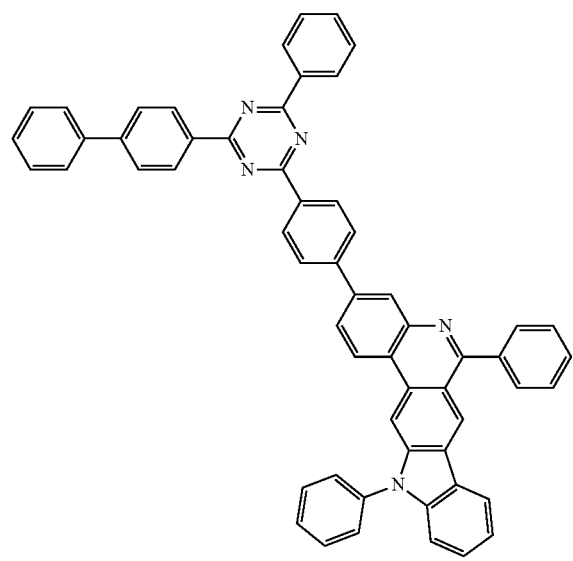
4-1
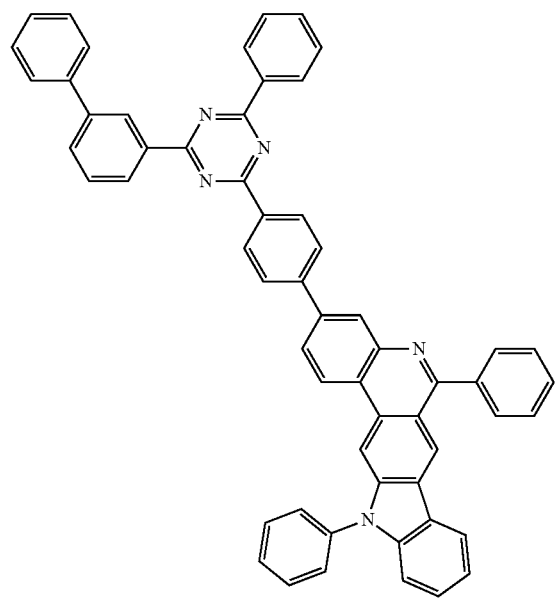
4-2
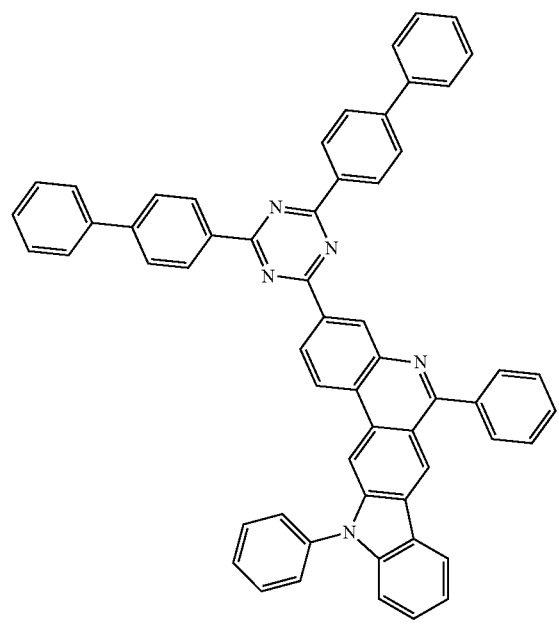
4-3
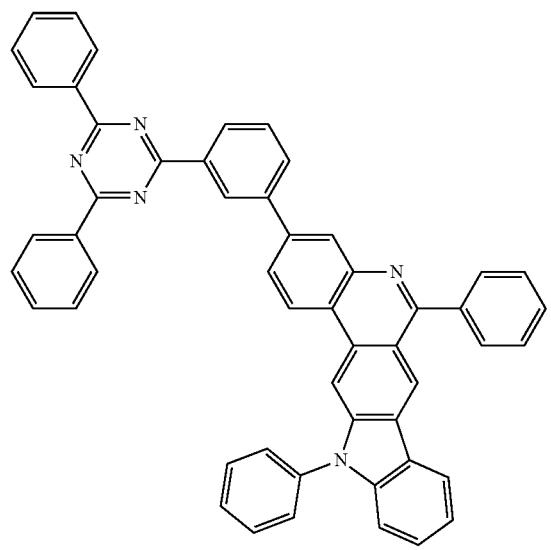
4-4

81
-continued
4-5
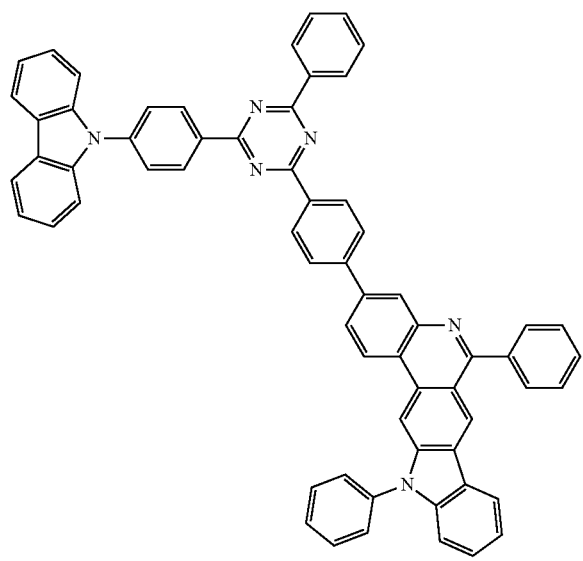
82
4-6
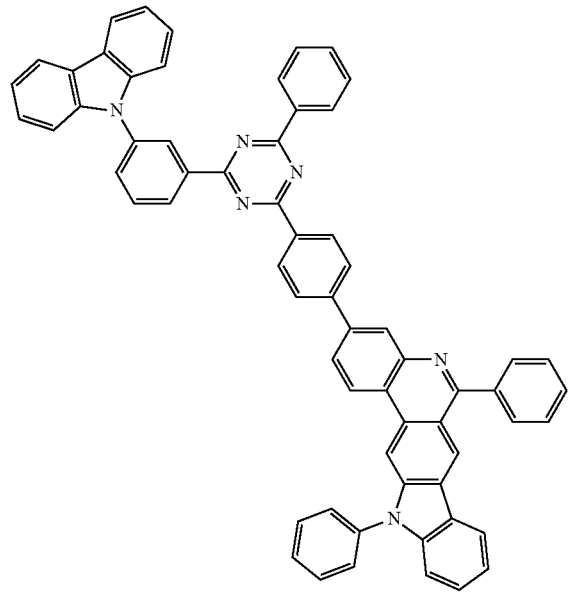
4-7
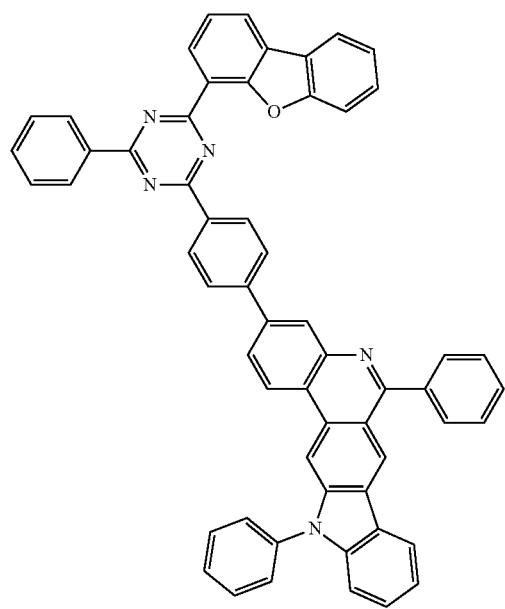
4-8
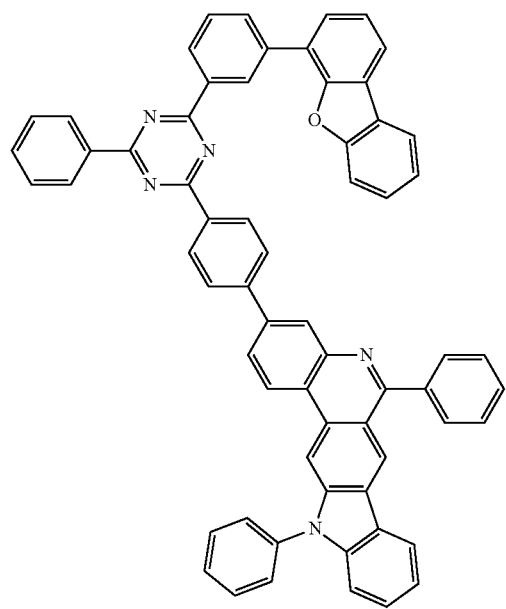

-continued
4-9
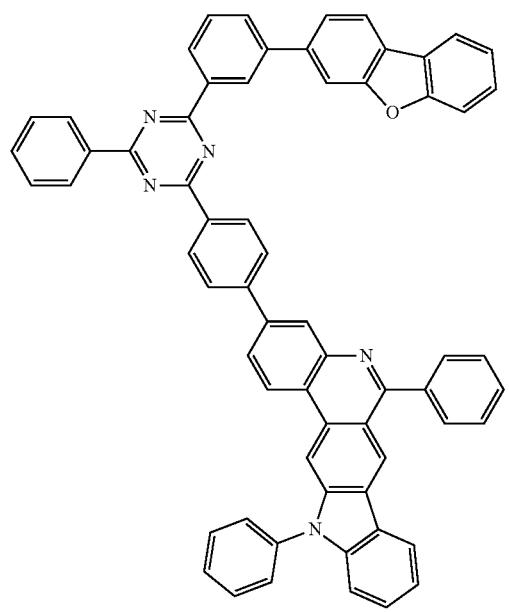
4-10
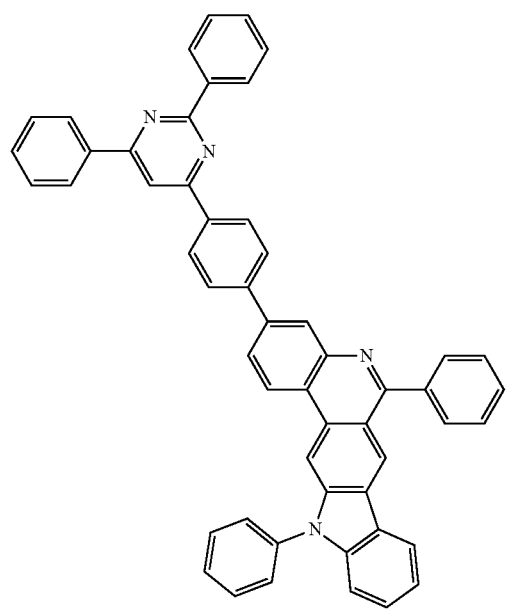
4-11
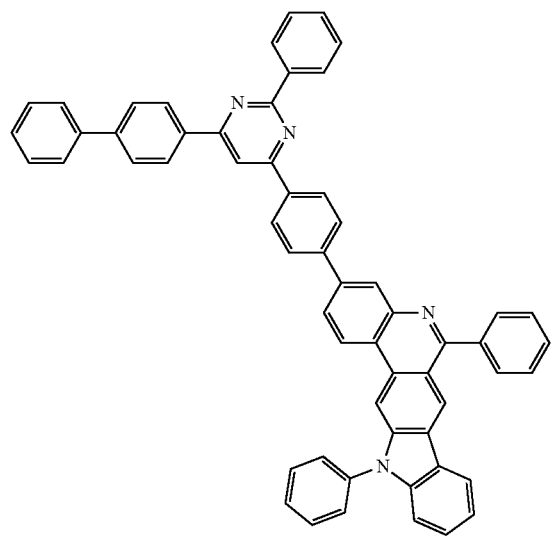
4-12
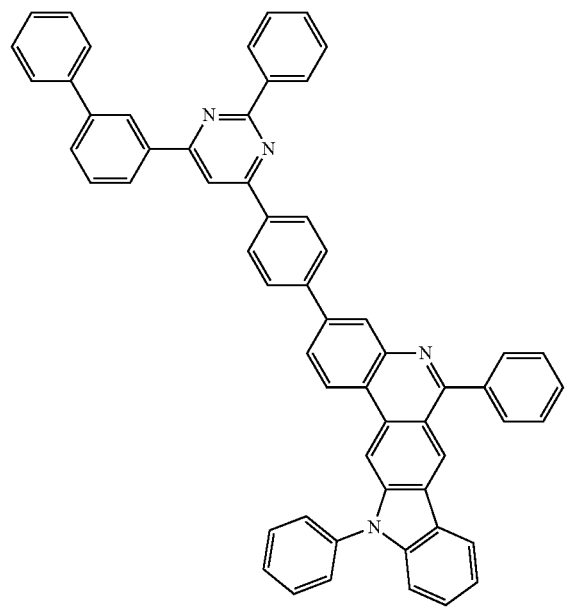

4-13
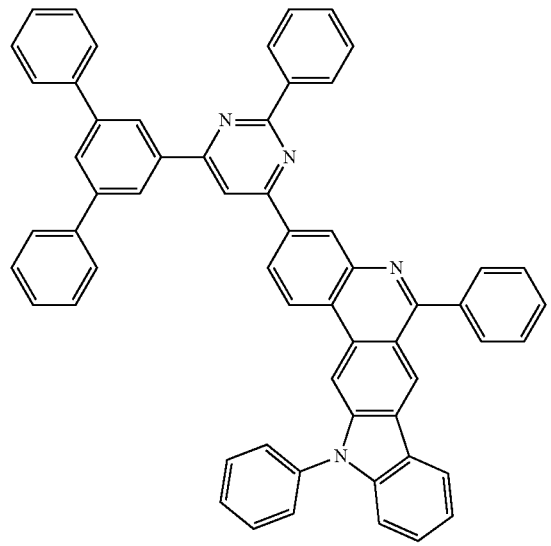
4-14
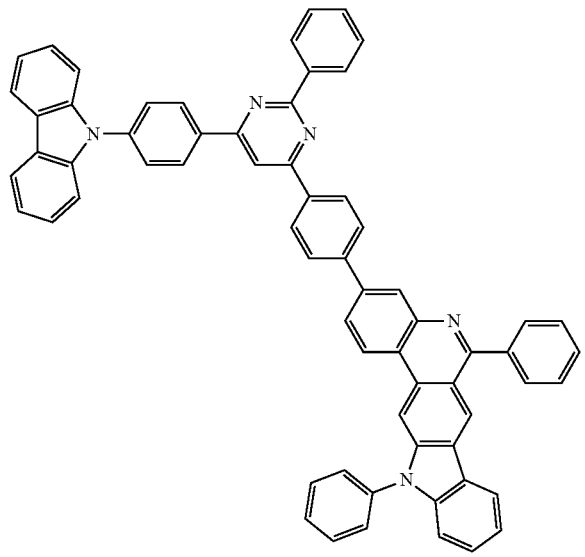
4-15
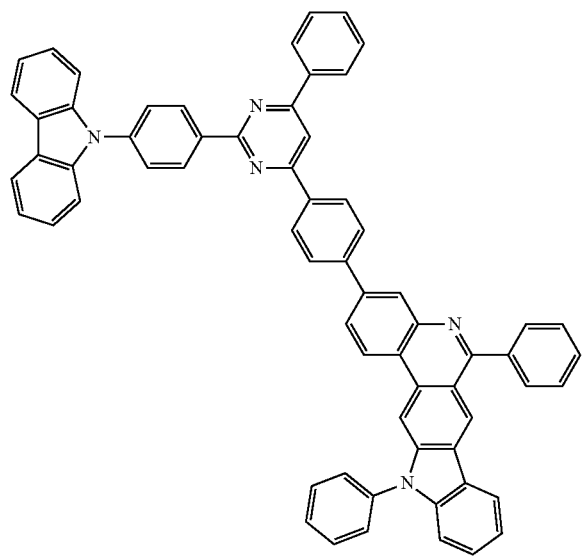
4-16
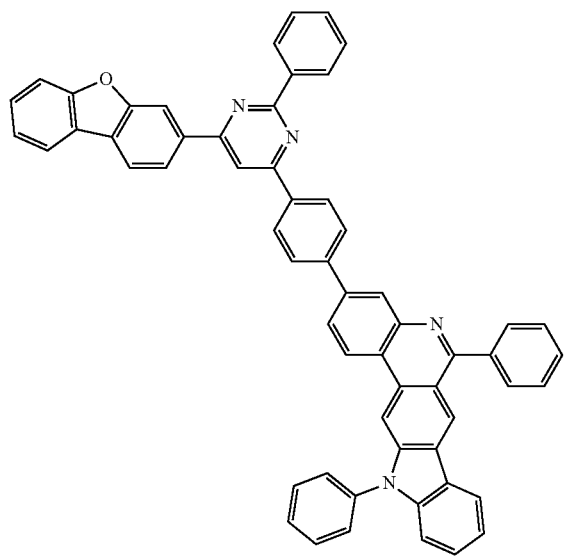

-continued
4-17
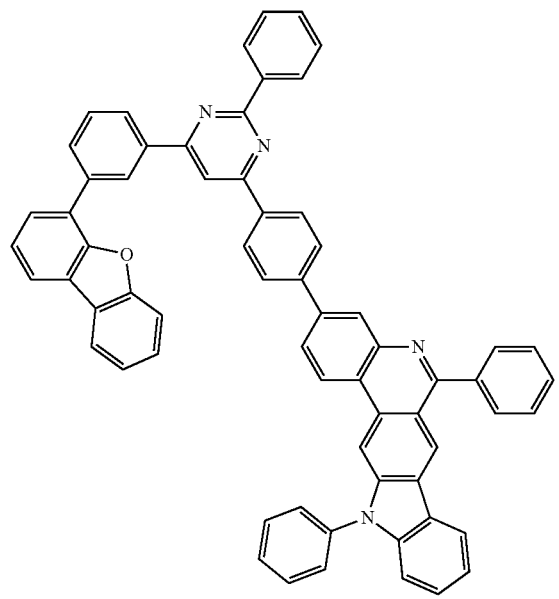
4-18
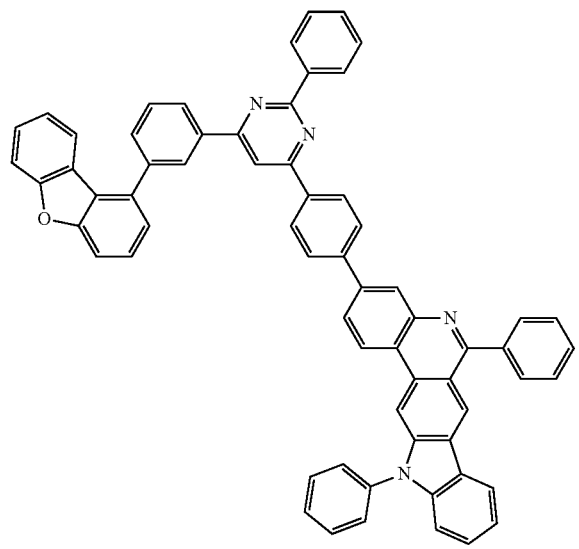
4-19
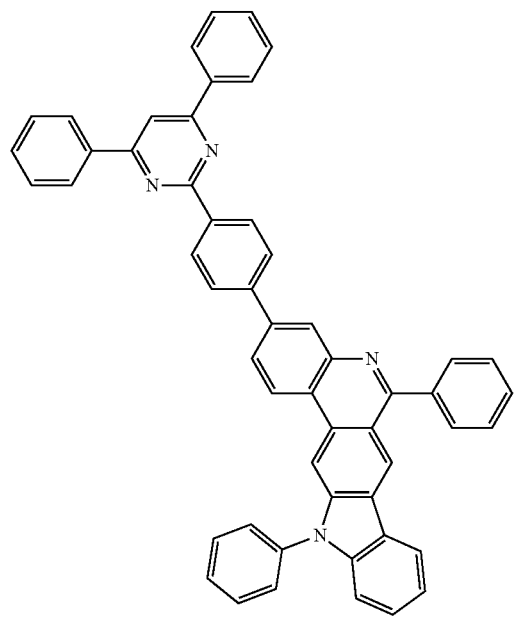
4-20
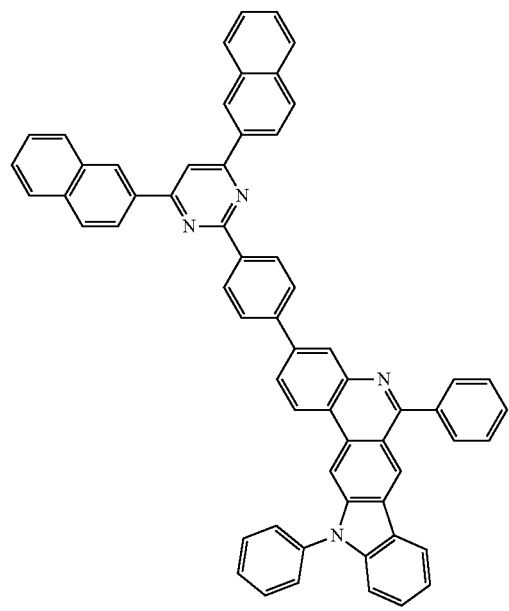

-continued
4-21
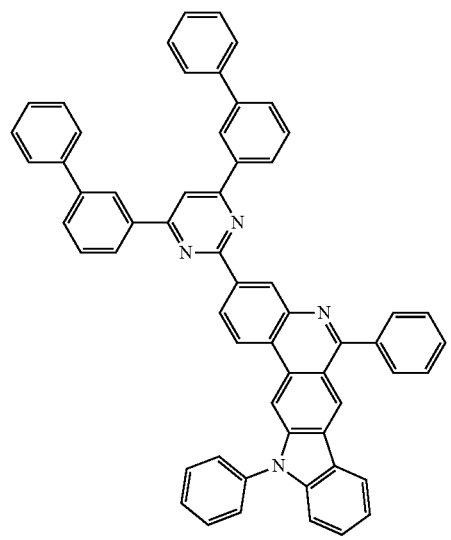
4-22
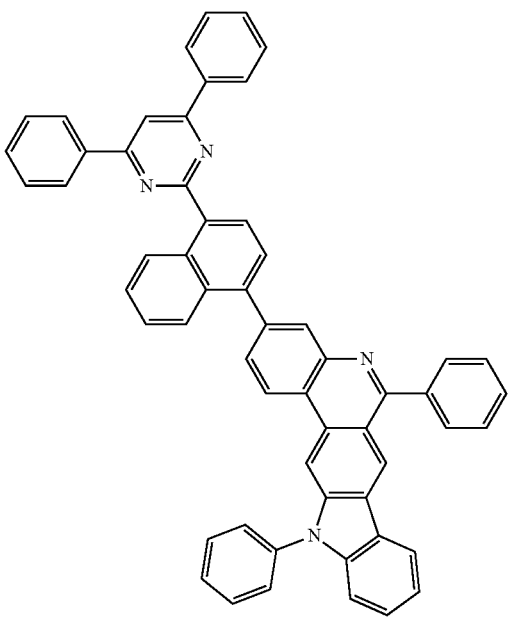
4-23
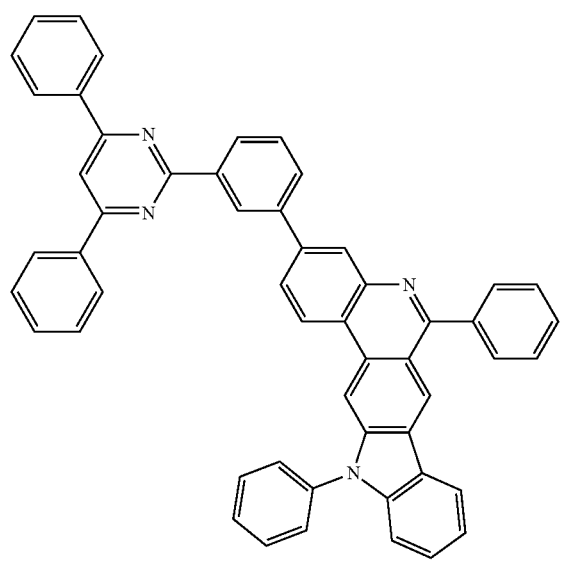
4-24
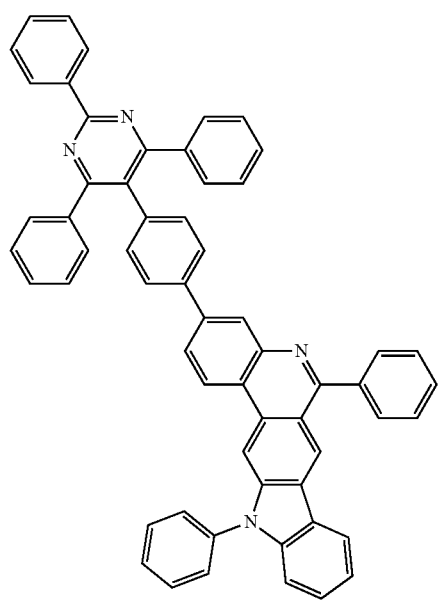

-continued
4-25
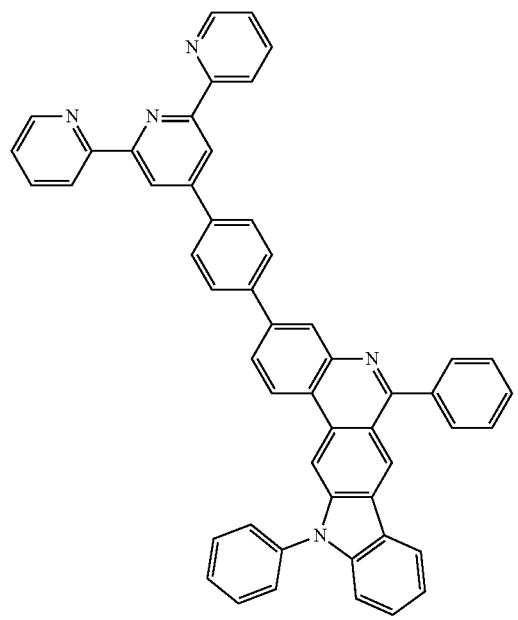
4-26
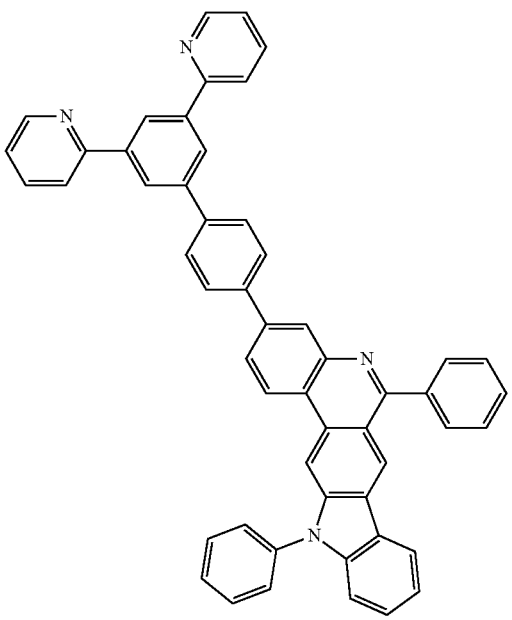
4-27
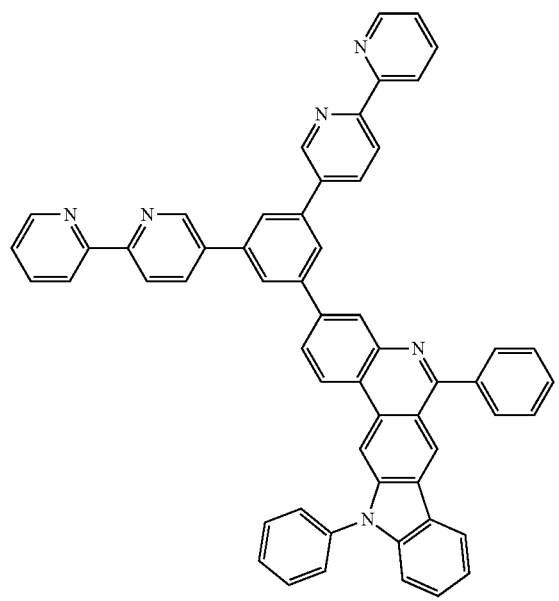
4-28
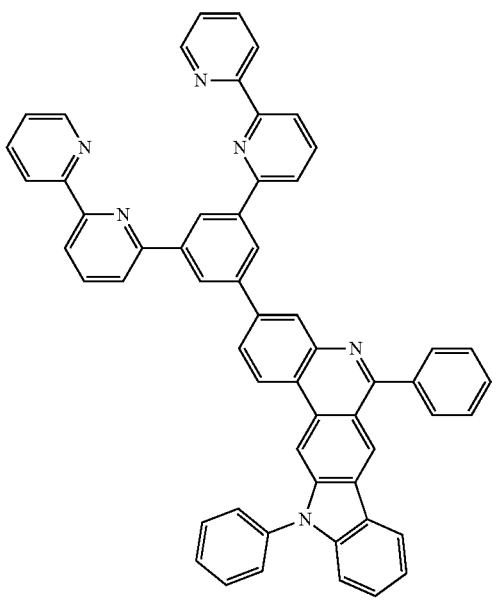

4-29
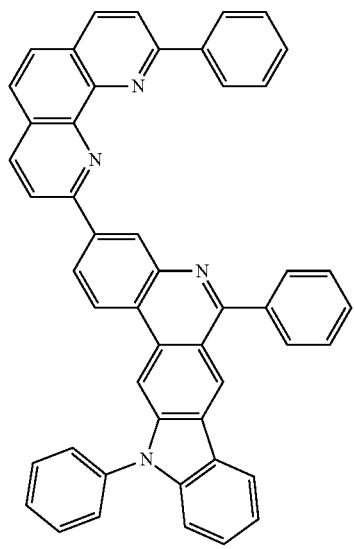
4-30
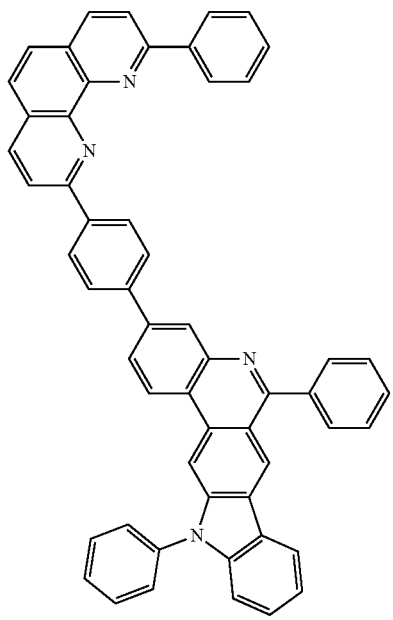
4-31
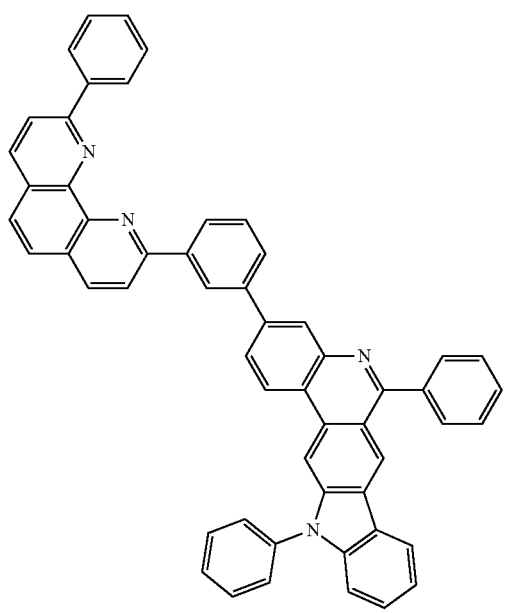
4-32

-continued
4-33
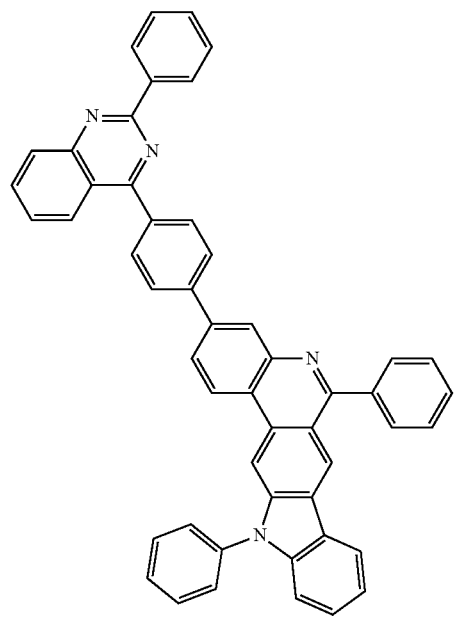
4-34
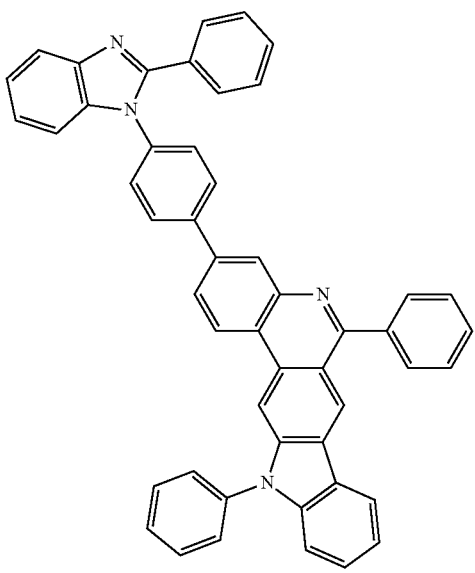
4-35
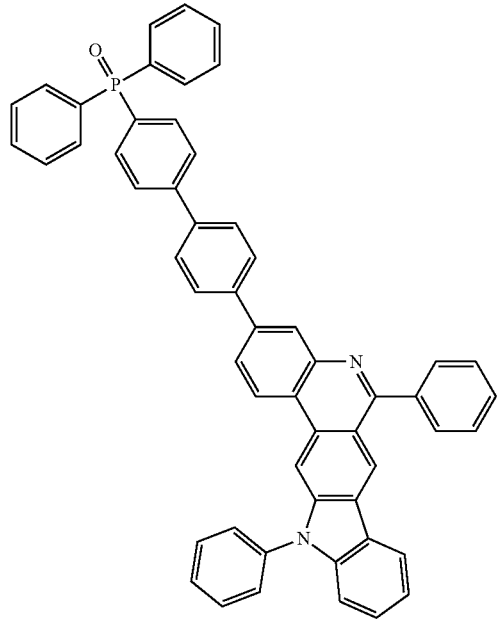
4-36
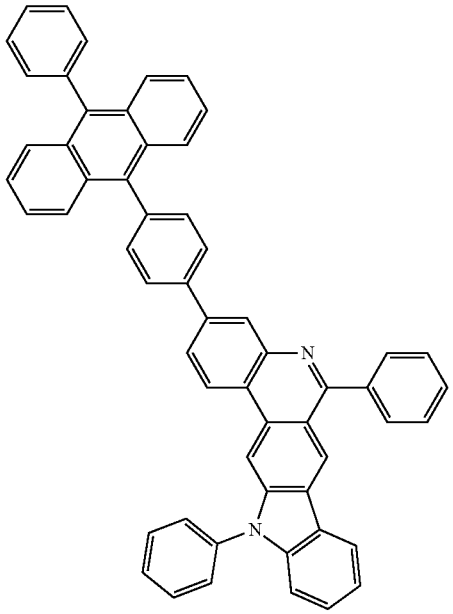

4-37
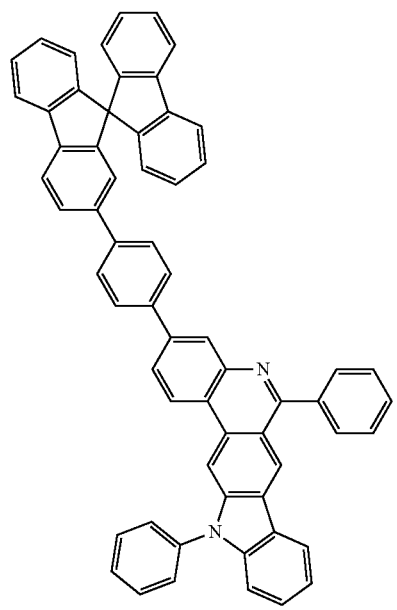
4-38
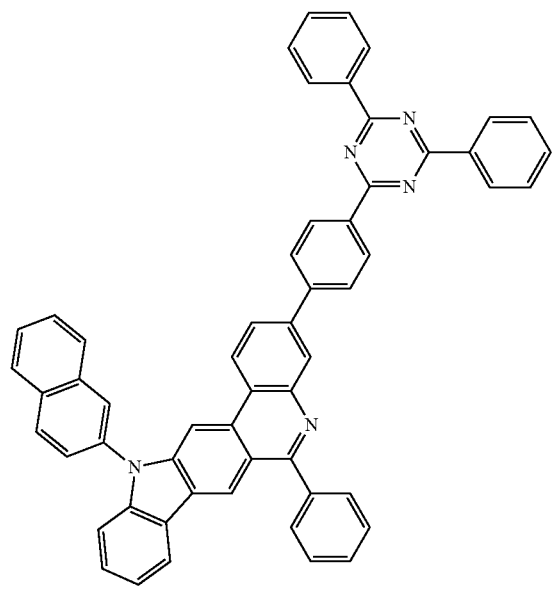
4-39
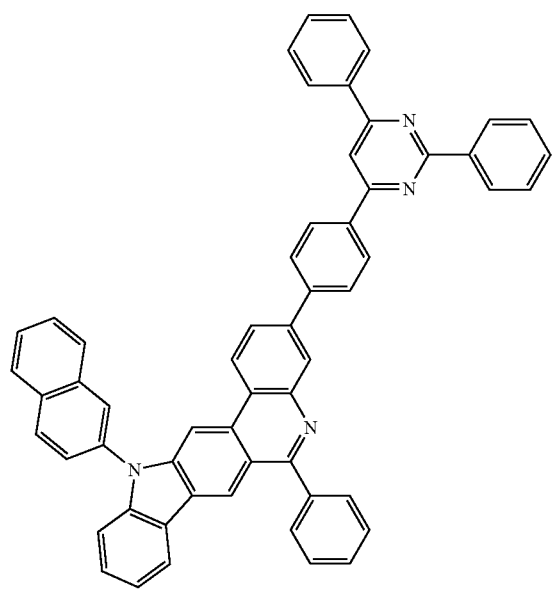
4-40
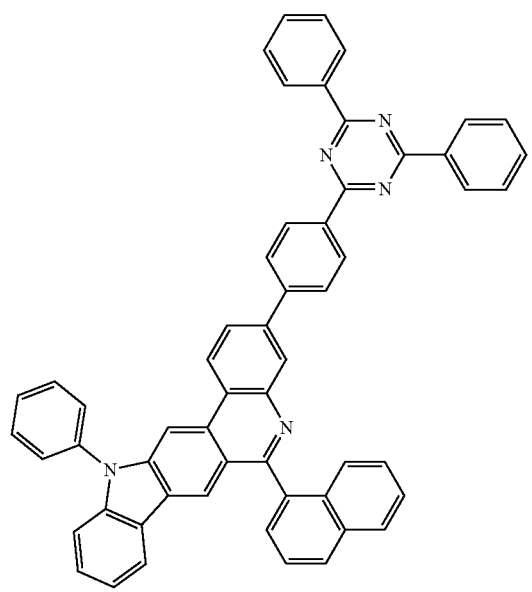

-continued
4-41
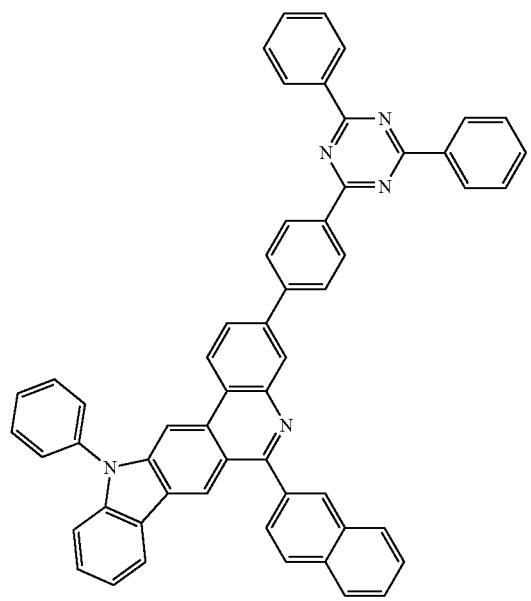
5
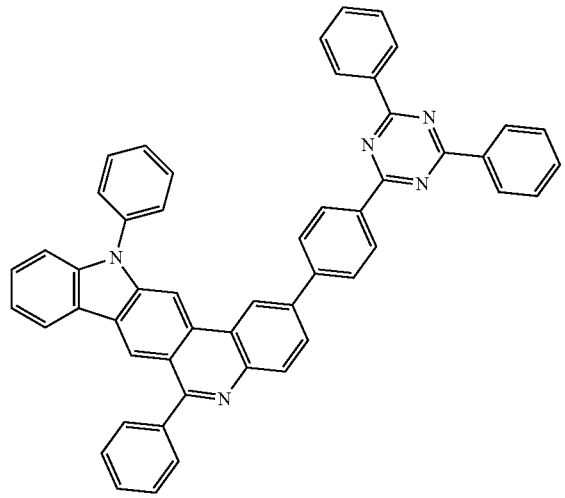
5-1
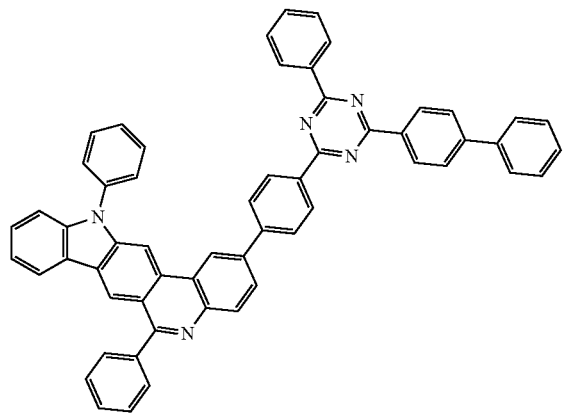
5-2
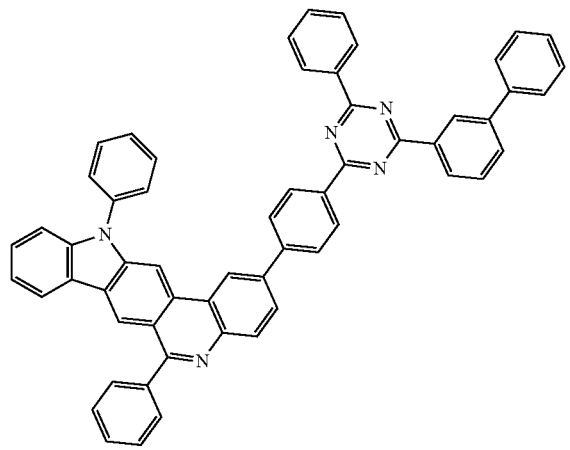
5-3
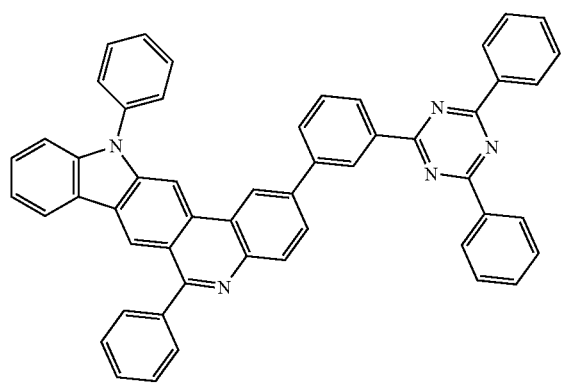
5-4
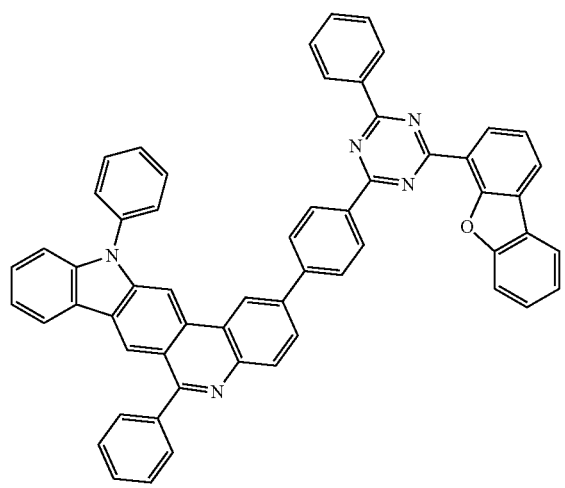

5-5
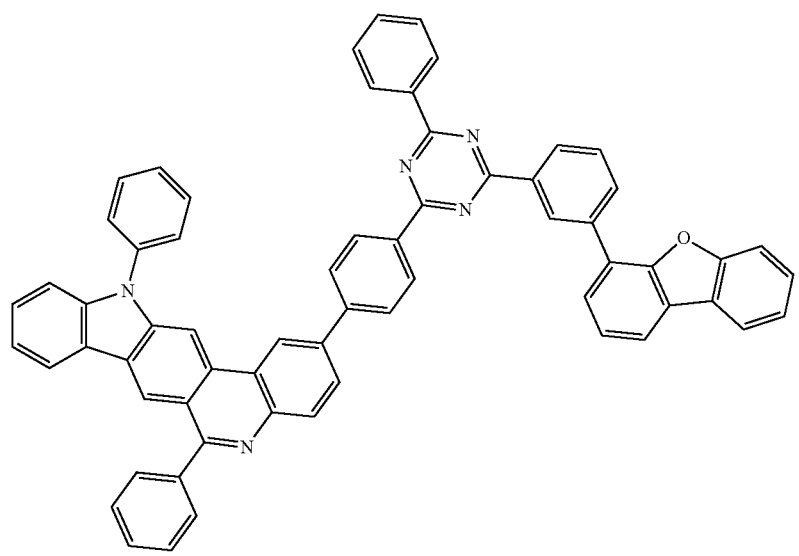
5-6 5-7
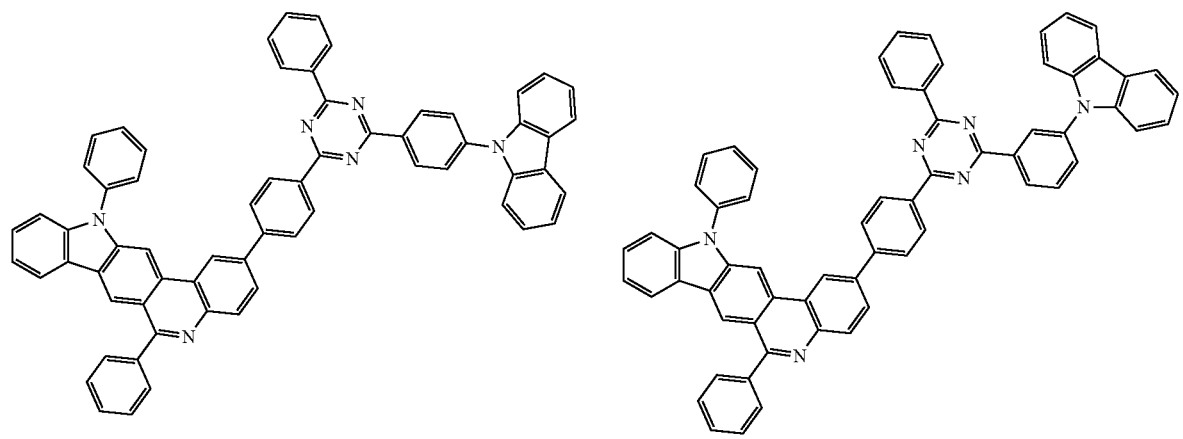
5-8 5-9
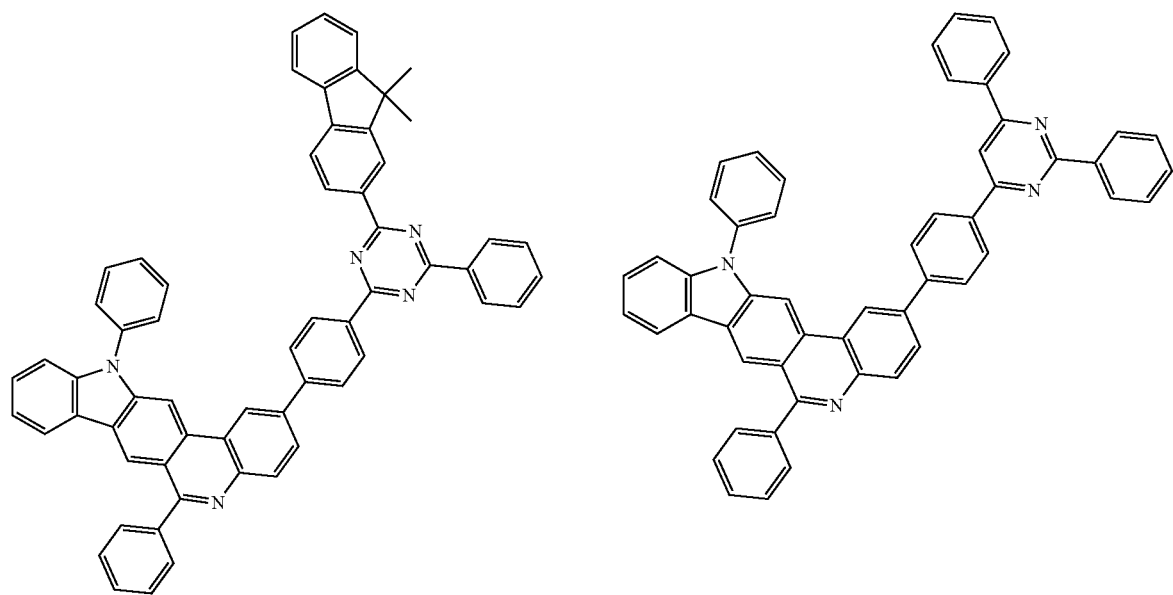

5-10
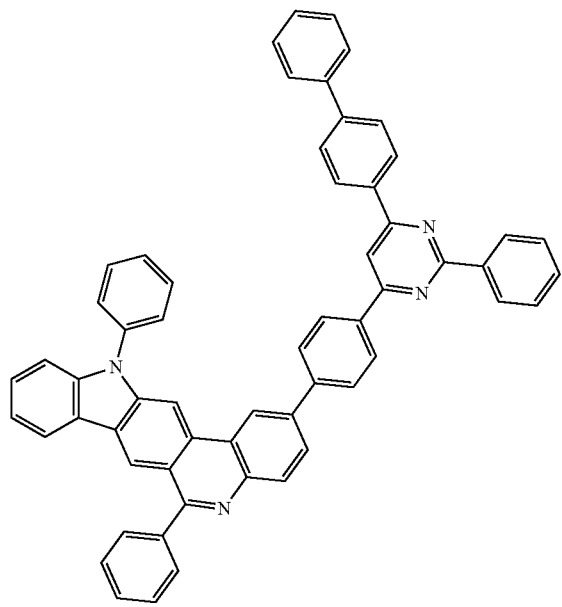
5-11
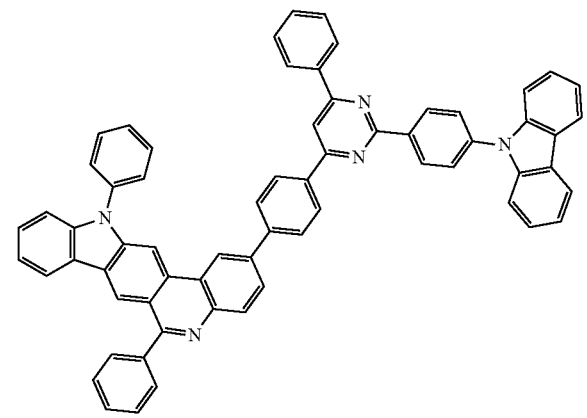
5-12
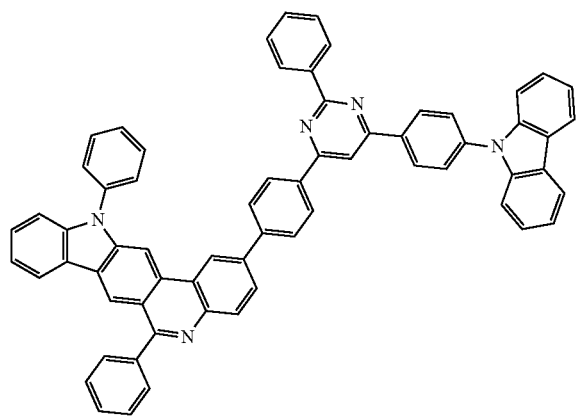
5-13
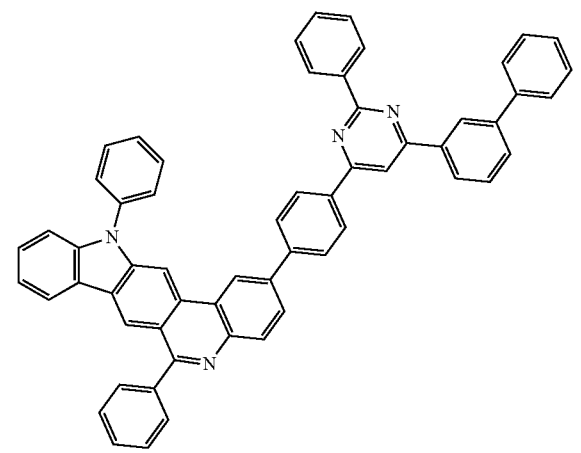
5-14
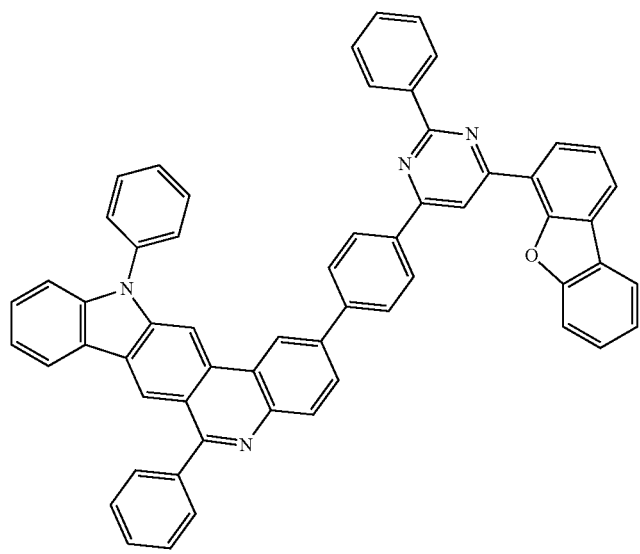

5-15
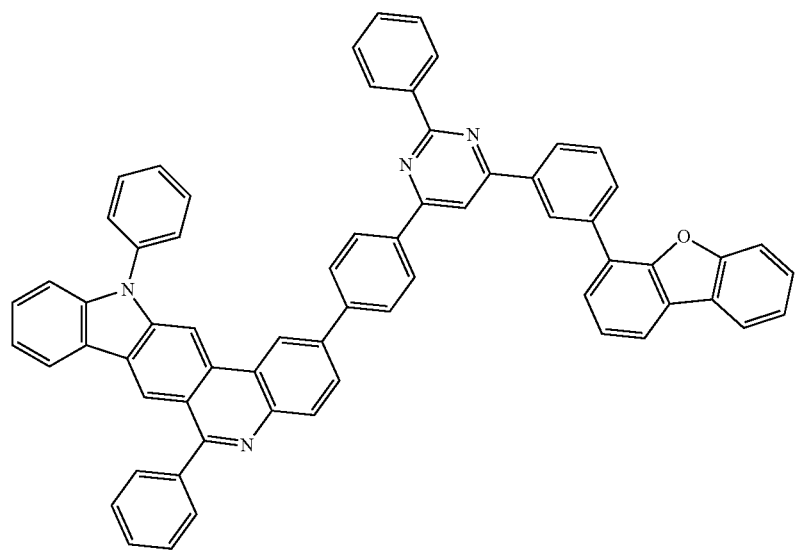
5-16
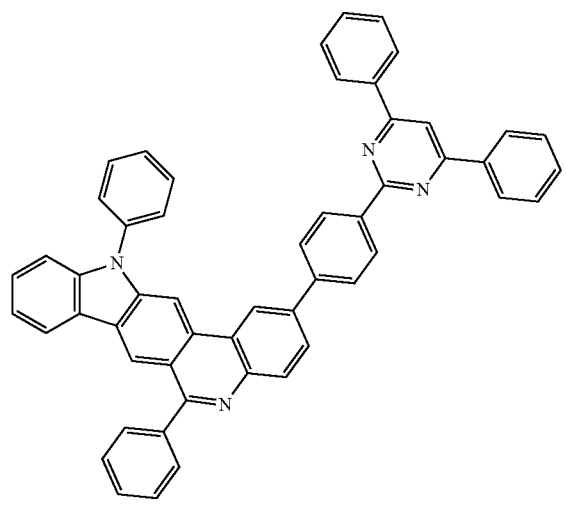
5-17
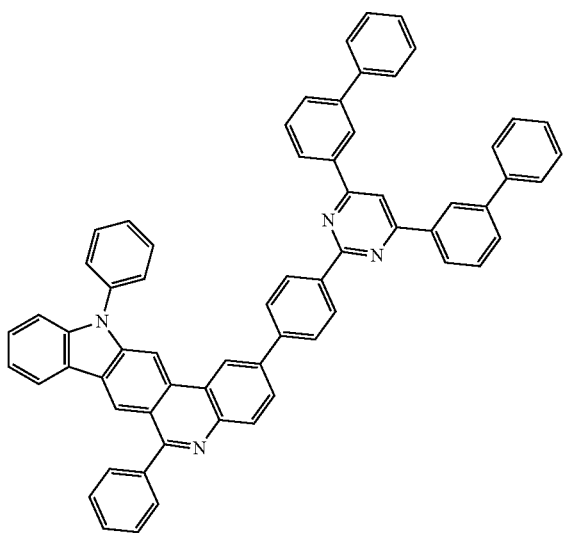

5-18
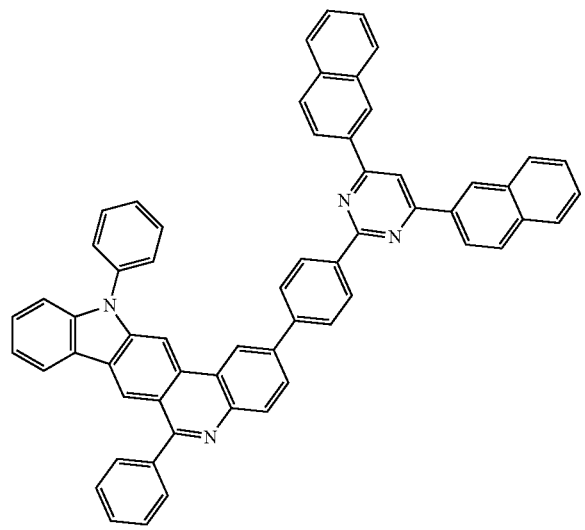
5-19
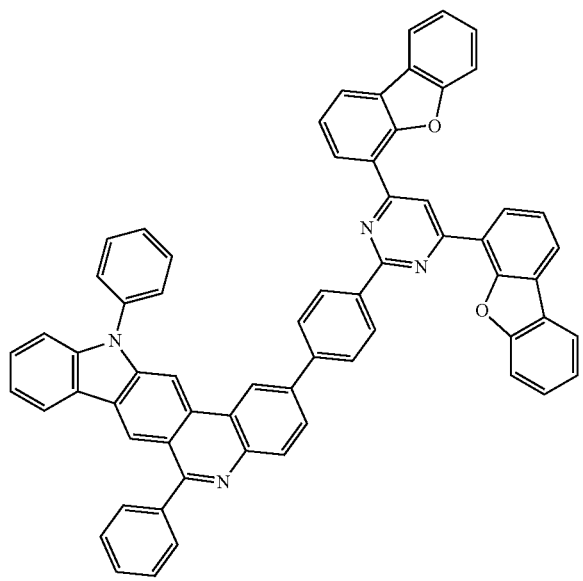
5-20
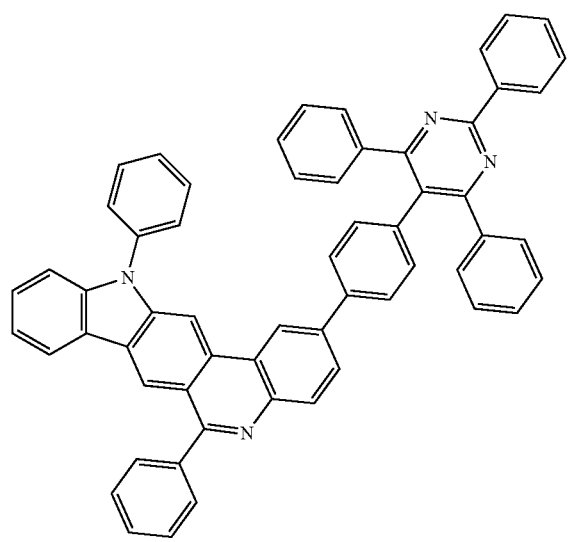
5-21
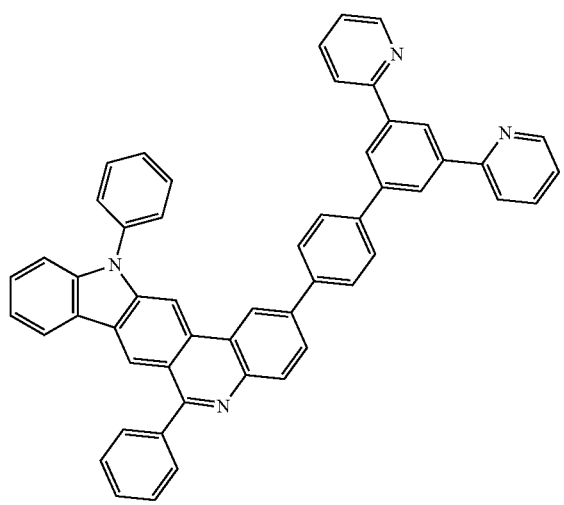
5-22
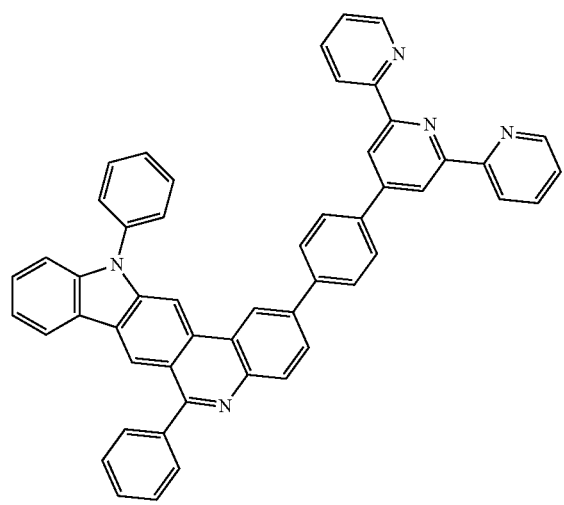
5-23
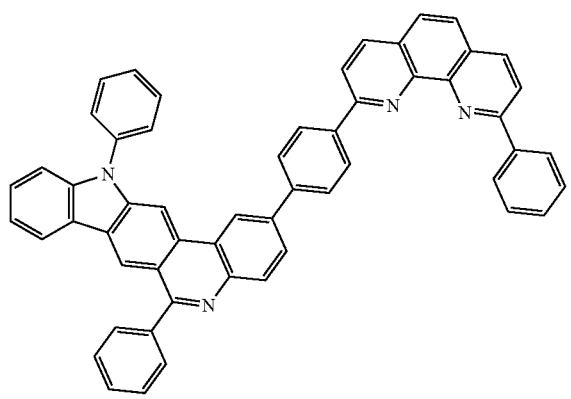

-continued
5-24
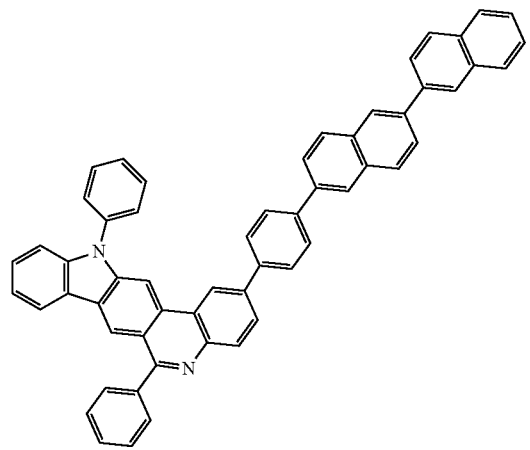
5-25
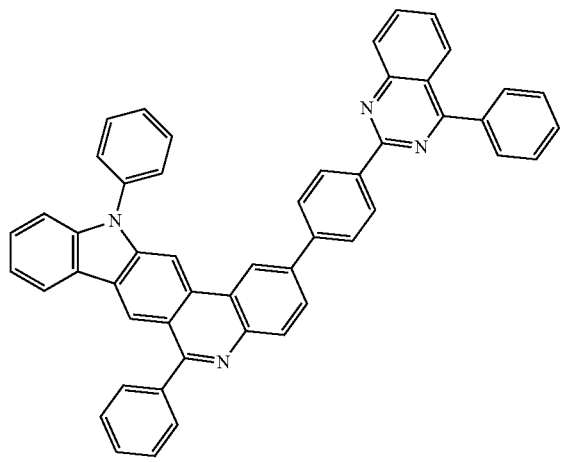
5-26
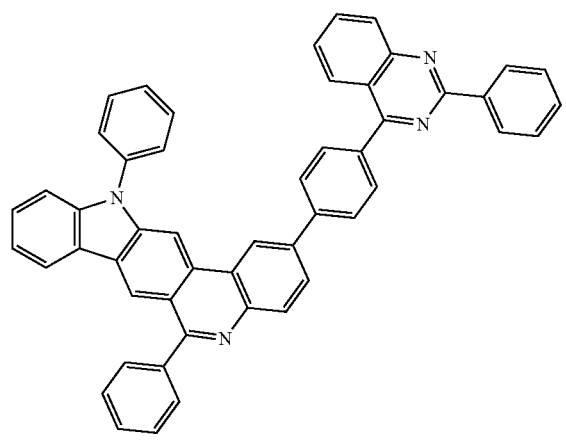
5-27
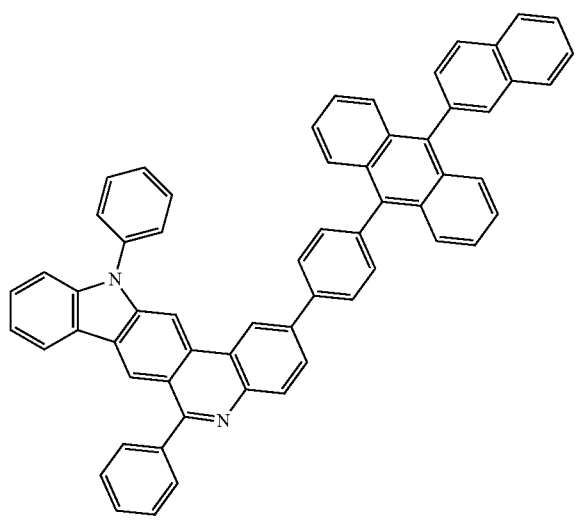
5-28
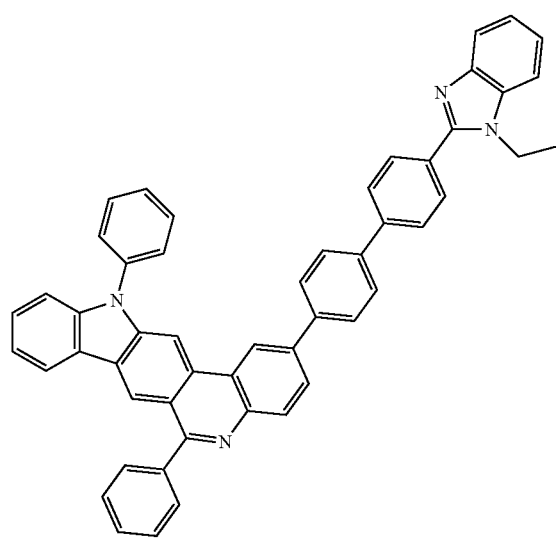
5-29
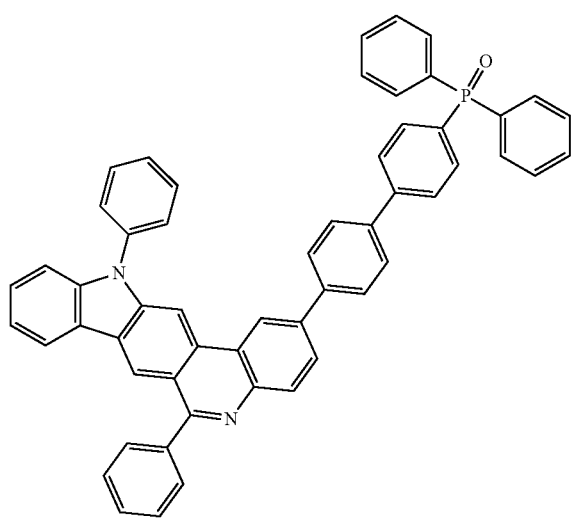

-continued
5-30
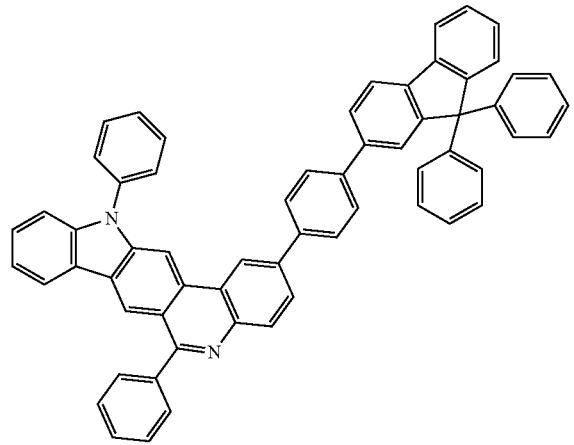
5-31
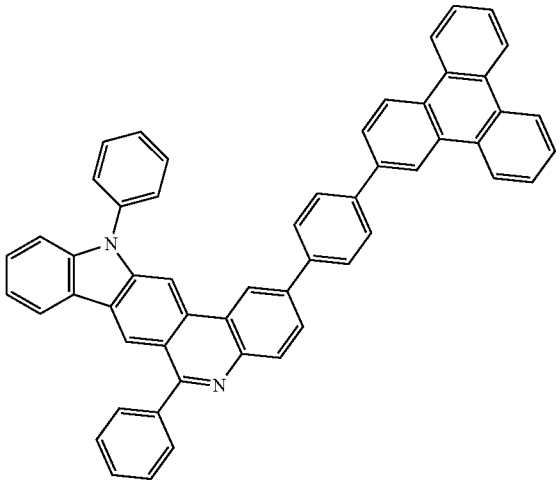
5-32
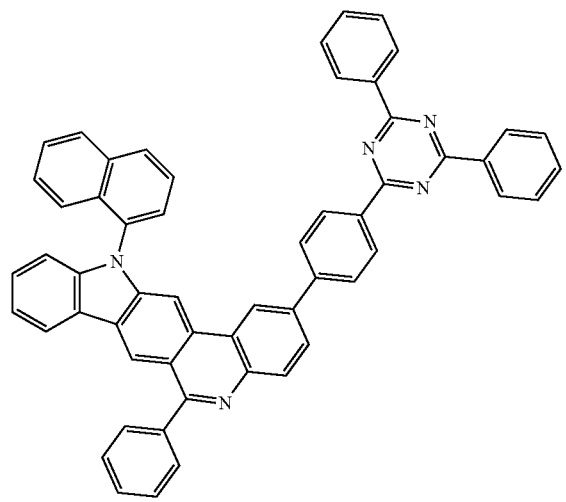
5-33
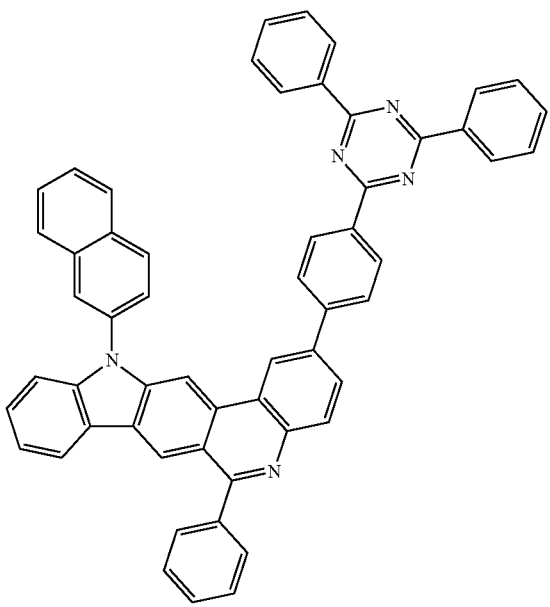

5-34
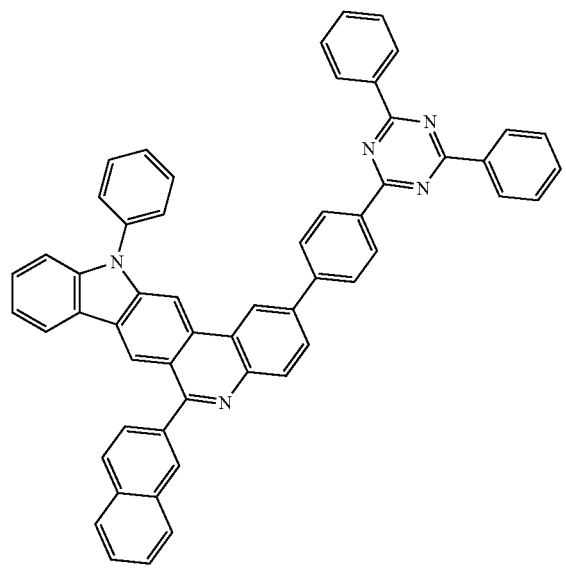
5-35
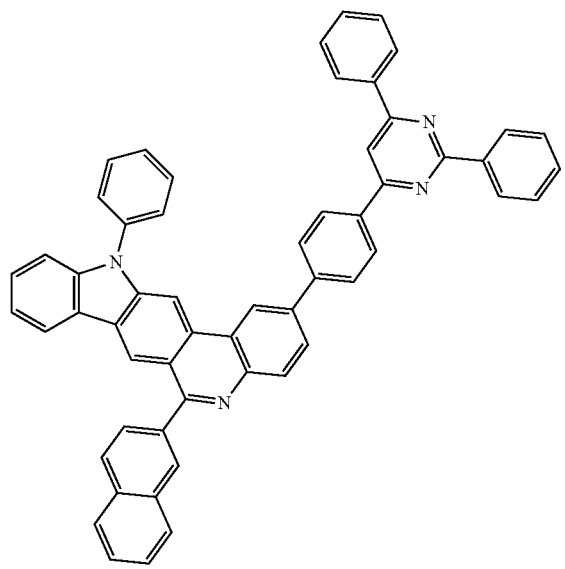
6
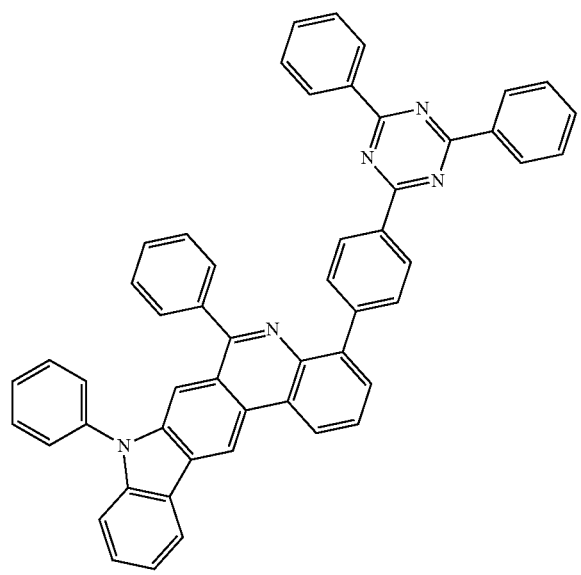
6-1
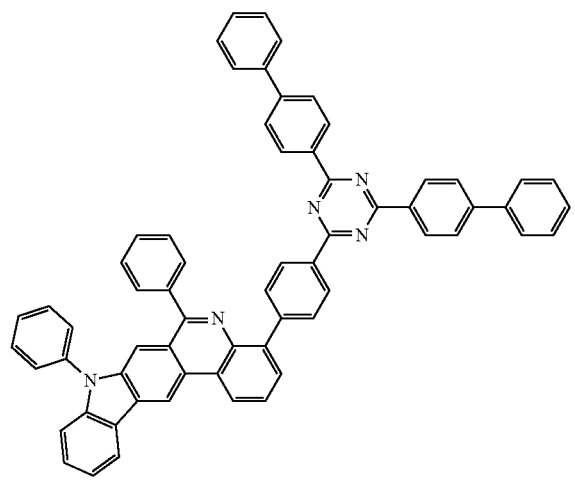

-continued
6-2
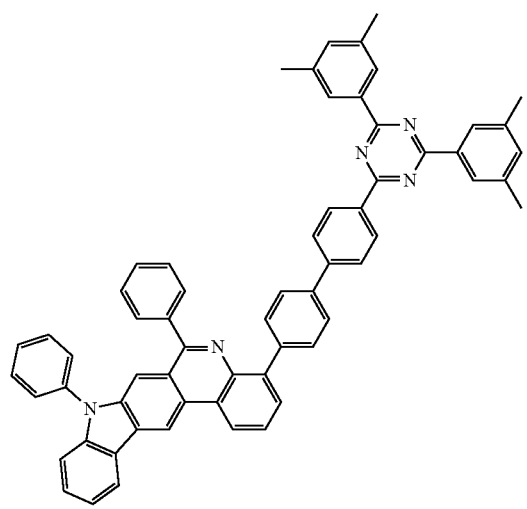
6-3
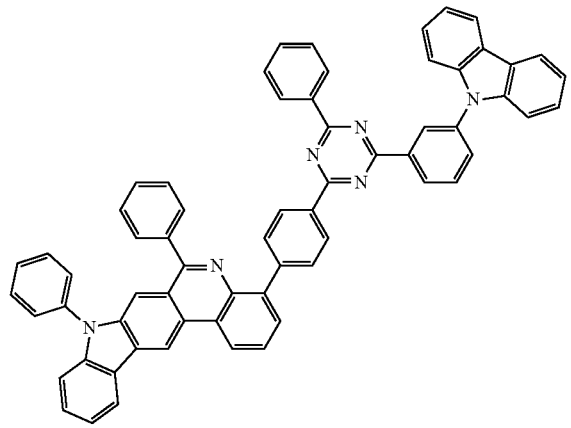
6-4
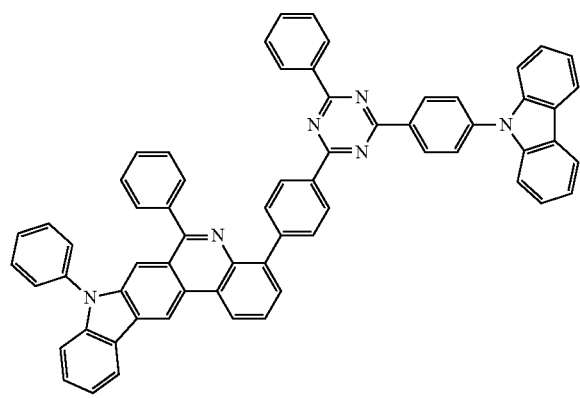
6-5
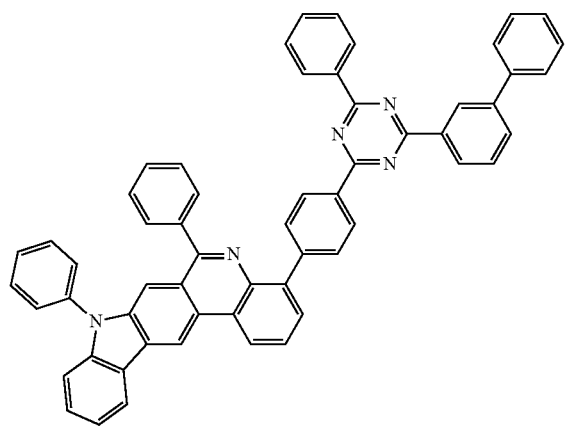
6-6
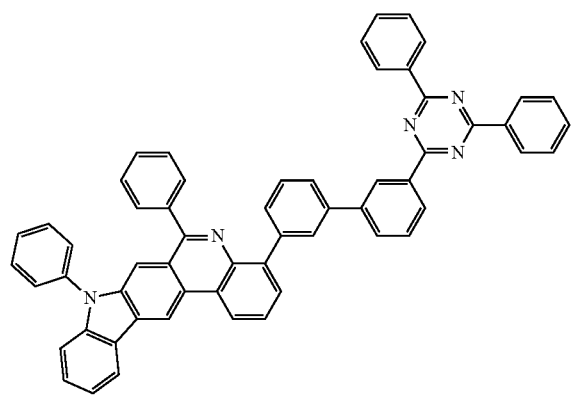
6-7
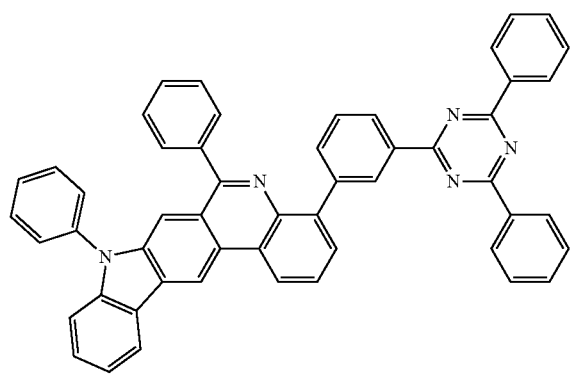

6-8
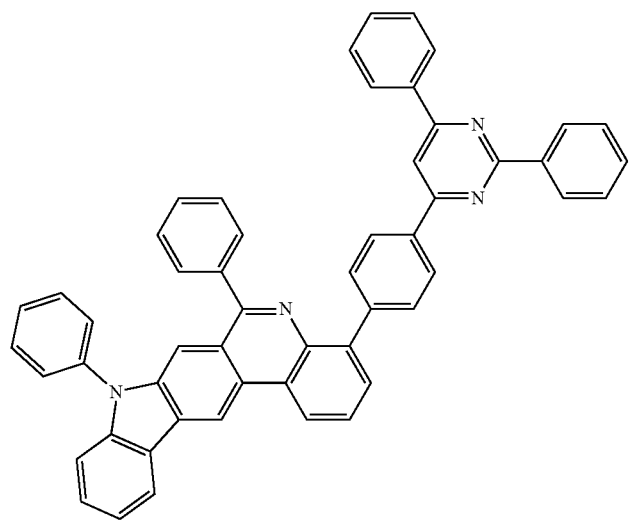
6-9
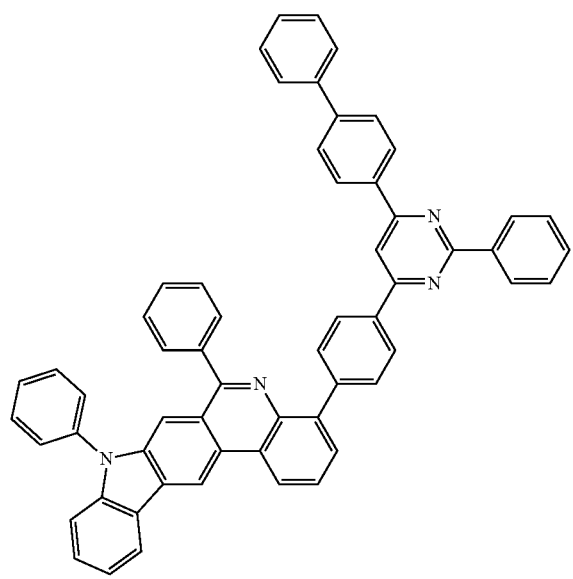
6-10
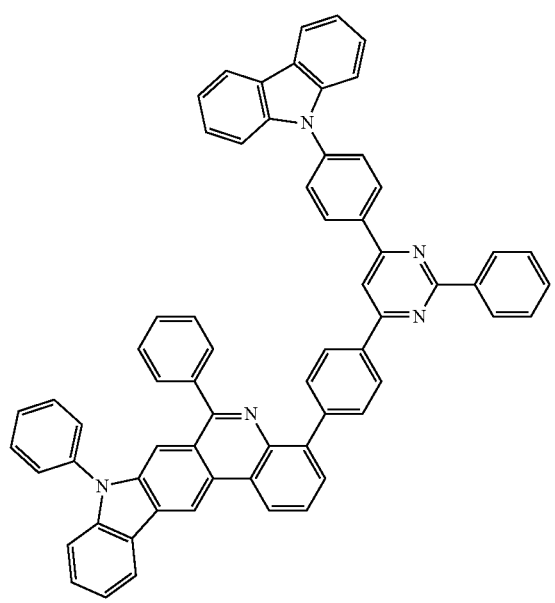

-continued
6-11
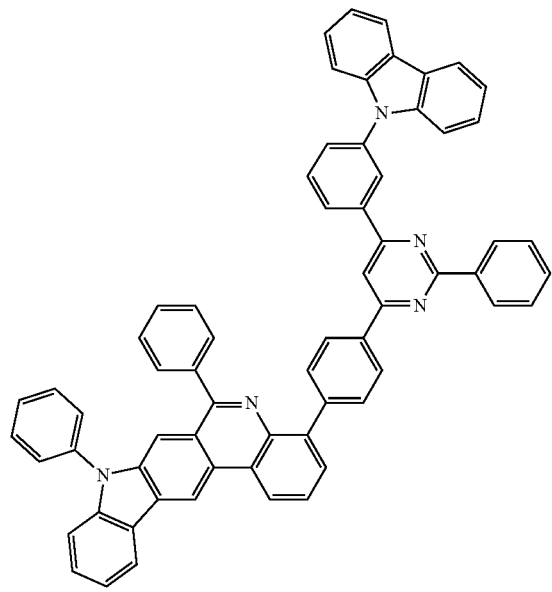
6-12
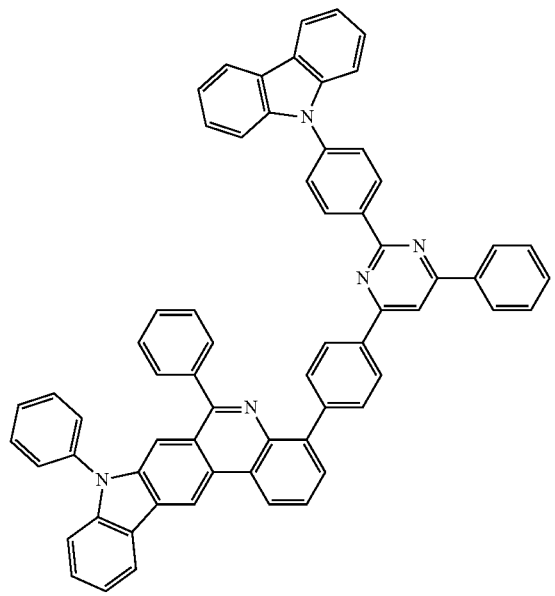
6-13
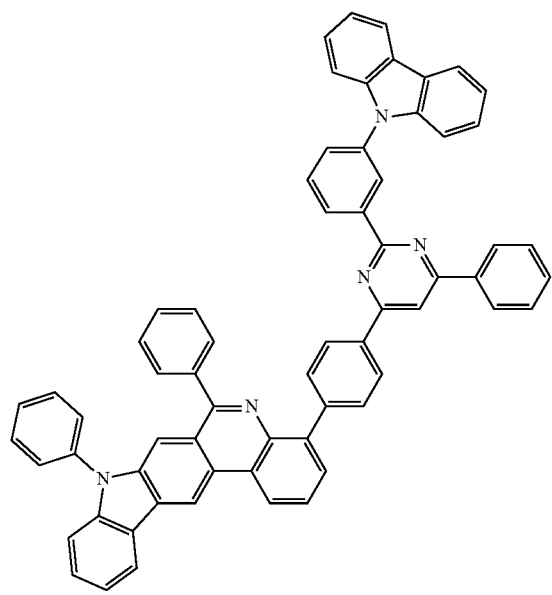
6-14
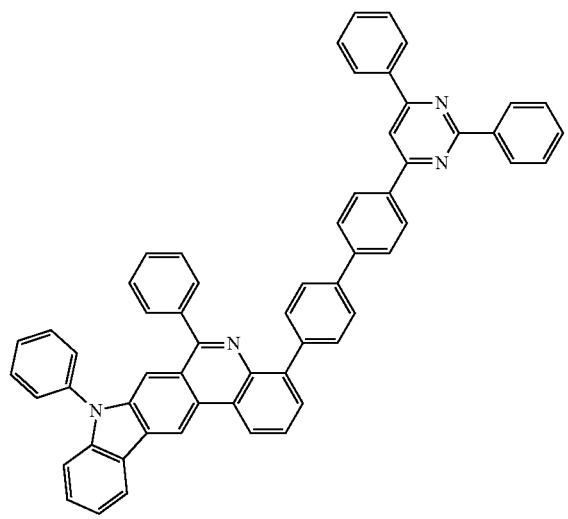

-continued
6-15
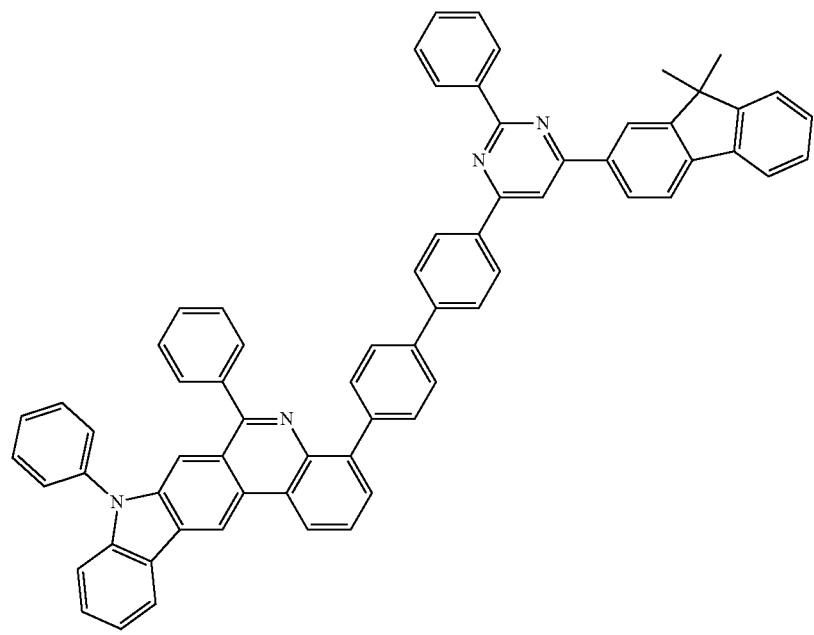
6-16
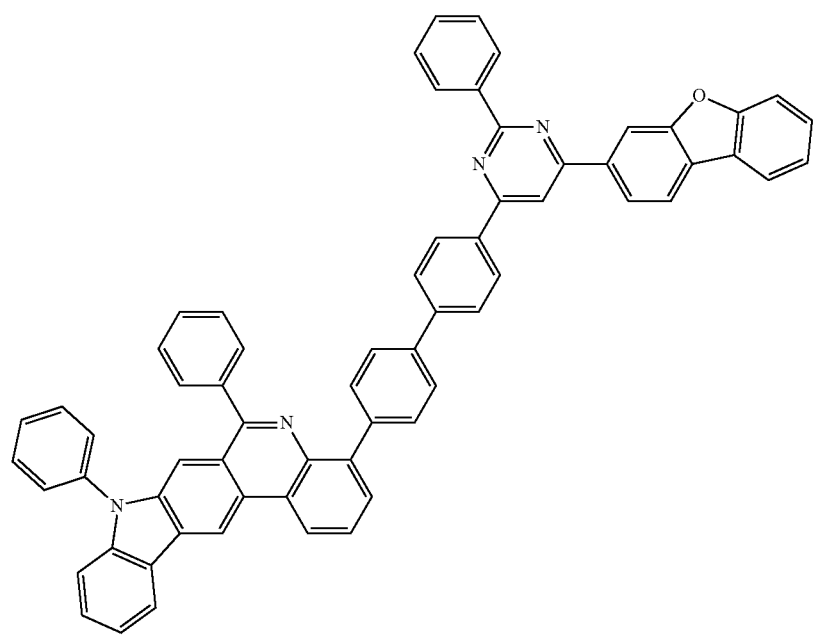

-continued
6-17
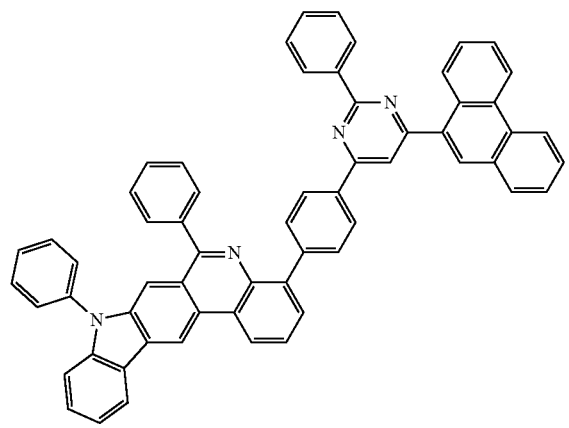
6-18
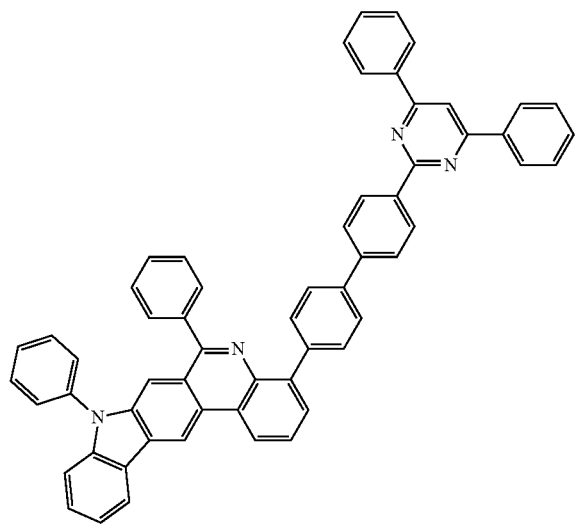
6-19
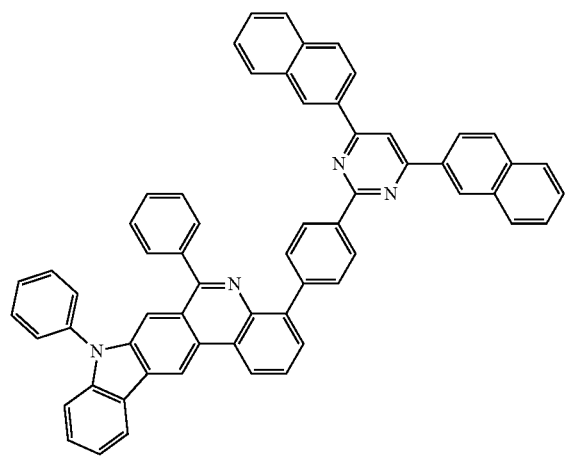
6-20
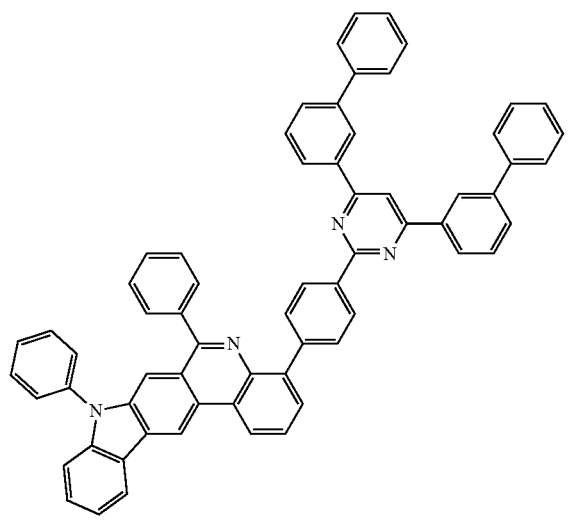
6-21
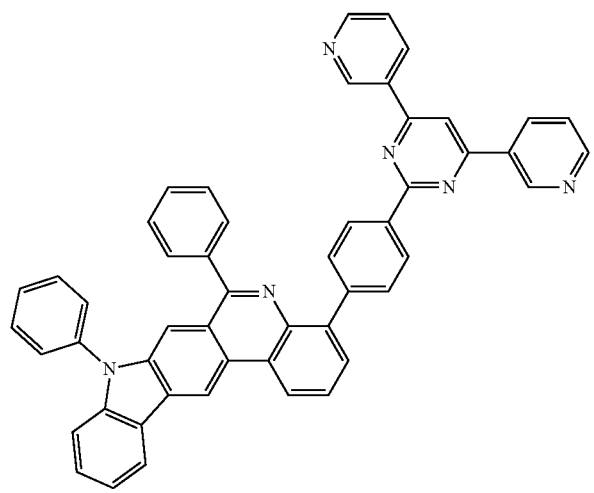
6-22
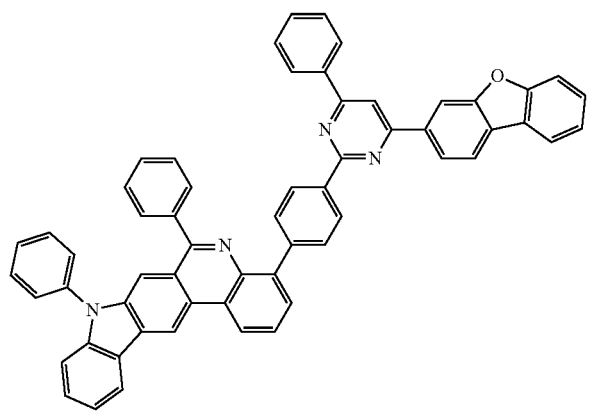

-continued
6-23
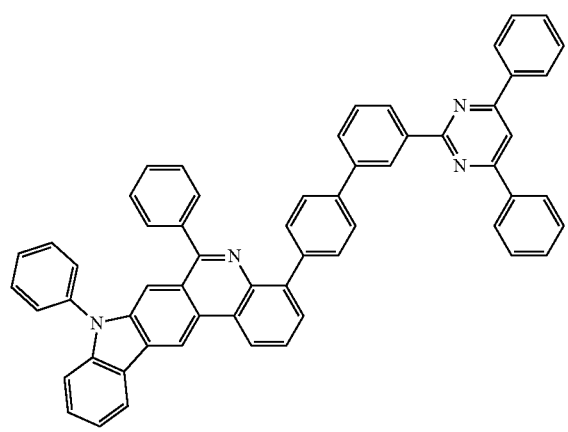
6-24
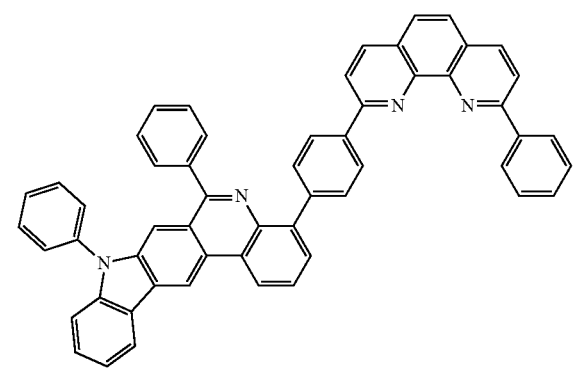
6-25
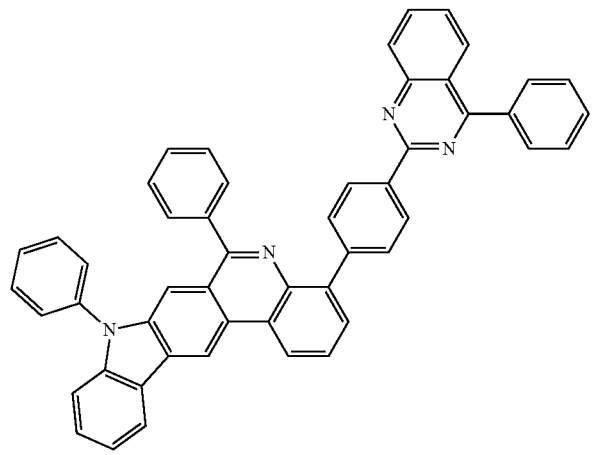
6-26
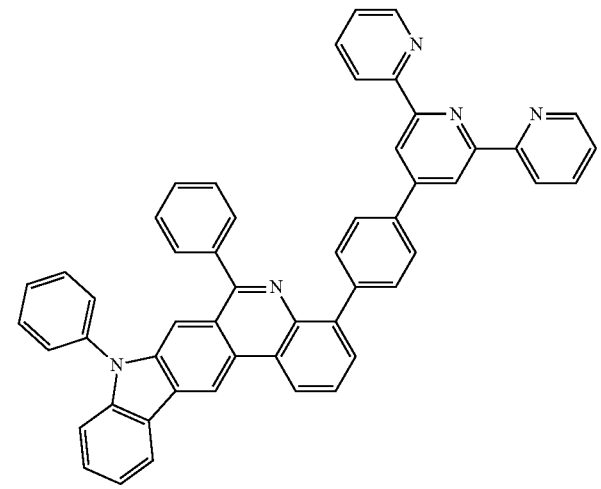
6-27
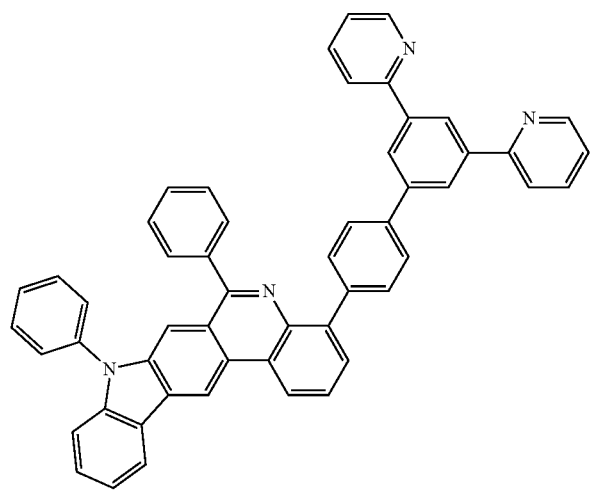
6-28
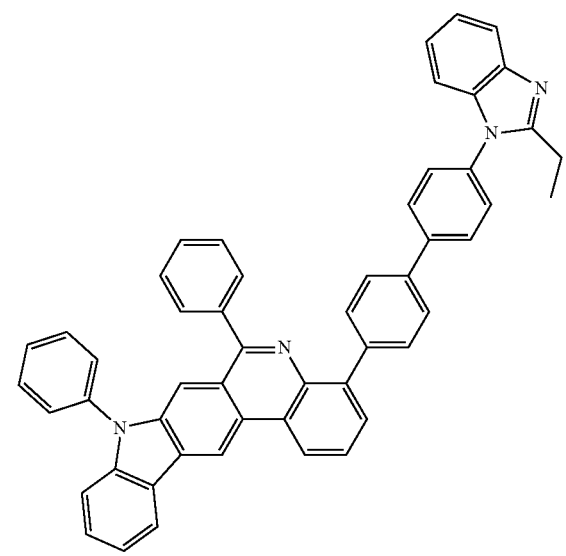

-continued
6-29
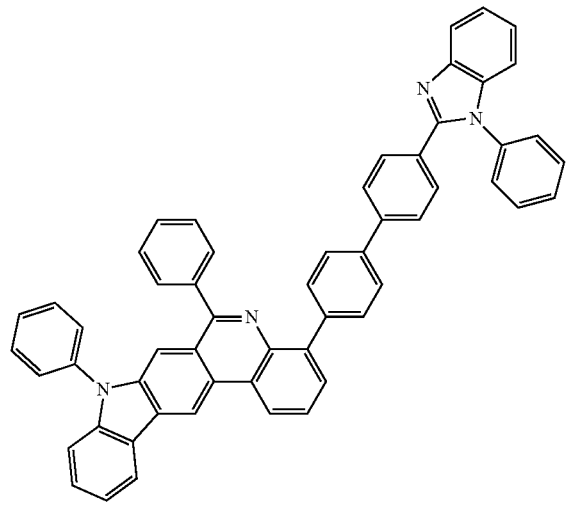
6-30
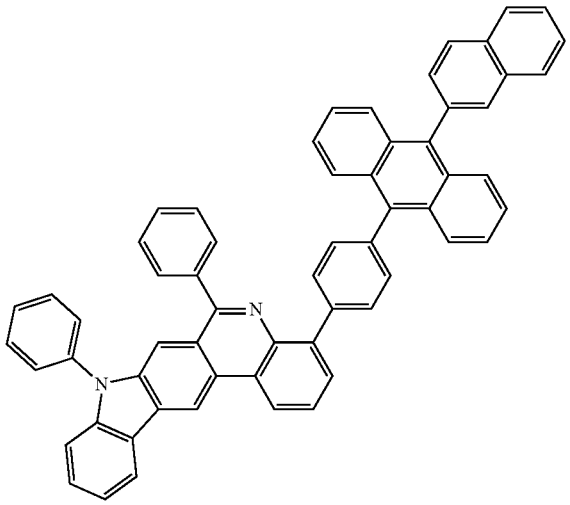
6-31
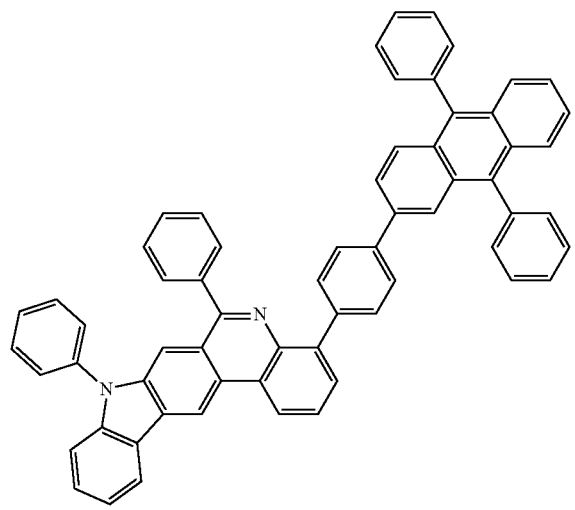
6-32
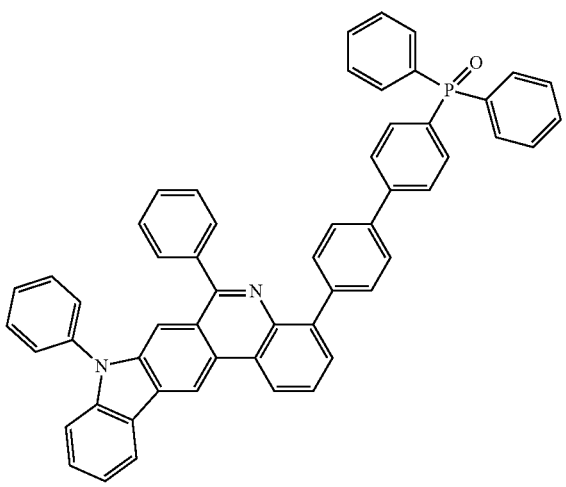

6-33
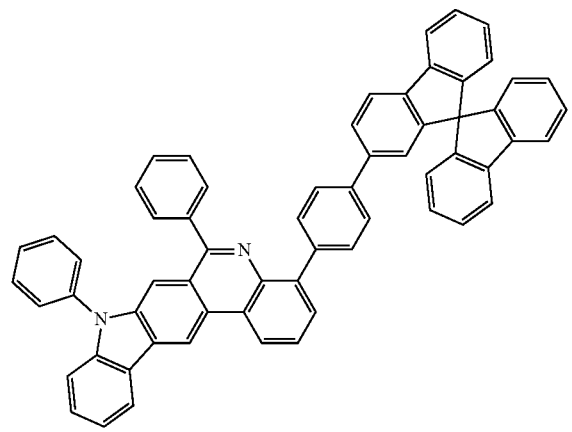
7
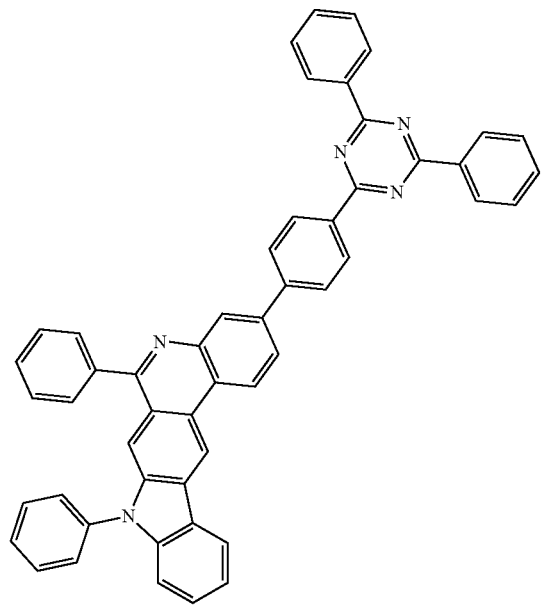
7-1
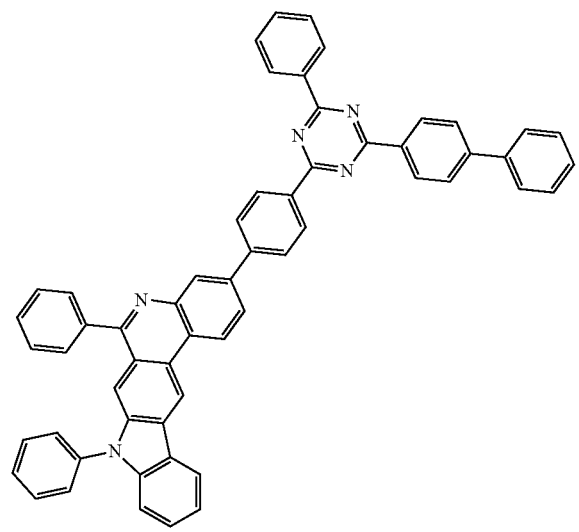
7-2
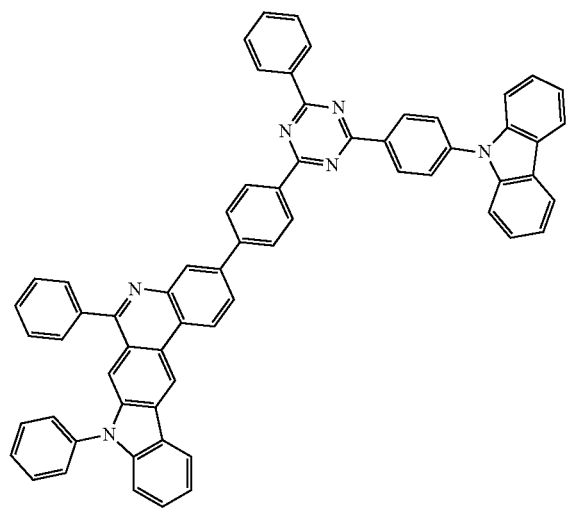

-continued
7-3
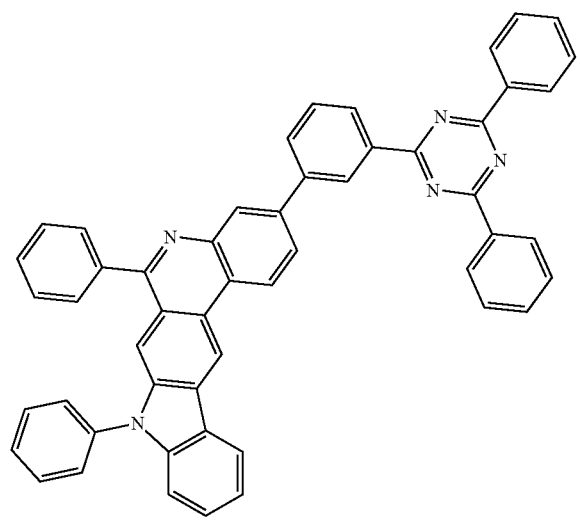
7-4
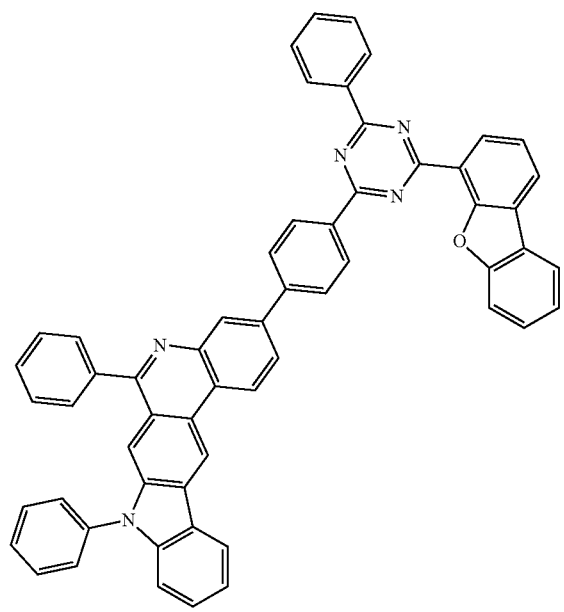
7-5
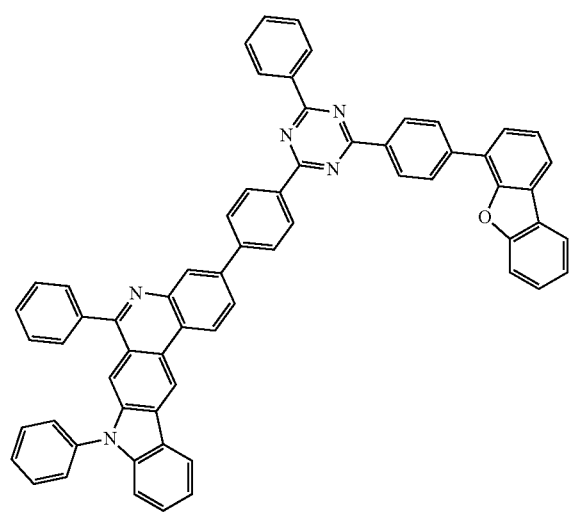
7-6
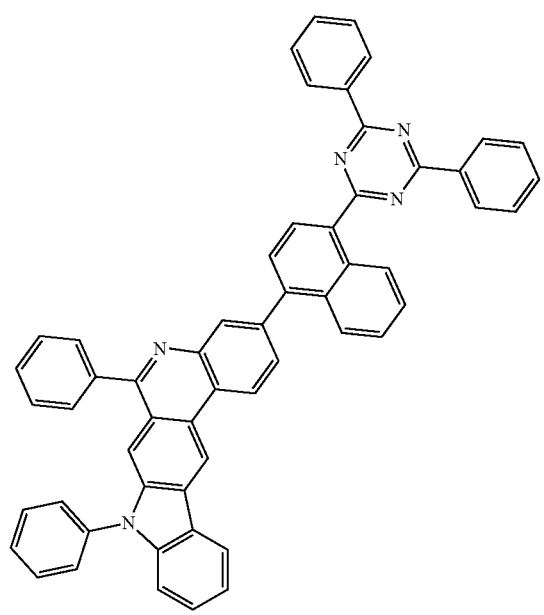

7-7
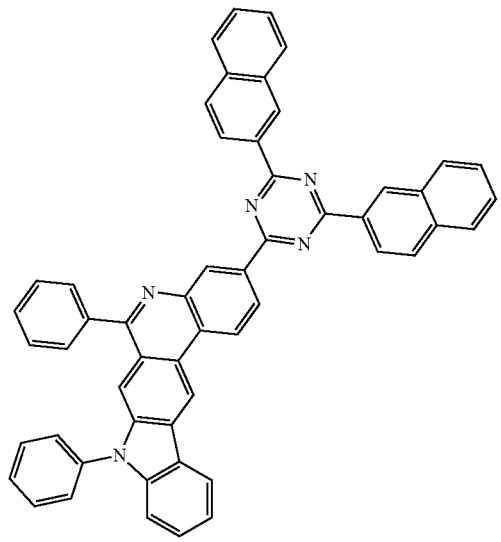
7-8
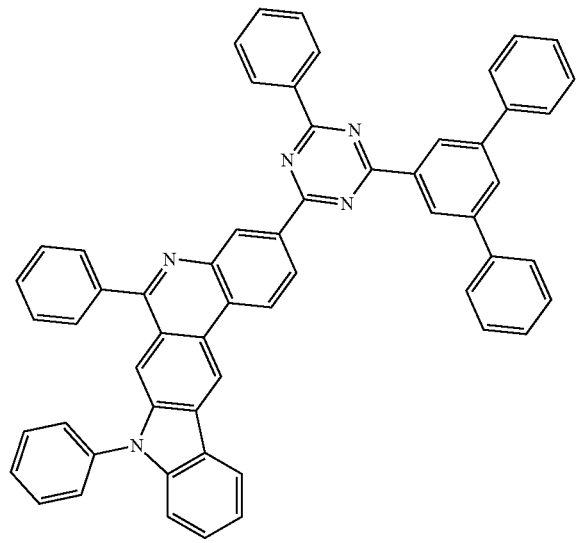
7-9
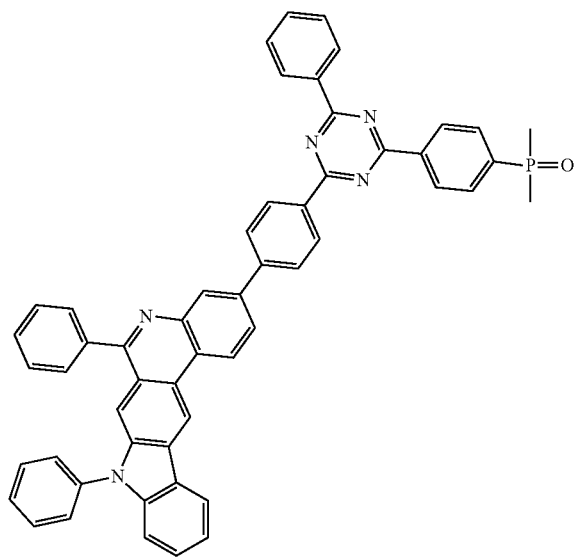
7-10
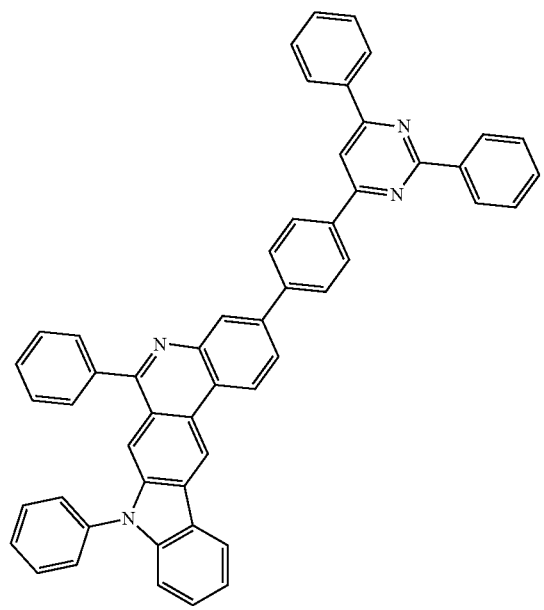

7-11
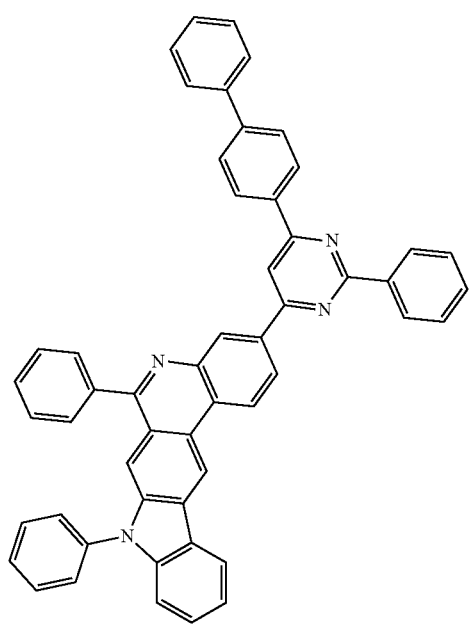
7-12
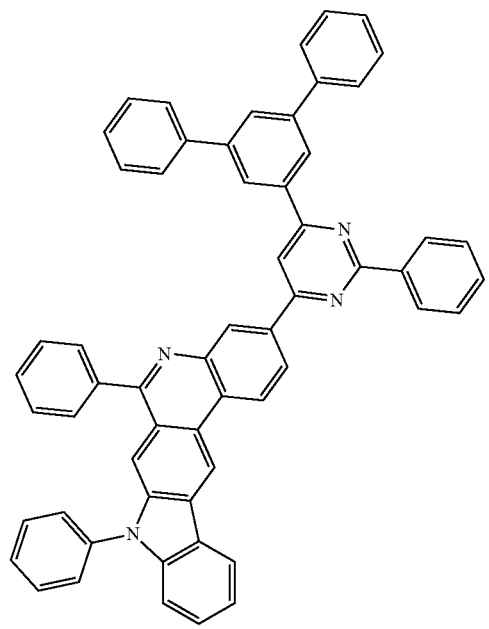
7-13
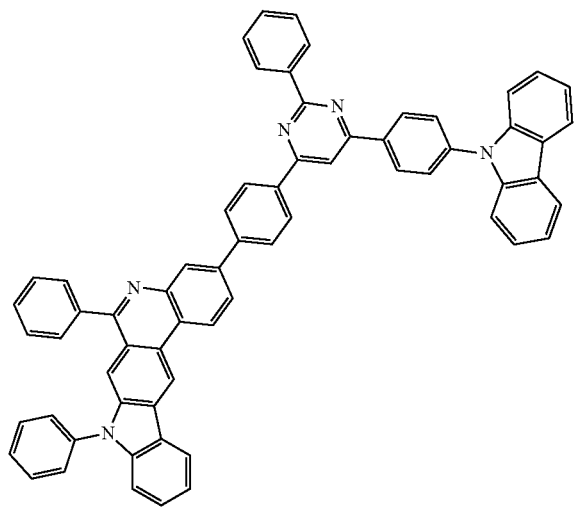
7-14
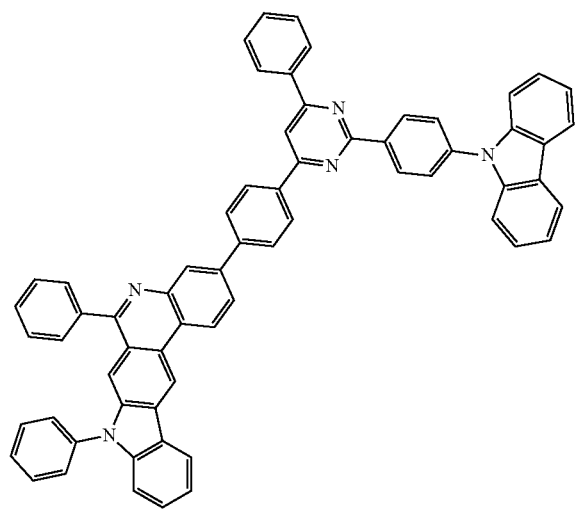

7-15
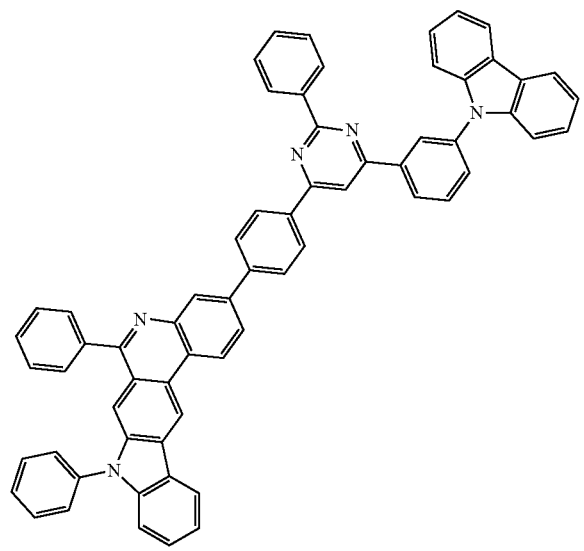
7-16
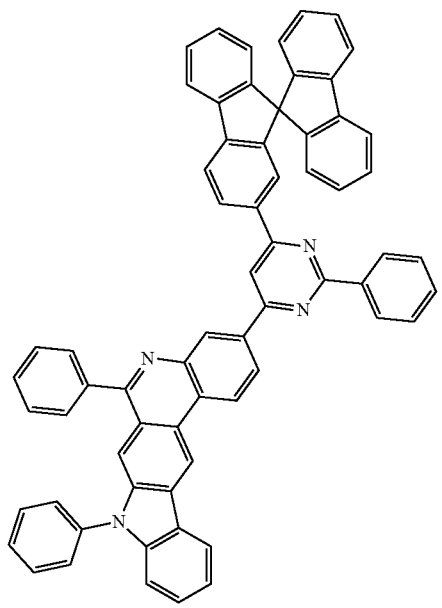
7-17
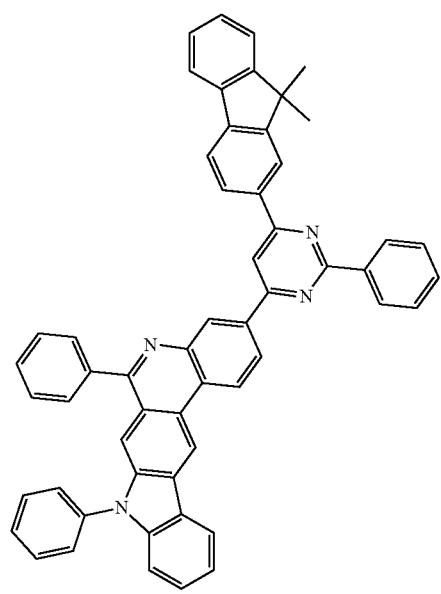
7-18
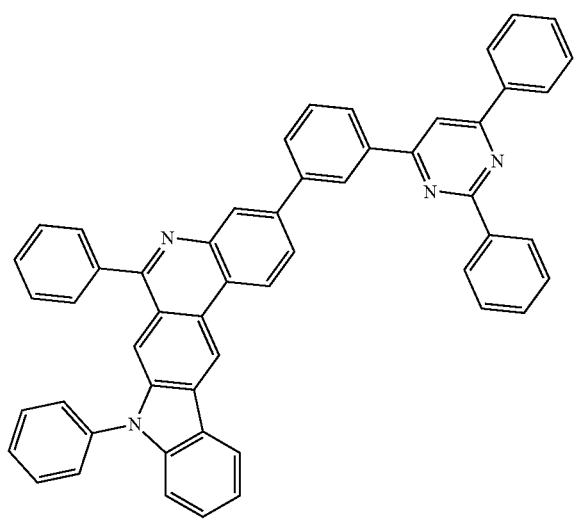

7-19
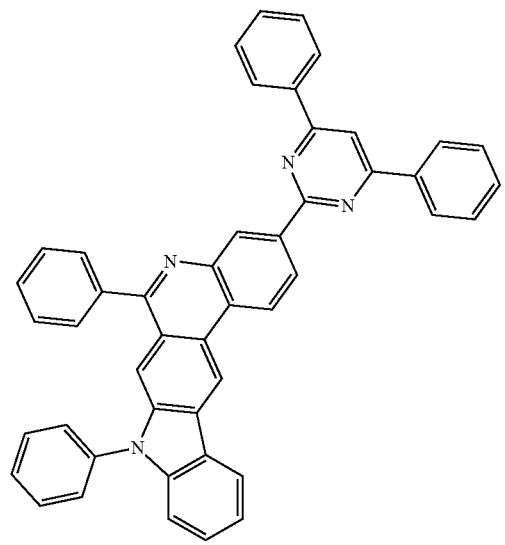
7-20
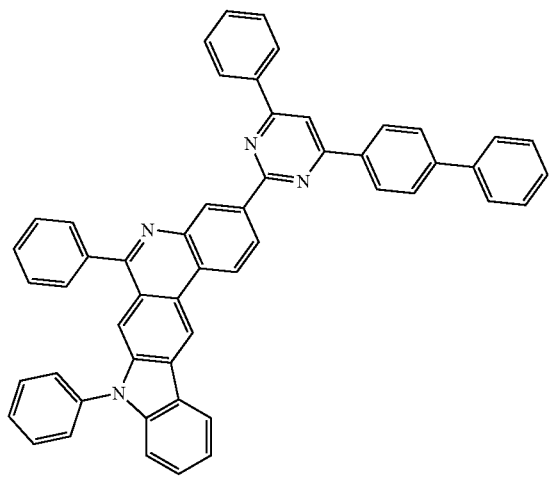
7-21
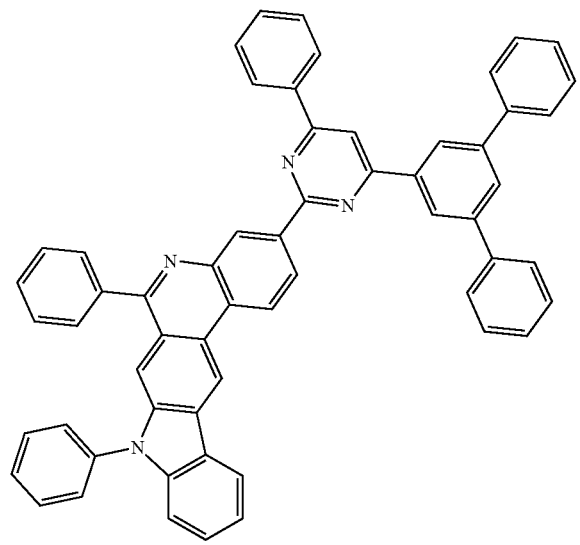
7-22
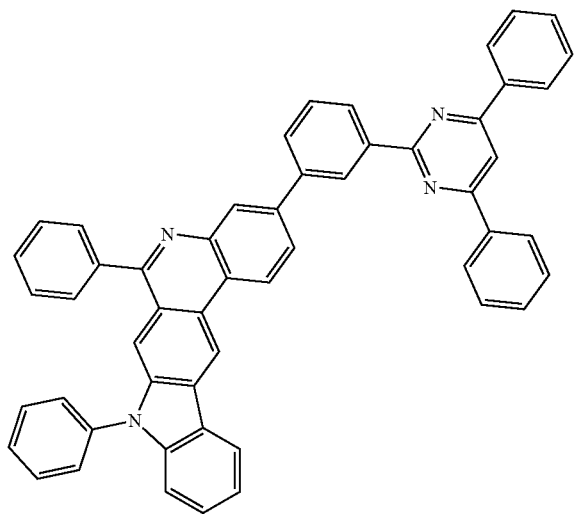

-continued
7-23
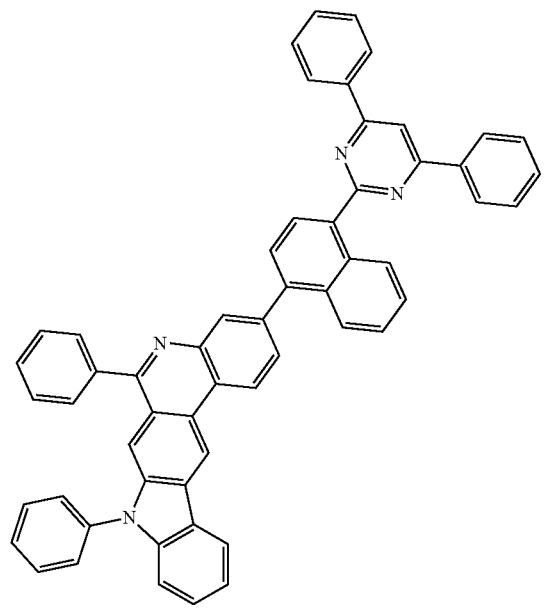
7-24
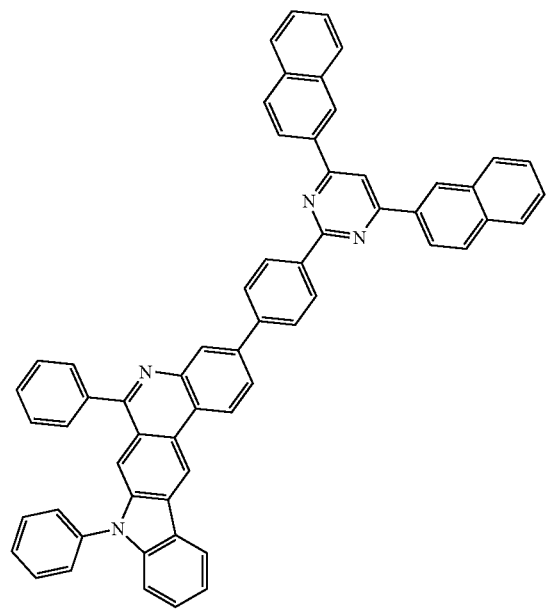
7-25
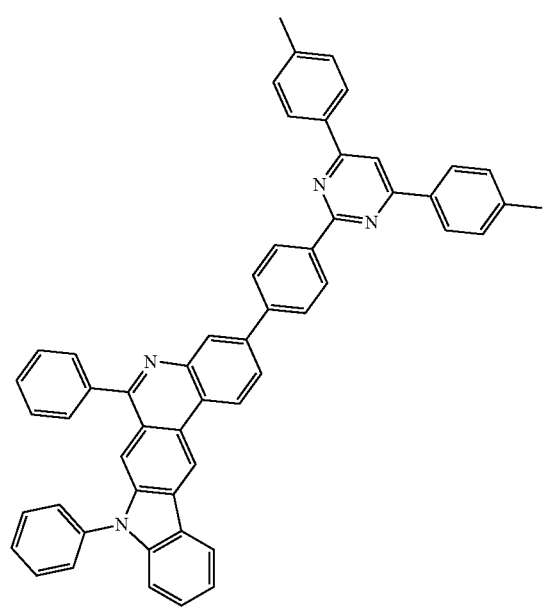
7-26
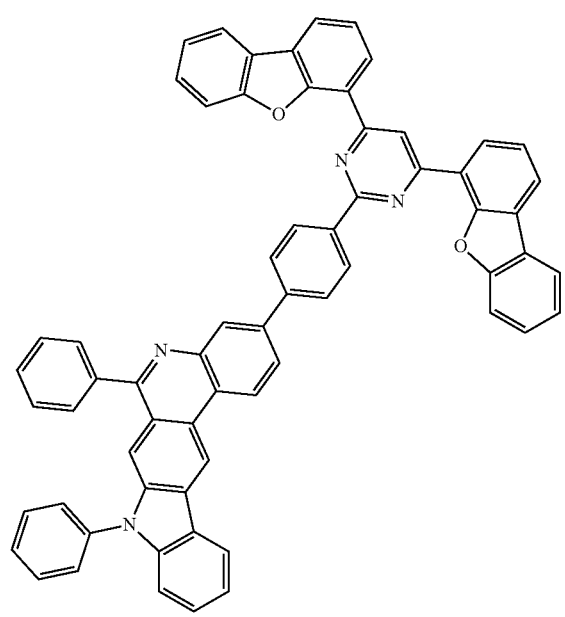

-continued
7-27
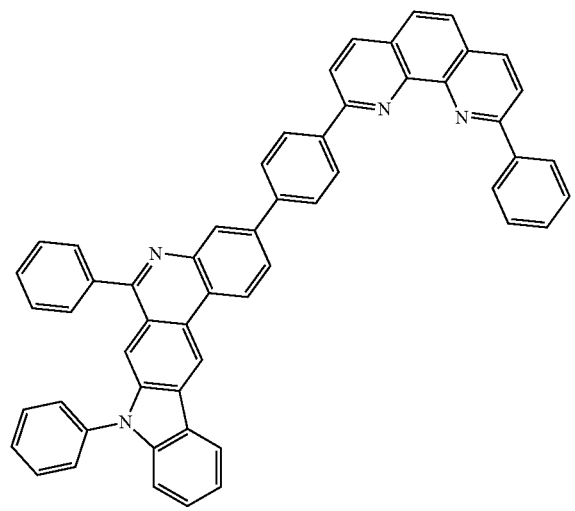
7-28
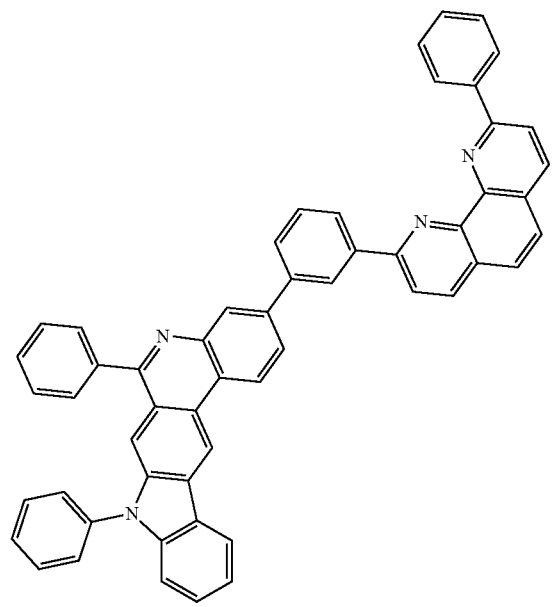
7-29
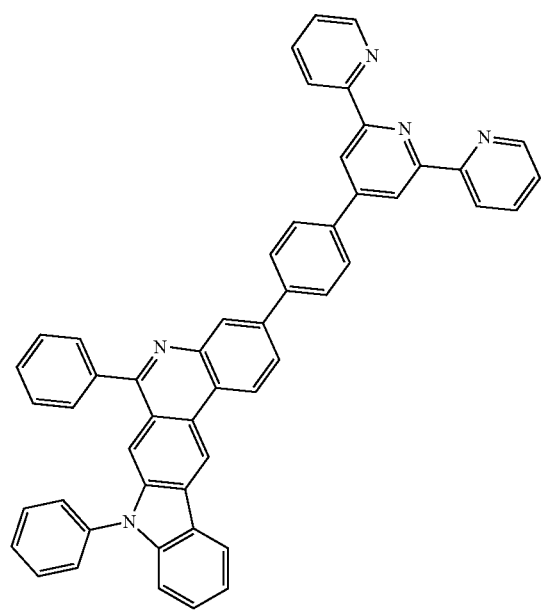
7-30
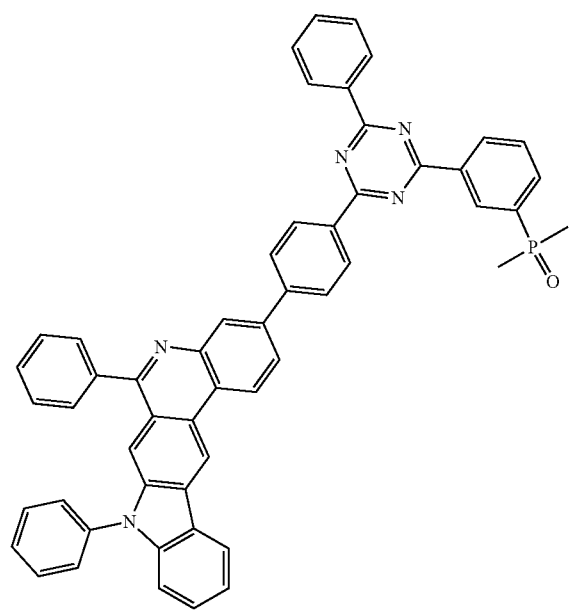

-continued
8
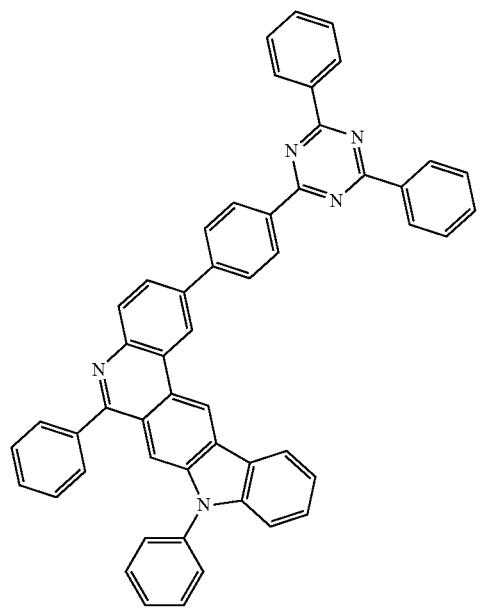
8-1
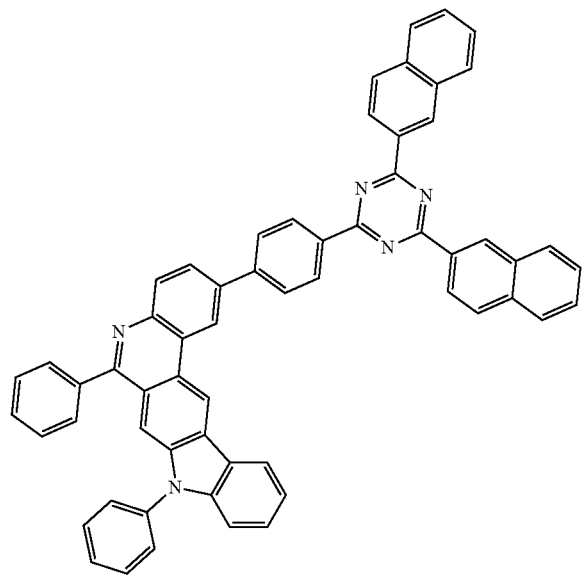
8-2
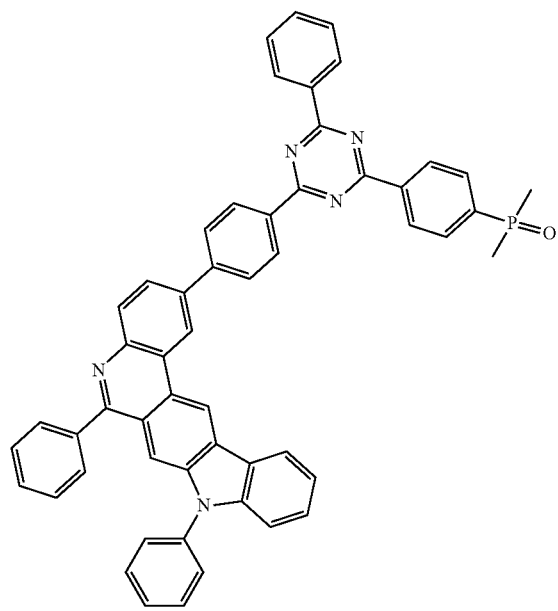
8-3
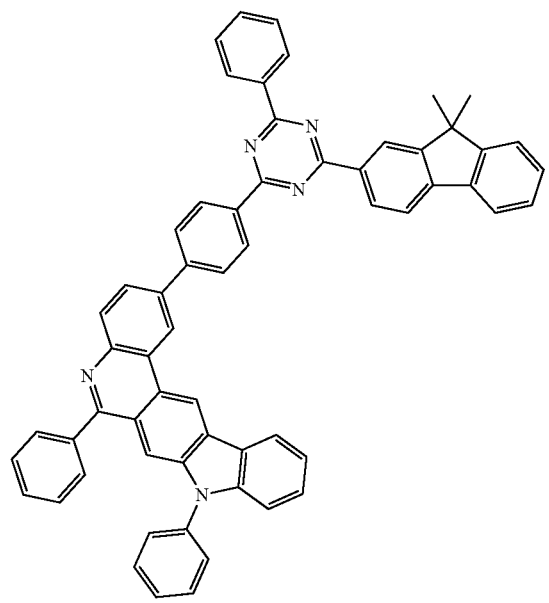

147
148
-continued
8-4
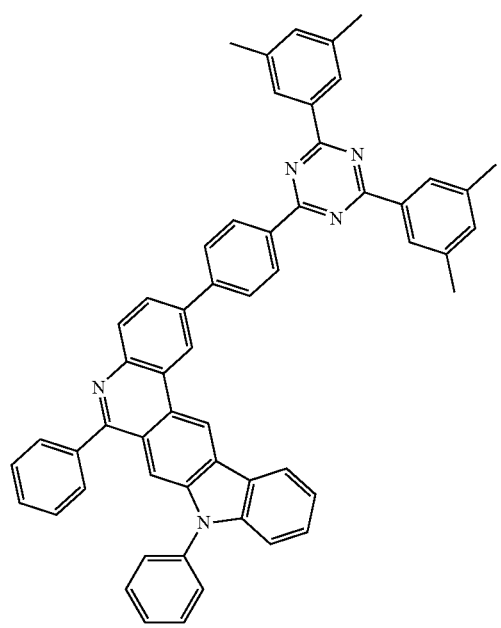
8-5
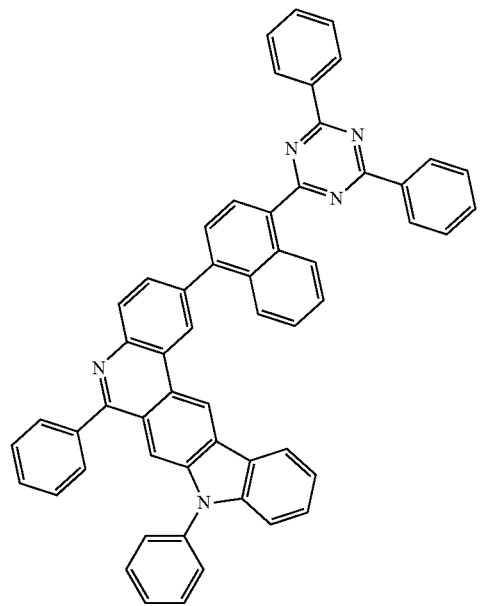
8-6
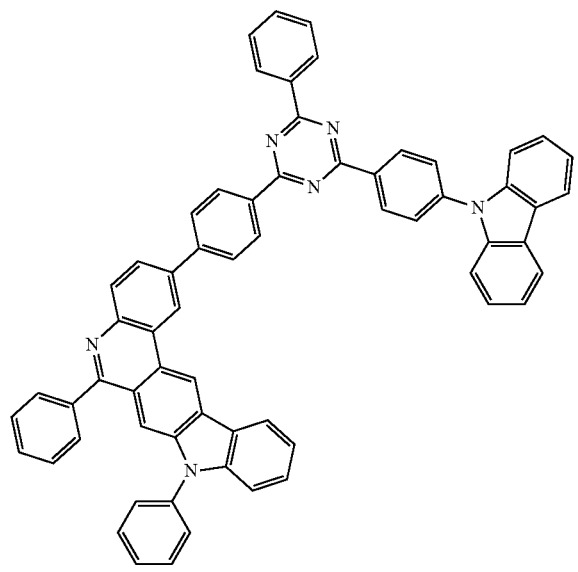
8-7
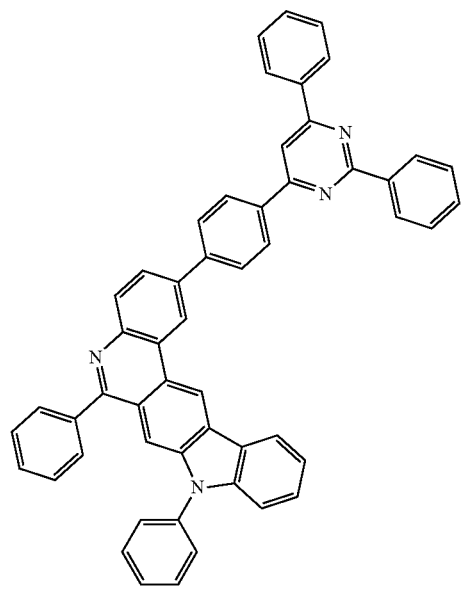

-continued
8-8
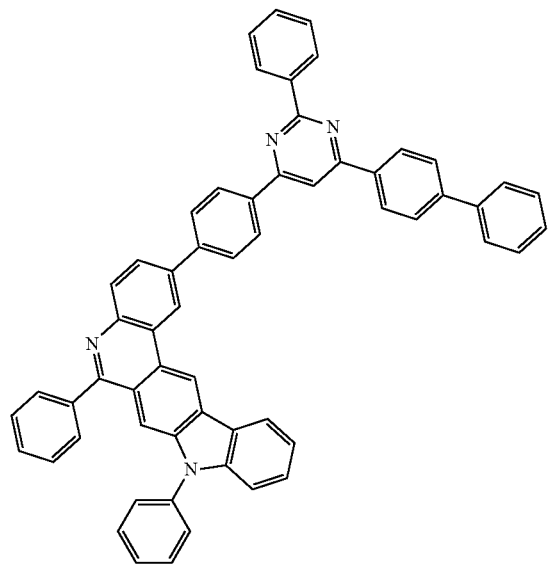
8-9
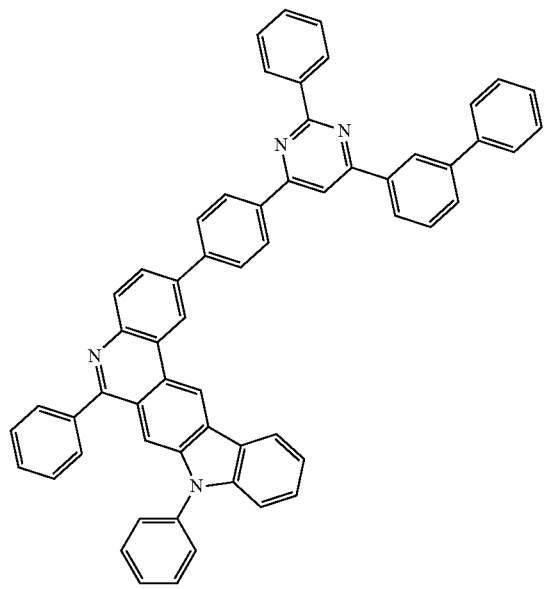
8-10
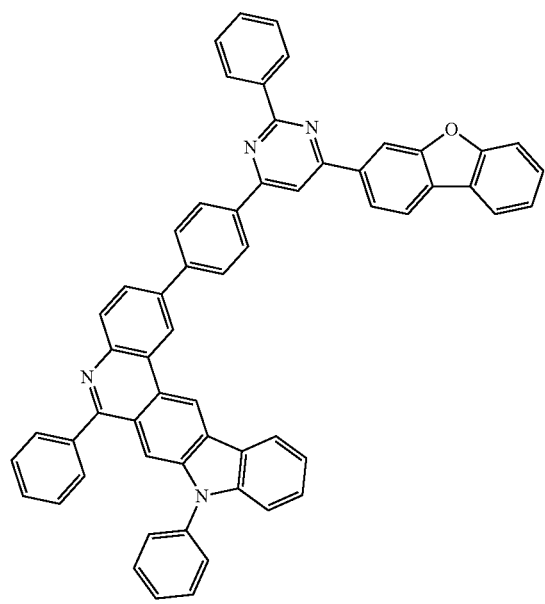
8-11
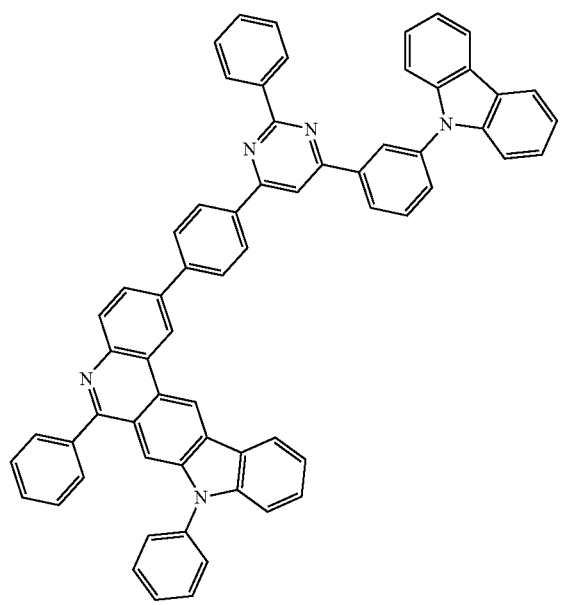

-continued
8-12
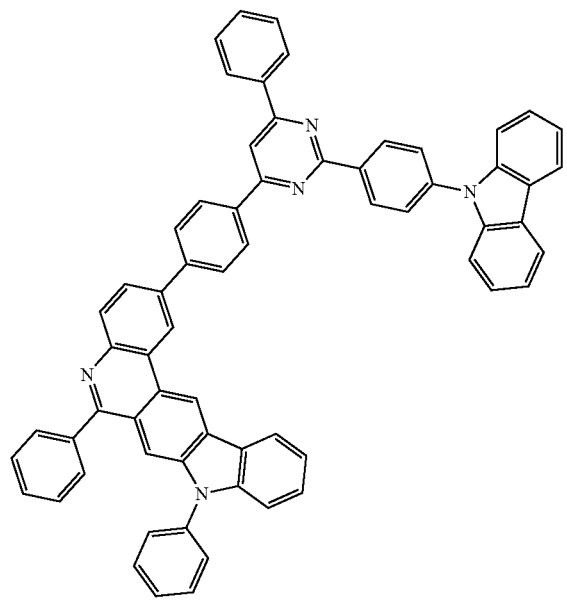
8-13
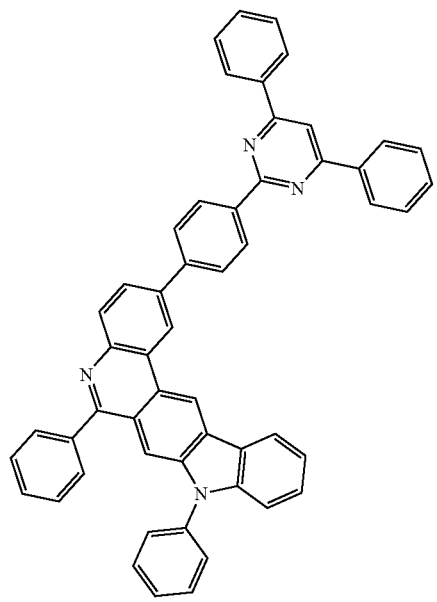
8-14
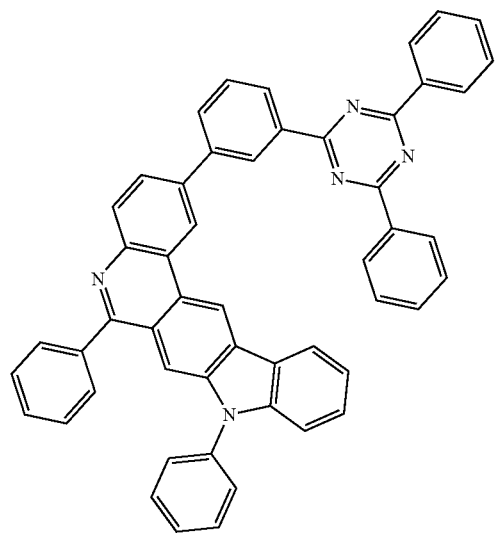
8-15
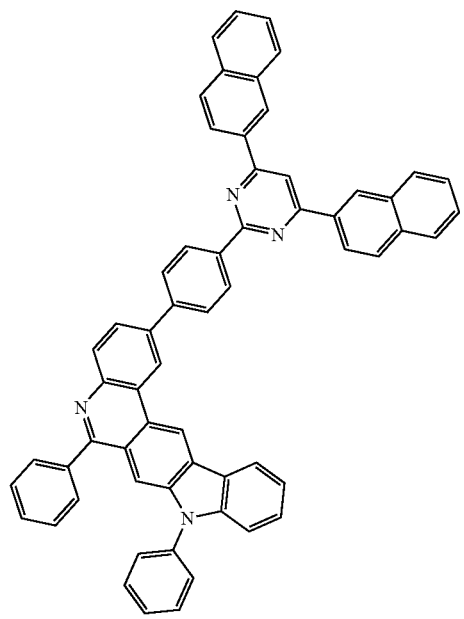

-continued
8-16
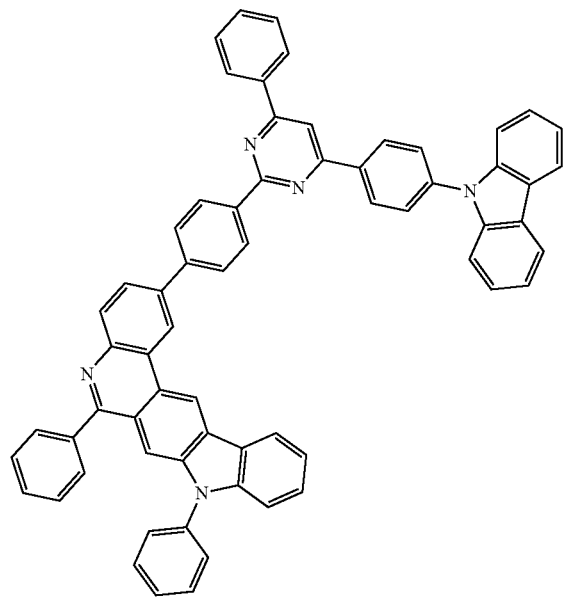
8-17
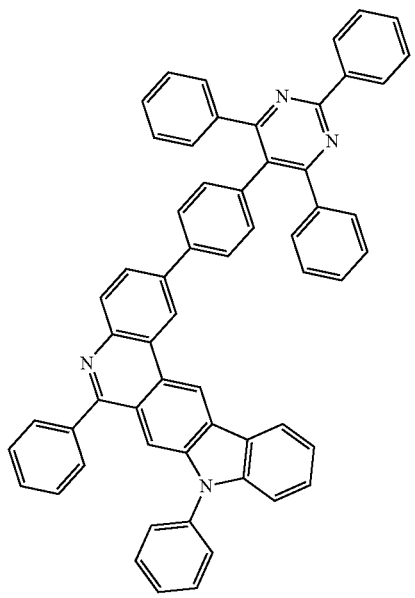
8-18
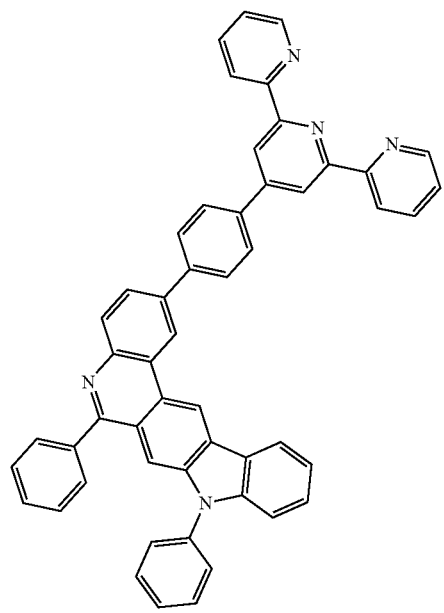
8-19
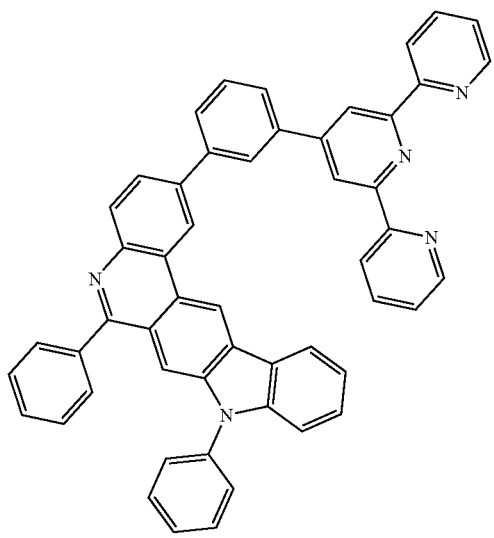

-continued
8-20
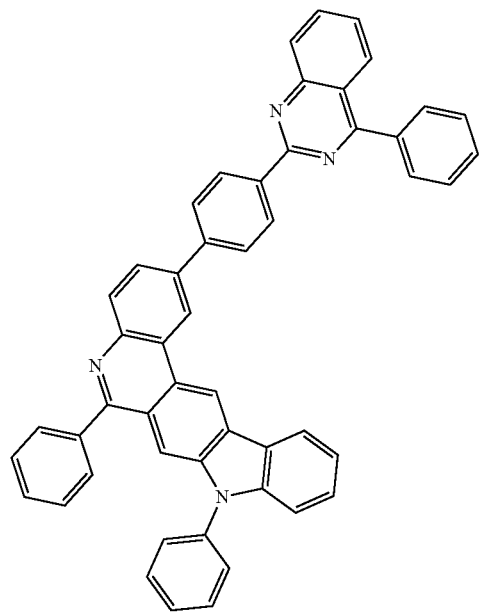
8-21
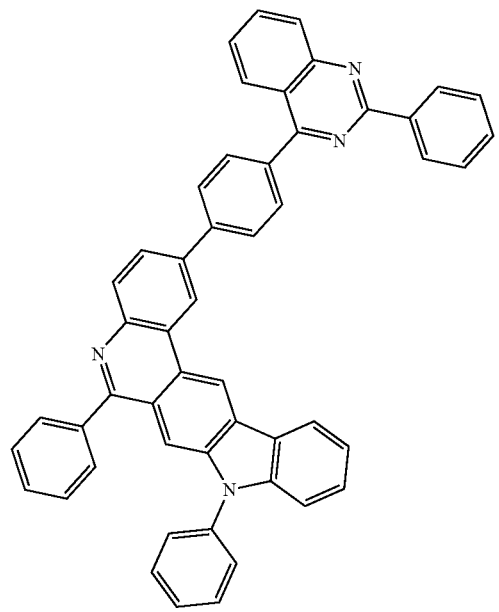
8-22
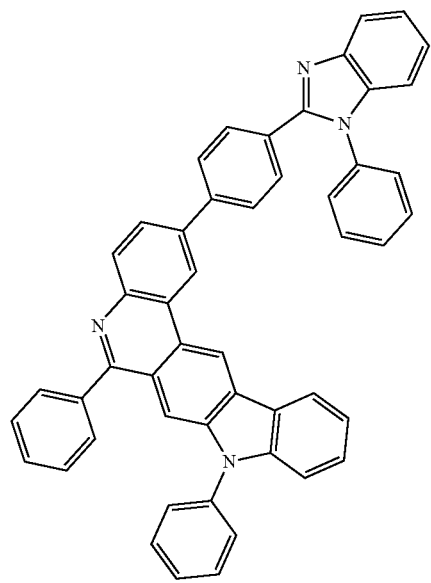
8-23
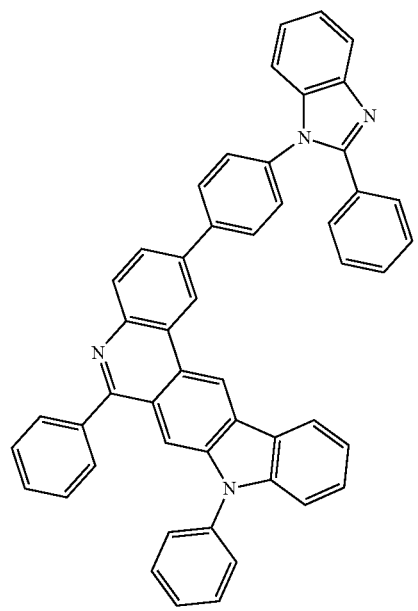

-continued
8-24
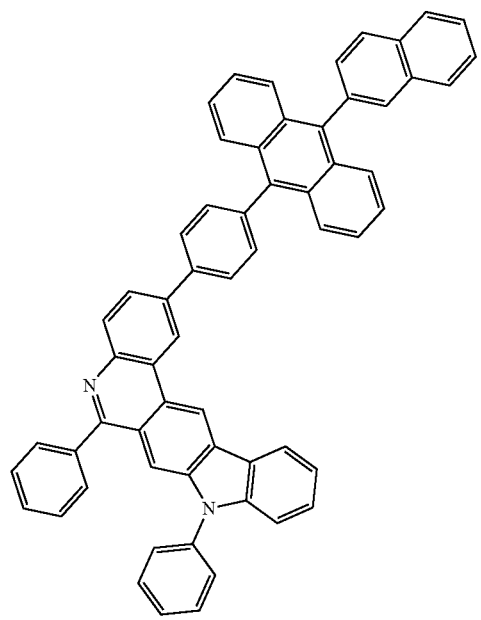
8-25
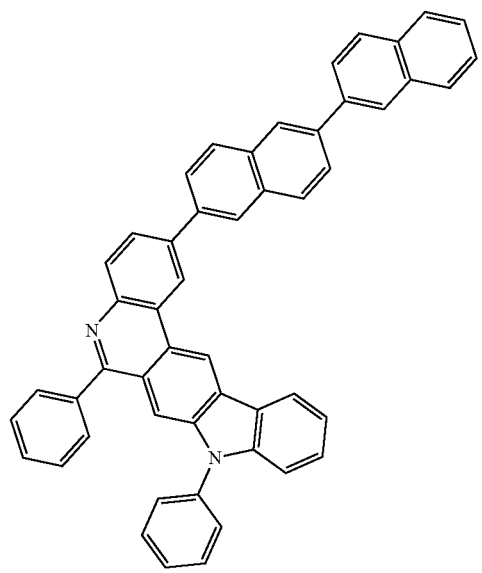
8-26
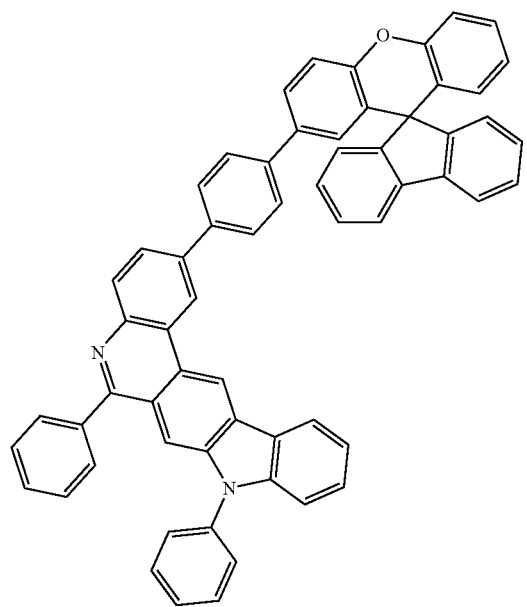
8-27
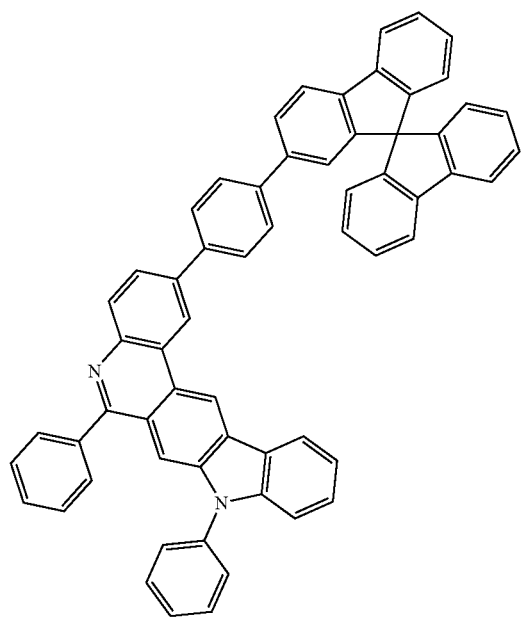

-continued
8-28
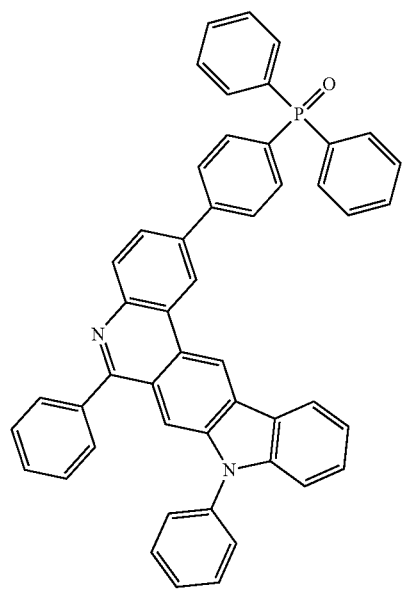
8-29
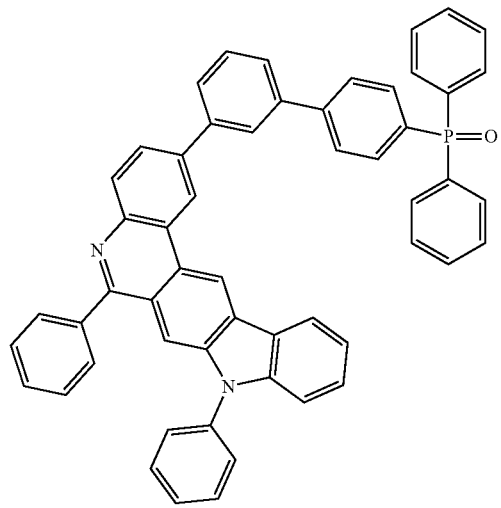
8-30
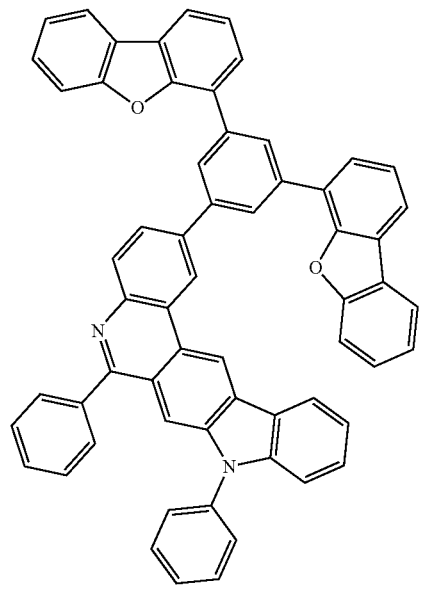
8-31
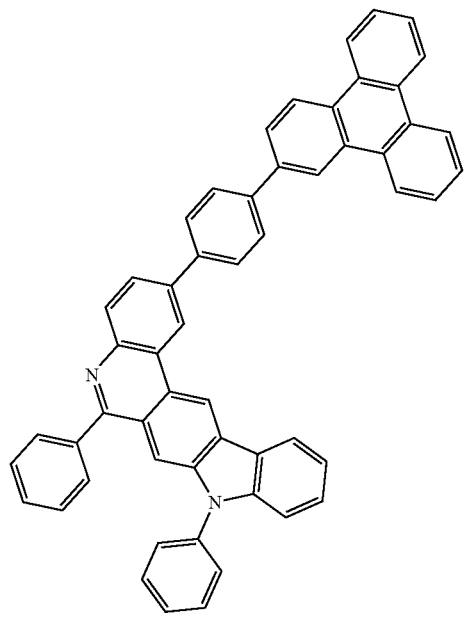

161
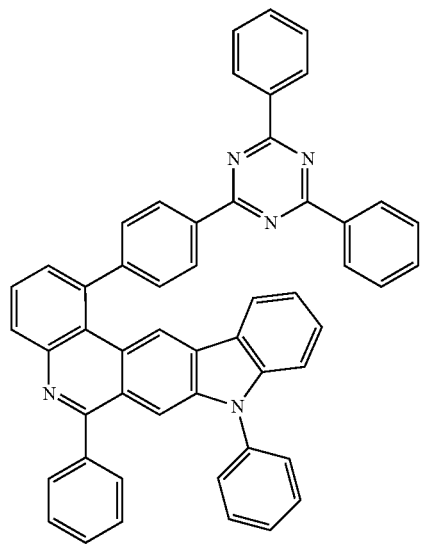
162
-continued
9
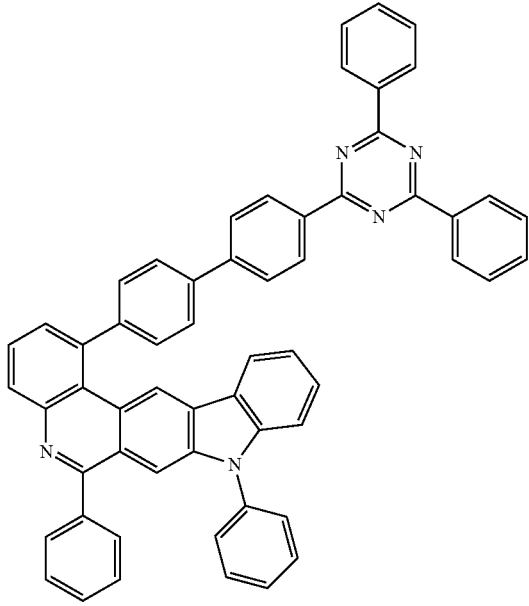
9-1
9-2
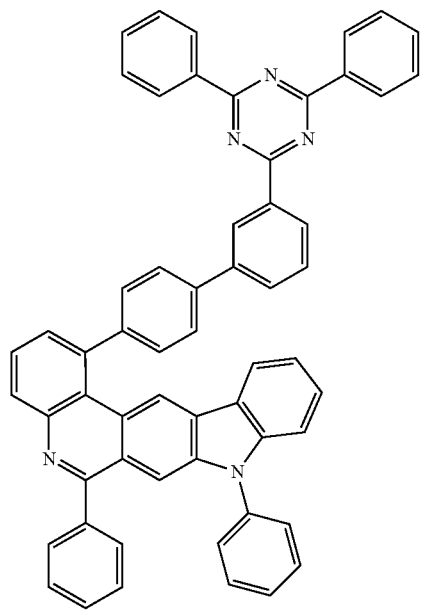
9-3
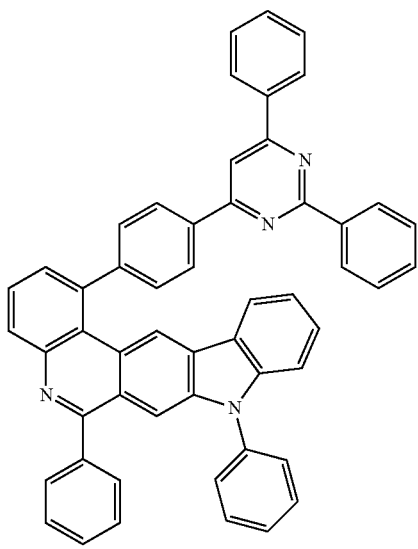

163
164
-continued
9-4
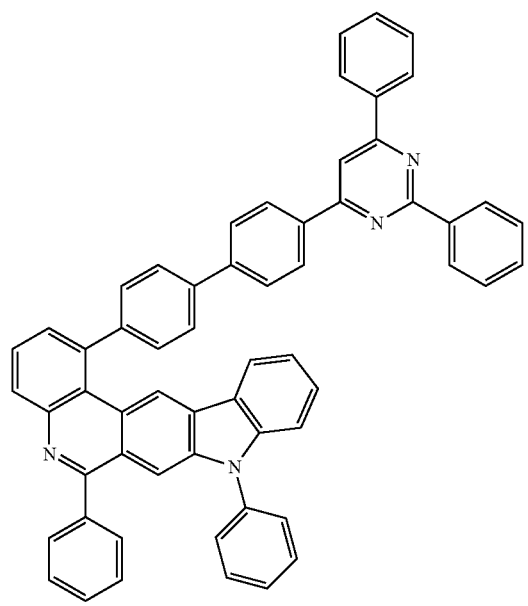
9-5
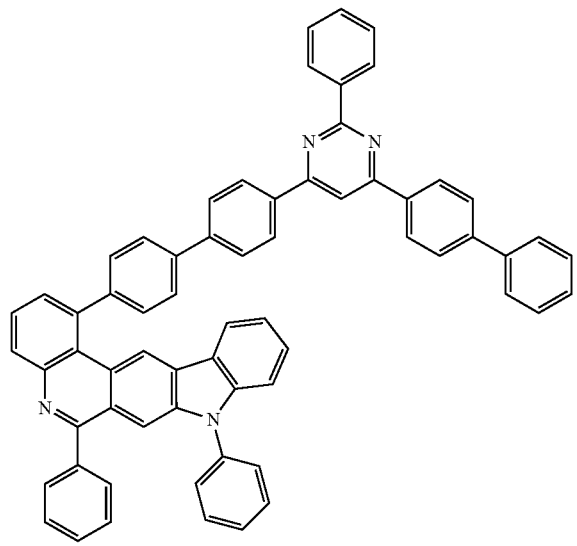
9-6
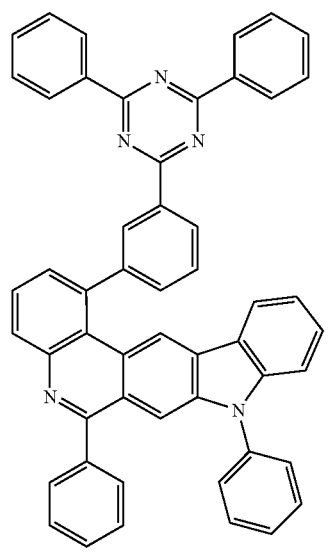
9-7
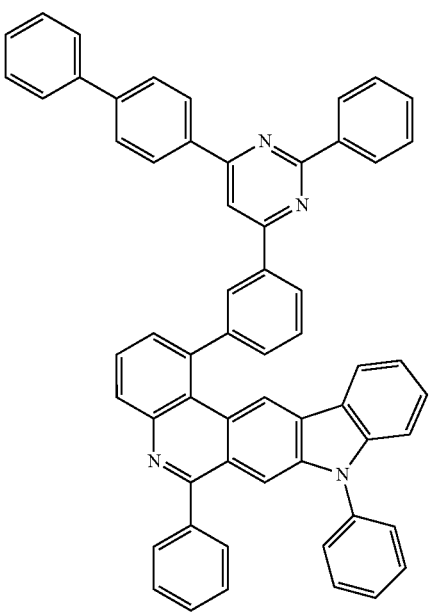

9-8
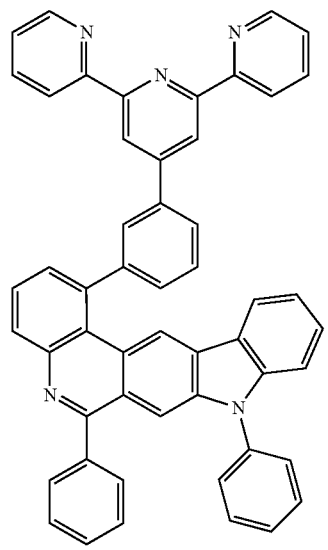
9-9
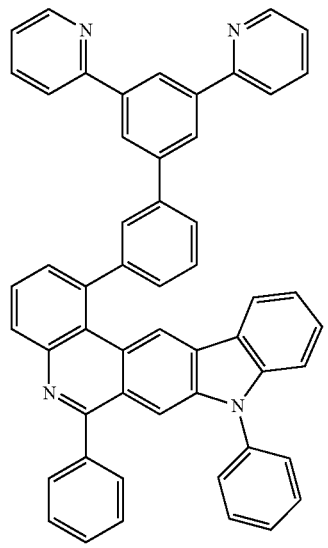 [SMILES: c1ccc(-c2nc3cccc(-c4cccc(-c5cc(-c6ccccn6)cc(-c6ccccn6)c5)c4)c3c3cc4c5ccccc5n(-c5ccccc5)c4cc23)cc1]
9-10
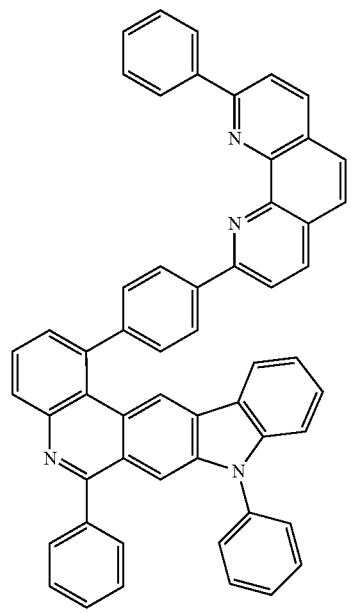
9-11
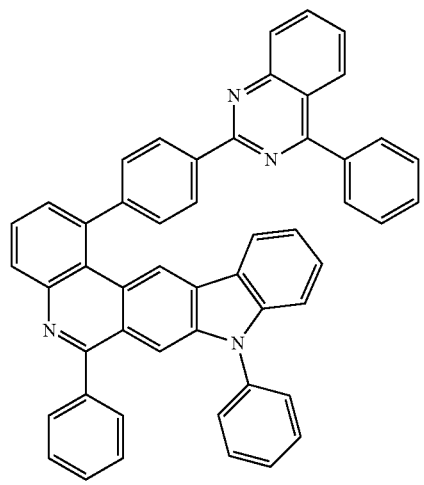

-continued
9-12
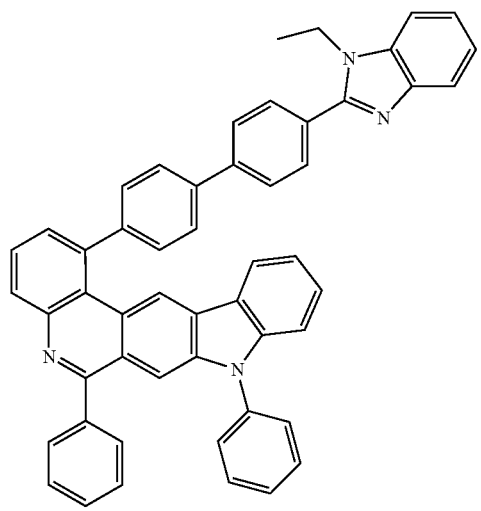
9-13
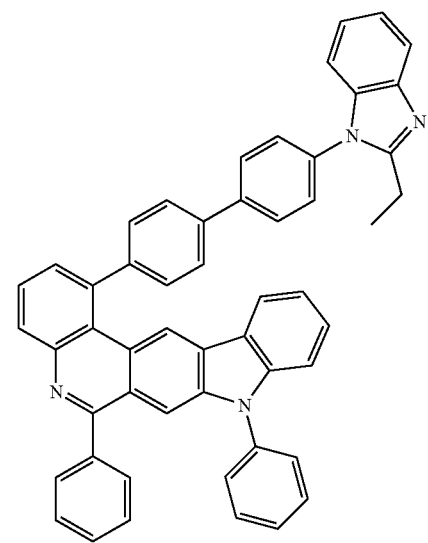
9-14
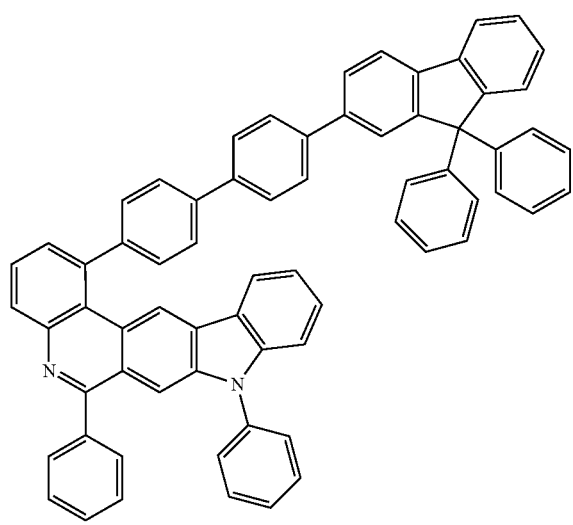
9-15
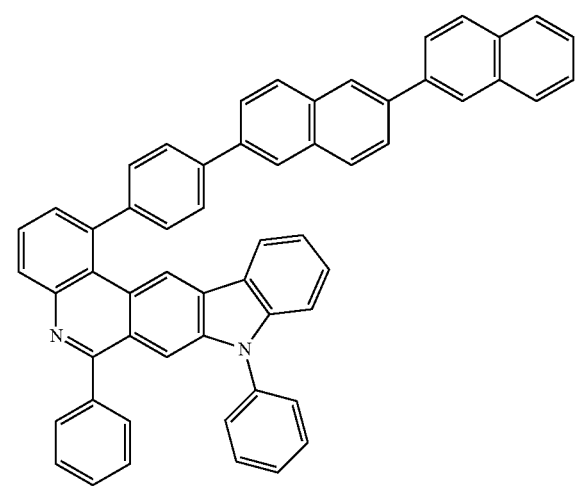
9-16
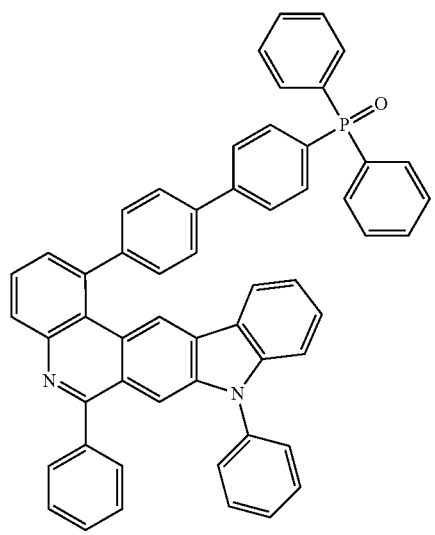
9-17
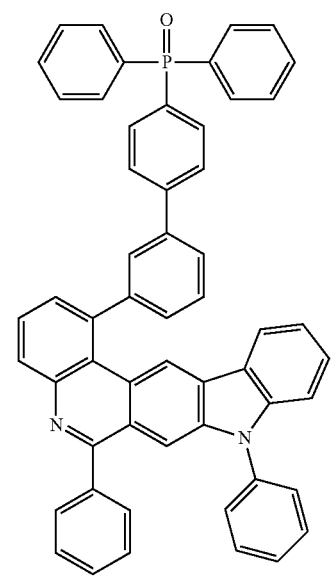

-continued
10
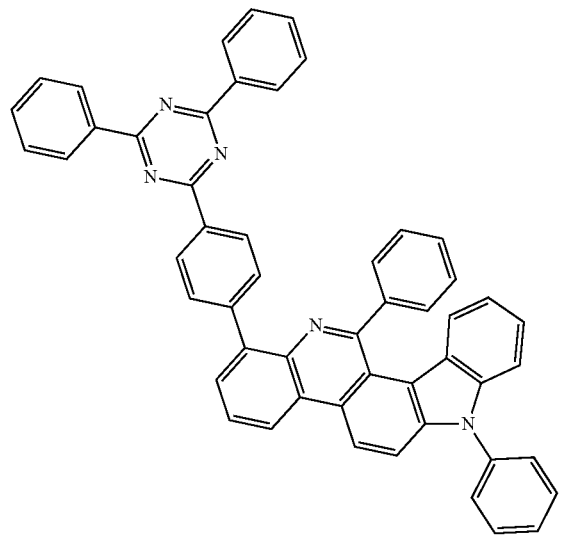
10-1
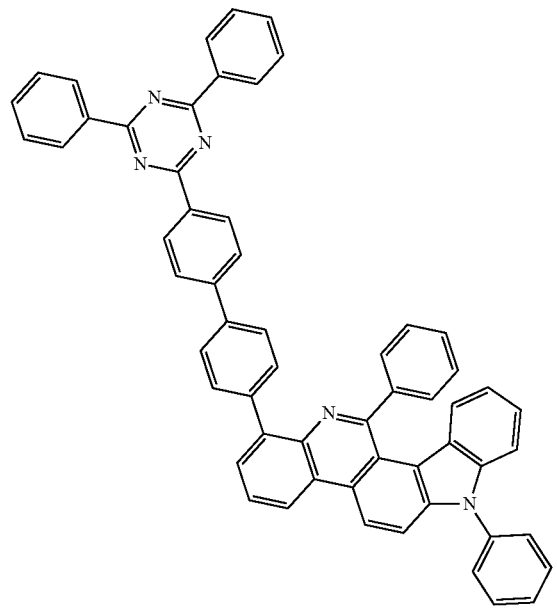
10-2
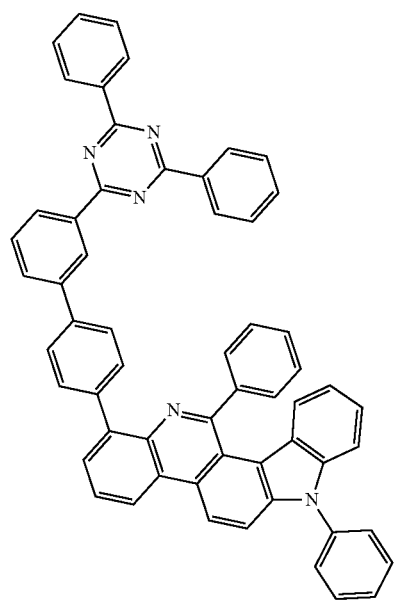
10-3
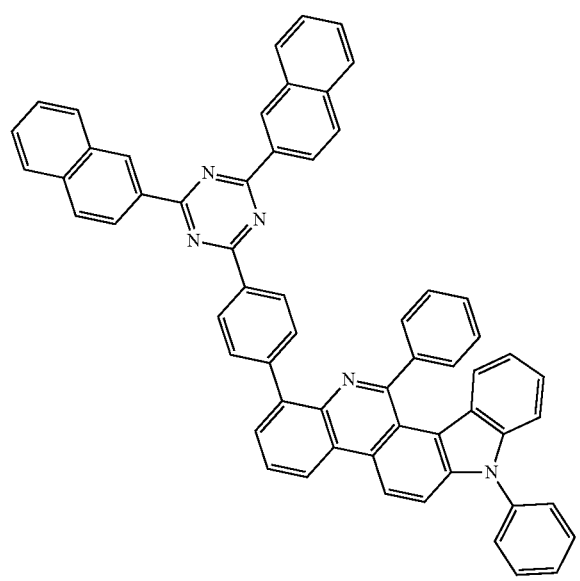

10-4
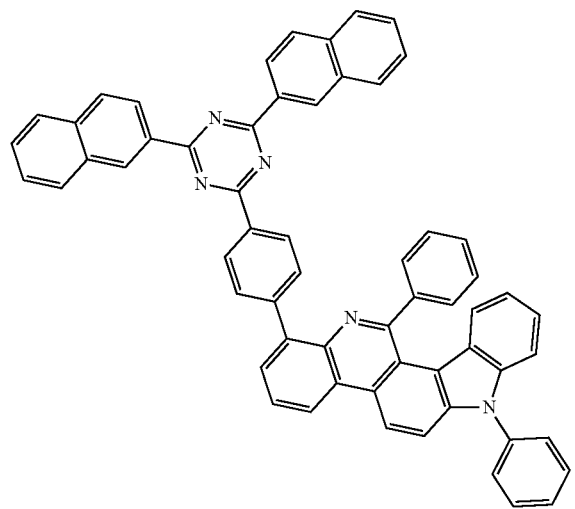
10-5
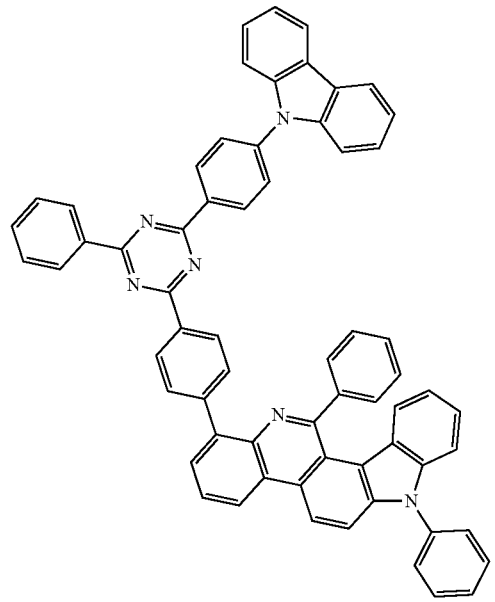
10-6
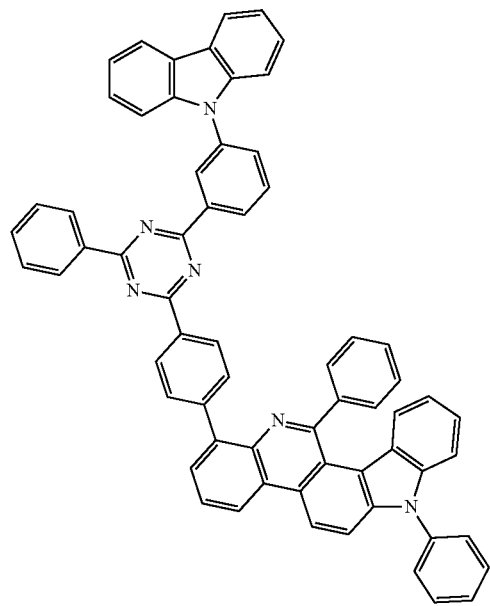
10-7
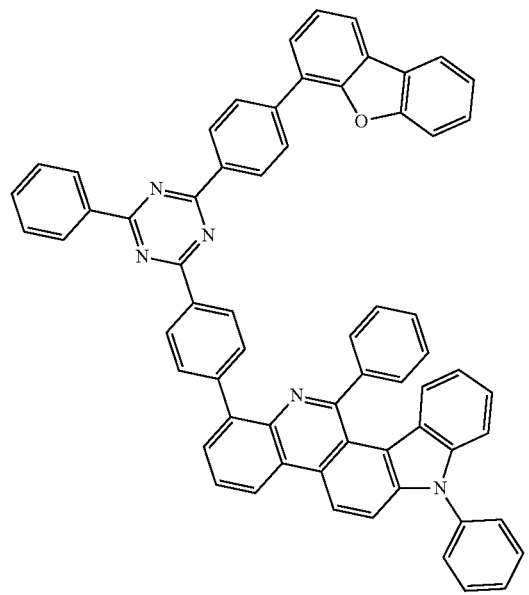

-continued
10-8
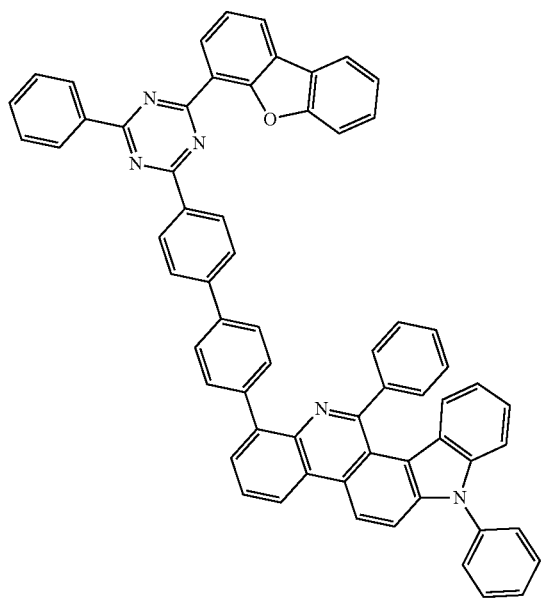
10-9
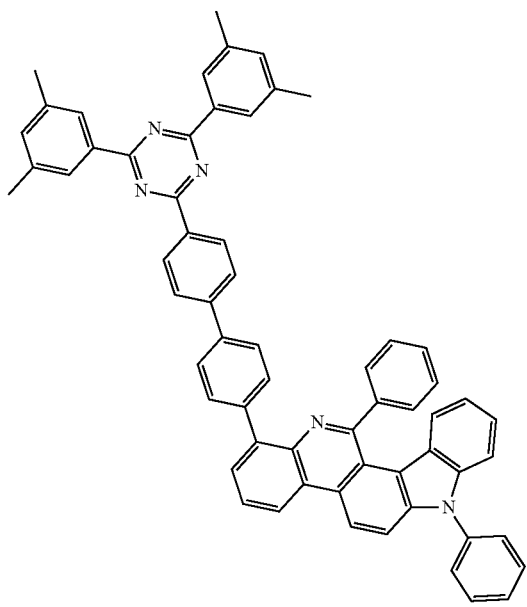
10-10
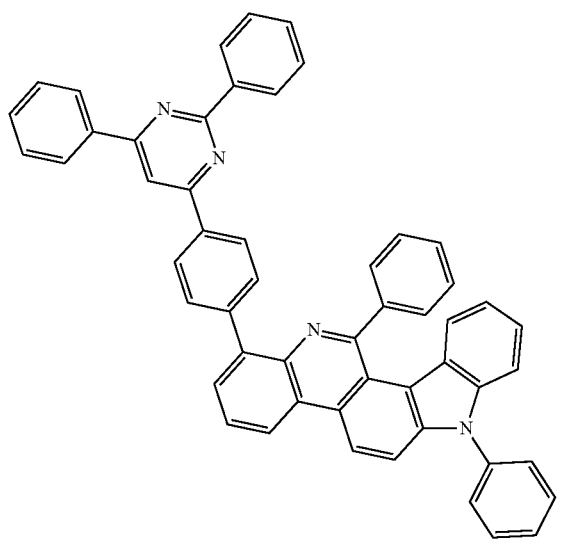
10-11
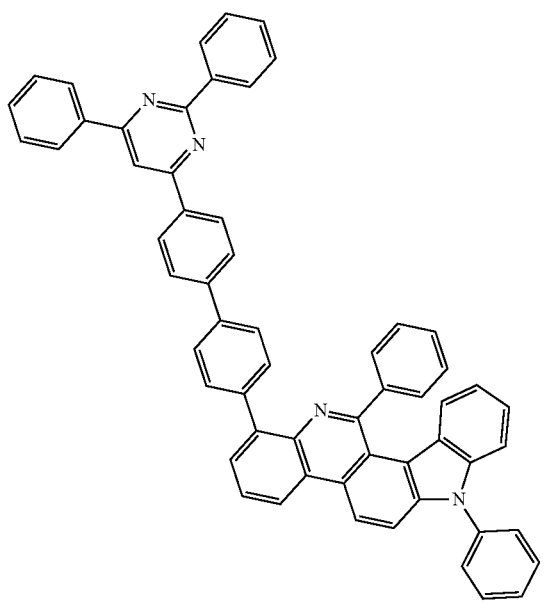

10-12
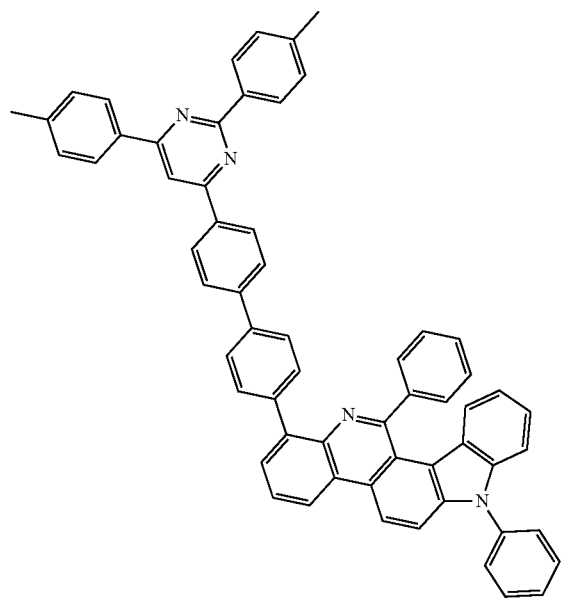
10-13
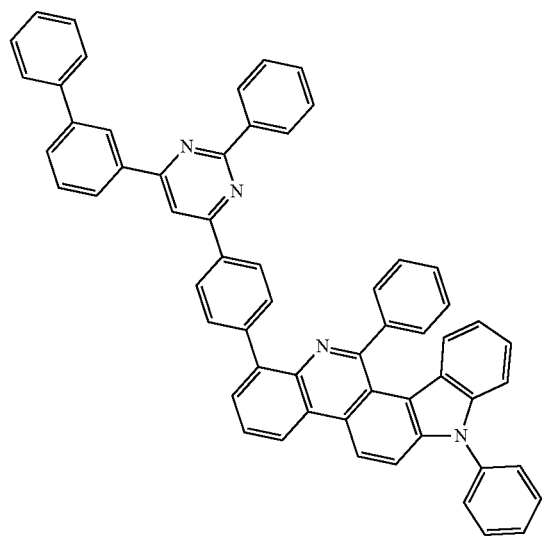
10-14
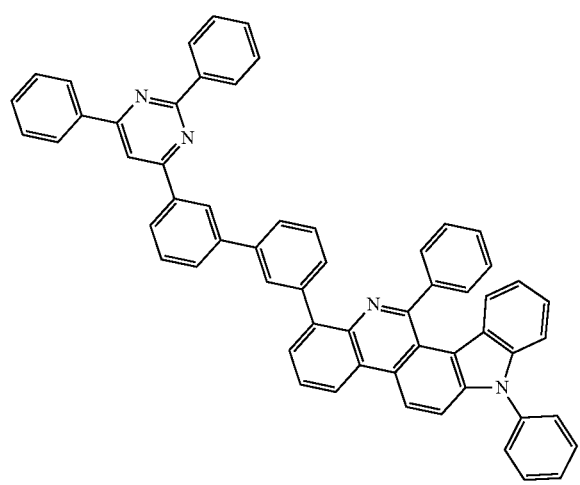
10-15
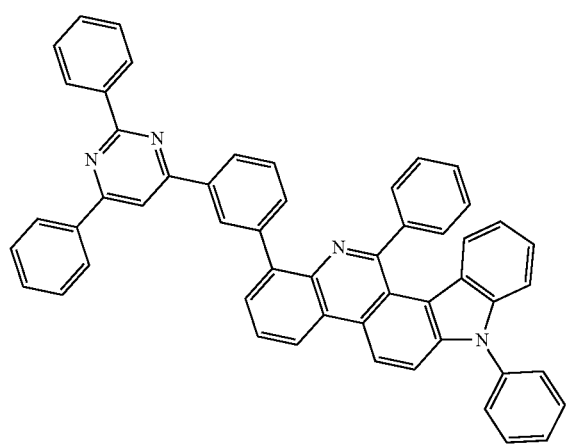

-continued
10-16
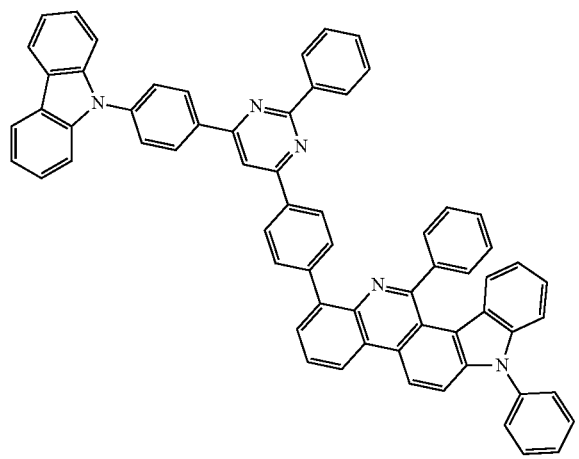
10-17
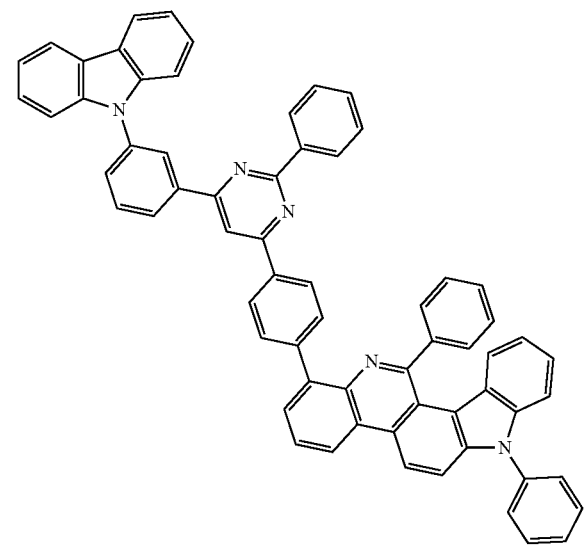
10-18
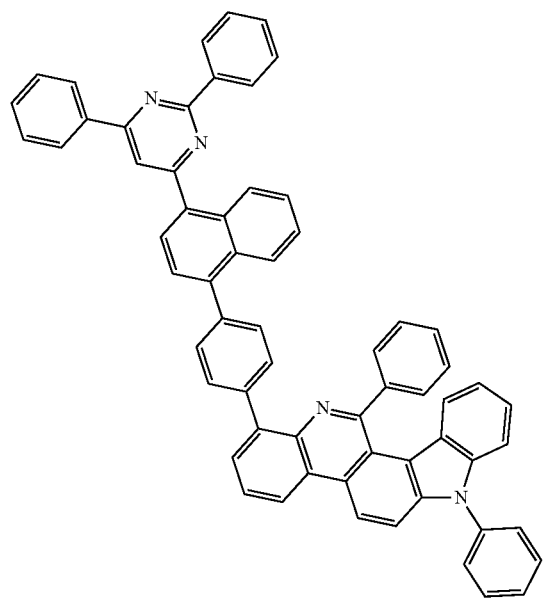
10-19
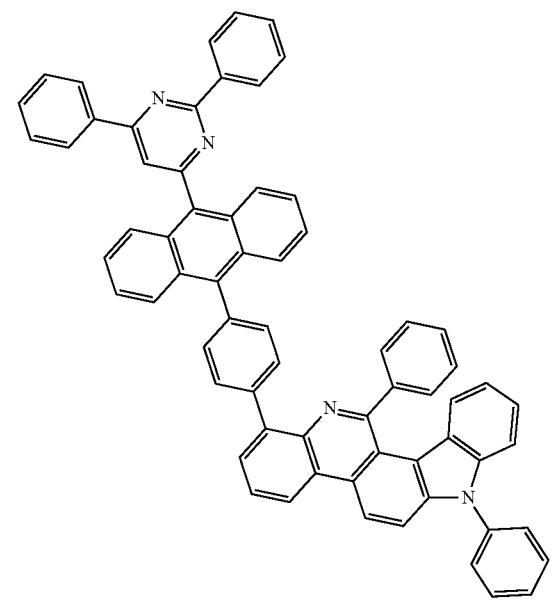

-continued
10-20
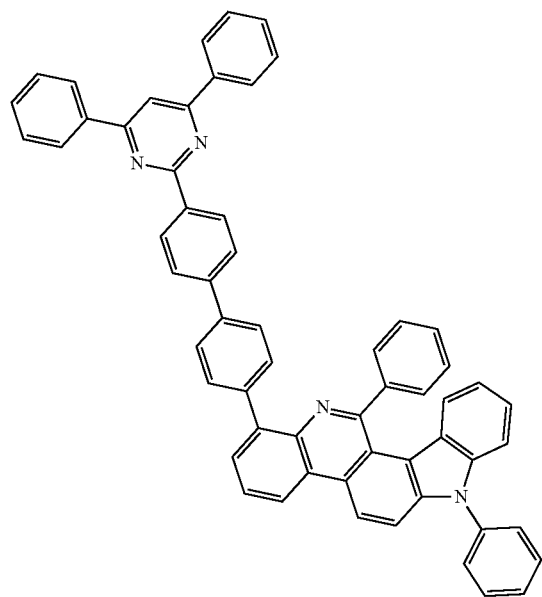
10-21
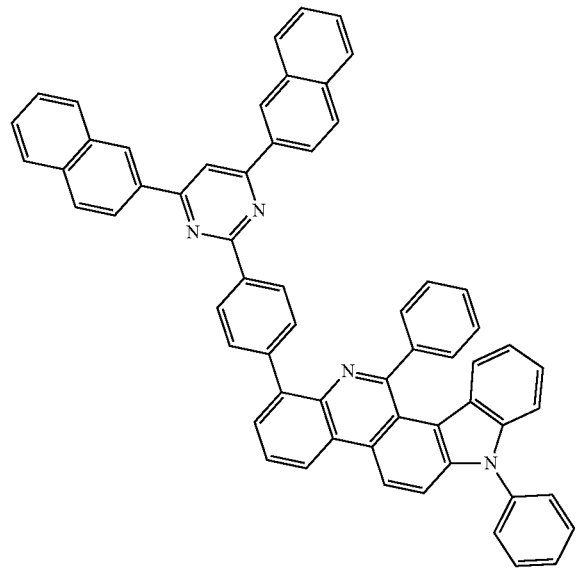
10-22
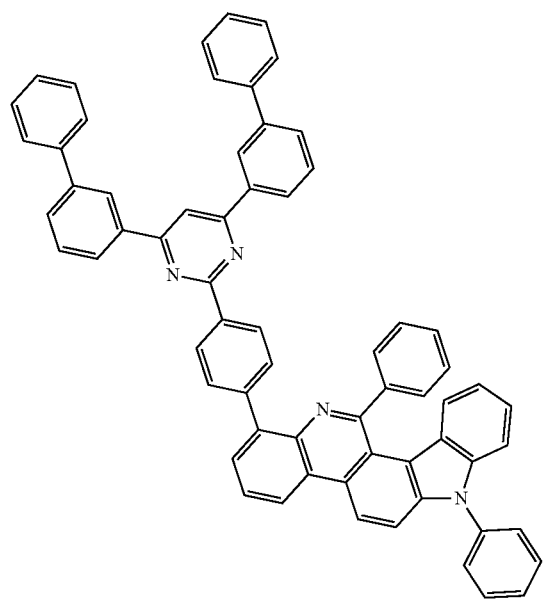
10-23
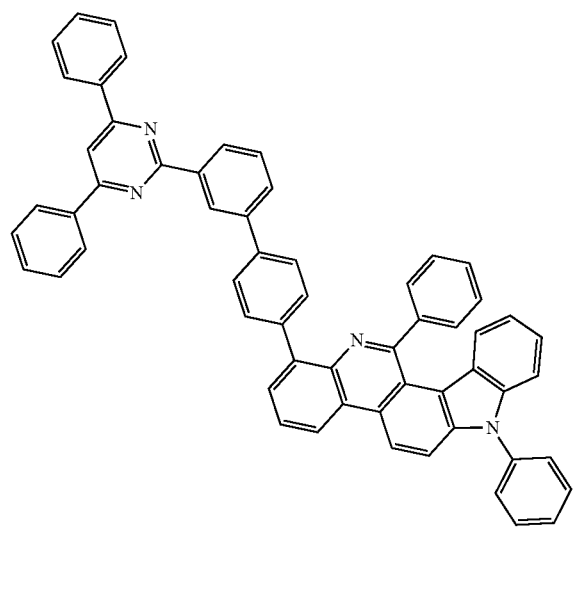

-continued
10-24
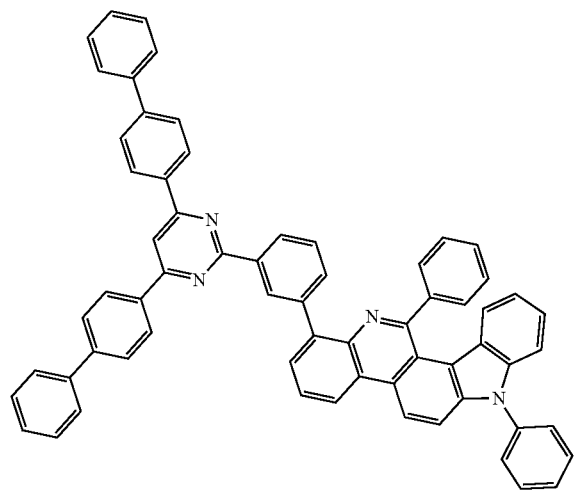
10-25
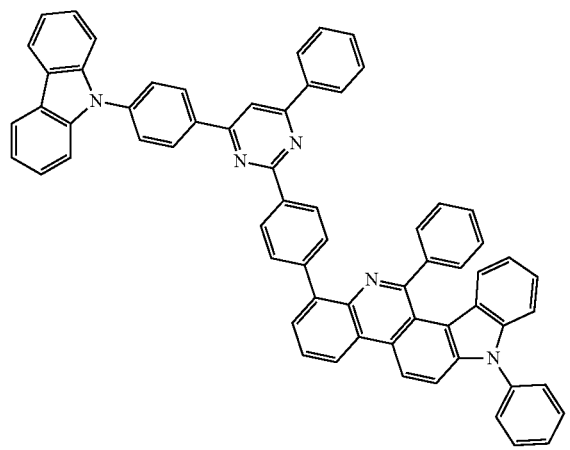
10-26
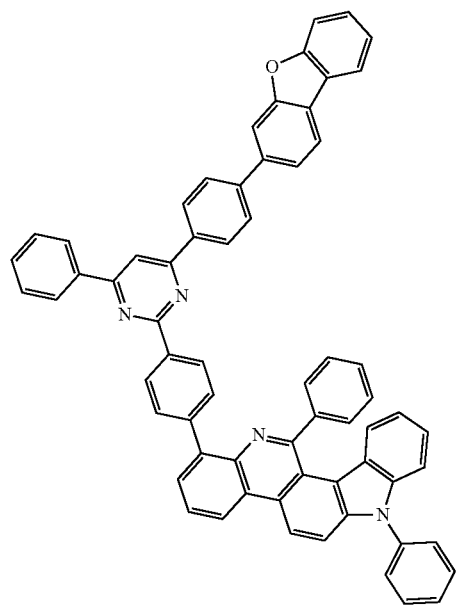
10-27
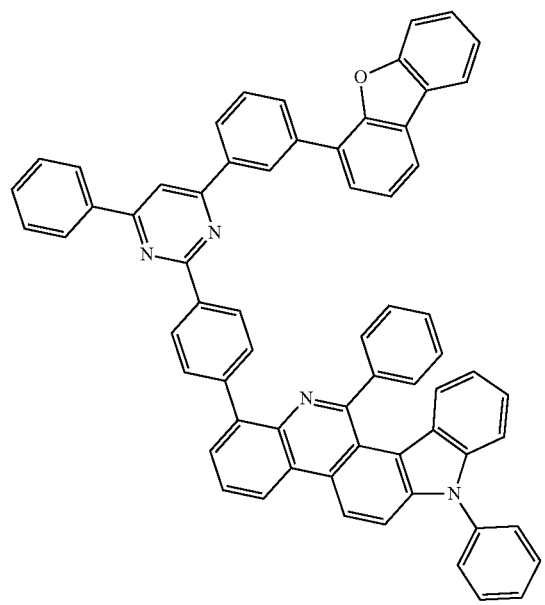

10-28
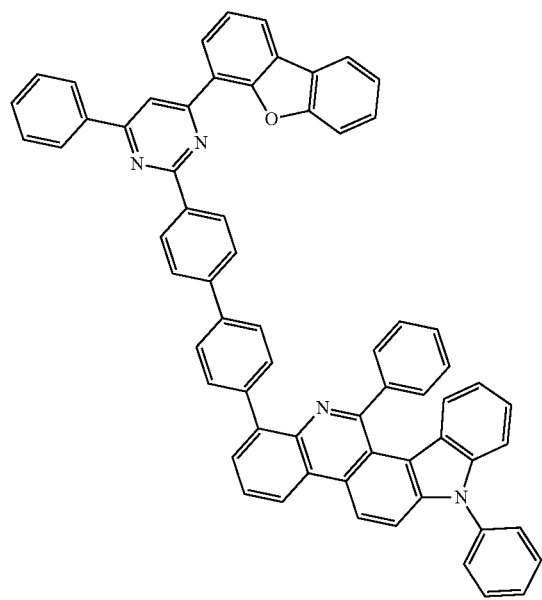
10-29
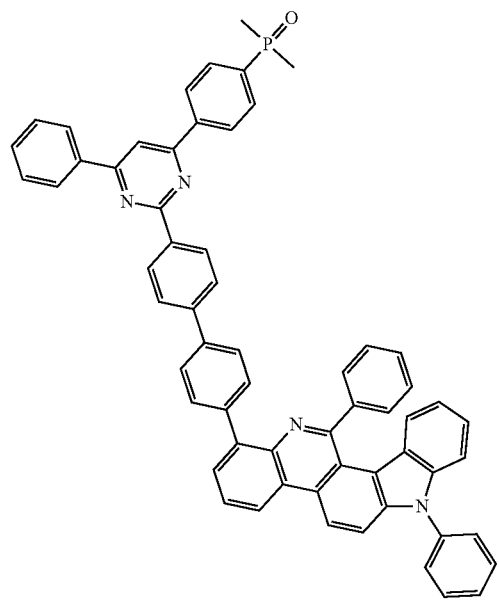
10-30
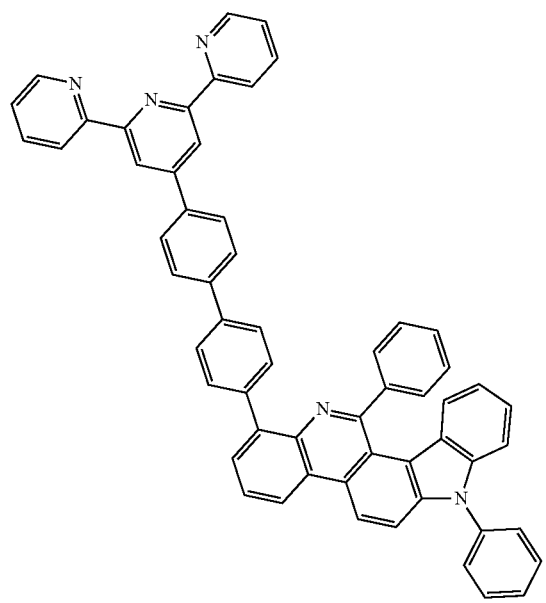
10-31
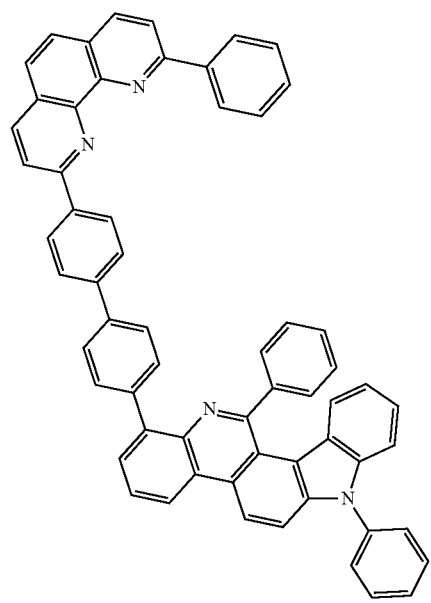

-continued
10-32
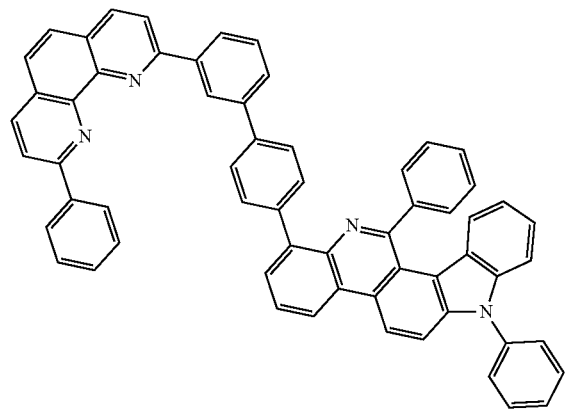
10-33
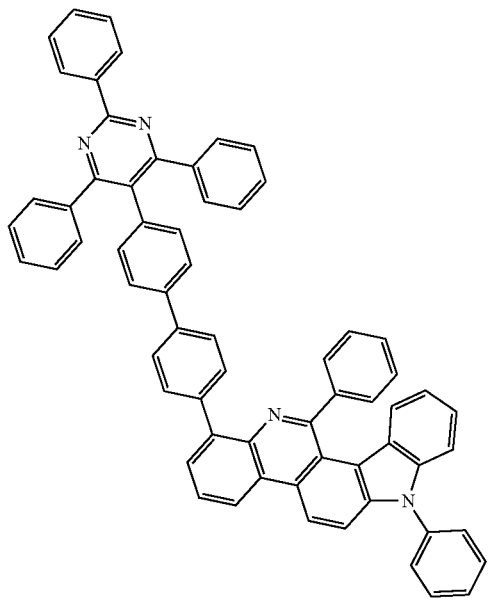
10-34
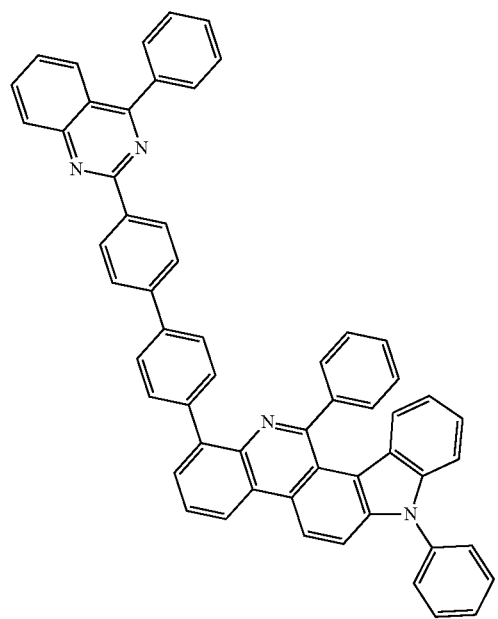
10-35
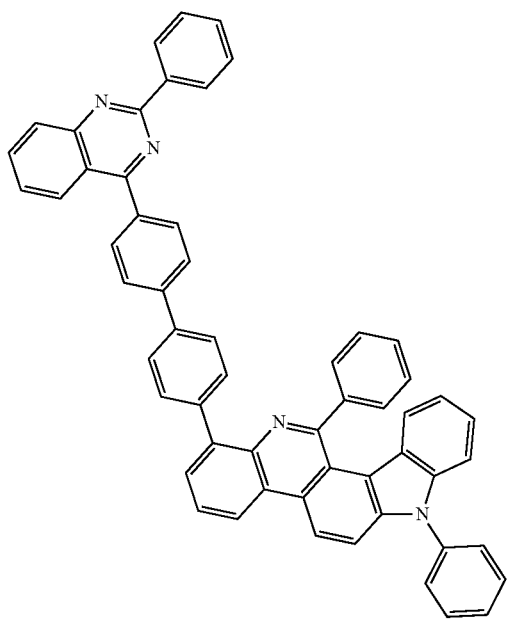

-continued
10-36
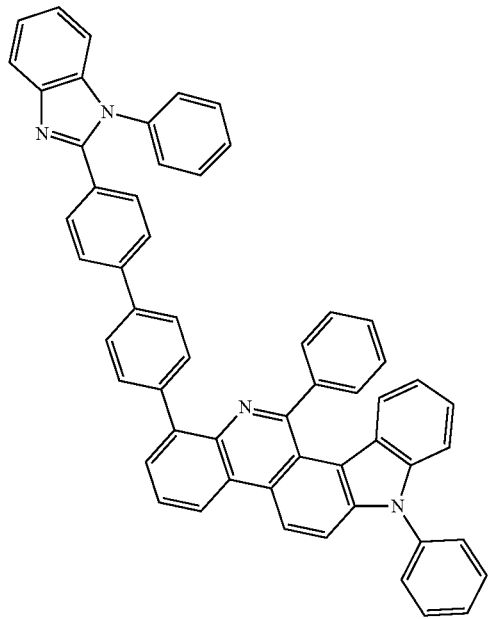
10-37
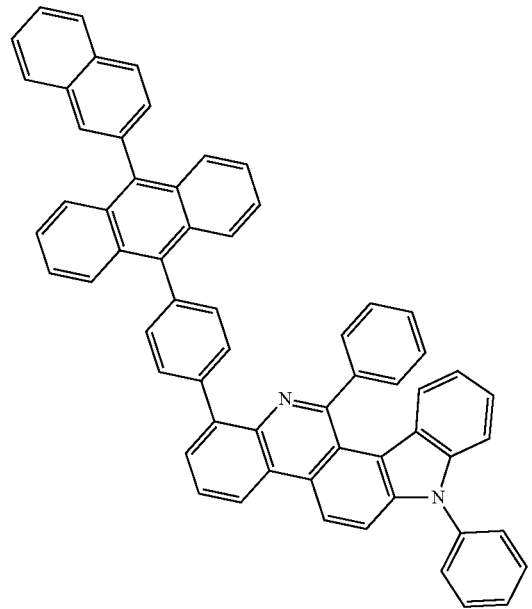
10-38
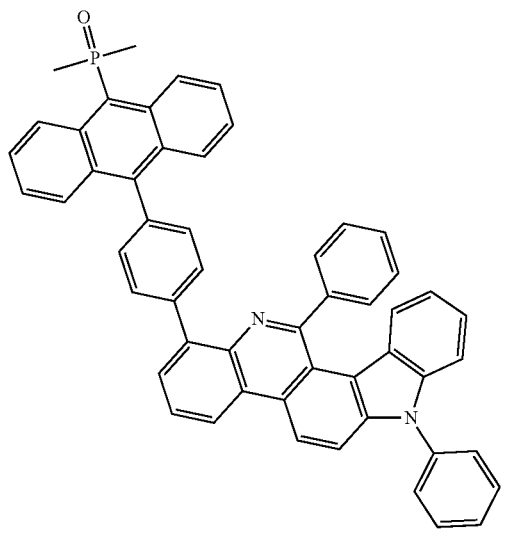
10-39
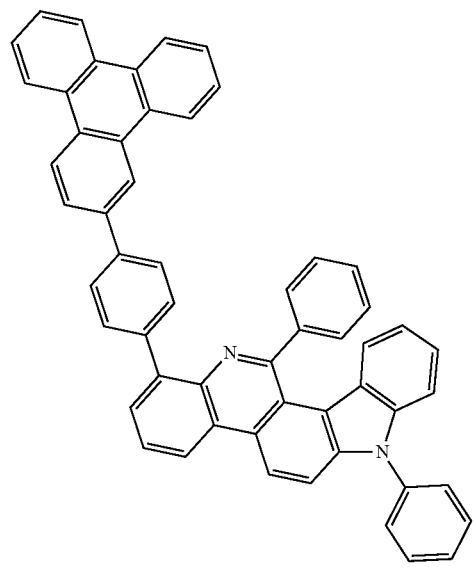

-continued
10-40
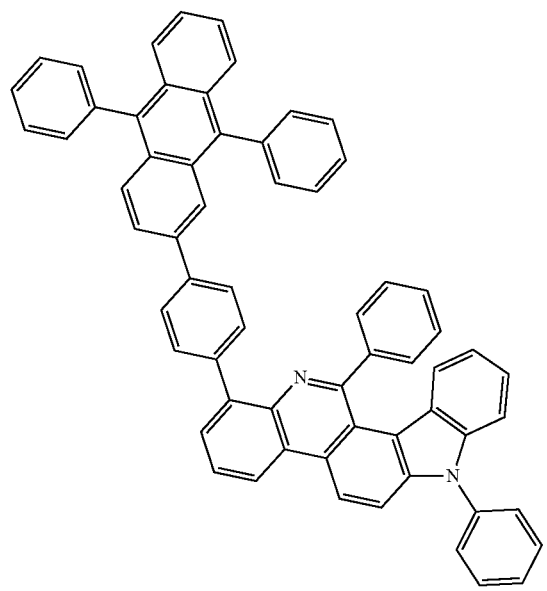
10-41
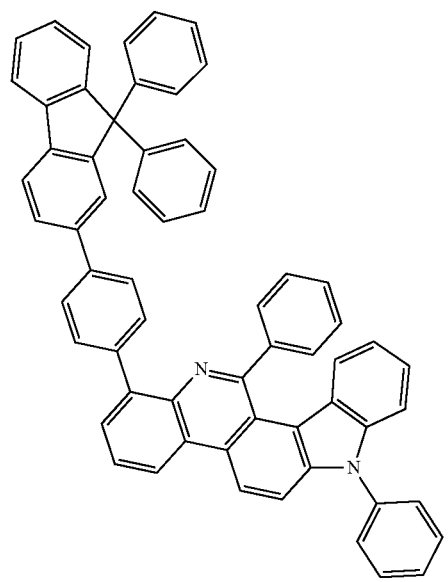
10-42
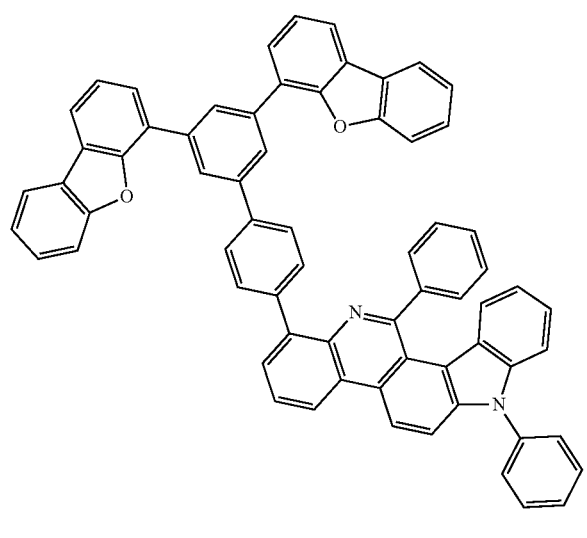
11
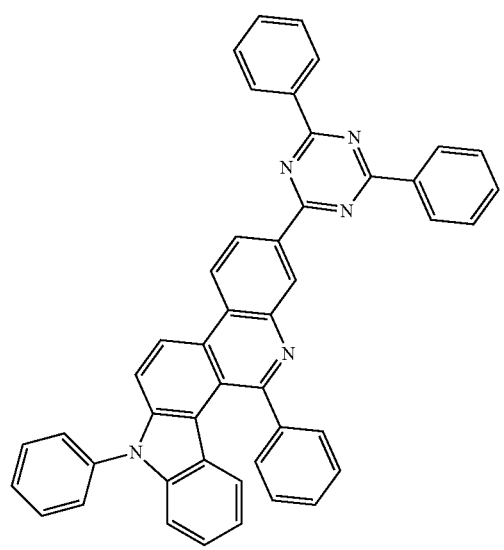

-continued
11-1
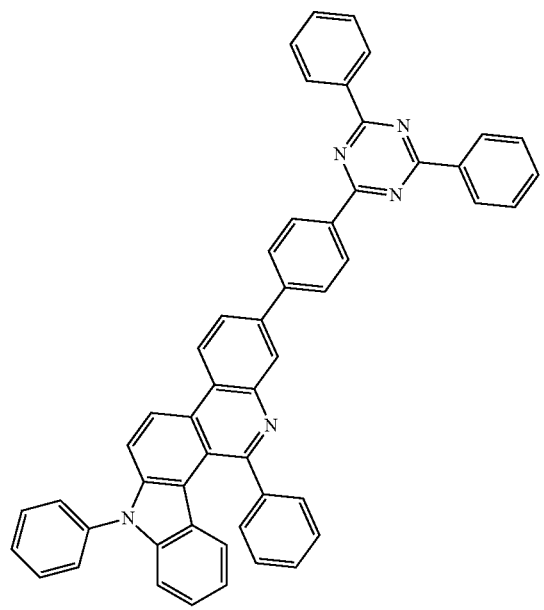
11-2
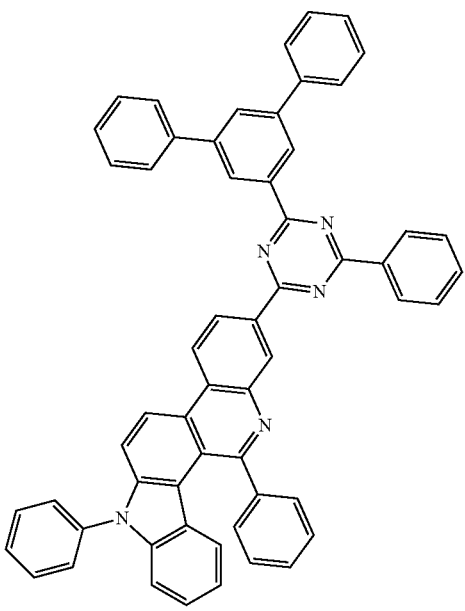
11-3
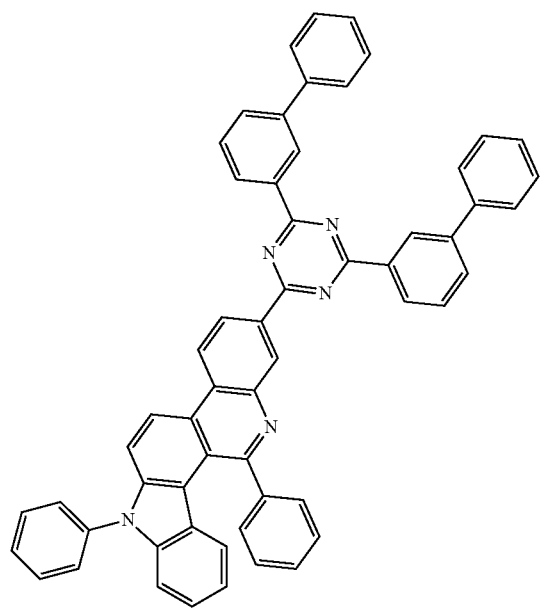
11-4
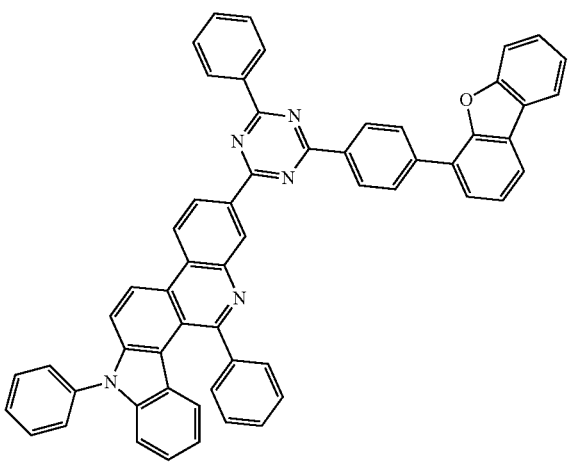

-continued
11-5
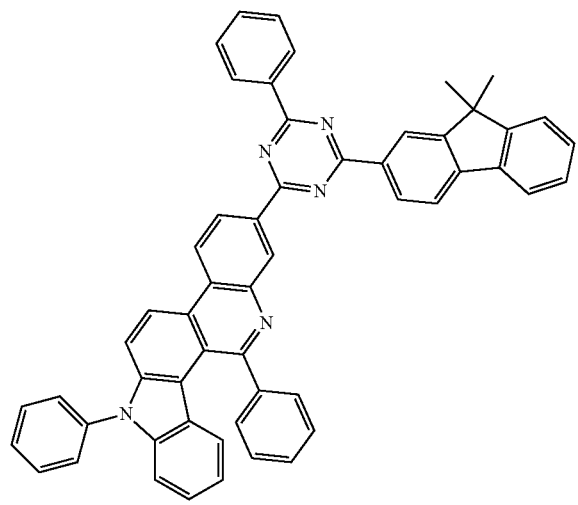
11-6
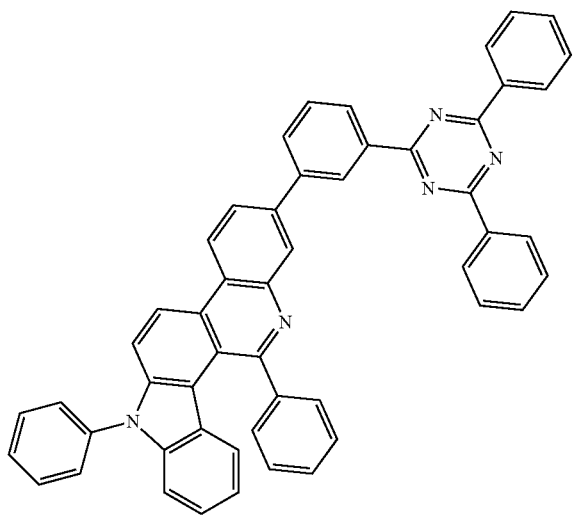
11-7
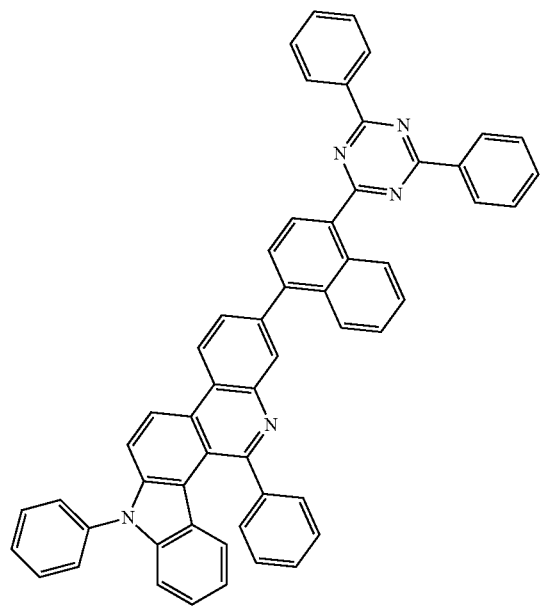
11-8
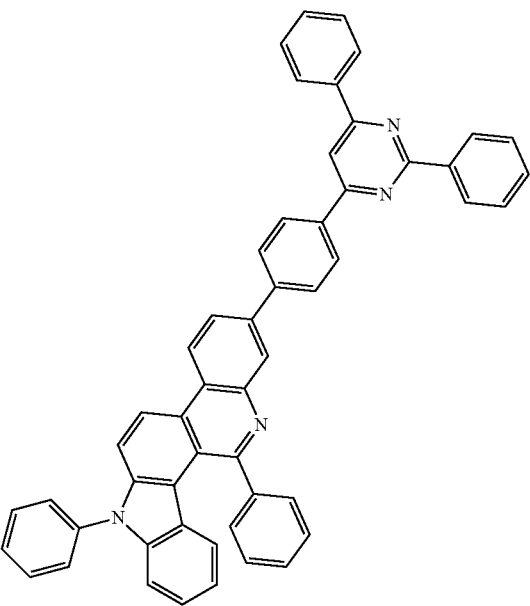

-continued
11-9
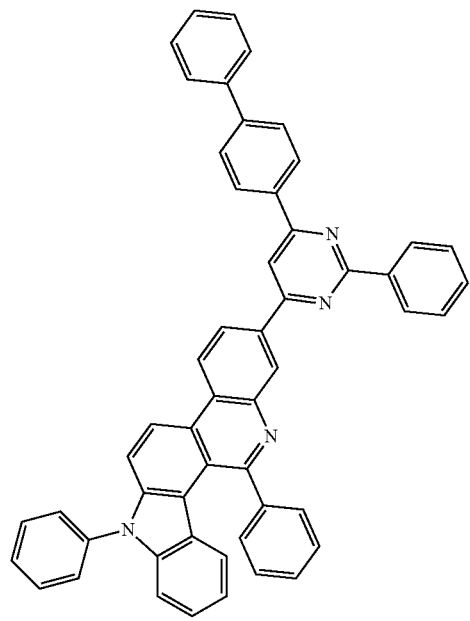
11-10
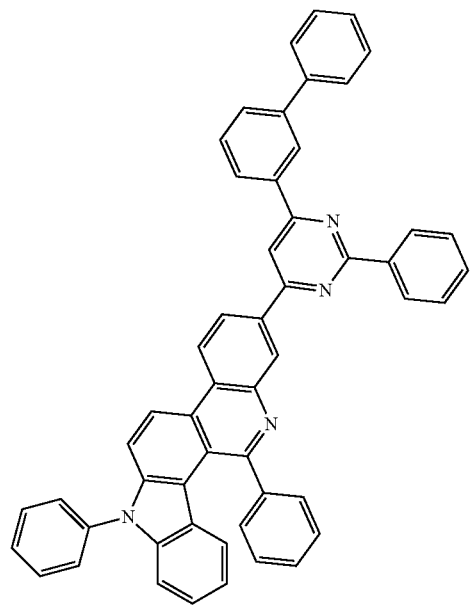
11-11
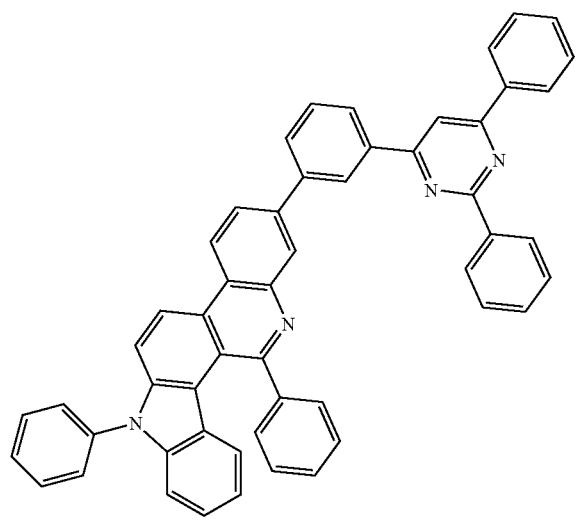
11-12
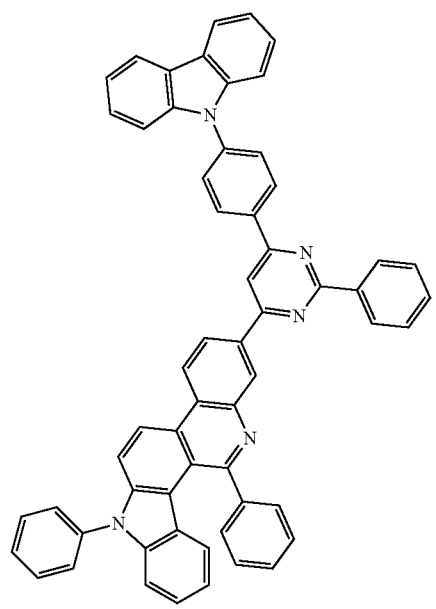

-continued
11-13
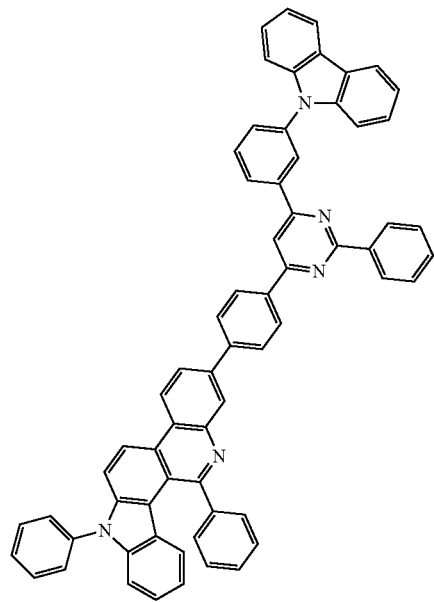
11-14
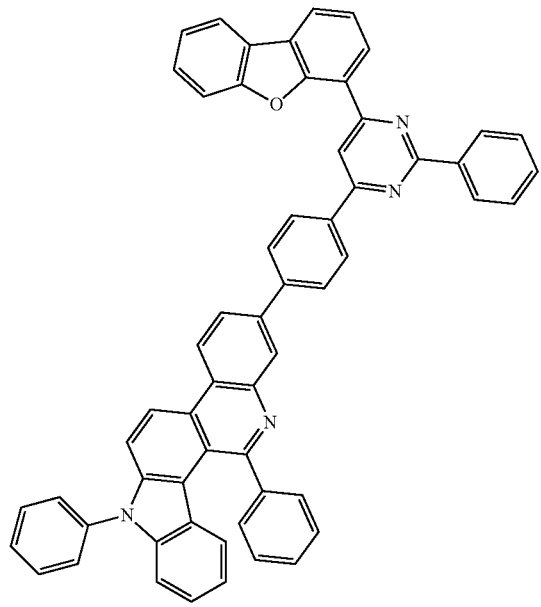
11-15
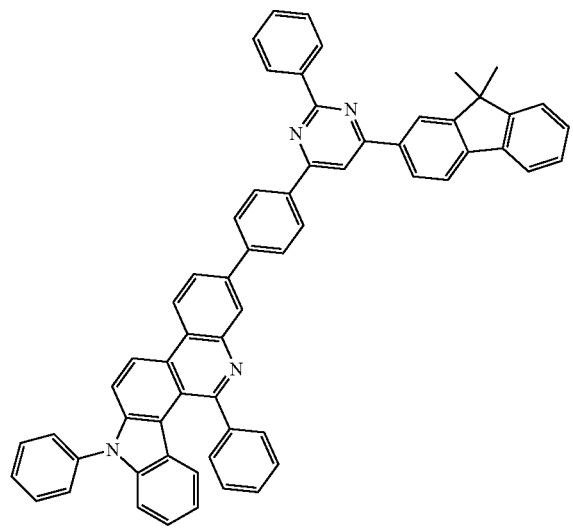
11-16
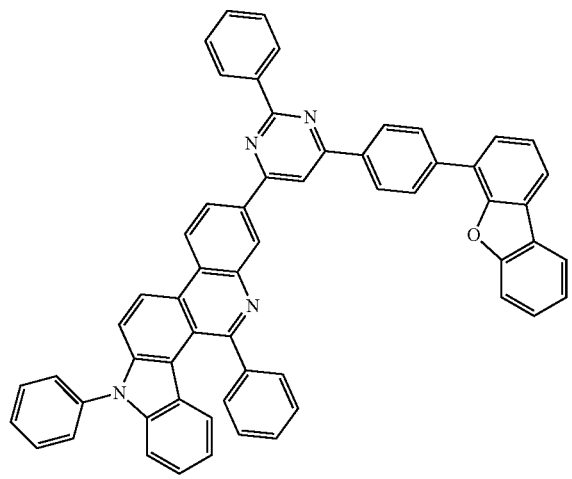

11-7
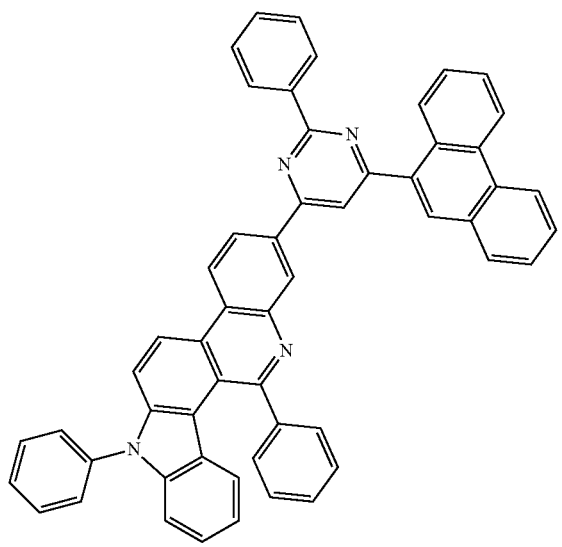
11-18
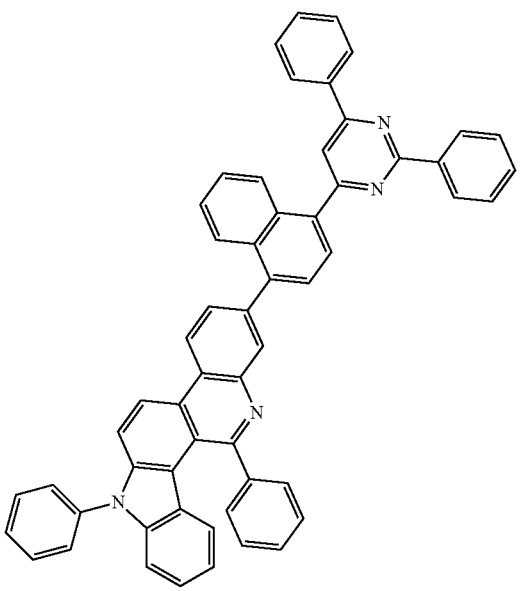
11-19
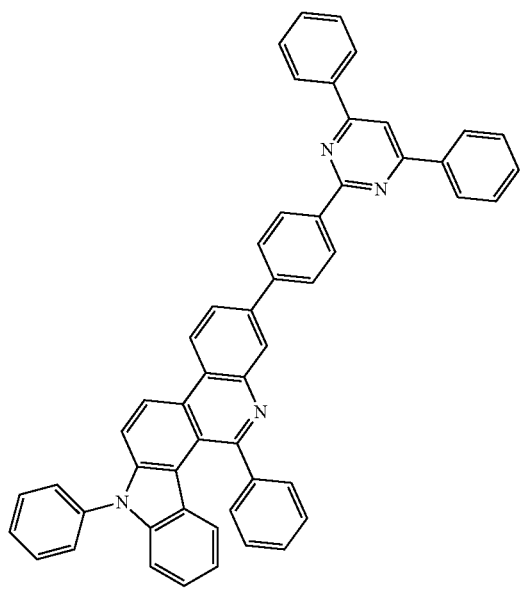
11-20
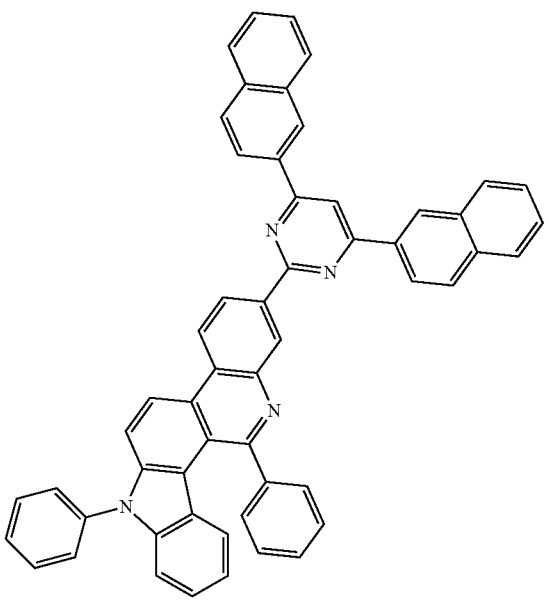

-continued
11-21
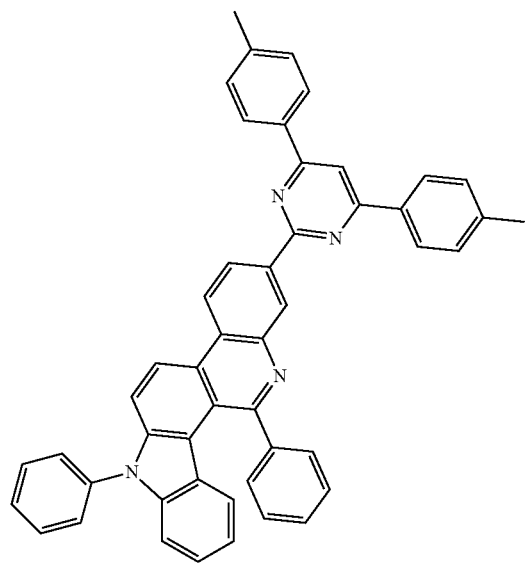
11-22
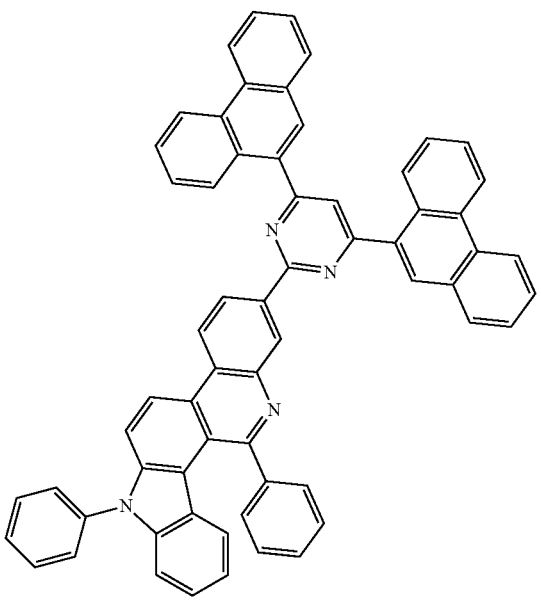
11-23
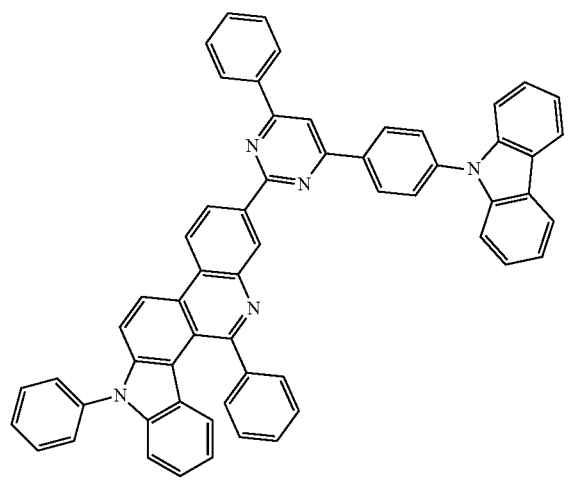
11-24
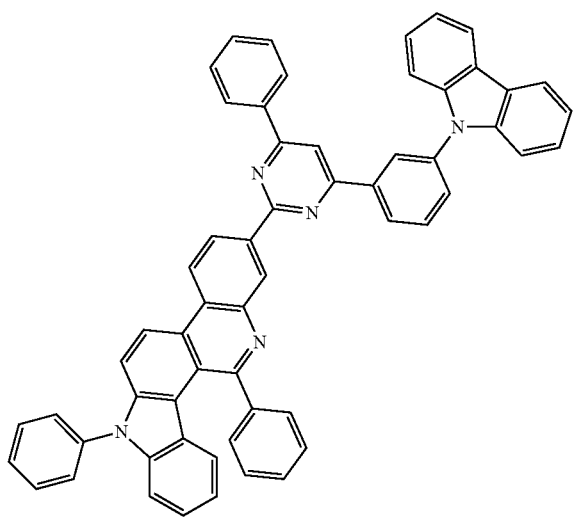

11-25
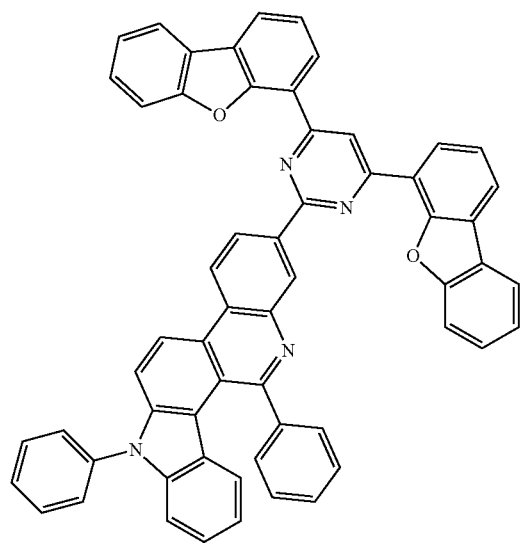
11-26
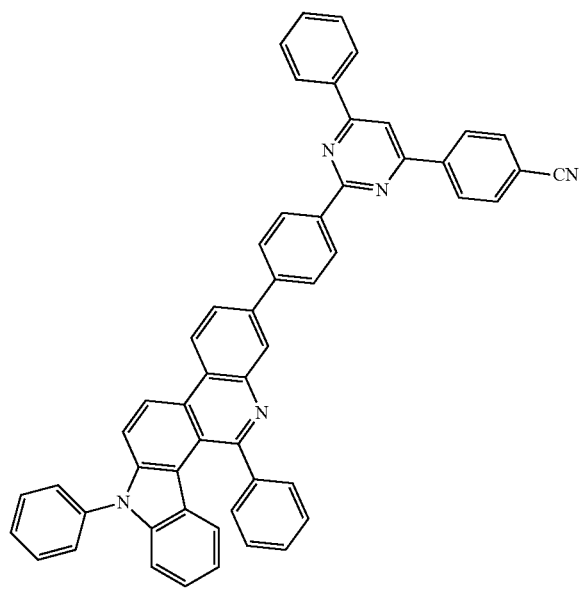
11-27
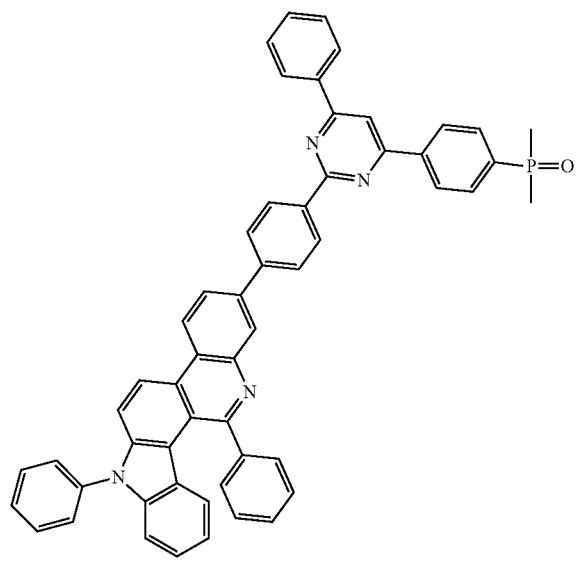
11-28
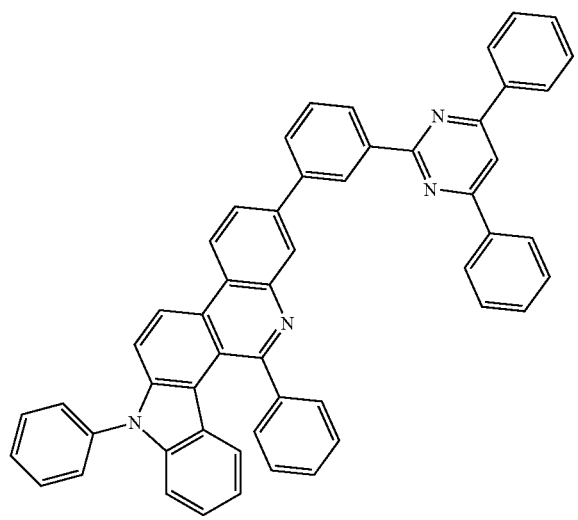

-continued
11-29
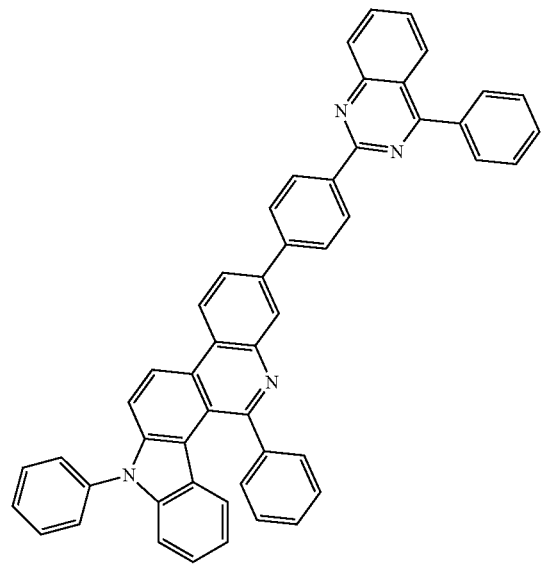
11-30
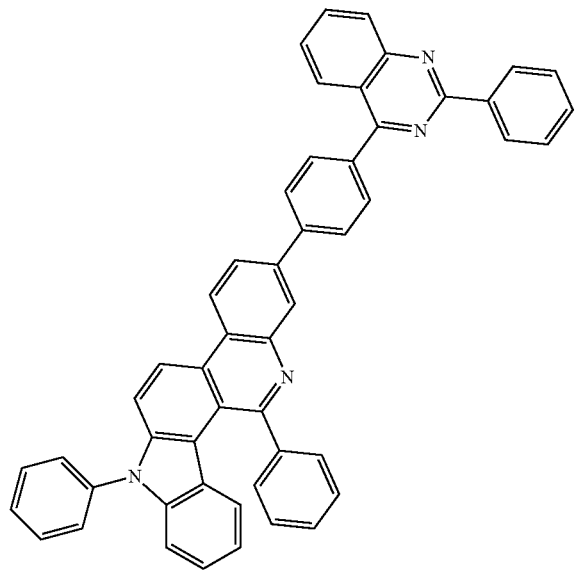
11-31
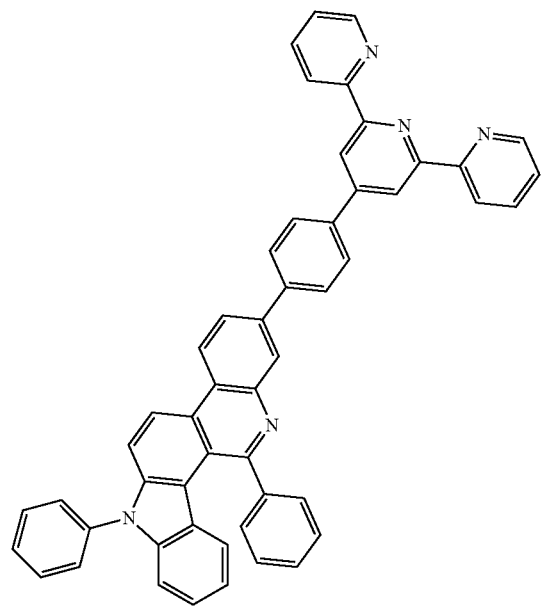
11-32
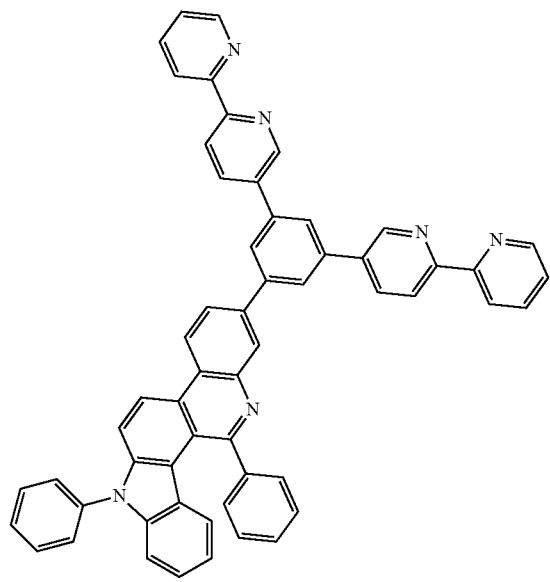

-continued
11-33
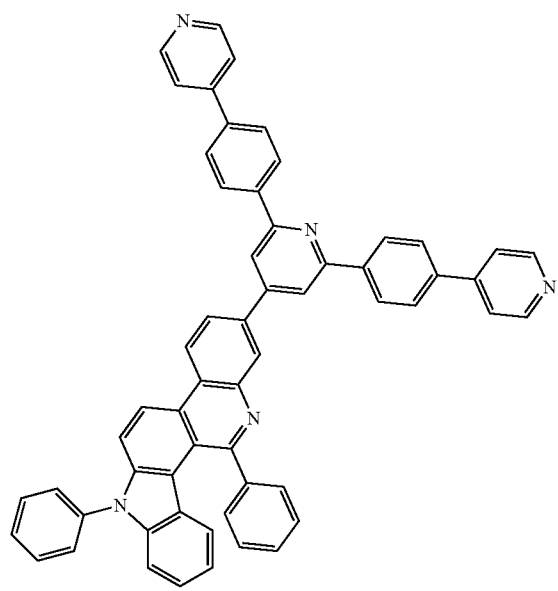
11-34
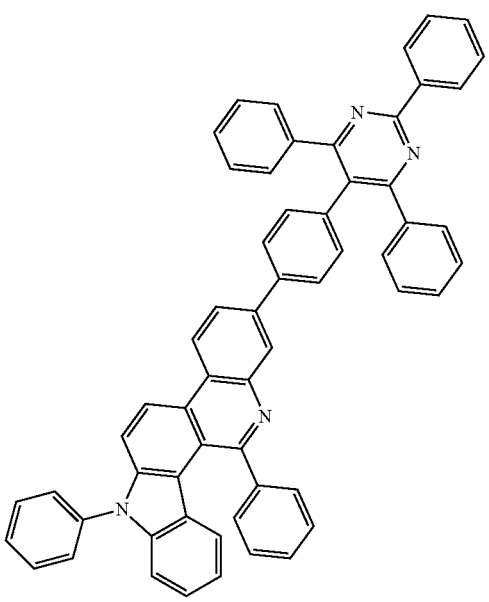
11-35
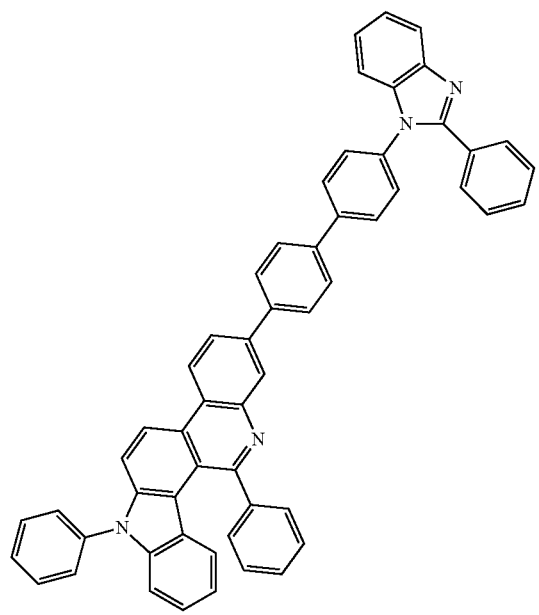
11-36
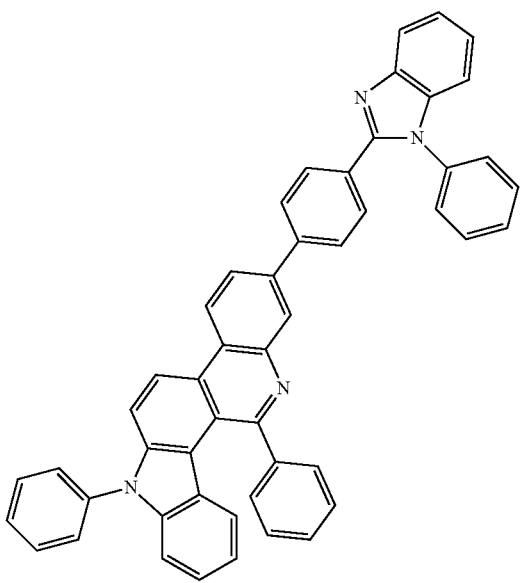

-continued
11-37
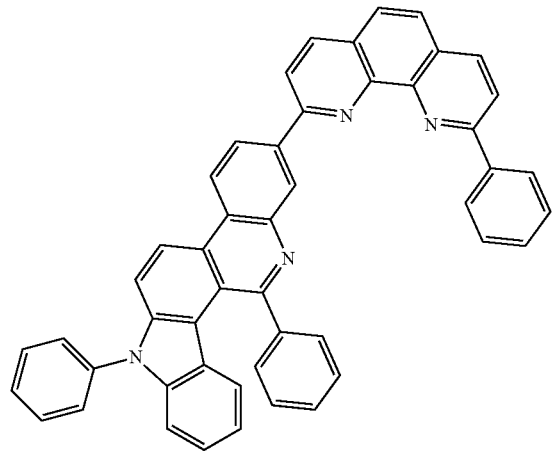
11-38
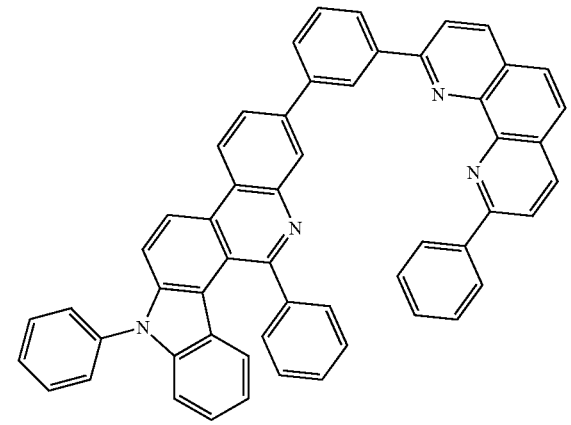
11-39
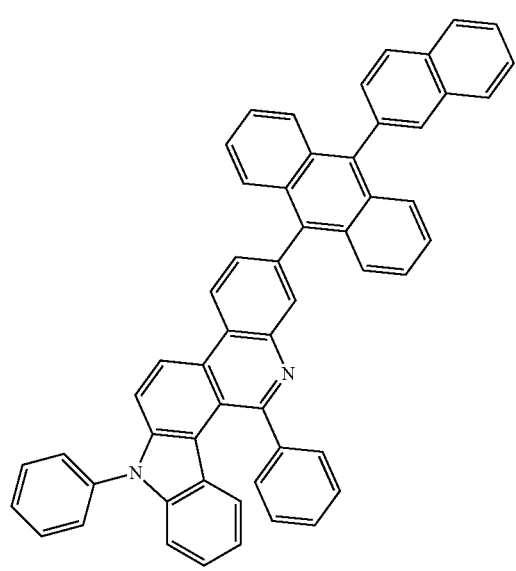
11-40
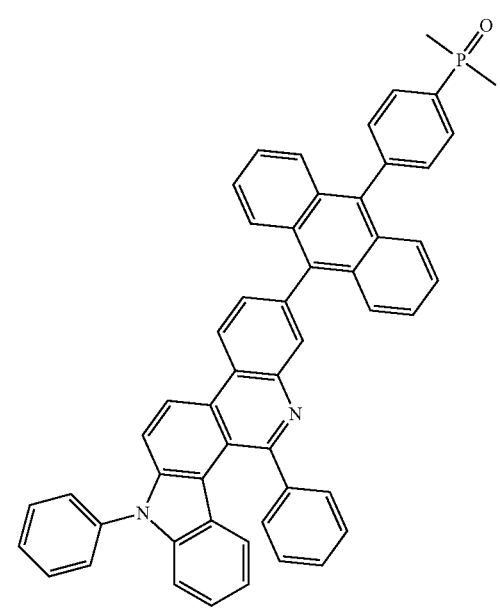
11-41
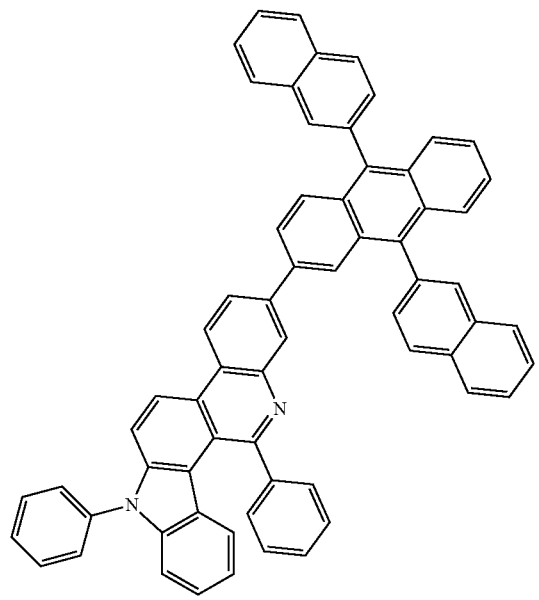
11-42
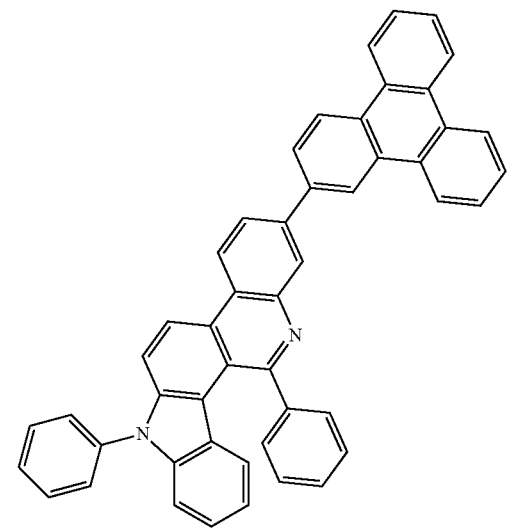

-continued
11-43
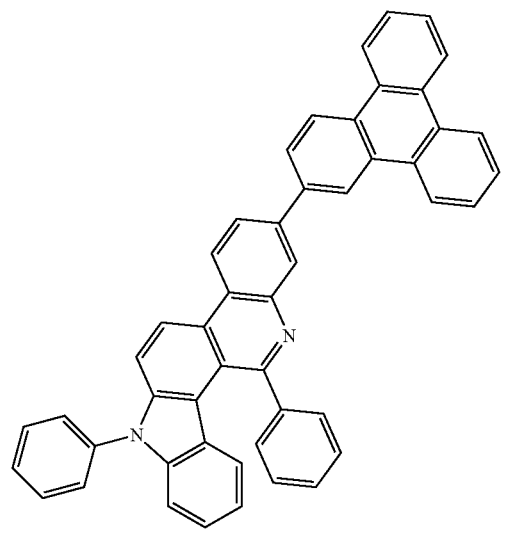
11-44
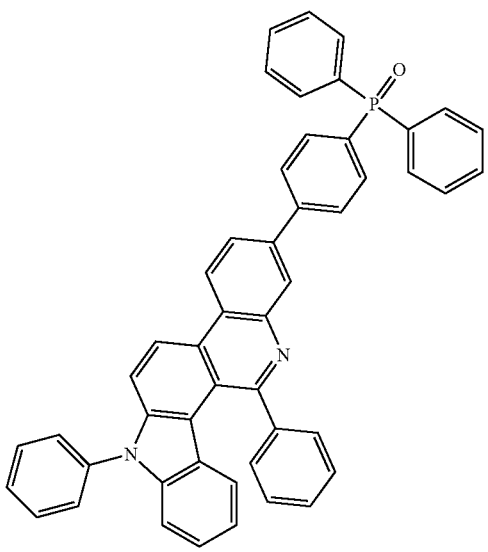
11-45
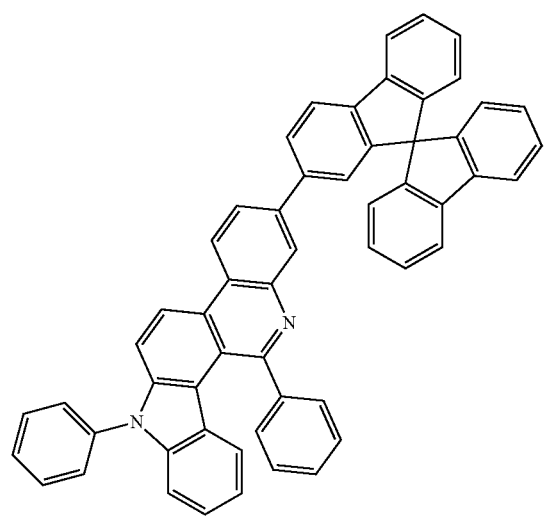
11-46
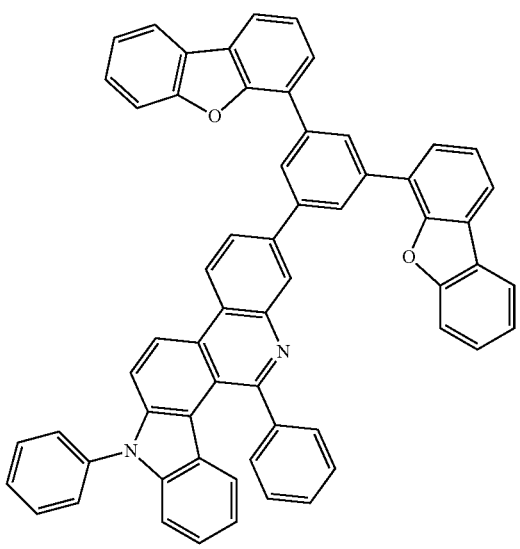

-continued
12
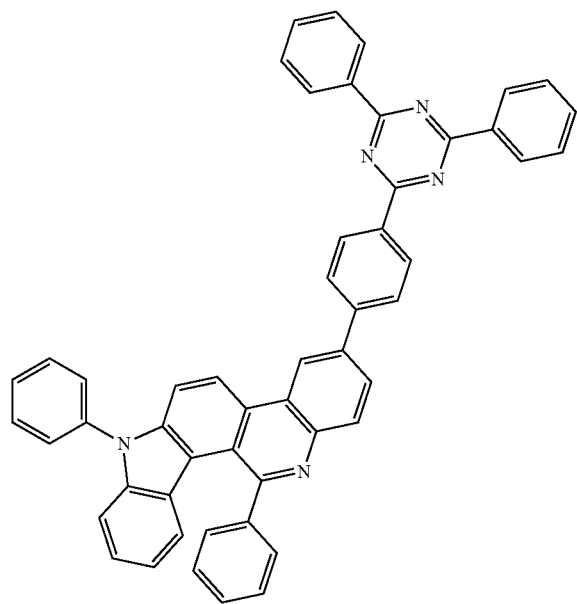
12-1
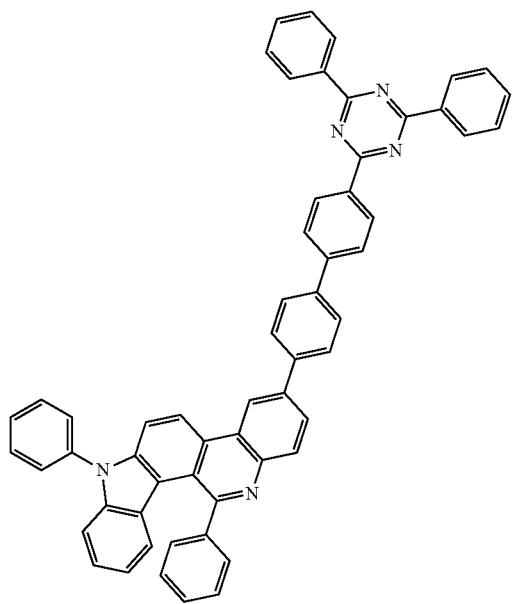
12-2
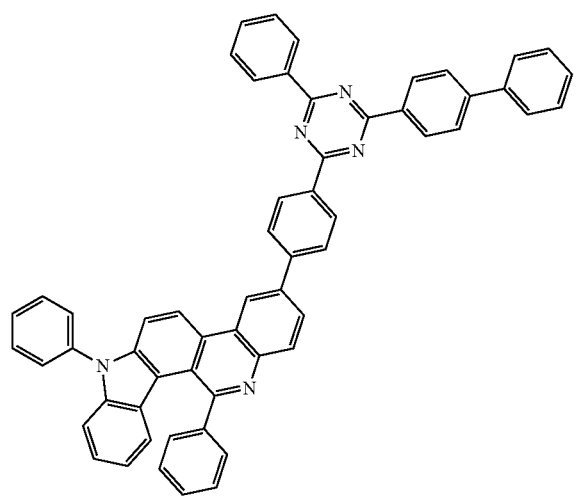
12-3
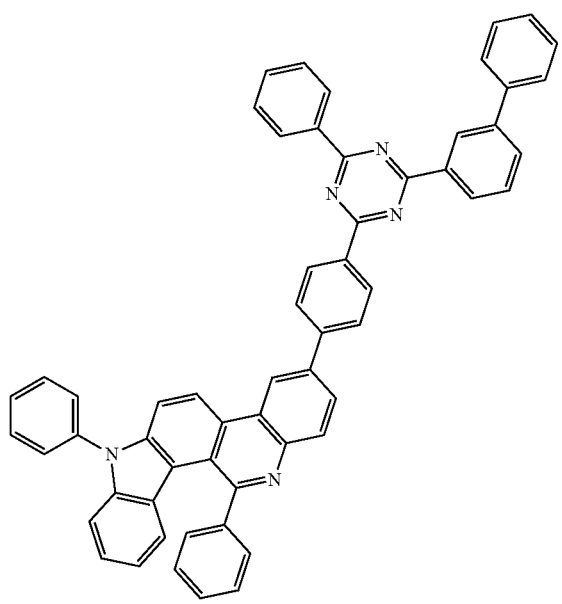

12-4
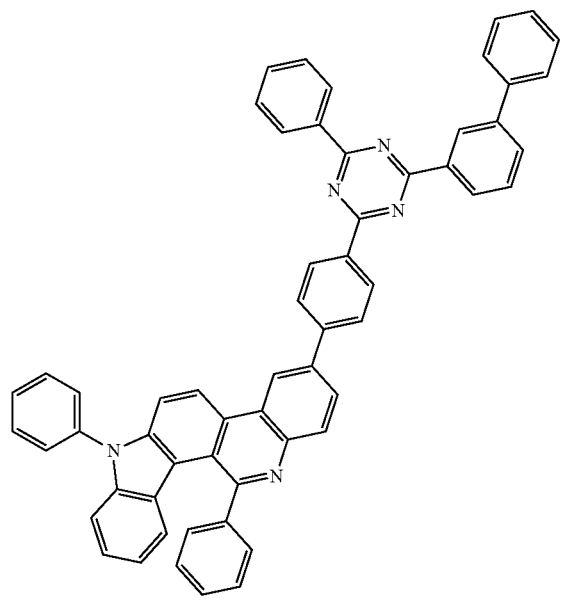
12-5
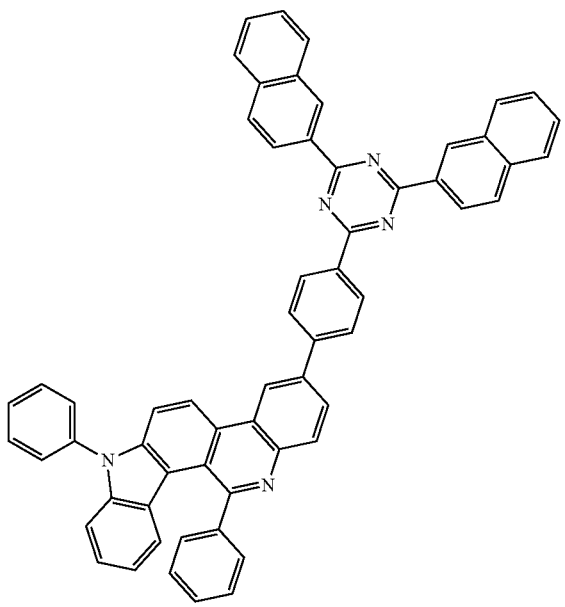
12-6
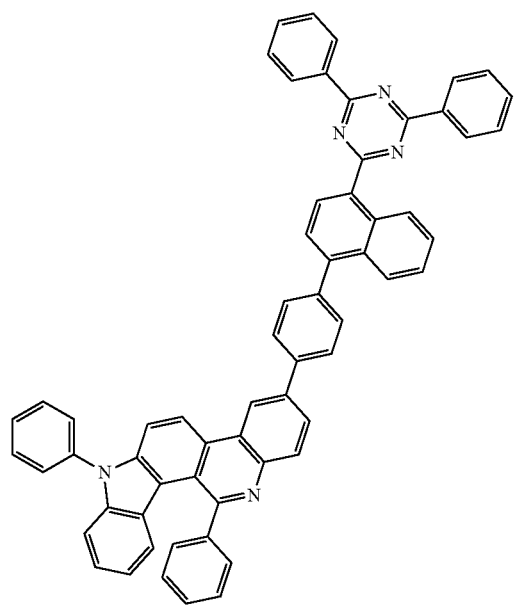
12-7
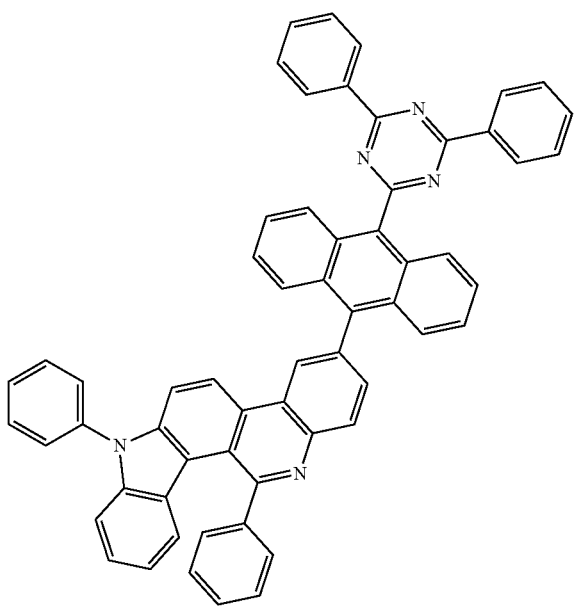

12-8
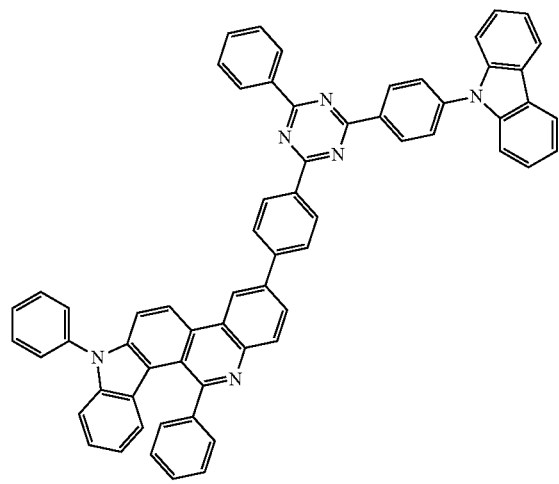
12-9
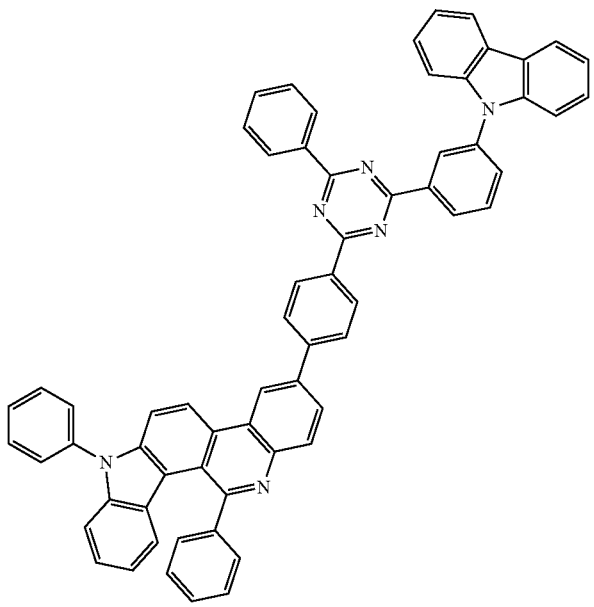
12-10
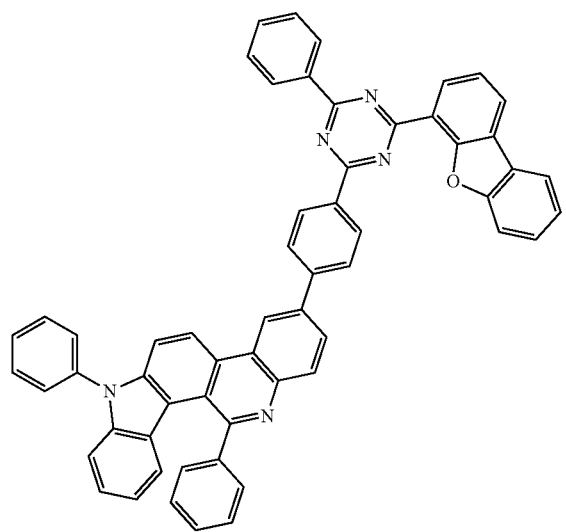
12-11
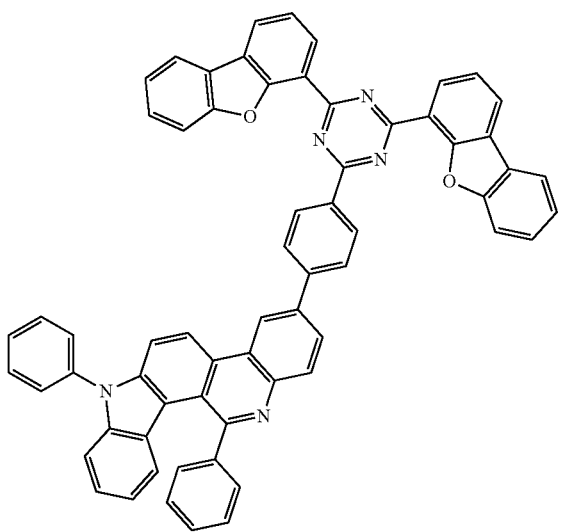

12-12
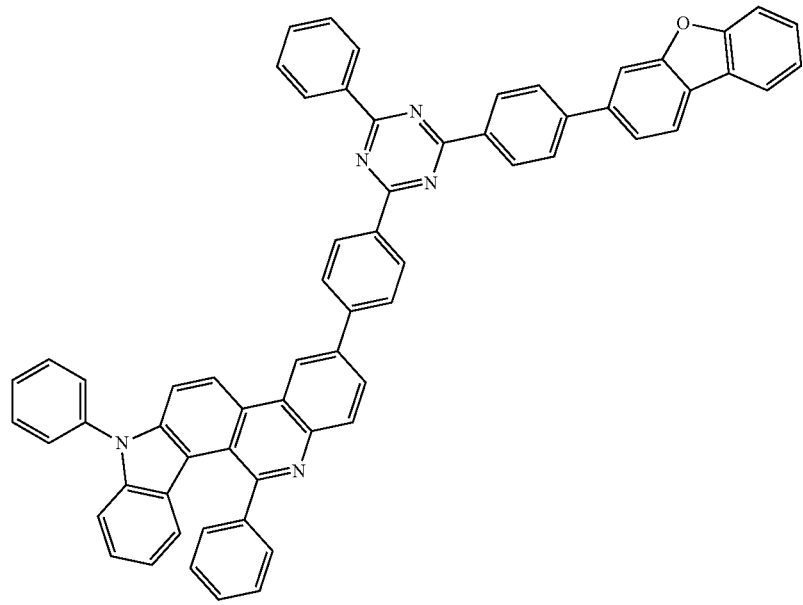
12-13
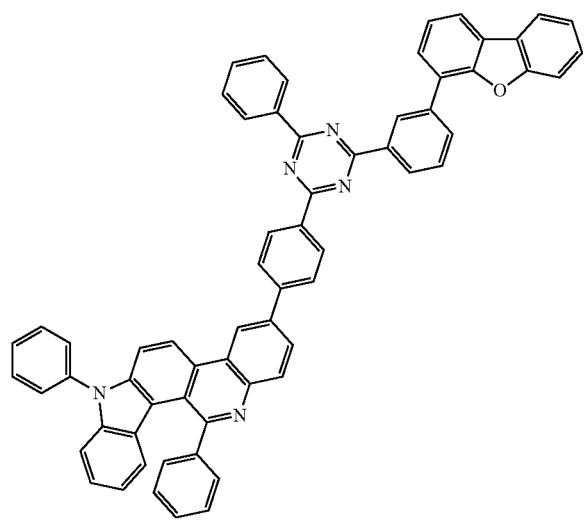
12-14
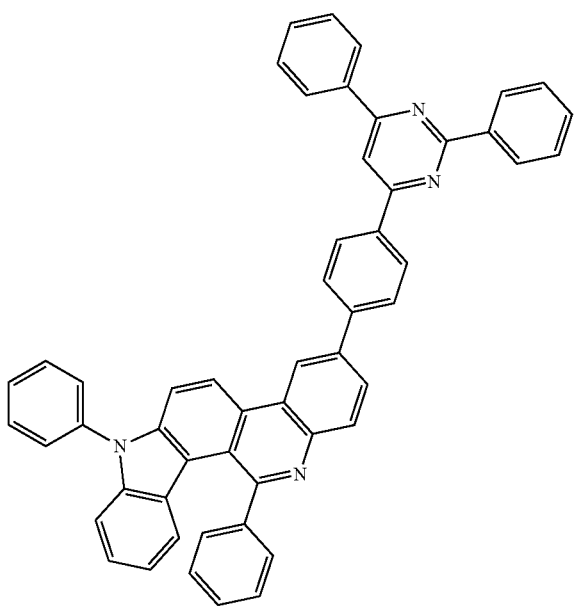

12-15
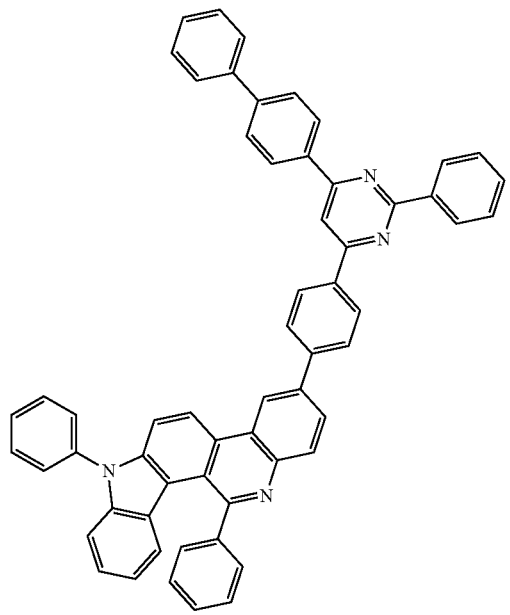
12-16
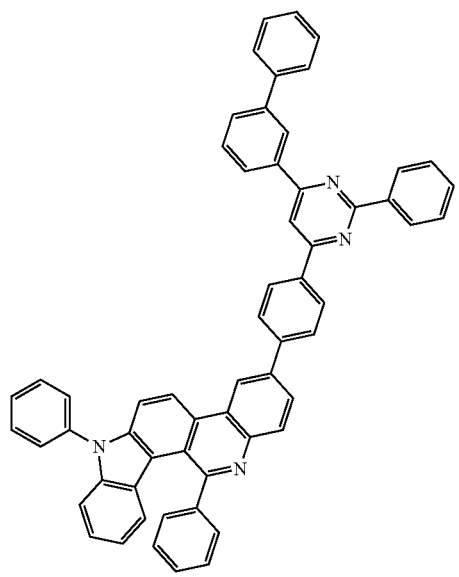
12-17
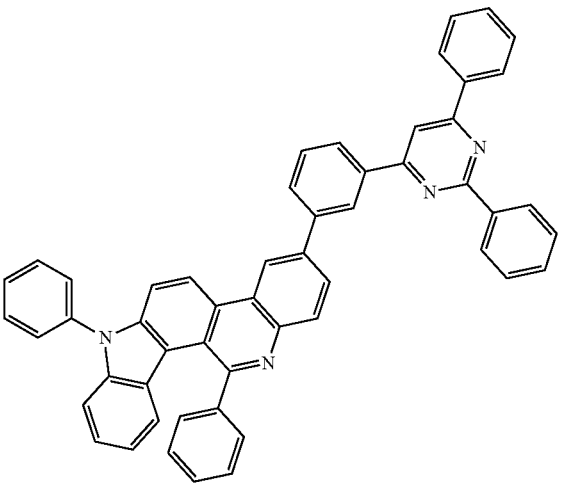

223
-continued
12-18
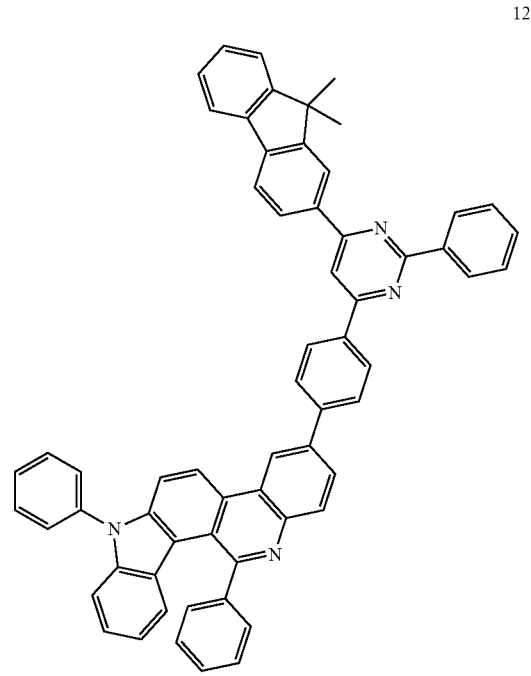
12-19
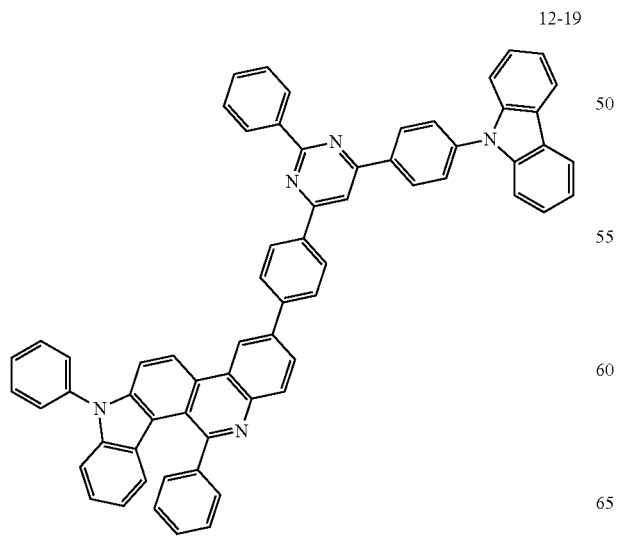
224
-continued
12-20
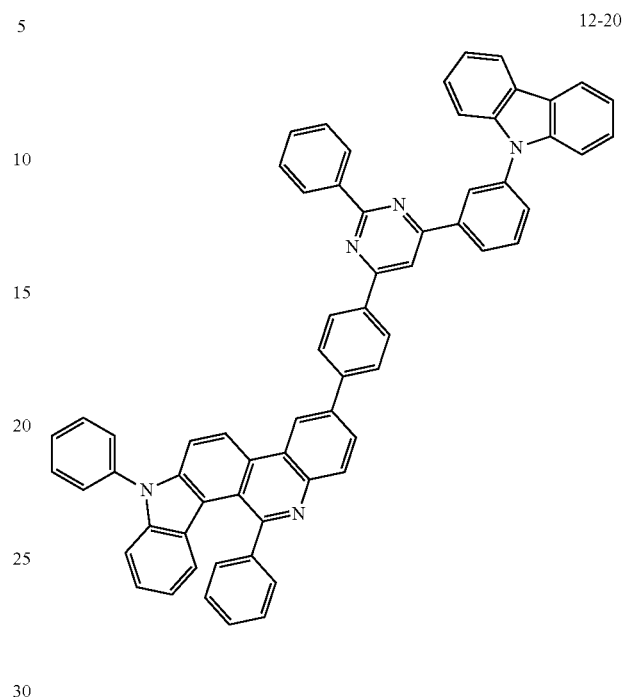
12-21
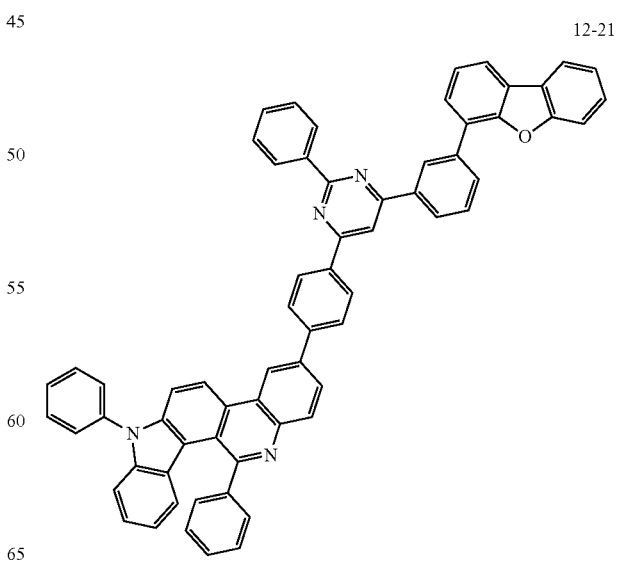

12-22
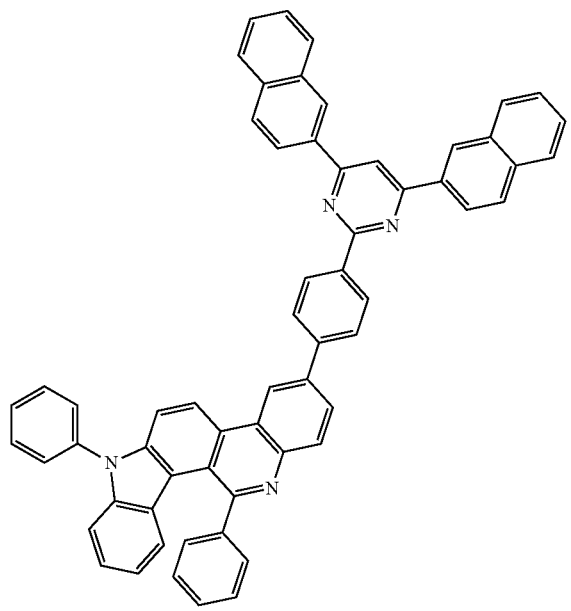
12-23
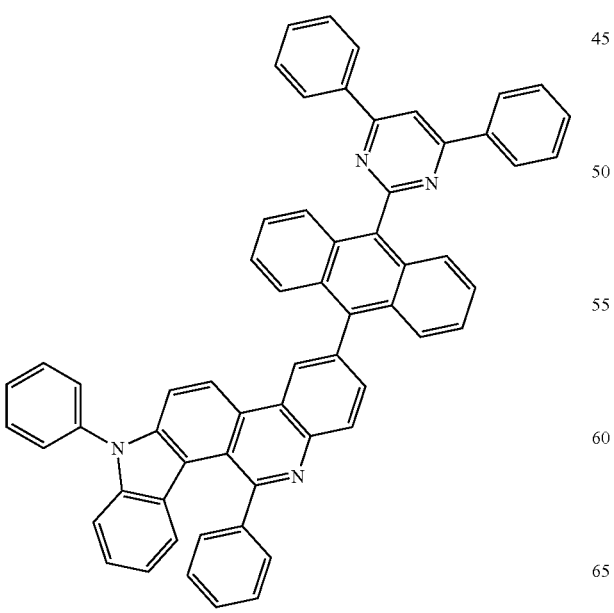
12-24
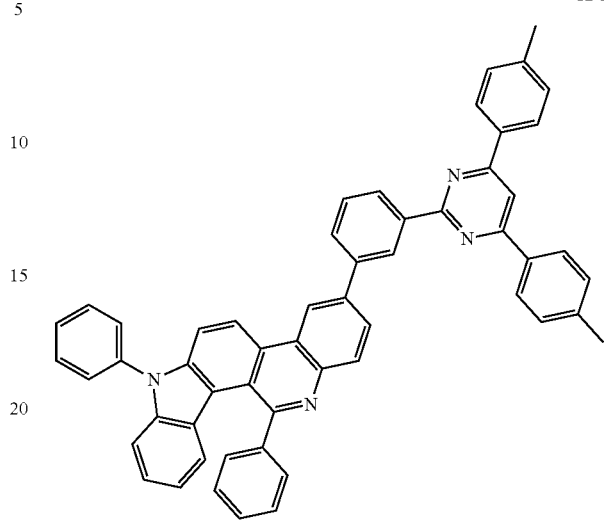
12-25
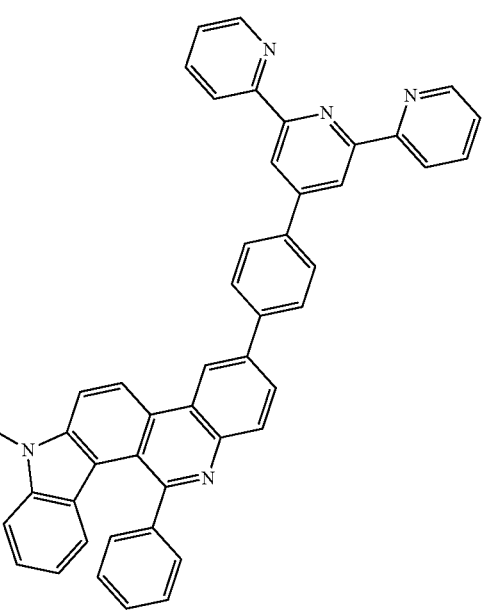

12-26
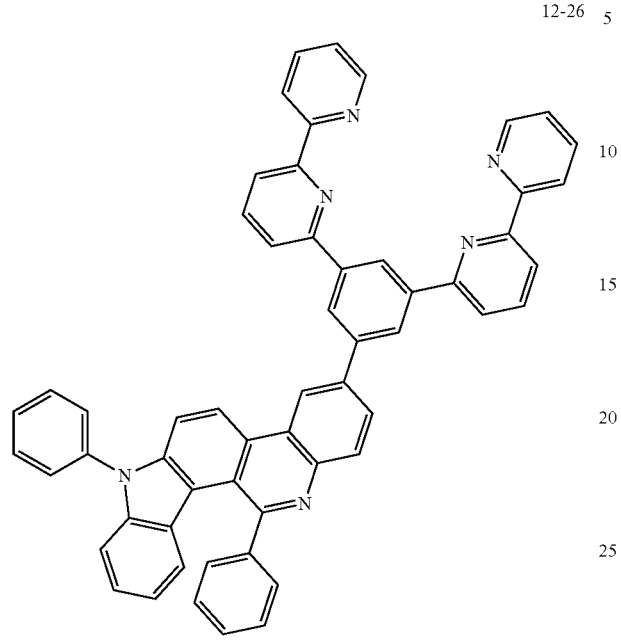
12-28
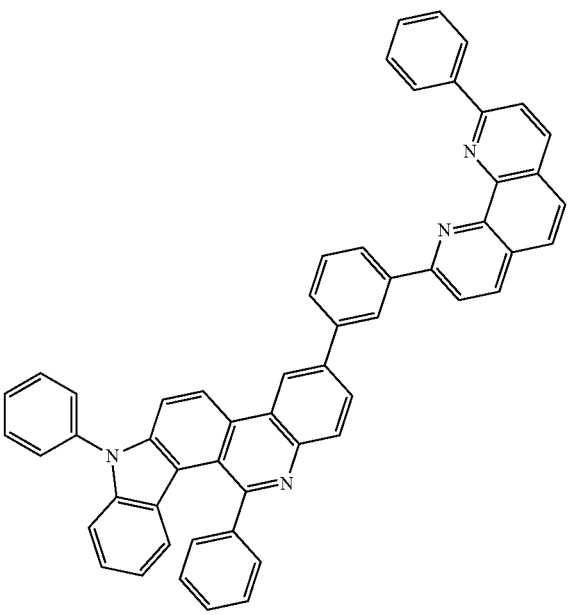
12-27
12-29
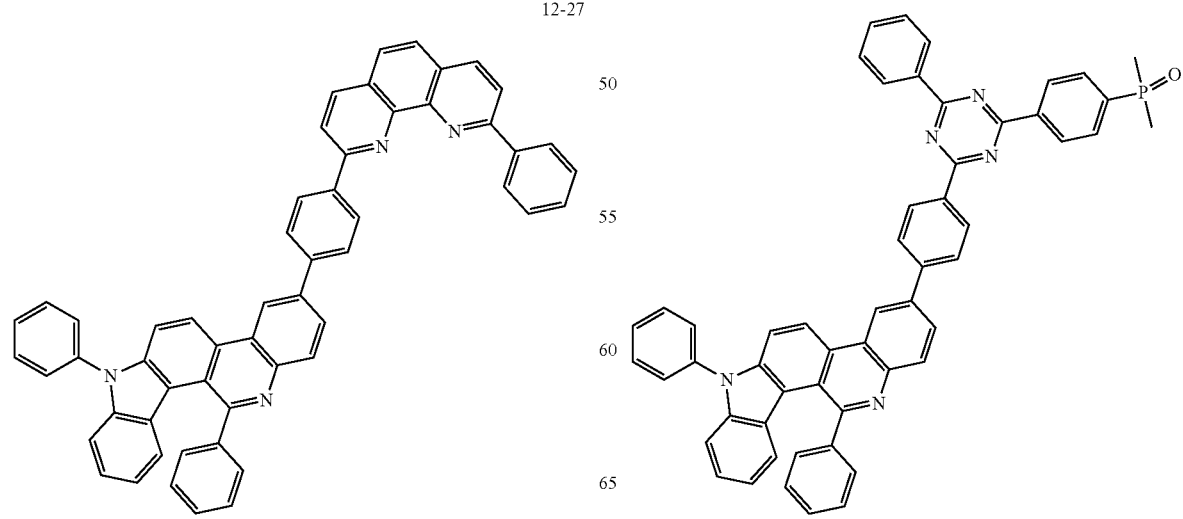

-continued
12-30
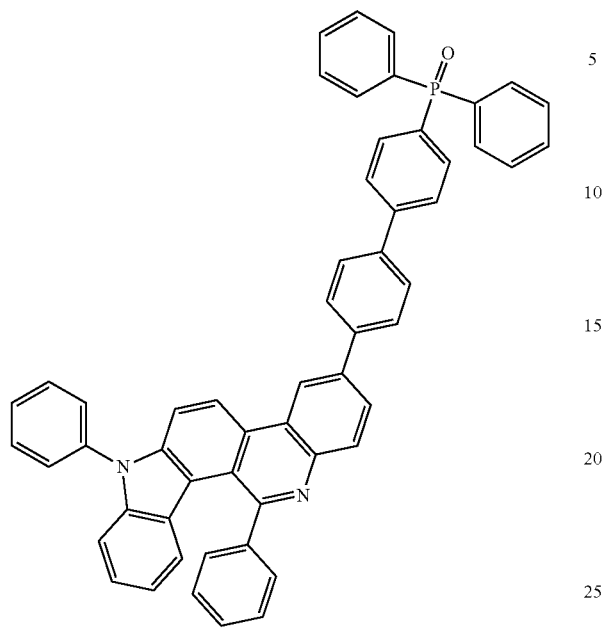
12-32
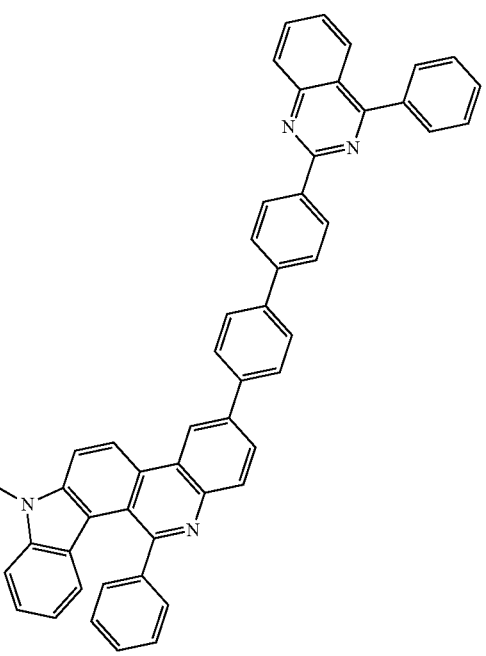
12-31
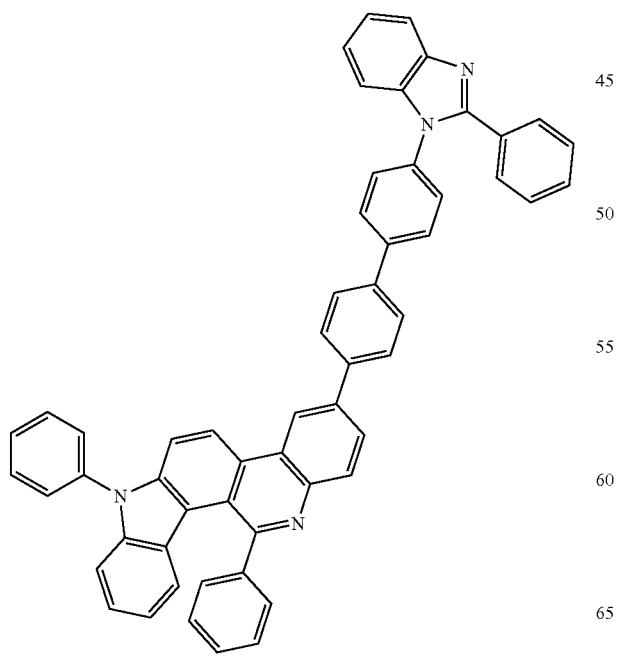
12-33
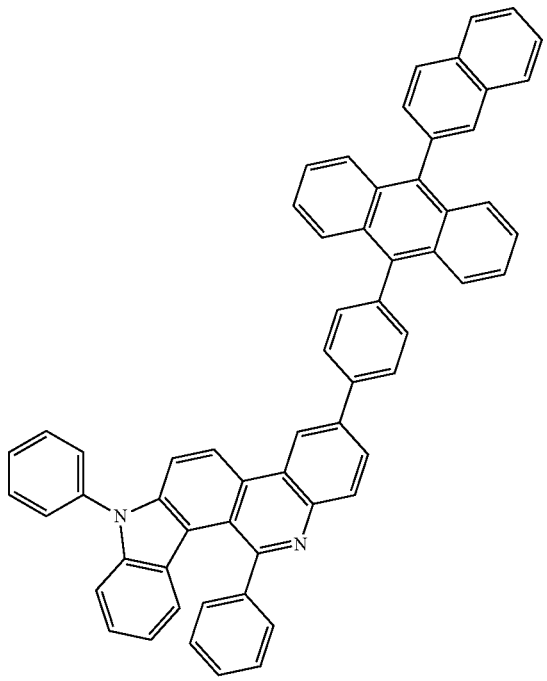

-continued
13
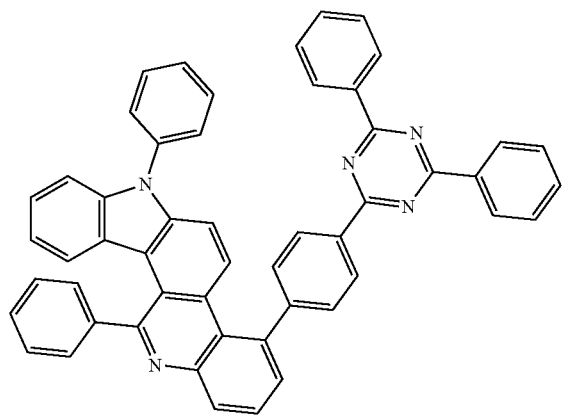
13-1
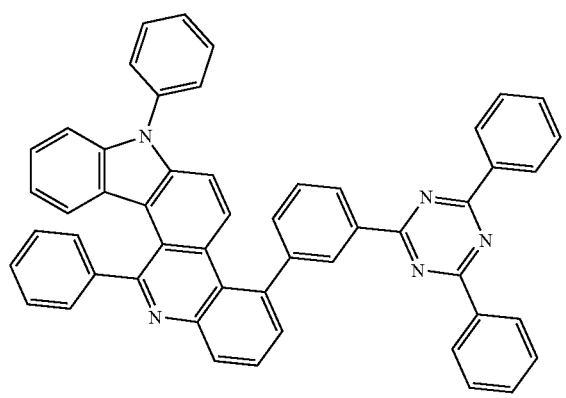
13-2
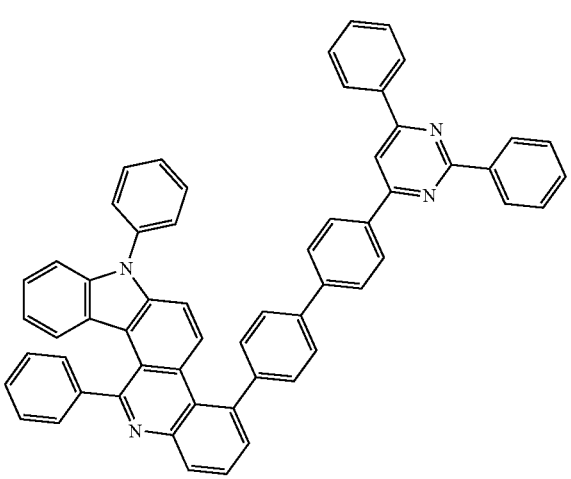
-continued
13-3
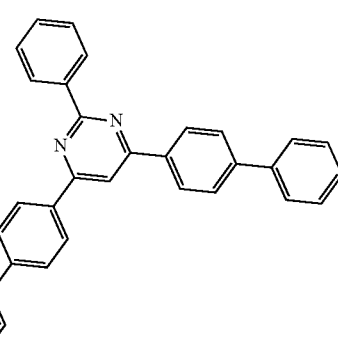
13-4
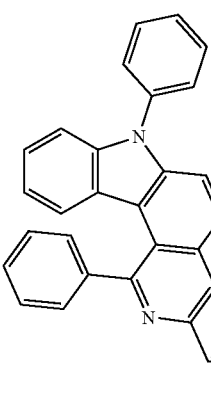
13-5
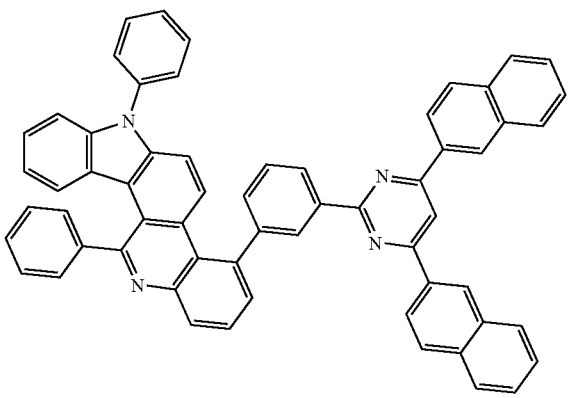
13-6
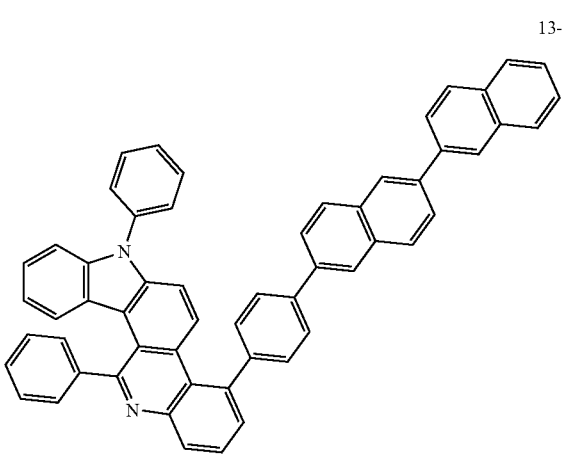

13-7
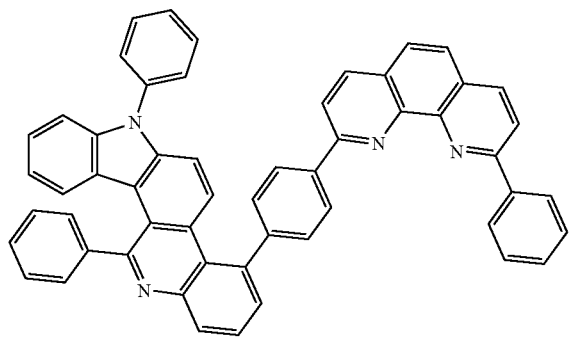
14
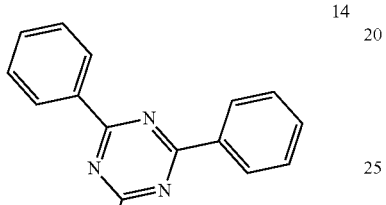
14-1
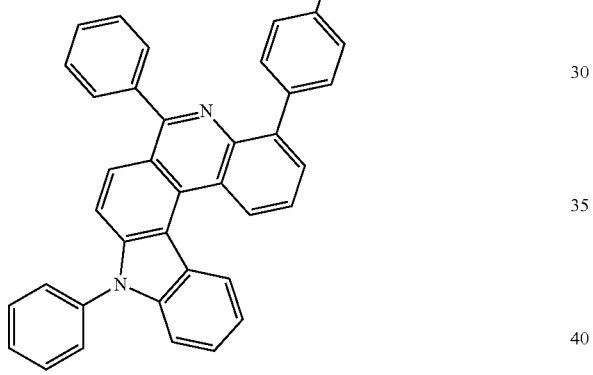
14-2
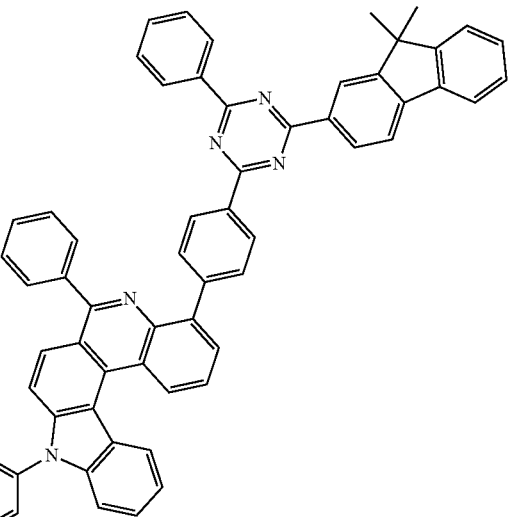
14-3
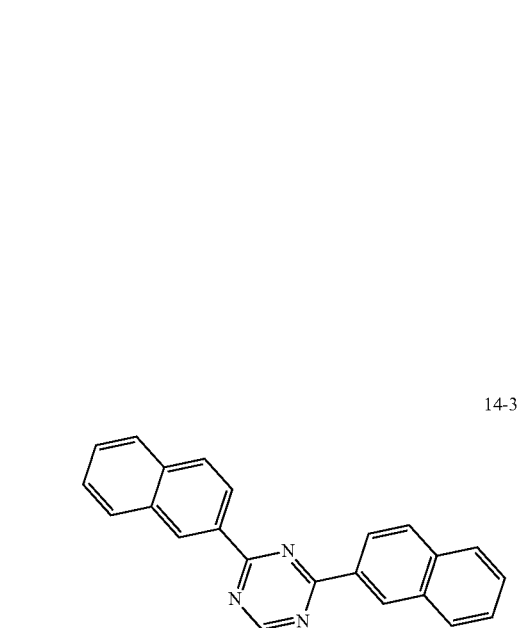

14-4
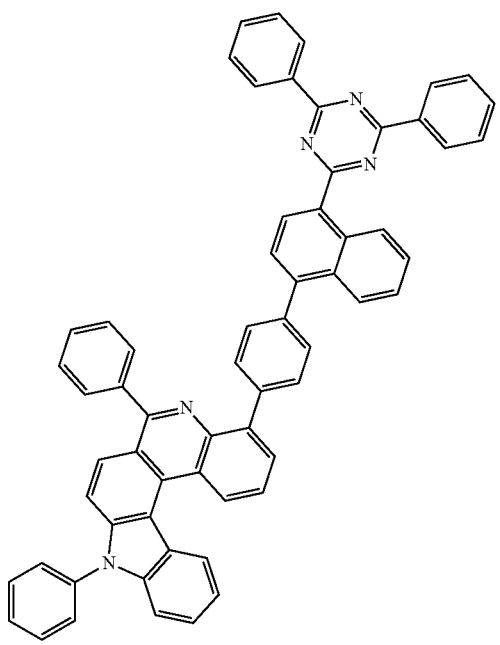
14-5
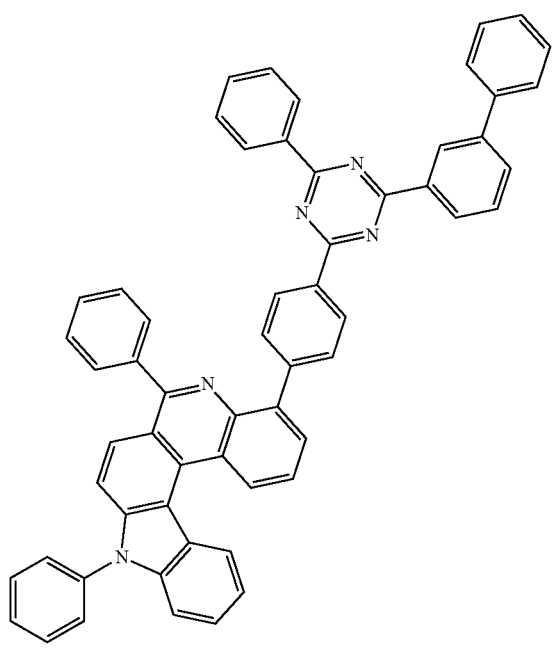
14-6
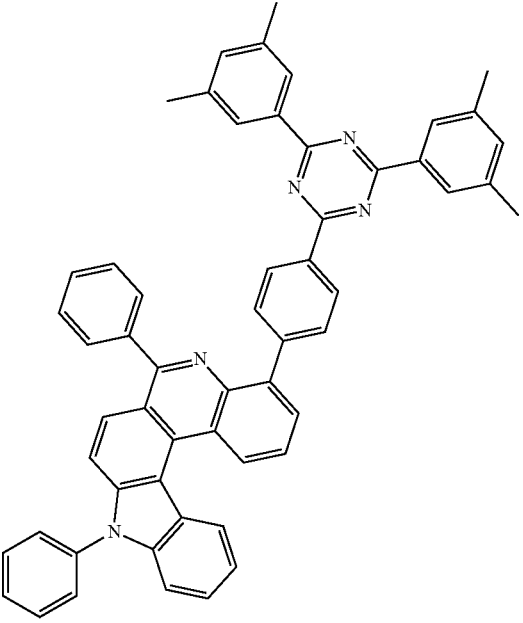
14-7
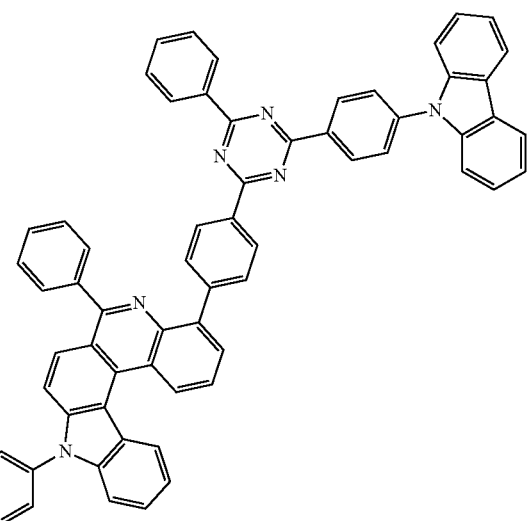

14-8
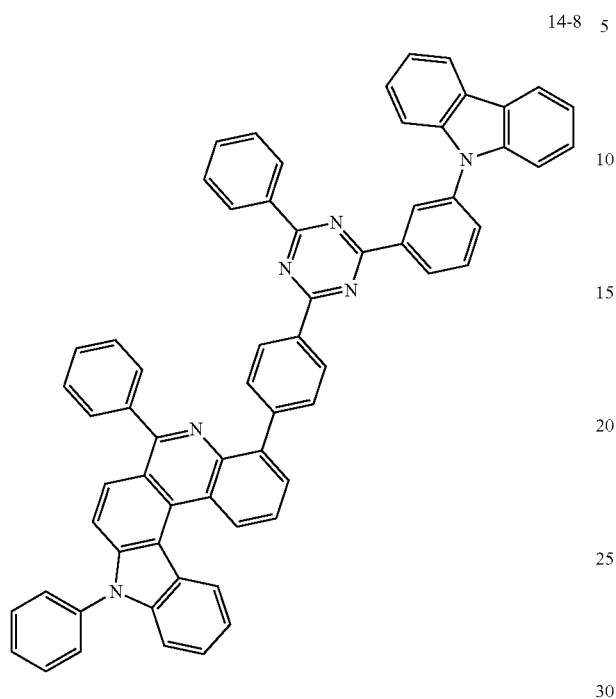
14-10
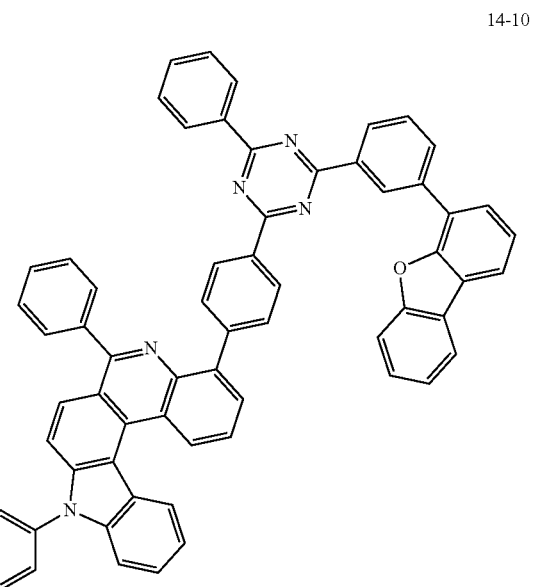
14-9
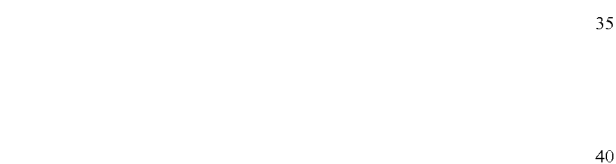
14-11
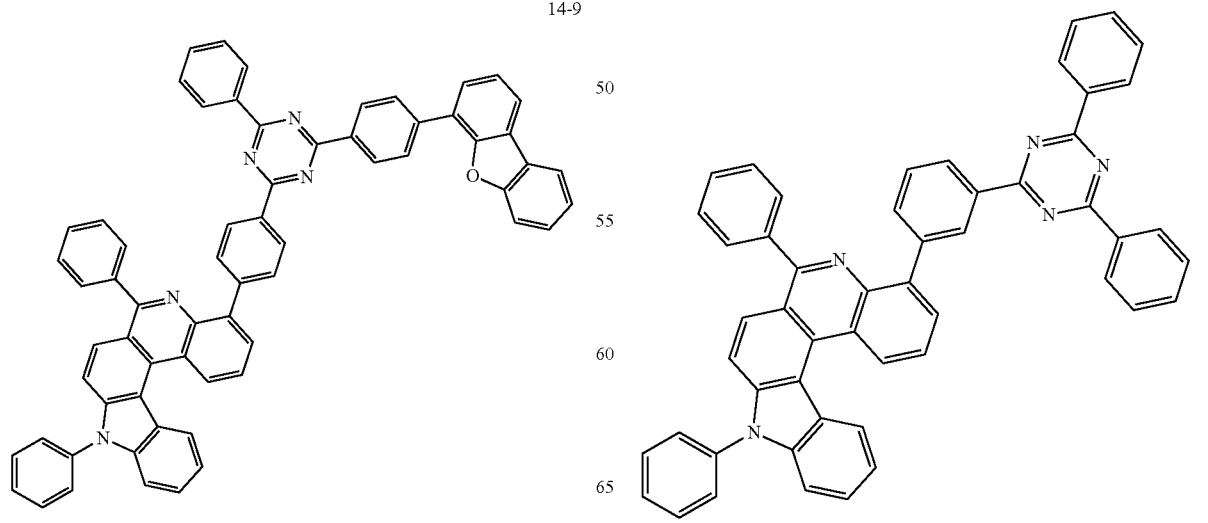

14-12
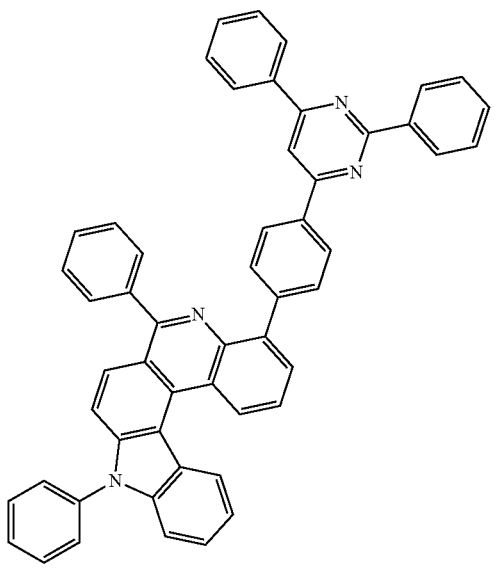
14-13
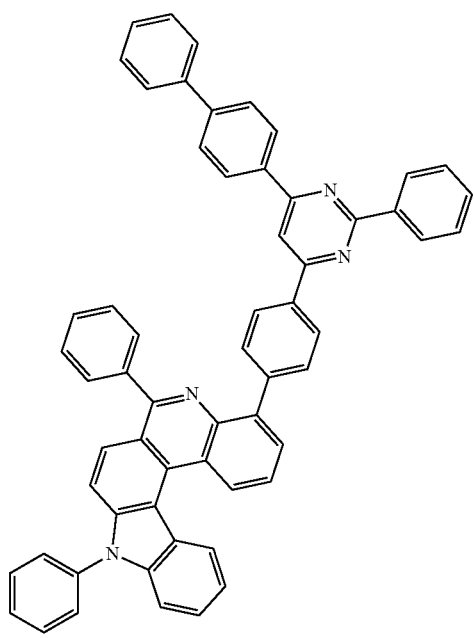
14-14
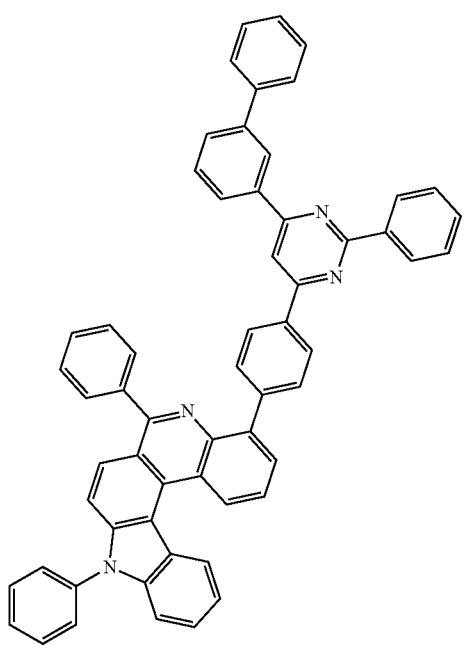
14-15
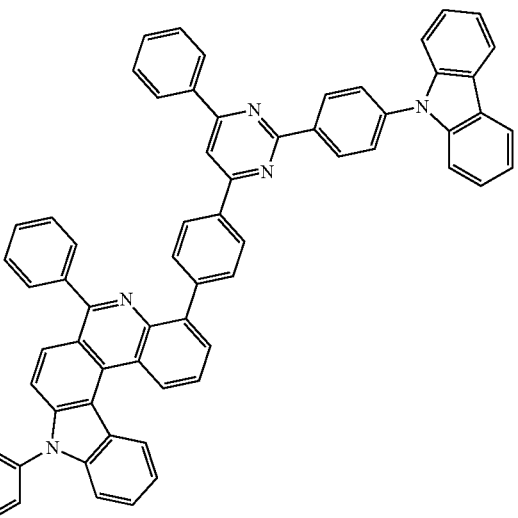

14-16
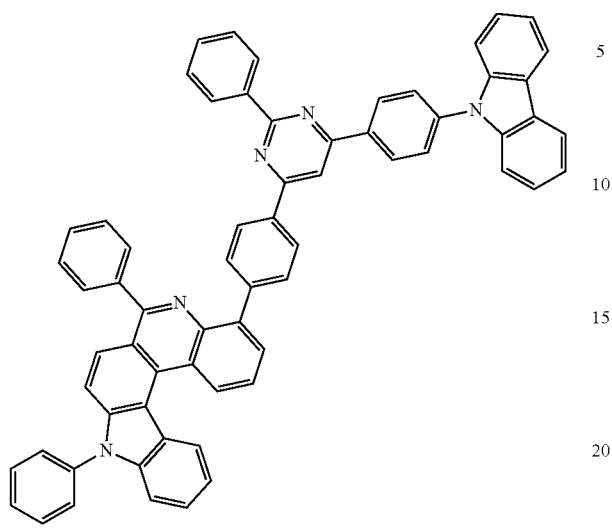
14-17
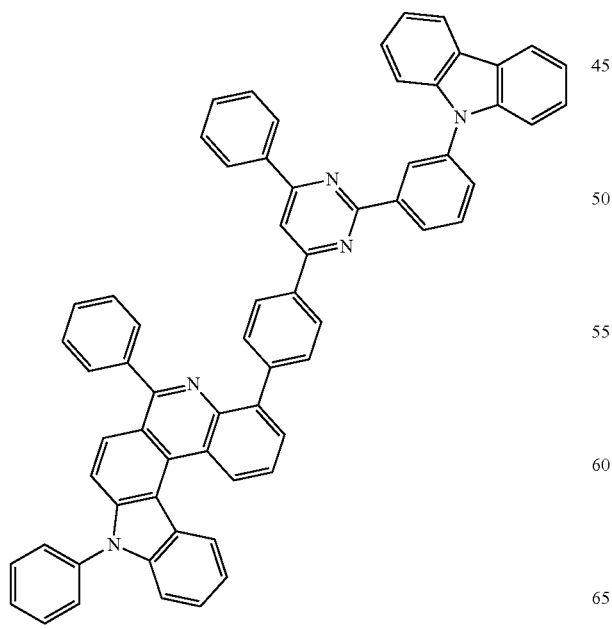
14-18
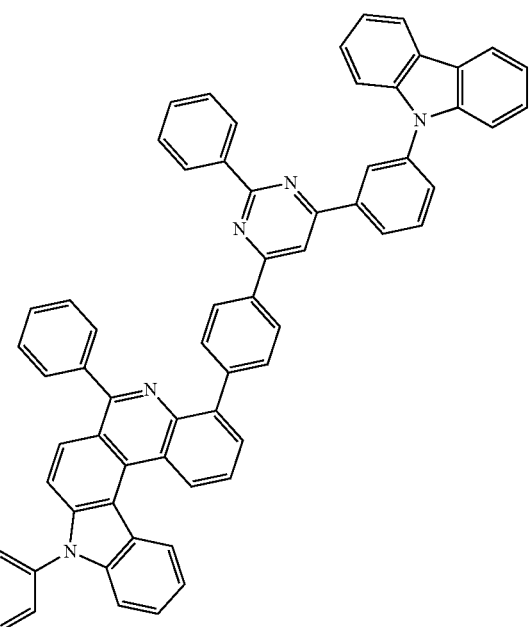
14-19
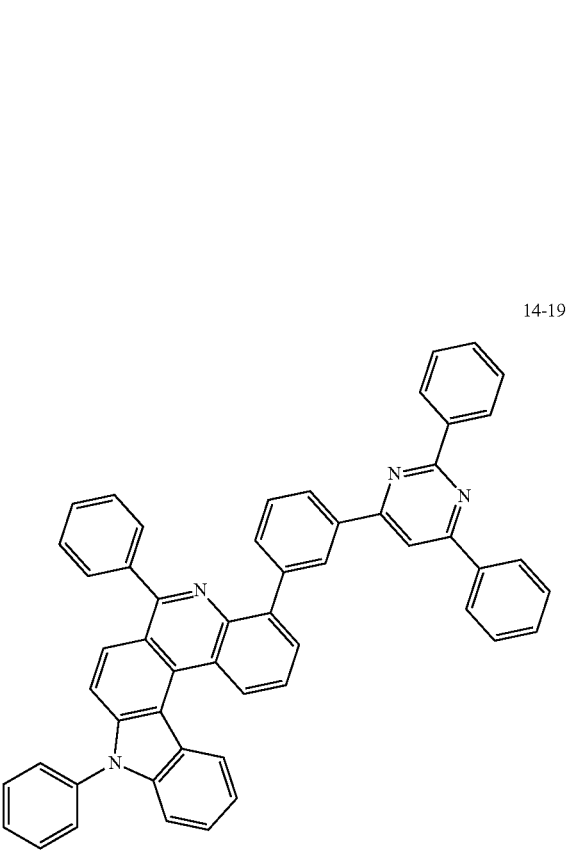

14-20
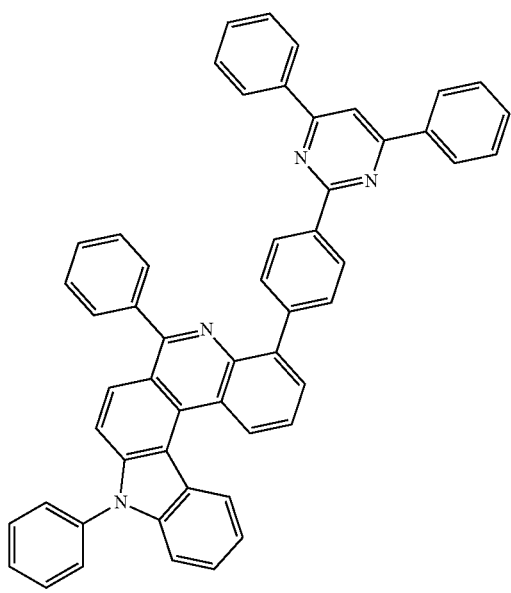
14-21
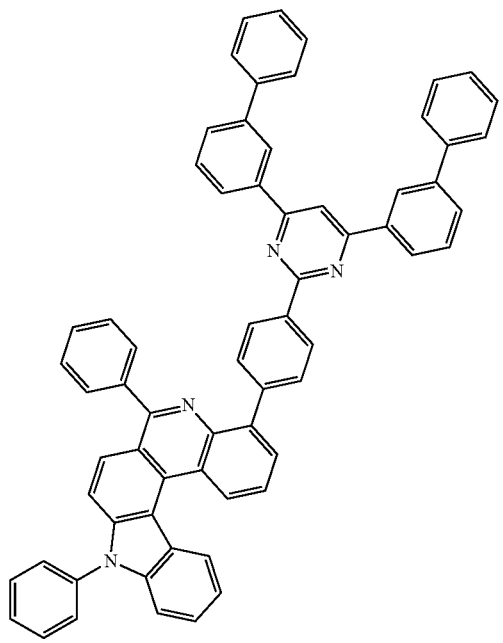
14-22
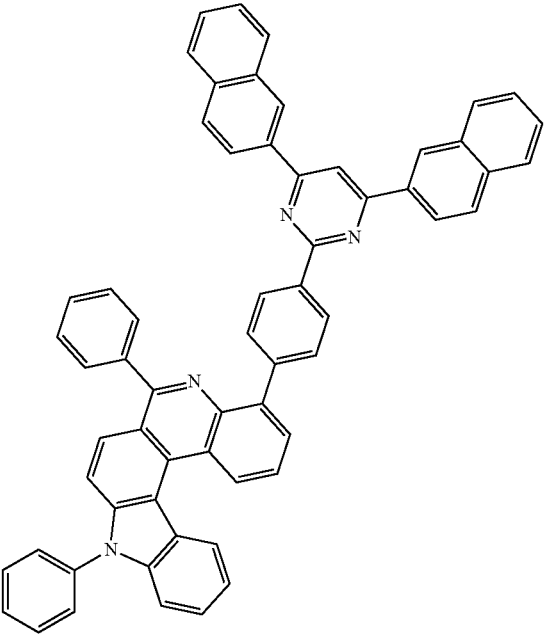
14-23
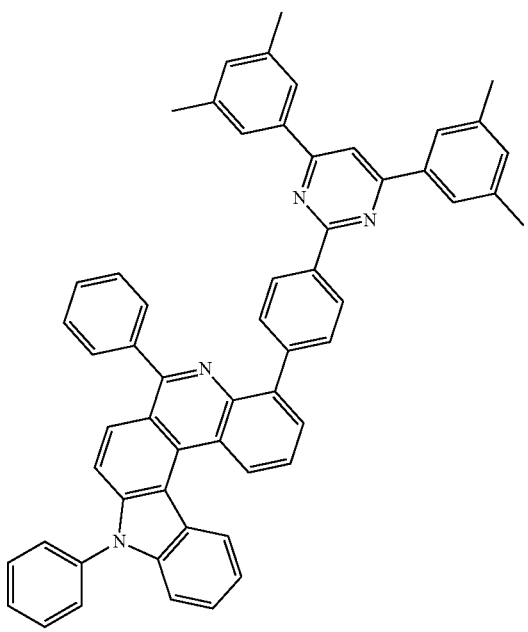

14-24
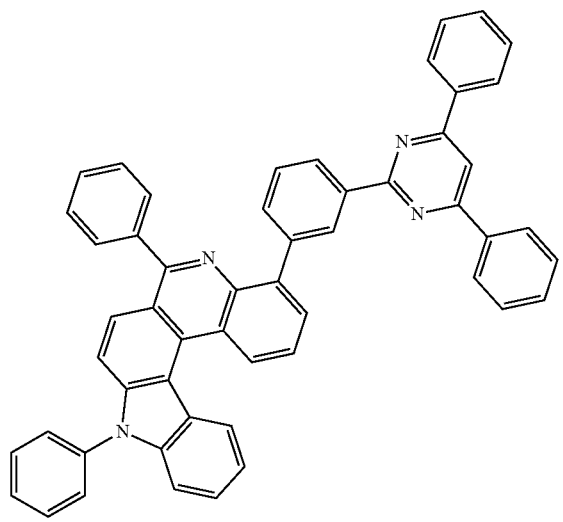
14-25
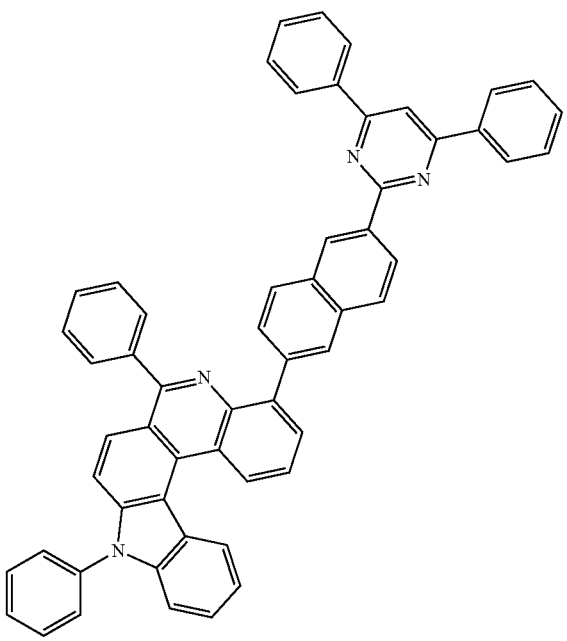
14-26
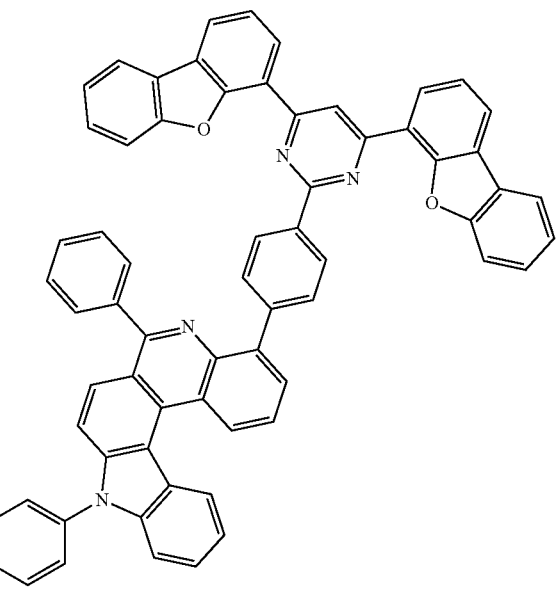
14-27
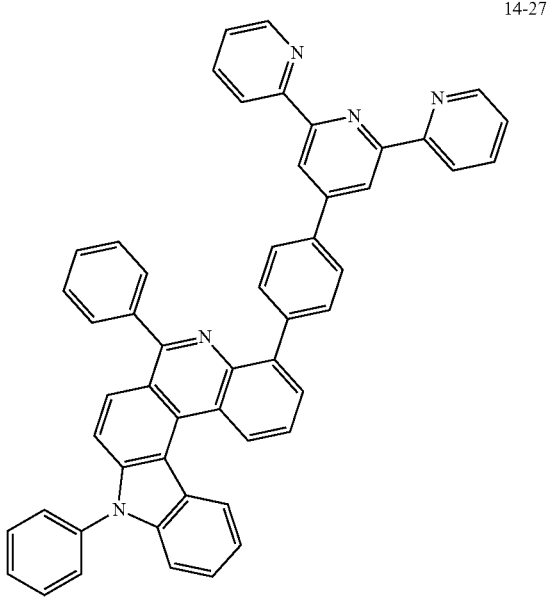

14-28
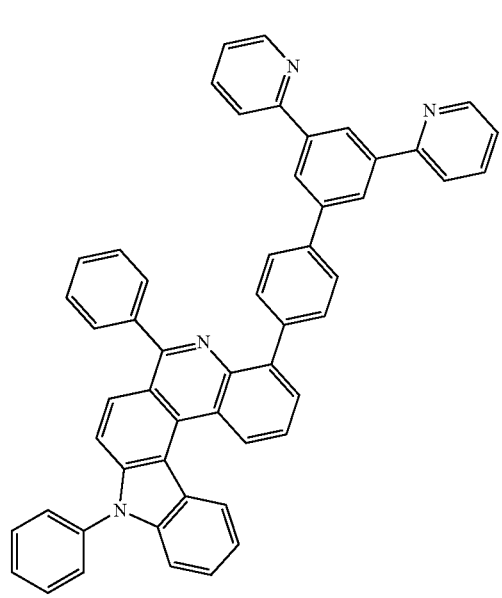
14-29
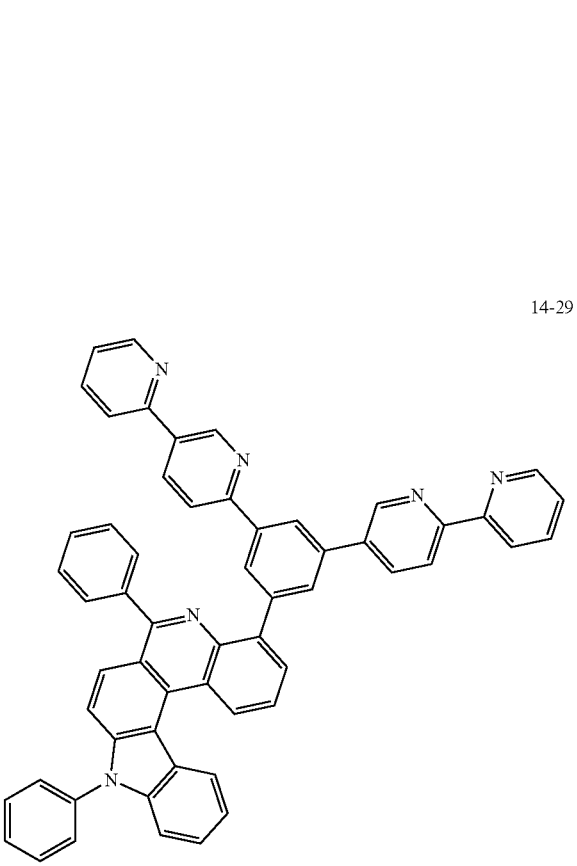
14-30
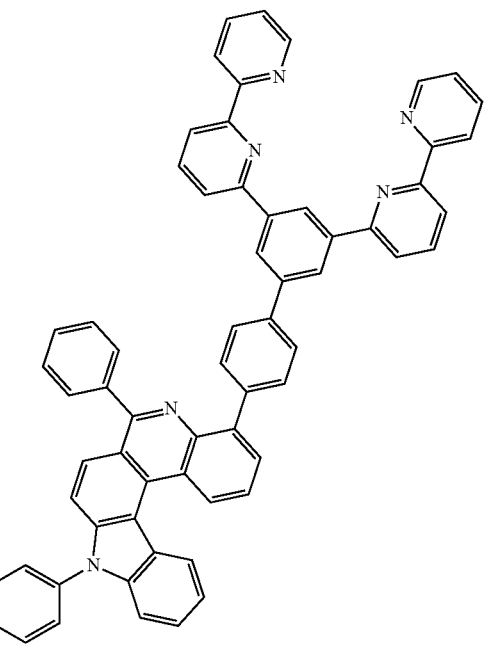
14-31
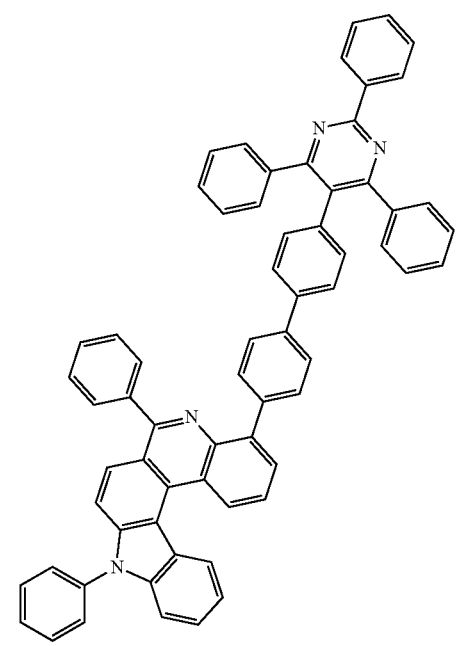

14-32
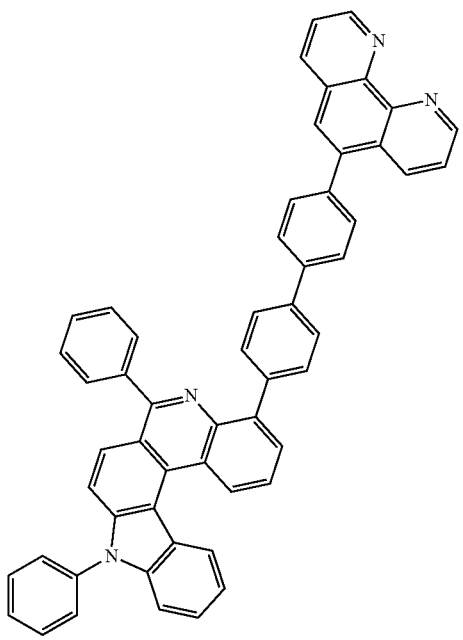
14-33
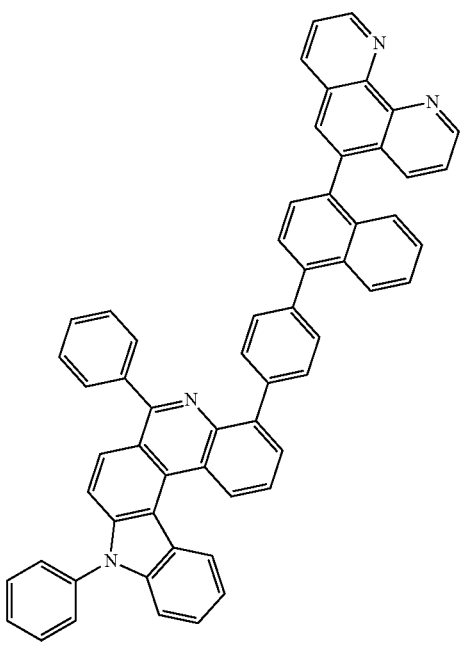
14-34
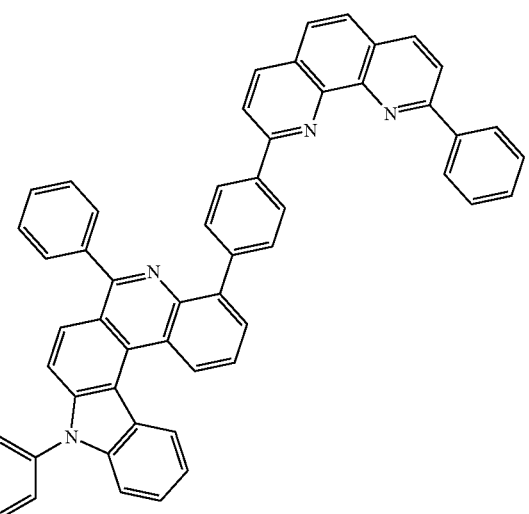
14-35
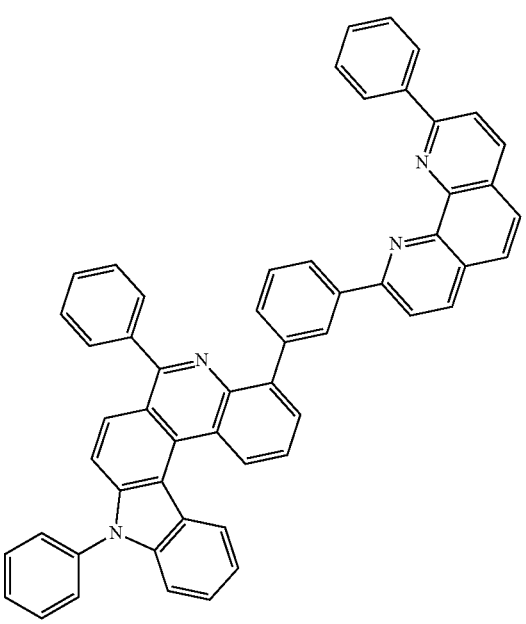

251
-continued
14-36
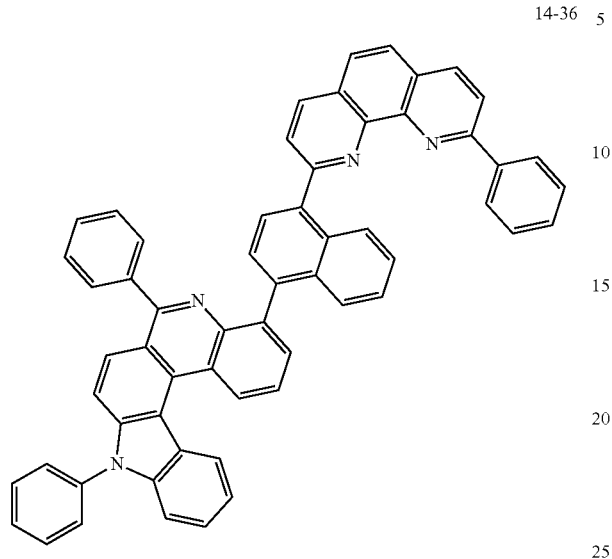
252
-continued
14-38
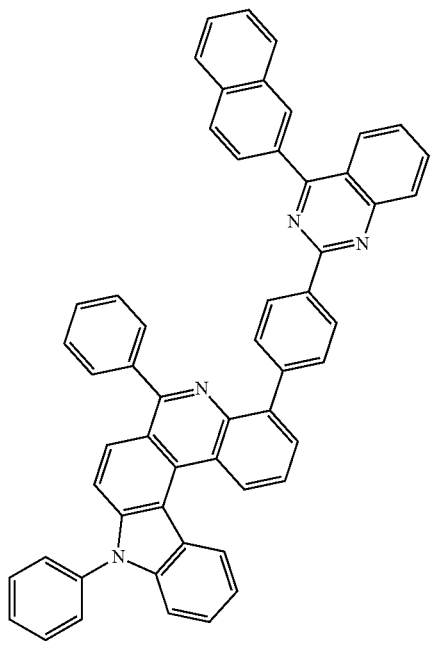
14-37
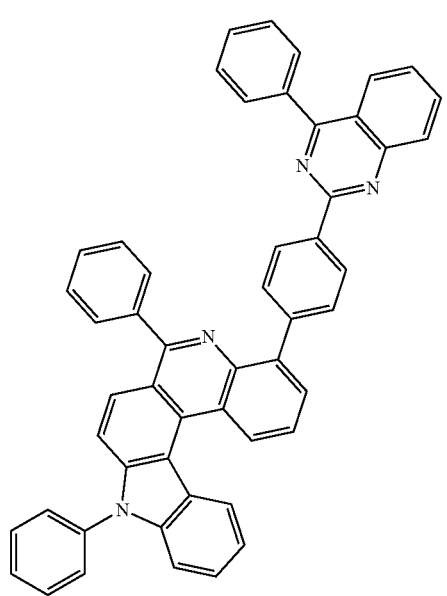
14-39
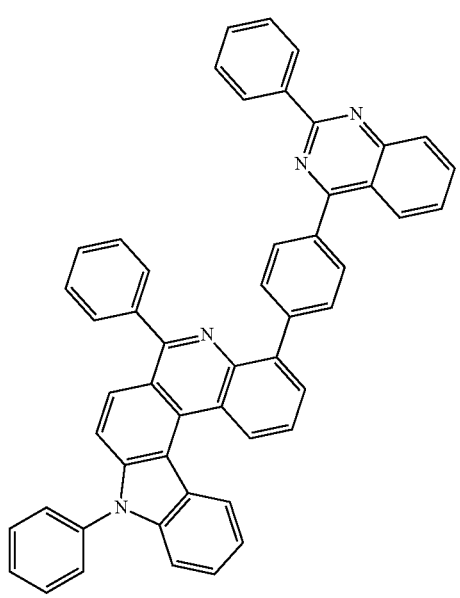

253
-continued
14-40
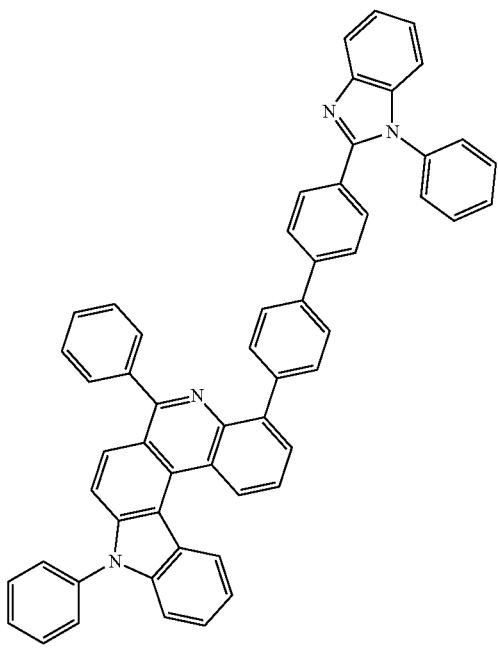
14-41
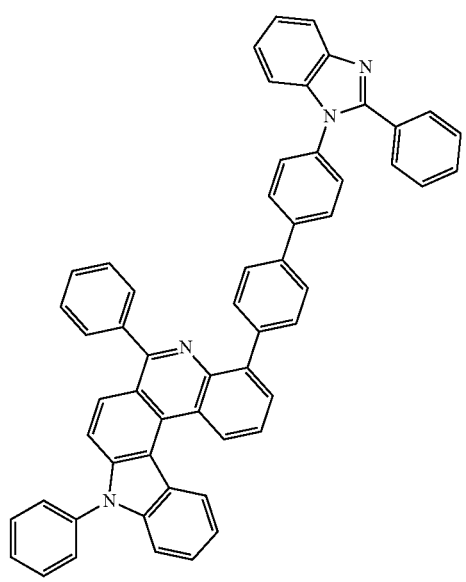
254
-continued
14-42
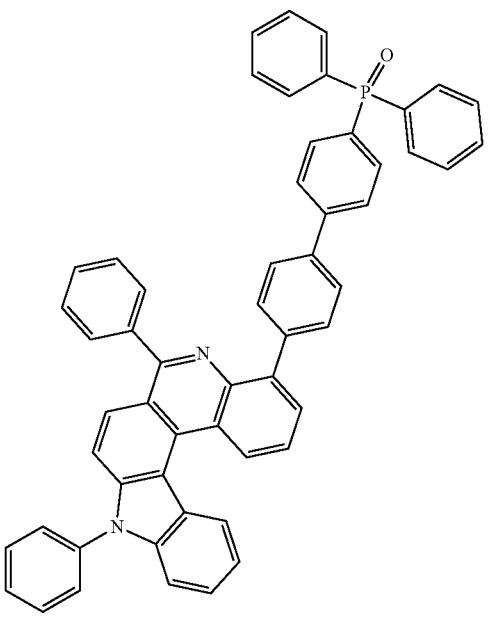
14-43
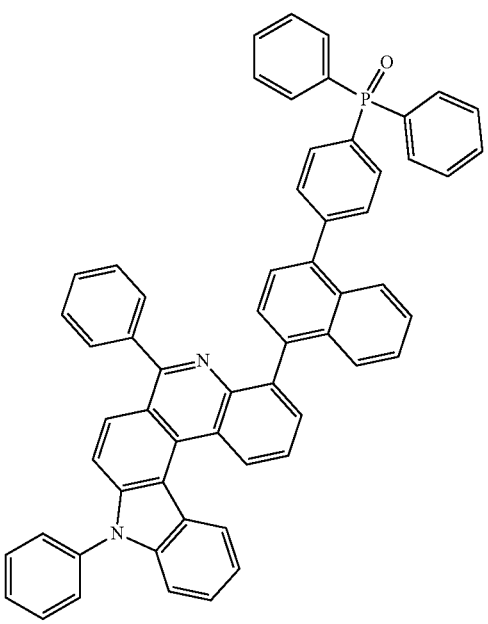

255
-continued
14-44
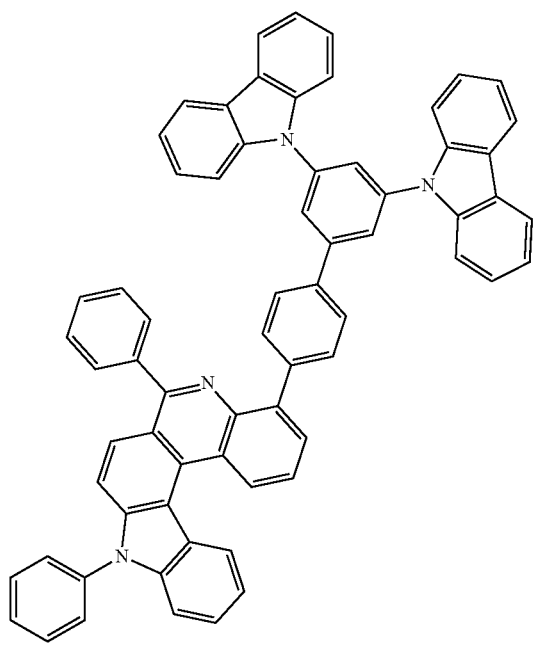
14-45
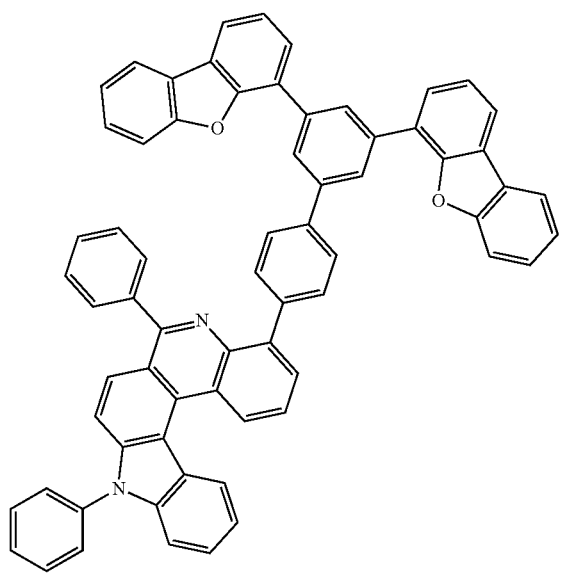
256
-continued
14-46
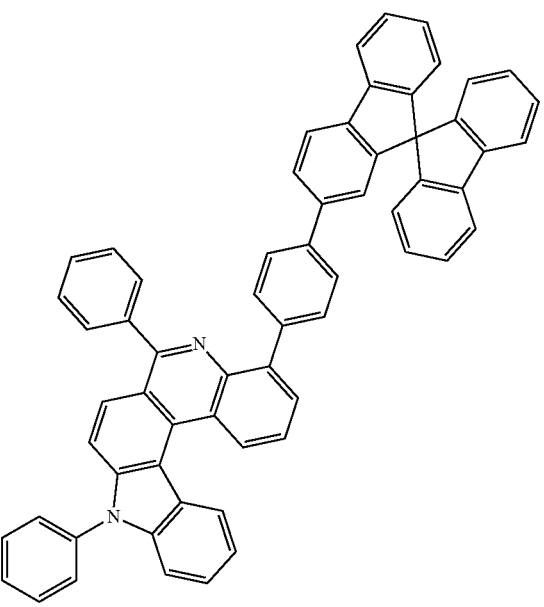
14-47
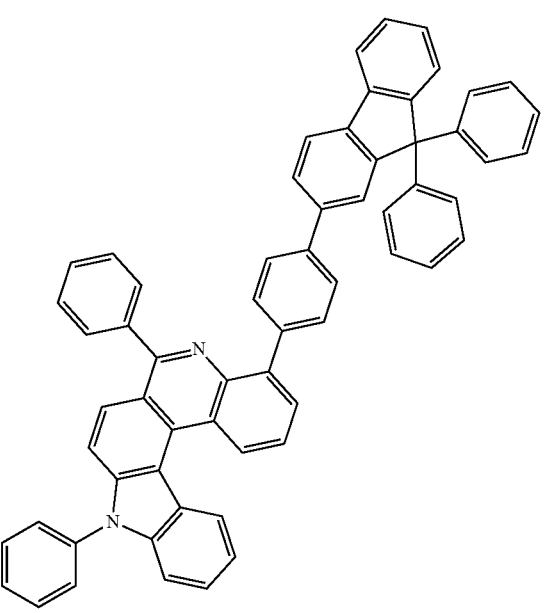

14-48
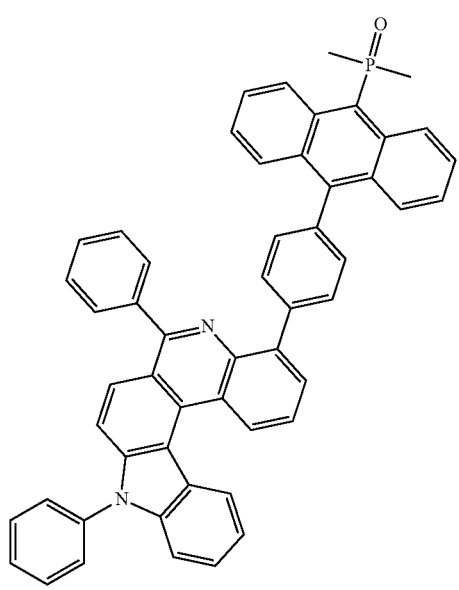
14-49
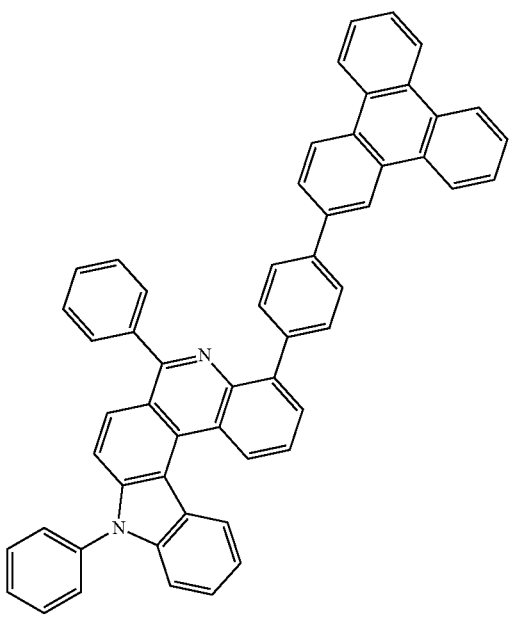
14-50
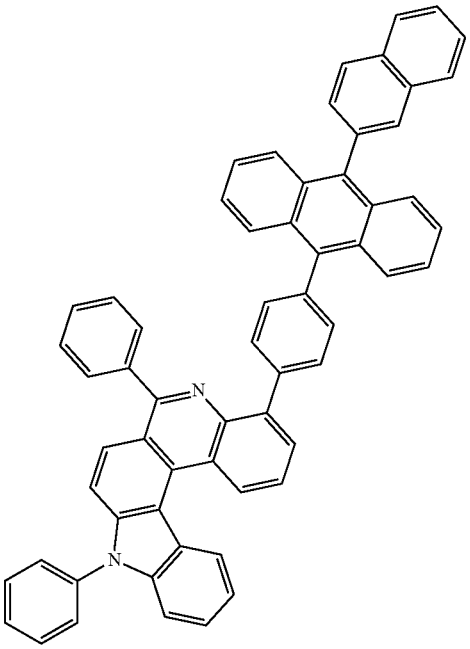
14-51
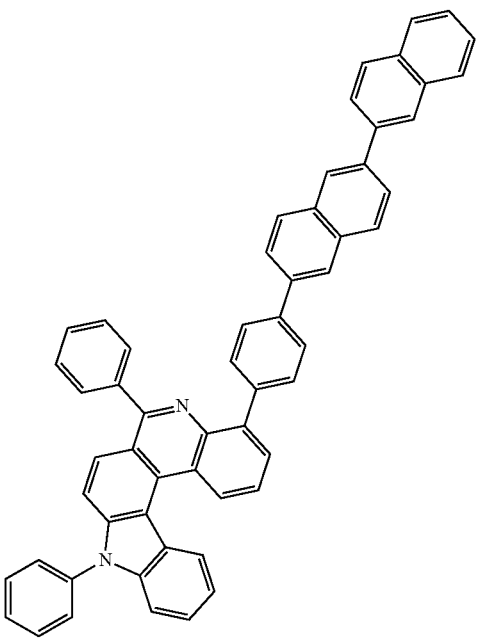

14-52
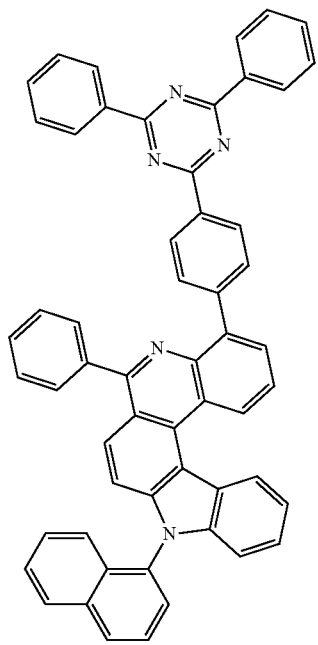
14-53
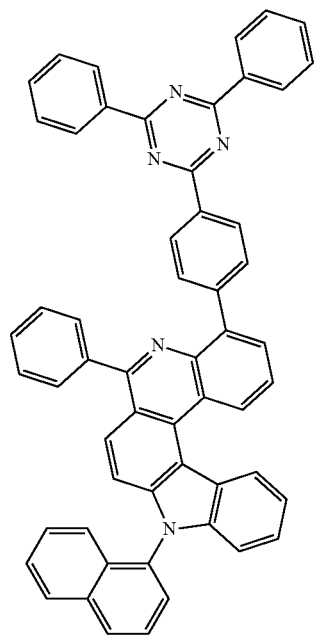
14-54
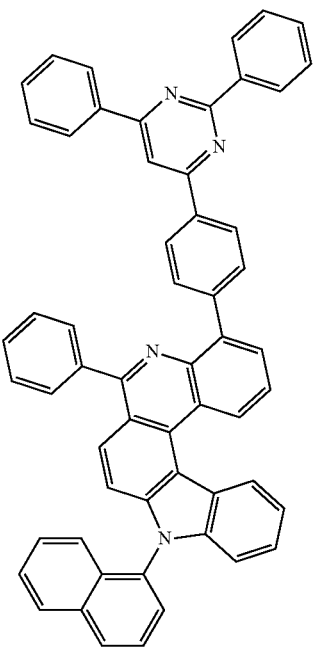
14-55
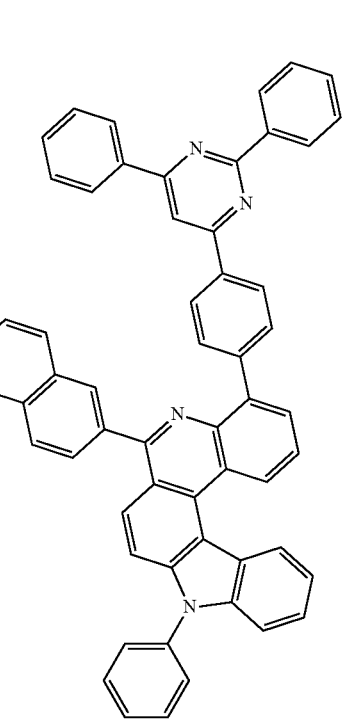

15
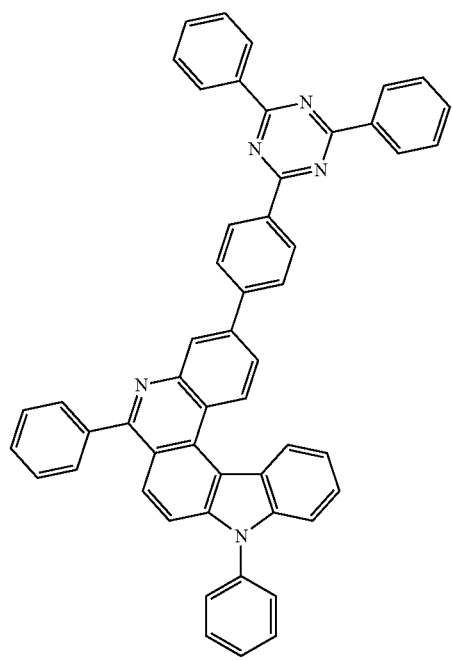
15-2
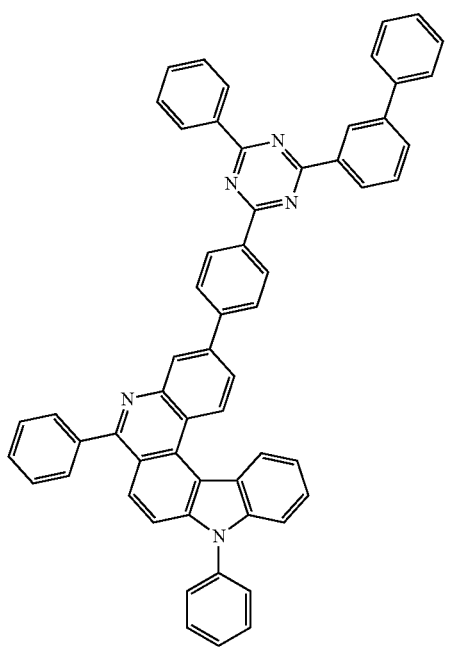
15-1
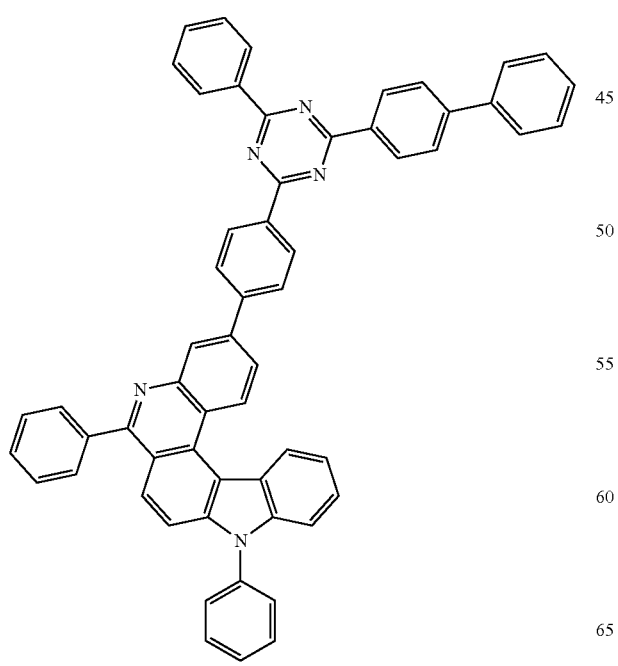
15-3
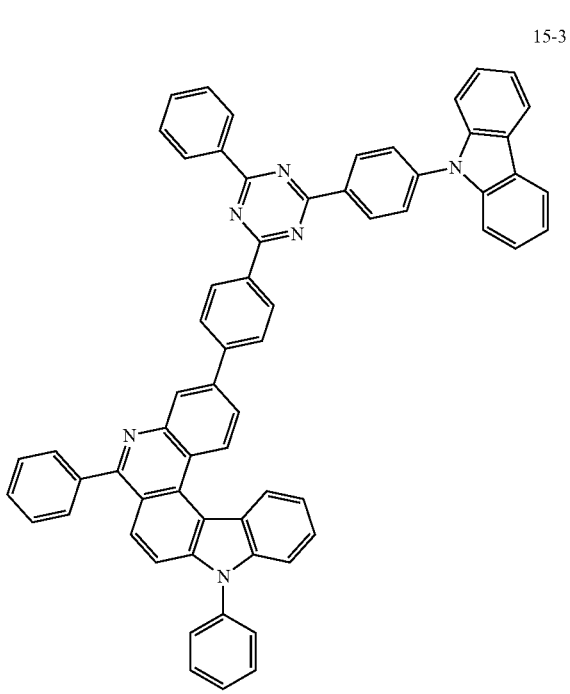

15-4
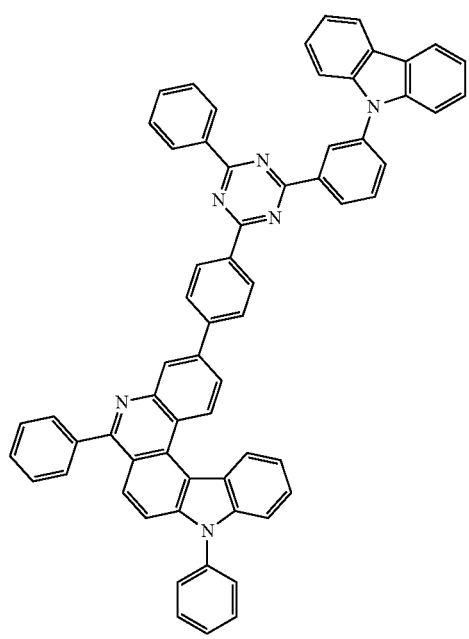
15-5
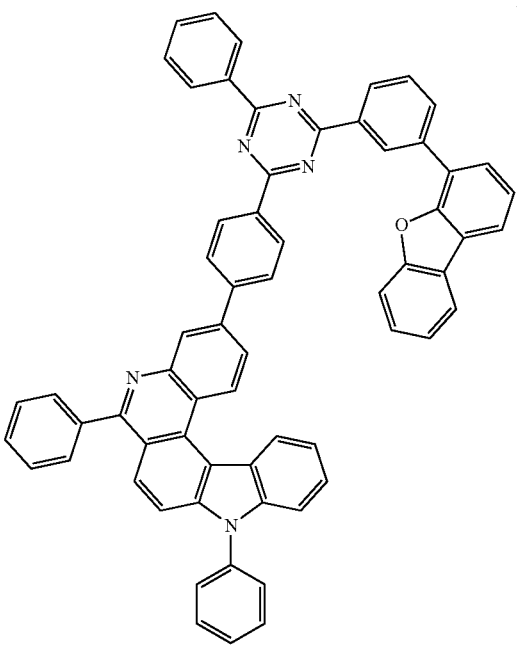
15-6
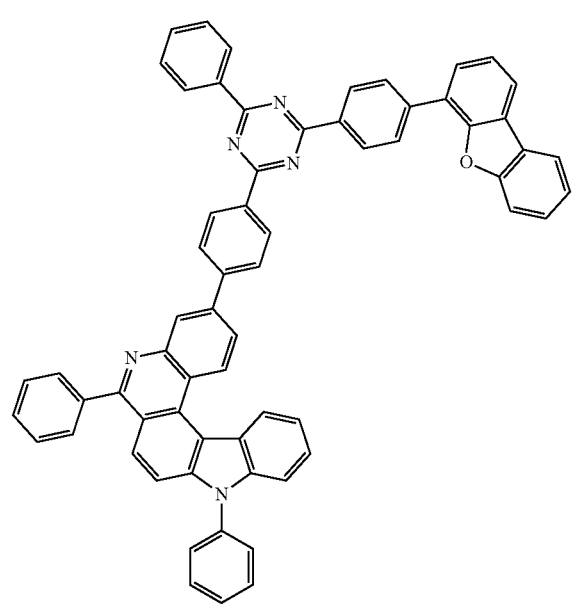
15-7

15-8
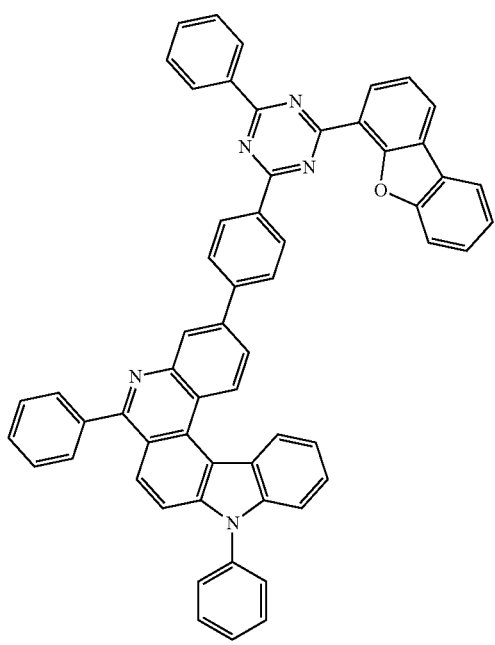
15-9
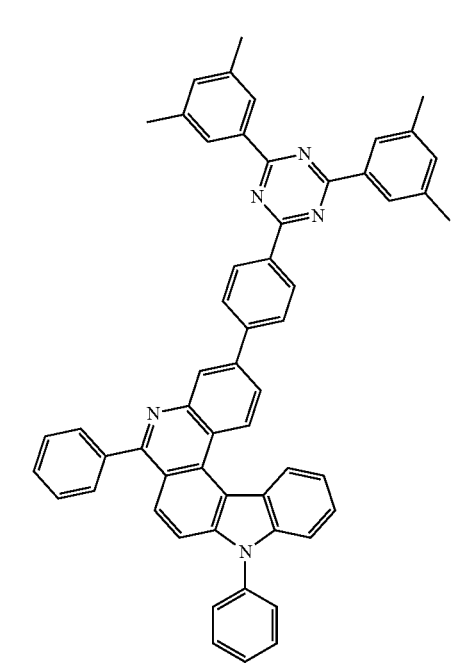
15-10
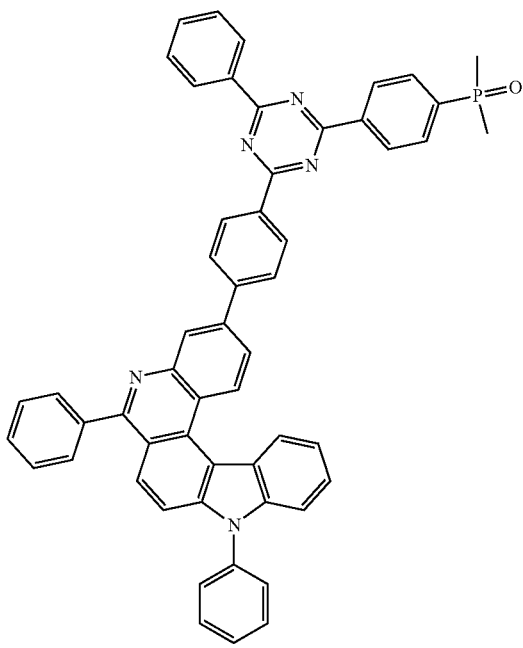
15-11
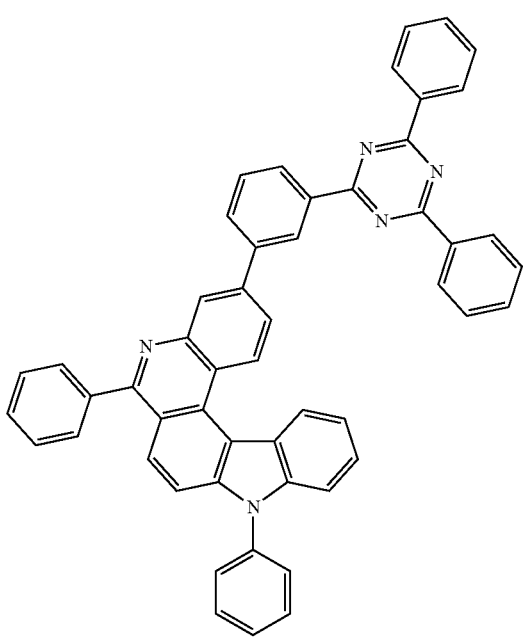

267
-continued
15-12
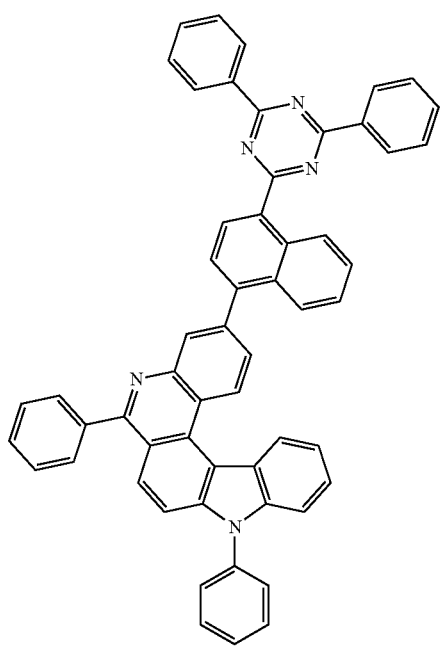
268
-continued
15-14
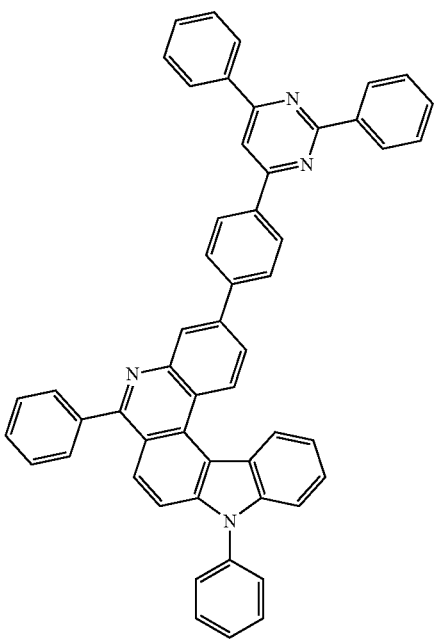
15-13
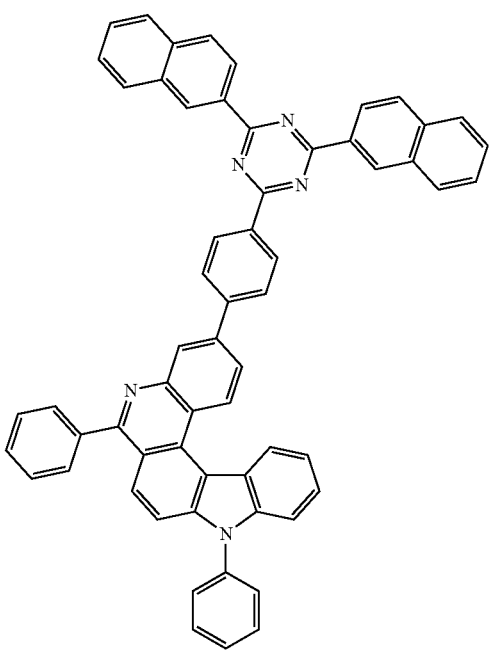
15-15
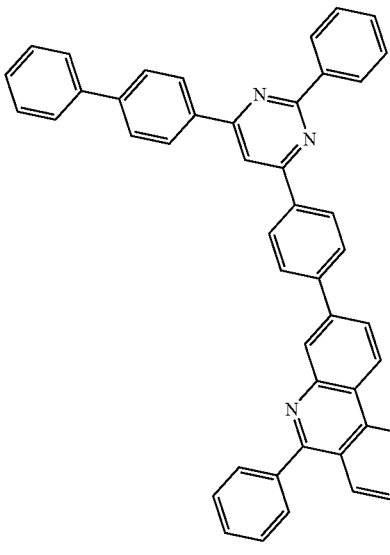

15-16
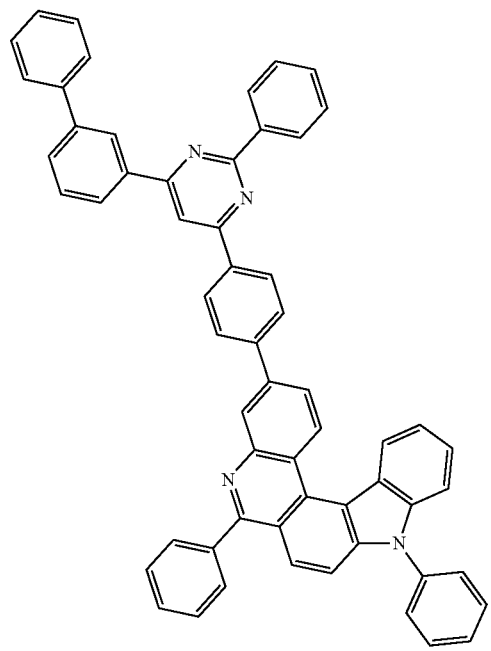
15-17
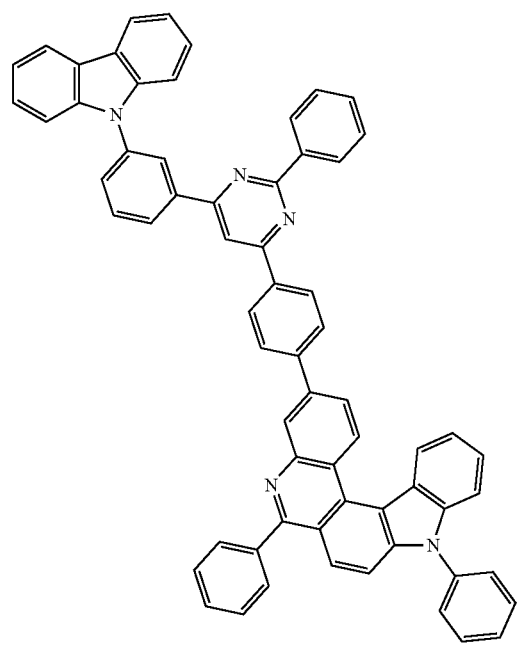
15-18
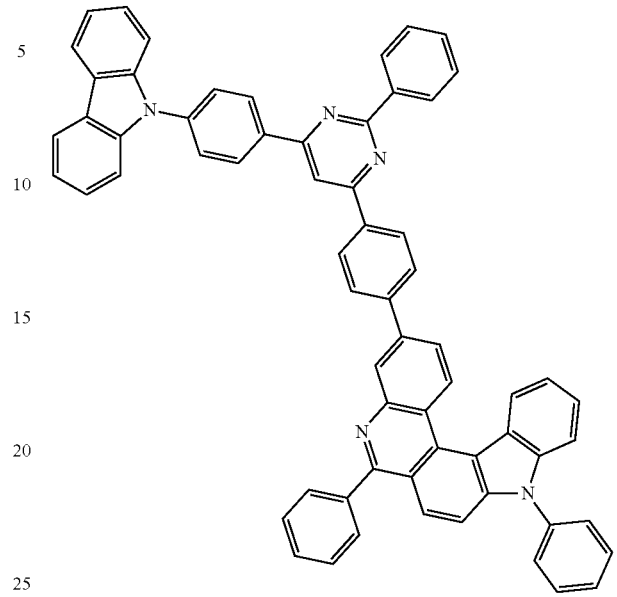
15-19
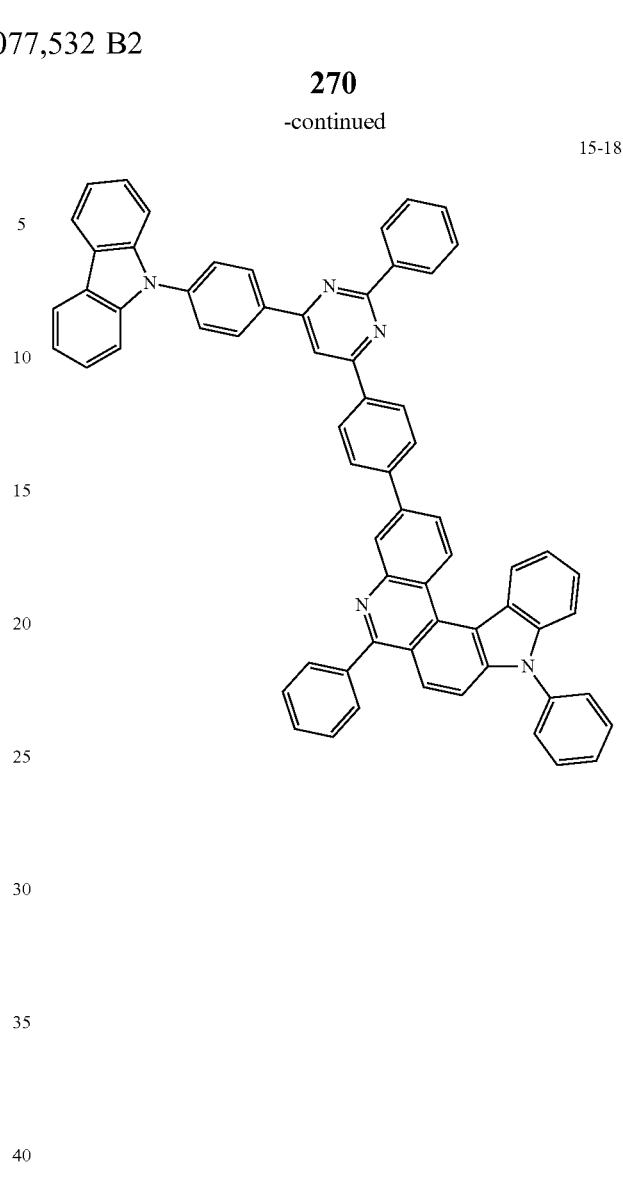

15-20
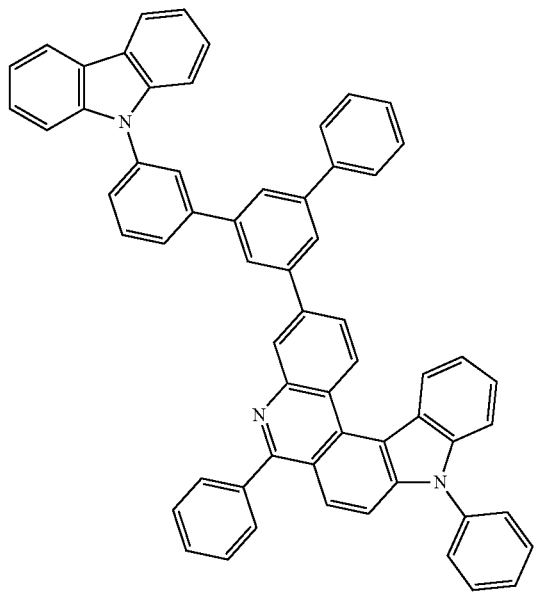
15-21
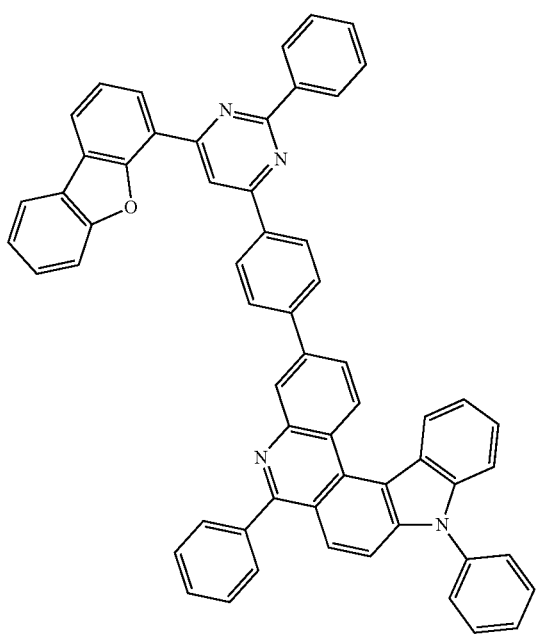
15-22
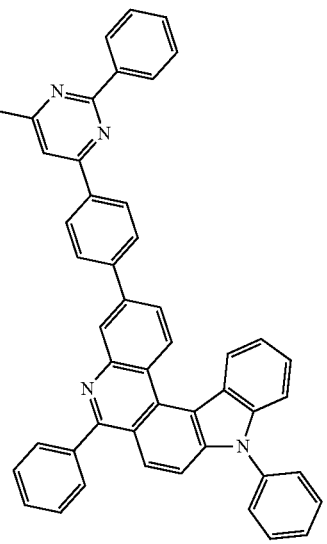
15-23

15-24
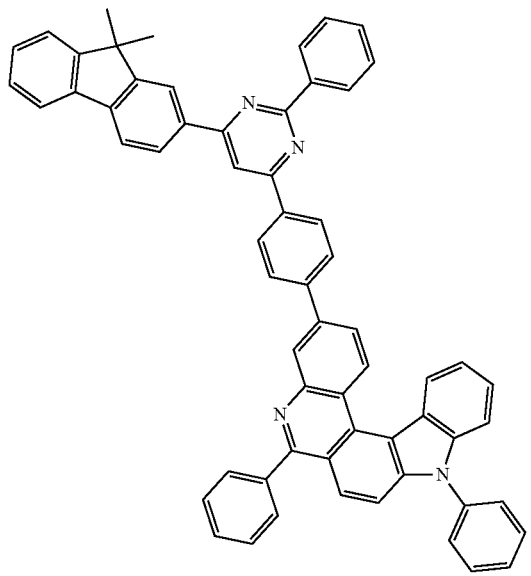
15-25
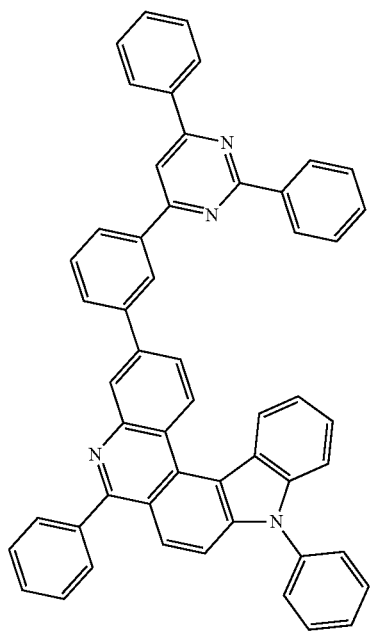
15-26
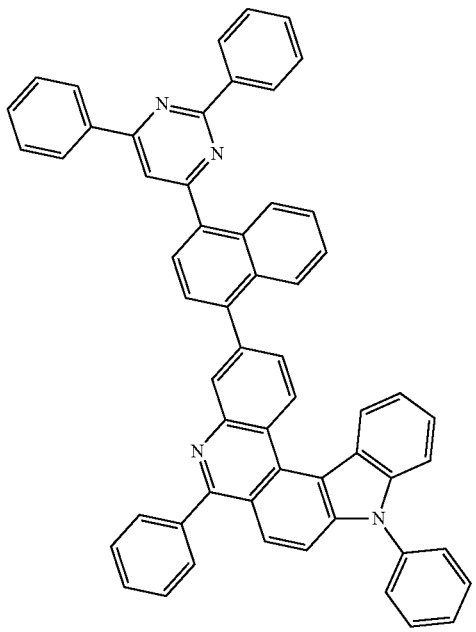
15-27
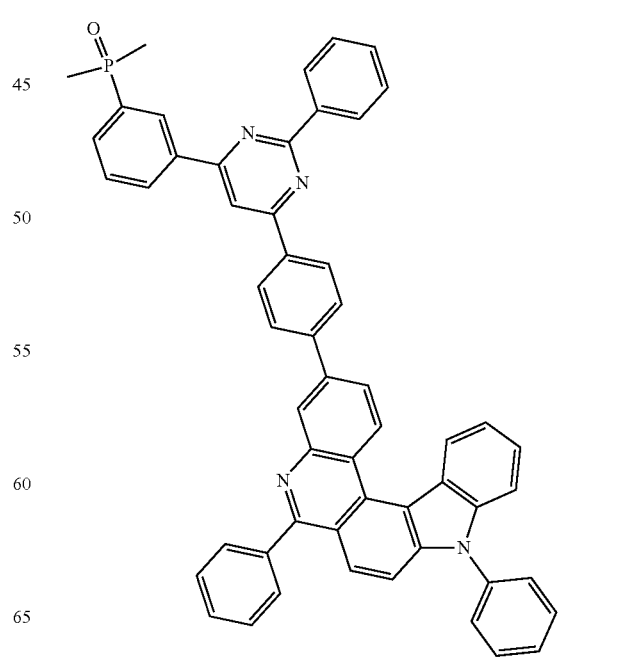

275
-continued
15-28
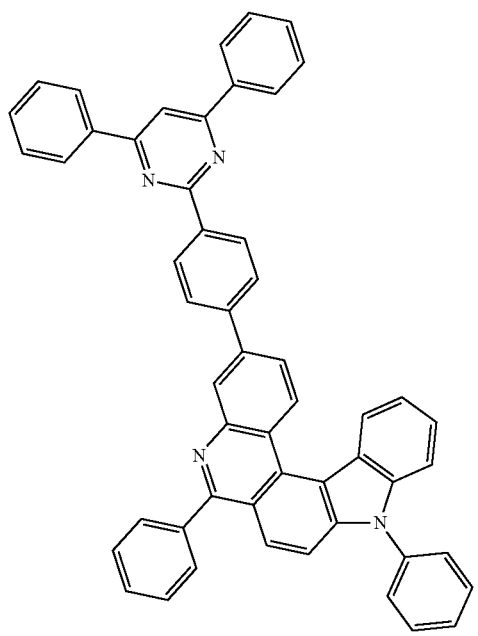
276
-continued
15-30
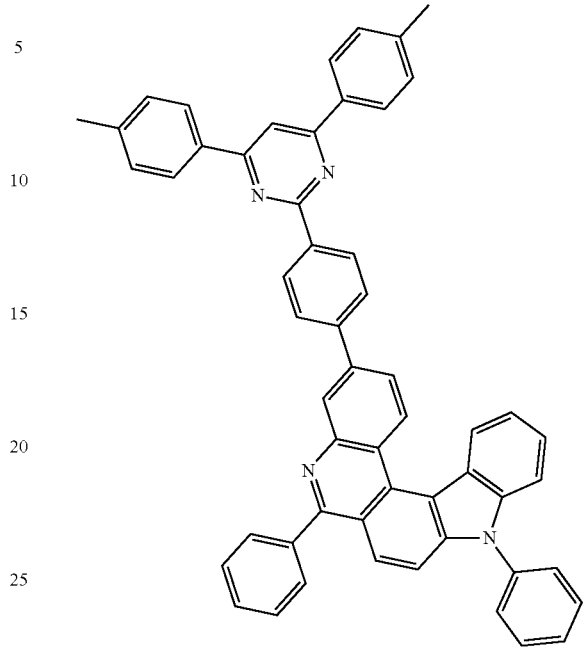
15-29
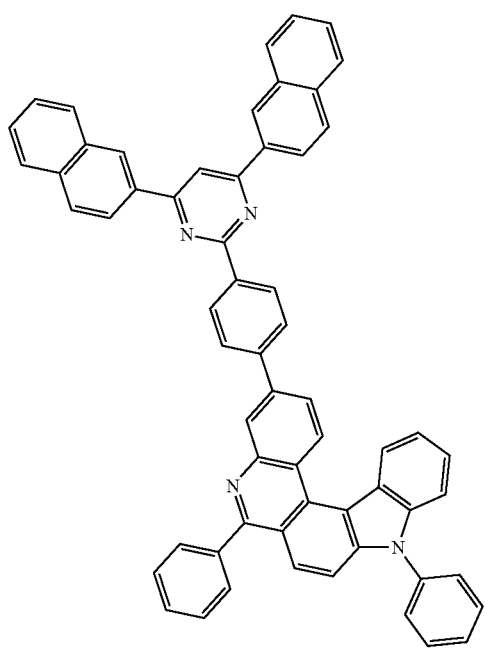
15-31
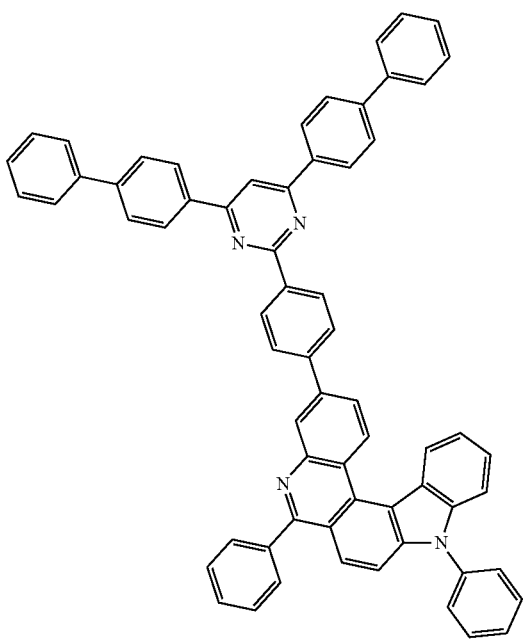

15-32
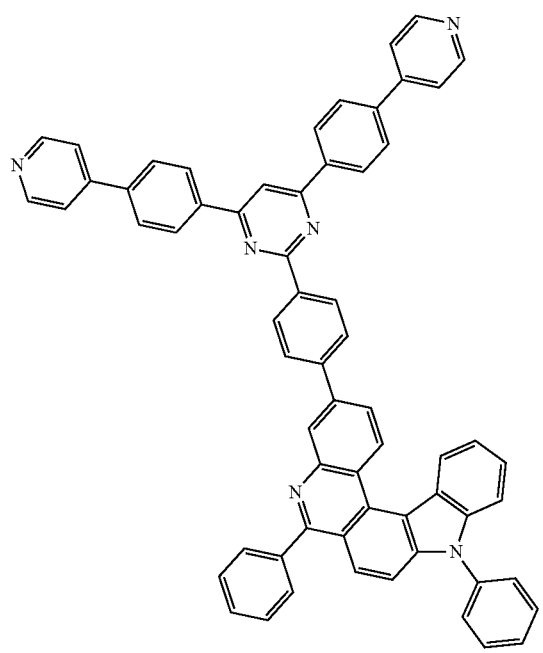
15-33
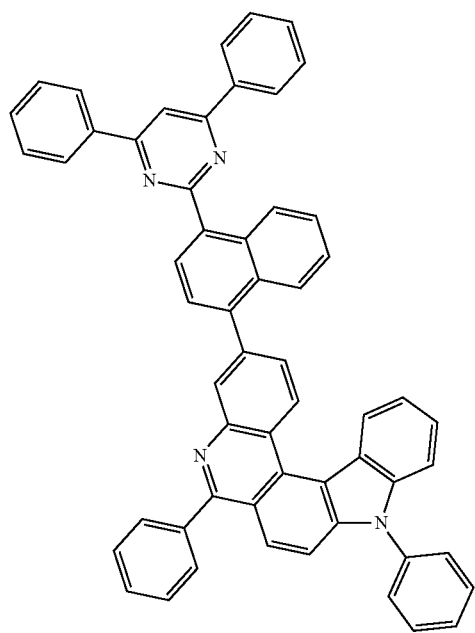
15-38
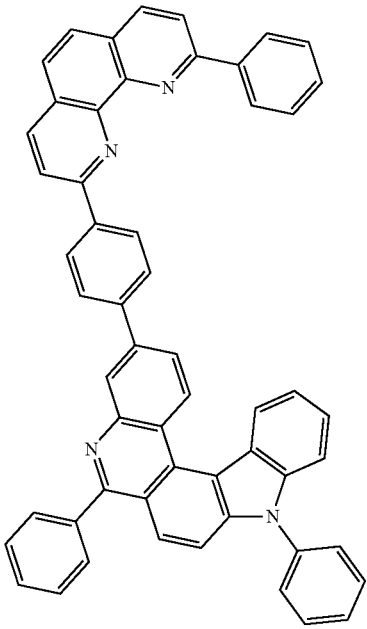
15-39
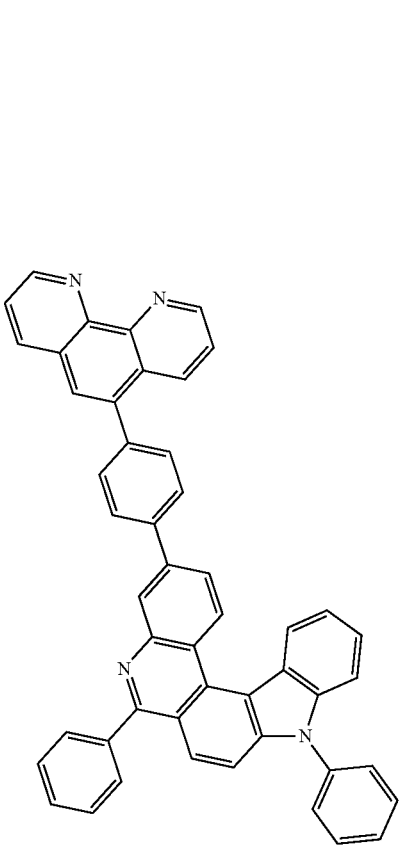

279
-continued
15-40
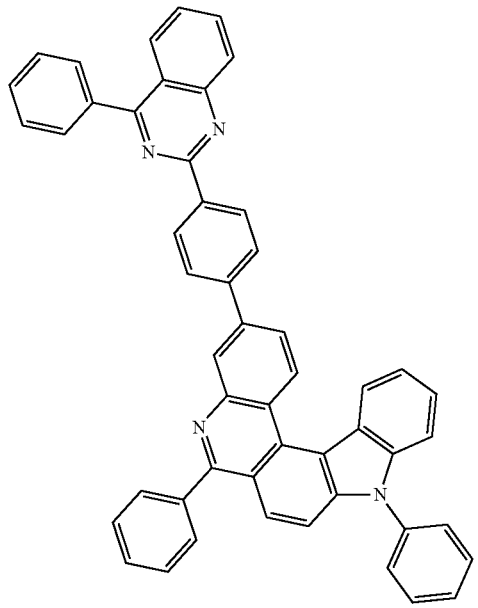
15-41
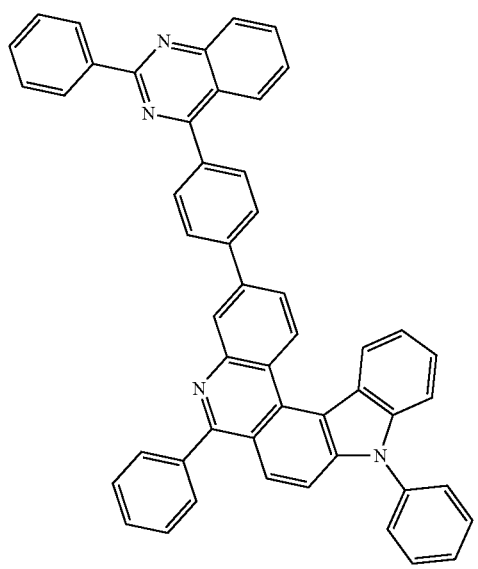
280
-continued
15-42
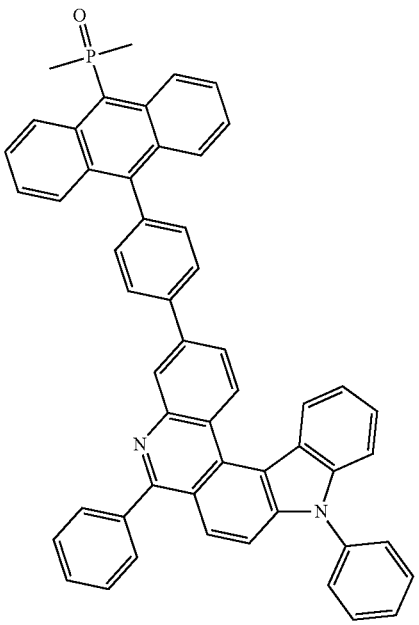
15-43
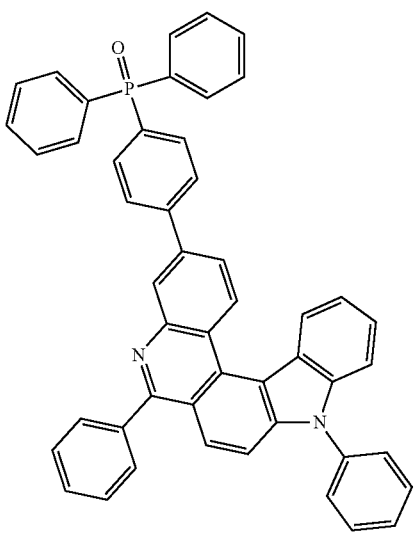

15-44
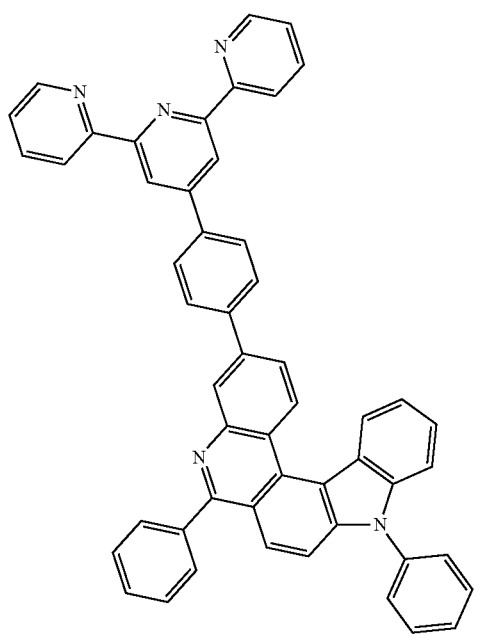
15-46
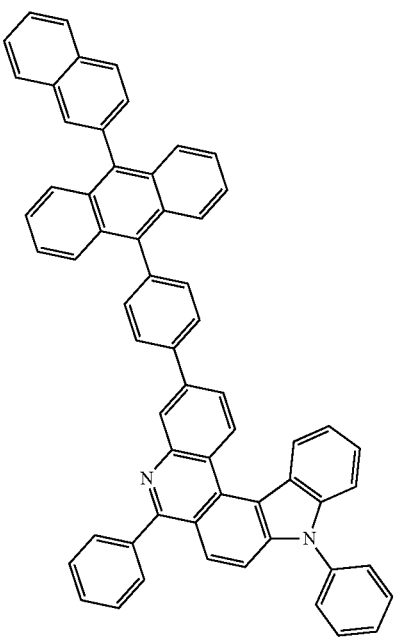
15-45
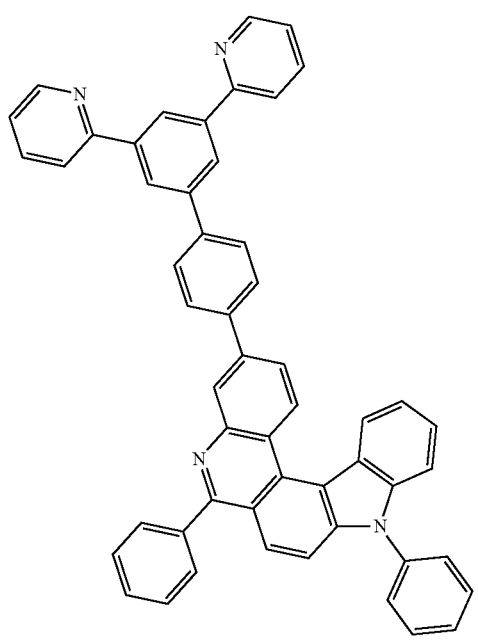
15-47
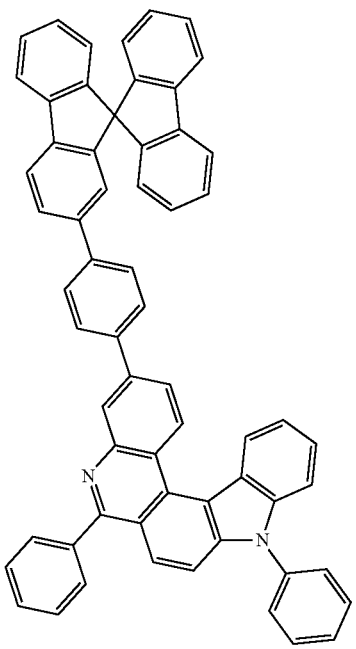

15-48
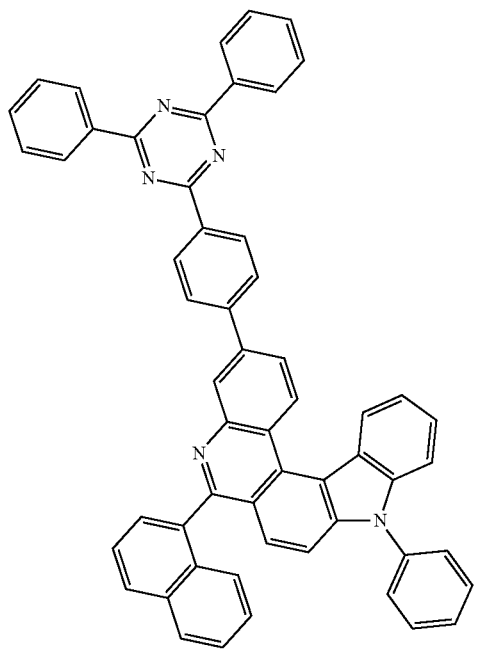
15-49
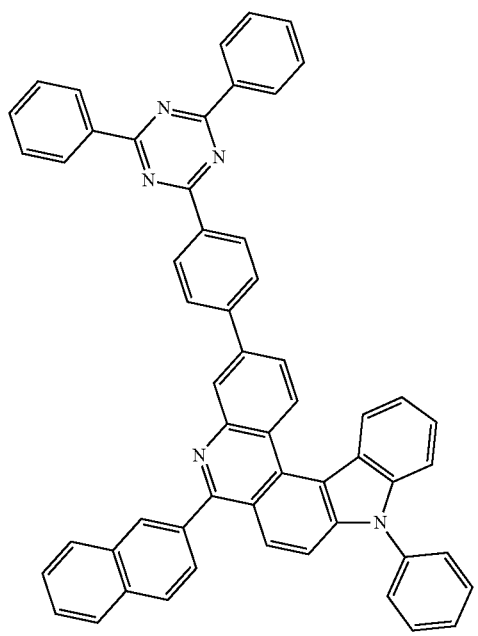
15-50
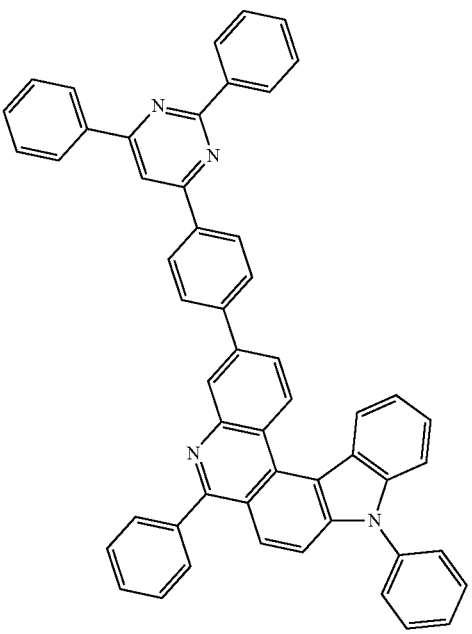
15-51
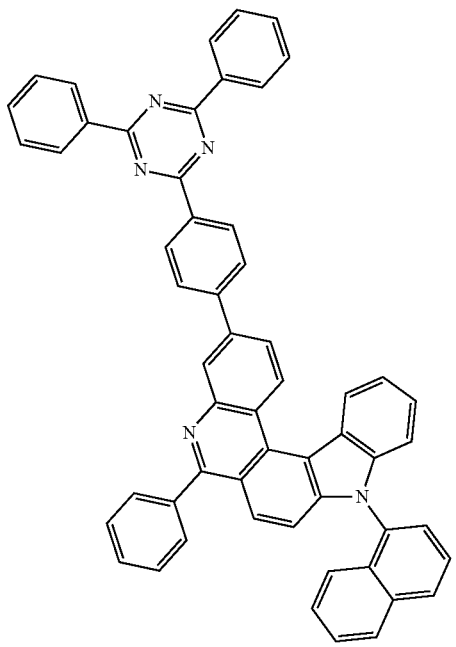

16
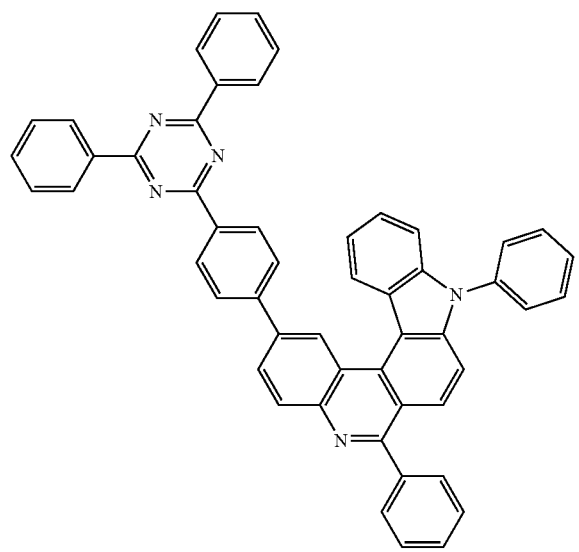
16-1
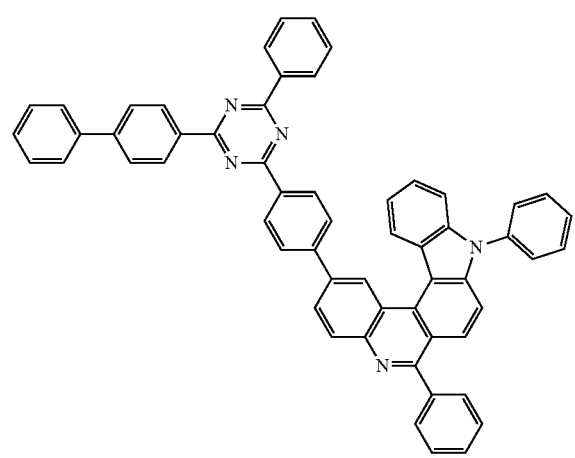
16-2
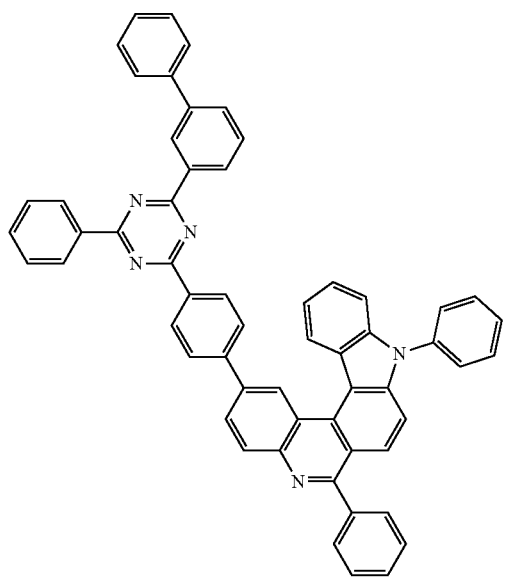
16-3
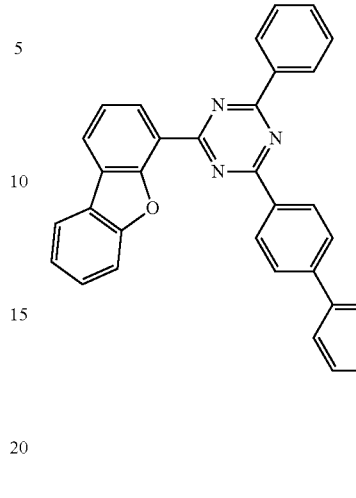
16-4
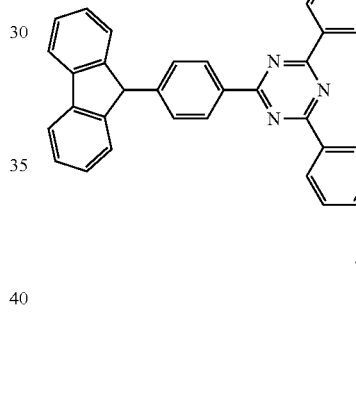
16-5
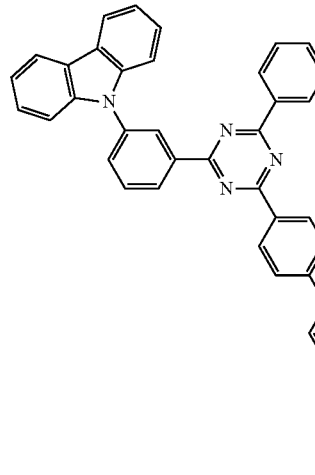

16-6
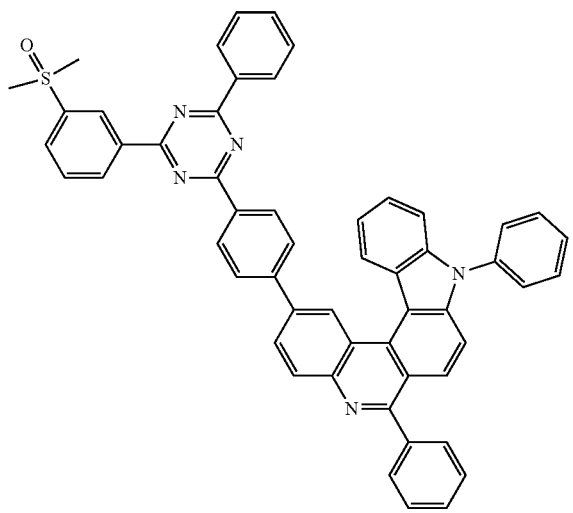
16-7
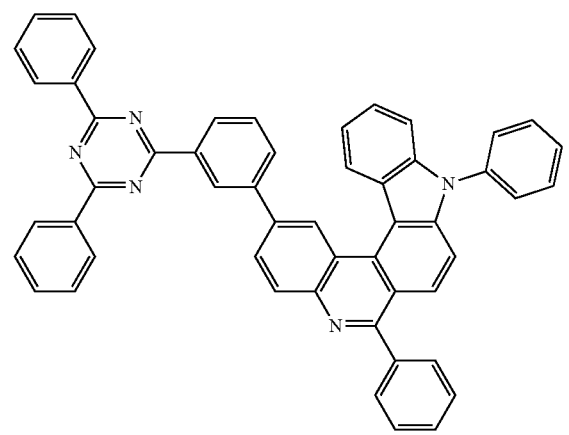
16-8
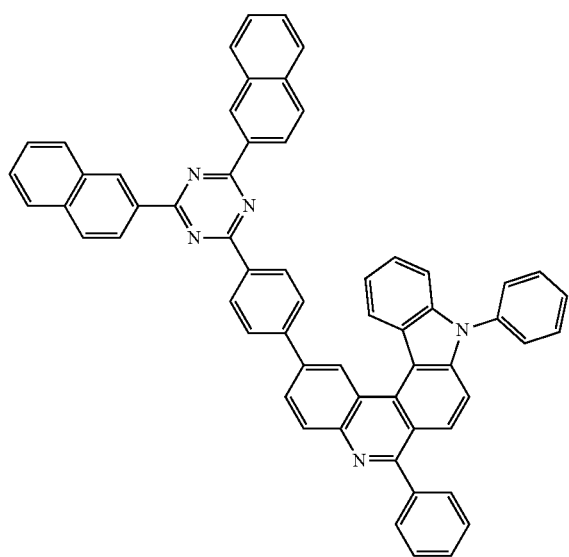
16-9
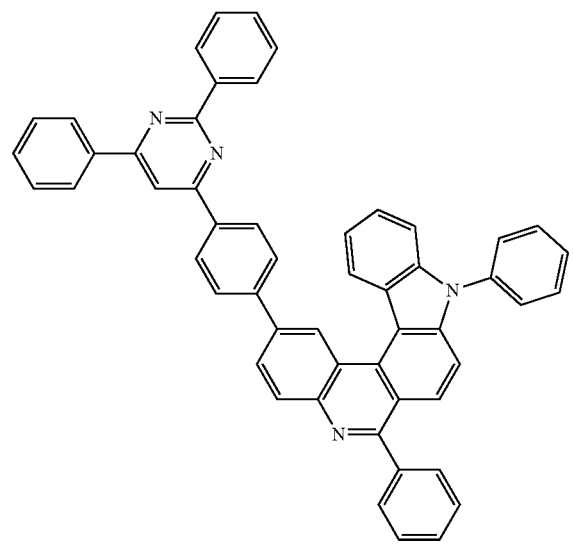
16-10
16-11
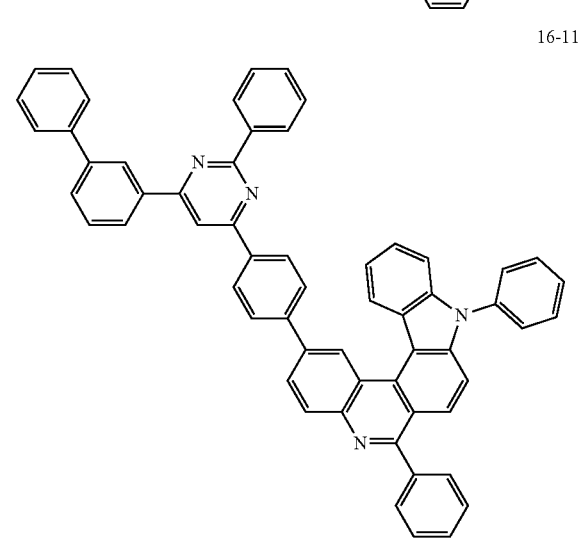

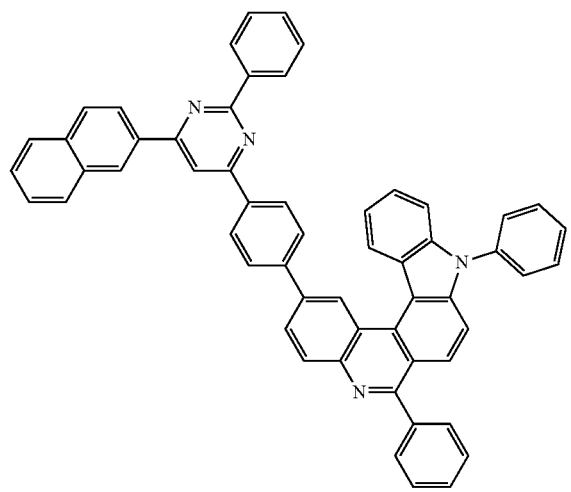
16-12
16-13
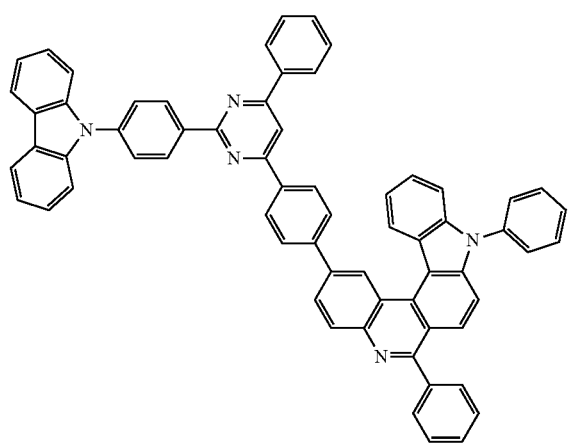
16-14
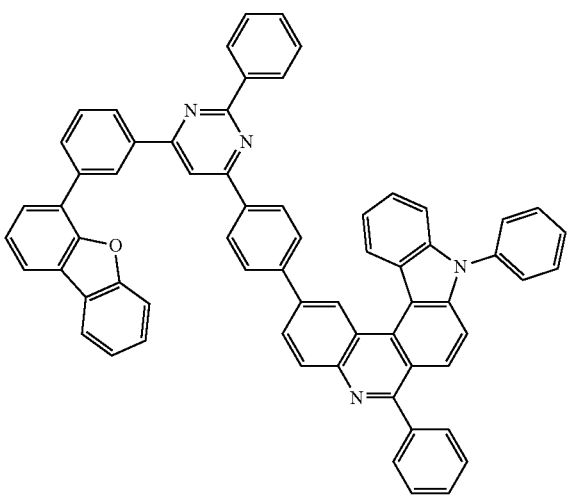
16-15
16-16
16-17

16-18
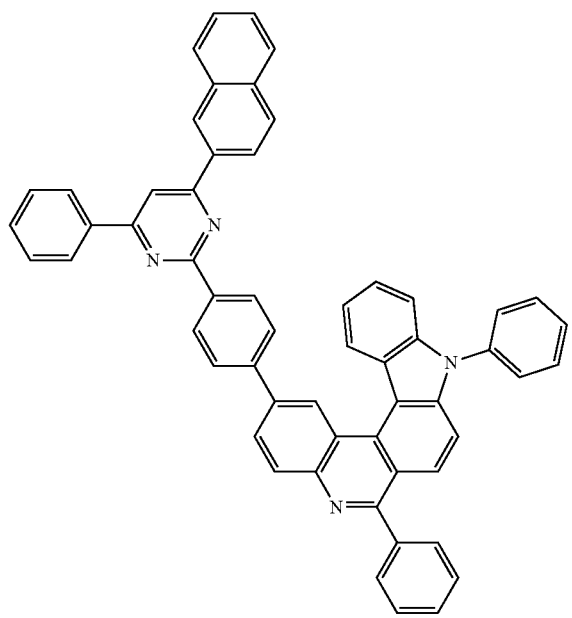
16-19
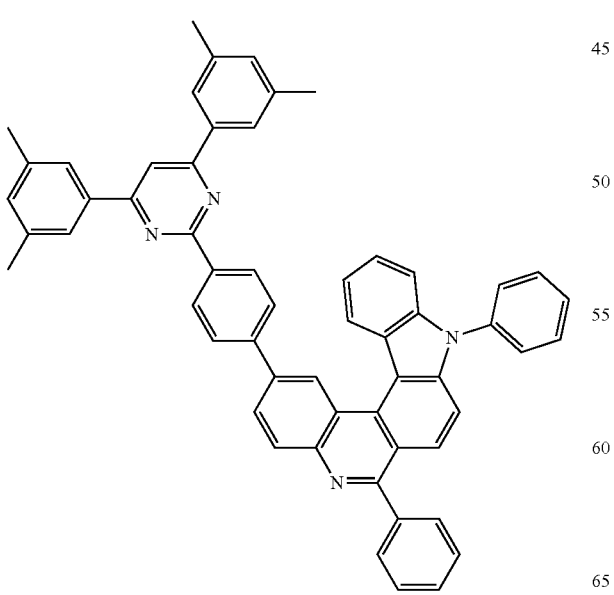
16-20
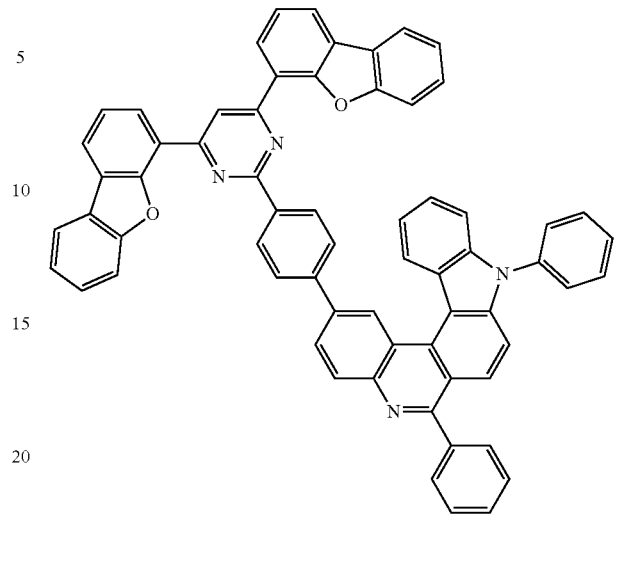
16-21
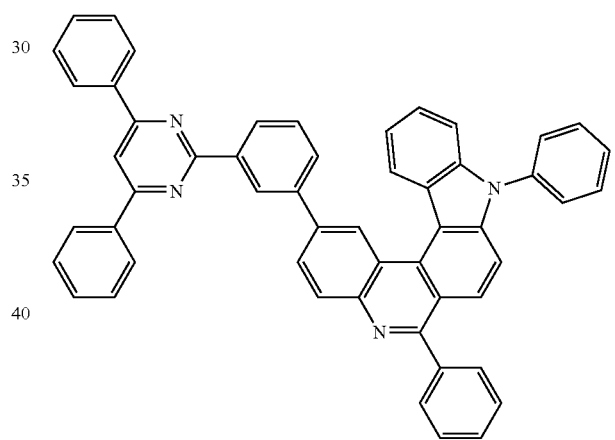
16-22
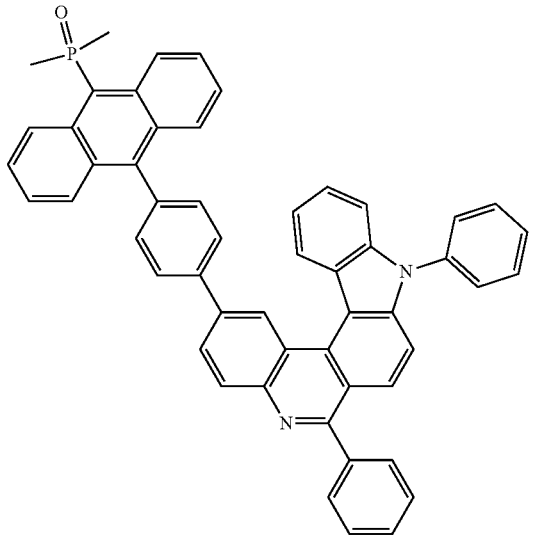

16-23
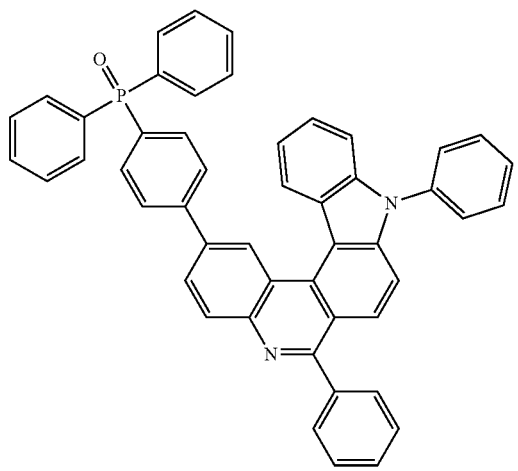
16-24
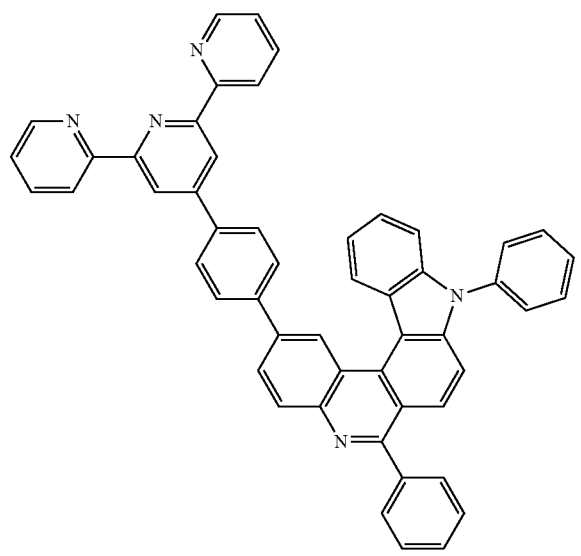
16-25
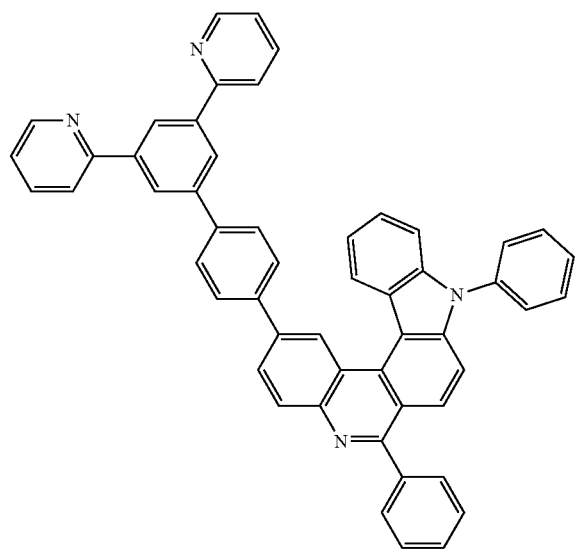
16-26
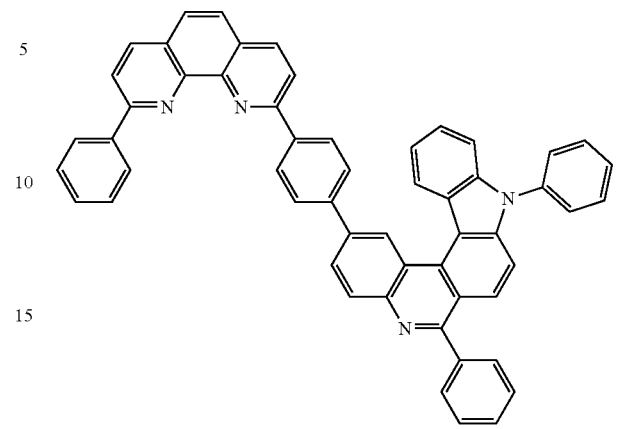
16-27
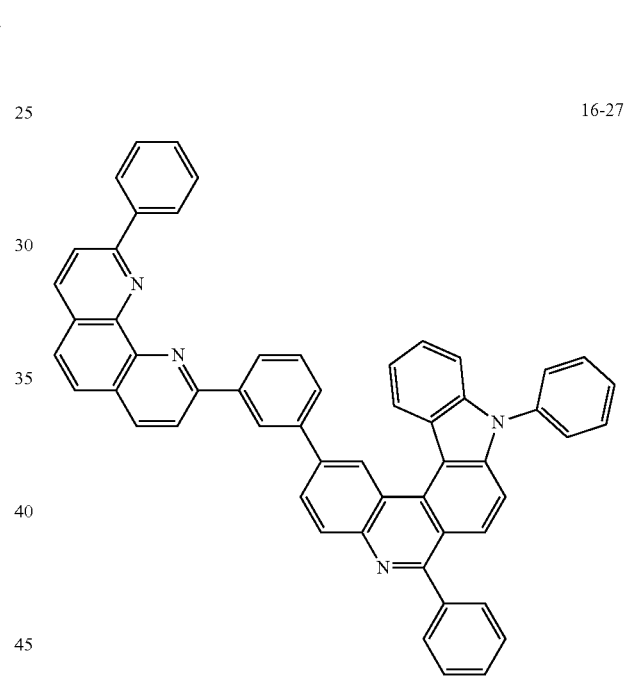
16-28
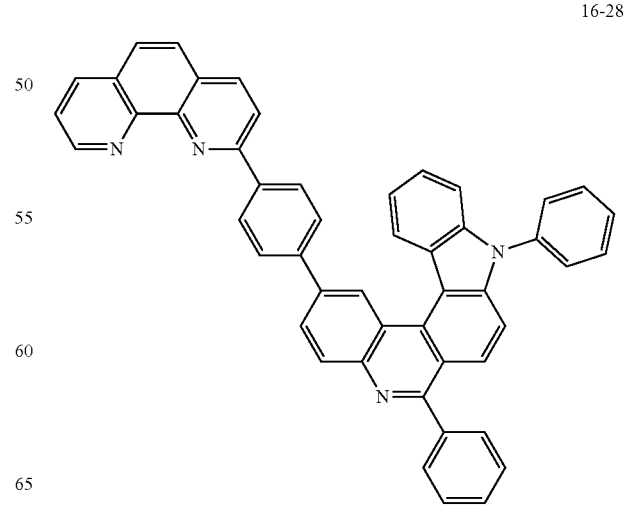

16-29
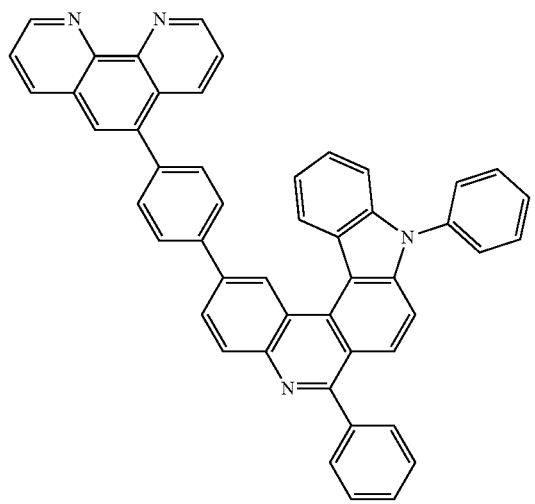
16-30
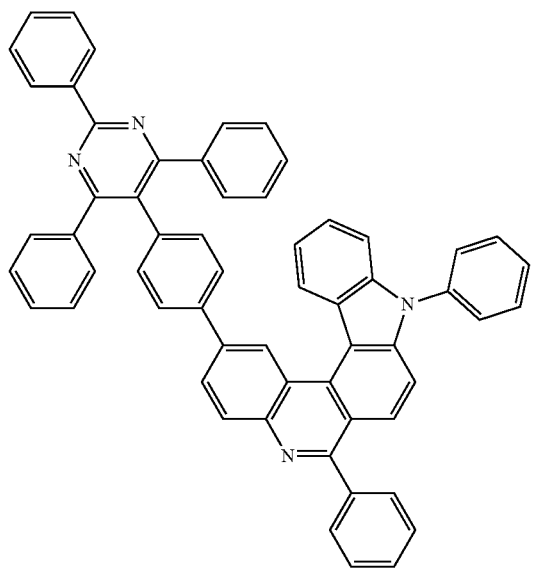
16-31
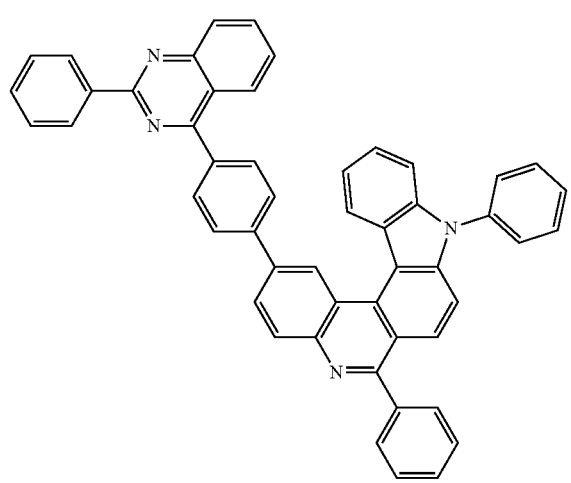
16-32
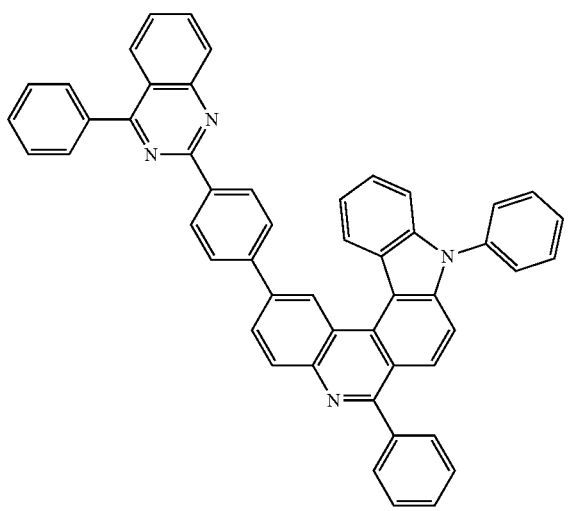
16-33
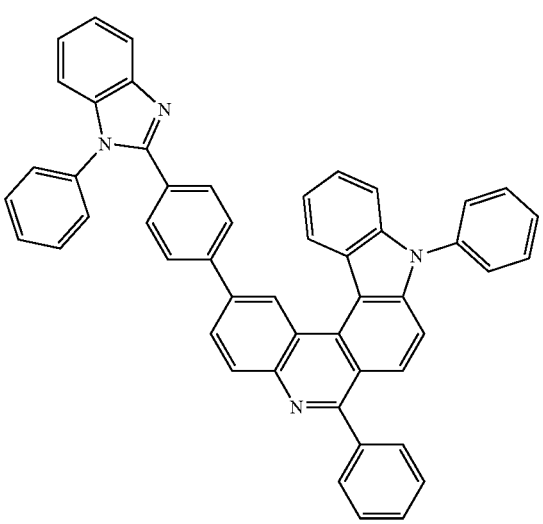
16-34
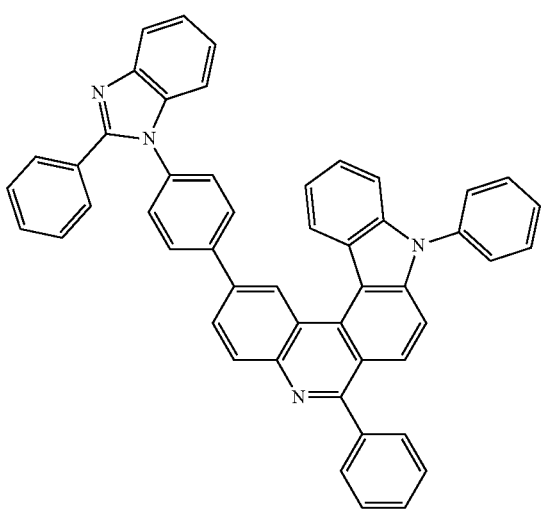

-continued
16-35
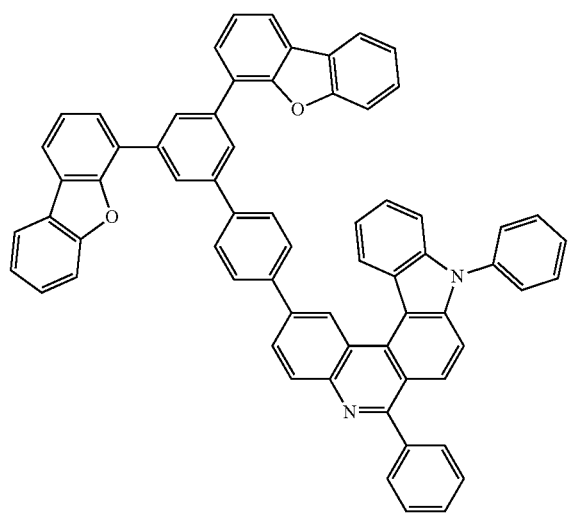
16-36
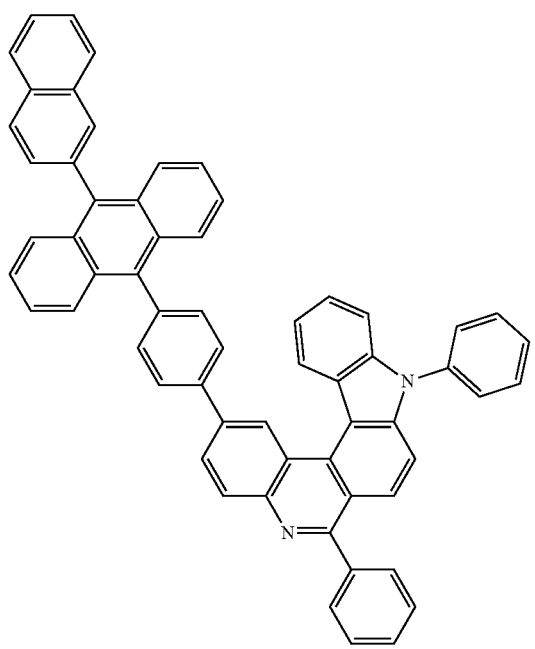
16-37
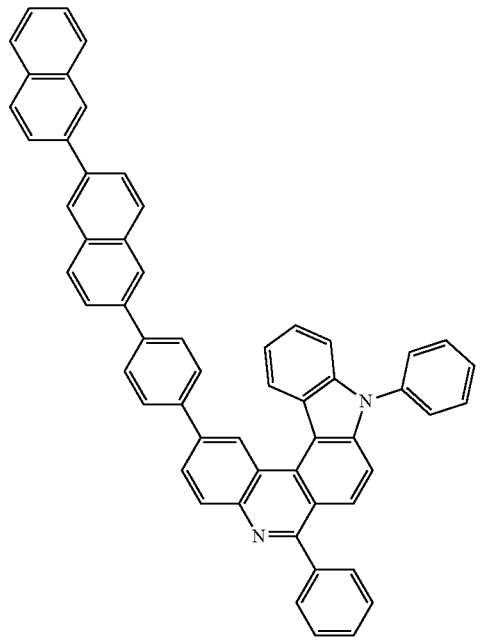
16-38
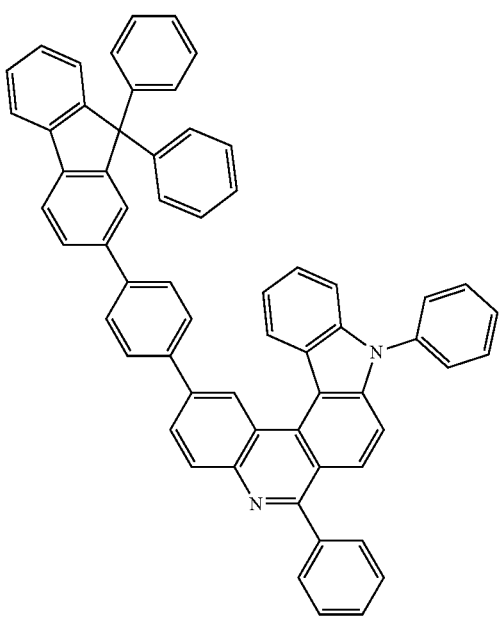

16-39
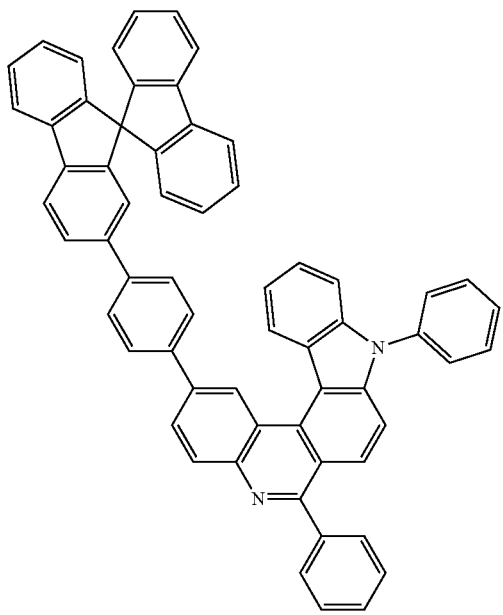
16-40
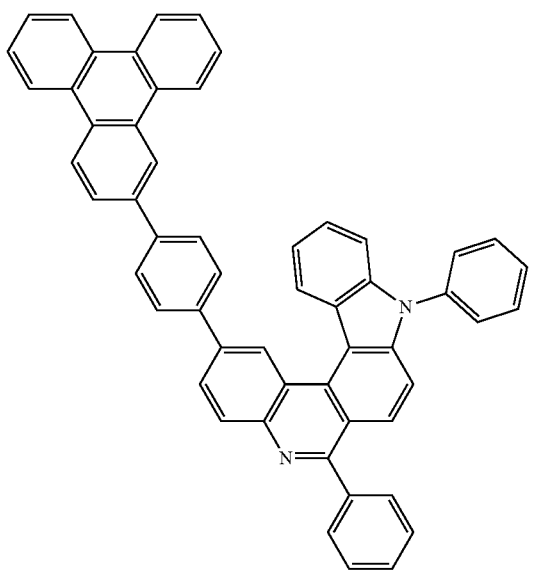
16-41
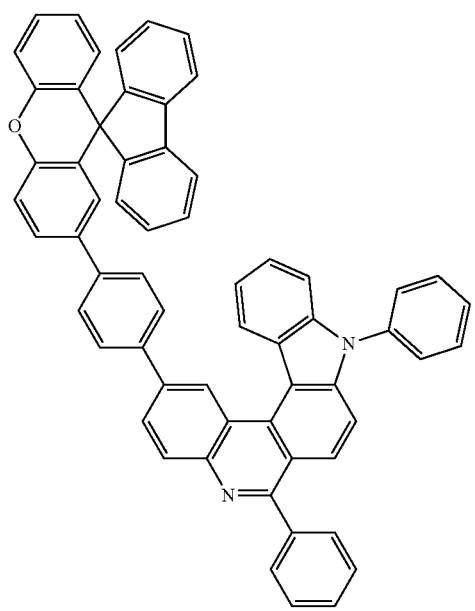
16-42
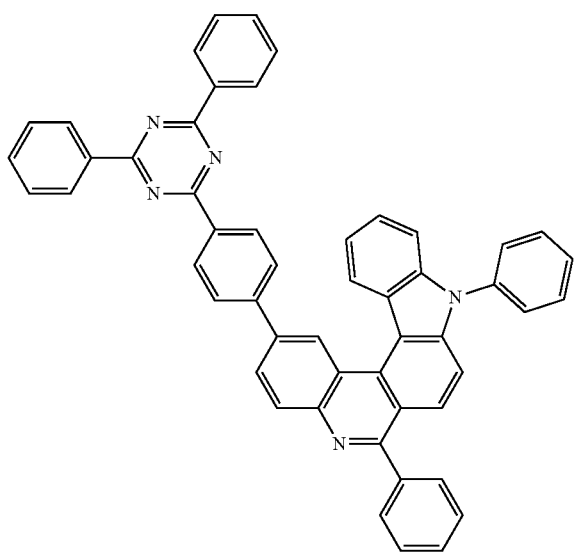

16-43

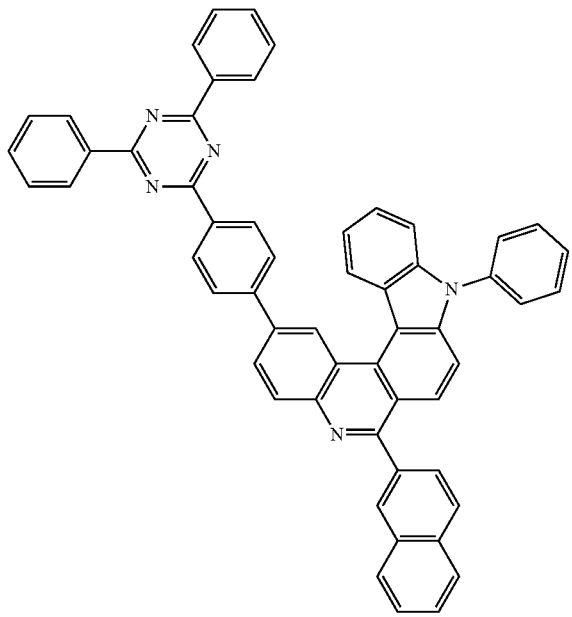

16-44

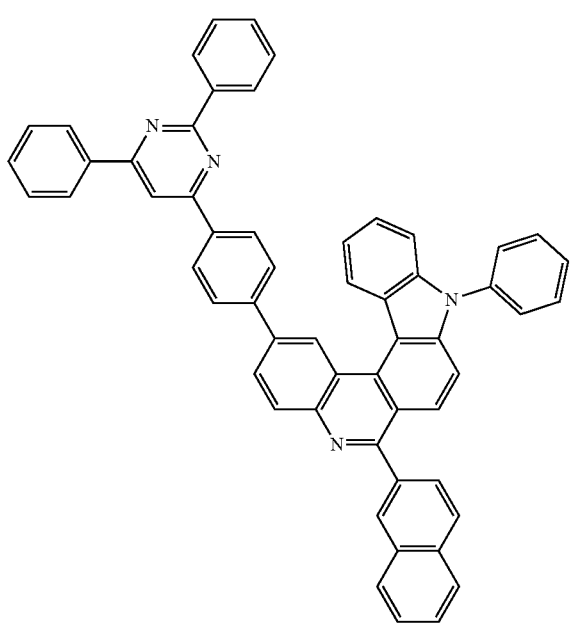

16-45

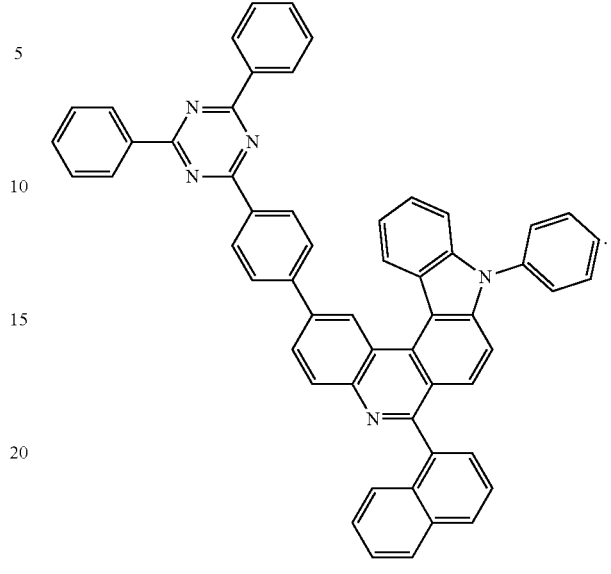

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the heterocyclic compound represented by Chemical Formula 1 are the same as the descriptions provided above.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 4 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100).

However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising the compound of Chemical Formula 1 may further comprise other materials as necessary.

In addition, the organic light emitting device according to one embodiment of the present application comprises an anode, a cathode, and two or more stacks provided between the anode and the cathode, and the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer and the like described above.

In the organic light emitting device provided in one embodiment of the present application, the charge generation layer is an N-type charge generation layer, and the charge generation layer comprises the heterocyclic compound.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in the following FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

[Preparation Example 1] Preparation of Compound 1

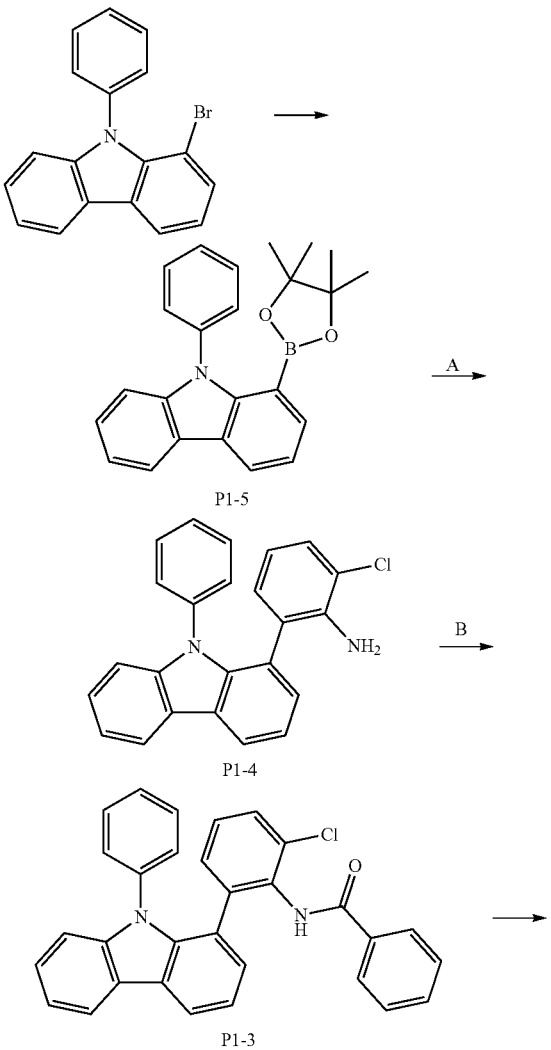

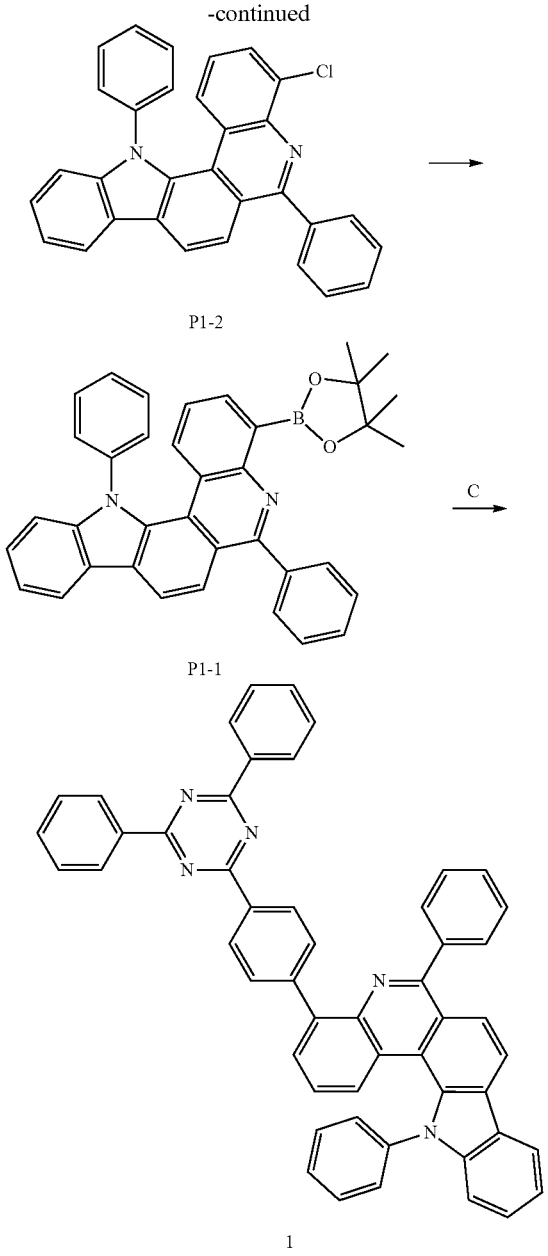

Preparation of Compound P1-5

After dissolving 4-bromo-9-phenyl-9H-carbazole (150 g, 465.55 mmol) and bis(pinacolato)diboron (236 g, 931.09 mmol) in 1,4-dioxane (2 L), (N₂ condition) PdCl₂(dppf) (17 g, 23.27 mmol) and KOAc (137 g, 1.39 mol) were introduced thereto, and the result was stirred for 14 hours at 100° C. After the reaction was completed, the mixture solution was dissolved in methylene chloride (MC) and extracted with water, and the organic layer was dried with anhydrous MgSO₄ and then silica gel filtered.

The filtered filtrate was, after removing the solvent using a rotary evaporator, precipitated with ethyl acetate (EA)/hexane (Hex), and then the precipitates were filtered to obtain Compound P1-5 (134.2 g, 78% yield).

Preparation of Compound P1-4

After dissolving Compound P1-5 (134.2 g, 363.33 mmol) and 2-bromo-6-chloroaniline (82.5 g, 399.66 mmol) in 1,4-dioxane (1 L) and H₂O (200 ml), (N₂ condition) Pd(PPh₃)₄ (12.6 g, 10.89 mmol) and K₃PO₄ (154.3 g, 726.66 mmol) were introduced thereto, and the result was stirred for 4 hours at 100° C. After the reaction was completed, the mixture solution was dissolved in MC and extracted with water, and the organic layer was dried with anhydrous MgSO₄ and then silica gel filtered. The filtered filtrate was, after removing the solvent using a rotary evaporator, precipitated with EA/Hex, and then the precipitates were filtered to obtain Compound P1-4 (92.5 g, 69% yield).

Preparation of Compound P1-3

After dissolving Compound P1-4 (92.5 g, 250.78 mmol) in MC (900 ml), triethylamine (106 ml, 752.34 mmol) was introduced thereto, and benzoyl chloride (32 ml, 275.85 mmol) was slowly added dropwise thereto at 0° C. The reaction temperature was raised to room temperature after 30 minutes (25° C.), and the result was stirred for 4 hours. After the reaction was completed, the mixture solution was extracted with distilled water, and the organic layer was dried with anhydrous MgSO₄ and then silica gel filtered. The filtered filtrate was, after removing the solvent using a rotary evaporator, precipitated with EA/Hex, and then the precipitates were filtered to obtain Compound P1-3 (88.9 g, 75% yield).

Preparation of Compound P1-2

After dissolving Compound P1-3 (88.9 g, 187.96 mmol) in nitrobenzene (800 ml), POCl₃ (18 ml, 187.96 mmol) was introduced thereto, and the result was stirred for 18 hours at 150° C. After the reaction was completed, the mixture solution was cooled to 0° C., and 1 M Na₂CO₃ (aq) was slowly added thereto to adjust the pH to 10 to 11. The organic layer extracted with distilled water was dried with anhydrous MgSO₄ and then silica gel filtered. The filtered filtrate was, after removing the solvent using a rotary evaporator, precipitated with MC/MeOH, and then the precipitates were filtered to obtain Compound P1-2 (70.8 g, 83% yield).

Preparation of Compound P1-1

After dissolving P1-2 (70.8 g, 155.79 mmol) and bis(pinacolato)diboron (80 g, 311.58 mmol) in 1,4-dioxane (800 ml), (N₂ condition) Pd(dba)₂ (8.9 g, 15.58 mmol), SPhos (12.7 g, 31.15 mmol) and KOAc (45.8 g, 467.37 mmol) were introduced thereto, and the result was stirred for 14 hours at 100° C. After the reaction was completed, the mixture solution was dissolved in MC and extracted with water, and the organic layer was dried with anhydrous MgSO₄ and then silica gel filtered. The filtered filtrate was, after removing the solvent using a rotary evaporator, precipitated with MC/MeOH, and then the precipitates were filtered to obtain Compound P1-1 (73.2 g, 86% yield).

Preparation of Compound 1

After dissolving Compound P1-1 (10 g, 18.29 mmol) and 2-(4-bromophenyl)-4,6-diphenyl-1,3,5-triazine (7.1 g, 18.29 mmol) in 1,4-dioxane (150 ml) and H₂O (30 ml), (N₂ condition) Pd(PPh₃)₄ (1.1 g, 0.91 mmol) and K₃PO₄ (11.6 g, 54.87 mmol) were introduced thereto, and the result was stirred for 14 hours at 100° C. After the reaction was completed, the result was cooled to room temperature, and precipitated solids were filtered and washed with solvents of H₂O and MeOH. The filtered solids were dried, then dissolved in an excess amount of hot 1,2-dichlorobenzene solvent, and silica gel filtered. The filtered filtrate was, after removing the solvent using a rotary evaporator, precipitated with MeOH, and then the precipitates were filtered to obtain Compound 1 (8.5 g, 64% yield).

Target compounds were synthesized in the same manner as in Preparation Example 1 except that Intermediate A of the following Table 1 was used instead of 2-bromo-6-chloroaniline, the compound of Reaction A, Intermediate B of the following Table 1 was used instead of benzoyl chloride of Reaction B, and Intermediate C was used instead of 2-(4-bromophenyl)-4,6-diphenyl-1,3,5-triazine of Reaction C.

TABLE 1
| Compound No. | A | B | C | Target Compound | Yield |
|---|---|---|---|---|---|
| 1-1 | 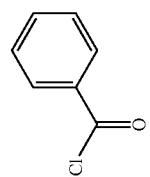 | 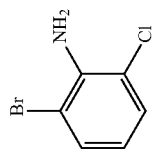 | |  | 56% |

TABLE 1-continued
| Compound No. | A | B | C | Target Compound | Yield |
|---|---|---|---|---|---|
| 1-7 | | | | | 68% |

TABLE 1-continued
| Compound No. | A | B | C | Target Compound | Yield |
|---|---|---|---|---|---|
| 1-20 | | | | 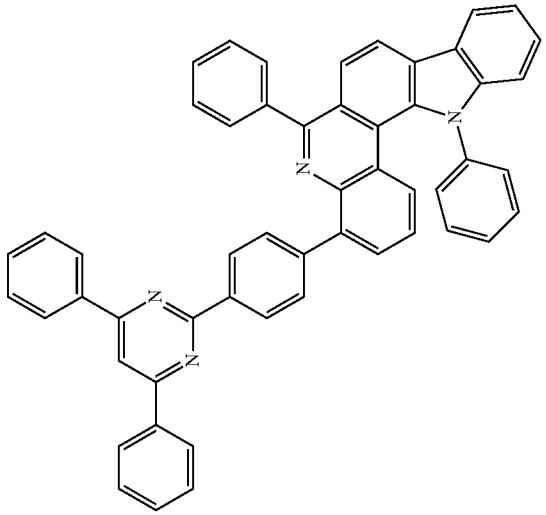 | 53% |

TABLE 1-continued
| Compound No. | A | B | C | Target Compound | Yield |
|---|---|---|---|---|---|
| 1-26 | 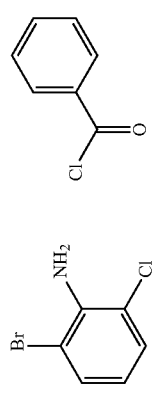 | 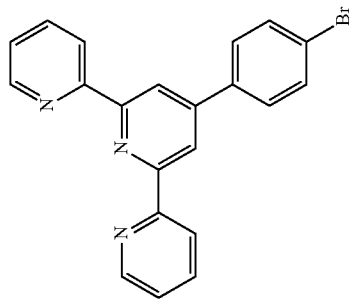 | 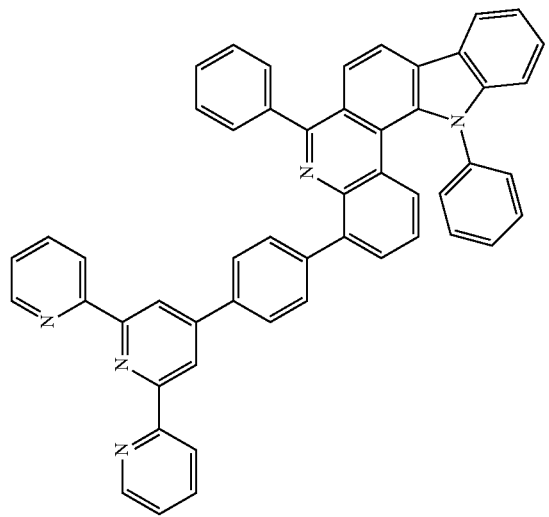 | 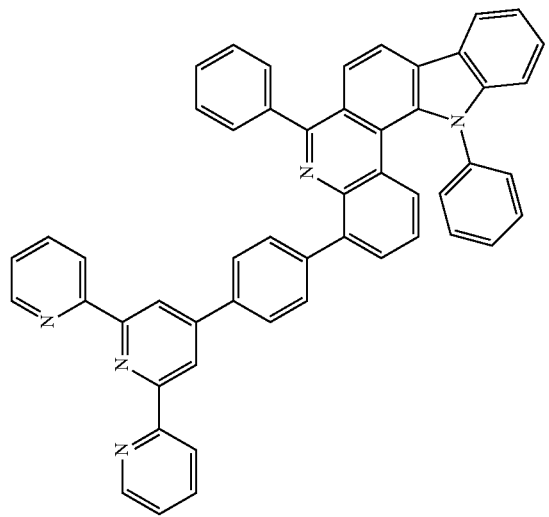 | 59% |

TABLE 1-continued
| Compound No. | A | B | C | Target Compound | Yield |
|---|---|---|---|---|---|
| 1-29 | 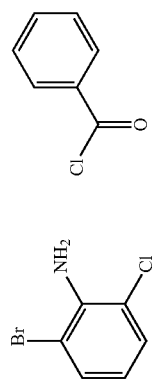 | 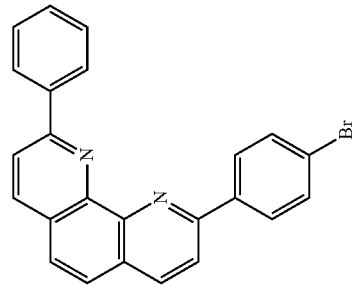 | 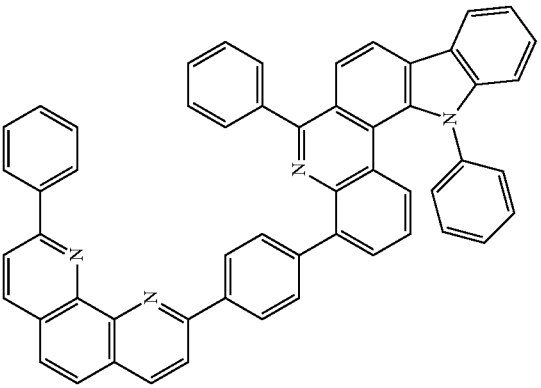 | 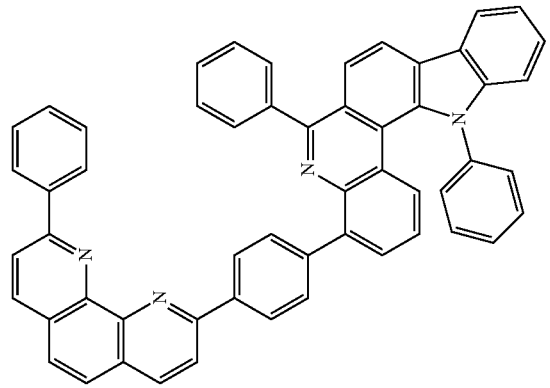 | 61% |

TABLE 1-continued
| Compound No. | A | B | C | Target Compound | Yield |
|---|---|---|---|---|---|
| 1-32 | | | |  | 70% |

TABLE 1-continued
| Compound No. | A | B | C | Target Compound | Yield |
|---|---|---|---|---|---|
| 1-40 | 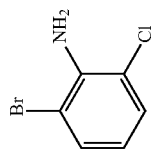 | 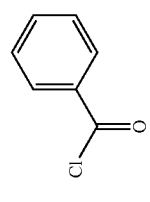 | 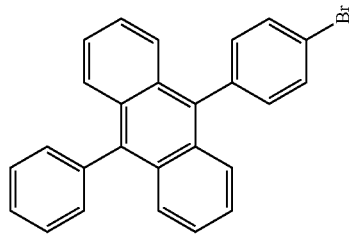 | 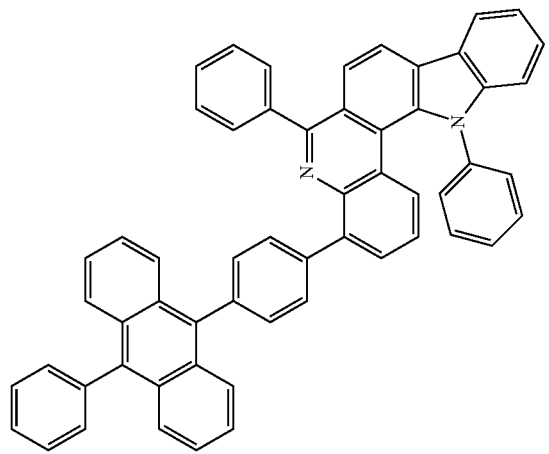 | 49% |

TABLE 1-continued
| Compound No. | A | B | C | Target Compound | Yield |
|---|---|---|---|---|---|
| 1-42 | 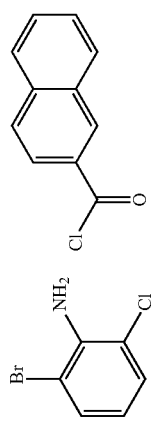 | 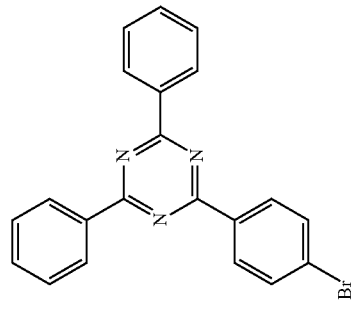 | 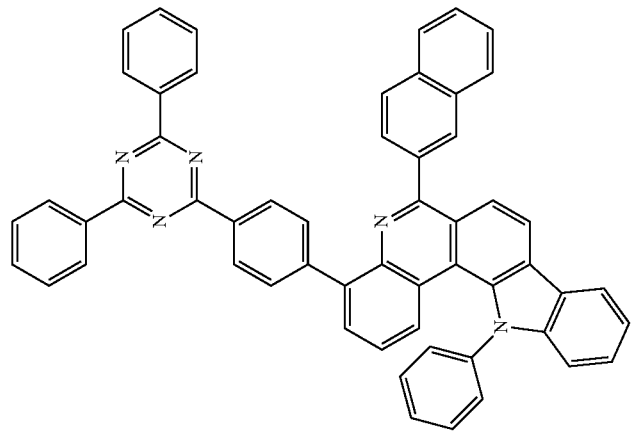 | 55% |

TABLE 1-continued
| Compound No. | A | B | C | Target Compound | Yield |
|---|---|---|---|---|---|
| 1-43 | | 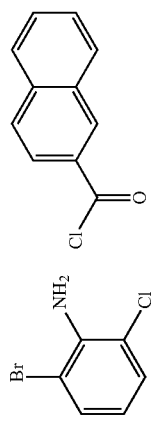 | 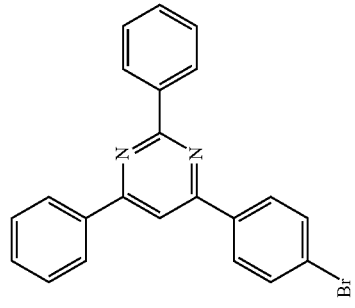 | 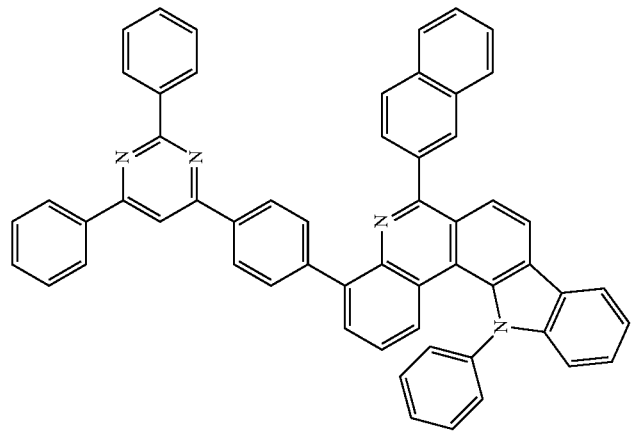 | 59% |

TABLE 1-continued
| Compound No. | A | B | C | Target Compound | Yield |
|---|---|---|---|---|---|
| 2-1 | 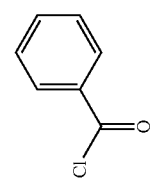 | 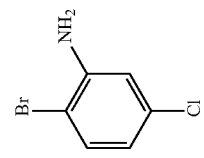 | 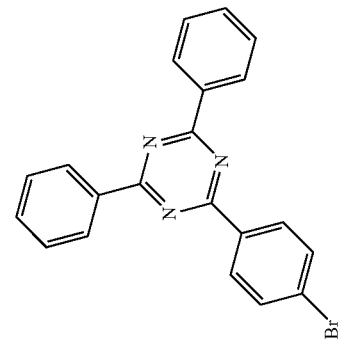 | 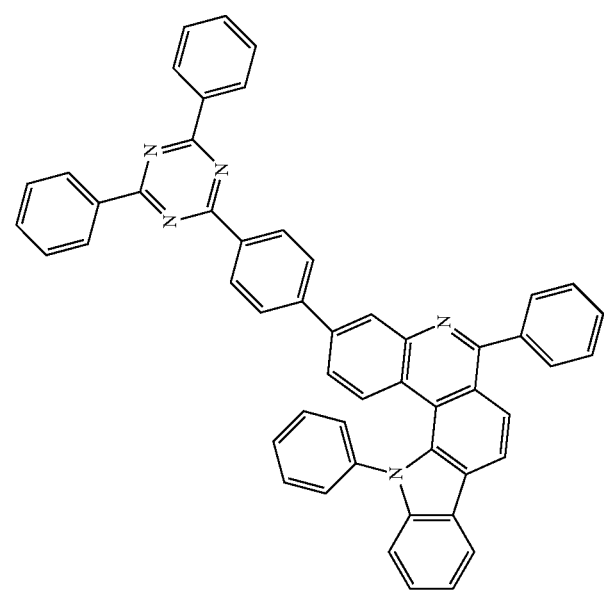 | 44% |

TABLE 1-continued
| Compound No. | A | B | C | Target Compound | Yield |
|---|---|---|---|---|---|
| 2-3 | 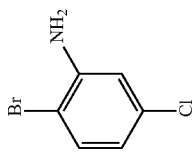 | 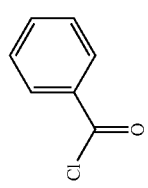 | 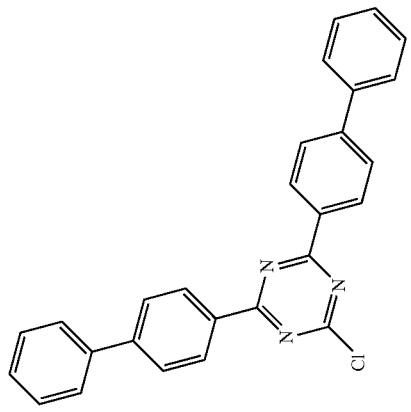 | 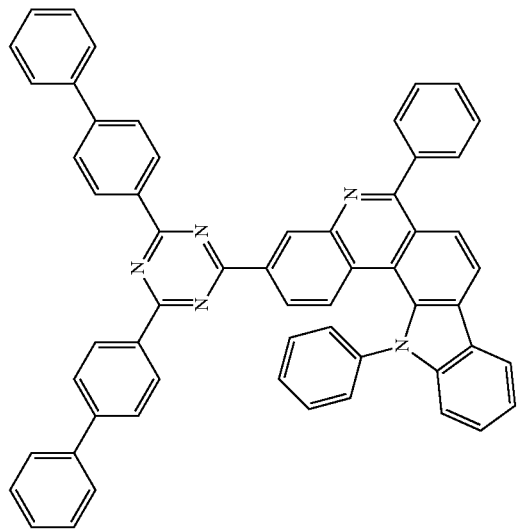 | 63% |

TABLE 1-continued
| Compound No. | A | B | C | Target Compound | Yield |
|---|---|---|---|---|---|
| 2-5 | | | | | 71% |
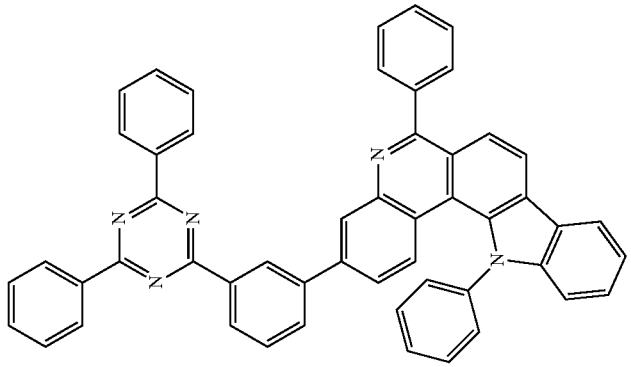

TABLE 1-continued
| Compound No. | A | B | C | Target Compound | Yield |
|---|---|---|---|---|---|
| 2-10 | 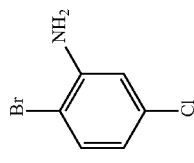 | 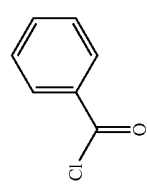 | 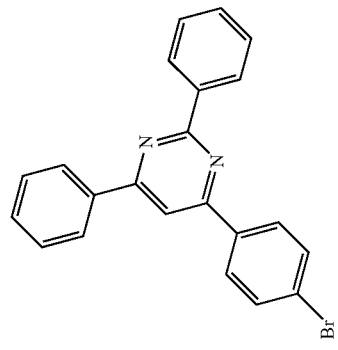 | 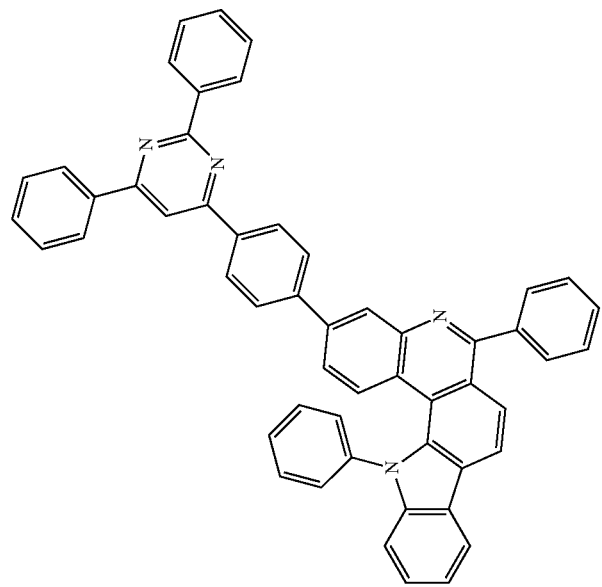 | 59% |

TABLE 1-continued
| Compound No. | A | B | C | Target Compound | Yield |
|---|---|---|---|---|---|
| 2-29 | 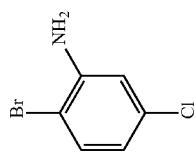 | 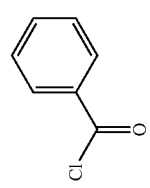 | 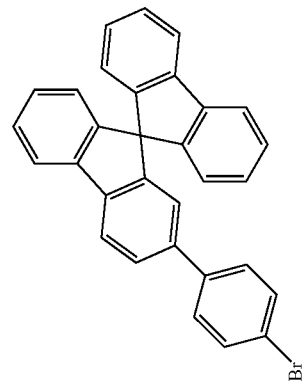 | 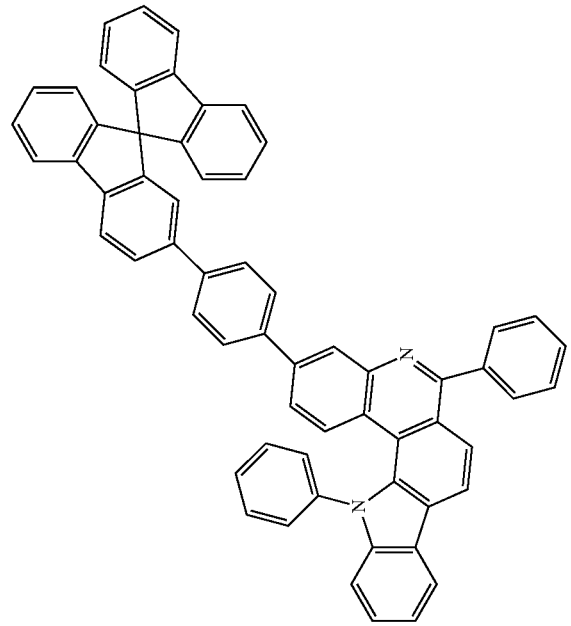 | 58% |

TABLE 1-continued
| Compound No. | A | B | C | Target Compound | Yield |
|---|---|---|---|---|---|
| 2-35 | | | | | 66% |
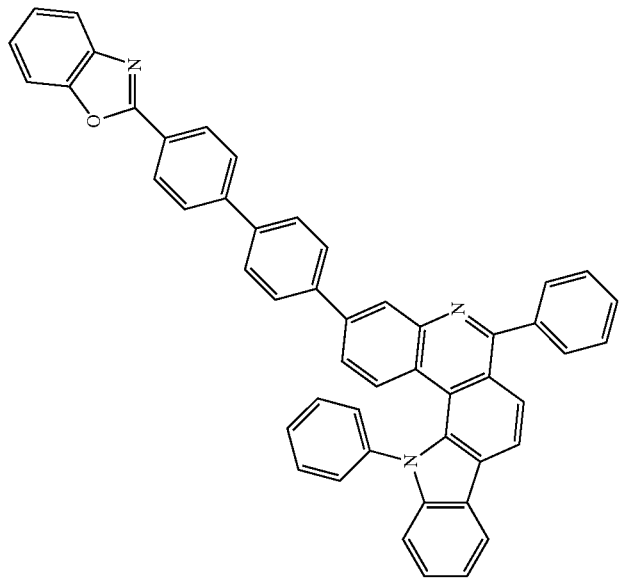

TABLE 1-continued
| Compound No. | A | B | C | Target Compound | Yield |
|---|---|---|---|---|---|
| 2-36 | 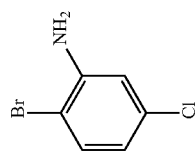 | 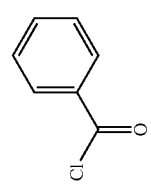 | 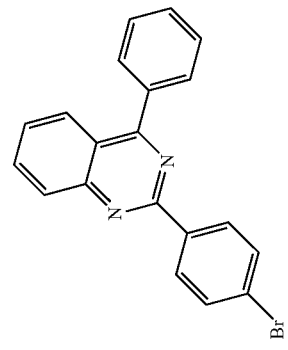 | 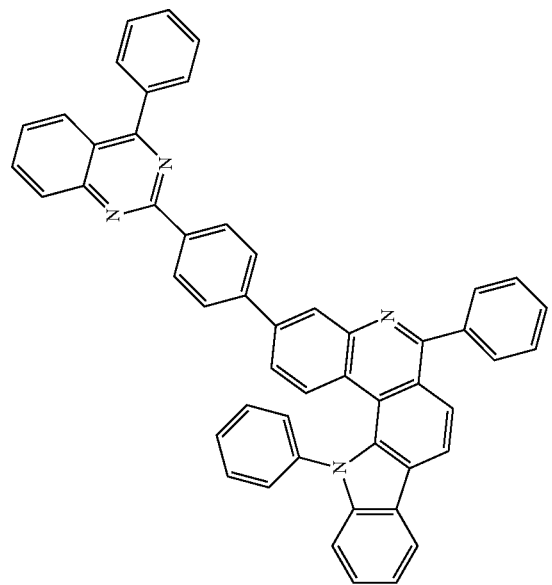 | 45% |

TABLE 1-continued
| Compound No. | A | B | C | Target Compound | Yield |
|---|---|---|---|---|---|
| 2-37 | | 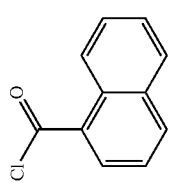 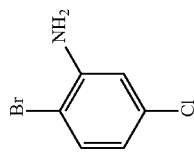 | 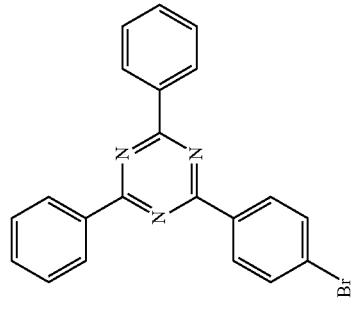 | 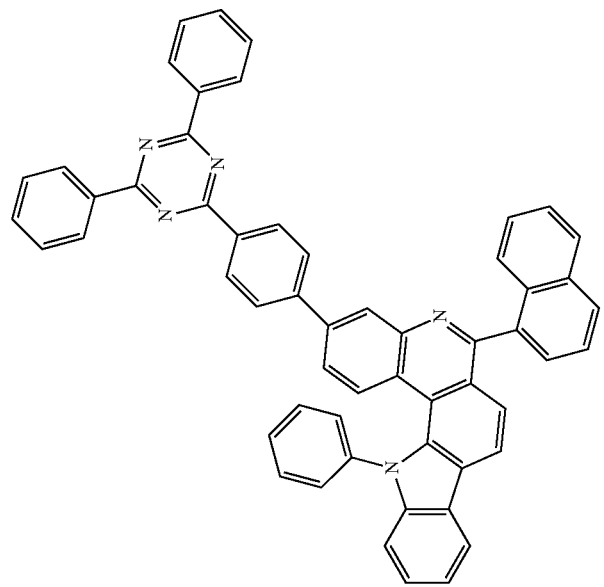 | 59% |

TABLE 1-continued
| Compound No. | A | B | C | Target Compound | Yield |
|---|---|---|---|---|---|
| 2-38 | | 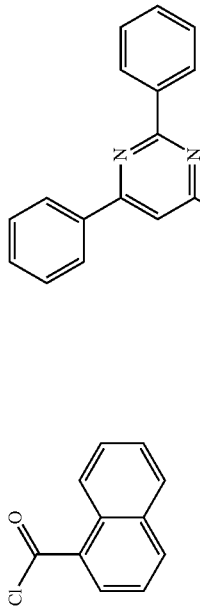 | 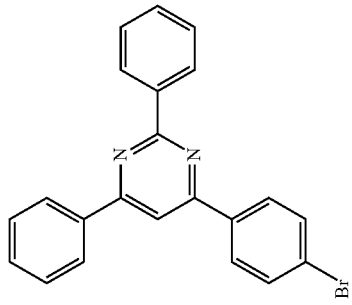 | 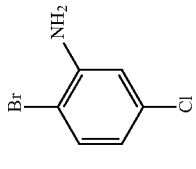 | 59% |
| | 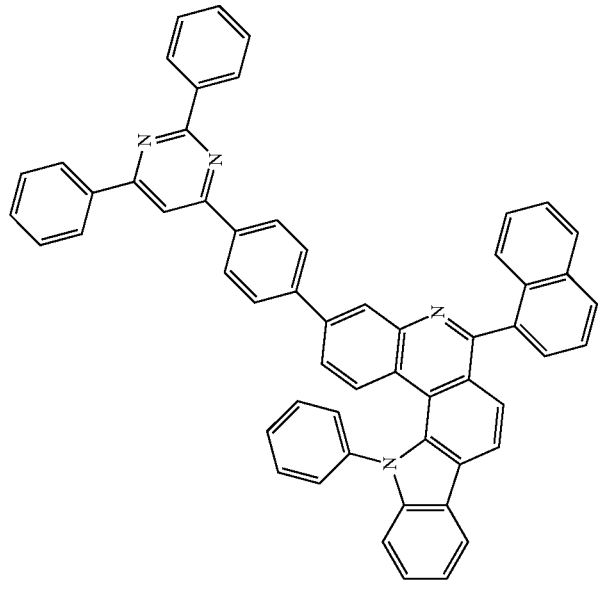 | | | | |

[Preparation Example 2] Preparation of Compound 3

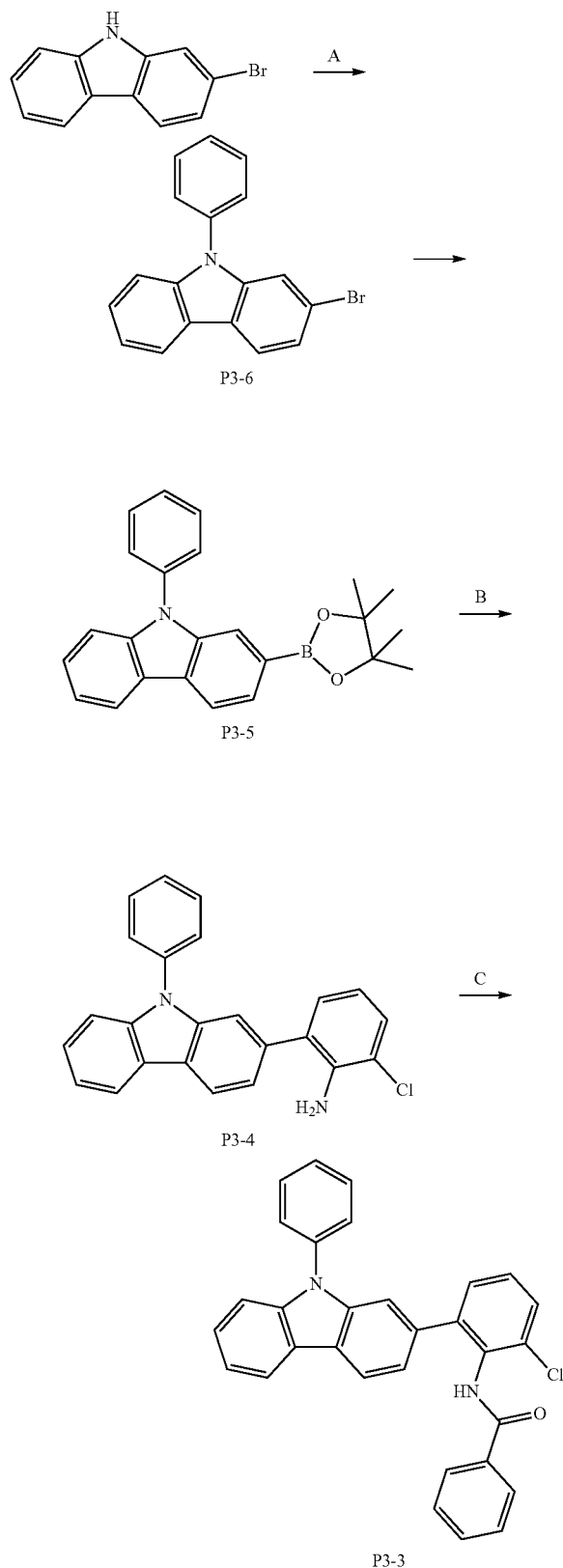

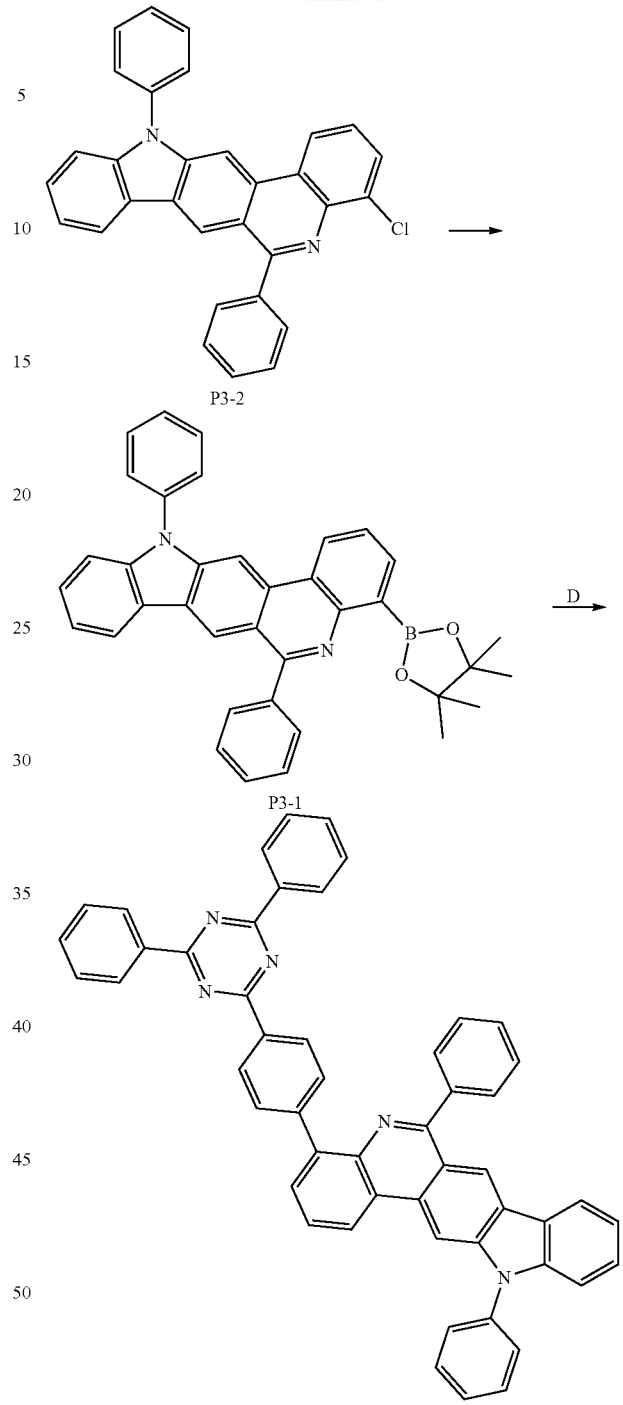

Preparation of Compound P3-6

After dissolving 2-bromo-9H-carbazole (100 g, 406.33 mmol), CuI (77.4 g, 406.33 mmol) and $K_3PO_4$ (258 g, 1.22 mol) in 1,4-dioxane (1.2 L), ($N_2$ condition) (±)-trans-1,2-diaminocyclohexane (49 mL, 406.33 mmol) and iodobenzene (59 mL, 528.23 mmol) were introduced thereto, and the result was stirred for 15 hours at 100° C. After the reaction was completed, the mixture solution was cooled to room temperature, the inorganic salt was filtered and removed, and the filtrate was concentrated and silica gel filtered. The solvent was removed from the filtered filtrate using a rotary evaporator to obtain Compound P3-6 (101 g, 77% yield).

Preparation of Compound P3-5

After dissolving P3-6 (100 g, 310.36 mmol) and bis(pinacolato)diboron (158 g, 620.73 mmol) in 1,4-dioxane (1 L), ($N_2$ condition) $PdCl_2$(dppf) (11 g, 15.52 mmol) and KOAc (91.3 g, 931.08 mmol) were introduced thereto, and the result was stirred for 14 hours at 100° C. After the reaction was completed, the mixture solution was dissolved in MC and extracted with water, and the organic layer was dried with anhydrous $MgSO_4$ and then silica gel filtered. The filtered filtrate was, after removing the solvent using a rotary evaporator, precipitated with EA/Hex, and then the precipitates were filtered to obtain Compound P3-5 (84 g, 74% yield).

Preparation of Compound P3-4

After dissolving Compound P3-5 (84 g, 227.48 mmol) and 2-bromo-6-chloroaniline (52 g, 250.23 mmol) in 1,4-dioxane (900 mL) and $H_2O$ (200 ml), ($N_2$ condition) Pd($PPh_3$) 4 (7.9 g, 6.82 mmol) and $K_3PO_4$ (92 g, 427.76 mmol) were introduced thereto, and the result was stirred for 4 hours at 100° C. After the reaction was completed, the mixture solution was dissolved in MC and extracted with water, and the organic layer was dried with anhydrous $MgSO_4$ and then silica gel filtered. The filtered filtrate was, after removing the solvent using a rotary evaporator, precipitated with EA/Hex, and then the precipitates were filtered to obtain Compound P3-4 (59 g, 71% yield).

Preparation of Compound P3-3

After dissolving Compound P3-4 (59 g, 159.95 mmol) in MC (700 ml), triethylamine (67 ml, 479.87 mmol) was introduced thereto, and benzoyl chloride (20 ml, 175.95 mmol) was slowly added dropwise thereto at 0° C. The reaction temperature was raised to room temperature after 30 minutes, and the result was stirred for 3 hours. After the reaction was completed, the mixture solution was extracted with distilled water, and the organic layer was dried with anhydrous $MgSO_4$ and then silica gel filtered. The filtered filtrate was, after removing the solvent using a rotary evaporator, precipitated with EA/Hex, and then the precipitates were filtered to obtain Compound P3-3 (50 g, 66% yield).

Preparation of Compound P3-2

After dissolving Compound P3-3 (50 g, 105.57 mmol) in nitrobenzene (400 ml), $POCl_3$ (10 ml, 105.57 mmol) was introduced thereto, and the result was stirred for 15 hours at 150° C. After the reaction was completed, the mixture solution was cooled to 0° C., and then 1 M $Na_2CO_3$ (aq) was slowly added thereto to adjust the pH to 10 to 11. The organic layer extracted with distilled water was dried with anhydrous $MgSO_4$ and then silica gel filtered. The filtered filtrate was, after removing the solvent using a rotary evaporator, precipitated with MC/MeOH, and then the precipitates were filtered to obtain Compound P3-2 (28 g 58% yield).

Preparation of Compound P3-1

After dissolving P3-2 (28 g, 61.55 mmol) and bis(pinacolato)diboron (32 g, 123.09 mmol) in 1,4-dioxane (300 ml), ($N_2$ condition) Pd(dba)$_2$ (3.5 g, 6.15 mmol), SPhos (4.9 g, 12.31 mmol) and KOAc (18.1 g, 184.52 mmol) were introduced thereto, and the result was stirred for 15 hours at 100° C. After the reaction was completed, the mixture solution was dissolved in MC and extracted with water, and the organic layer was dried with anhydrous $MgSO_4$ and then silica gel filtered. The filtered filtrate was, after removing the solvent using a rotary evaporator, precipitated with MC/MeOH, and then the precipitates were filtered to obtain Compound P3-1 (28 g, 85% yield).

Preparation of Compound 3

After dissolving Compound P3-1 (7 g, 12.81 mmol) and 2-(4-bromophenyl)-4,6-diphenyl-1,3,5-triazine (5.5 g, 14.09 mmol) in 1,4-dioxane (100 ml) and $H_2O$ (20 ml), ($N_2$ condition) Pd($PPh_3$)$_4$ (0.74 g, 0.64 mmol) and $K_3PO_4$ (5.4 g, 25.62 mmol) were introduced thereto, and the result was stirred for 6 hours at 100° C. After the reaction was completed, the result was cooled to room temperature, and precipitated solids were filtered and washed with solvents of $H_2O$ and MeOH. The filtered solids were dried, then dissolved in an excess amount of hot 1,2-dichlorobenzene solvent, and silica gel filtered. The filtered filtrate was, after removing the solvent using a rotary evaporator, precipitated with MeOH, and then the precipitates were filtered to obtain Compound 3 (5.5 g, 59% yield).

Target compounds were synthesized in the same manner as in Preparation Example 2 except that Intermediate A of the following Table 2 was used instead of iodobenzene, the compound of Reaction A, Intermediate B of the following Table 2 was used instead of 2-bromo-6-chloroaniline, the compound of Reaction B, Intermediate C of the following Table 2 was used instead of benzoyl chloride of Reaction C, and Intermediate D of the following Table 2 was used instead of 2-(4-bromophenyl)-4,6-diphenyl-1,3,5-triazine of Reaction D.

TABLE 2

| Compound No. | A | B | C | D | Target Compound | Yield |
|---|---|---|---|---|---|---|
| 3-1 | (iodobenzene) | (2-bromo-6-chloroaniline) | (benzoyl chloride) | (2-([1,1'-biphenyl]-4-yl)-4-(4-bromophenyl)-6-phenyl-1,3,5-triazine) | (target compound structure) | 68% |

TABLE 2-continued

| Compound No. | A | B | C | D | Target Compound | Yield |
|---|---|---|---|---|---|---|
| 3-5 | (iodobenzene) | (2-bromo-6-chloroaniline) | (benzoyl chloride) | (triazine-carbazole-phenyl intermediate with Br) | (target compound) | 47% |

TABLE 2-continued
| Compound No. | A | B | C | D | Target Compound | Yield |
|---|---|---|---|---|---|---|
| 3-6 | 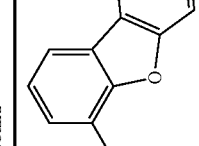 | 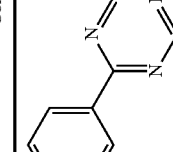 | 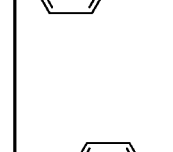 | 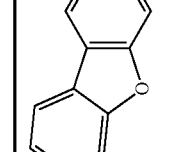 | 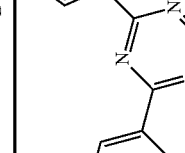 | 44% |

TABLE 2-continued

| Compound No. | A | B | C | D | Target Compound | Yield |
|---|---|---|---|---|---|---|
| 3-8 | [phenyl iodide] | [2-bromo-6-chloroaniline] | [benzoyl chloride] | [structure D] | [target compound structure] | 56% |

TABLE 2-continued

| Compound No. | A | B | C | D | Target Compound | Yield |
|---|---|---|---|---|---|---|
| 3-13 | (iodobenzene) | 2-bromo-6-chloroaniline | benzoyl chloride | (intermediate structure) | (target structure) | 61% |

TABLE 2-continued

| Compound No. | A | B | C | D | Target Compound | Yield |
|---|---|---|---|---|---|---|
| 3-38 | (iodobenzene) | 2-bromo-6-chloroaniline | benzoyl chloride | 4'-bromo-biphenyl-4-yl diphenylphosphine oxide | (target compound structure) | 58% |

TABLE 2-continued

| Compound No. | A | B | C | D | Target Compound | Yield |
|---|---|---|---|---|---|---|
| 3-39 | (iodobenzene) | 2-bromo-6-chloroaniline | 2-naphthoyl chloride | 2-(4-bromophenyl)-4,6-diphenyl-1,3,5-triazine | (target compound structure) | 74% |

TABLE 2-continued

| Compound No. | A | B | C | D | Target Compound | Yield |
|---|---|---|---|---|---|---|
| 3-42 | 2-iodonaphthalene | 2-bromo-6-chloroaniline | benzoyl chloride | 4-(4-bromophenyl)-2,6-diphenylpyrimidine | (structure shown) | 71% |

TABLE 2-continued
| Compound No. | A | B | C | D | Target Compound | Yield |
|---|---|---|---|---|---|---|
| 4 | 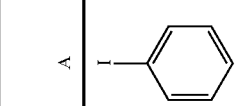 | 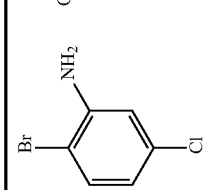 | 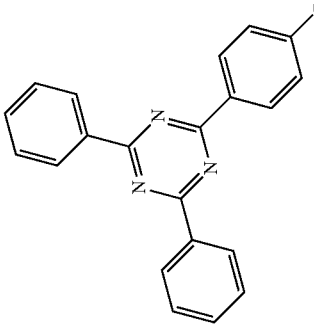 | 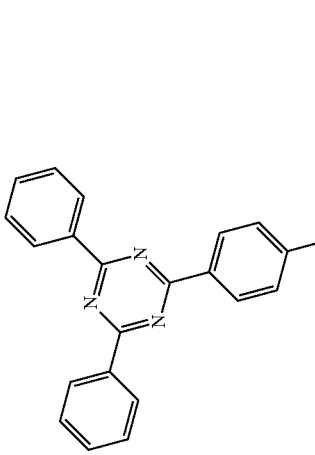 | 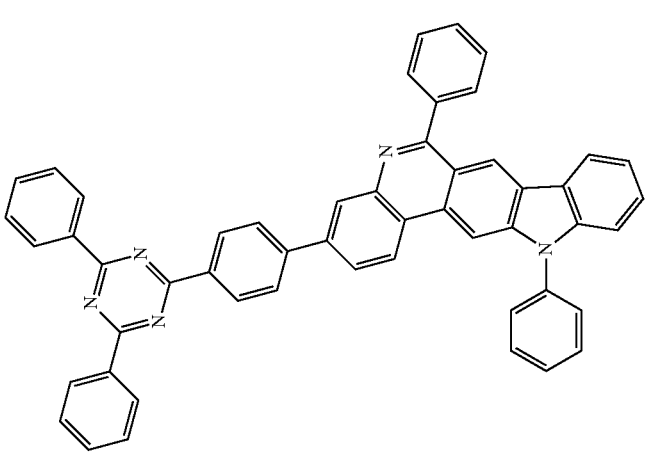 | 69% |

TABLE 2-continued
| Compound No. | A | B | C | D | Target Compound | Yield |
|---|---|---|---|---|---|---|
| 4-3 |  | 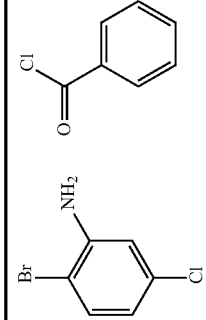 | 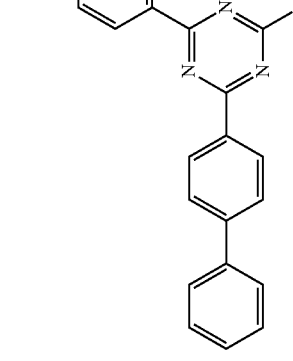 | 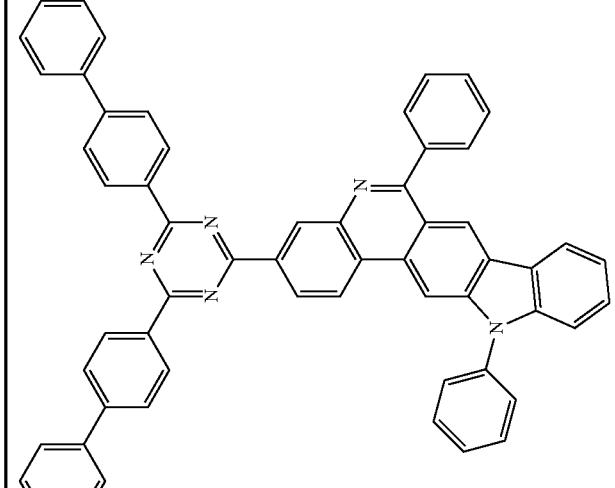 | 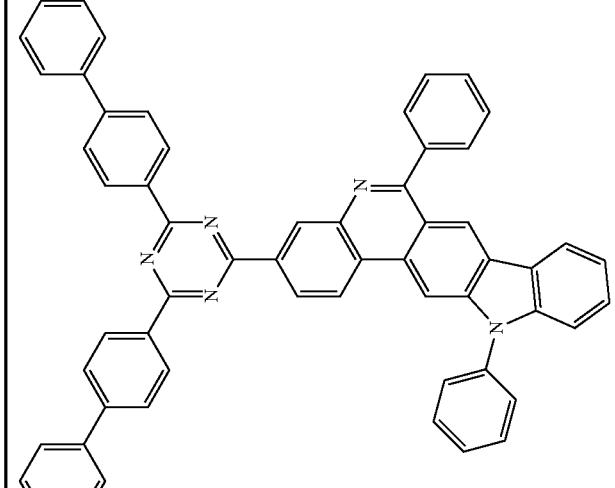 | 52% |

TABLE 2-continued

| Compound No. | A | B | C | D | Target Compound | Yield |
|---|---|---|---|---|---|---|
| 4-10 | phenyl iodide | 2-bromo-4-chloroaniline | benzoyl chloride | 2,4-diphenyl-6-(4-bromophenyl)pyrimidine | (structure shown) | 70% |

TABLE 2-continued

| Compound No. | A | B | C | D | Target Compound | Yield |
|---|---|---|---|---|---|---|
| 4-13 | (iodobenzene) | 2-bromo-4-chloroaniline | benzoyl chloride | (chloropyrimidine intermediate) | (target compound structure) | 63% |

TABLE 2-continued

| Compound No. | A | B | C | D | Target Compound | Yield |
|---|---|---|---|---|---|---|
| 4-22 | (iodobenzene) | 2-bromo-4-chloroaniline | benzoyl chloride | 2-(4-bromonaphthalen-1-yl)-4,6-diphenylpyrimidine | (target compound structure) | 49% |

TABLE 2-continued

| Compound No. | A | B | C | D | Target Compound | Yield |
|---|---|---|---|---|---|---|
| 4-29 | (3-iodopyridine) | (2-bromo-4-chloroaniline) | (benzoyl chloride) | (2-chloro-9-phenyl-1,10-phenanthroline) | (target compound structure) | 60% |

TABLE 2-continued
| Compound No. | A | B | C | D | Target Compound | Yield |
|---|---|---|---|---|---|---|
| 4-34 | 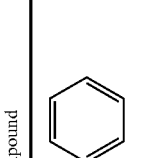 | 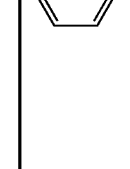 | 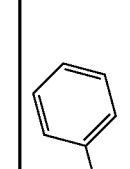 | 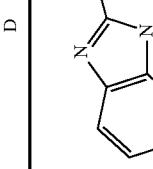 | 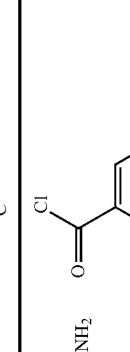 | 54% |

TABLE 2-continued

| Compound No. | A | B | C | D | Target Compound | Yield |
|---|---|---|---|---|---|---|
| 4-39 | 2-iodonaphthalene | 2-bromo-4-chloroaniline | benzoyl chloride | 2-(4-bromophenyl)-4,6-diphenylpyrimidine | (structure shown) | 55% |

TABLE 2-continued
| Compound No. | A | B | C | D | Target Compound | Yield |
|---|---|---|---|---|---|---|
| 4-40 |  | 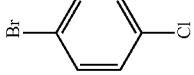 | 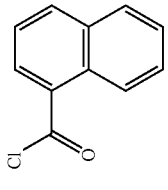 | 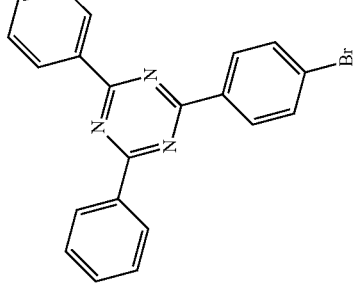 | 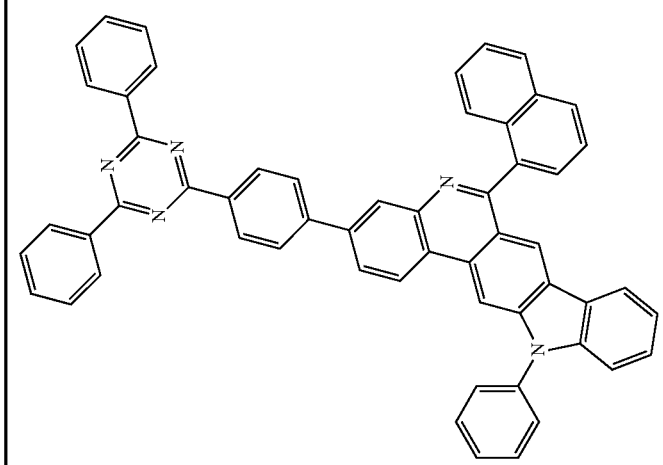 | 60% |

TABLE 2-continued
| Compound No. | A | B | C | D | Target Compound | Yield |
|---|---|---|---|---|---|---|
| 5-12 |  | 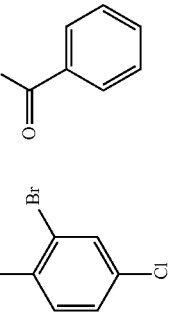 | 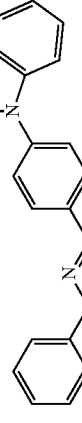 | 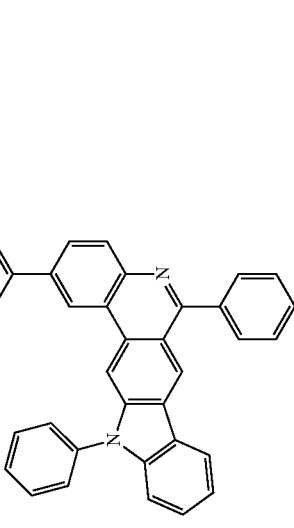 | 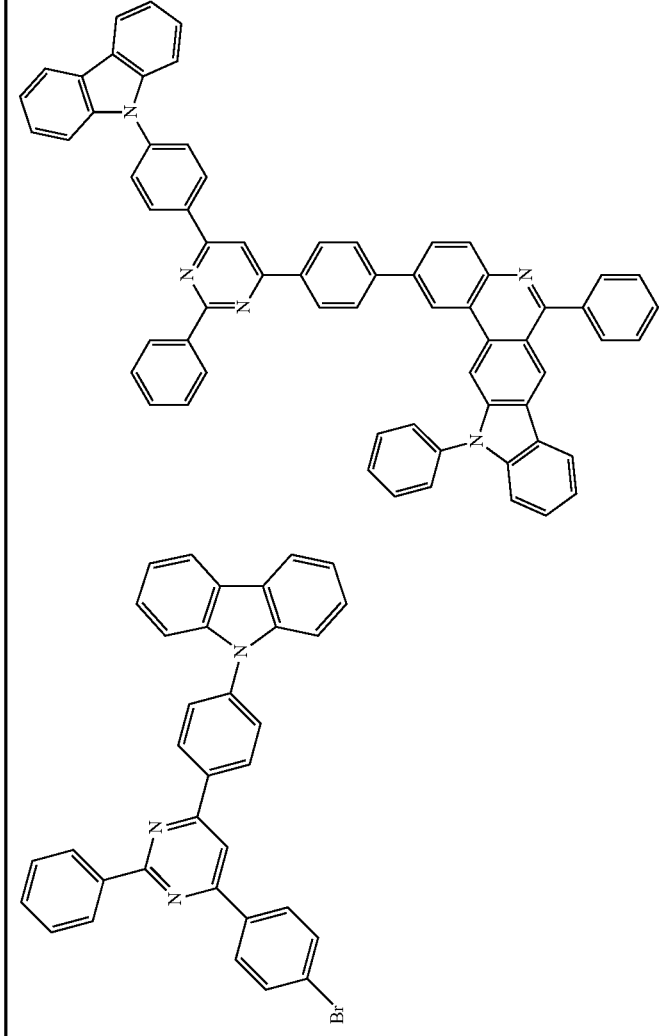 | 51% |

TABLE 2-continued

| Compound No. | A | B | C | D | Target Compound | Yield |
|---|---|---|---|---|---|---|
| 5-15 | phenyl iodide | 2-bromo-4-chloroaniline | benzoyl chloride | (structure) | (structure) | 44% |

TABLE 2-continued

| Compound No. | A | B | C | D | Target Compound | Yield |
|---|---|---|---|---|---|---|
| 5-20 | (iodobenzene) | 2-bromo-4-chloroaniline | benzoyl chloride | (pyrimidine intermediate with Br) | (target compound) | 64% |

TABLE 2-continued
| Compound No. | A | B | C | D | Target Compound | Yield |
|---|---|---|---|---|---|---|
| 5-27 | 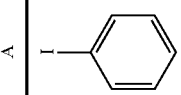 |  |  | 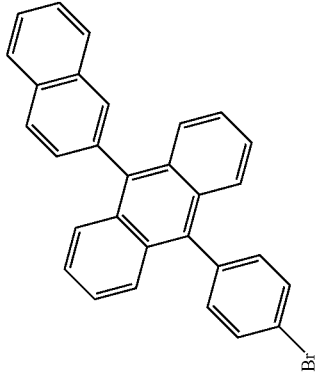 | 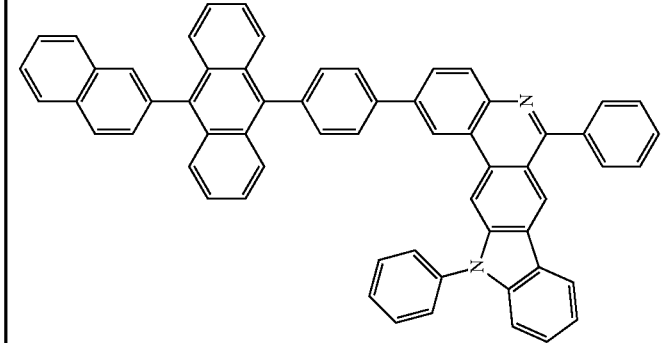 | 55% |

TABLE 2-continued
| Compound No. | A | B | C | D | Target Compound | Yield |
|---|---|---|---|---|---|---|
| 5-32 | 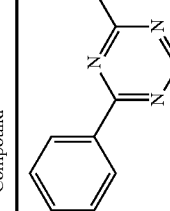 | 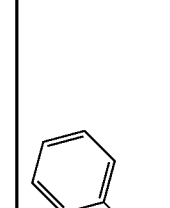 | 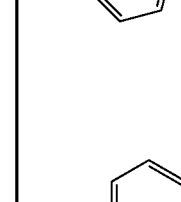 | 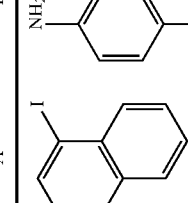 | 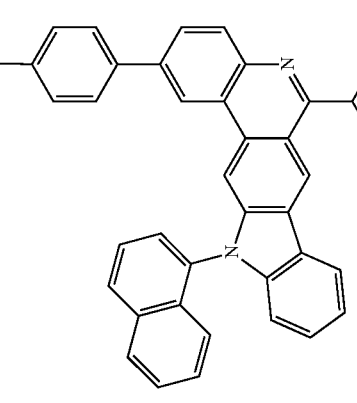 | 60% |

TABLE 2-continued
| Compound No. | A | B | C | D | Target Compound | Yield |
|---|---|---|---|---|---|---|
| 5-35 |  | 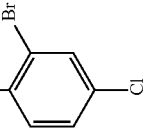 | 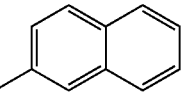 | 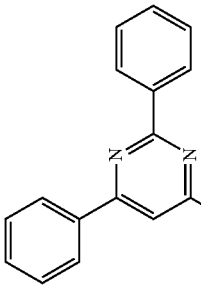 | 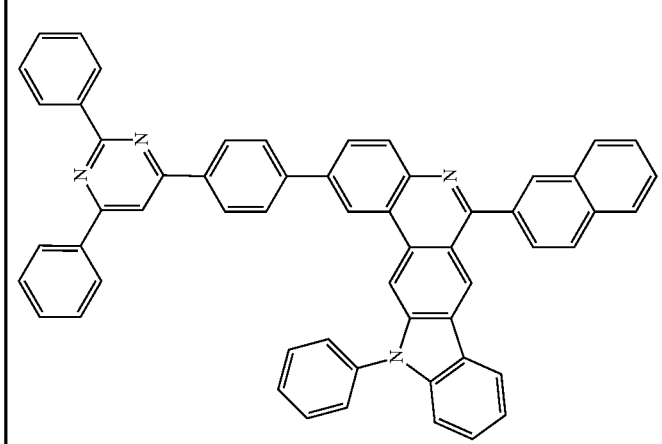 | 63% |

[Preparation Example 3] Preparation of Compound 6

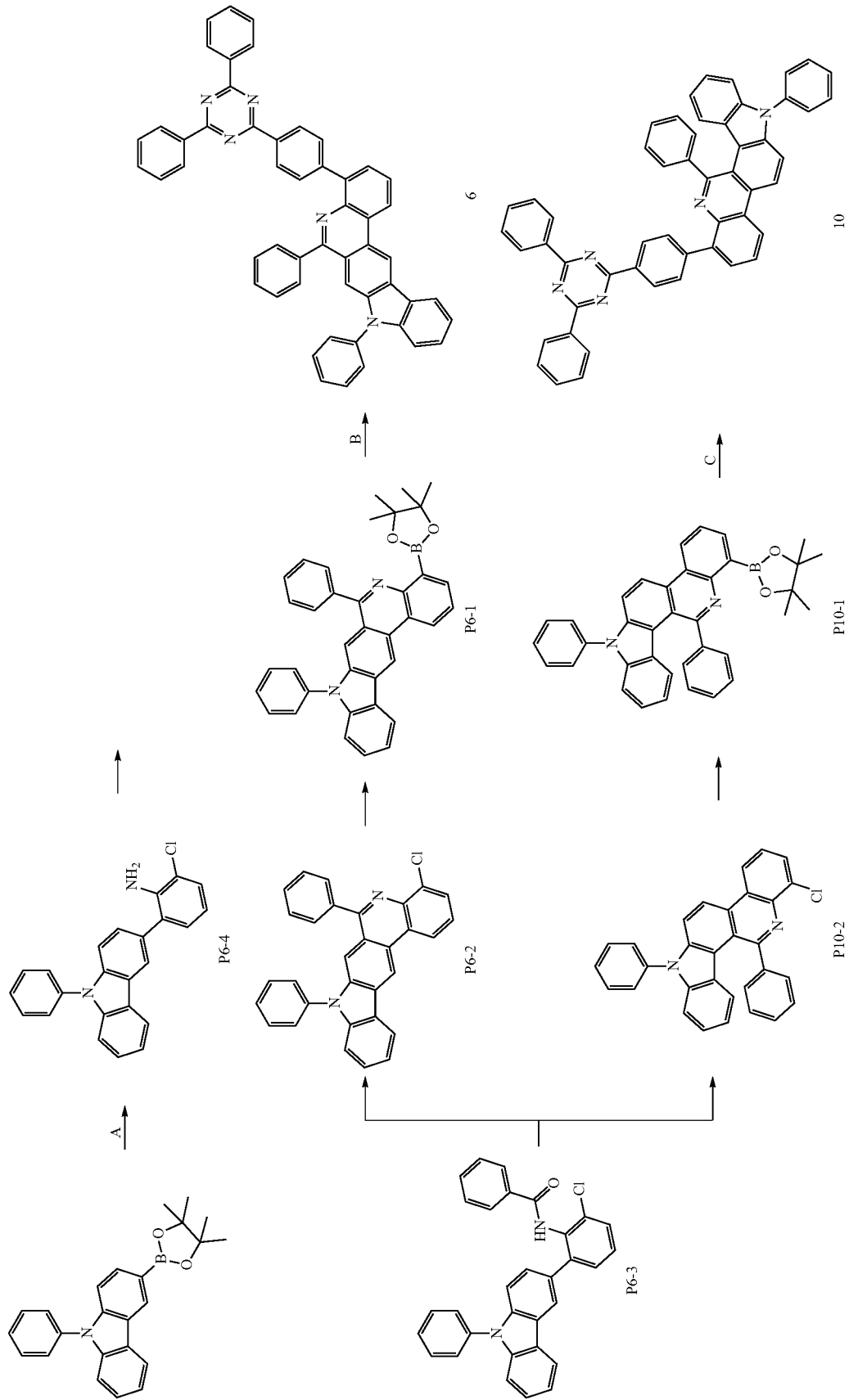

Preparation of Compound P6-4

After dissolving 9-phenyl-3-(4,4,5,5-tetramethyl-1,3,2-dioxaborolan-2-yl)-9H-carbazole (107 g, 289.69 mmol) and 2-bromo-6-chloroaniline (66 g, 318.65 mmol) in 1,4-dioxane (1 L) and $H_2O$ (300 ml), ($N_2$ condition) Pd(PPh$_3$)$_4$ (10 g, 8, 69 mmol) and $K_3PO_4$ (123 g, 579.38 mmol) were introduced thereto, and the result was stirred for 6 hours at 100° C. After the reaction was completed, the mixture solution was dissolved in MC and extracted with water, and the organic layer was dried with anhydrous $MgSO_4$ and then silica gel filtered. The filtered filtrate was, after removing the solvent using a rotary evaporator, precipitated with EA/Hex, and then the precipitates were filtered to obtain Compound P6-4 (64 g, 60% yield).

Preparation of Compound P6-3

After dissolving Compound P6-4 (64 g, 173.51 mmol) in MC (700 ml), triethylamine (73 ml, 520.54 mmol) was introduced thereto, and benzoyl chloride (22 ml, 190.86 mmol) was slowly added dropwise thereto at 0° C. The reaction temperature was raised to room temperature after 30 minutes, and the result was stirred for 4 hours. After the reaction was completed, the mixture solution was extracted with distilled water, and the organic layer was dried with anhydrous $MgSO_4$ and then silica gel filtered. The filtered filtrate was, after removing the solvent using a rotary evaporator, precipitated with EA/Hex, and then the precipitates were filtered to obtain Compound P6-3 (62 g, 75% yield).

Preparation of Compound P6-2

After dissolving Compound P6-3 (62 g, 131.08 mmol) in nitrobenzene (500 ml), POCl$_3$ (12 ml, 131.08 mmol) was introduced thereto, and the result was stirred for 15 hours at 150° C. After the reaction was completed, the mixture solution was cooled to 0° C., and then 1 M $Na_2CO_3$ (aq) was slowly added thereto to adjust the pH to 10 to 11. The organic layer extracted with distilled water was dried with anhydrous $MgSO_4$ and then silica gel filtered. The filtered filtrate was, after removing the solvent using a rotary evaporator, column chromatographed <MC/Hex=2/1> to obtain each of P6-2 (23 g) and P10-2 (17.2 g).

Preparation of Compound P6-1

After dissolving Compound P6-2 (23 g, 42.13 mmol) and bis(pinacolato)diboron (21.5 g, 84.29 mmol) in 1,4-dioxane (200 ml), ($N_2$ condition) Pd(dba)$_2$ (2.4 g, 4.21 mmol), SPhos (3.5 g, 8.42 mmol) and KOAc (12.3 g, 126.39 mmol) were introduced thereto, and the result was stirred for 17 hours at 100° C. After the reaction was completed, the mixture solution was dissolved in MC and extracted with water, and the organic layer was dried with anhydrous $MgSO_4$ and then silica gel filtered. The filtered filtrate was, after removing the solvent using a rotary evaporator, precipitated with MC/MeOH, and then the precipitates were filtered to obtain Compound P6-1 (18 g, 80% yield).

Preparation of Compound 6

After dissolving Compound P6-1 (7 g, 12.81 mmol) and 2-(4-bromophenyl)-4,6-diphenyl-1,3,5-triazine (5.5 g, 14.09 mmol) in 1,4-dioxane (100 ml) and $H_2O$ (20 ml), ($N_2$ condition) Pd(PPh$_3$)$_4$ (0.74 g, 0.64 mmol) and $K_3PO_4$ (5.4 g, 25.62 mmol) were introduced thereto, and the result was stirred for 13 hours at 100° C. After the reaction was completed, the result was cooled to room temperature, and precipitated solids were filtered and washed with solvents of $H_2O$ and MeOH. The filtered solids were dried, then dissolved in an excess amount of hot 1,2-dichlorobenzene solvent, and silica gel filtered. The filtered filtrate was, after removing the solvent using a rotary evaporator, precipitated with MeOH, and then the precipitates were filtered to obtain Compound 6 (6.8 g, 72% yield).

Target compounds were synthesized in the same manner as in Preparation Example 3 except that Intermediate A of the following Table 3 was used instead of 2-bromo-6-chloroaniline, the compound of Reaction A, and Intermediate B or C of the following Table 3 was used instead of 2-(4-bromophenyl)-4,6-diphenyl-1,3,5-triazine of Reactions B and C.

TABLE 3
| Compound No. | A | B | C | Target Compound | Yield |
|---|---|---|---|---|---|
| 6-1 |  |  | — |  | 62% |
| 6-2 |  |  | — |  | 58% |

TABLE 3-continued
| Compound No. | A | B | C | Target Compound | Yield |
|---|---|---|---|---|---|
| 6-12 | 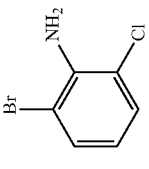 | 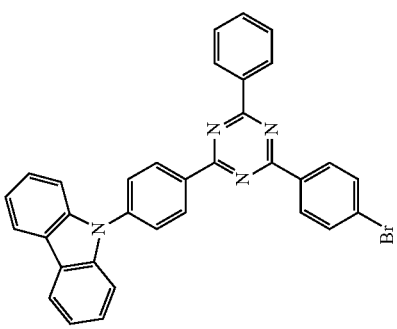 | — | 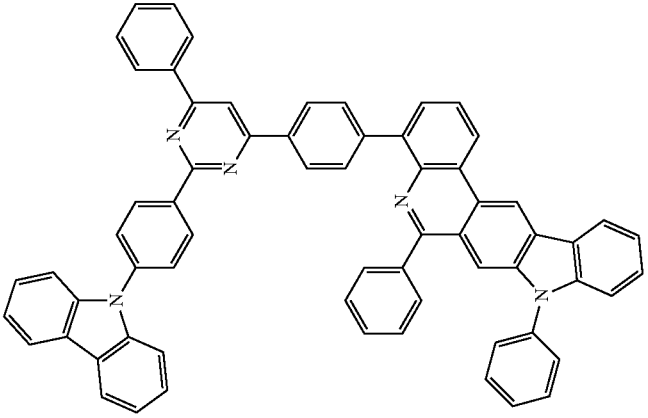 | 49% |

TABLE 3-continued
| Compound No. | A | B | C | Target Compound | Yield |
|---|---|---|---|---|---|
| 6-17 | | 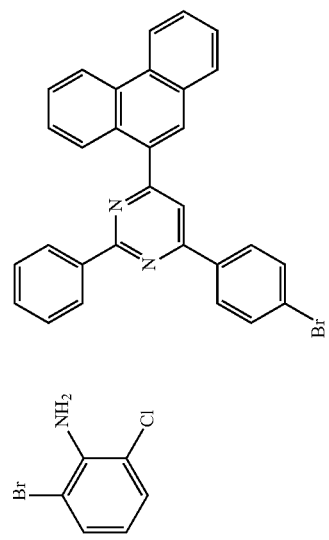 | — | 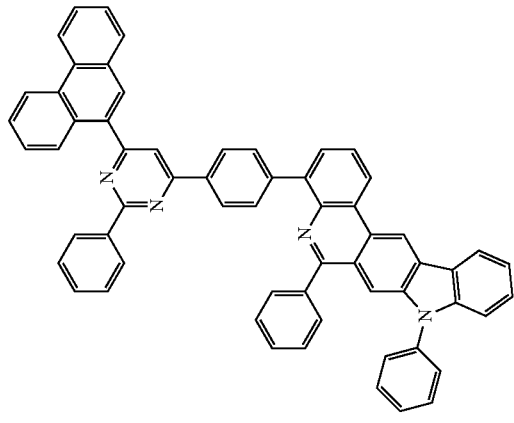 | 46% |

TABLE 3-continued
| Compound No. | A | B | C | Target Compound | Yield |
|---|---|---|---|---|---|
| 6-21 | | | — | 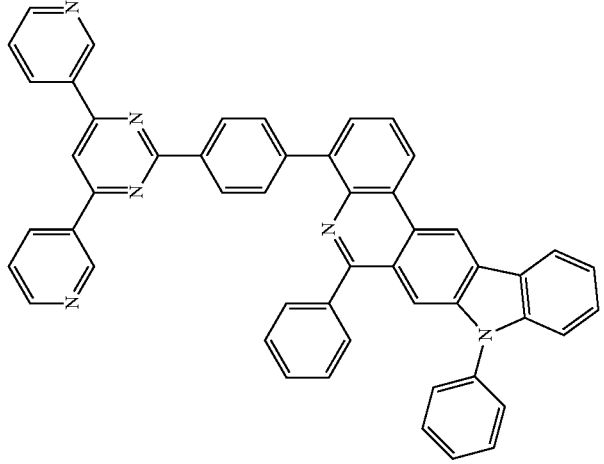 | 52% |

TABLE 3-continued
| Compound No. | A | B | C | Target Compound | Yield |
|---|---|---|---|---|---|
| 6-28 | 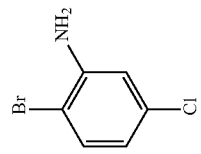 | 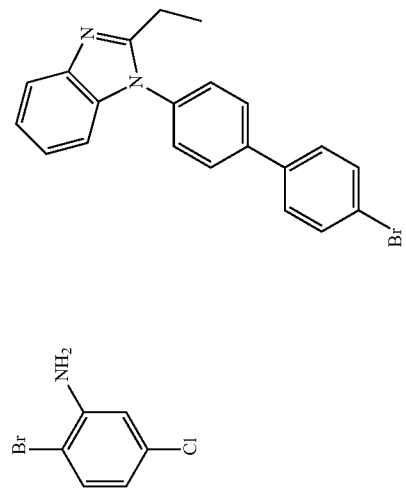 | — | 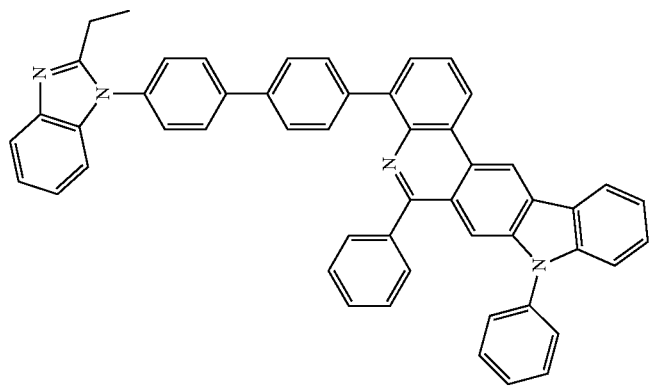 | 63% |

TABLE 3-continued
| Compound No. | A | B | C | Target Compound | Yield |
|---|---|---|---|---|---|
| 7-1 | 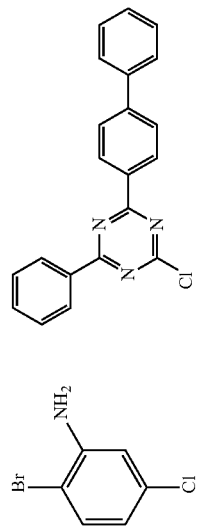 | | — | | 60% |

TABLE 3-continued
| Compound No. | A | B | C | Target Compound | Yield |
|---|---|---|---|---|---|
| 7-8 | | | — | | 51% |
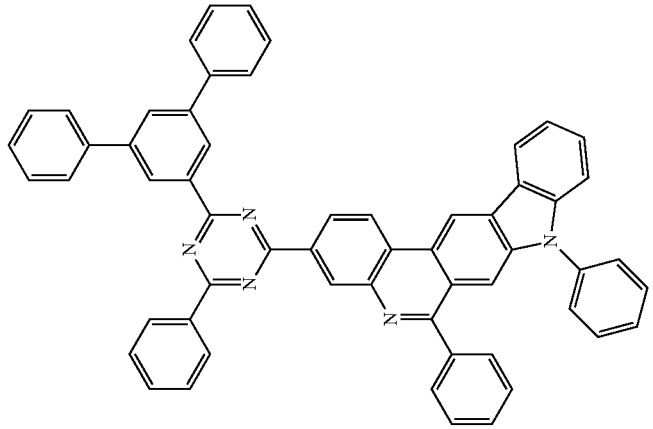

TABLE 3-continued
| Compound No. | A | B | C | Target Compound | Yield |
|---|---|---|---|---|---|
| 7-11 | | | — | | 68% |
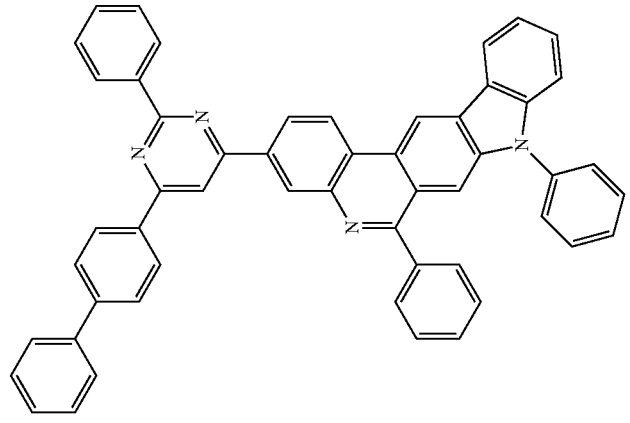

TABLE 3-continued
| Compound No. | A | B | C | Target Compound | Yield |
|---|---|---|---|---|---|
| 7-17 | | | — | | 63% |
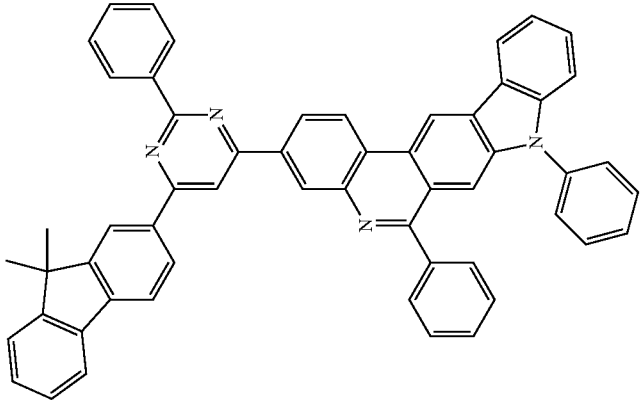

TABLE 3-continued
| Compound No. | A | B | C | Target Compound | Yield |
|---|---|---|---|---|---|
| 7-19 | | | — | | 72% |
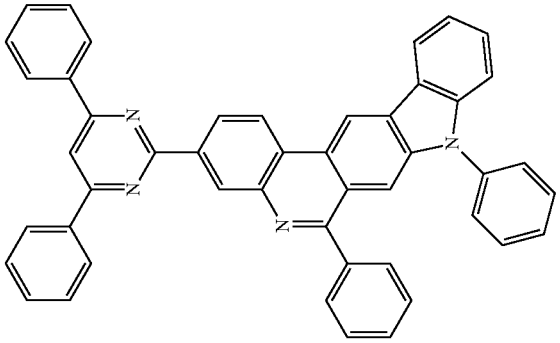

TABLE 3-continued

| Compound No. | A | B | C | Target Compound | Yield |
|---|---|---|---|---|---|
| 7-29 | | | — | | 76% |

TABLE 3-continued
| Compound No. | A | B | C | Target Compound | Yield |
|---|---|---|---|---|---|
| 8-1 | | | — | 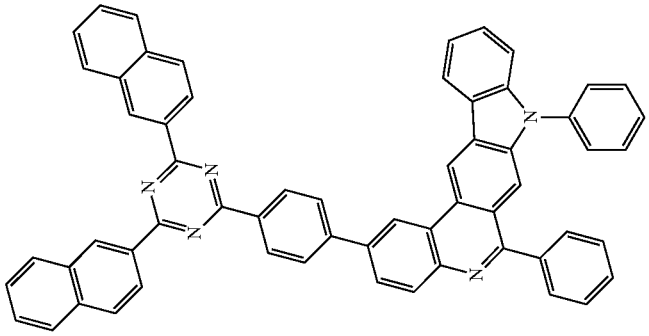 | 52% |

TABLE 3-continued
| Compound No. | A | B | C | Target Compound | Yield |
|---|---|---|---|---|---|
| 8-5 | 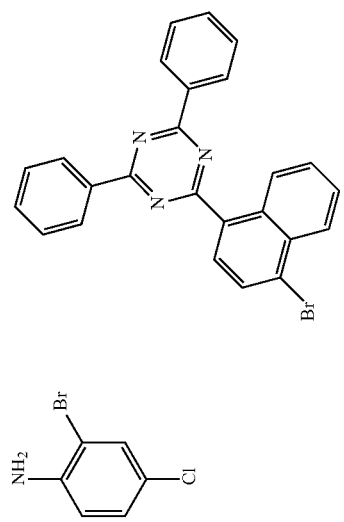 | 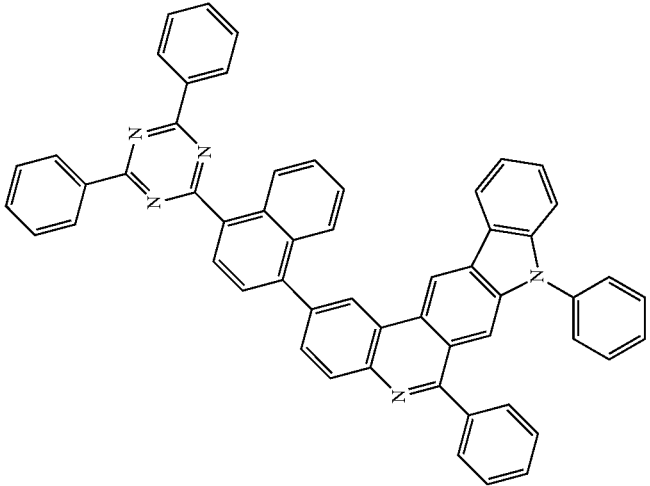 | — | | 47% |

| Compound No. | A | B | C | Target Compound | Yield |
|---|---|---|---|---|---|
| 8-10 | 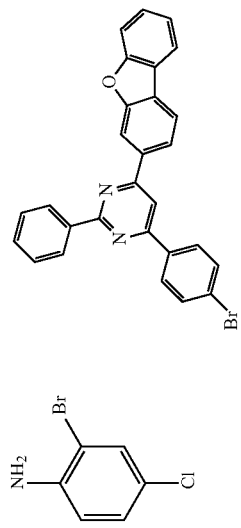 | 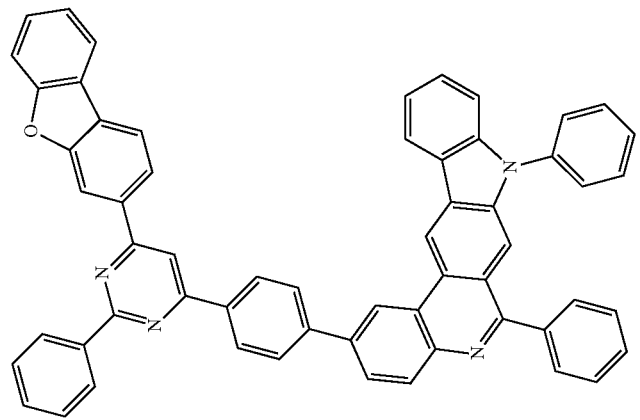 | — | | 51% |

TABLE 3-continued
| Compound No. | A | B | C | Target Compound | Yield |
|---|---|---|---|---|---|
| 8-15 | | | — | | 46% |
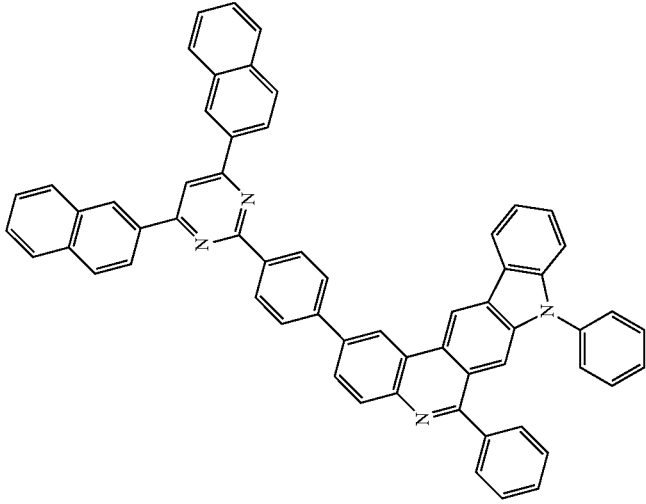

TABLE 3-continued
| Compound No. | A | B | C | Target Compound | Yield |
|---|---|---|---|---|---|
| 8-19 | | | — | | 68% |
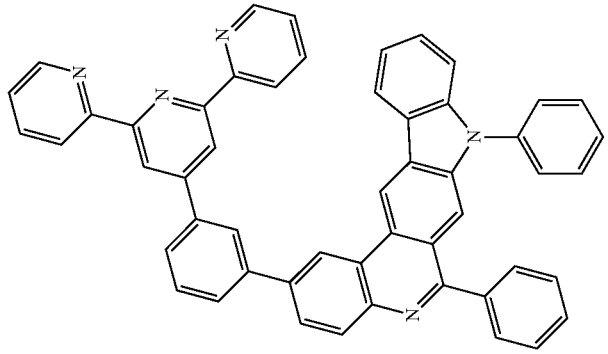

| Compound No. | A | B | C | Target Compound | Yield |
|---|---|---|---|---|---|
| 8-26 | 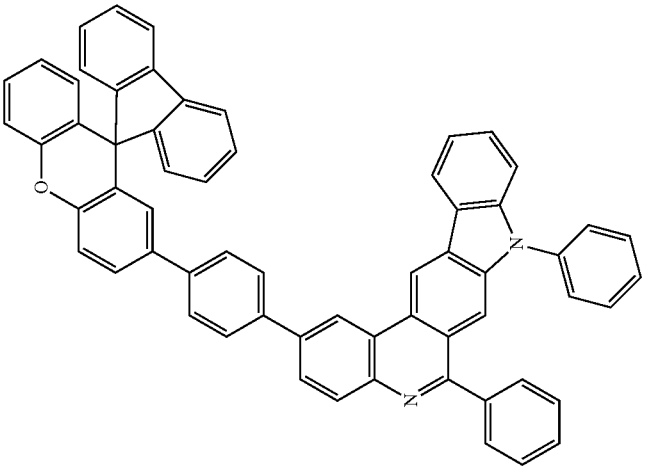 | | — | | 43% |

| Compound No. | A | B | C | Target Compound | Yield |
|---|---|---|---|---|---|
| 9-6 | 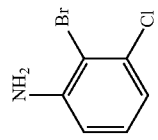 | 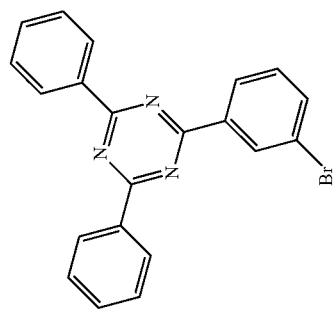 | — | 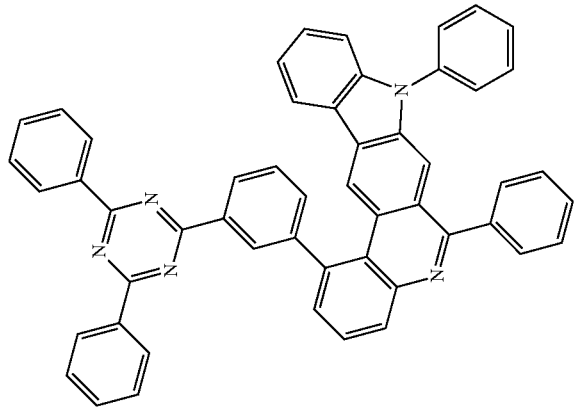 | 41% |

TABLE 3-continued
| Compound No. | A | B | C | Target Compound | Yield |
|---|---|---|---|---|---|
| 9-9 | 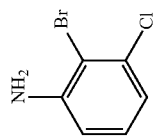 | 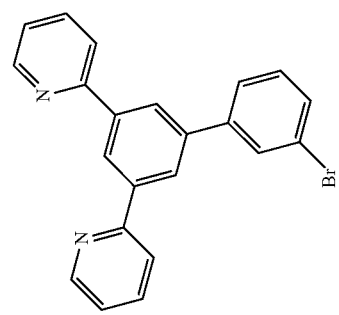 | — | 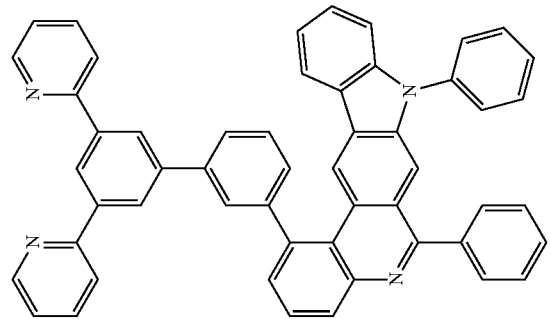 | 38% |

TABLE 3-continued

| Compound No. | A | B | C | Target Compound | Yield |
|---|---|---|---|---|---|
| 9-12 | 2-bromo-3-chloroaniline | 1-ethyl-2-(4'-bromobiphenyl-4-yl)benzimidazole | — | (structure) | 45% |
| 10 | 2-bromo-6-chloroaniline | — | 2-(4-bromophenyl)-4,6-diphenyl-1,3,5-triazine | (structure) | 66% |

TABLE 3-continued

| Compound No. | A | B | C | Target Compound | Yield |
|---|---|---|---|---|---|
| 10-4 | 2-bromo-6-chloroaniline | — | 2,4-di(naphthalen-2-yl)-6-(4-bromophenyl)-1,3,5-triazine | (structure) | 68% |
| 10-18 | 2-bromo-6-chloroaniline | — | 4-(4-bromophenyl)-1-(2,6-diphenylpyrimidin-4-yl)naphthalene | (structure) | 57% |

TABLE 3-continued
| Compound No. | A | B | C | Target Compound | Yield |
|---|---|---|---|---|---|
| 10-22 | 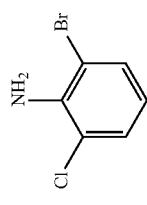 | — | 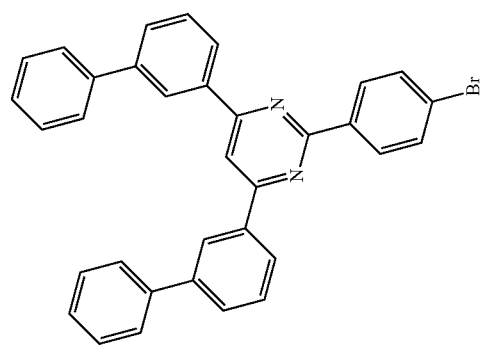 | 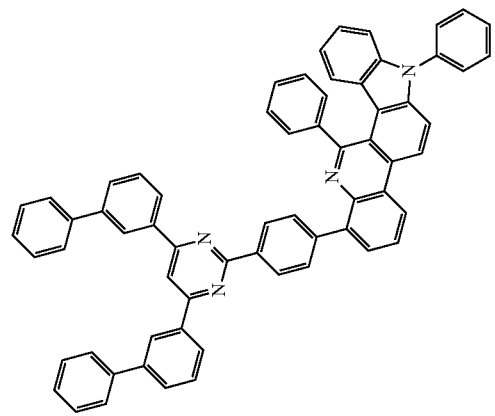 | 55% |

TABLE 3-continued
| Compound No. | A | B | C | Target Compound | Yield |
|---|---|---|---|---|---|
| 10-36 | 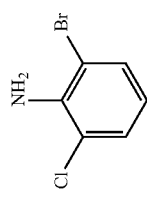 | — | 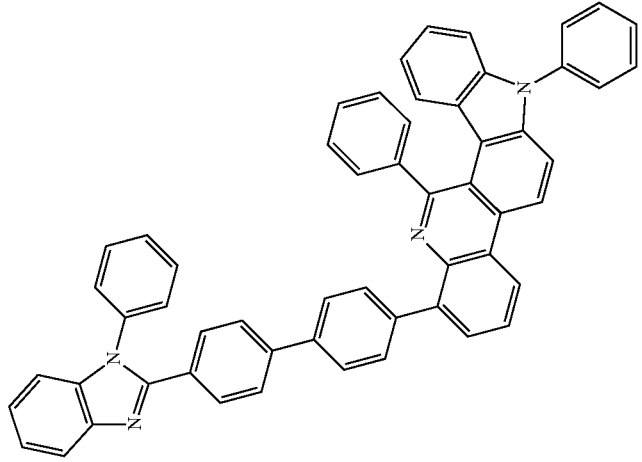 | | 50% |

TABLE 3-continued

| Compound No. | A | B | C | Target Compound | Yield |
|---|---|---|---|---|---|
| 10-40 | 2-bromo-6-chloroaniline (NH₂, Br, Cl substituted benzene) | — | [anthracene-phenyl-Br structure] | [target polycyclic structure] | 47% |

TABLE 3-continued
| Compound No. | A | B | C | Target Compound | Yield |
|---|---|---|---|---|---|
| 11 | 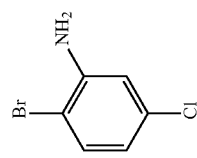 | — | (structure) | (structure) | 51% |

TABLE 3-continued
| Compound No. | A | B | C | Target Compound | Yield |
|---|---|---|---|---|---|
| 11-1 | | — | | | 59% |
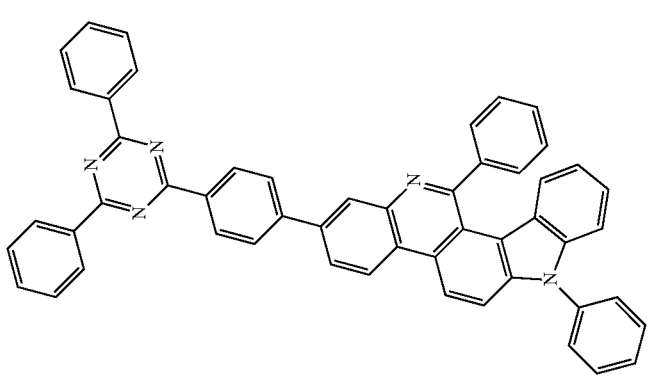

TABLE 3-continued
| Compound No. | A | B | C | Target Compound | Yield |
|---|---|---|---|---|---|
| 11-4 | 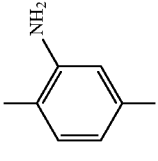 | — | 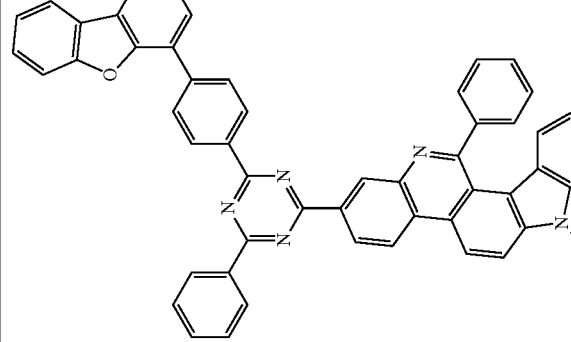 | | 605 |

TABLE 3-continued
| Compound No. | A | B | C | Target Compound | Yield |
|---|---|---|---|---|---|
| 11-9 | 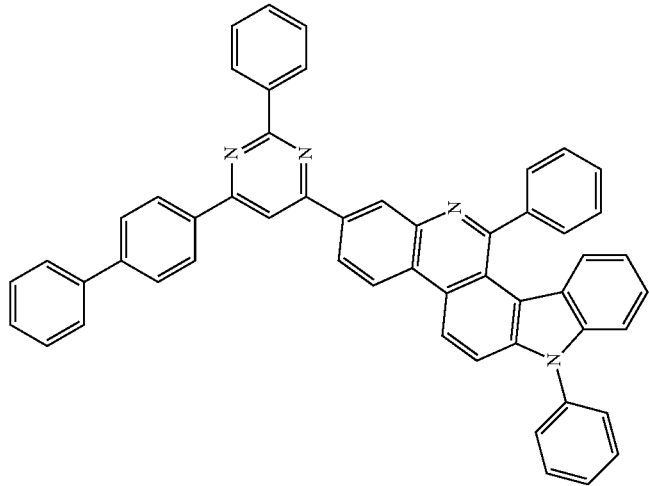 | — | | | 74% |

TABLE 3-continued
| Compound No. | A | B | C | Target Compound | Yield |
|---|---|---|---|---|---|
| 11-22 | 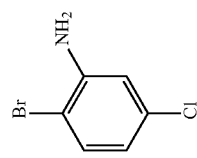 | — | 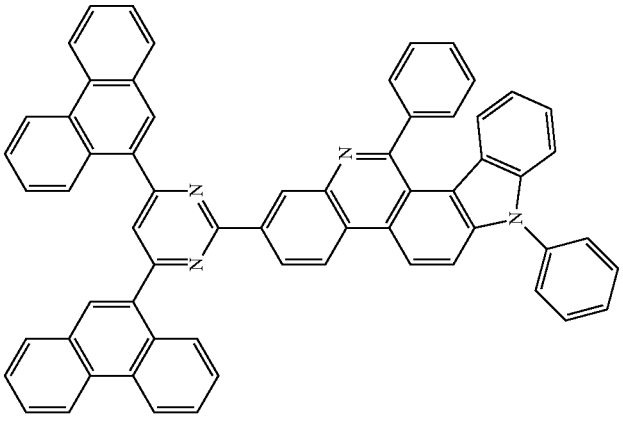 | | 55% |

TABLE 3-continued
| Compound No. | A | B | C | Target Compound | Yield |
|---|---|---|---|---|---|
| 11-32 | 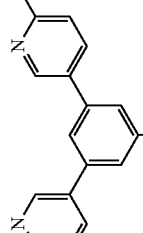 | — | 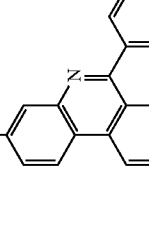 | 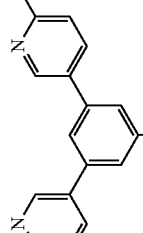 | 50% |
| 11-42 | 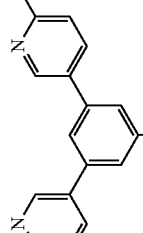 | — | 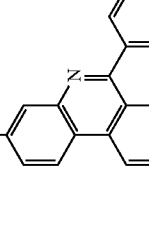 | 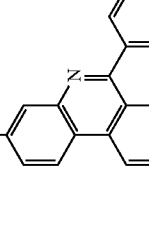 | 63% |

TABLE 3-continued
| Compound No. | A | B | C | Target Compound | Yield |
|---|---|---|---|---|---|
| 12-1 | 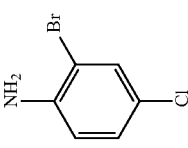 | — | 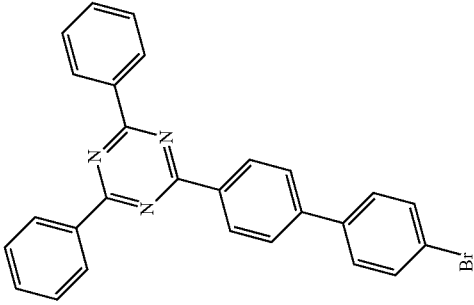 | 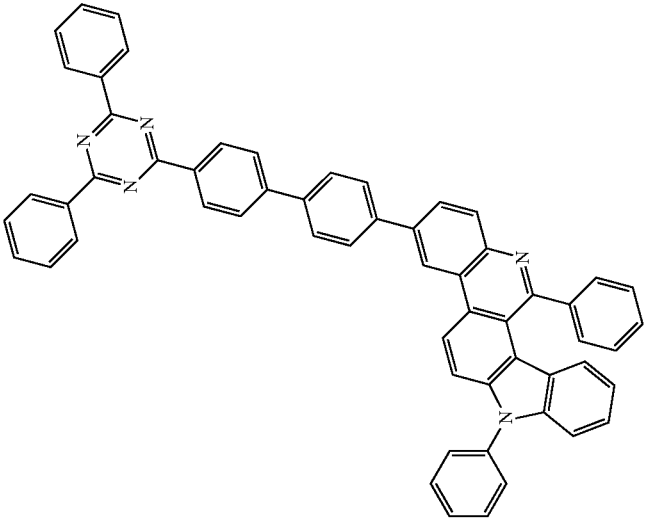 | 77% |

TABLE 3-continued
| Compound No. | A | B | C | Target Compound | Yield |
|---|---|---|---|---|---|
| 12-7 | 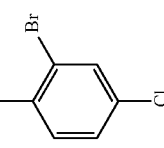 | — | 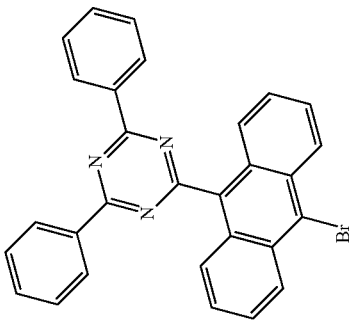 | 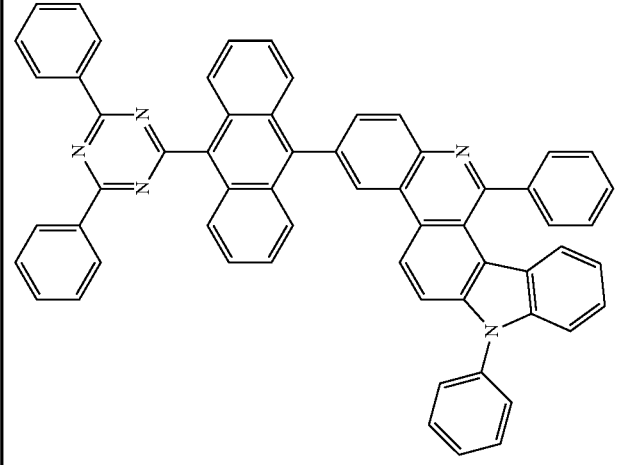 | 52% |

TABLE 3-continued
| Compound No. | A | B | C | Target Compound | Yield |
|---|---|---|---|---|---|
| 12-11 | 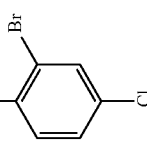 | — | 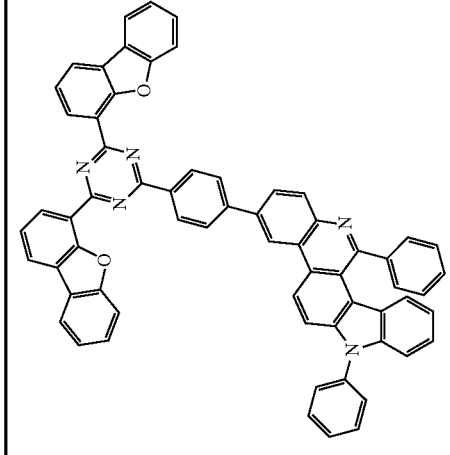 | 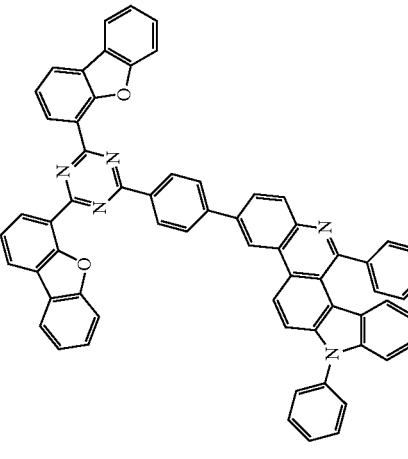 | 48% |
| 12-17 | 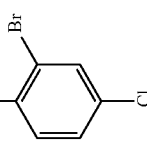 | — | 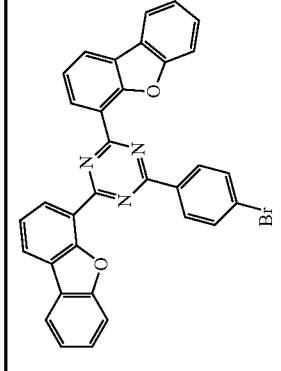 | 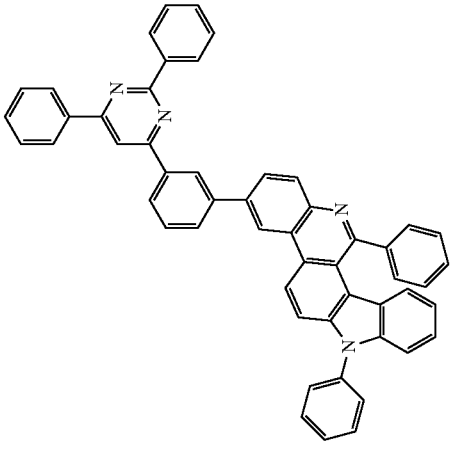 | 46% |

TABLE 3-continued

| Compound No. | A | B | C | Target Compound | Yield |
|---|---|---|---|---|---|
| 12-29 | 2-bromo-4-chloroaniline | — | 2-(4-bromophenyl)-4-(4-(dimethylphosphoryl)phenyl)-6-phenyl-1,3,5-triazine | (structure) | 67% |
| 13-1 | 2-bromo-3-chloroaniline | — | 2-(3-bromophenyl)-4,6-diphenyl-1,3,5-triazine | (structure) | 56% |

TABLE 3-continued

| Compound No. | A | B | C | Target Compound | Yield |
|---|---|---|---|---|---|
| 13-3 | 2-bromo-3-chloroaniline | — | (pyrimidine intermediate with biphenyl and bromophenyl) | (target compound structure) | 44% |
| 13-4 | 2-bromo-3-chloroaniline | — | (pyrimidine intermediate with diphenyl and bromophenyl) | (target compound structure) | 41% |

[Preparation Example 4] Preparation of Compound 14
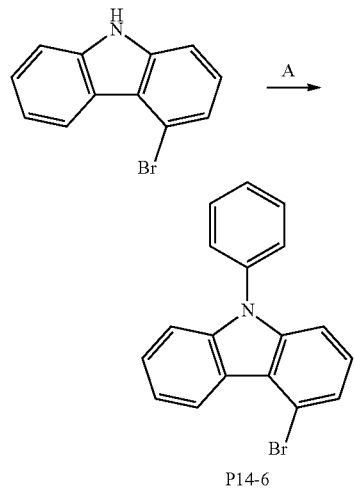
P14-6
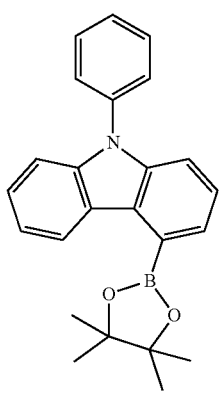
P14-5
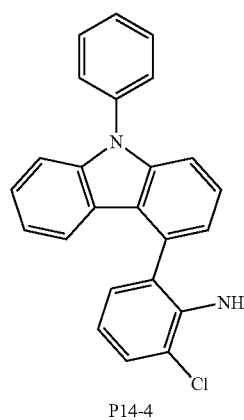
P14-4
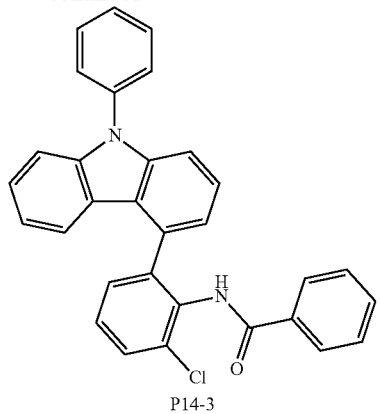
P14-3
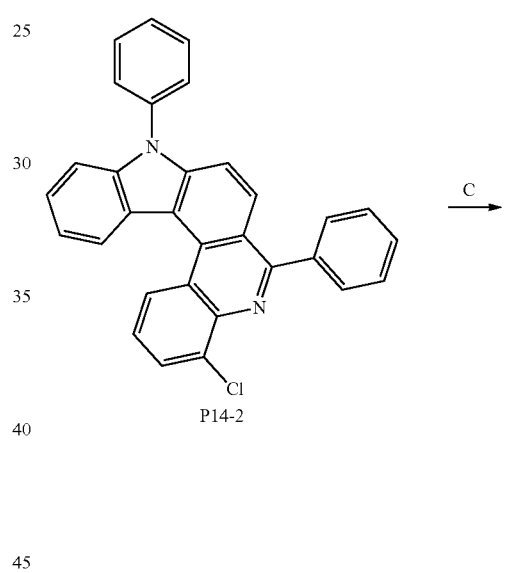
P14-2
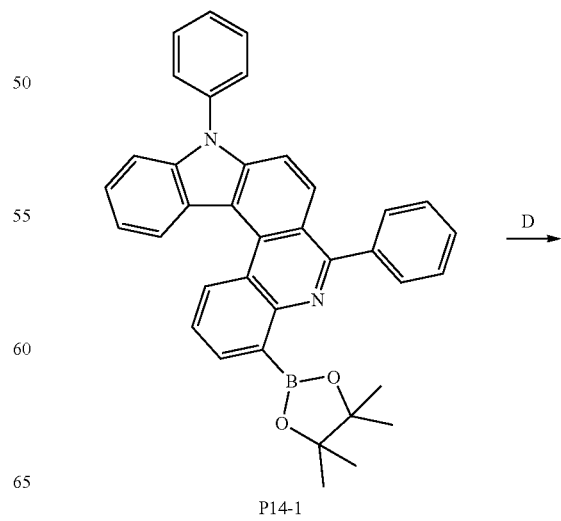
P14-1

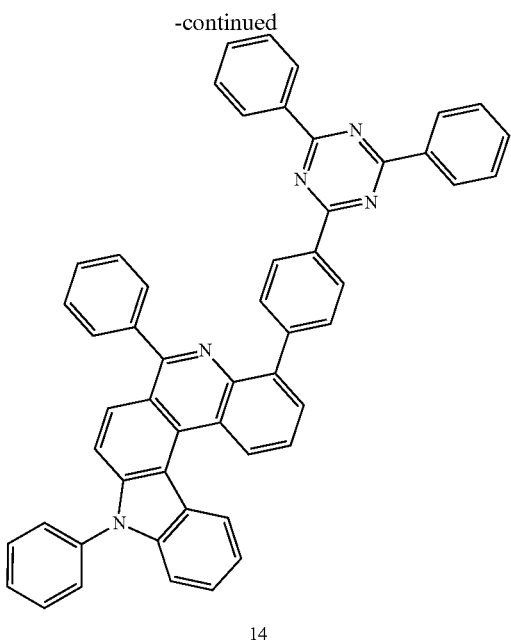

14

Preparation of Compound P14-6

After dissolving 4-bromo-9H-carbazole (100 g, 406.33 mmol), CuI (77.4 g, 406.33 mmol) and K₃PO₄ (258 g, 1.22 mol) in 1,4-dioxane (1.2 L), (N₂ condition) (±)-trans-1,2-diaminocyclohexane (49 mL, 406.33 mmol) and iodobenzene (59 mL, 528.23 mmol) were introduced thereto, and the result was stirred for 15 hours at 100° C. After the reaction was completed, the mixture solution was cooled to room temperature, the inorganic salt was filtered and removed, and the filtrate was concentrated and silica gel filtered. The solvent was removed from the filtered filtrate using a rotary evaporator to obtain Compound P14-6 (112 g, 85% yield).

Preparation of Compound P14-5

After dissolving P14-6 (112 g, 347.76 mmol) and bis(pinacolato)diboron (176 g, 695.22 mmol) in 1,4-dioxane (1 L), (N₂ condition) PdCl₂(dppf) (12.7 g, 17.39 mmol) and KOAc (102.2 g, 1.04 mol) were introduced thereto, and the result was stirred for 19 hours at 100° C. After the reaction was completed, the mixture solution was dissolved in MC and extracted with water, and the organic layer was dried with anhydrous MgSO₄ and then silica gel filtered. The filtered filtrate was, after removing the solvent using a rotary evaporator, precipitated with EA/Hex, and then the precipitates were filtered to obtain Compound P14-5 (91 g, 72% yield).

Preparation of Compound P14-4

After dissolving Compound P14-5 (91 g, 246.44 mmol) and 2-bromo-6-chloroaniline (55 g, 271.08 mmol) in 1,4-dioxane (900 mL) and H₂O (200 ml), (N₂ condition) Pd(PPh₃)₄ (8.5 g, 7.39 mmol) and K₃PO₄ (104.5 g, 492.88 mmol) were introduced thereto, and the result was stirred for 8 hours at 100° C. After the reaction was completed, the mixture solution was dissolved in MC and extracted with water, and the organic layer was dried with anhydrous MgSO₄ and then silica gel filtered. The filtered filtrate was, after removing the solvent using a rotary evaporator, precipitated with EA/Hex, and then the precipitates were filtered to obtain Compound P14-4 (62 g, 69% yield).

Preparation of Compound P14-3

After dissolving Compound P14-4 (62 g, 168.08 mmol) in MC (700 ml), triethylamine (71 ml, 504.26 mmol) was introduced thereto, and benzoyl chloride (21 ml, 184.88 mmol) was slowly added dropwise thereto at 0° C. The reaction temperature was raised to room temperature after 30 minutes, and the result was stirred for 3 hours. After the reaction was completed, the mixture solution was extracted with distilled water, and the organic layer was dried with anhydrous MgSO₄ and then silica gel filtered. The filtered filtrate was, after removing the solvent using a rotary evaporator, precipitated with EA/Hex, and then the precipitates were filtered to obtain Compound P14-3 (62 g, 79% yield).

Preparation of Compound P14-2

After dissolving Compound P14-3 (62 g, 131.09 mmol) in nitrobenzene (500 ml), POCl₃ (12.2 ml, 131.09 mmol) was introduced thereto, and the result was stirred for 19 hours at 150° C. After the reaction was completed, the mixture solution was cooled to 0° C., and then 1 M Na₂CO₃ (aq) was slowly added thereto to adjust the pH to 10 to 11. The organic layer extracted with distilled water was dried with anhydrous MgSO₄ and then silica gel filtered. The filtered filtrate was, after removing the solvent using a rotary evaporator, precipitated with MC/MeOH, and then the precipitates were filtered to obtain Compound P14-2 (39 g, 66% yield).

Preparation of Compound P14-1

After dissolving Compound P14-2 (39 g, 71.51 mmol) and bis(pinacolato)diboron (36 g, 143.02 mmol) in 1,4-dioxane (400 ml), (N₂ condition) Pd(dba)₂ (4.1 g, 7.15 mmol), SPhos (5.8 g, 14.32 mmol) and KOAc (21 g, 214.53 mmol) were introduced thereto, and the result was stirred for 16 hours at 100° C. After the reaction was completed, the mixture solution was dissolved in MC and extracted with water, and the organic layer was dried with anhydrous MgSO₄ and then silica gel filtered. The filtered filtrate was, after removing the solvent using a rotary evaporator, precipitated with MC/MeOH, and then the precipitates were filtered to obtain Compound P14-1 (30 g, 78% yield).

Preparation of Compound 14

After dissolving Compound P14-1 (10 g, 18.29 mmol) and 2-(4-bromophenyl)-4,6-diphenyl-1,3,5-triazine (7.8 g, 20.12 mmol) in 1,4-dioxane (120 ml) and H₂O (30 ml), (N₂ condition) Pd(PPh₃)₄ (1 g, 0.91 mmol) and K₃PO₄ (7.7 g, 36.58 mmol) were introduced thereto, and the result was stirred for 14 hours at 100° C. After the reaction was completed, precipitated solids were filtered and washed with solvents of H₂O and MeOH. The filtered solids were dried, then dissolved in an excess amount of hot 1,2-dichlorobenzene solvent, and silica gel filtered. The filtered filtrate was, after removing the solvent using a rotary evaporator, precipitated with MeOH, and then the precipitates were filtered to obtain Compound 14 (9.2 g, 65% yield).

Target compounds were synthesized in the same manner as in Preparation Example 4 except that Intermediate A of the following Table 4 was used instead of iodobenzene, the compound of Reaction A, Intermediate B of the following Table 4 was used instead of 2-bromo-6-chloroaniline, the compound of Reaction B, Intermediate C of the following Table 4 was used instead of benzoyl chloride of Reaction C, and Intermediate D of the following Table 4 was used instead of 2-(4-bromophenyl)-4,6-diphenyl-1,3,5-triazine of Reaction D.

TABLE 4
| Compound | A | B | C | D | Target Compound | Yield |
|---|---|---|---|---|---|---|
| 14-3 | 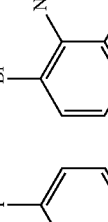 | 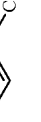 |  | | | 66% |

TABLE 4-continued
| Compound | A | B | C | D | Target Compound | Yield |
|---|---|---|---|---|---|---|
| 14-5 | 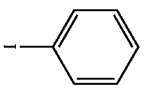 | 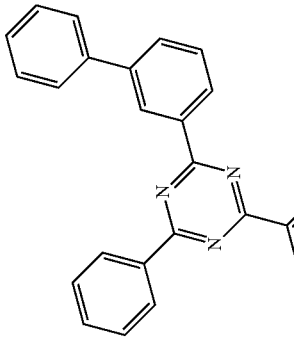 | 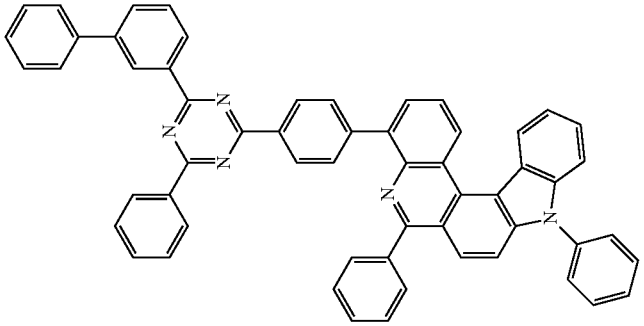 | 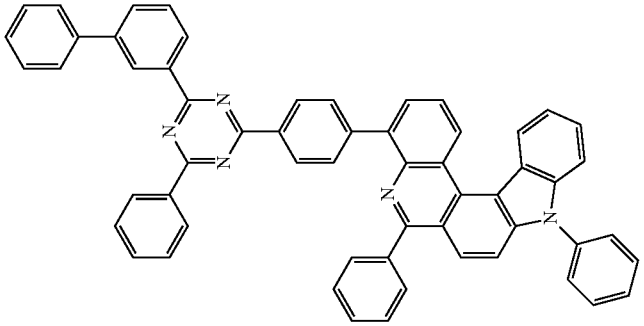 |  | 69% |

TABLE 4-continued
| Compound | A | B | C | D | Target Compound | Yield |
|---|---|---|---|---|---|---|
| 14-7 | 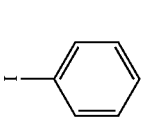 | 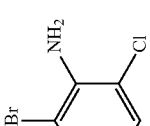 | 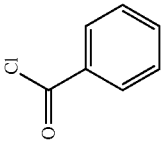 | 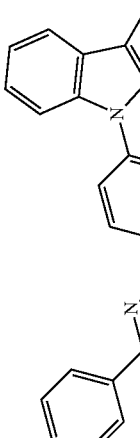 | 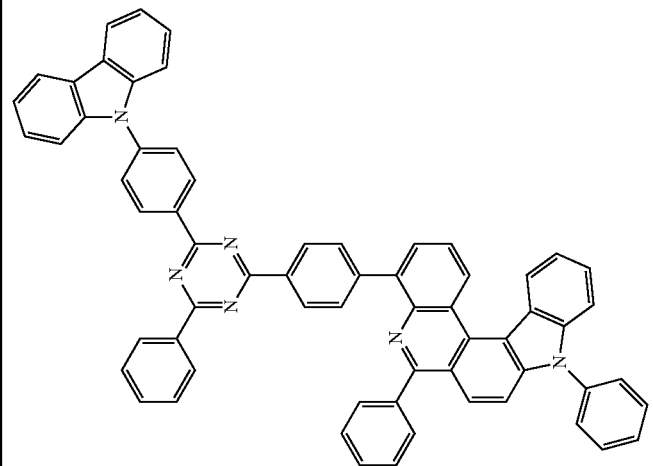 | 59% |

TABLE 4-continued
| Compound | A | B | C | D | Target Compound | Yield |
|---|---|---|---|---|---|---|
| 14-12 | 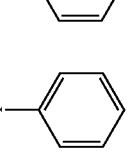 | 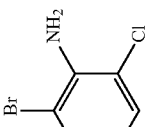 | 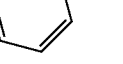 | 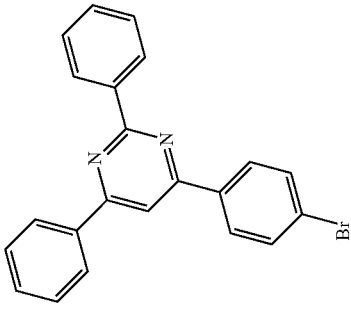 | 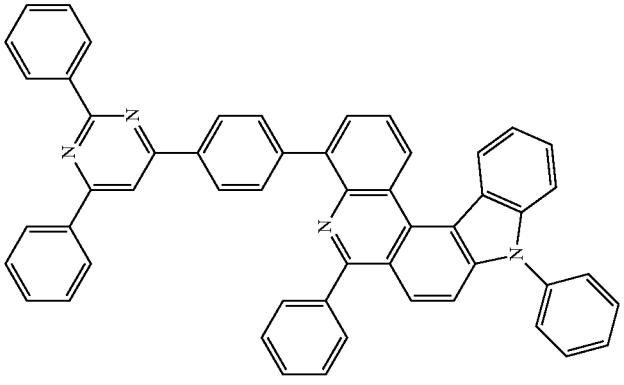 | 70% |

TABLE 4-continued
| Compound | A | B | C | D | Target Compound | Yield |
|---|---|---|---|---|---|---|
| 14-16 | 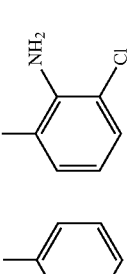 |  |  |  |  | 51% |

TABLE 4-continued
| Compound | A | B | C | D | Target Compound | Yield |
|---|---|---|---|---|---|---|
| 14-22 | 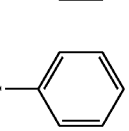 | 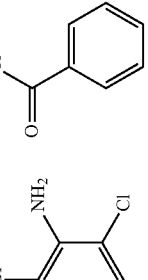 | 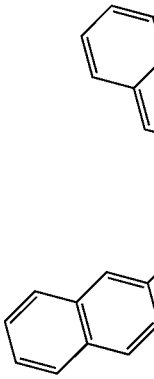 | 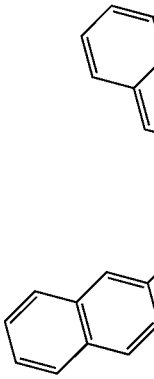 | 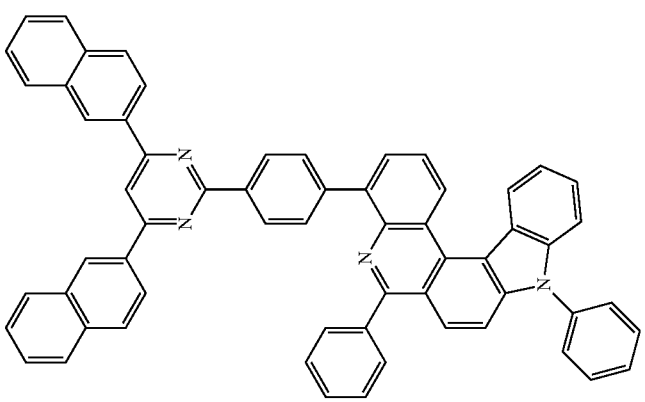 | 52% |

TABLE 4-continued
| Compound | A | B | C | D | Target Compound | Yield |
|---|---|---|---|---|---|---|
| 14-33 | 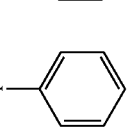 | 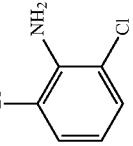 | 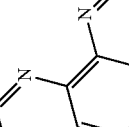 | 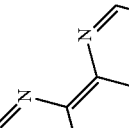 | 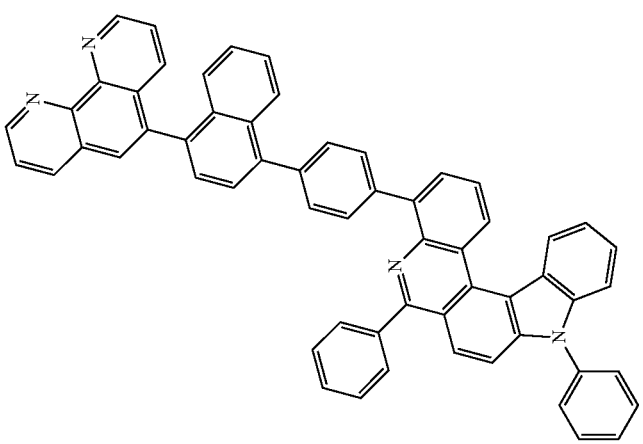 | 57% |

TABLE 4-continued
| Compound | A | B | C | D | Target Compound | Yield |
|---|---|---|---|---|---|---|
| 14-43 | 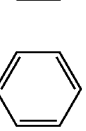 | 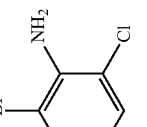 | 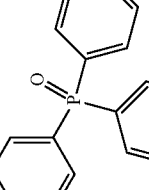 | 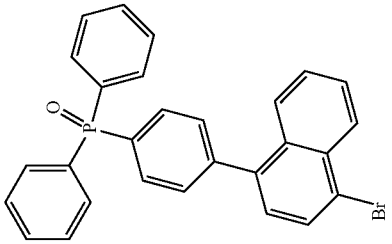 | 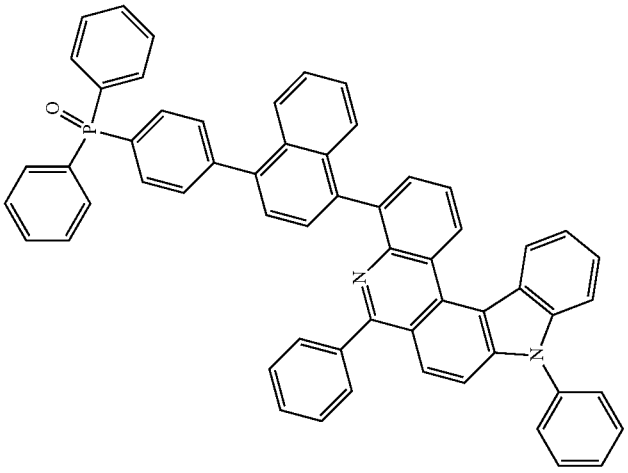 | 60% |

TABLE 4-continued
| Compound | A | B | C | D | Target Compound | Yield |
|---|---|---|---|---|---|---|
| 14-52 | 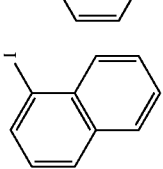 | 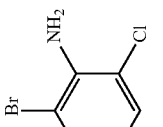 | 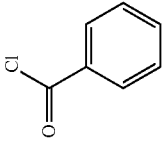 | 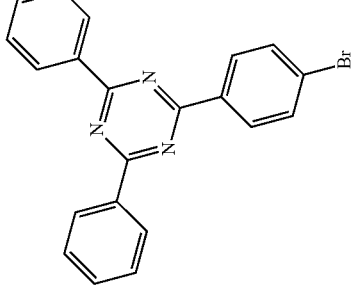 | 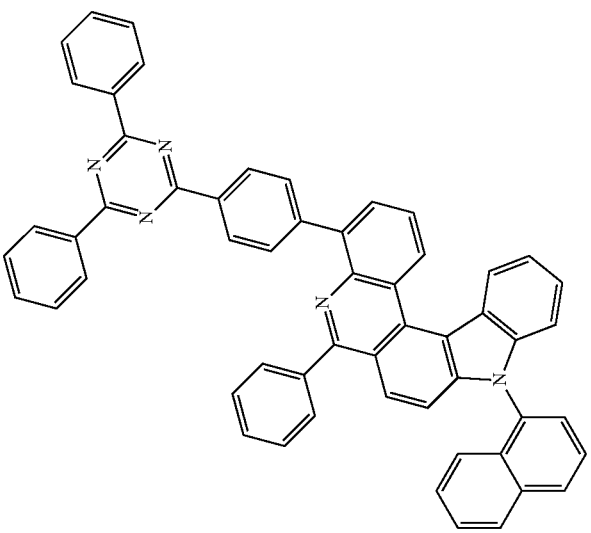 | 66% |

TABLE 4-continued
| Compound | A | B | C | D | Target Compound | Yield |
|---|---|---|---|---|---|---|
| 14-53 | 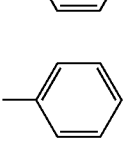 | 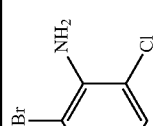 | 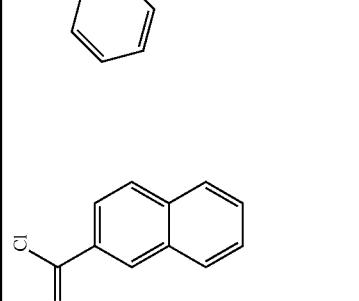 | 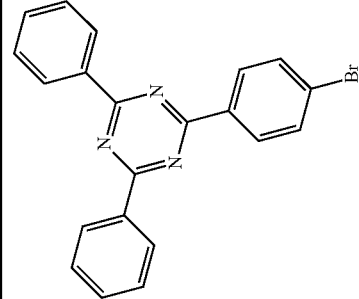 | 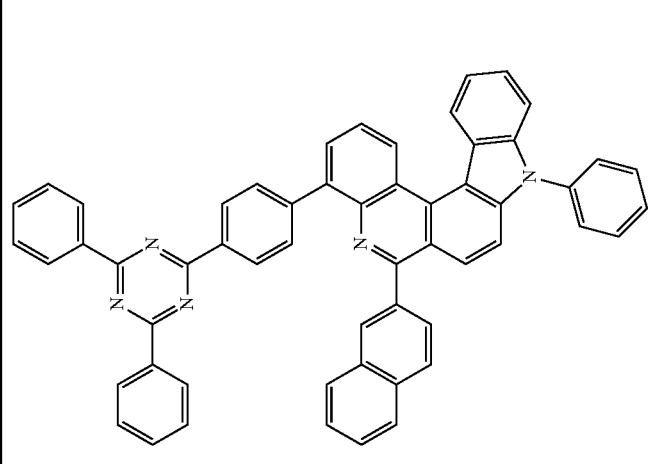 | 68% |

TABLE 4-continued
| Compound | A | B | C | D | Target Compound | Yield |
|---|---|---|---|---|---|---|
| 14-55 | 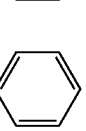 | 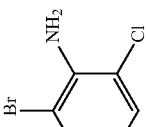 | 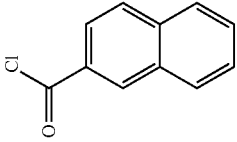 | 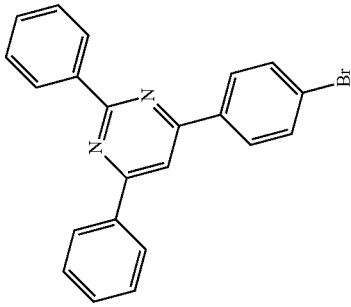 | 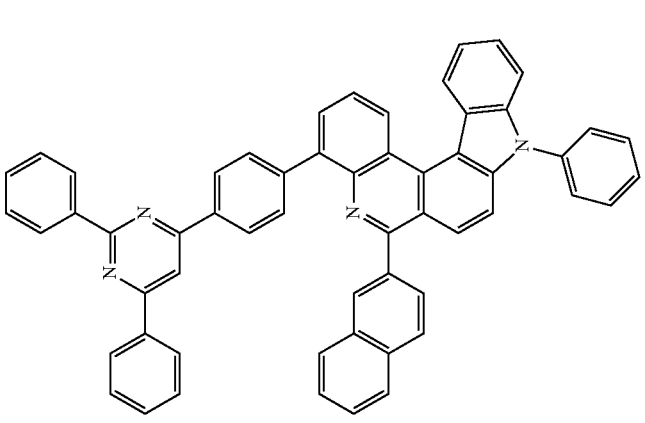 | 59% |

TABLE 4-continued
| Compound | A | B | C | D | Target Compound | Yield |
|---|---|---|---|---|---|---|
| 15 | 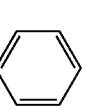 | 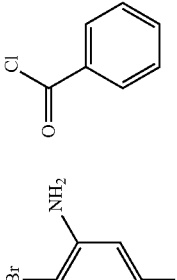 | 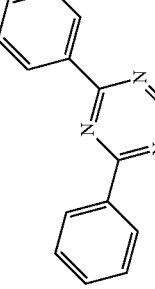 | 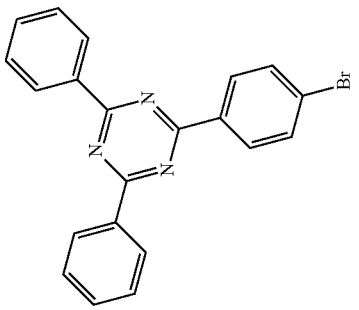 | 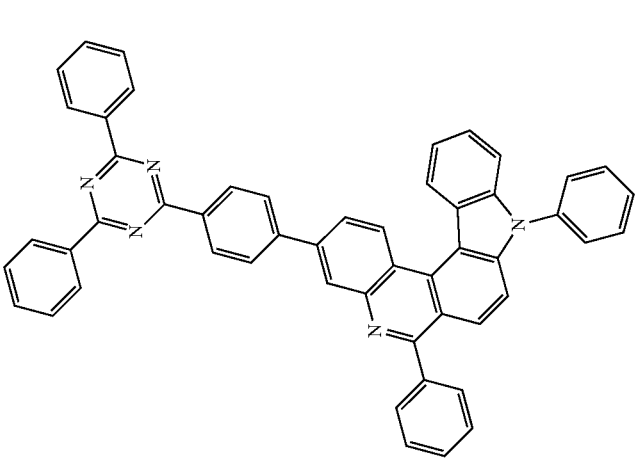 | 60% |

TABLE 4-continued
| Compound | A | B | C | D | Target Compound | Yield |
|---|---|---|---|---|---|---|
| 15-2 | 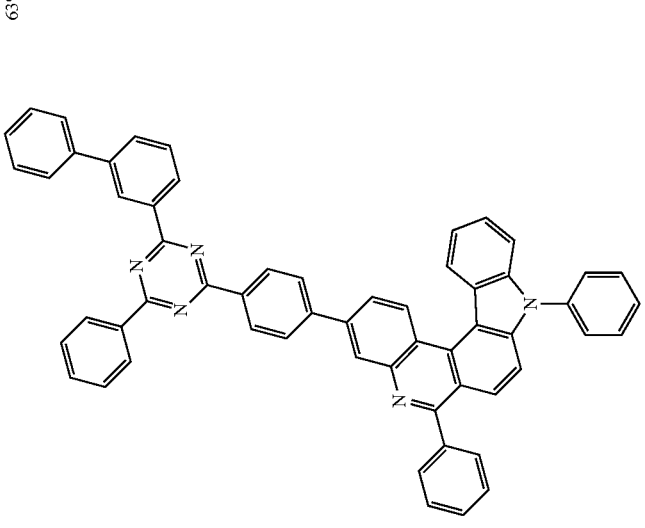 | 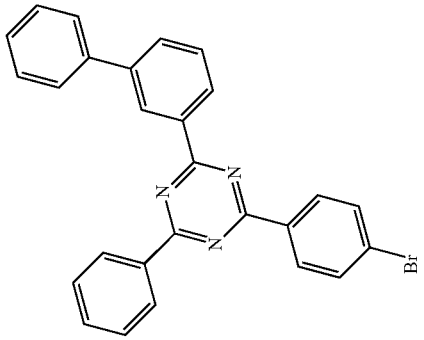 | 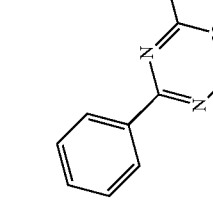 | 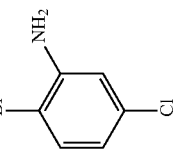 | 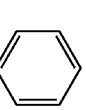 | 63% |

TABLE 4-continued
| Compound | A | B | C | D | Target Compound | Yield |
|---|---|---|---|---|---|---|
| 15-4 | 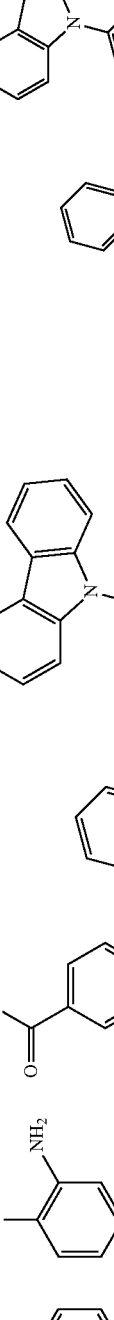 | 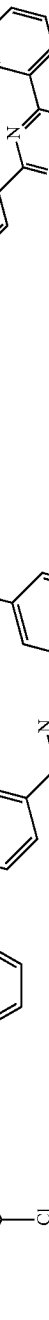 | 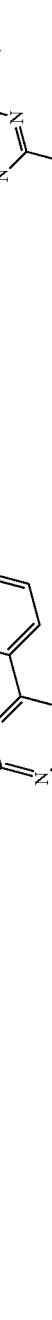 |  | 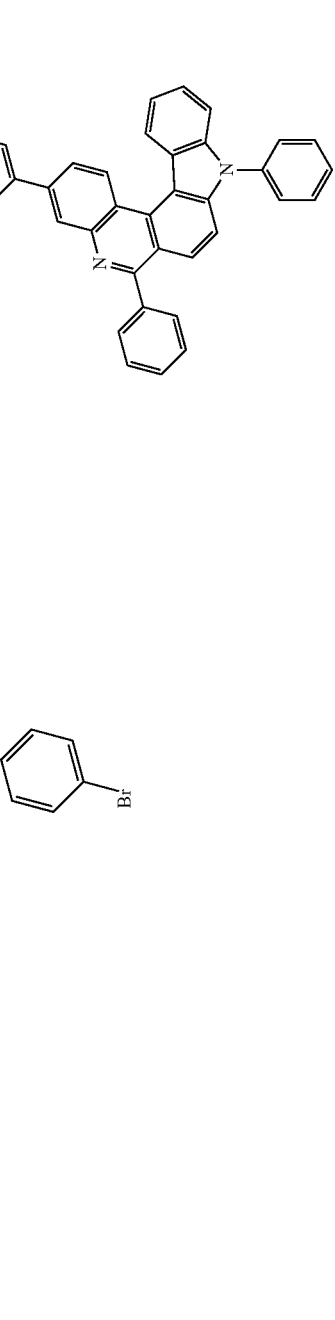 | 55% |

TABLE 4-continued
| Compound | A | B | C | D | Target Compound | Yield |
|---|---|---|---|---|---|---|
| 15-8 | 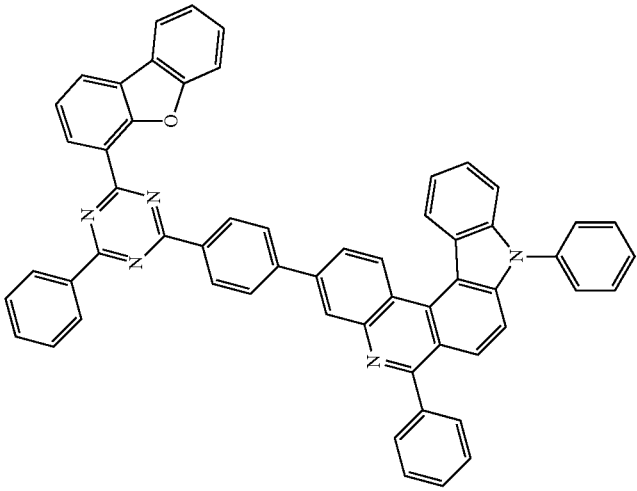 | 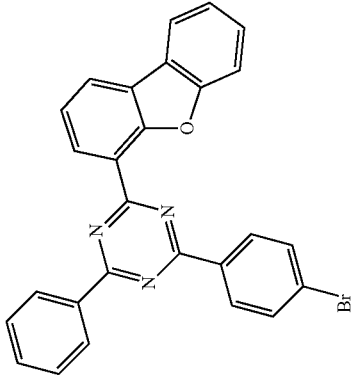 | 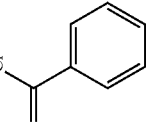 | 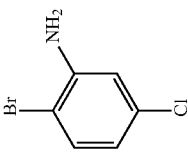 |  | 52% |

TABLE 4-continued
| Compound | A | B | C | D | Target Compound | Yield |
|---|---|---|---|---|---|---|
| 15-11 | 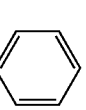 | 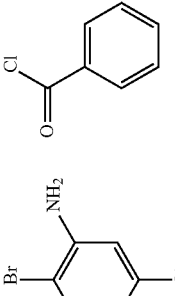 | 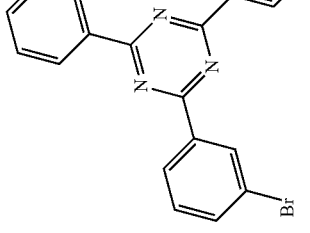 | 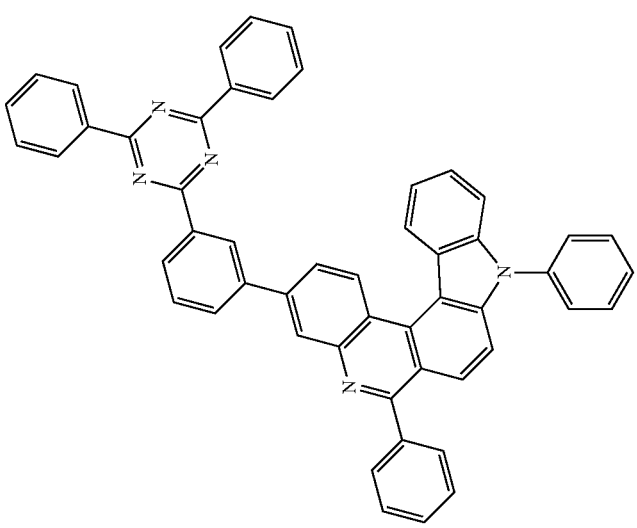 | 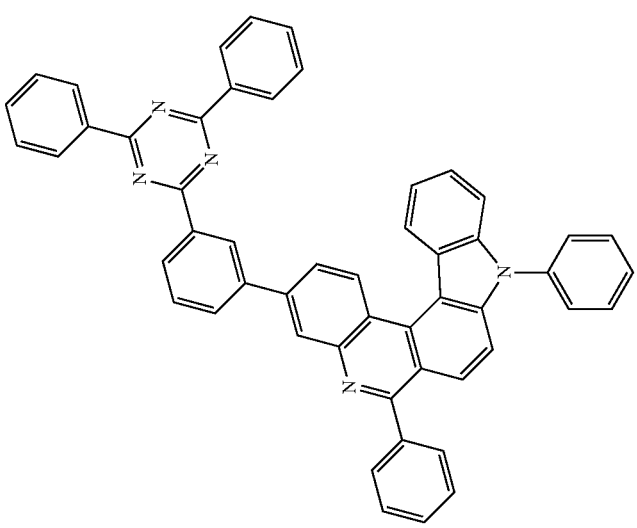 | 60% |

TABLE 4-continued
| Compound | A | B | C | D | Target Compound | Yield |
|---|---|---|---|---|---|---|
| 15-15 |  | 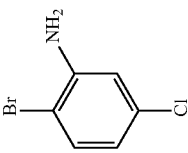 | 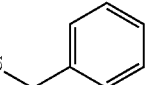 |  | 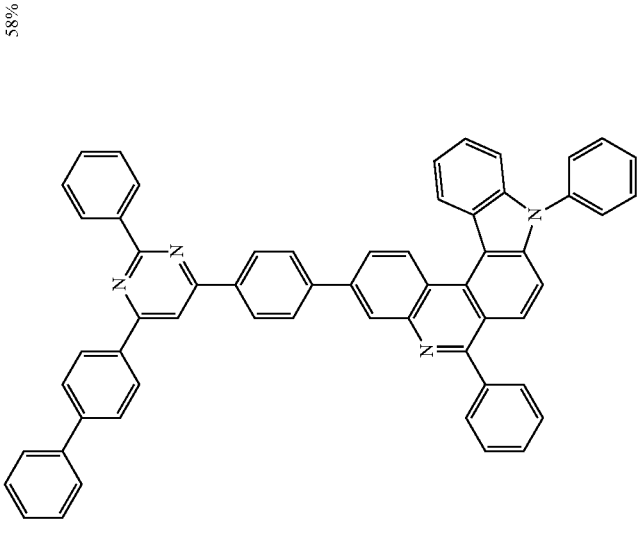 | 58% |

TABLE 4-continued
| Compound | A | B | C | D | Target Compound | Yield |
|---|---|---|---|---|---|---|
| 15-30 |  | 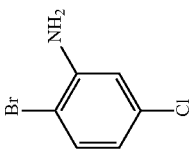 | 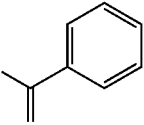 | 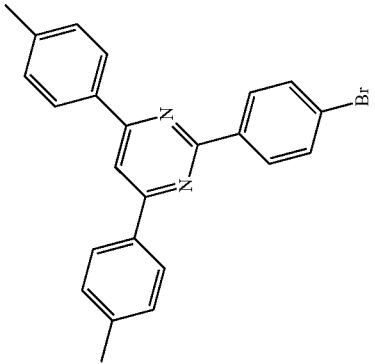 | 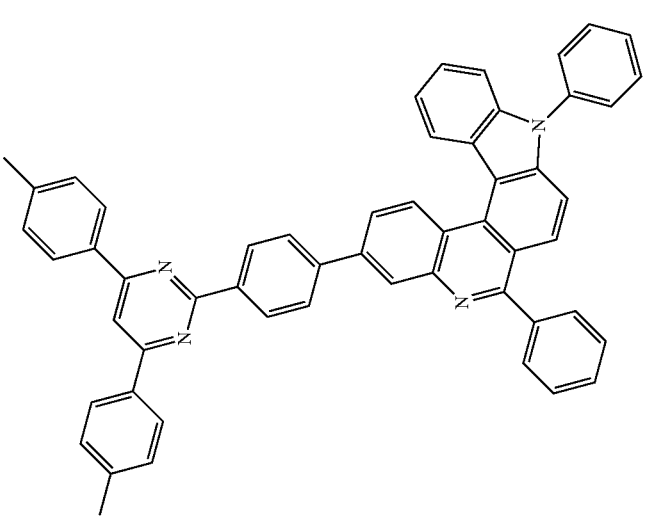 | 57% |

TABLE 4-continued
| Compound | A | B | C | D | Target Compound | Yield |
|---|---|---|---|---|---|---|
| 15-42 |  | 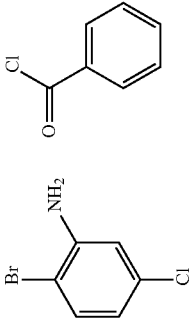 | 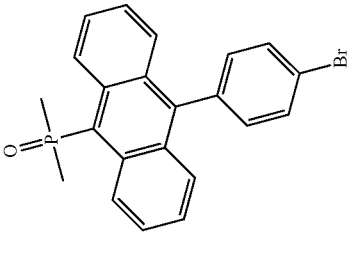 | 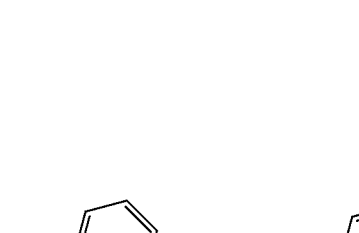 | 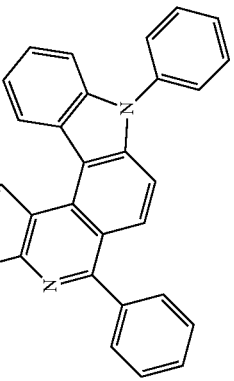 | 58% |

TABLE 4-continued
| Compound | A | B | C | D | Target Compound | Yield |
|---|---|---|---|---|---|---|
| 15-48 | 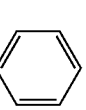 | 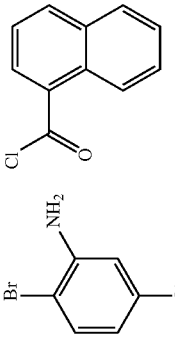 | 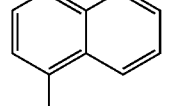 | 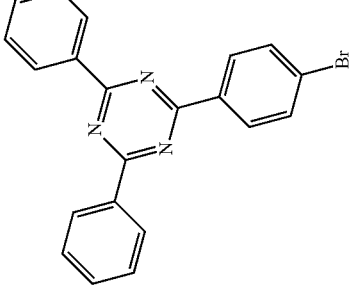 | 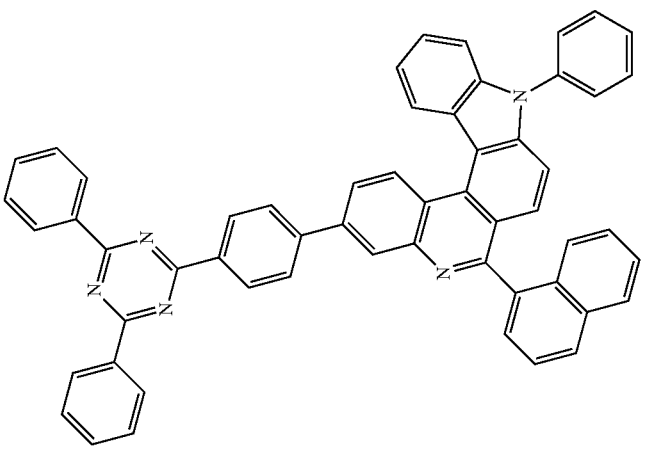 | 68% |

TABLE 4-continued
| Compound | A | B | C | D | Target Compound | Yield |
|---|---|---|---|---|---|---|
| 15-50 |  | 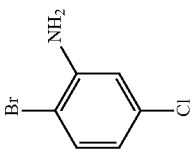 | 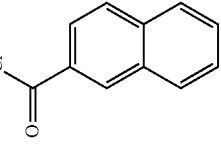 | 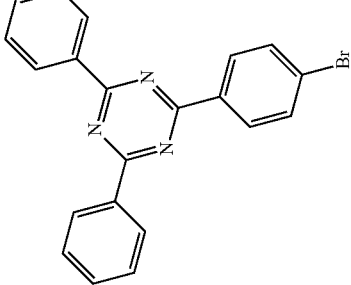 | 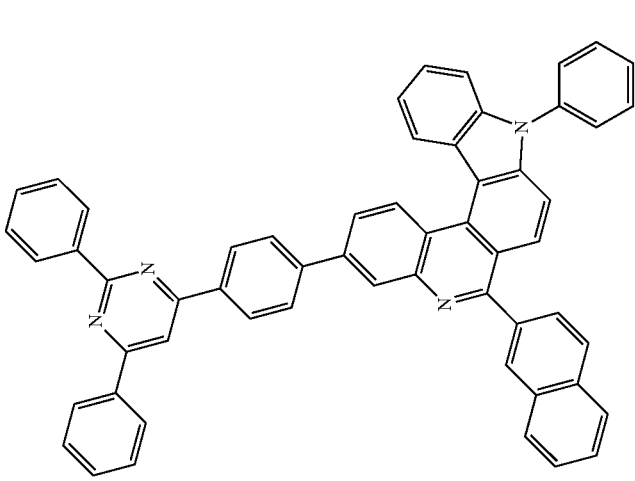 | 66% |

| Compound | A | B | C | D | Target Compound | Yield |
|---|---|---|---|---|---|---|
| 15-51 | 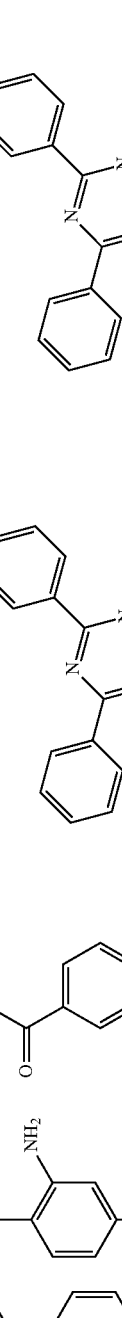 | 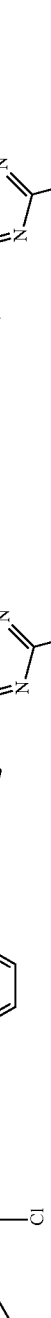 | 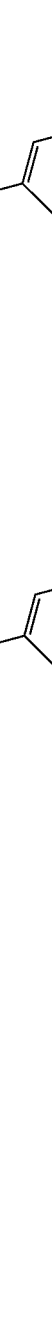 | 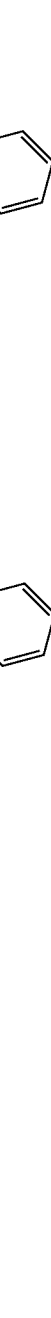 | 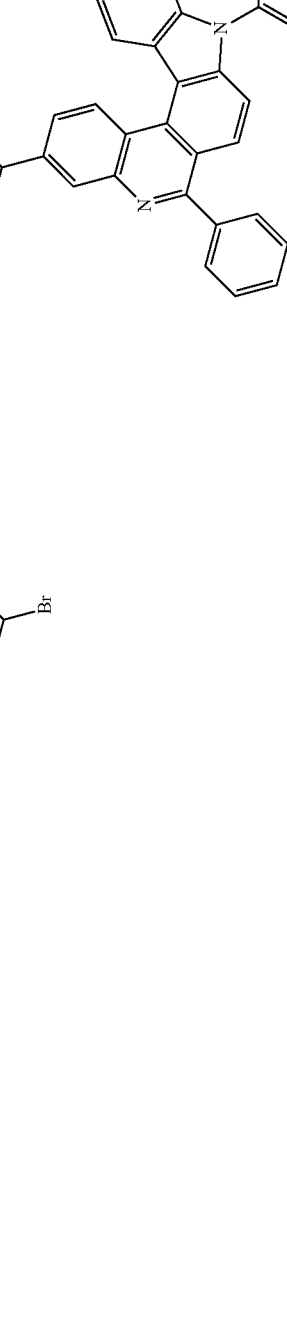 | 76% |

TABLE 4-continued
| Compound | A | B | C | D | Target Compound | Yield |
|---|---|---|---|---|---|---|
| 16 | 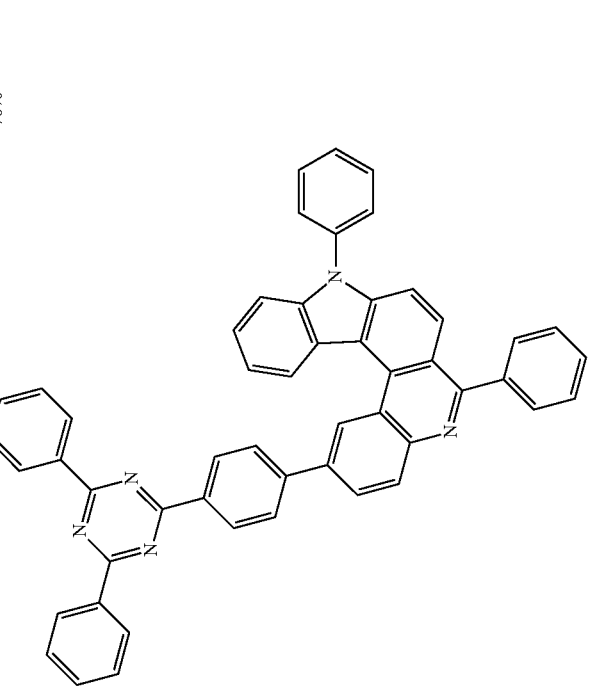 | 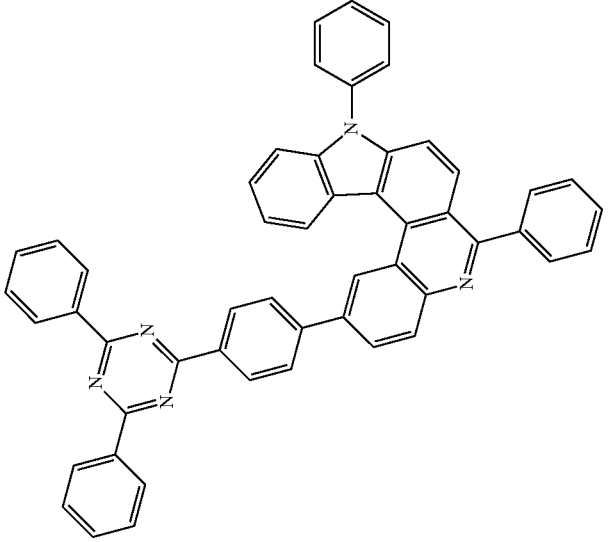 | 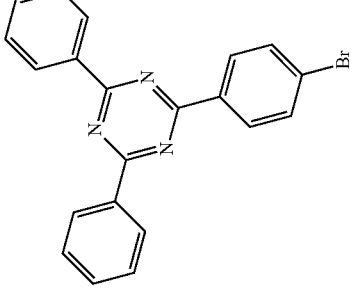 | 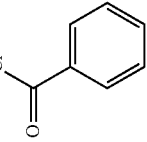 |  | 70% |

TABLE 4-continued
| Compound | A | B | C | D | Target Compound | Yield |
|---|---|---|---|---|---|---|
| 16-8 | 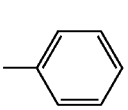 | 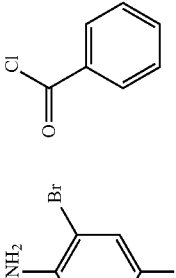 | 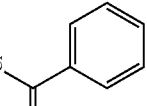 | 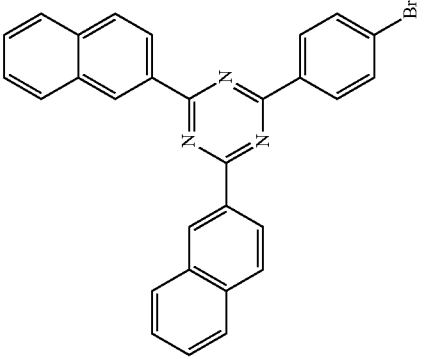 | 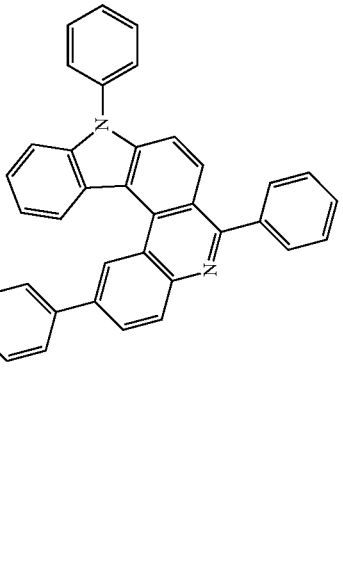 | 56% |

TABLE 4-continued
| Compound | A | B | C | D | Target Compound | Yield |
|---|---|---|---|---|---|---|
| 16-11 | 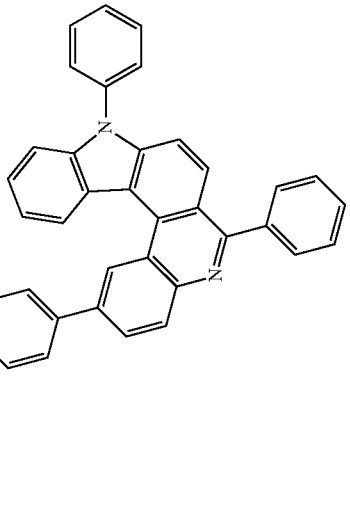 | 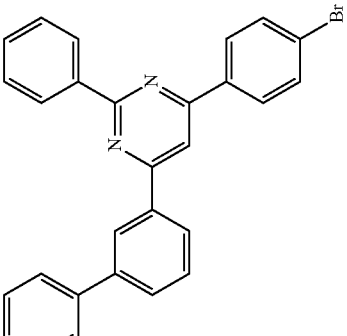 | 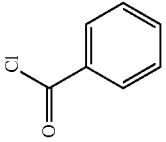 | 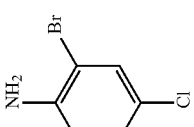 | 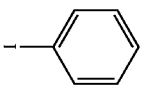 | 51% |

TABLE 4-continued
| Compound | A | B | C | D | Target Compound | Yield |
|---|---|---|---|---|---|---|
| 16-14 | 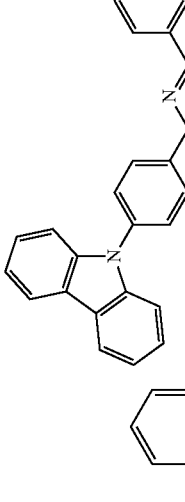 |  | 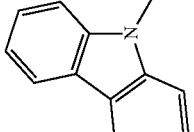 | 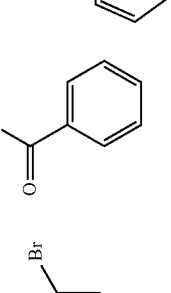 | 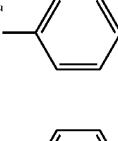 | 49% |

TABLE 4-continued
| Compound | A | B | C | D | Target Compound | Yield |
|---|---|---|---|---|---|---|
| 16-20 | 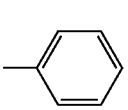 | 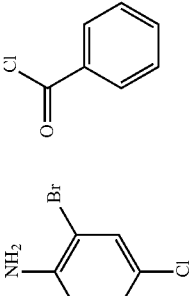 | 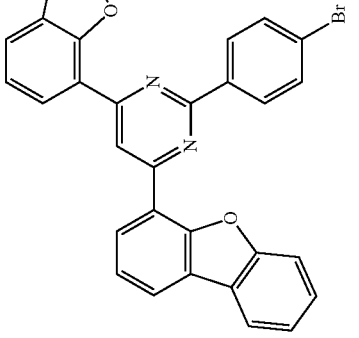 | 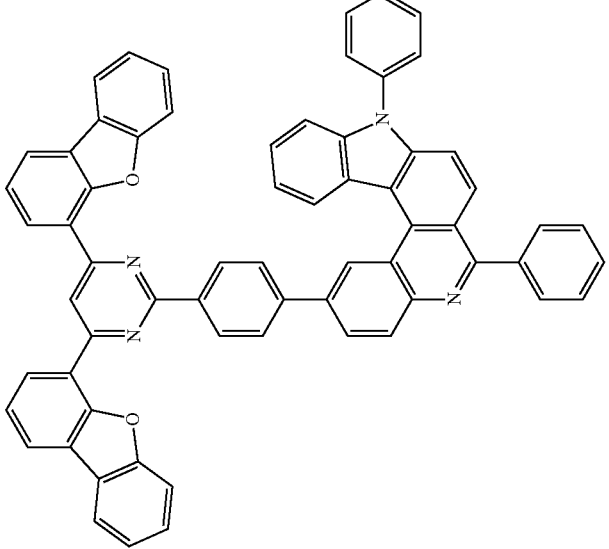 | 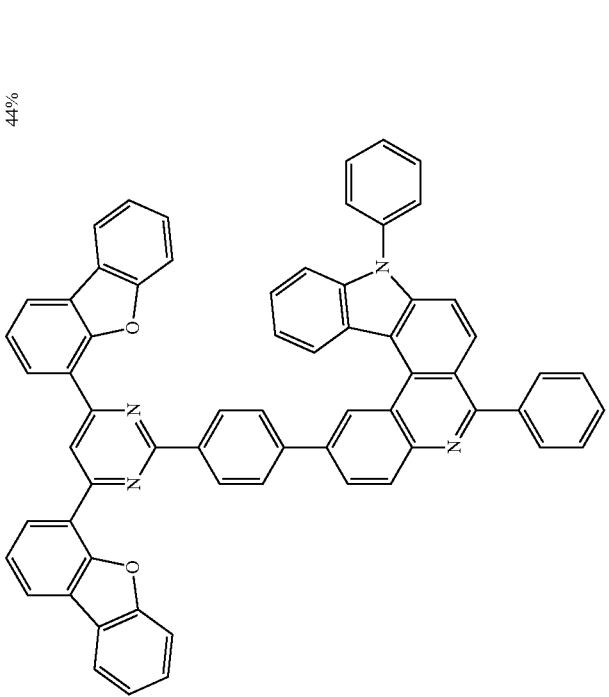 | 44% |

TABLE 4-continued
| Compound | A | B | C | D | Target Compound | Yield |
|---|---|---|---|---|---|---|
| 16-28 | 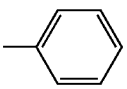 | 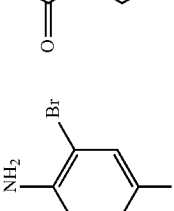 |  | 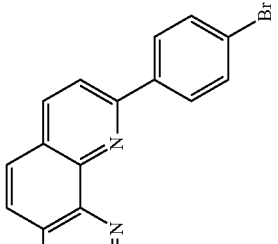 | 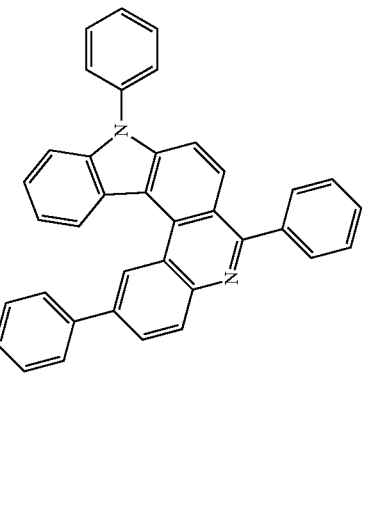 | 56% |
| 16-35 | 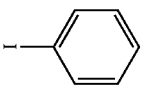 |  |  | 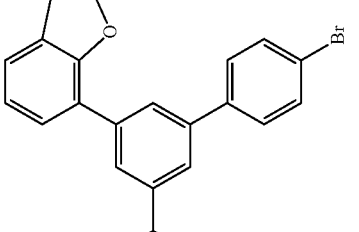 | 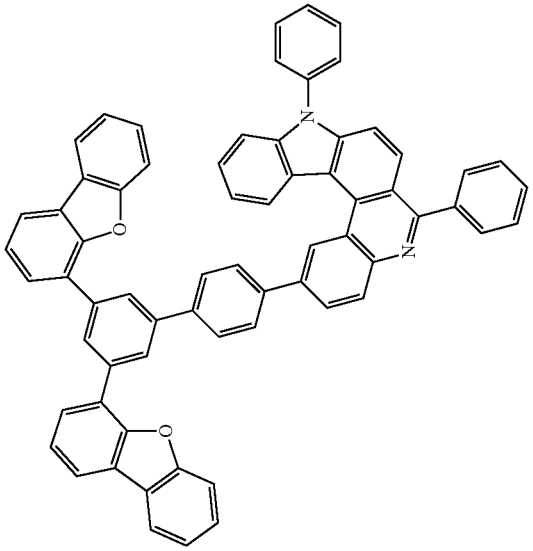 | 57% |

TABLE 4-continued
| Compound | A | B | C | D | Target Compound | Yield |
|---|---|---|---|---|---|---|
| 16-42 | 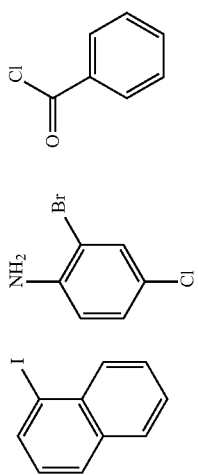 | 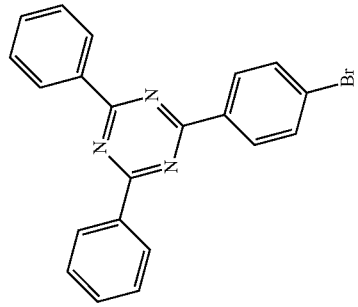 | 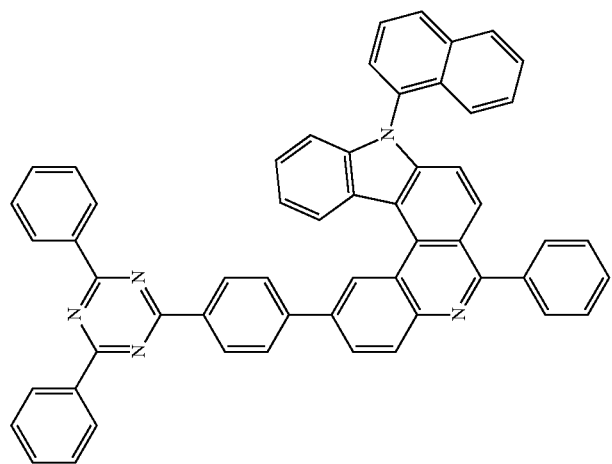 | 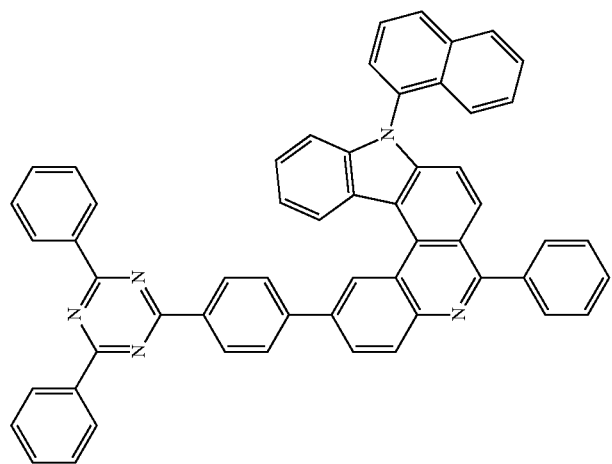 | 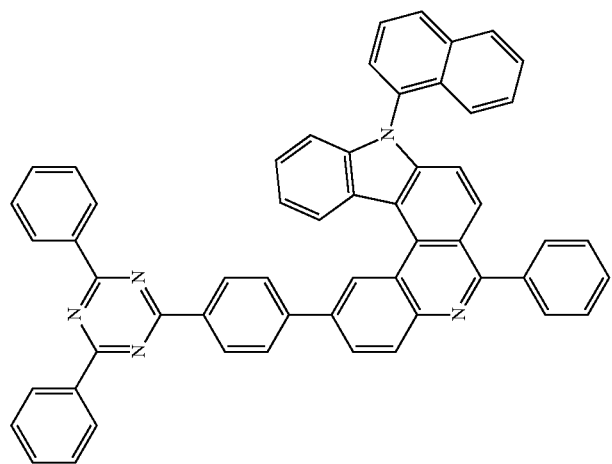 | 69% |

TABLE 4-continued
| Compound | A | B | C | D | Target Compound | Yield |
|---|---|---|---|---|---|---|
| 16-44 |  |  | 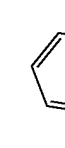 | 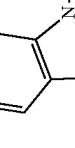 | 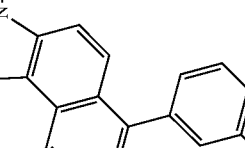 | 68% |

Compounds other than the compounds described in Preparation Examples 1 to 4 and Tables 1 to 4 were also prepared in the same manner as the compounds described in Preparation Examples 1 to 4 and Tables 1 to 4, and the synthesis identification results are shown in the following Table 5 and Table 6.

TABLE 5

| NO | ¹H NMR (CDCl₃, 300 Mz) |
|---|---|
| 1 | 7.25-7.33 (m, 4H), 7.41-7.58 (m, 16H), 7.85 (m, 2H), 7.92-7.94 (m, 2H), 8.02 (d, 1H), 8.22-8.30 (m, 7H), 8.55 (m, 1H) |
| 1-1 | 7.25-7.33 (m, 8H), 7.41-7.47 (m, 4H), 7.50-7.58 (m, 15H), 7.66 (m, 1H), 7.85 (m, 6H), 7.92-7.94 (m, 2H), 8.02 (d, 1H), 8.21 (d, 1H), 8.30 (m, 2H), 8.55 (d, 1H) |
| 1-7 | 7.25-7.33 (m, 2H), 7.41-7.48 (m, 7H), 7.50-7.58 (m, 13H), 7.66-7.70 (m, 3H), 7.92-7.94 (m, 2H), 8.02 (d, 1H), 8.21-8.24 (m, 2H), 8.28-8.30 (m, 6H), 8.55 (d, 1H) |
| 1-20 | 7.25-7.33 (m, 4H), 7.41-7.47 (m, 4H), 7.50-7.58 (m, 12H), 7.79 (m, 4H), 7.85 (m, 2H), 7.92-7.94 (m, 2H), 8.02 (d, 1H), 8.21-8.23 (m 2H), 8.30 (m, 2H), 8.55 (d, 1H) |
| 1-26 | 7.14 (td, 2H), 7.25-7.33 (m, 6H), 7.45-7.58 (m, 10H), 7.70 (m, 2H), 7.92-7.94 (m, 2H), 8.02 (d, 1H), 8.21 (d, 1H), 8.30 (m, 2H), 8.53-8.55 (m, 3H), 9.15 (s, 2H), 9.30 (d, 1H) |
| 1-29 | 7.25-7.35 (m, 6H), 7.45-7.58 (m, 12H), 7.66 (m, 1H), 7.81 (d, 1H), 7.92-7.94 (m, 2H), 8.02-8.10 (m, 4H), 8.21 (d, 1H), 8.30 (m, 4H), 8.55 (d, 1H), 8.81 (d, 2H) |
| 1-32 | 7.25-7.33 (m, 4H), 7.41-7.66 (m, 14H), 7.83-7.84 (m, 2H), 7.92-7.94 (m, 2H), 8.02 (dd, 1H), 8.16-8.21 (m, 2H), 8.28-8.30 (m, 6H), 8.55 (dd, 1H) |
| 1-40 | 7.25-7.33 (m, 6H), 7.39-7.66 (m, 19H), 7.91-7.94 (m, 6H), 8.02 (d, 1H), 8.21 (d, 1H), 8.30 (m, 2H), 8.55 (dd, 1H) |
| 1-42 | 7.25-7.33 (m, 4H), 7.41-7.66 (m, 15H), 7.85 (m, 2H), 7.92-8.02 (m, 6H), 8.21 (m, 1H), 8.28 (m, 4H), 8.38 (dd, 1H), 8.55 (d, 1H), 8.85 (s, 1H) |
| 1-43 | 7.25-7.33 (m, 4H), 7.41-7.66 (m, 15H), 7.79 (dd, 2H), 7.92-8.02 (m, 6H), 8.21-8.23 (m, 2H), 8.28-8.30 (m, 4H), 8.38 (d, 1H), 8.55 (d, 1H), 8.85 (s, 1H) |
| 2-1 | 7.25-7.33 (m, 4H), 7.41-7.47 (m, 4H), 7.50-7.58 (m, 11H), 7.85 (m, 2H), 7.92-7.94 (m, 2H), 8.12 (d, 1H), 8.27-8.30 (m, 7H), 8.55 (d, 1H) |
| 2-3 | 7.25-7.33 (m, 6H), 7.41-7.58 (m, 19H), 7.85 (m, 4H), 7.92-7.94 (m, 2H), 8.03 (d, 1H), 8.12 (d, 1H), 8.27-8.30 (m, 3H), 8.55 (dd, 1H) |
| 2-5 | 7.25-7.33 (m, 2H), 7.41-7.58 (m, 17H), 7.70 (s, 1H), 7.92-7.94 (m, 2H), 8.03 (d, 1H), 8.12 (d, 1H), 8.24-8.30 (m, 8H), 8.55 (d, 1H) |
| 2-10 | 7.25-7.33 (m, 2H), 7.41-7.58 (m, 15H), 7.79 (dd, 2H), 7.85 (m, 2H), 7.92-7.94 (m, 2H), 8.03 (d, 1H), 8.12 (d, 1H), 8.23 (s, 1H), 8.27-8.30 (m, 7H), 8.55 (d, 1H) |
| 2-29 | 7.16-7.19 (m, 4H), 7.25-7.28 (m, 6H), 7.33-7.38 (m, 4H), 7.45-7.58 (m, 10H), 7.63 (m, 1H), 7.75-7.77 (m, 3H), 7.87-7.94 (m, 4H), 8.03 (d, 1H), 8.12 (d, 1H), 8.27-8.30 (m, 3H), 8.55 (dd, 1H) |
| 2-35 | 7.25 (m, 7H), 7.33-7.39 (m, 3H), 7.45-7.58 (m, 9H), 7.74 (m, 2H), 7.85 (m, 2H), 7.92-7.94 (m, 2H), 8.03 (d, 1H), 8.12 (d, 1H), 8.27-8.30 (m, 3H), 8.55 (d, 1H) |
| 2-36 | 7.24-7.33 (m, 5H), 7.41-7.58 (m, 12H), 7.79 (dd, 2H), 7.83-7.85 (m, 4H), 7.92-7.94 (m, 2H), 8.03 (d, 1H), 8.12-8.16 (m, 2H), 8.27-8.30 (m, 3H), 8.55 (d, 1H) |
| 2-37 | 7.26-7.33 (m, 4H), 7.41-7.58 (m, 14H), 7.64 (m, 1H), 7.85 (dd, 2H), 7.92-7.94 (m, 2H), 8.03-8.12 (m, 4H), 8.27-8.28 (m, 5H), 8.46 (d, 1H), 8.55 (m, 2H) |
| 2-38 | 7.25-7.33 (m, 2H), 7.41-7.63 (m, 15H), 7.79 (m, 2H), 7.85 (d, 2H), 7.92-7.94 (m, 2H), 8.03-8.12 (m, 4H), 8.23-8.30 (m, 6H), 8.46 (d, 1H), 8.55 (m, 2H) |
| 3 | 7.25-7.33 (m, 4H), 7.41-7.71 (m, 16H), 7.85-7.87 (m, 3H), 7.94 (d, 1H), 8.02 (d, 1H), 8.28-8.30 (m, 7H), 8.55 (d, 1H) |
| 3-1 | 7.25-7.33 (m, 6H), 7.41-7.47 (m, 4H), 7.50-7.58 (m, 12H), 7.66-7.71 (m, 2H), 7.85-7.87 (m, 5H), 7.94 (d, 1H), 8.02 (d, 1H), 8.21 (dd, 1H), 8.30 (m, 2H), 8.55 (dd, 1H) |
| 3-5 | 7.25-7.34 (m, 6H), 7.41-7.47 (m, 4H), 7.50-7.58 (m, 9H), 7.63-7.71 (m, 5H), 7.79 (dd, 2H), 7.85-7.87 (m, 3H), 7.94 (m, 2H), 8.02 (d, 1H), 8.12 (m, 1H), 8.21-8.30 (m, 5H), 8.55 (d, 1H) |
| 3-6 | 7.26-7.33 (m, 4H), 7.38-7.41 (m, 3H), 7.45-7.47 (m, 3H), 7.50-7.58 (m, 8H), 7.66-7.71 (m, 3H), 7.81-7.94 (m, 7H), 8.02 (dd, 1H), 8.21 (m, 1H), 8.28-8.30 (m, 4H), 8.55 (d, 1H) |
| 3-8 | 1.72 (s, 6H), 7.25-7.33 (m, 5H), 7.42-7.47 (m, 4HH), 7.51-7.63 (m, 11H), 7.71 (s, 1H), 7.77 (s, 1H), 7.85-7.87 (m, 4H), 7.93-7.94 (m, 2H), 8.02 (dd, 1H), 8.21 (d, 1H), 8.28-8.30 (m, 4H), 8.55 (d, 1H) |
| 3-13 | 7.26-7.33 (m, 7H), 7.41-7.47 (m, 3H), 7.50-7.58 (m, 9H), 7.63-7.71 (m, 5H), 7.79 (m, 2H), 7.87 (s, 1H), 7.94 (m, 1H), 8.02 (dd, 1H), 8.12 (m, 1H), 8.21-8.23 (m, 2H), 8.28-8.30 (m, 4H), 8.55 (dd, 1H) |
| 3-38 | 7.25-7.33 (m, 6H), 7.45-7.47 (m, 8H), 7.50-7.58 (m, 6H), 7.66-7.79 (m, 8H), 7.83-7.87 (m, 3H), 7.94 (m, 1H), 8.02 (dd, 1H), 8.21 (d, 1H), 8.30 (m, 2H), 8.55 (dd, 1H) |
| 3-39 | 7.25-7.33 (m, 4H), 7.41-7.45 (m, 3H), 7.50-7.71 (m, 12H), 7.85-7.87 (m, 3H), 7.94-8.02 (m, 5H), 8.21-8.28 (m, 5H), 8.38 (d, 1H), 8.55 (d, 1H), 8.85 (m, 1H) |
| 3-41 | 7.25-7.36 (m, 5H), 7.41-7.47 (m, 3H), 7.51-7.71 (m, 10H), 7.79-7.87 (m, 4H), 7.94-8.02 (m, 5H), 8.21-8.30 (m, 8H), 8.55 (dd, 1H) |
| 4 | 7.25-7.33 (m, 4H), 7.41-7.47 (m, 4H), 7.50-7.58 (m, 10H), 7.71 (s, 1H), 7.85-7.87 (m, 3H), 7.94 (dd, 1H), 8.03 (m, 1H), 8.27-8.30 (m, 7H), 8.55 (d, 1H) |
| 4-3 | 7.25-7.33 (m, 6H), 7.41-7.47 (m, 4H), 7.50-7.58 (m, 14H), 7.71 (s, 1H), 7.85-7.87 (m, 5H), 7.94 (m, 1H), 8.03 (m, 1H), 8.12 (dd, 1H), 8.30 (m, 2H), 8.55 (d, 1H) |
| 4-10 | 7.25-7.33 (m, 2H), 7.41-7.58 (m, 14H), 7.71 (s, 1H), 7.79-7.87 (m, 5H), 7.94 (m, 1H), 8.03 (m, 1H), 8.12 (d, 1H), 8.23-8.30 (m, 8H), 8.55 (dd, 1H) |
| 4-13 | 7.25-7.33 (m, 2H), 7.41-7.58 (m, 21H), 7.66 (s, 3H), 7.71 (s, 1H), 7.87 (s, 1H), 7.94 (m, 1H), 8.03 (m, 1H), 8.12 (dd, 1H), 8.23-8.30 (m, 6H), 8.55 (dd, 1H) |
| 4-22 | 7.25-7.33 (m, 2H), 7.41-7.58 (m, 16H), 7.71 (s, 1H), 7.79 (m, 4H), 7.87 (s, 1H), 7.94 (d, 1H), 8.01-8.03 (m, 3H), 8.12 (m, 1H), 8.23 (s, 1H), 8.27-8.30 (m, 3H), 8.55 (m, 2H) |
| 4-29 | 7.25 (t, 1H), 7.33-7.35 (m, 3H), 7.45-7.28 (m, 11H), 7.71 (s, 1H), 7.81-7.87 (m, 2H), 7.94 (dd, 1H), 8.06-8.15 (m, 4H), 8.30 (m, 4H), 8.54-8.55 (m, 2H), 8.78 (s, 1H) |
| 4-34 | 7.22-7.25 (m, 3H), 7.33 (m, 1H), 7.41-7.59 (m, 12H), 7.68-7.71 (m, 3H), 7.79 (m, 2H), 7.79 (s, 1H), 7.94 (m, 1H), 8.03 (m, 1H), 8.12 (d, 1H), 8.27-8.30 (m, 5H), 8.55-8.56 (m, 2H) |
| 4-39 | 7.25 (t, 1H), 7.33-7.36 (m, 2H), 7.41-7.59 (m, 11H), 7.71 (s, 1H), 7.79-7.87 (m, 6H), 7.94-8.03 (m, 5H), 8.12 (m, 1H), 8.23-8.30 (m, 8H), 8.55 (dd, 1H) |
| 4-40 | 7.25-7.33 (m, 4H), 7.41-7.58 m, 13H), 7.64-7.71 (m, 2H), 7.85 (m, 2H), 7.94 (dd, 1H), 8.03-8.12 (m, 4H), 8.27-8.28 (m, 5H), 8.46 (m, 1H), 8.55 (m, 2H) |
| 5-12 | 7.25-7.33 (m, 5H), 7.41-7.58 (m, 12H), 7.63-7.71 (m, 3H), 7.79-7.94 (m, 8H), 8.04 (d, 1H), 8.12 (dd, 1H), 8.21-8.30 (m, 8H), 8.55 (dd, 1H) |
| 5-15 | 7.25-7.38 (m, 5H), 7.41-7.58 (m, 14H), 7.66-7.94 (m, 11H), 8.04 (d, 1H), 8.21-8.30 (m, 8H), 8.55 (d, 1H) |
| 5-20 | 7.25-7.33 (m, 6H), 7.41-7.58 (m, 17H), 7.71 (s, 1H), 7.79 (m, 4H), 7.87-7.94 (m, 3H), 8.04 (d, 1H), 8.21 (m, 1H), 8.28-8.30 (m, 4H), 8.55 (d, 1H) |
| 5-27 | 7.25 (m, 5H), 7.33-7.39 (m, 5H), 7.45-7.59 (m, 11H), 7.71-7.73 (m, 2H), 7.87-8.04 (m, 11H), 8.21 (d, 1H), 8.30 (m, 2H), 8.55 (d, 1H) |
| 5-32 | 7.25-7.33 (m, 4H), 7.41-7.60 (m, 13H), 7.71 (s, 1H), 7.85-7.94 (m, 5H), 8.04-8.08 (m, 4H), 8.21 (m, 1H), 8.28-8.30 (m, 6H), 8.55 (d, 1H) |
| 5-35 | 7.25-7.33 (m, 2H), 7.41-7.59 (m, 13H), 7.71 (s, 1H), 7.79 (m, 2H), 7.85-7.87 (m, 3H), 7.90-8.04 (m, 6H), 8.21-8.23 (m, 2H), 8.28-8.30 (m, 4H), 8.38 (d, 1H), 8.55 (d, 1H), 8.85 (m, 1H) |
| 6 | 7.25-7.33 (m, 4H), 7.41-7.69 (m, 16H), 7.85-7.87 (m, 3H), 7.94 (d, 1H), 8.02 (d, 1H), 8.28-8.30 (m, 7H), 8.55 (d, 1H) |
| 6-1 | 7.25-7.33 (m, 8H), 7.41-7.58 (m, 18H), 7.66-7.71 (m, 2H), 7.85-7.87 (m, 7H), 7.94 (d, 1H), 8.02 (d, 1H), 8.21 (d, 1H), 8.30 (m, 2H), 8.55 (d, 1H) |
| 6-2 | 2.34 (s, 12H), 7.25 (m, 7H), 7.31-7.33 (m, 3H), 7.45-7.58 (m, 8H), 7.60-7.66 (m, 5H), 7.71 (s, 1H), 7.85-7.87 (m, 3H), 7.94 (m, 1H), 8.02 (m, 1H), 8.21 (m, 1H), 8.30 (m, 2H), 8.55 (d, 1H) |
| 6-12 | 7.25-7.33 (m, 7H), 7.41-7.58 (m, 12H), 7.63-7.71 (m, 5H), 7.79 (m, 4H), 7.87 (s, 1H), 7.94 (m, 2H), 8.02 (m, 1H), 8.12 (dd, 1H), 8.21-8.23 (m, 2H), 8.30 (m, 4H), 8.55 (d, 1H) |
| 6-17 | 7.25-7.33 (m, 4H), 7.41-7.58 (m, 11H), 7.66-7.71 (m, 2H), 7.82-7.94 (m, 7H), 8.02 (d, 1H), 8.12 (m, 2H), 8.21-8.30 (m, 8H), 8.55 (d, 1H), 8.93 (m, 2H) |
| 6-21 | 7.25-7.33 (m, 4H), 7.45-7.71 (m, 12H), 7.85 (m, 2H), 7.87 (d, 1H), 7.94 (d, 1H), 8.21 (d, 1H), 8.30 (m, 2H), 8.35 (s, 1H), 8.42 (m, 2H), 8.55 (d, 1H), 8.70 (m, 2H), 9.24 (s, 2H) |

TABLE 5-continued

| NO | $^1$H NMR (CDCl$_3$, 300 Mz) |
|---|---|
| 6-28 | 1.25 (t, 3H), 2.85 (t, 2H), 7.22-7.31 (m, 8H), 7.45-7.59 (m, 9H), 7.66-7.71 (m, 4H), 7.79 (m, 2H), 7.87 (s, 1H), 7.94 (d, 1H), 8.02 (m, 1H), 8.21 (d, 1H), 8.30 (m, 2H), 8.55-8.56 (m, 2H) |
| 7-1 | 7.25-7.31 (m, 4H), 7.41-7.58 (m, 16H), 7.71 (s, 1H), 7.85-7.87 (m, 3H), 7.94 (d, 1H), 8.03 (m, 1H), 8.12 (d, 1H), 8.27-8.30 (m, 5H), 8.55 (d, 1H) |
| 7-8 | 7.25-7.31 (m, 2H), 7.41-7.58 (m, 21H), 7.33 (s, 3H), 7.71 (s, 1H), 7.87 (s, 1H), 7.94 (m, 1H), 8.03 (d, 1H), 8.12 (d, 1H), 8.27-8.30 (m, 5H), 8.55 (dd, 1H) |
| 7-11 | 7.25-7.32 (m, 2H), 7.41-7.58 (m, 16H), 7.71 (s, 1H), 7.85-7.87 (m, 3H), 7.95 (d, 1H), 8.03 (m, 1H), 8.12 (m, 1H), 8.23 (s, 1H), 8.27-8.30 (m, 7H), 8.55 (d, 1H) |
| 7-17 | 1.72 (s, 6H), 7.26-7.38 (m, 4H), 7.41-7.58 (m, 12H), 7.63 (m, 1H), 7.71 (s, 1H), 7.87 (m, 2H), 7.93-7.94 (m, 2H), 8.03 (m, 1H), 8.12 (m, 1H), 8.23 (s, 1H), 8.27-8.30 (m, 5H), 8.55 (m, 1H) |
| 7-19 | 7.25-7.33 (m, 2H), 7.41-7.58 (m, 14H), 7.71 (s, 1H), 7.79 (m, 4H), 7.87 (s, 1H), 7.94 (m, 1H), 8.03 (m, 1H), 8.12 (d, 1H), 8.23 (s, 1H), 8.27-8.30 (m, 3h), 8.55 (m, 1H) |
| 7-29 | 7.14 (m, 2H), 7.25-7.33 (m, 6H), 7.47-7.58 (m, 8H), 7.70-7.71 (m, 3H), 7.87 (s, 1H), 7.94 (m, 1H), 8.04 (d, 1H), 8.12 (m, 1H), 8.27-8.30 (m, 3H), 8.53-8.55 (m, 3H), 9.15 (s, 2H), 9.30 (m, 2H) |
| 8-1 | 7.25 (m, 3H), 7.34 (m, 1H), 7.45-7.59 (m, 12H), 7.85-8.04 (m, 12H), 8.21 (m, 1H), 8.30 (d, 1H), 8.49 (m, 2H), 8.55 (d, 1H), 9.09 (m, 2H) |
| 8-5 | 7.25-7.32 (m, 2H), 7.41-7.58 (m, 16H), 7.71 (s, 1H), 7.87-7.94 (m, 3H), 8.01-8.04 (m, 3H), 8.21 (d, 1H), 8.28-8.30 (m, 6H), 8.55 (m, 3H) |
| 8-10 | 7.26-7.58 (m, 15H), 7.64-7.71 (m, 4H), 7.85-7.95 (m, 7H), 8.04 (d, 1H), 8.21-8.23 (m, 2H), 8.28-8.30 (m, 6H), 8.55 (d, 1H) |
| 8-15 | 7.25 (m, 3H), 7.33 (t, 1H), 7.45-7.59 (m, 12H), 7.71 (s, 1H), 7.85-7.87 (m, 5H), 7.90-8.04 (m, 9H), 8.21-8.23 (m, 2H), 8.30-8.34 (m, 4H), 8.55 (d, 1H) |
| 8-19 | 7.14 (t, 2H), 7.25-7.33 (m, 2H), 7.40-7.58 (m, 11H), 7.87-7.94 (m, 3H), 8.04 (d, 1H), 8.21 (m, 1H), 8.30 (m, 2H), 8.53-8.55 (m, 3H), 9.15 (s, 2H), 9.30 (d, 2H) |
| 8-26 | 7.05-7.08 (m, 2H), 7.19-7.38 (m, 13H), 7.47-7.58 (m, 11H), 7.71 (s, 1H), 7.75 (m, 1H), 7.87-7.94 (m, 5H), 8.04 (d, 1H), 8.21 (m, 1H), 8.30 (m, 2H), 8.55 (m, 1H) |
| 9-6 | 7.25-7.33 (m, 2H), 7.41-7.58 (m, 15H), 7.70-7.71 (m, 2H), 7.87 (s, 1H), 7.94-7.95 (m, 3H), 8.24-8.30 (m, 7H), 8.55 (d, 1H) |
| 9-9 | 7.00 (m, 2H), 7.25-7.33 (m, 4H), 7.45-7.58 (m, 13H), 7.70-7.71 (m, 2H), 7.87 (s, 1H), 7.94-8.03 (m, 4H), 8.23 (s, 2H), 8.30 (m, 2H), 8.50-8.55 (m, 3H), 8.68 (1H) |
| 9-12 | 1.29 (t, 3H), 4.12 (t, 2H), 7.22-7.33 (m, 10H), 7.45-7.59 (m, 10H), 7.71 (s, 1H), 7.85-7.87 (m, 3H), 7.94-8.03 (m, 4H), 8.30 (m, 2H), 8.55 (d, 1H) |
| 10 | 7.25-7.33 (m, 4H), 7.41-7.66 (m, 16H), 7.76 (m, 1H), 7.85 (m, 2H), 7.94 (d, 1H), 8.02 (m, 1H), 8.21 (d, 1H), 8.28-8.30 (m, 6H), 8.55 (d, 1H) |
| 10-4 | 7.25-7.33 (m, 2H), 7.45-7.66 (m, 14H), 7.76 (d, 1H), 7.85-8.02 (m, 10H), 8.21 (d, 1H), 8.30 (m, 2H), 8.49-8.55 (m, 3H), 9.09 (s, 2H) |
| 10-18 | 7.25-7.33 (m, 6H), 7.41-7.66 (m, 18H), 7.79 (m, 2H), 7.94 (d, 1H), 8.01-8.02 (m, 3H), 8.21-8.30 (m, 6H), 8.55 (m, 3H) |
| 10-22 | 7.25-7.33 (m, 4H), 7.41-7.58 (m, 23H), 7.66-7.76 (m, 6H), 7.85 (m, 2H), 7.94 (m, 1H), 8.02 (m, 1H), 8.21-8.23 (m, 2H), 8.30 (m, 2H), 8.55 (m, 1H) |
| 10-36 | 7.22-7.33 (m, 10H), 7.45-7.66 (m, 16H), 7.76 (d, 1H), 7.85 (m, 2H), 7.94 (d, 1H), 8.02 (m, 1H), 8.21 (d, 1H), 8.30 (m, 2H), 8.55-8.56 (m, 2H) |
| 10-40 | 7.25-7.33 (m, 6H), 7.39-7.58 (m, 21H), 7.61-7.66 (m, 2H), 7.76 (d, 1H), 7.91-8.02 (m, 5H), 8.13 (s, 1H), 8.31 (d, 1H), 8.30 (m, 2H), 8.55 (d, 1H) |
| 11 | 7.25-7.32 (m, 2H), 7.41-7.58 (m, 15H), 7.76 (d, 1H), 7.94 (d, 1H), 8.03 (dd, 1H), 8.12 (dd, 1H), 8.28-8.30 (m, 7H), 8.55 (d, 1H) |
| 11-1 | 7.25-7.31 (m, 4H), 7.41-7.58 (m, 15H), 7.76 (d, 1H), 7.85 (m, 2H), 7.94 (m, 1H), 8.03 (dd, 1H), 8.12 (d, 1H), 8.27-8.30 (m, 7H), 8.55 (d, 1H) |
| 11-4 | 7.25-7.31 (m, 5H), 7.38-7.66 (m, 15H), 7.76-7.94 (m, 7H), 8.03 (d, 1H), 8.12 (d, 1H), 8.27-8.30 (m, 5H), 8.55 (dd, 1H) |
| 11-9 | 7.25-7.33 (m, 2H), 7.41-7.58 (m, 17H), 7.76 (d, 1H), 7.85 (m, 2H), 7.94 (m, 1H), 8.03, (m, 1H), 8.12 (d, 1H), 8.23-8.30 (m, 8H), 8.55 (d, 1H) |
| 11-22 | 7.25-7.33 ((m, 2H), 7.45-7.58 (m, 8H), 7.76-7.94 (m, 12H), 8.03 (d, 1H), 8.12 (m, 5H), 8.23 (s, 1H), 8.27-8.30 (m, 3H), 8.55 (m, 1H), 8.93 (m, 4H) |
| 11-32 | 7.14 (m, 2H), 7.25-7.33 (m, 2H), 7.45-7.58 (m, 9H), 7.66-7.76 (m, 6H), 7.88 (m, 2H), 7.94 (d, 1H), 8.03 (d, 1H), 8.12 (d, 1H), 8.27-8.30 (m, 3H), 8.53-8.55 (m, 3H), 8.81 (s, 2H), 8.99 (s, 2H), 9.30 (d, 2H) |
| 11-42 | 7.25-7.33 (m, 2H), 7.45-7.58 (m, 9H), 7.76-7.94 (m, 6H), 8.03-8.04 (m, 2H), 8.12-8.18 (m, 4H), 8.27-8.30 (m, 3H), 8.55 (d, 1H), 8.93 (m, 2H), 9.15 (s, 1H) |
| 12-1 | 7.25-7.33 (m, 8H), 7.41-7.58 (m, 15H), 7.76 (d, 1H), 7.85 (m, 2H), 7.90-7.94 (m, 2H), 8.04 (d, 1H), 8.21-8.30 (m, 7H), 8.55 (d, 1H) |
| 12-7 | 7.25 (m, 1H), 7.33-7.58 (m, 20H), 7.76 (d, 1H), 7.90-7.94 (m, 6H), 8.04 (d, 1H), 8.21 (d, 1H), 8.28-8.30 (m, 6H), 8.55 (d, 1H) |
| 12-11 | 7.25-7.38 (m, 10H), 7.45-7.66 (m, 11H), 7.76-7.94 (m, 9H), 8.04 (m, 1H), 8.21 (d, 1H), 8.30 (m, 2H), 8.55 (d, 1H) |
| 12-17 | 7.25-7.33 (m, 2H), 7.41-7.58 (m, 17H), 7.70-7.79 (m, 5H), 7.90-7.94 (m, 2H), 8.04 (d, 1H), 8.21-8.30 (m, 6H), 8.55 (d, 1H) |
| 12-29 | 1.76 (d, 6H), 7.25-7.33 (m, 4H), 7.41-7.58 (m, 12H), 7.76-7.94 (m, 9H), 8.04 (d, 1H), 8.21-8.30 (m, 5H), 8.55 (d, 1H) |
| 13-1 | 7.25-7.33 (m, 2H), 7.41-7.58 (m, 17H), 7.70-7.76 (m, 2H), 7.94-7.95 (m, 3H), 8.03 (m, 1H), 8.24-8.30 (m, 7H), 8.55 (m, 1H) |
| 13-3 | 7.25-7.33 (m, 4H), 7.41-7.58 (m, 17H), 7.76 (d, 1H), 7.85 (m, 2H), 7.94-7.95 (m, 3H), 8.03 (m, 1H), 8.23-8.30 (m, 9H), 8.55 (m, 1H) |
| 13-4 | 7.25-7.33 (m, 2H), 7.41-7.58 (m, 17H), 7.70-7.79 (m, 5h), 7.94-7.95 (m, 3H), 8.03 (m, 1H), 8.23-8.30 (m, 5H), 8.55 (1H) |
| 14 | 7.25-7.33 (m, 4H), 7.45-7.66 (m, 16H), 7.85 (m, 2H), 7.92-7.93 (m, 2H), 8.02 (m, 1H), 8.25-8.30 (m, 7H), 8.55 (d, 1H) |
| 14-3 | 7.25-7.33 (m, 2H), 7.45-7.66 (m, 14H), 7.85-8.00 (m, 11H), 8.21 (m, 1H), 8.30 (m, 2H), 8.49 (m, 2H), 8.55 (dd, 1H), 9.09 (s, 2H) |
| 14-5 | 7.25-7.33 (m, 4H), 7.41-7.58 (m, 19H), 7.66-7.70 (m, 2H), 7.85 (m, 2H), 7.92-7.94 (m, 2H), 8.21-8.30 (m, 6H), 8.55 (d, 1H) |
| 14-7 | 7.26-7.33 (m, 6H), 7.41-7.68 (m, 18H), 7.79 (m, 2H), 7.85 (m, 2H), 7.92-7.94 (m, 3H), 8.02 (d, 1H), 8.12 (d, 1H), 8.21-8.30 ((m, 5H), 8.55 (m, 2H) |
| 14-12 | 7.25-7.33 (m, 4H), 7.41-7.66 (m, 16H), 7.79 (m, 2H), 7.92-7.94 (m, 2H), 8.02 (d, 1H), 8.21-8.30 (m, 8H), 8.55 (d, 1H) |
| 14-16 | 7.25-7.33 (m, 7H), 7.41-7.66 (m, 17H), 7.79 (dd, 2H), 7.92-7.94 (m, 3H0, 8.02 (m, 1H), 8.12 (m, 1H), 8.21-8.30 (m, 8H), 8.55 (m, 1H) |
| 14-22 | 7.25-7.32 (m, 4H), 7.47-7.66 (m, 14H), 7.85-8.02 (m, 13H), 8.21-8.23 (m, 2H), 8.30-8.34 (m, 4H), 8.55 (m, 1H) |
| 14-33 | 7.25-7.31 (m, 6H), 7.47-7.65 (m, 15H), 7.92-7.94 (m, 2H), 8.01-8.02 (m, 3H), 8.21 (d, 1H), 8.30 (m, 2H), 8.38 (m, 2H), 8.55 (m, 3H), 8.83 (m, 2H) |
| 14-43 | 7.25-7.33 (m, 2H), 7.45-7.65 (m, 18H), 7.77-7.79 (m, 8H), 7.92-7.94 (m, 2H), 8.01-8.02 (m, 3H), 8.21 (d, 1H), 8.30 (m, 2H), 8.55 (m, 2H) |
| 14-52 | 7.25-7.33 (m, 4H), 7.41-7.66 (m, 15H), 7.85 (m, 2H), 7.92-7.94 (m, 2H), 8.02-8.08 (m, 4H), 8.21-8.29 (m, 7H), 8.55 (d, 1H) |
| 14-53 | 7.25-7.32 (m, 4H), 7.41-7.59 (m, 15H), 7.92-8.02 (m, 8H), 8.21 (d, 1H), 8.28 (m, 4H), 8.38 (dd, 1H), 8.55 (d, 1H), 8.85 (s, 1H) |
| 14-55 | 7.25-7.31 (m, 4H), 7.41-7.62 (m, 15h), 7.79 (m, 2H), 7.92-8.02 (m, 6H), 8.21-8.30 (m, 6H), 8.38 (m, 1H), 8.55 (d, 1H), 8.85 (s, 1H) |
| 15 | 7.26-7.33 (m, 4H), 7.41-7.58 (m, 15H), 7.85 (m, 2H), 7.92-7.94 (m, 2H), 8.03 (m, 1H), 8.12 (d, 1H), 8.27-8.30 (m, 7H), 8.55 (d, 1H) |
| 15-2 | 7.25-7.33 (m, 4H), 7.41-7.58 (m, 19H), 7.70 (s, 1H), 7.85 (d, 2H), 7.92-7.94 (m, 2H), 8.03 (m, 1H), 8.12 (d, 1H), 8.24-8.30 (m, 6H), 8.55 (d, 1H) |
| 15-4 | 7.25-7.33 (m, 7H), 7.41-7.58 (m, 16H), 7.85 (m, 2H), 7.92-7.94 (m, 3H), 8.03 (d, 1H), 8.09-8.12 (m, 3H), 8.27-8.28 (m, 6H), 8.55 (m, 2H) |

TABLE 5-continued

| NO | $^1$H NMR (CDCl$_3$, 300 Mz) |
|---|---|
| 15-8 | 7.25-7.57 (m, 20H), 7.81-7.94 (m, 7H), 8.03 (d, 1H), 8.12 (d, 1H), 8.28-8.30 (m, 5H), 8.55 (d, 1H) |
| 15-11 | 7.25-7.32 (m, 2H), 7.41-7.58 (m, 17H), 7.70 (s, 1H), 7.92-7.94 (m, 2H), 8.03 (m, 1H), 8.12 (d, 1H), 8.24-8.30 (m, 8H), 8.55 (d, 1H) |
| 15-15 | 7.25-7.33 (m, 2H), 7.41-7.58 (m, 17H), 7.85 (m, 4H), 7.92-7.94 (m, 2H), 8.03 (m, 1H), 8.12 (d, 1H), 8.27-8.30 (m, 9H), 8.55 (m, 1H) |
| 15-30 | 2.34 (s, 6H), 7.25-7.32 (m, 8H), 7.47-7.58 (m, 9H), 7.67 (m, 4H), 7.85 (m, 2H), 7.92-7.94 (m, 2H), 8.03 (m, 1H), 8.12 (d, 1H), 8.23, 8.27-8.30 (m, 3H), 8.55 (d, 1H) |
| 15-42 | 1.76 (s, 6H), 7.25-7.30 (m, 6H), 7.45-7.58 (m, 13H), 7.90-7.94 (m, 6H), 8.03 (m, 1H), 8.12 (d, 1H), 8.27-8.30 (m, 3H), 8.55 (d, 1H) |
| 15-48 | 7.25-7.32 (m, 4H), 7.41-7.58 (m, 15H), 7.85 (m, 2H), 7.92-7.94 (m, 2H), 8.03-8.10 (m, 4H), 8.27-8.28 (m, 5H), 8.46 (m, 1H), 8.55 (m, 2H) |
| 15-50 | 7.25-7.33 (m, 2H), 7.41-7.59 (m, 14H), 7.79-7.85 (m, 4H), 7.92-8.00 (m, 6H), 8.12 (d, 1H), 8.23-8.30 (m, 6H), 8.38 (d, 1H), 8.55 (d, 1H), 8.85 (s, 1H) |
| 15-51 | 7.26-7.33 (m, 4H), 7.42-7.58 (m, 14H), 7.85 (m, 2H), 7.92-7.94 (m, 2H), 8.03-8.12 (m, 5H), 8.27-8.30 (m, 7H), 8.55 (d, 1H) |
| 16 | 7.25-7.33 (m, 4H), 7.41-7.58 (m, 15H), 7.85 (m, 2H), 7.90-7.94 (m, 3H), 8.04 (d, 1H), 8.21 (m, 1H), 8.28-8.30 (m, 6H), 8.55 (m, 1H) |
| 16-8 | 7.25-7.33 (m, 4H), 7.45-7.58 (m, 13H), 7.85-8.04 (m, 12H), 8.21 (m, 1H), 8.30 (m, 2H), 8.49-8.55 (m, 3H), 9.09 (s, 2H) |
| 16-11 | 7.25-7.33 (m, 2H), 7.41-7.58 (m, 19H), 7.70-7.75 (m, 2H), 7.85-7.94 (m, 5H), 8.04 (d, 1H), 8.21-8.30 (m, 8H), 8.55 (d, 1H) |
| 16-14 | 7.25-7.33 (m, 5H), 7.41-7.65 (m, 16H), 7.79-7.94 (m, 10H), 8.04 (d, 1H), 8.12 (m, 1H), 8.21-8.30 (m, 6H), 8.55 (m, 1H) |
| 16-20 | 7.25-7.35 (m, 10H), 7.45-7.66 (m, 13H), 7.85-7.94 (m, 9H), 8.04 (d, 1H), 8.21-8.29 (m, 4H), 8.55 (d, 1H) |
| 16-28 | 7.25-7.33 (m, 3H), 7.45-7.58 (m, 10H), 7.81-7.94 (m, 6H), 8.04-8.10 (m, 3H), 8.21 (m, 1H), 8.32-8.38 (m, 3H), 8.55 (d, 1H), 8.81-8.83 (m, 3H) |
| 16-35 | 7.25-7.36 (m, 12H), 7.45-7.58 (m, 9H), 7.66 (m, 5H), 7.81-7.94 (m, 9H), 8.04 (d, 1H), 8.21 (d, 1H), 8.30 (m, 2H), 8.55 (d, 1H) |
| 16-42 | 7.25-7.31 (m, 4H), 7.42-7.58 (m, 14H), 7.85-7.94 (m, 5H), 8.04-8.08 (m, 4H), 8.22-8.30 (m, 7H), 8.55 (d, 1H) |
| 16-44 | 7.25-7.33 (m, 2H), 7.41-7.58 (m, 14H), 7.79-8.03 (m, 11H), 8.22-8.30 (m, 6H), 8.38 (d, 1H), 8.55 (d, 1H), 8.85 (s, 1H) |

TABLE 6

| Compound | FD-MS | Compound | FD-MS |
|---|---|---|---|
| 1 | m/z = 727.27 (C$_{52}$H$_{33}$N$_5$ = 727.85) | 1-1 | m/z = 879.34 (C$_{64}$H$_{41}$N$_5$ = 880.04) |
| 1-7 | m/z = 803.30 (C$_{58}$H$_{37}$N$_5$ = 803.95) | 1-20 | m/z = 726.28 (C$_{53}$H$_{34}$N$_4$ = 726.86) |
| 1-26 | m/z = 727.28 (C$_{52}$H$_{33}$N$_5$ = 727.85) | 1-29 | m/z = 750.28 (C$_{55}$H$_{34}$N$_4$ = 750.89) |
| 1-32 | m/z = 700.26 (C$_{51}$H$_{32}$N$_4$ = 700.83) | 1-40 | m/z = 748.29 (C$_{57}$H$_{35}$N$_{52}$ = 748.91) |
| 1-42 | m/z = 777.29 (C$_{56}$H$_{35}$N$_3$ = 777.91) | 1-43 | m/z = 776.29 (C$_{57}$H$_{35}$N$_4$ = 776.92) |
| 2-1 | m/z = 727.27 (C$_{52}$H$_{33}$N$_5$ = 727.85) | 2-3 | m/z = 803.30 (C$_{58}$H$_{37}$N$_5$ = 803.95) |
| 2-5 | m/z = 727.27 (C$_{52}$H$_{33}$N$_5$ = 727.85) | 2-10 | m/z = 726.28 (C$_{53}$H$_{34}$N$_4$ = 726.86) |
| 2-29 | m/z = 810.30 (C$_{62}$H$_{38}$N$_2$ = 810.98) | 2-35 | m/z = 689.25 (C$_{50}$H$_{31}$N$_3$O = 689.80) |
| 2-36 | m/z = 700.26 (C$_{51}$H$_{32}$N$_4$ = 700.83) | 2-37 | m/z = 777.29 (C$_{56}$H$_{35}$N$_5$ = 777.91) |
| 2-38 | m/z = 776.29 (C$_{57}$H$_{35}$N$_4$ = 776.92) | 3 | m/z = 727.27 (C$_{52}$H$_{33}$N$_5$ = 727.85) |
| 3-1 | m/z = 803.30 (C$_{58}$H$_{37}$N$_5$ = 803.95) | 3-5 | m/z = 892.33 (C$_{64}$H$_{40}$N$_6$ = 893.04) |
| 3-6 | m/z = 817.28 (C$_{58}$H$_{35}$N$_5$O = 817.93) | 3-8 | m/z = 843.34 (C$_{61}$H$_{41}$N$_5$ = 844.01) |
| 3-13 | m/z = 891.34 (C$_{65}$H$_{41}$N$_5$ = 892.05) | 3-38 | m/z = 772.26 (C$_{55}$H$_{37}$N$_2$OP = 772.87) |
| 3-39 | m/z = 777.29 (C$_{56}$H$_{35}$N$_5$ = 777.91) | 3-41 | m/z = 776.29 (C$_{57}$H$_{36}$N$_4$ = 776.92) |
| 4 | m/z = 727.27 (C$_{52}$H$_{33}$N$_5$ = 727.85) | 4-3 | m/z = 803.30 (C$_{58}$H$_{37}$N$_5$ = 803.95) |
| 4-10 | m/z = 726.28 (C$_{53}$H$_{34}$N$_4$ = 726.86) | 4-13 | m/z = 802.31 (C$_{59}$H$_{38}$N$_4$ = 802.96) |
| 4-22 | m/z = 776.29 (C$_{57}$H$_{36}$N$_4$ = 776.92) | 4-29 | m/z = 674.25 (C$_{49}$H$_{30}$N = 674.79) |
| 4-34 | m/z = 688.26 (C$_{50}$H$_{32}$N$_4$ = 688.82) | 4-39 | m/z = 776.29 (C$_{57}$H$_{36}$N$_4$ = 776.92) |
| 4-40 | m/z = 777.29 (C$_{56}$H$_{35}$N$_5$ = 777.91) | 5-12 | m/z = 891.34 (C$_{56}$H$_{41}$N$_5$ = 892.05) |
| 5-15 | m/z = 892.32 (C$_{65}$H$_{40}$N$_4$O = 893.04) | 5-20 | m/z = 802.31 (C$_{59}$H$_{38}$N$_4$ = 802.96) |
| 5-27 | m/z = 798.30 (C$_{61}$H$_{38}$N$_2$ = 798.97) | 5-32 | m/z = 777.29 (C$_{56}$H$_{35}$N$_5$ = 777.91) |
| 5-35 | m/z = 776.29 (C$_{54}$H$_{36}$N$_4$ = 776.92) | 6 | m/z = 727.27 (C$_{52}$H$_{33}$N$_5$ = 727.85) |
| 6-1 | m/z = 879.34 (C$_{64}$H$_{41}$N$_5$ = 880.04) | 6-2 | m/z = 859.37 (C$_{62}$H$_{45}$N$_5$ = 860.05) |
| 6-12 | m/z = 891.34 (C$_{65}$H$_{41}$N$_5$ = 892.05) | 6-17 | m/z = 826.31 (C$_{61}$H$_{38}$N$_4$ = 826.98) |

TABLE 6-continued

| Compound | FD-MS | Compound | FD-MS |
|---|---|---|---|
| 6-21 | m/z = 728.27 ($C_{51}H_{32}N_6$ = 728.84) | 6-28 | m/z = 716.29 ($C_{62}H_{36}N_4$ = 716.87) |
| 7-1 | m/z = 727.27 ($C_{52}H_{33}N_5$ = 727.85) | 7-8 | m/z = 803.30 ($C_{58}H_{37}N_5$ = 803.95) |
| 7-11 | m/z = 726.28 ($C_{53}H_{34}N_4$ = 726.86) | 7-17 | m/z = 766.31 ($C_{56}H_{38}N_4$ = 766.93) |
| 7-19 | m/z = 650.25 ($C_{47}H_{30}N_4$ = 650.77) | 7-29 | m/z = 727.27 ($C_{52}H_{33}N_5$ = 772.85) |
| 8-1 | m/z = 827.30 ($C_{60}H_{37}N_5$ = 827.97) | 8-5 | m/z = 777.29 ($C_{56}H_{35}N_5$ = 777.91) |
| 8-10 | m/z = 816.29 ($C_{59}H_{36}N_4O$ = 816.94) | 8-15 | m/z = 826.31 ($C_{61}H_{38}N_4$ = 826.98) |
| 8-19 | m/z = 727.27 ($C_{52}H_{33}N_5$ = 727.85) | 8-26 | m/z = 826.30 ($C_{62}H_{38}N_2O$ = 826.98) |
| 9-6 | m/z = 727.27 ($C_{52}H_{33}N_5$ = 727.85) | 9-9 | m/z = 726.28 ($C_{53}H_{34}N_4$ = 726.86) |
| 9-12 | m/z = 716.29 ($C_{52}H_{36}N_4$ = 716.87) | 10 | m/z = 727.27 ($C_{52}H_{33}N_5$ = 727.85) |
| 10-4 | m/z = 827.30 ($C_{60}H_{37}N_5$ = 827.97) | 10-18 | m/z = 852.33 ($C_{63}H_{40}N_4$ = 853.02) |
| 10-22 | m/z = 878.34 ($C_{65}H_{42}N_4$ = 879.06) | 10-36 | m/z = 764.29 ($C_{56}H_{36}N_4$ = 764.91) |
| 10-40 | m/z = 824.32 ($C_{63}H_{40}N_2$ = 825.01) | 11 | m/z = 651.24 ($C_{46}H_{29}N_5$ = 651.76) |
| 11-1 | m/z = 727.27 ($C_{52}H_{33}N_5$ = 727.85) | 11-4 | m/z = 817.28 ($C_{58}H_{35}N_5O$ = 817.93) |
| 11-9 | m/z = 726.28 ($C_{53}H_{34}N_4$ = 726.86) | 11-22 | m/z = 850.31 ($C_{63}H_{38}N_4$ = 851.00) |
| 11-32 | m/z = 804.30 ($C_{57}H_{36}N_6$ = 804.94) | 11-42 | m/z = 64 6.24 ($C_{49}H_{30}N_2$ = 646.78) |
| 12-1 | m/z = 803.30 ($C_{58}H_{37}N_5$ = 803.95) | 12-7 | m/z = 827.30 ($C_{60}H_{37}N_5$ = 827.97) |
| 12-11 | m/z = 907.29 ($C_{64}H_{37}N_5O_2$ = 908.01) | 12-17 | m/z = 726.28 ($C_{53}H_{34}N_4$ = 726.86) |
| 12-29 | m/z = 803.28 ($C_{54}H_{38}N_5OP$ = 803.89) | 13-1 | m/z = 727.27 ($C_{52}H_{33}N_5$ = 727.85) |
| 13-3 | m/z = 802.31 ($C_{59}H_{38}N_4$ = 802.96) | 13-4 | m/z = 726.28 ($C_{53}H_{34}N_4$ = 726.86) |
| 14 | m/z = 727.27 ($C_{52}H_{33}N_5$ = 727.85) | 14-3 | m/z = 827.30 ($C_{60}H_{37}N_5$ = 827.97) |
| 14-5 | m/z = 803.30 ($C_{58}H_{37}N_5$ = 803.95) | 14-7 | m/z = 892.33 ($C_{64}H_{40}N_6$ = 893.04) |
| 14-12 | m/z = 726.28 ($C_{53}H_{34}N_4$ = 726.86) | 14-16 | m/z = 891.34 ($C_{65}H_{41}N_5$ = 892.05) |
| 14-22 | m/z = 826.31 ($C_{61}H_{38}N_4$ = 826.98) | 14-33 | m/z = 800.29 ($C_{59}H_{36}N_4$ = 800.94) |
| 14-43 | m/z = 822.29 ($C_{59}H_{39}N_2OP$ = 822.93) | 14-52 | m/z = 777.29 ($C_{56}H_{35}N_5$ = 777.91) |
| 14-53 | m/z = 777.29 ($C_{56}H_{35}N_5$ = 777.91) | 14-55 | m/z = 776.29 ($O_{57}H_{36}N_4$ = 776.92) |
| 15 | m/z = 727.27 ($C_{52}H_{33}N_5$ = 727.85) | 15-2 | m/z = 803.30 ($C_{58}H_{37}N_5$ = 803.95) |
| 15-4 | m/z = 892.33 ($C_{64}H_{40}N_6$ = 893.04) | 15-8 | m/z = 817.28 ($C_{58}H_{35}N_5O$ = 817.93) |
| 15-11 | m/z = 727.27 ($C_{52}H_{33}N_5$ = 727.85) | 15-15 | m/z = 802.31 ($C_{59}H_{38}N_4$ = 802.96) |
| 15-30 | m/z = 754.31 ($C_{55}H_{38}N_4$ = 754.92) | 15-42 | m/z = 748.26 ($C_{53}H_{37}N_2OP$ = 748.85) |
| 15-48 | m/z = 777.29 ($C_{56}H_{35}N_5$ = 777.91) | 15-50 | m/z = 776.29 ($C_{57}H_{36}N_4$ = 776.92) |
| 15-51 | m/z = 777.29 ($C_{56}H_{35}N_5$ = 777.91) | 16 | m/z = 727.27 ($C_{52}H_{33}N_5$ = 727.85) |
| 16-8 | m/z = 827.30 ($C_{60}H_{37}N_5$ = 827.97) | 16-11 | m/z = 802.31 ($C_{59}H_{38}N_4$ = 802.96) |
| 16-14 | m/z = 891.34 ($C_{65}H_{41}N_5$ = 892.05) | 16-20 | m/z = 906.30 ($C_{65}H_{38}N_4O_2$ = 907.02) |
| 16-28 | m/z = 674.25 ($C_{49}H_{30}N_4$ = 674.79) | 16-35 | m/z = 904.31 ($C_{67}H_{40}N_2O_2$ = 905.05) |
| 16-42 | m/z = 777.29 ($C_{56}H_{35}N_5$ = 777.91) | 16-44 | m/z = 776.29 ($C_{57}H_{36}N_4$ = 776.92) |

Experimental Example

Experimental Example 1

1) Manufacture of Organic Light Emitting Device

A glass substrate on which indium tin oxide (ITO) was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and ultraviolet ozone (UVO) treated for 5 minutes using UV in an ultraviolet (UV) cleaner. After that, the substrate was transferred to a plasma cleaner (PT), and plasma treatment was performed under vacuum for ITO work function and residual film removal, and the substrate was transferred to a thermal deposition apparatus for organic deposition.

On the transparent ITO electrode (anode), organic materials were formed in a 2-stack white organic light emitting device (WOLED) structure. As for the first stack, TAPC was thermal vacuum deposited first to a thickness of 300 Å to form a hole transfer layer. After forming the hole transfer layer, a light emitting layer was thermal vacuum deposited thereon as follows. As the light emitting layer, TCz1, a host, was 8% doped with FIrpic, a blue phosphorescent dopant, and deposited to 300 Å. After forming an electron transfer layer to 400 Å using TmPyPB, the compound described in the following Table 7 was 20% doped with $Cs_2CO_3$ to form a charge generation layer to 100 Å.

As for the second stack, $MoO_3$ was thermal vacuum deposited first to a thickness of 50 Å to form a hole injection layer. A hole transfer layer, a common layer, was formed to 100 Å by 20% doping $MoO_3$ to TAPC and then depositing TAPC to 300 Å. A light emitting layer was formed by 8% doping Ir(ppy)$_3$, a green phosphorescent dopant, to TCz1, a host, and depositing the result to 300 Å, and then an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

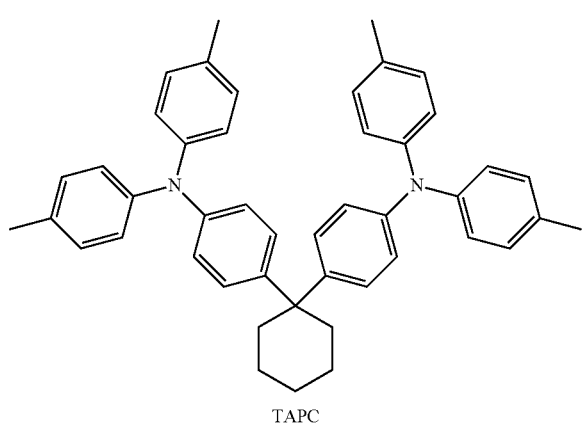

TAPC

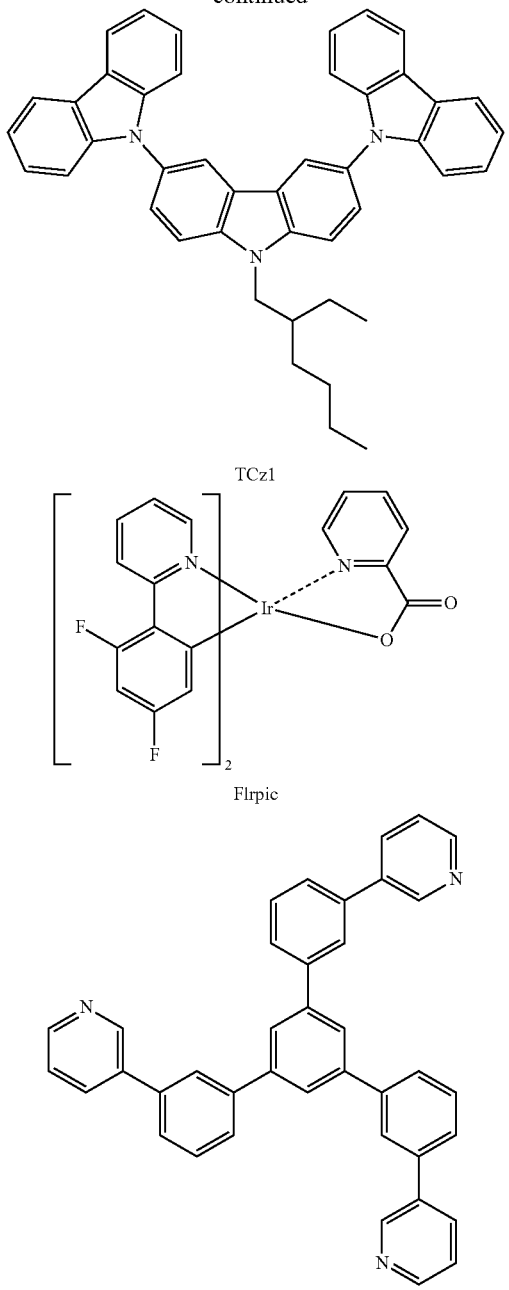

TCz1

FIrpic

TmPyPB

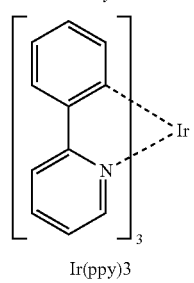

Ir(ppy)3

Meanwhile, all the organic compounds required to manufacture the OLED were vacuum sublimation purified under $10^{-6}$ torr to $10^{-8}$ torr for each material to be used in the OLED manufacture.

2) Driving Voltage and Light Emission Efficiency of Organic Light Emitting Device For the organic light emitting devices manufactured as above, electroluminescent (EL) properties were measured using M7000 manufactured by McScience Inc., and with the measurement results, T95 when standard luminance was 3,500 cd/m$^2$ was measured using a lifetime measurement system (M6000) manufactured by McScience Inc. Results of measuring driving voltage, light emission efficiency, external quantum efficiency and color coordinate (CIE) of the white organic light emitting devices manufactured according to the present disclosure are as shown in Table 7.

TABLE 7

| Compound | Driving Voltage (V) | Light Emission Efficiency (cd/A) | CIE (x, y) | Lifetime (T95) |
|---|---|---|---|---|
| Example 1 | 1-20 | 7.71 | 60.95 | (0.210, 0.439) | 40 |
| Example 2 | 1-26 | 7.42 | 65.51 | (0.220, 0.445) | 50 |
| Example 3 | 1-29 | 7.36 | 64.78 | (0.220, 0.440) | 45 |
| Example 4 | 2-5 | 7.69 | 62.88 | (0.208, 0.421) | 38 |
| Example 5 | 3-39 | 7.72 | 60.55 | (0.220, 0.436) | 35 |
| Example 6 | 4-29 | 7.44 | 66.04 | (0.223, 0.442) | 50 |
| Example 7 | 4-34 | 7.66 | 62.99 | (0.220, 0.430) | 35 |
| Example 8 | 6-21 | 7.39 | 65.12 | (0,218, 0.435) | 42 |
| Example 9 | 7-11 | 7.72 | 63.13 | (0.222, 0.433) | 38 |
| Example 10 | 7-29 | 7.57 | 65.89 | (0.238, 0.438) | 41 |
| Example 11 | 8-19 | 7.45 | 66.11 | (0.210, 0.440) | 45 |
| Example 12 | 9-9 | 7.51 | 65.56 | (0.209, 0.415) | 47 |
| Example 13 | 10 | 7.74 | 60.89 | (0.231, 0.420) | 38 |
| Example 14 | 11 | 7.69 | 61.71 | (0.221, 0.425) | 40 |
| Example 15 | 11-32 | 7.59 | 65.26 | (0.229, 0.429) | 41 |
| Example 16 | 12-17 | 7.71 | 63.11 | (0.207, 0.409) | 30 |
| Example 17 | 14-33 | 7.63 | 66.67 | (0.208, 0.415) | 36 |
| Example 18 | 15-11 | 7.65 | 63.06 | (0.214, 0.420) | 40 |
| Example 19 | 16 | 7.71 | 61.56 | (0.214, 0.429) | 37 |
| Example 20 | 16-28 | 7.35 | 67.21 | (0.221, 0.434) | 45 |
| Comparative Example 1-1 | TmPyPB | 8.57 | 57.61 | (0.212, 0.433) | 24 |
| Comparative Example 1-2 | BBQB | 8.43 | 58.11 | (0.220, 0.429) | 27 |
| Comparative Example 1-3 | TBQB | 8.47 | 58.90 | (0.222, 0.430) | 28 |
| Comparative Example 1-4 | E2 | 8.45 | 58.05 | (0.221, 0.431) | 25 |
| Comparative Example 1-5 | DPBC | 8.60 | 58.06 | (0.222, 0.433) | 26 |

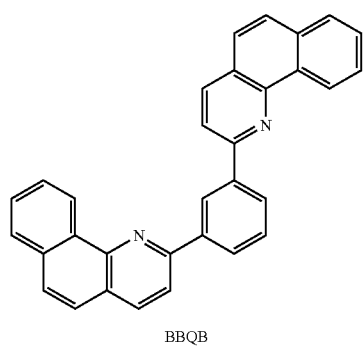

BBQB

TBQB

E2

DPBC

As seen from the results of Table 7, the organic light emitting device using the charge generation layer material of the 2-stack white organic light emitting device of the present disclosure had lower driving voltage and improved light emission efficiency compared to the comparative examples. Particularly, it was identified that Compounds 1-26, 1-29, 4-29, 8-19, 9-9 and 16-28 were significantly superior in all aspects of driving, efficiency and lifetime.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

Experimental Example 2

1) Manufacture of Organic Light Emitting Device

A glass substrate on which indium tin oxide (ITO) was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treated for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), organic materials were formed in a single stack structure. As a hole injection layer, HAT-CN was deposited to a thickness of 50 Å, and subsequently, as a hole transfer layer, NPD doped with DNTPD in 10% or less was deposited to a thickness of 1500 Å, and TCTA was continuously deposited to a thickness of 200 Å. Subsequently, a light emitting layer comprising a t-Bu-perylene dopant in an ADN host was formed to a thickness of 250 Å. Subsequently, Alq$_3$, an electron transfer layer, was formed as a film to a thickness of 250 Å, and as an N-type charge generation layer, a compound described in the following Table 8 was doped with lithium, an alkali metal, and formed as a film to a thickness of 100 Å. Al, a cathode, was formed as a film to a thickness of approximately 1,000 Å, and as a result, an organic light emitting device was manufactured.

2) Driving Voltage and Light Emission Efficiency of Organic Light Emitting Device For the organic light emitting devices manufactured as above, electroluminescent (EL) properties were measured using M7000 manufactured by McScience Inc., and with the measurement results, T95 when standard luminance was 750 cd/m$^2$ was measured using a lifetime measurement system (M6000) manufactured by McScience Inc. Results of measuring driving voltage, light emission efficiency, external quantum efficiency and color coordinate (CIE) of the blue organic electroluminescent devices manufactured according to the present disclosure are as shown in Table 8.

TABLE 8

| | Compound | Driving Voltage (V) | Light Emission Efficiency (cd/A) | CIE (x, y) | Lifetime (T95) |
|---|---|---|---|---|---|
| Example 1 | 1 | 5.30 | 6.94 | (0.134, 0.102) | 42 |
| Example 2 | 1-26 | 5.11 | 7.10 | (0.134, 0.101) | 50 |
| Example 3 | 1-29 | 5.05 | 7.25 | (0.134, 0.100) | 48 |
| Example 4 | 2-1 | 5.38 | 6.77 | (0.134, 0.102) | 40 |
| Example 5 | 2-5 | 5.33 | 6.57 | (0.134, 0.102) | 36 |
| Example 6 | 3 | 5.25 | 6.66 | (0.134, 0.102) | 39 |
| Example 7 | 3-39 | 5.30 | 6.88 | (0.133, 0.102) | 41 |
| Example 8 | 4 | 5.28 | 6.85 | (0.134, 0.102) | 40 |
| Example 9 | 4-29 | 5.07 | 7.28 | (0.133, 0.101) | 55 |

TABLE 8-continued

| | Compound | Driving Voltage (V) | Light Emission Efficiency (cd/A) | CIE (x, y) | Lifetime (T95) |
|---|---|---|---|---|---|
| Example 10 | 4-34 | 5.28 | 6.95 | (0.134, 0.102) | 39 |
| Example 11 | 5-20 | 5.25 | 6.88 | (0.134, 0.101) | 41 |
| Example 12 | 6-2 | 5.31 | 6.75 | (0.134, 0,104) | 40 |
| Example 13 | 6-21 | 5.18 | 7.15 | (0.133, 0.101) | 43 |
| Example 14 | 6-28 | 5.28 | 6.74 | (0.133, 0.104) | 42 |
| Example 15 | 7-29 | 5.10 | 7.11 | (0.134, 0.101) | 46 |
| Example 16 | 8-19 | 5.18 | 7.10 | (0.133, 0.101) | 43 |
| Example 17 | 9-6 | 5.30 | 6.55 | (0.134, 0.101) | 42 |
| Example 18 | 9-9 | 5.18 | 7.20 | (0.133, 0.100) | 40 |
| Example 19 | 11 | 5.25 | 6.59 | (0.134, 0.101) | 41 |
| Example 20 | 11-32 | 5.05 | 7.29 | (0.133, 0.102) | 43 |
| Example 21 | 12-7 | 5.30 | 6.99 | (0.134, 0.103) | 39 |
| Example 22 | 13-1 | 5.25 | 7.10 | (0.134, 0.102) | 41 |
| Example 23 | 14-33 | 5.15 | 7.12 | (0.134, 0.101) | 40 |
| Example 24 | 15-11 | 5.25 | 7.26 | (0.133, 0.103) | 41 |
| Example 25 | 16-28 | 5.05 | 7.20 | (0.134, 0.101) | 52 |
| Comparative Example 2-1 | Bphen | 5.82 | 6.23 | (0.134, 0.110) | 27 |
| Comparative Example 2-2 | BBQB | 5.80 | 6.32 | (0.134, 0.111) | 29 |
| Comparative Example 2-3 | TBQB | 5.84 | 6.39 | (0.134, 0.111) | 25 |
| Comparative Example 2-4 | E2 | 5.81 | 6.33 | (0.134, 0.111) | 23 |

As seen from the results of Table 8, the organic light emitting device using the charge generation layer material of the blue organic light emitting device of the present disclosure had lower driving voltage and improved light emission efficiency compared to the comparative examples. Particularly, it was identified that Compounds 1-26, 1-29, 4-29, 7-29 and 16-28 were significantly superior in all aspects of driving, efficiency and lifetime.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

Experimental Example 3

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was introduced to a cell in the vacuum deposition apparatus.

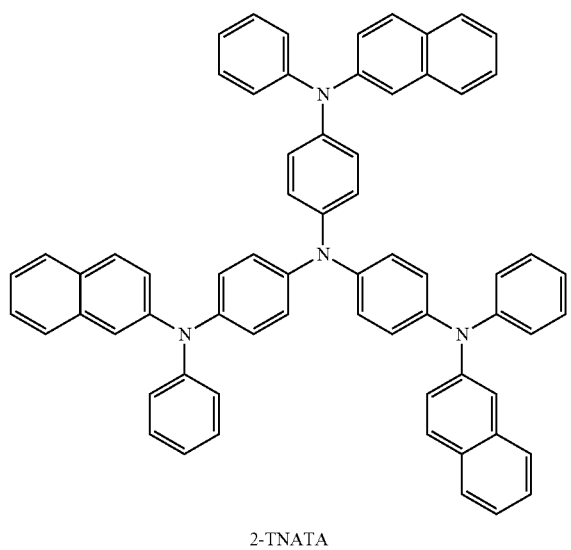

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

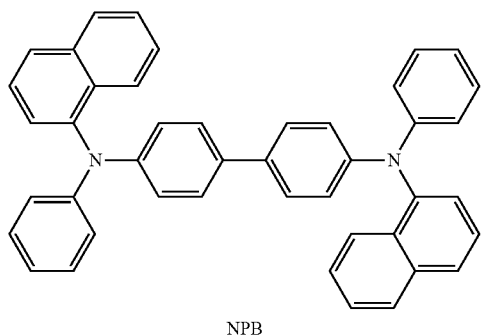

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

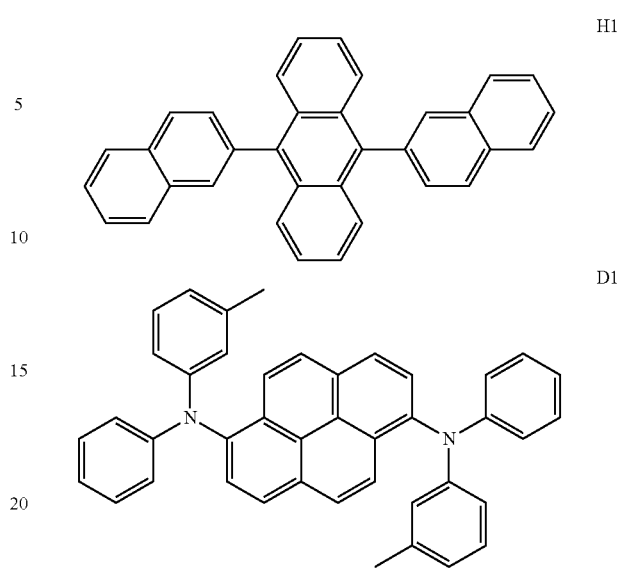

Subsequently, a compound of the following Table 9 was deposited to a thickness of 300 Å as an electron transfer layer.

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

2) Driving Voltage and Light Emission Efficiency of Organic Light Emitting Device For the organic light emitting devices manufactured as above, electroluminescent (EL) properties were measured using M7000 manufactured by McScience Inc., and with the measurement results, T95 when standard luminance was 700 cd/m² was measured using a lifetime measurement system (M6000) manufactured by McScience Inc. Results of measuring driving voltage, light emission efficiency, external quantum efficiency and color coordinate (CIE) of the blue organic light emitting devices manufactured according to the present disclosure are as shown in Table 9.

TABLE 9

|  | Compound | Driving Voltage (V) | Light Emission Efficiency (cd/A) | CIE (x, y) | Lifetime (T95) |
|---|---|---|---|---|---|
| Example 1 | 1 | 4.53 | 6.68 | (0.134, 0.100) | 55 |
| Example 2 | 1-7 | 4.97 | 6.56 | (0.134, 0.101) | 42 |
| Example 3 | 1-42 | 4.95 | 6.98 | (0.134, 0.103) | 41 |
| Example 4 | 2-1 | 4.80 | 6.58 | (0.134, 0.100) | 49 |
| Example 5 | 2-37 | 4.90 | 6.66 | (0.134, 0.101) | 40 |
| Example 6 | 3 | 4.72 | 7.11 | (0.134, 0.101) | 42 |
| Example 7 | 3-5 | 4.88 | 7.00 | (0.134, 0.102) | 50 |
| Example 8 | 3-8 | 4.85 | 6.88 | (0.134, 0.100) | 44 |
| Example 9 | 3-38 | 4.98 | 6.65 | (0.134, 0.101) | 40 |
| Example 10 | 4-10 | 4.82 | 7.05 | (0.134, 0.101) | 46 |
| Example 11 | 4-22 | 4.96 | 6.77 | (0.134, 0.101) | 41 |
| Example 12 | 4-34 | 4.89 | 6.70 | (0.134, 0.100) | 43 |
| Example 13 | 5-15 | 4.81 | 6.81 | (0.134, 0.101) | 45 |
| Example 14 | 5-20 | 4.88 | 6.90 | (0.134, 0.100) | 39 |
| Example 15 | 5-27 | 4.95 | 6.56 | (0.134, 0.102) | 40 |

TABLE 9-continued

| Compound | Driving Voltage (V) | Light Emission Efficiency (cd/A) | CIE (x, y) | Lifetime (T95) |
|---|---|---|---|---|
| Example 16 | 6 | 4.90 | 6.88 | (0.134, 0.101) | 44 |
| Example 17 | 6-12 | 4.81 | 6.85 | (0.134, 0.101) | 47 |
| Example 18 | 7-1 | 4.80 | 7.01 | (0.134, 0.100) | 50 |
| Example 19 | 7-11 | 4.70 | 6.88 | (0.134, 0.101) | 45 |
| Example 20 | 8-26 | 4.95 | 6.63 | (0.134, 0.100) | 37 |
| Example 21 | 9-12 | 4.93 | 6.56 | (0.134, 0.100) | 37 |
| Example 22 | 10 | 4.80 | 6.98 | (0.134, 0.100) | 45 |
| Example 23 | 11-1 | 4.87 | 6.62 | (0.134, 0.102) | 43 |
| Example 24 | 12-1 | 4.90 | 6.71 | (0.134, 0.102) | 45 |
| Example 25 | 12-29 | 4.85 | 6.55 | (0.134, 0.099) | 40 |
| Example 26 | 13-4 | 4.99 | 6.77 | (0.134, 0.101) | 43 |
| Example 27 | 14 | 4.77 | 6.91 | (0.134, 0.100) | 46 |
| Example 28 | 14-7 | 4.96 | 6.88 | (0.134, 0.102) | 49 |
| Example 29 | 14-12 | 4.70 | 6.85 | (0.134, 0.100) | 45 |
| Example 30 | 14-53 | 4.89 | 6.65 | (0.134, 0.101) | 41 |
| Example 31 | 15 | 4.77 | 7.00 | (0.134, 0.100) | 46 |
| Example 32 | 15-42 | 4.88 | 6.55 | (0.134, 0.099) | 39 |
| Example 33 | 16 | 4.85 | 6.99 | (0.134, 0.100) | 42 |
| Example 34 | 16-11 | 4.95 | 6.75 | (0.134, 0.101) | 41 |
| Example 35 | 16-20 | 4.98 | 6.38 | (0.134, 0.102) | 40 |
| Comparative Example 3-1 | E1 | 5.56 | 5.91 | (0.134, 0.100) | 28 |
| Comparative Example 3-2 | E2 | 5.52 | 6.09 | (0.134, 0.101) | 28 |
| Comparative Example 3-3 | BBQB | 5.50 | 6.10 | (0.134, 0.101) | 30 |
| Comparative Example 3-4 | TBQB | 5.51 | 6.15 | (0.134, 0.102) | 29 |
| Comparative Example 3-5 | DTBC-1 | 5.52 | 5.89 | (0.134, 0.102) | 30 |
| Comparative Example 3-6 | DTBC-2 | 5.55 | 5.99 | (0.134, 0.101) | 35 |
| Comparative Example 3-7 | DPBC | 5.61 | 6.01 | (0.134, 0.102) | 32 |
| Comparative Example 3-8 | DPBP-1 | 5.01 | 6.44 | (0.134, 0.100) | 39 |
| Comparative Example 3-9 | DPBP-2 | 5.05 | 6.45 | (0.134, 0.101) | 38 |

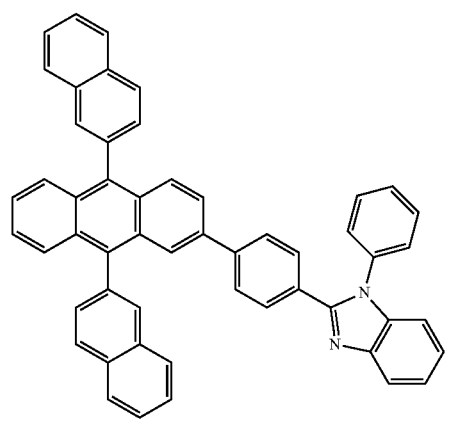

E1

E2

BBQB

TBQB

DTBC-1

TABLE 9-continued

| Compound | Driving Voltage (V) | Light Emission Efficiency (cd/A) | CIE (x, y) | Lifetime (T95) |
|---|---|---|---|---|
| 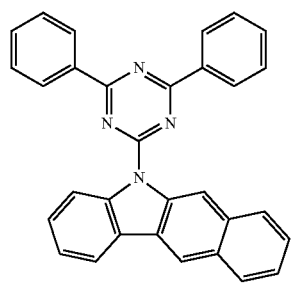 DTBC-2 | | | | |
| 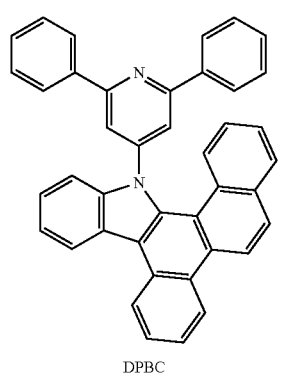 DPBC | | | | |
| 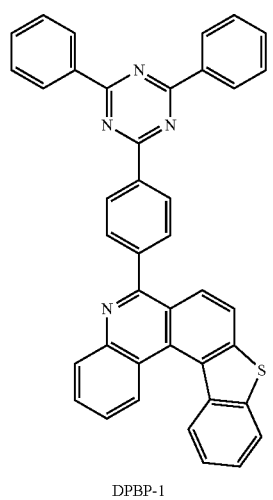 DPBP-1 | | | | |

TABLE 9-continued

| Compound | Driving Voltage (V) | Light Emission Efficiency (cd/A) | CIE (x, y) | Lifetime (T95) |
|---|---|---|---|---|
| 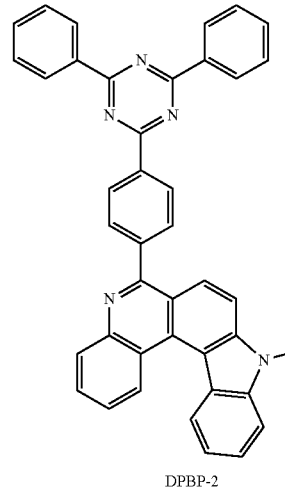 DPBP-2 | | | | |

As seen from the results of Table 9, the organic light emitting device using the electron transfer layer material of the blue organic light emitting device of the present disclosure had lower driving voltage and significantly improved light emission efficiency and lifetime compared to the comparative examples. Particularly, it was identified that Compounds 1, 3-5, 3-8, 4-10, 6-12, 7-1, 7-11, 10, 14-7 and 15 were superior in all aspects of driving, efficiency and lifetime.

Such a result is considered to be due to the fact that, when using the disclosed compound having proper length and strength, and flatness as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

Experimental Example 4

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was introduced to a cell in the vacuum deposition apparatus.

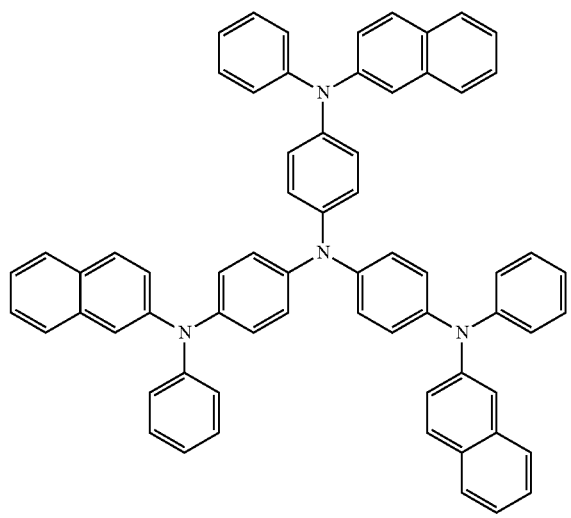

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

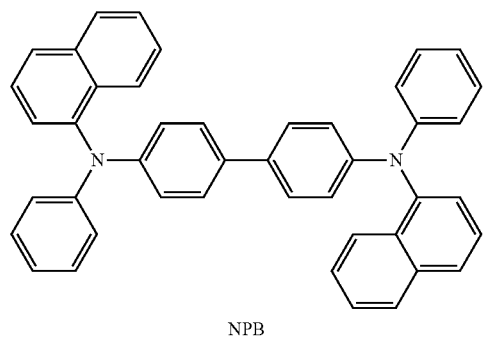

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

Subsequently, a compound of the following structural formula E1 was deposited to a thickness of 300 Å as an electron transfer layer.

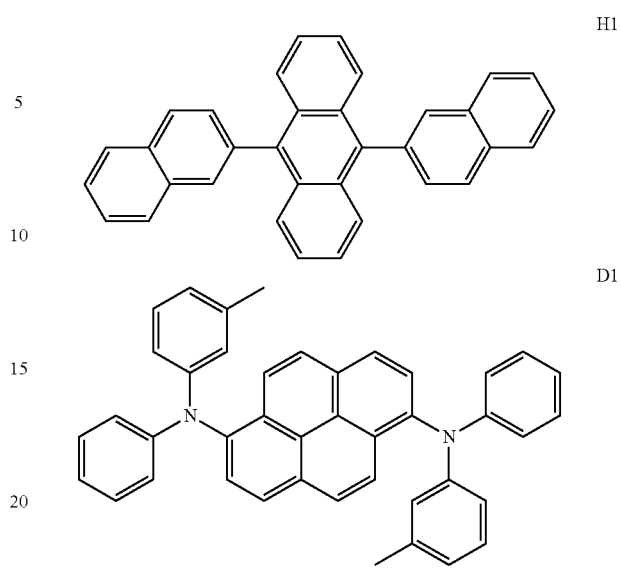

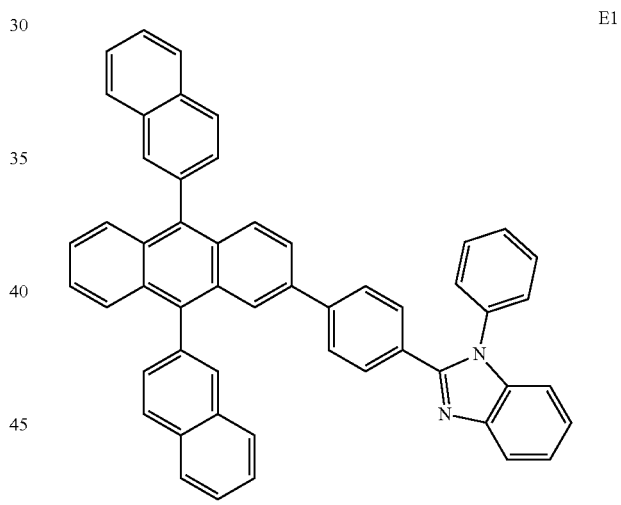

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

An electron transfer layer E1 was formed to a thickness of 250 Å, and then a hole blocking layer was formed on the electron transfer layer using a compound presented in Table 9 to a thickness of 50 Å, and as a result, an organic electroluminescent device was manufactured.

Results of measuring driving voltage, light emission efficiency, color coordinate (CIE) and lifetime of the blue organic light emitting devices manufactured according to the present disclosure are as shown in Table 10.

TABLE 10

| | Compound | Driving Voltage (V) | Light Emission Efficiency (cd/A) | CIE (x, y) | Lifetime (T95) |
|---|---|---|---|---|---|
| Example 1 | 1-7 | 5.02 | 6.75 | (0.134, 0.101) | 52 |
| Example 2 | 2-5 | 5.10 | 6.89 | (0.134, 0.102) | 54 |
| Example 3 | 2-29 | 5.40 | 6.50 | (0.134, 0.101) | 45 |
| Example 4 | 3-39 | 5.39 | 6.51 | (0.134, 0.102) | 41 |
| Example 5 | 4-13 | 5.25 | 6.66 | (0.134, 0.102) | 43 |
| Example 6 | 6-17 | 5.42 | 6.21 | (0.134, 0.101) | 54 |
| Example 7 | 7-8 | 5.33 | 6.68 | (0.134, 0.102) | 49 |
| Example 8 | 9-6 | 5.05 | 6.90 | (0.134, 0.101) | 50 |
| Example 9 | 9-9 | 5.40 | 6.13 | (0.134, 0.101) | 41 |
| Example 10 | 10-22 | 5.04 | 6.80 | (0.134, 0.100) | 48 |
| Example 11 | 10-40 | 5.27 | 6.17 | (0.134, 0.101) | 46 |
| Example 12 | 12-17 | 5.32 | 6.25 | (0.134, 0.101) | 41 |
| Example 13 | 13-1 | 5.14 | 6.26 | (0.134, 0.102) | 51 |
| Example 14 | 13-4 | 5.01 | 6.77 | (0.134, 0.101) | 55 |
| Example 15 | 14-5 | 5.22 | 6.34 | (0.134, 0.101) | 42 |
| Example 16 | 15-11 | 5.03 | 6.72 | (0.134, 0.100) | 48 |
| Example 17 | 16-11 | 5.33 | 6.37 | (0.134, 0.101) | 46 |
| Comparative Example 4-1 | - | 5.51 | 5.94 | (0.134, 0.100) | 31 |
| Comparative Example 4-2 | DTBC-1 | 5.50 | 5.88 | (0.134, 0.101) | 30 |
| Comparative Example 4-3 | DTBC-2 | 5.55 | 5.79 | (0.134, 0.102) | 25 |
| Comparative Example 4-4 | DPBC | 5.52 | 5.90 | (0.134, 0.101) | 28 |
| Comparative Example 4-5 | DPBP-1 | 5.35 | 6.00 | (0.134, 0.100) | 35 |
| Comparative Example 4-6 | DPBP-2 | 5.39 | 5.99 | (0.134, 0.101) | 39 |

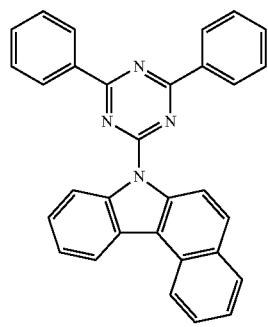

DTBC-1

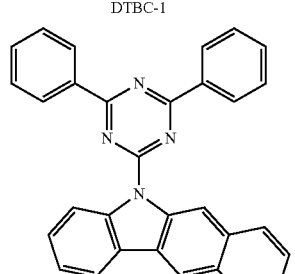

DTBC-2

As seen from the results of Table 10, the organic light emitting device using the hole blocking layer material of the blue organic light emitting device of the present disclosure had lower driving voltage and significantly improved light emission efficiency and lifetime compared to Comparative Example 4-1.

Such a result is due to the fact that, as a bipolar type having both a p-type and an n-type, hole leakage is blocked, and excitons are effectively locked in the light emitting layer.

From Table 7 to Table 10, it was identified that, when having a substituent of -(L)m-(Z)n in the benzene ring of the fused quinoline group in the core structure of Chemical Formula 1, an electron transfer ability was enhanced due to planarity and an increase in the conjugation range of the compound. Accordingly, the excited hetero skeleton site was stabilized efficiently transferring electrons without being decomposed or destroyed, and as a result, excellent driving and light emission efficiency were obtained when using the compound of Chemical Formula 1 in the organic light emitting device.

In addition, it was identified that, by having a substituent in the benzene ring of the fused quinoline group as in Chemical Formula 1, properties of increased bipolar with obvious p-type and n-type were obtained, and efficient electron migration was induced by having uniform molecular arrangement, and excitons were effectively locked in the light emitting layer by blocking hole leakage, and as a result, results of improved light emission efficiency and lifetime were obtained.

The invention claimed is:

1. A heterocyclic compound represented by the following Chemical Formula 1:

[Chemical Formula 1]

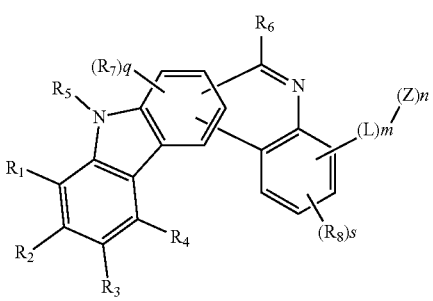

wherein, in Chemical Formula 1, $R_1$ to $R_4$, $R_7$ and $R_8$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aromatic hydrocarbon ring or a substituted or unsubstituted heteroring;

$R_5$ and $R_6$ are the same as or different from each other, and each independently a substituted or unsubstituted C6 to C40 aryl group;

L is a direct bond; a substituted or unsubstituted arylene group; or a substituted or unsubstituted heteroarylene group;

Z is selected from the group consisting of deuterium; —CN; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group;

R, R' and R" are the same as or different from each other, and each independently hydrogen; a substituted or unsubstituted alkyl group; a substituted or unsubstituted aryl group; or a substituted or unsubstituted heteroaryl group;

m is an integer of 0 to 5;

n is an integer of 1 to 6;

q is an integer of 0 to 2; and s is an integer of 0 to 3.

2. The heterocyclic compound of claim 1, wherein the "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted; and R, R' and R" have the same definitions as in Chemical Formula 1.

3. The heterocyclic compound of claim 1, wherein Chemical Formula 1 is represented by any one of the following Chemical Formula 2 to Chemical Formula 7:

[Chemical Formula 2]

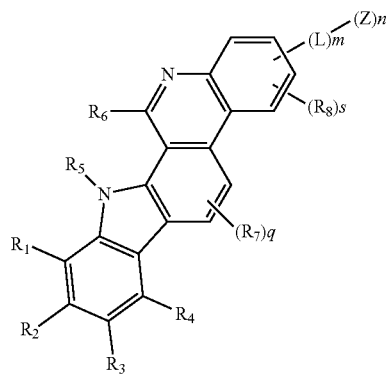

[Chemical Formula 3]

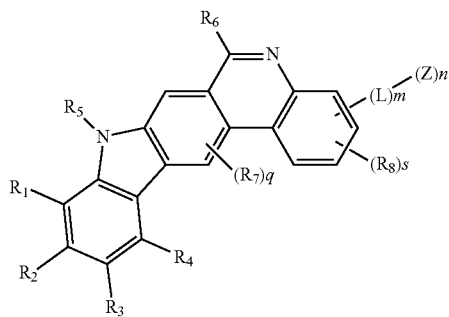

[Chemical Formula 4]

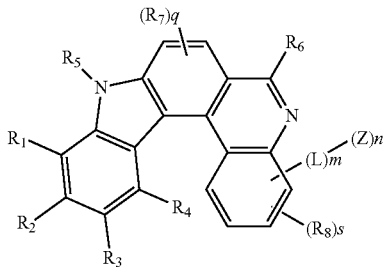

[Chemical Formula 5]

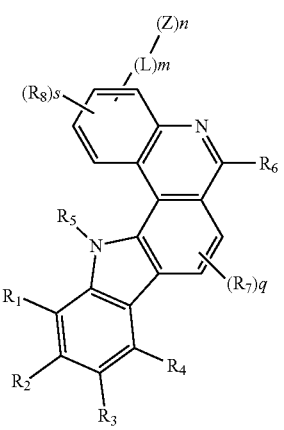

[Chemical Formula 6]

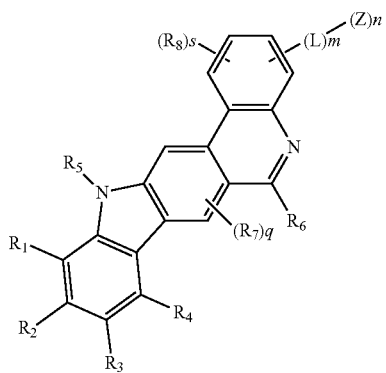

[Chemical Formula 7]

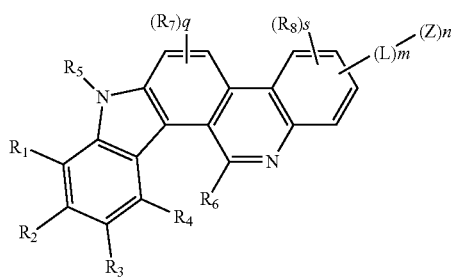

in Chemical Formulae 2 to 7, $R_1$ to $R_8$, L, Z, m, n, s and q have the same definitions as in Chemical Formula 1.

4. The heterocyclic compound of claim 1, wherein Chemical Formula 1 is represented by any one of the following Chemical Formulae 8 to 11:

[Chemical Formula 8]

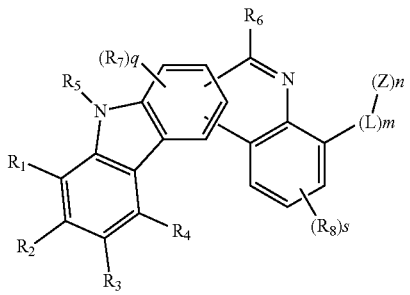

[Chemical Formula 9]

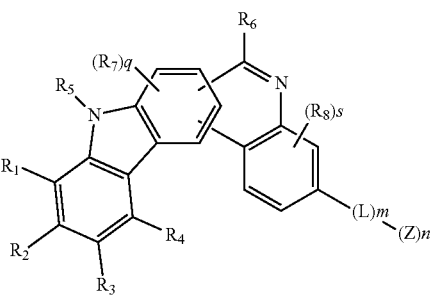

[Chemical Formula 10]

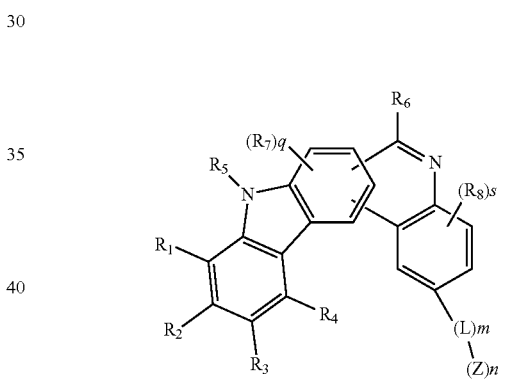

[Chemical Formula 11]

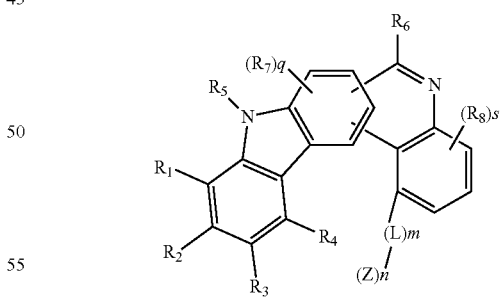

in Chemical Formulae 8 to 11, $R_1$ to $R_8$, L, Z, m, n, s and q have the same definitions as in Chemical Formula 1.

5. The heterocyclic compound of claim 1, wherein $R_1$ to $R_4$, $R_7$ and $R_8$ are hydrogen.

6. The heterocyclic compound of claim 1, wherein Chemical Formula 1 is represented by any one of the following compounds:

563
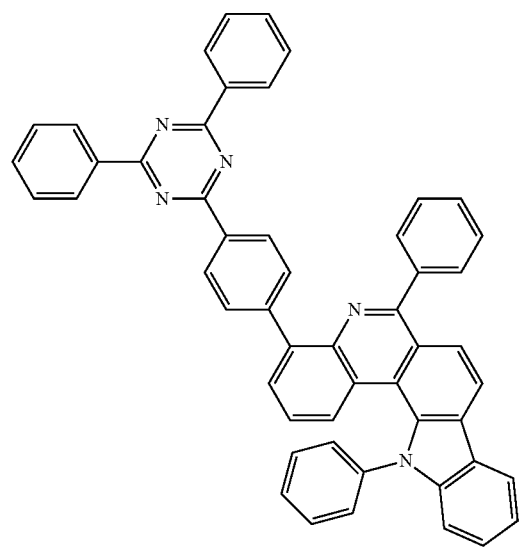
1
564
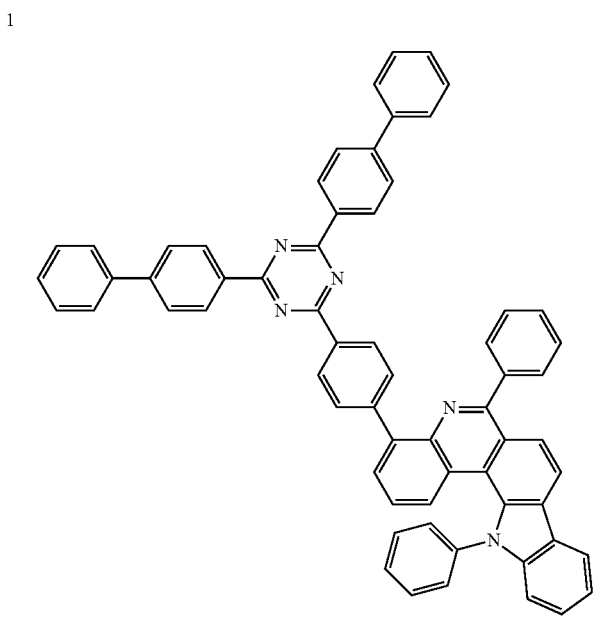
1-1
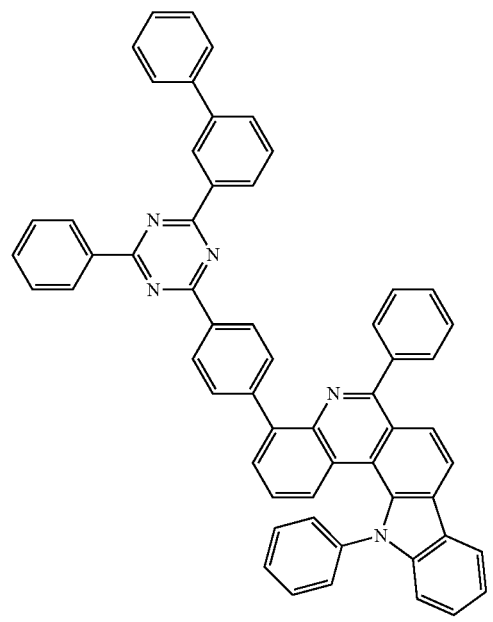
1-2
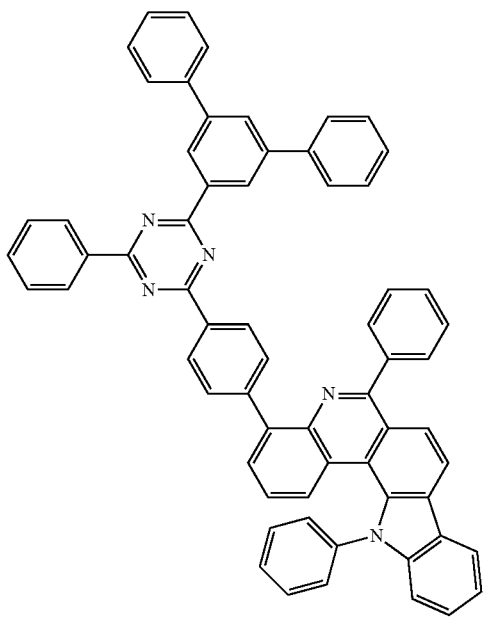
1-3

-continued
1-4
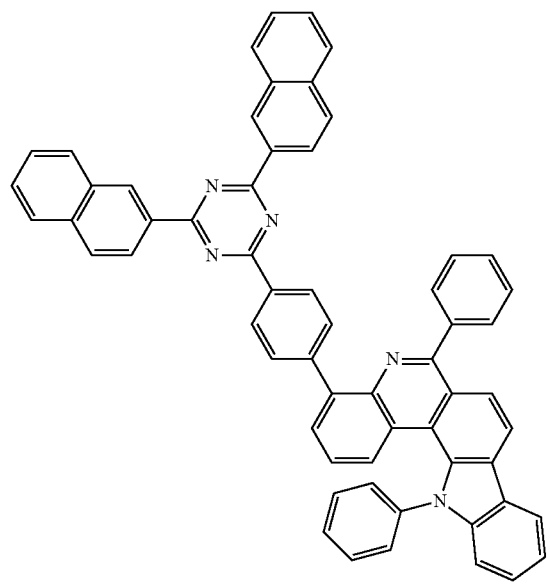
1-5
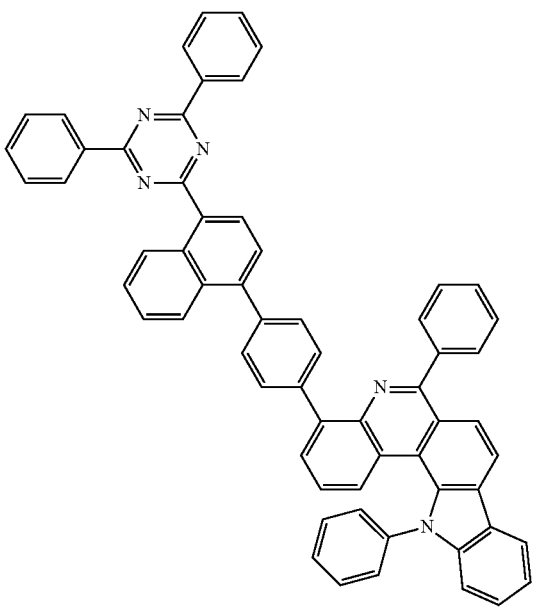
1-6
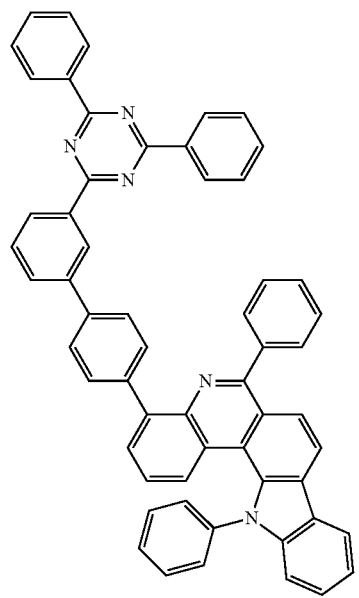
1-7
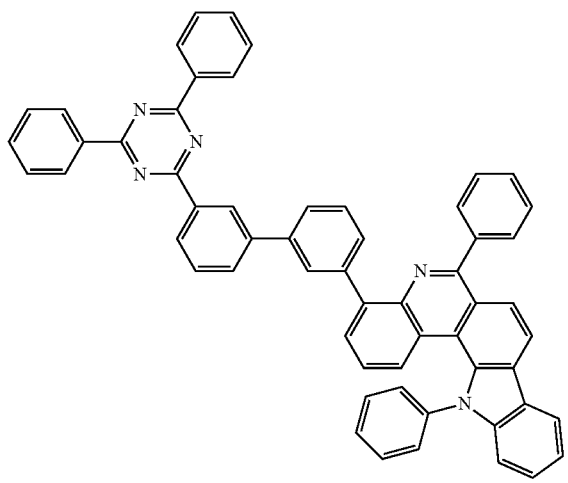

-continued
1-8
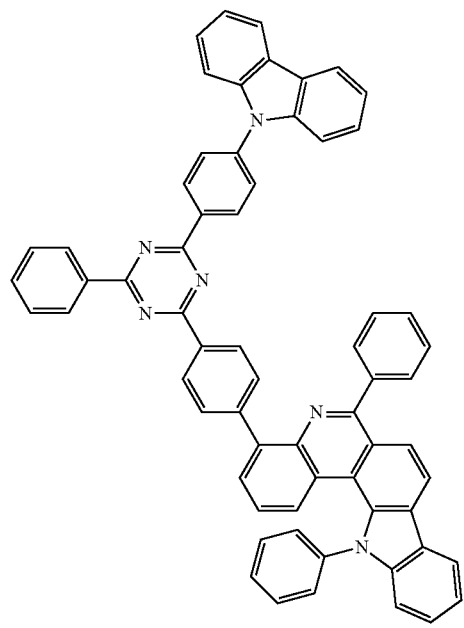
1-9
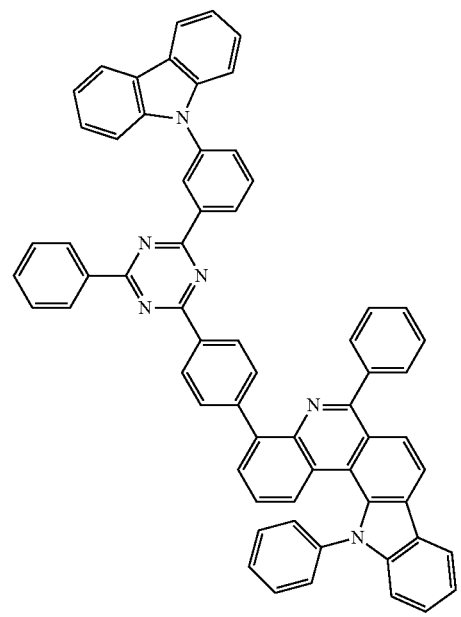
1-10
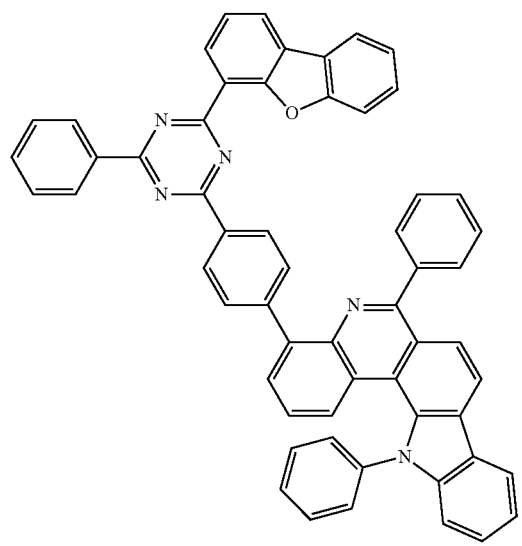
1-11
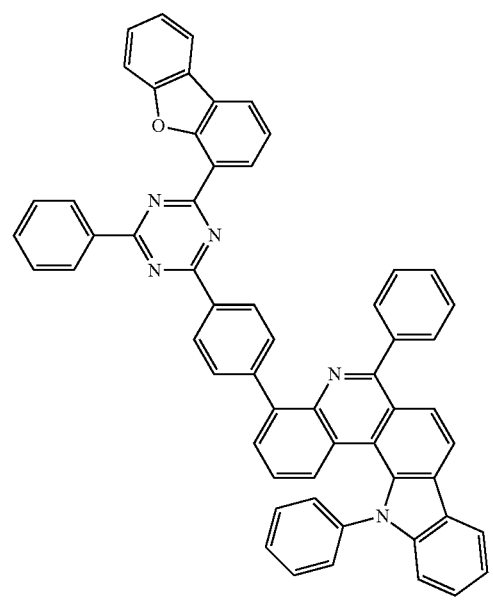

-continued
1-12
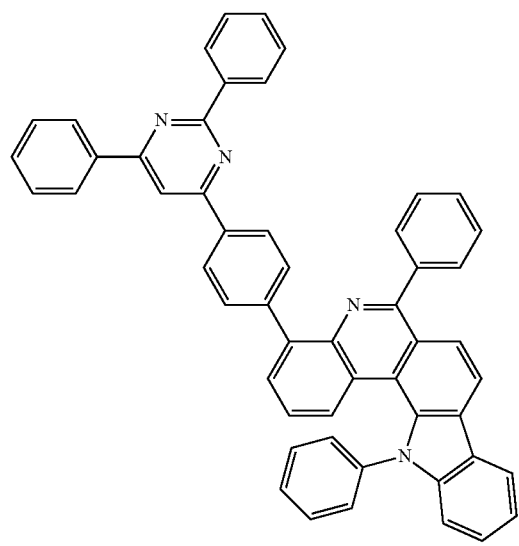
1-13
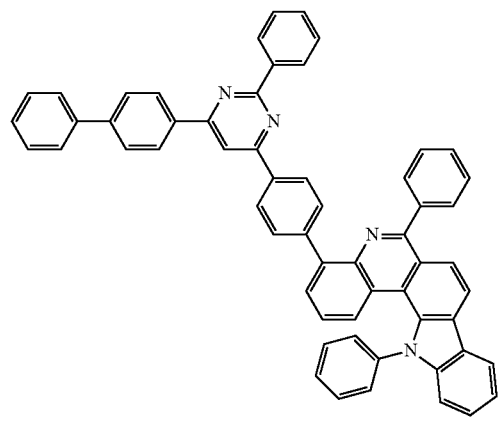
1-14
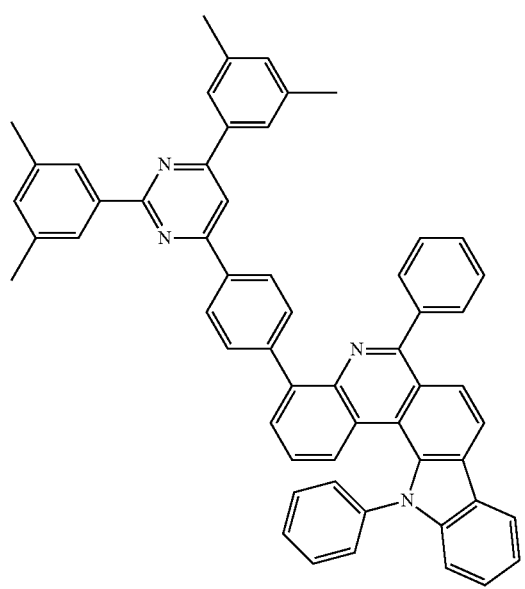
1-15
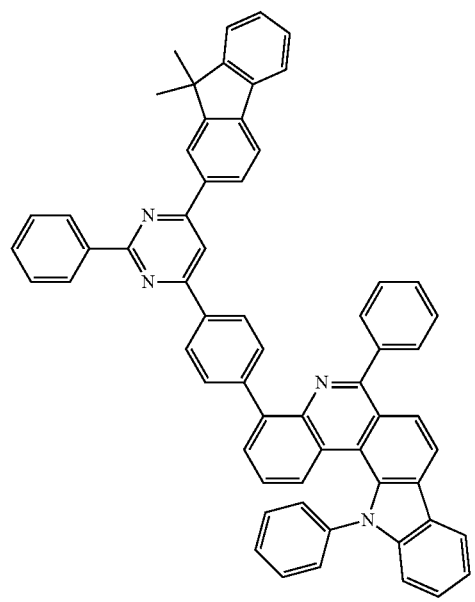

1-16
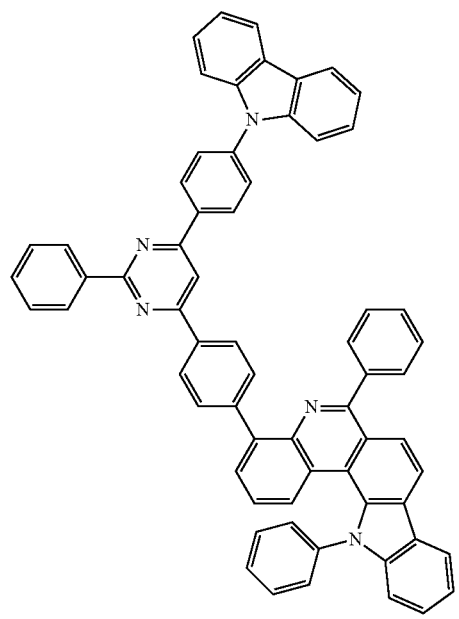
1-17
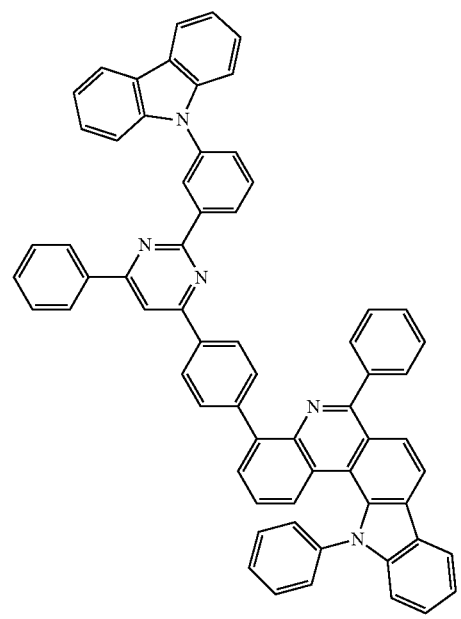
1-18
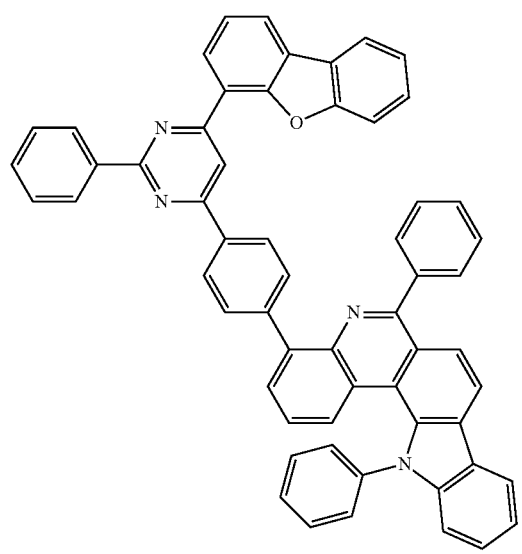
1-19
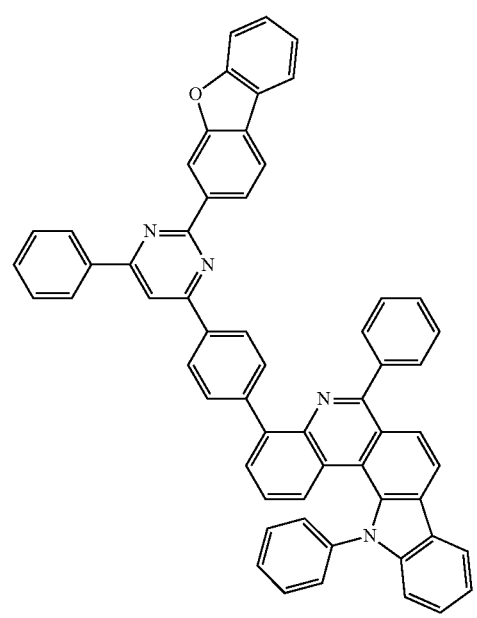

-continued
1-20
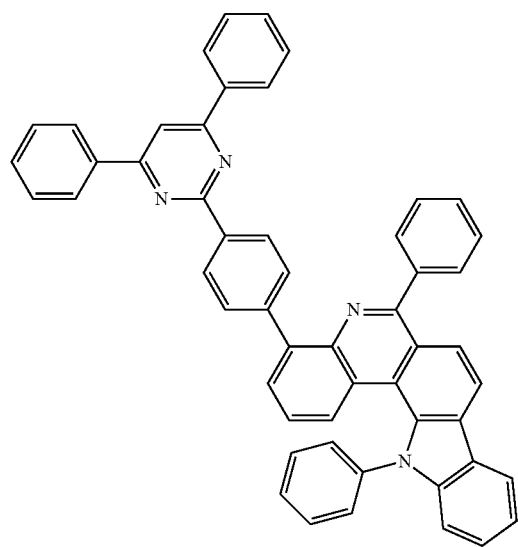
1-21
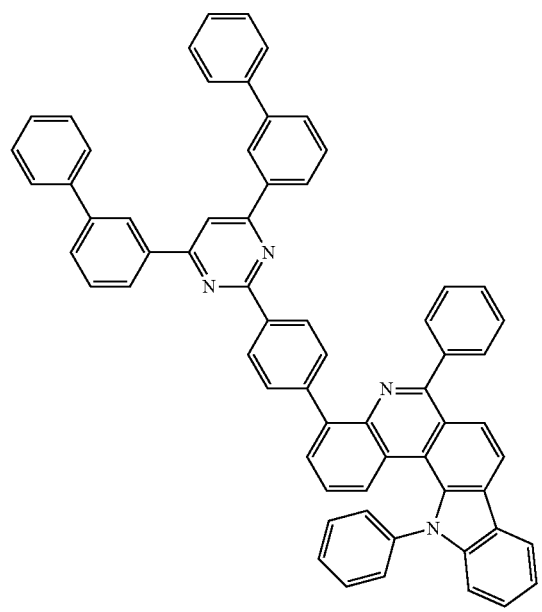
1-22
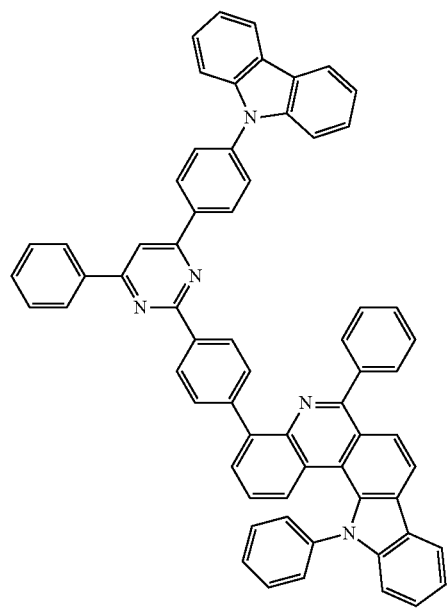
1-23
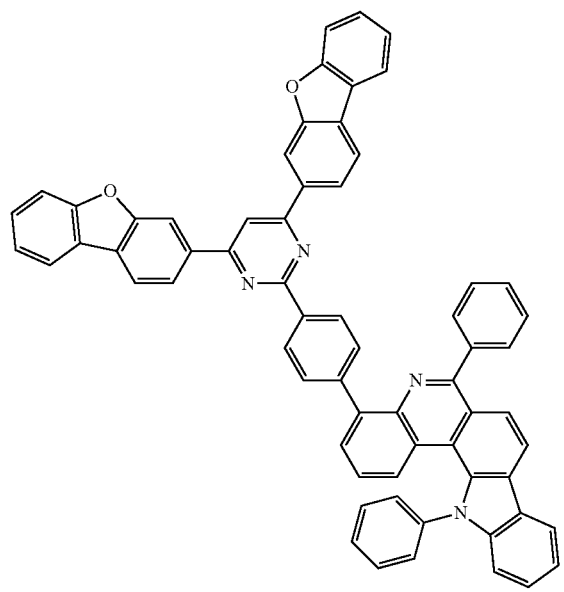

1-24
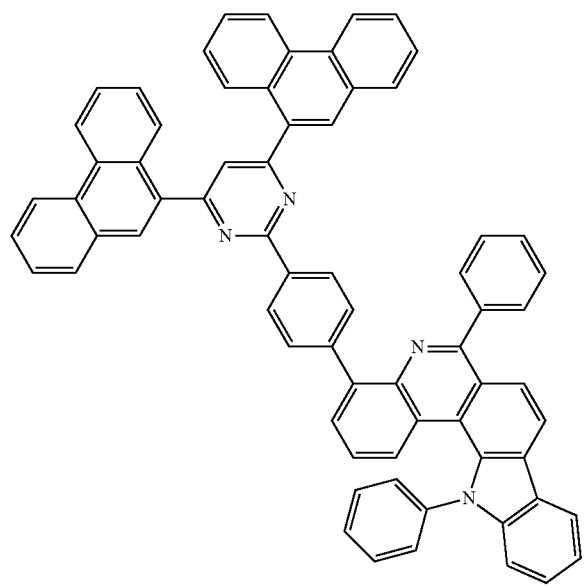
1-25
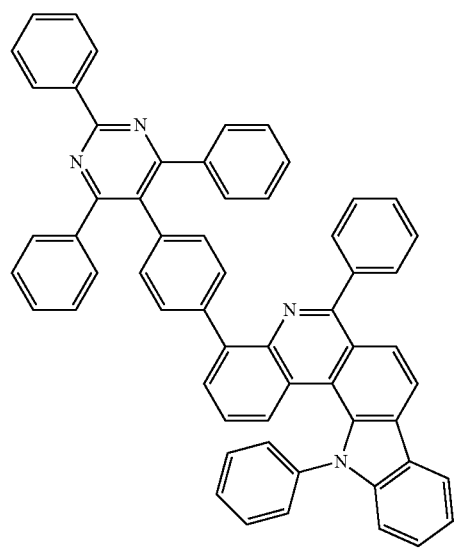
1-26
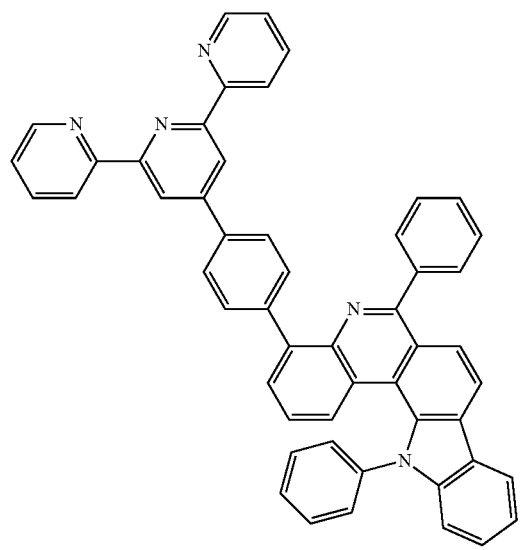
1-27
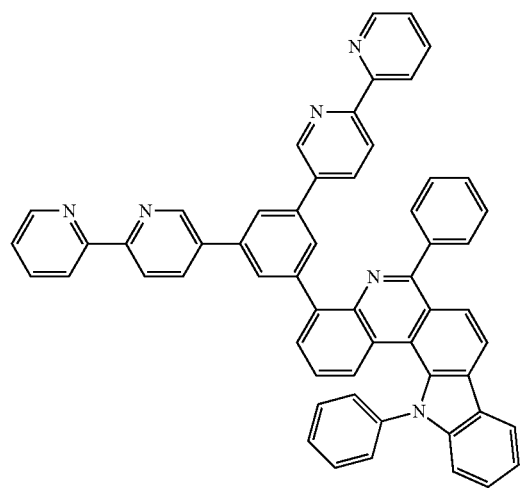

-continued
1-28
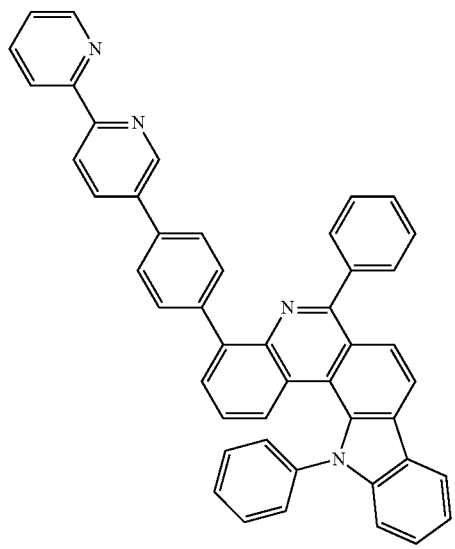
1-29
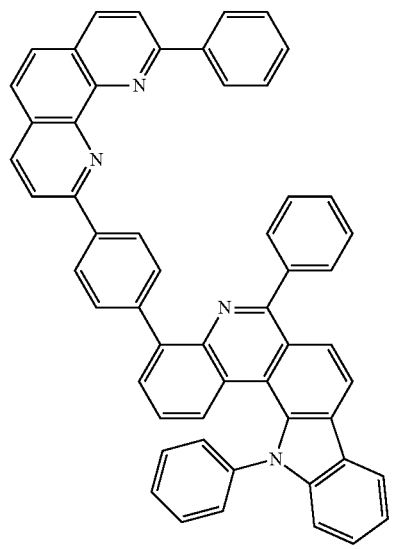
1-30
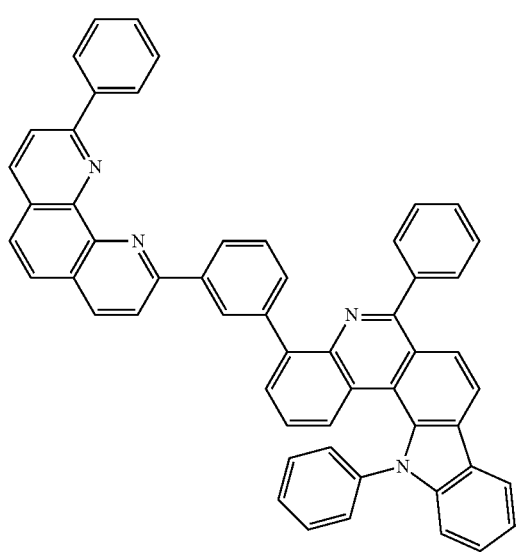
1-31
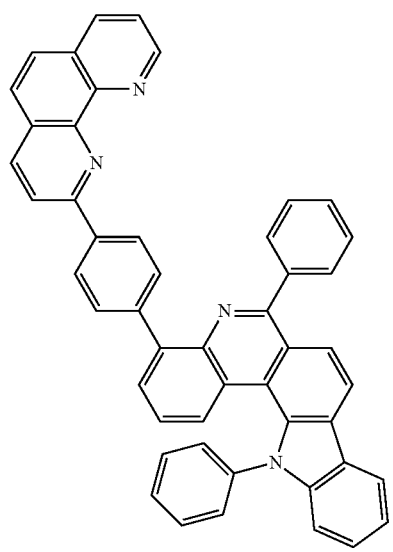
1-32
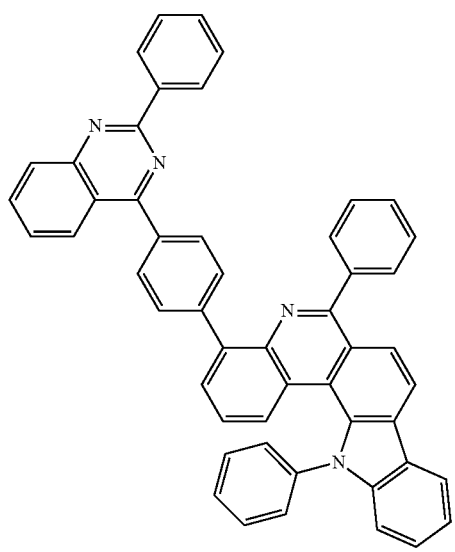
1-33
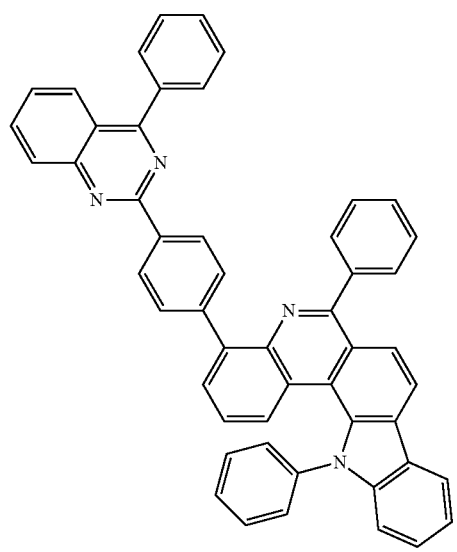

-continued
1-34
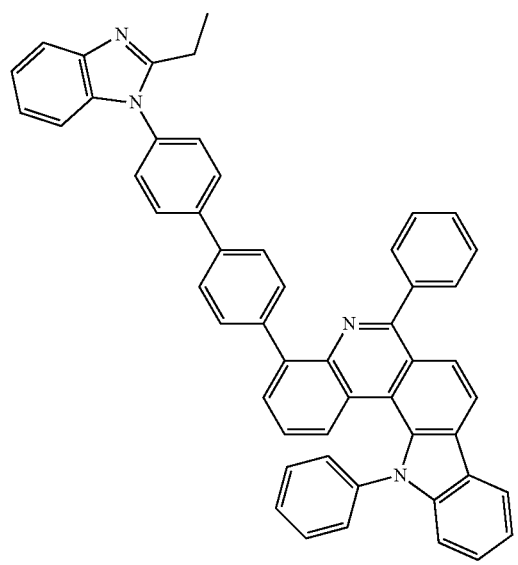
1-35
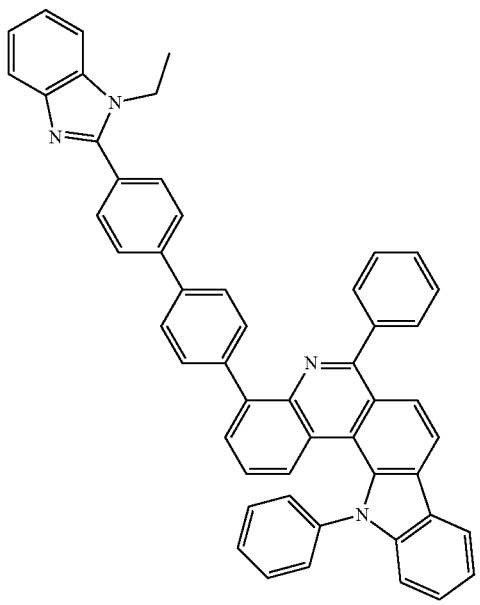
1-36
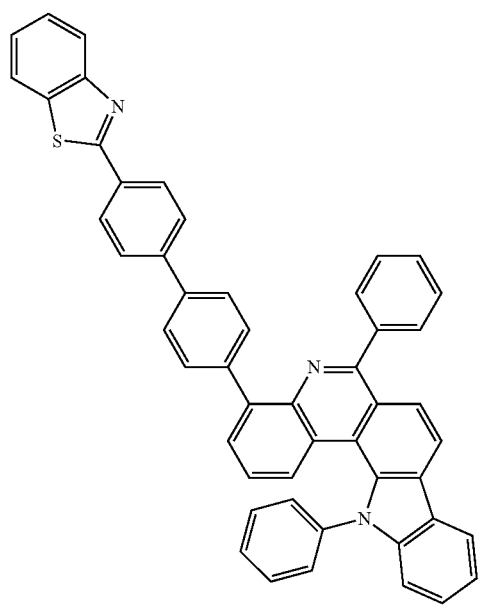
1-37
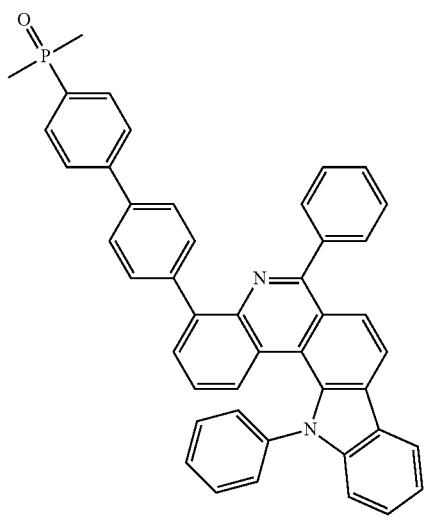

-continued
1-38
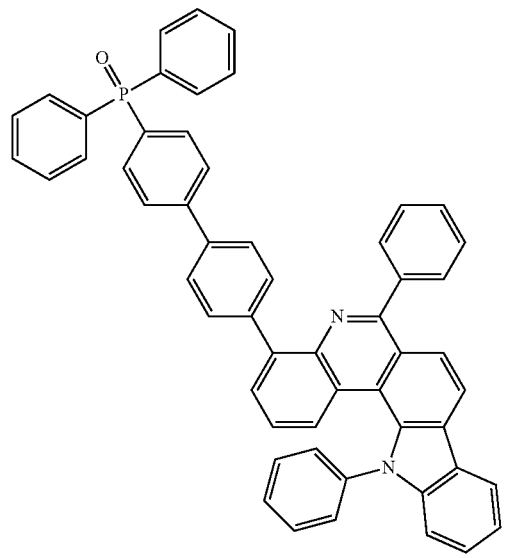
1-39
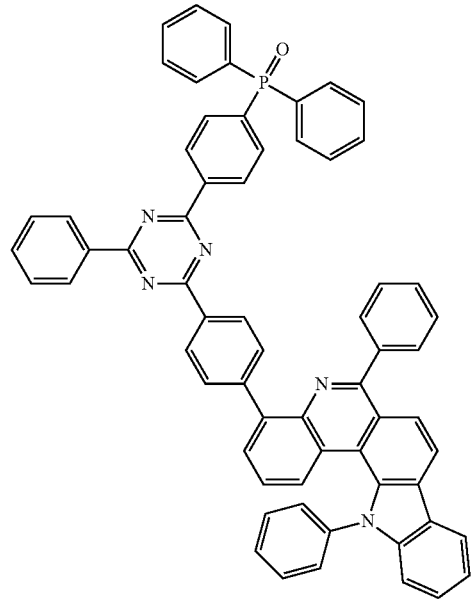
1-40
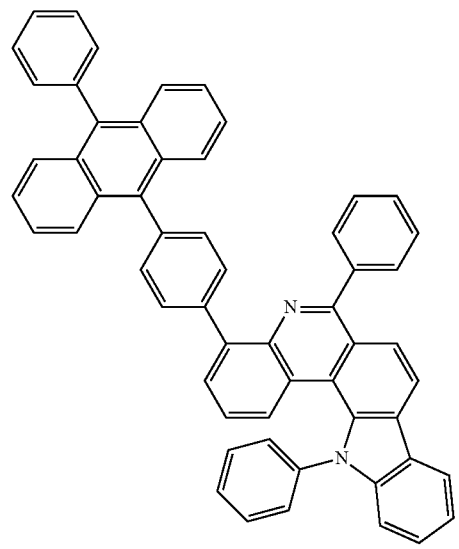
1-41
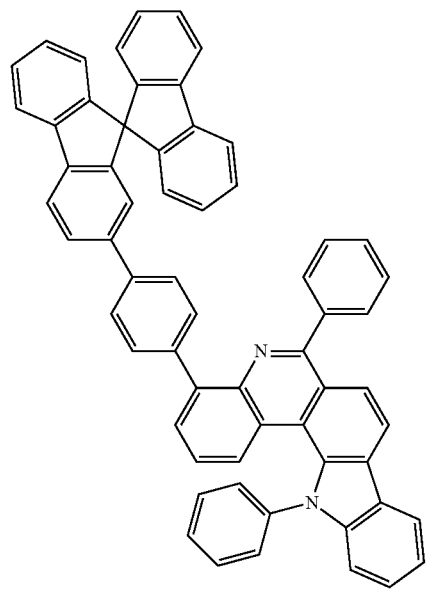

583
-continued
1-42
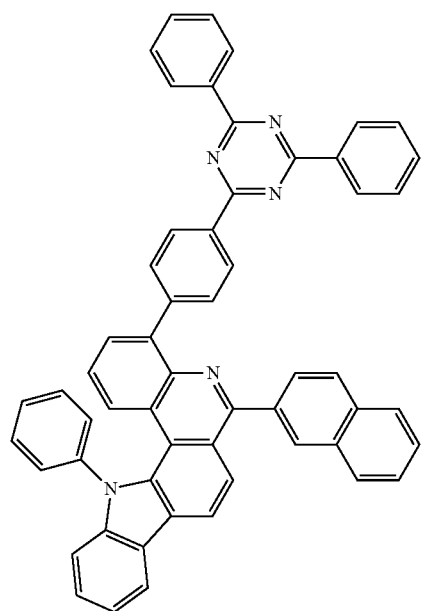
584
1-43
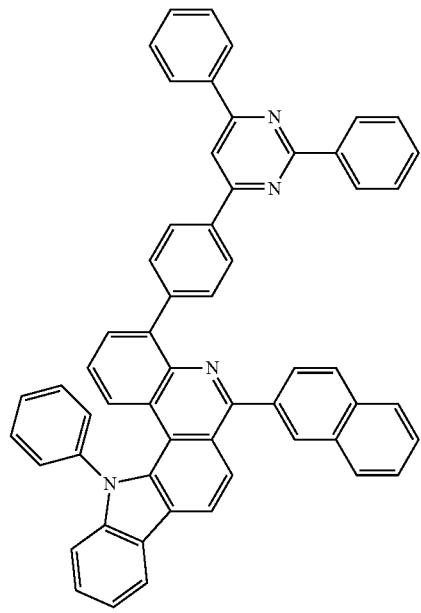
2
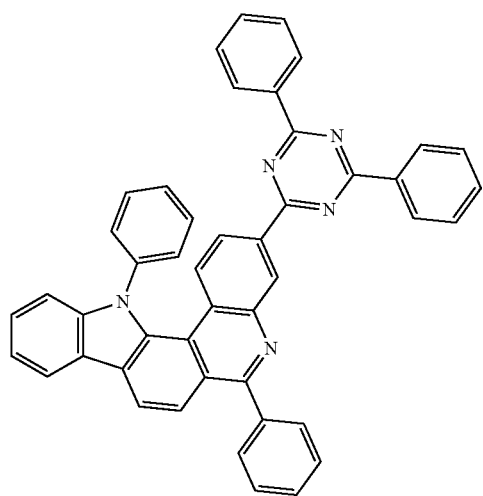
2-1
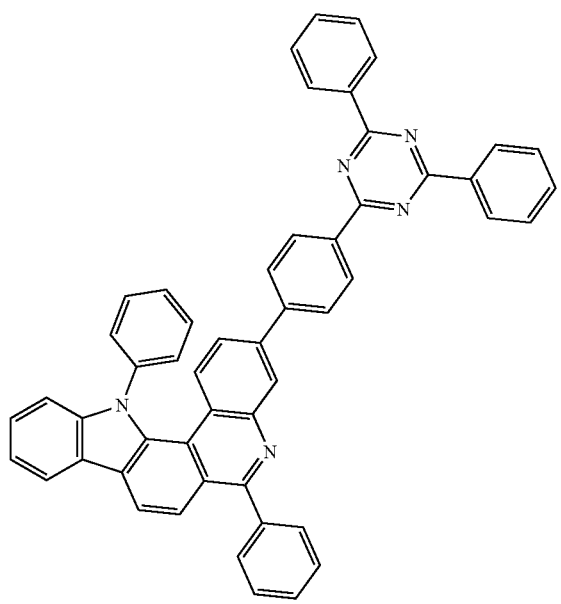

-continued
2-2
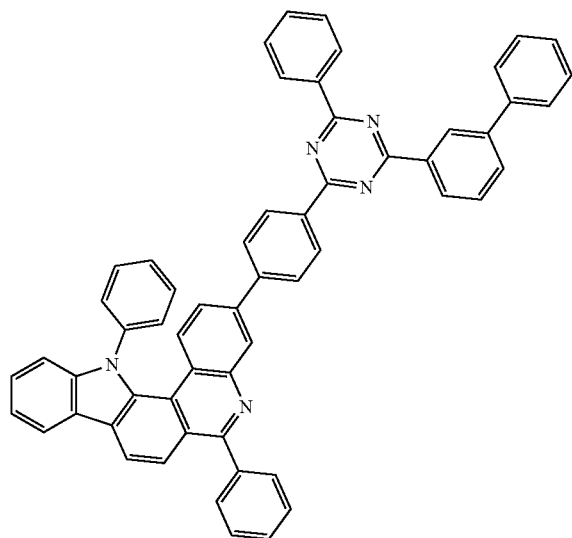
2-3
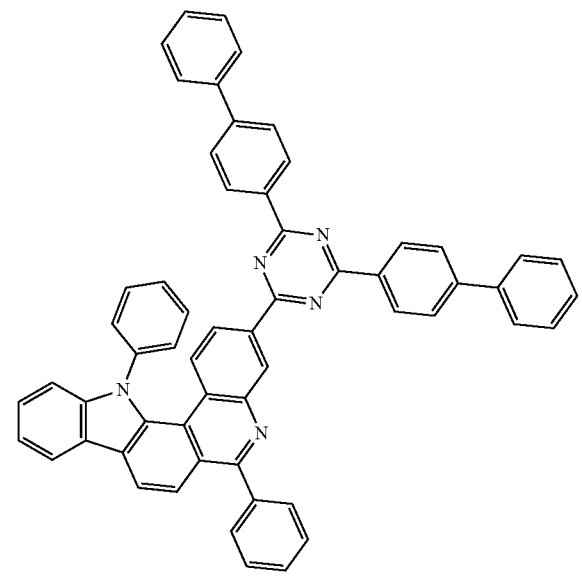
2-4
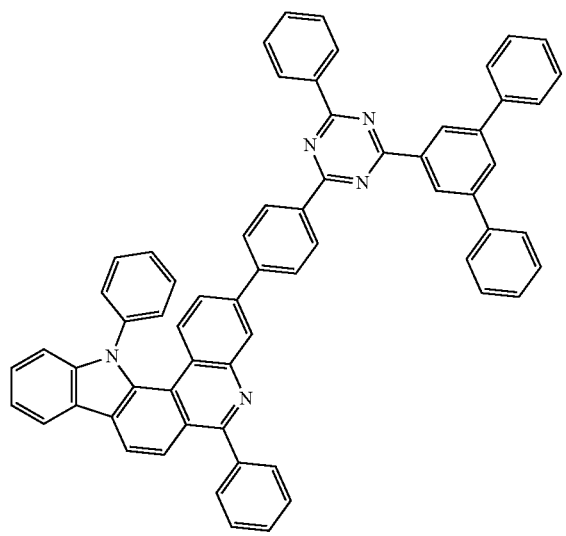
2-5
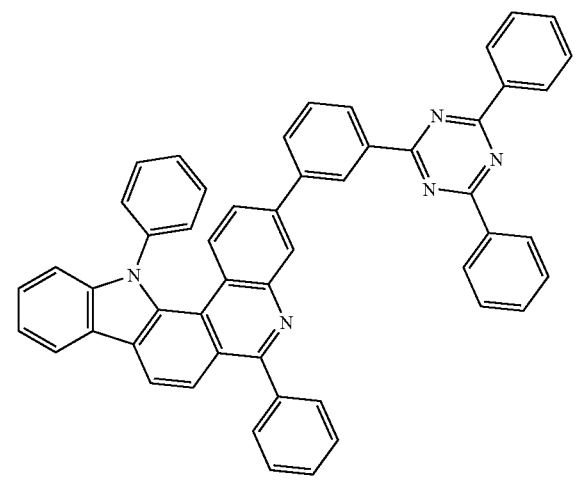
2-6
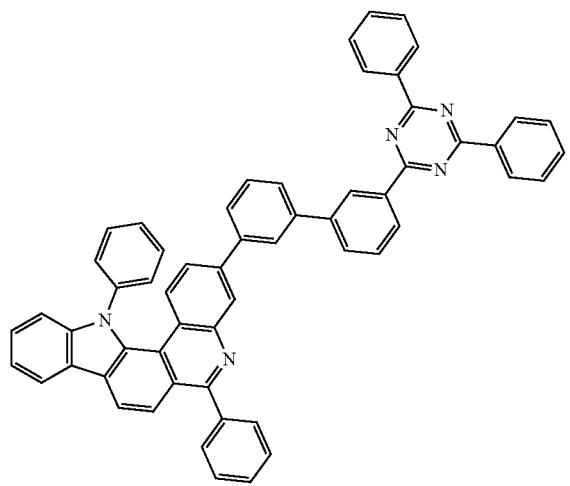
2-7
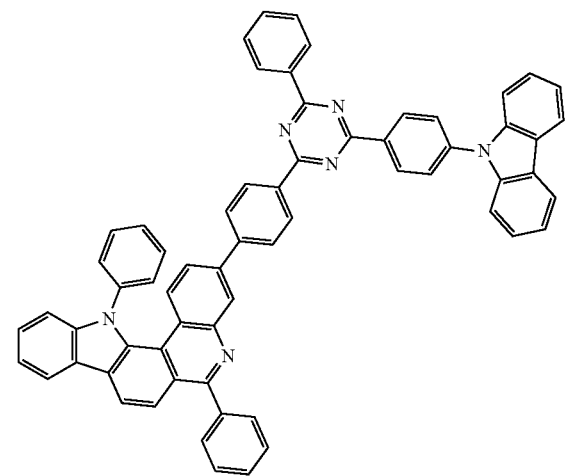

587 588
2-8
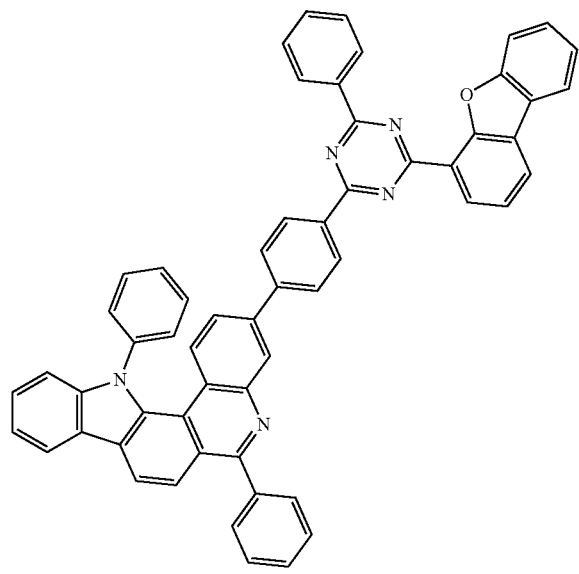
2-9
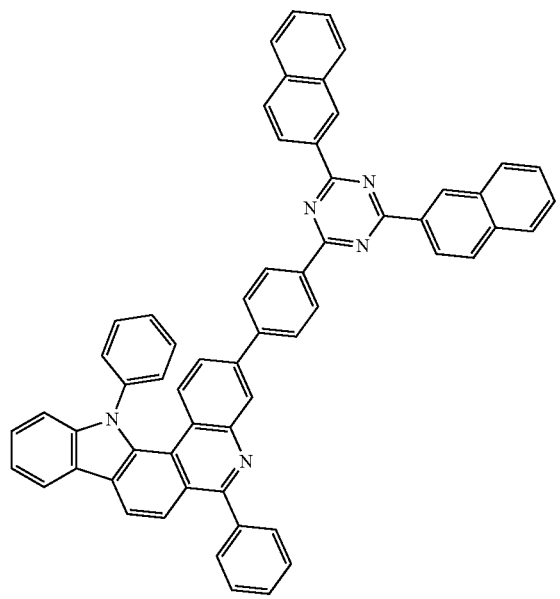
2-10
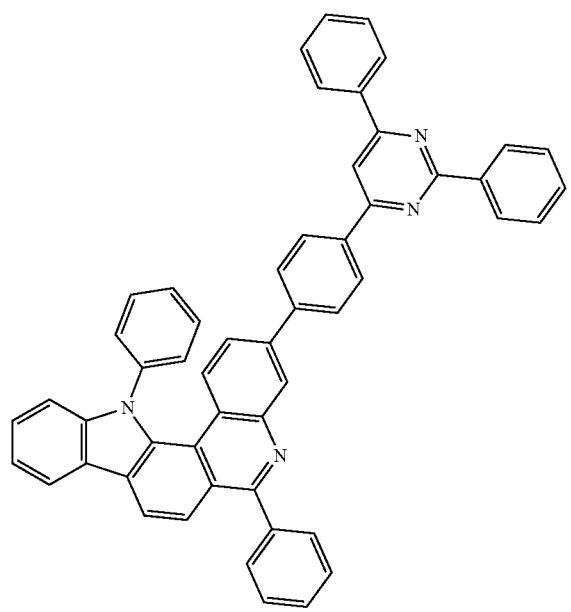
2-11
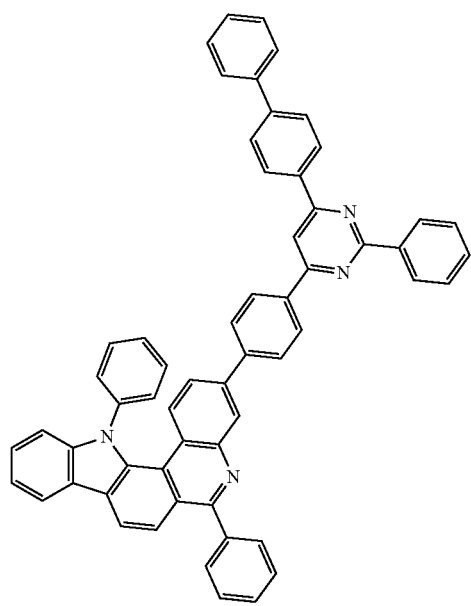

-continued
2-12
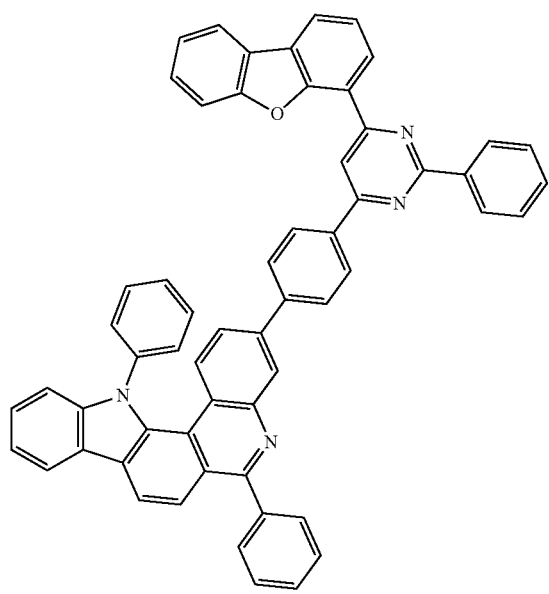
2-13
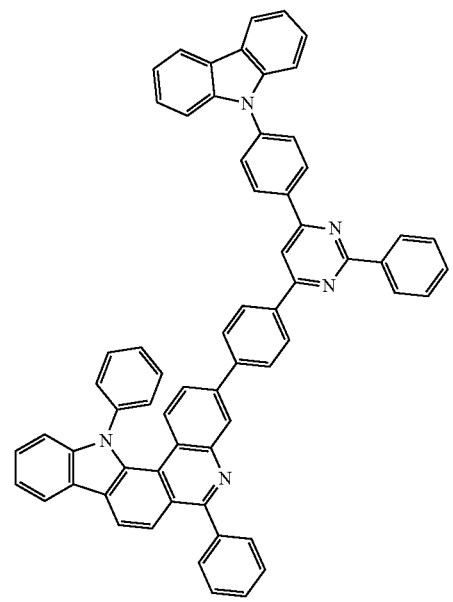
2-14
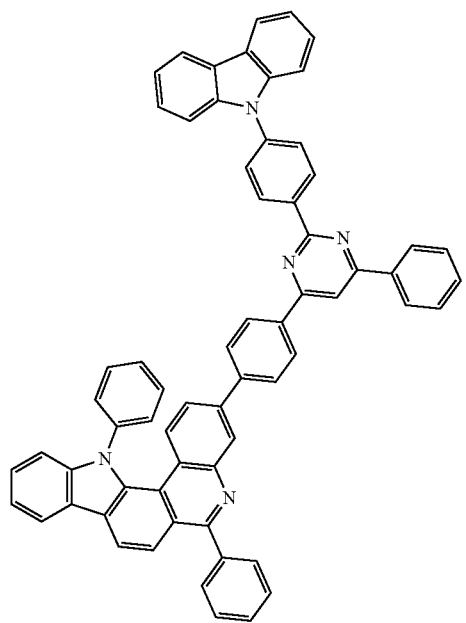
2-16
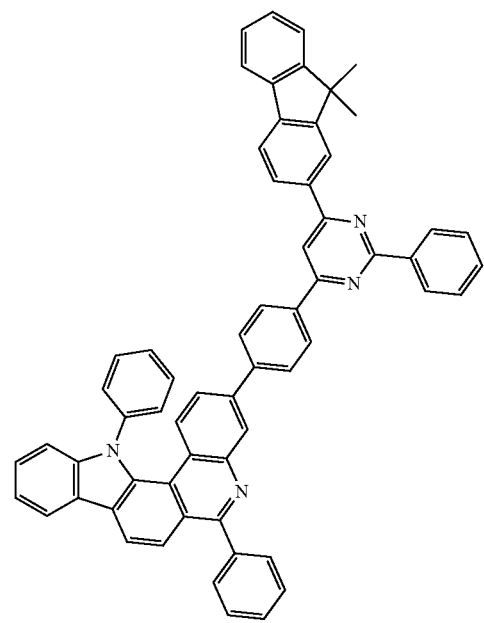

-continued
2-17
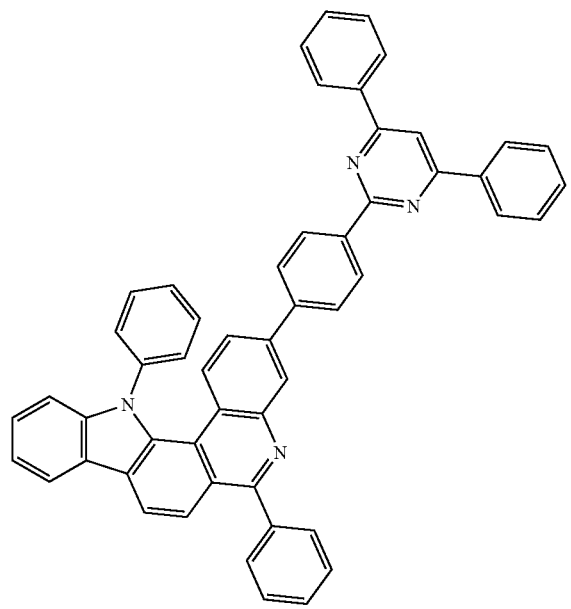
2-18
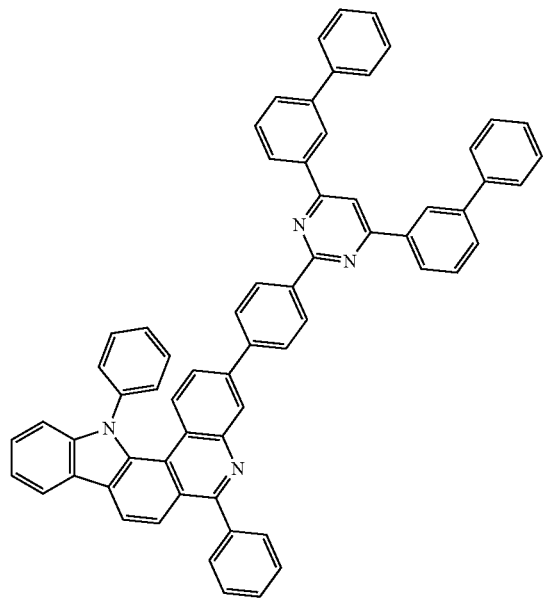
2-19
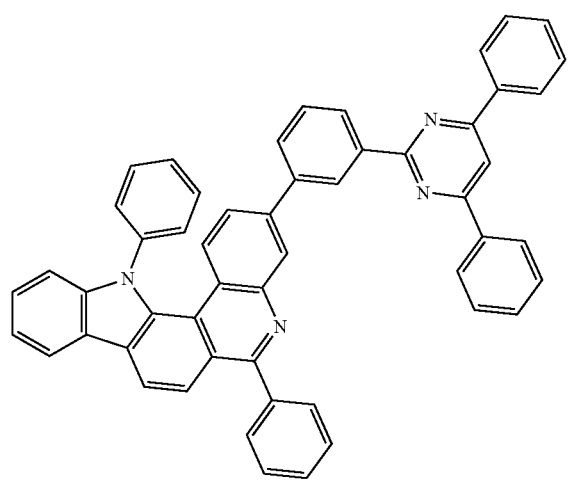
2-20
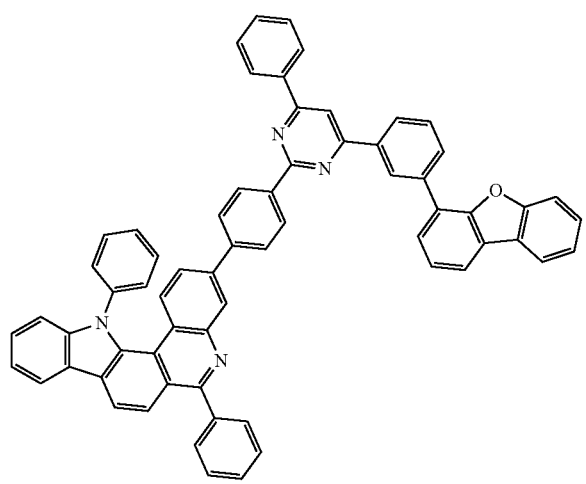

593 594
-continued
2-21
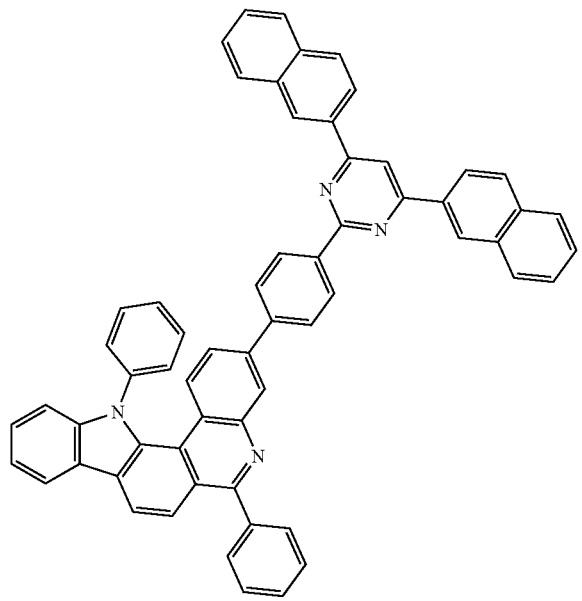
2-22
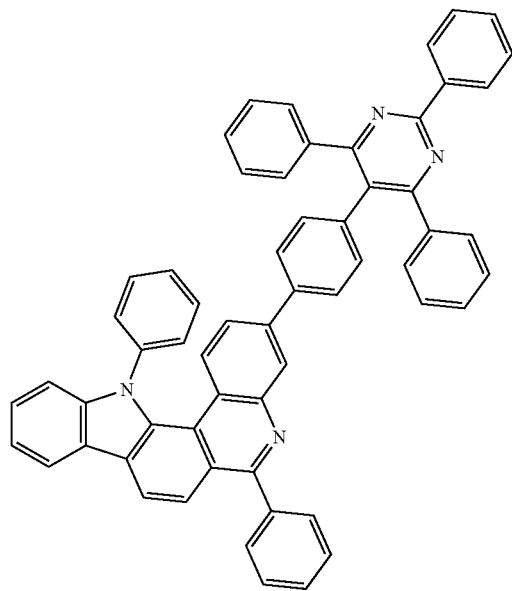
2-23
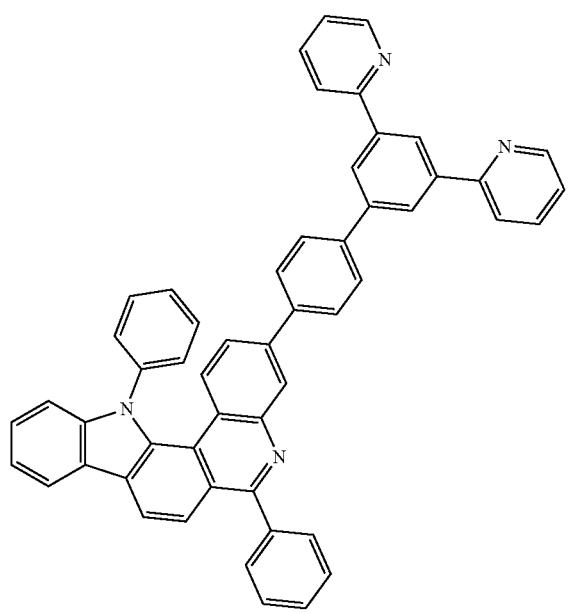
2-24
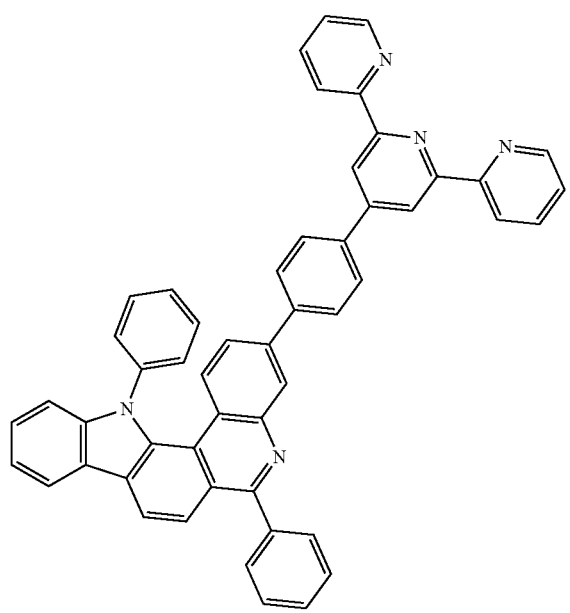

-continued
2-25
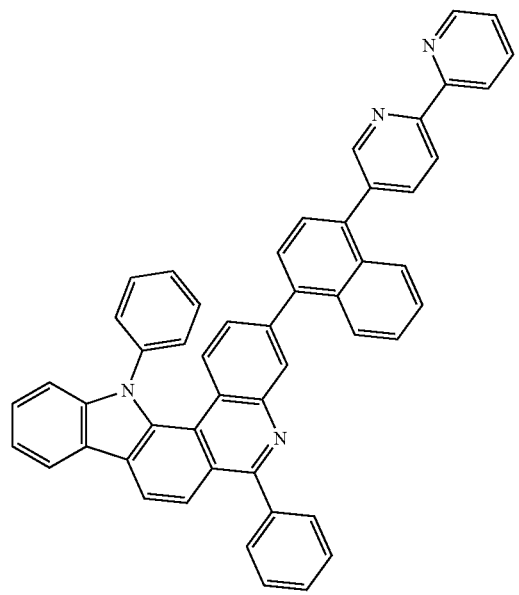
2-26
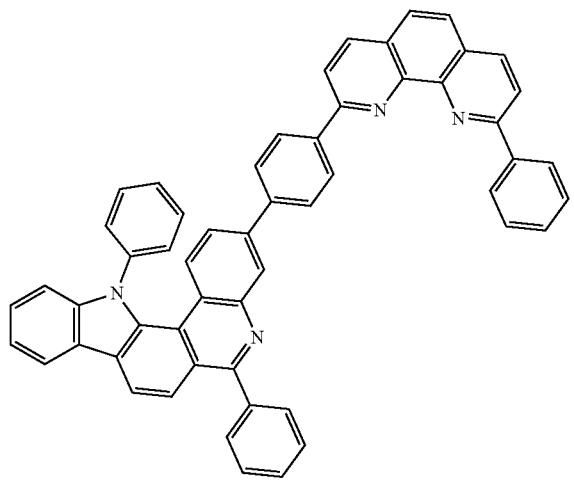
2-27
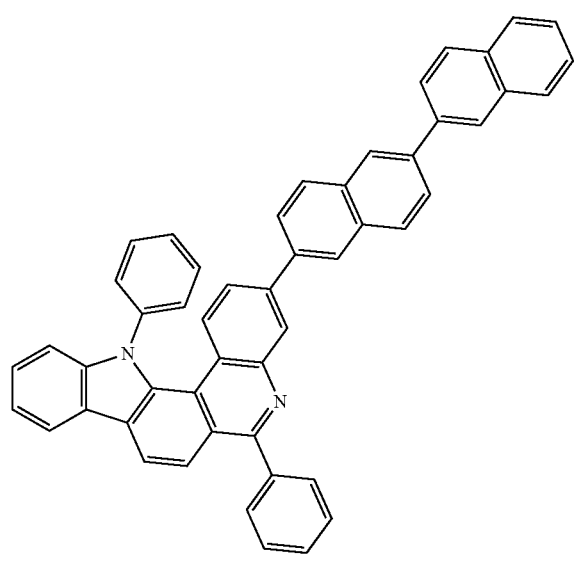
2-28
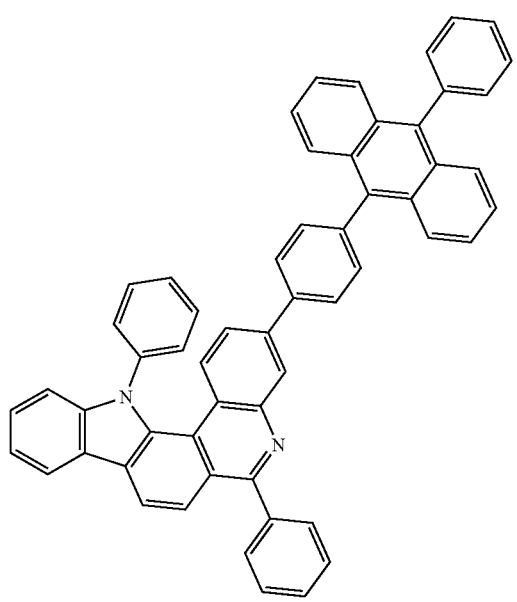

2-29
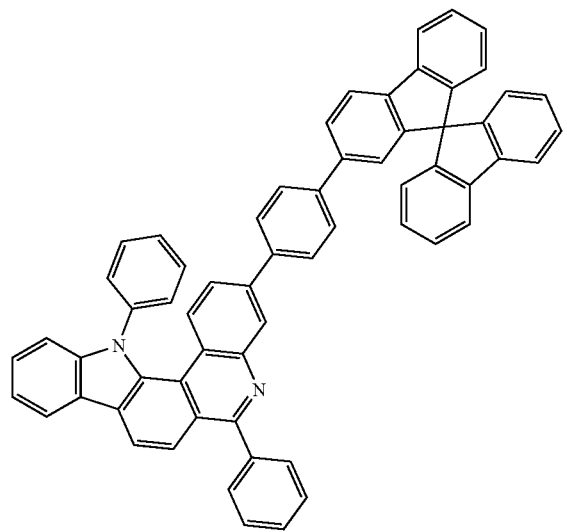
2-30
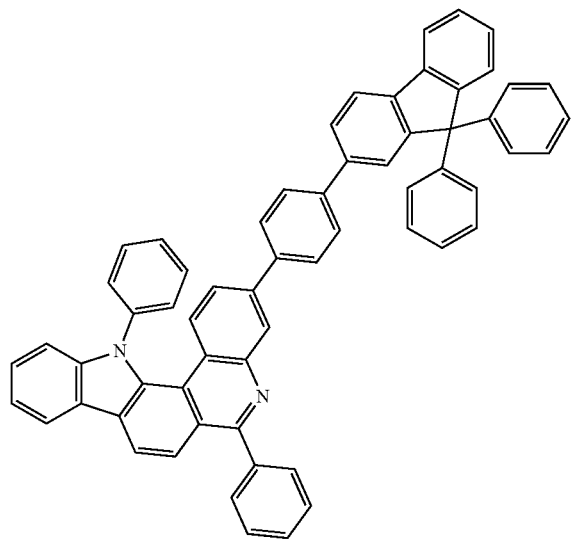
2-31
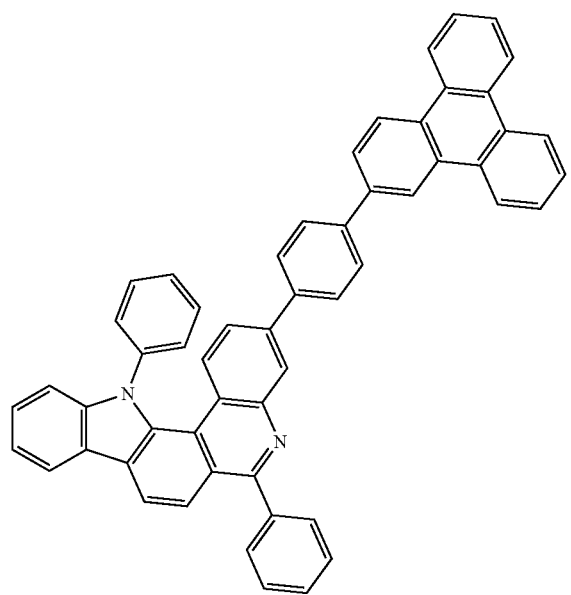
2-32
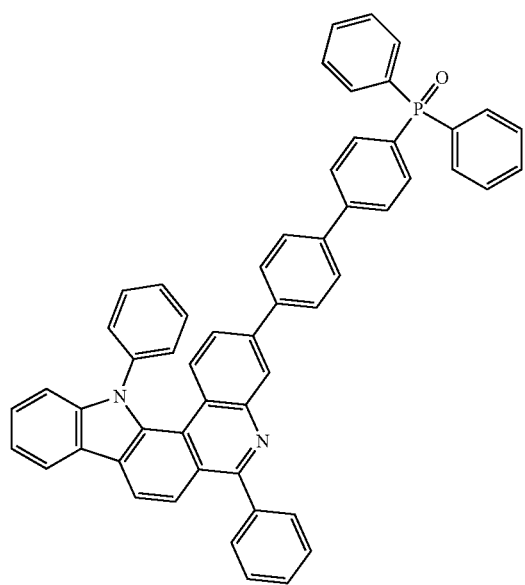

-continued
2-33
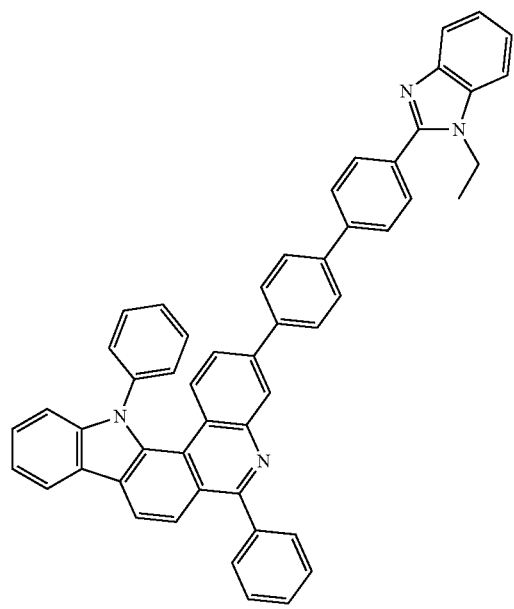
2-34
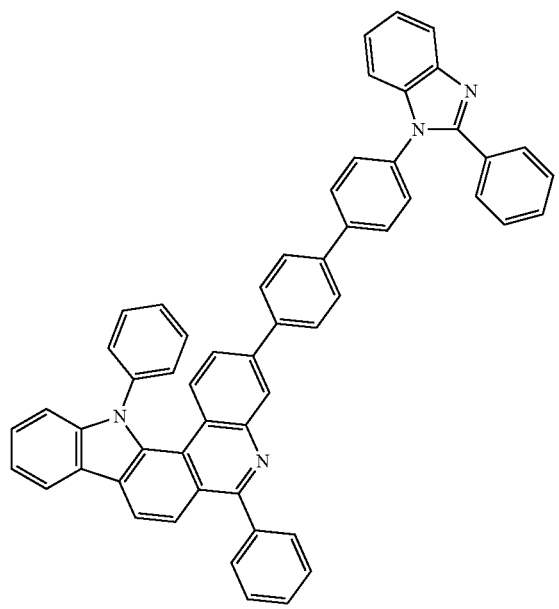
2-35
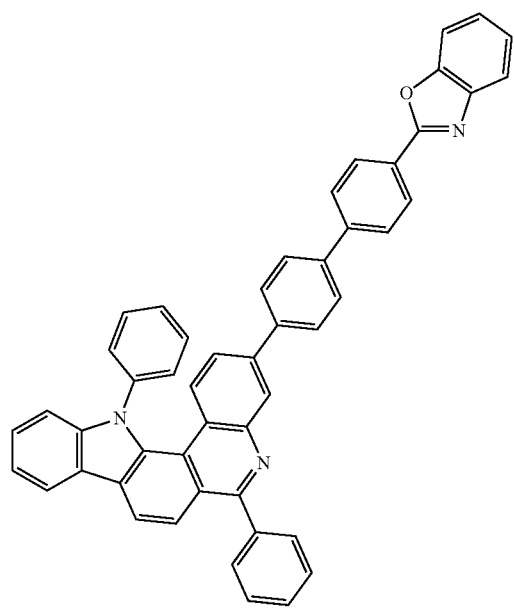
2-36
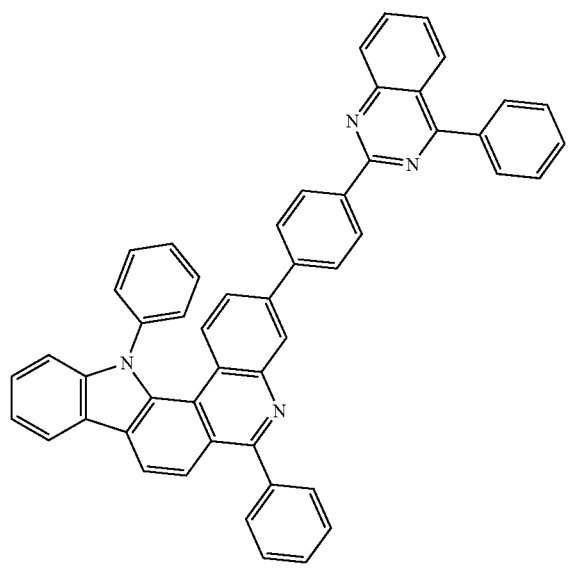

-continued
601
2-37
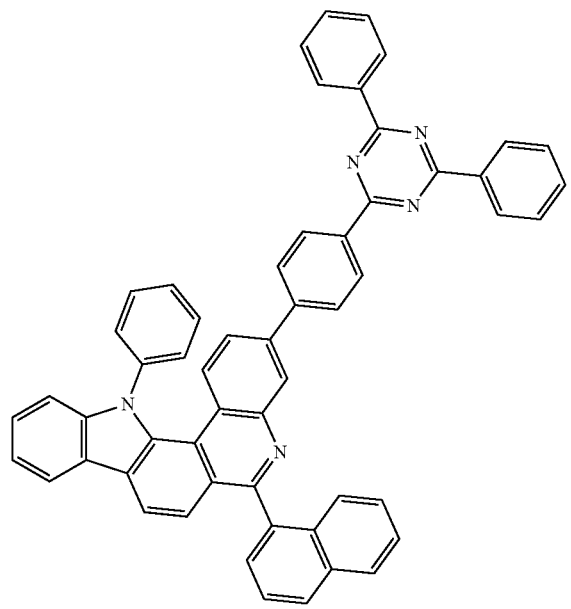
602
2-38
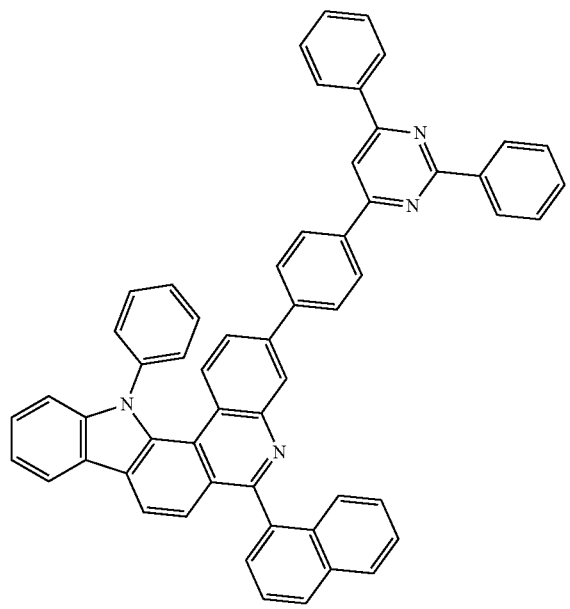
3
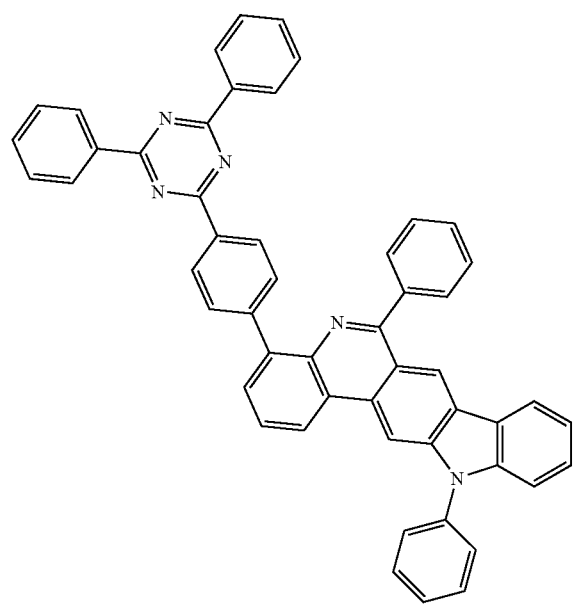
3-1
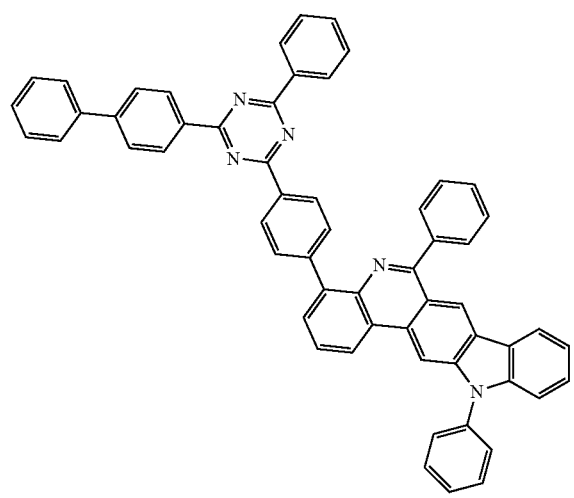

-continued
603
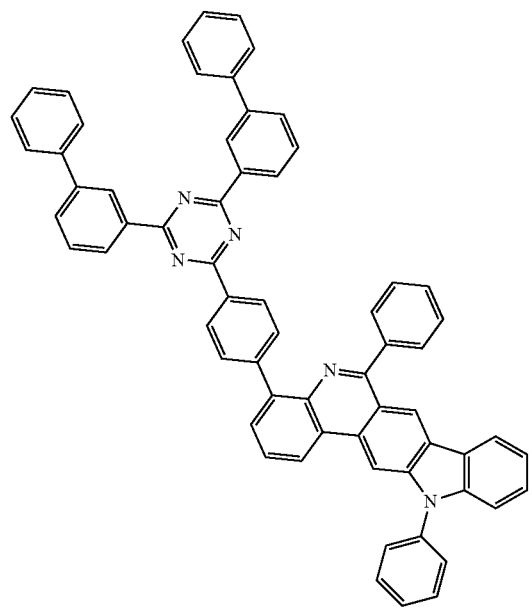
3-2
604
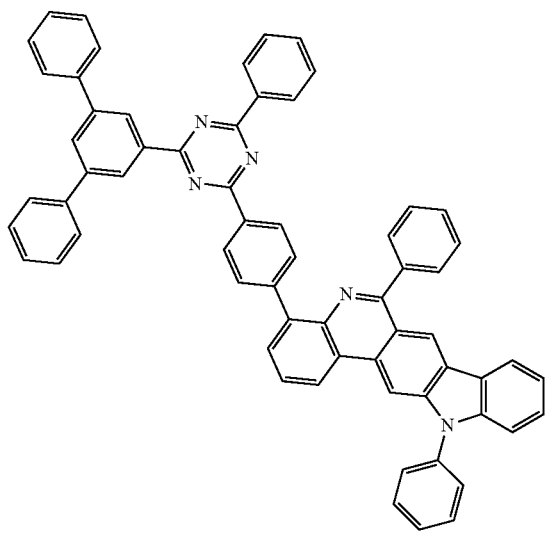
3-3
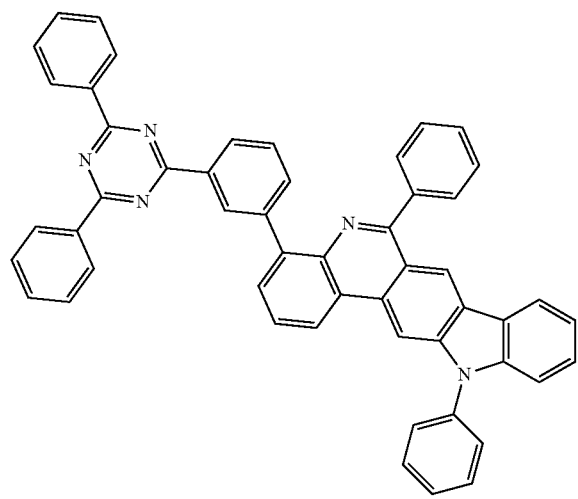
3-4
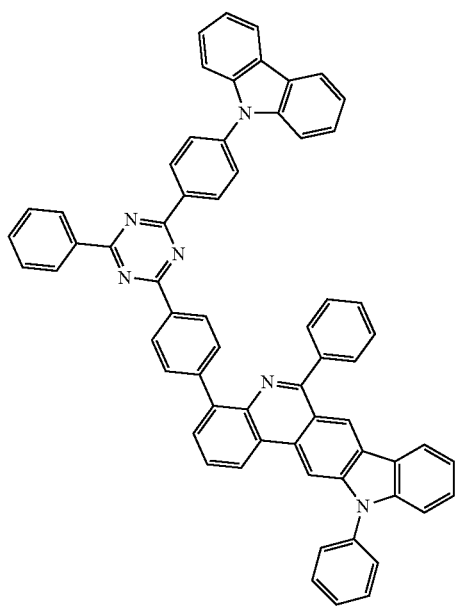
3-5

605 | 606
-continued
3-6
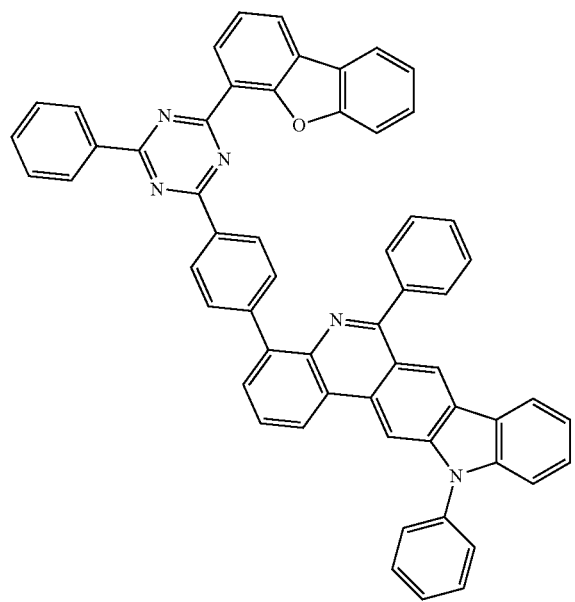
3-7
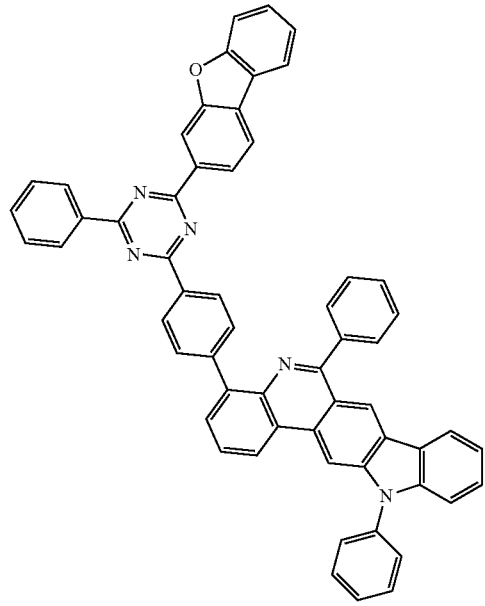
3-8
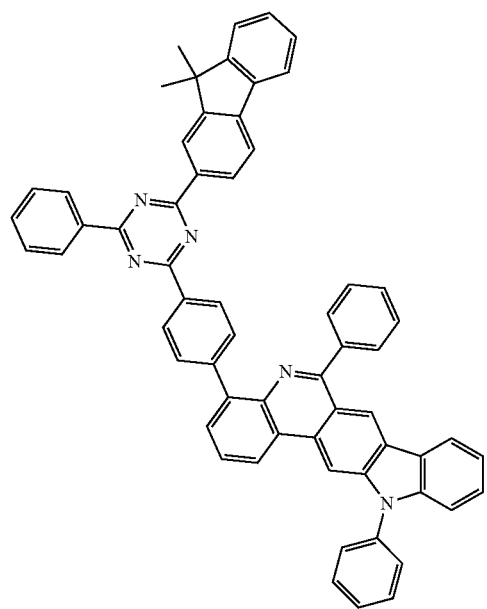
3-9
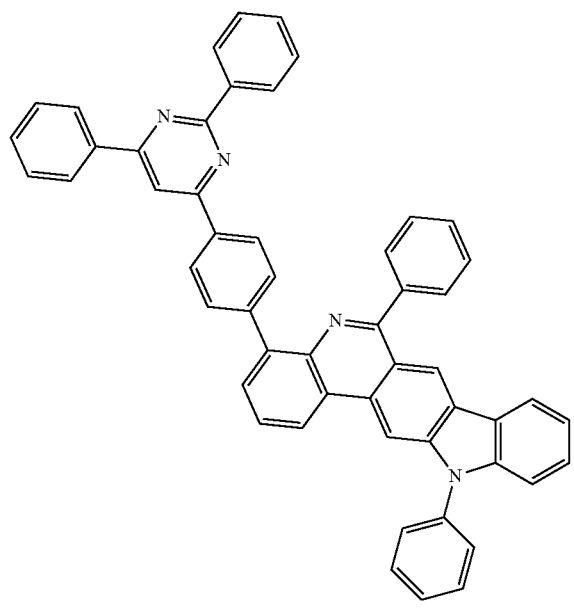

-continued
3-10
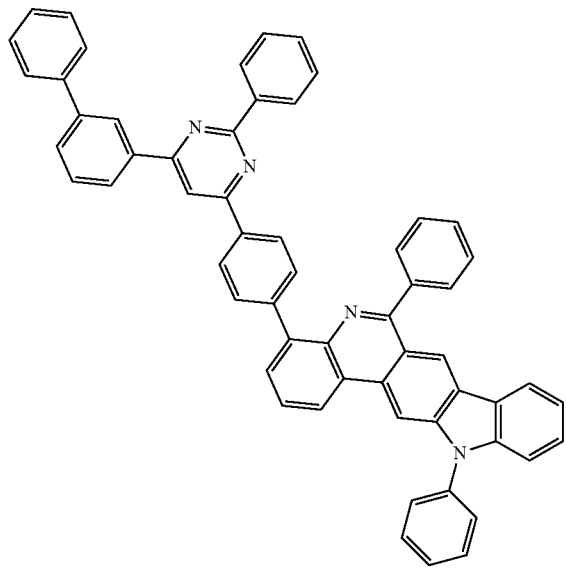
3-11
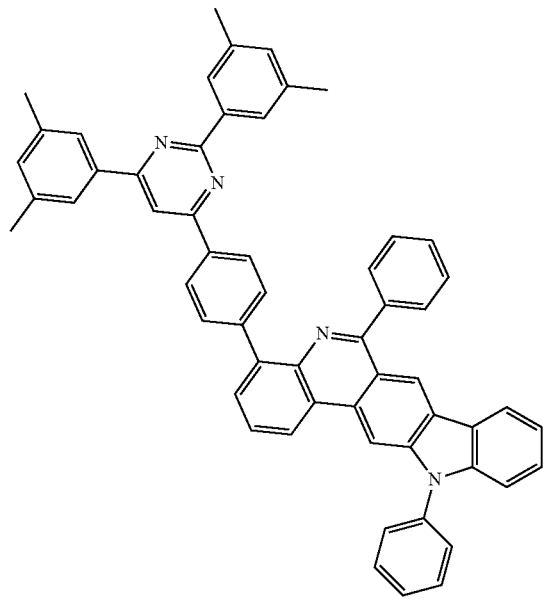
3-12
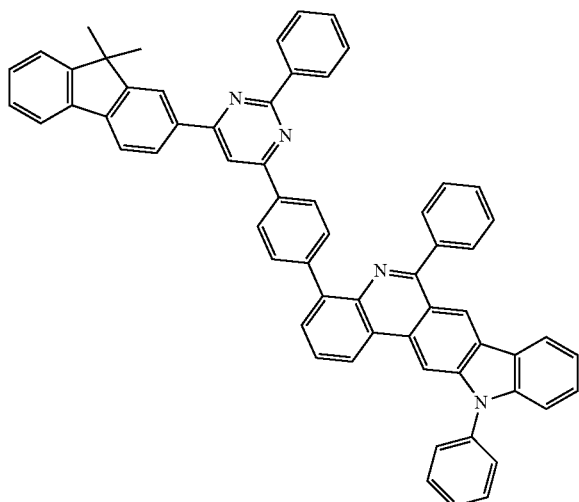
3-13
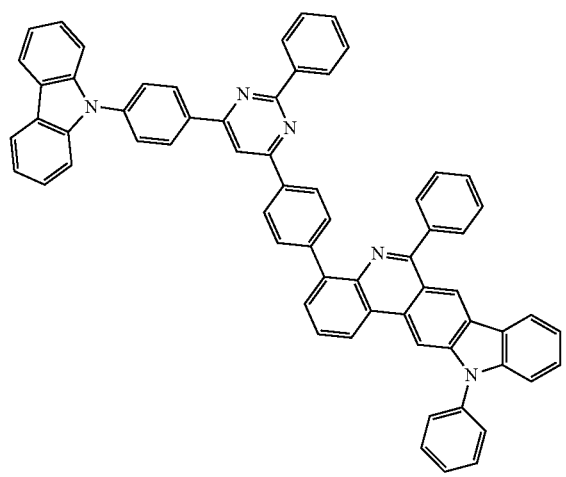
3-14
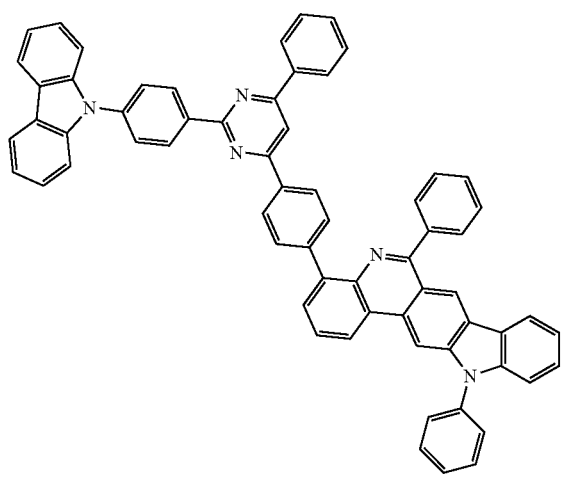
3-15
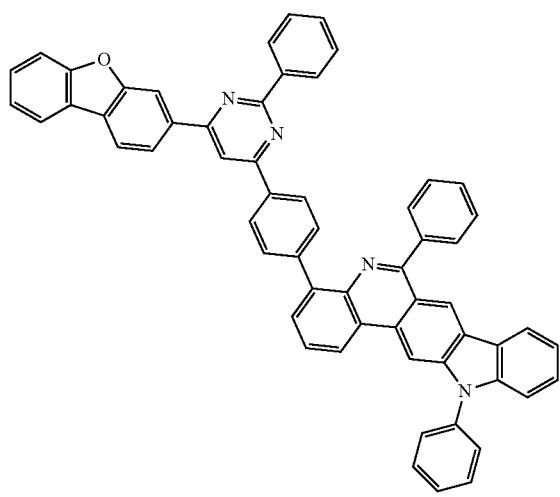

-continued
3-16
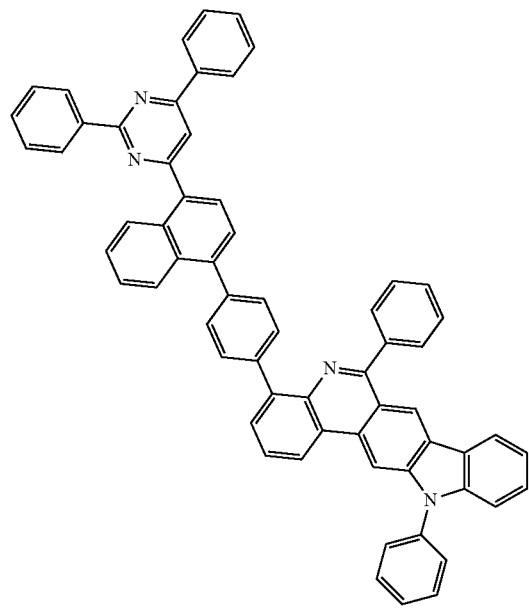
3-17
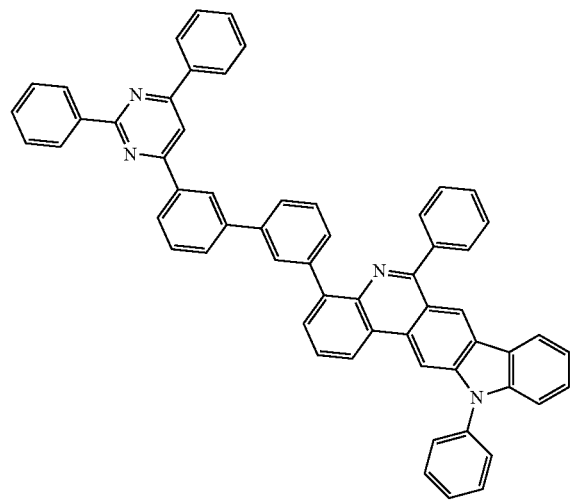
3-18
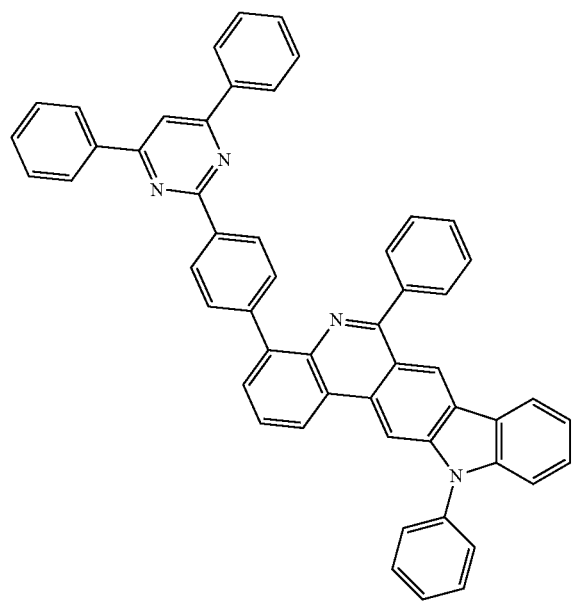
3-19
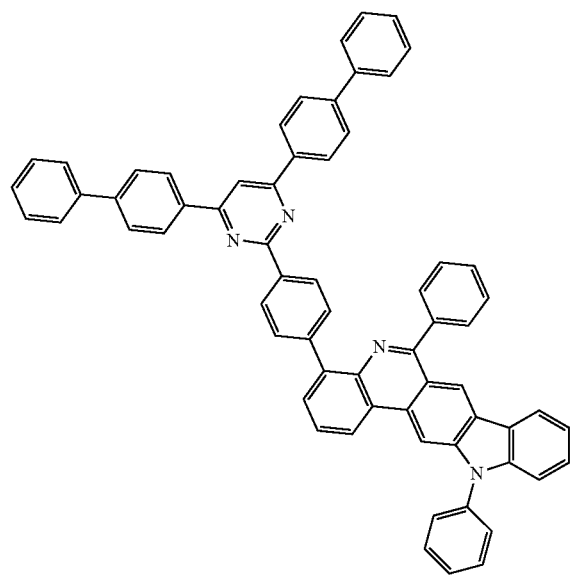

-continued
611
3-20
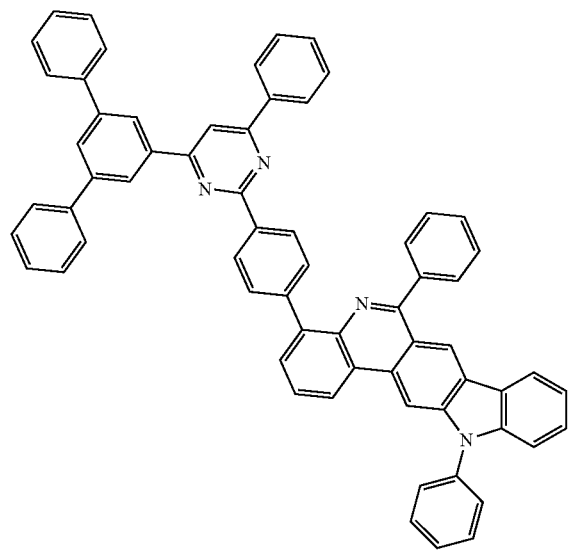
612
3-21
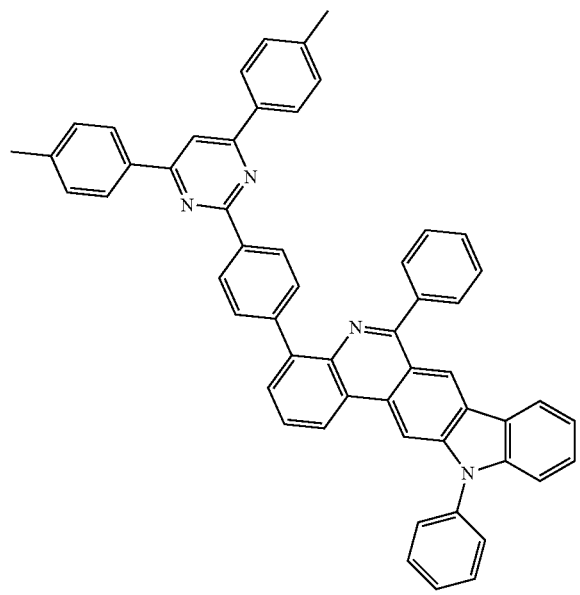
3-22
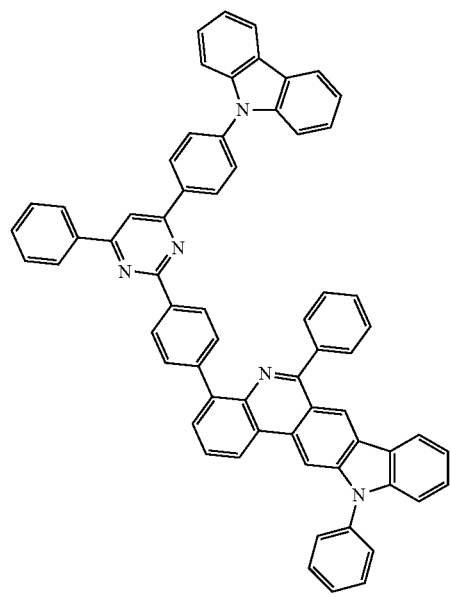
3-23
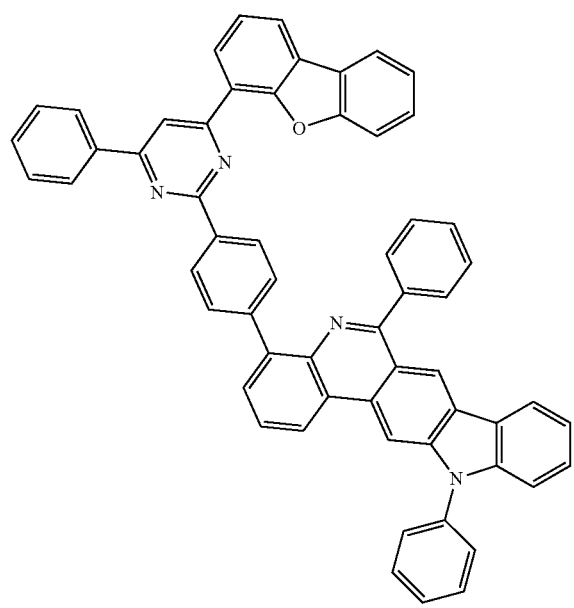

613 614
3-24 3-25
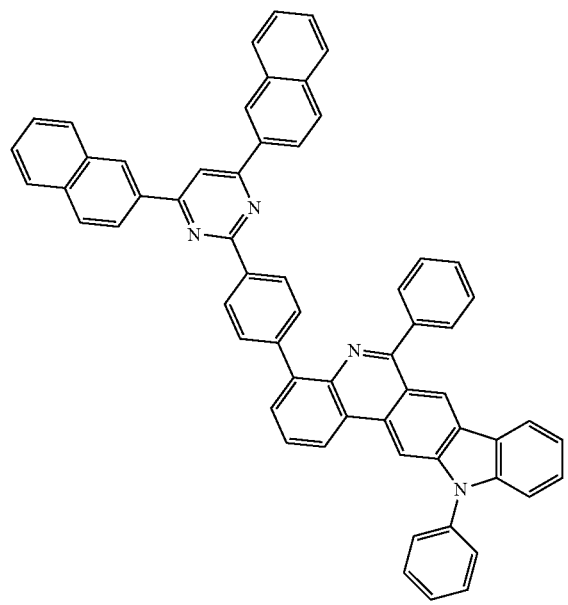
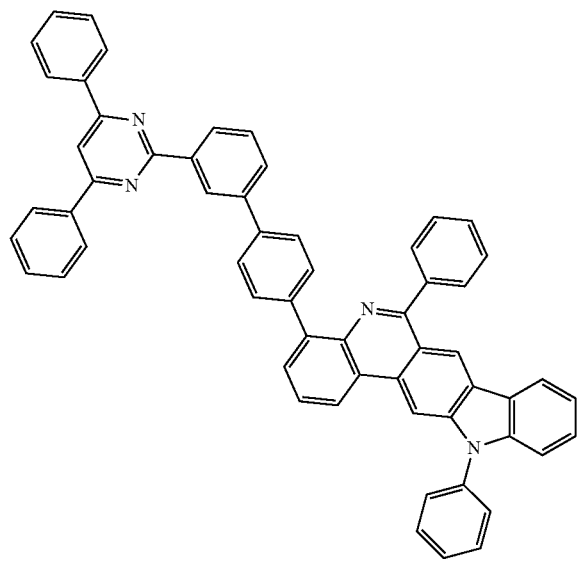
3-26 3-27
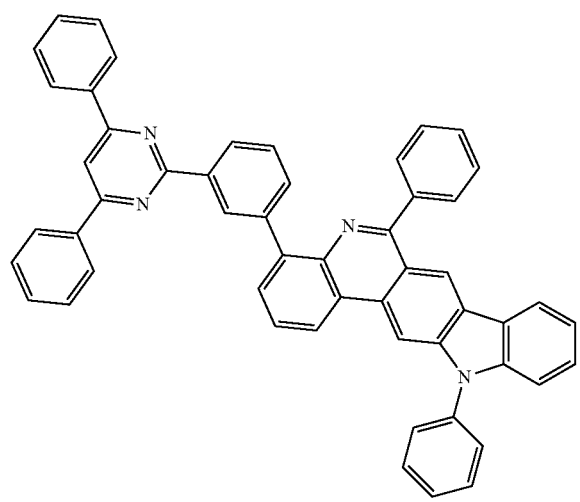
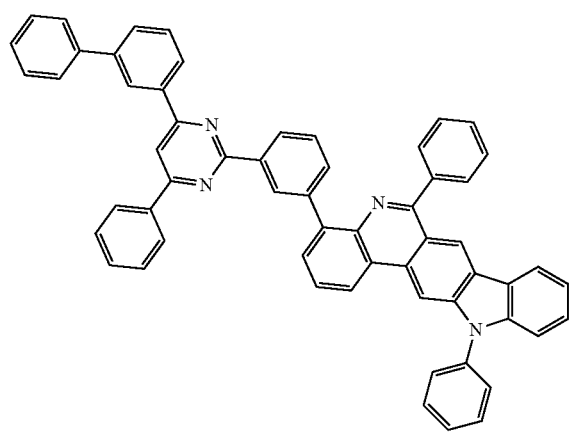

-continued
3-28
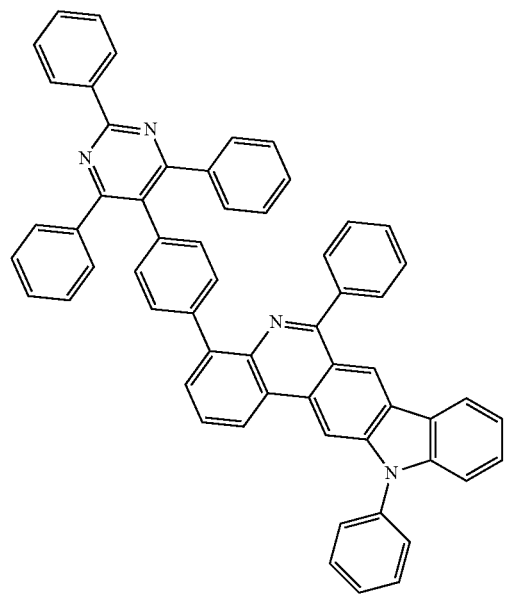
3-29
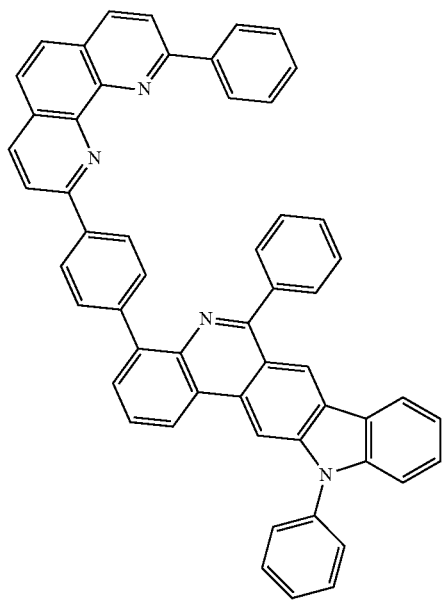
3-30
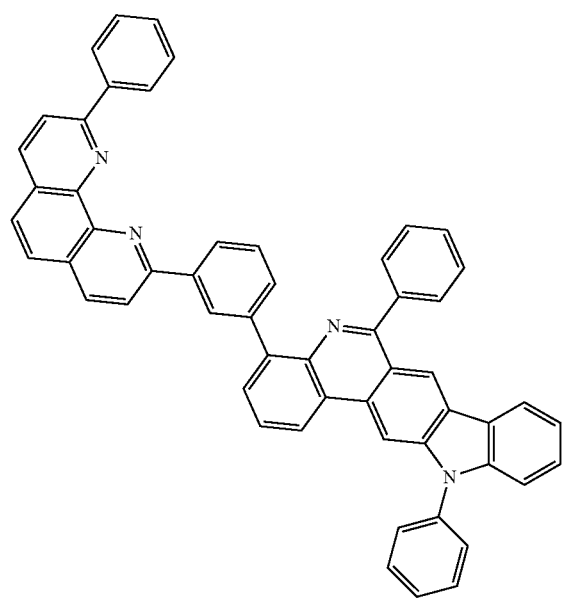
3-31
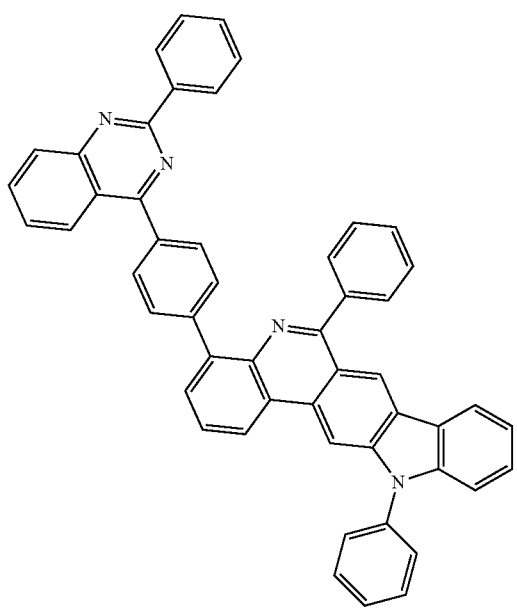

3-32
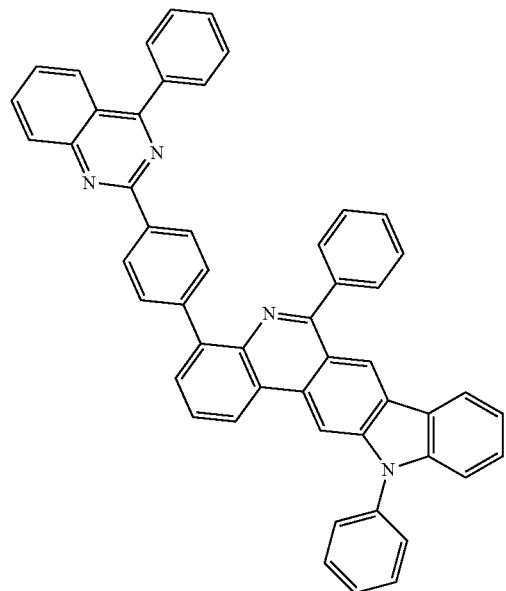
3-33
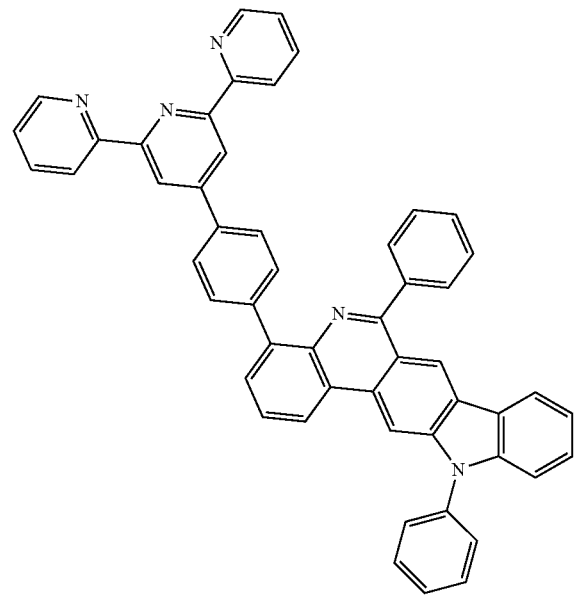
3-34
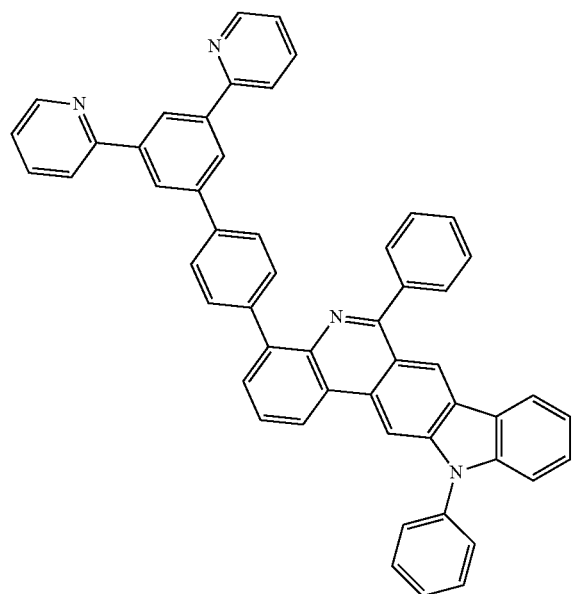
3-35
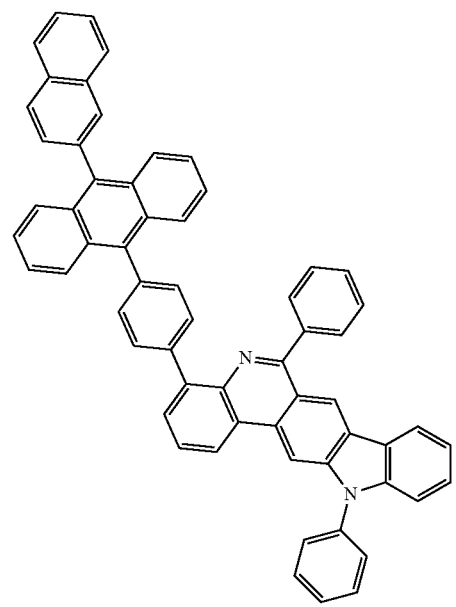

-continued
3-36
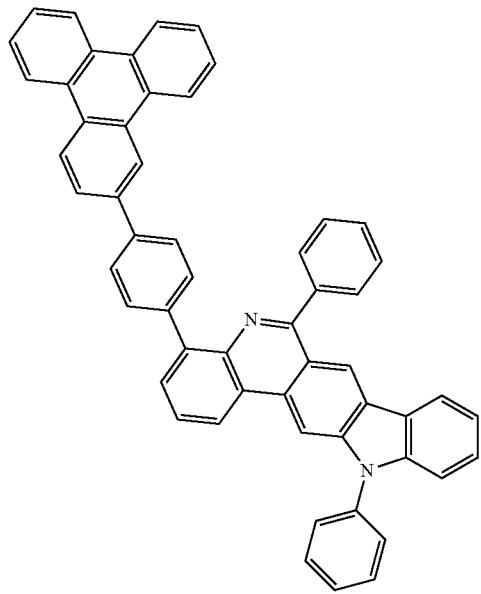
3-37
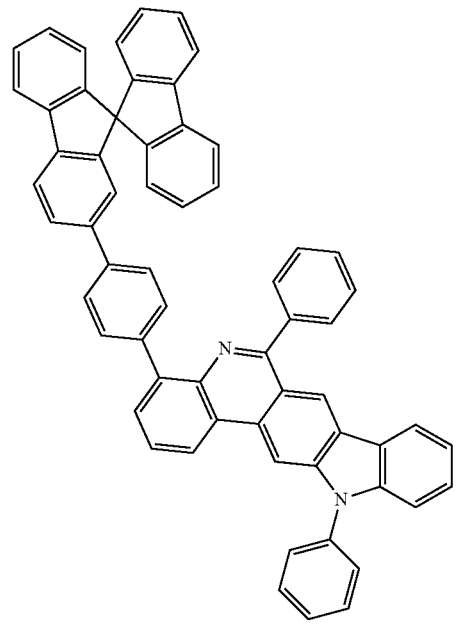
3-38
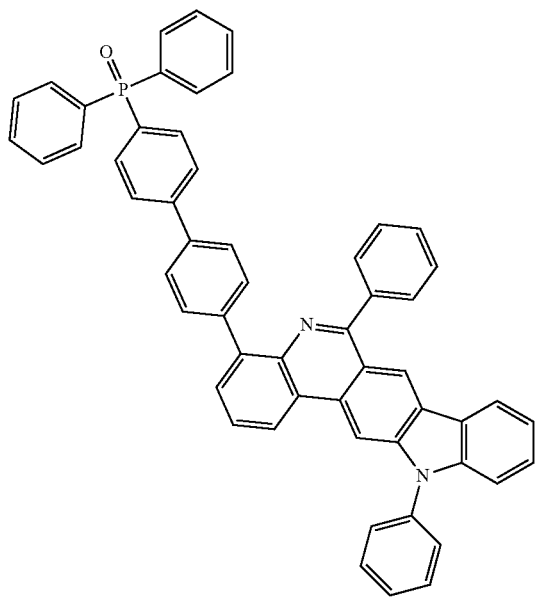
3-39
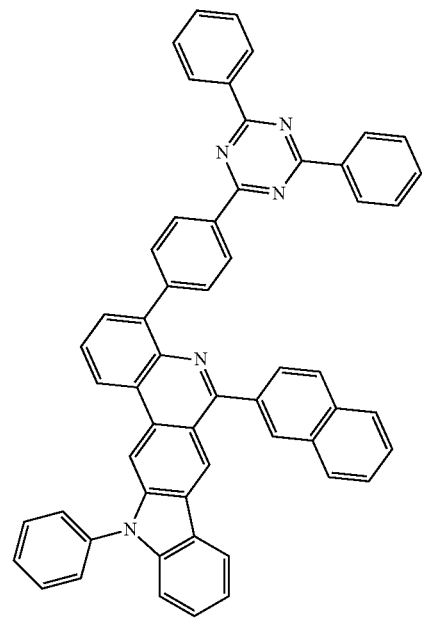

-continued
621
3-40
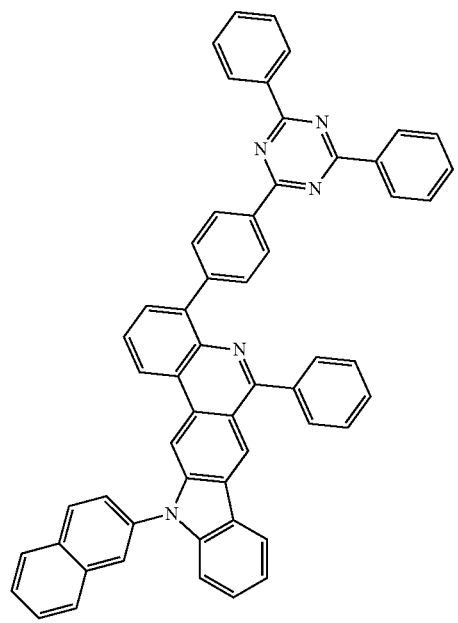
622
3-41
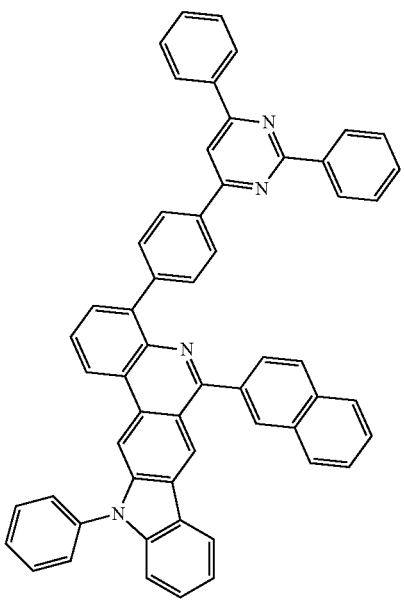
3-42
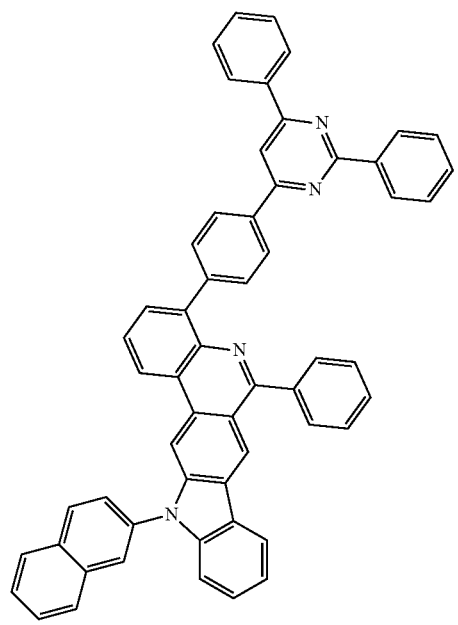
4
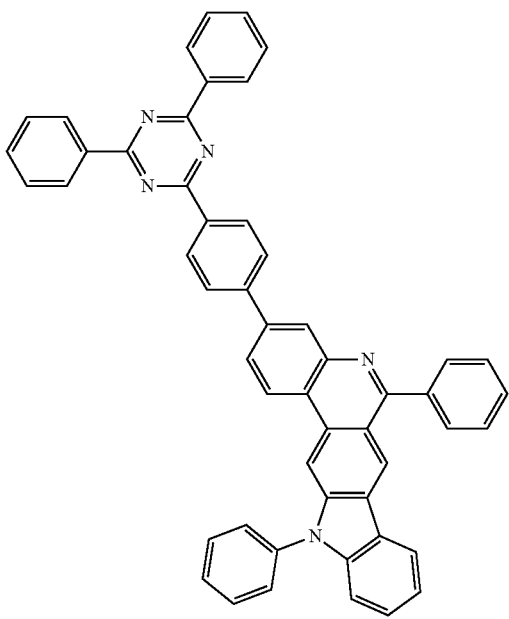

-continued
4-1
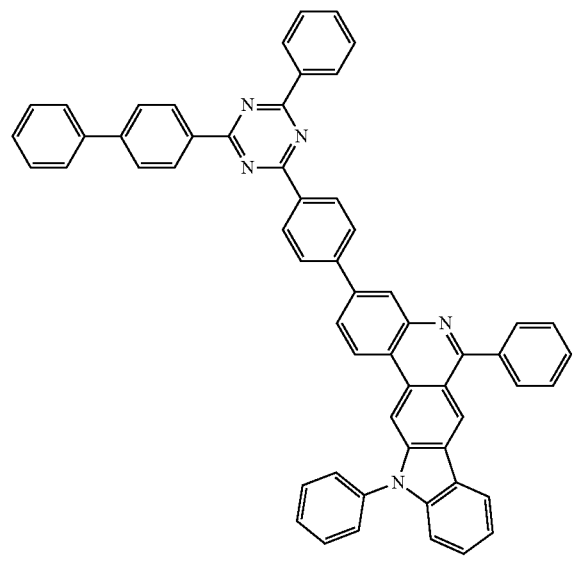
4-2
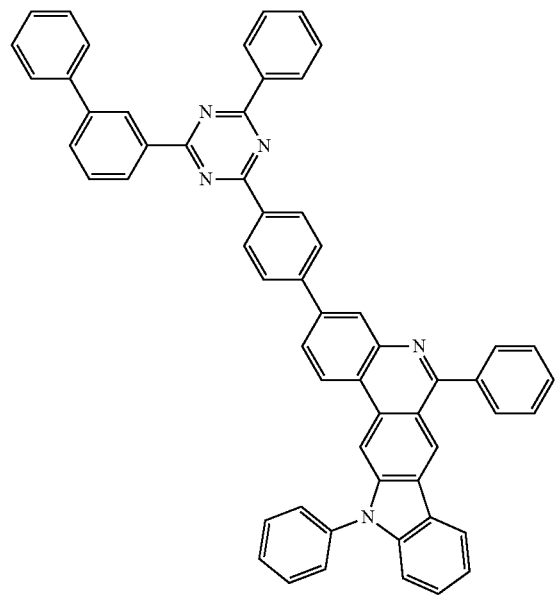
4-3
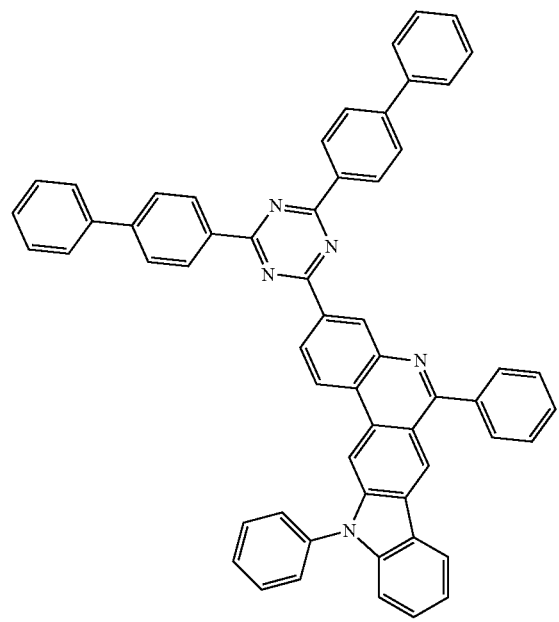
4-4
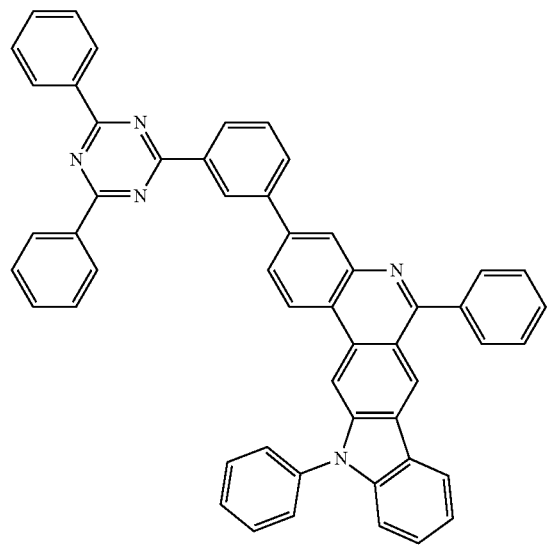

-continued
4-5
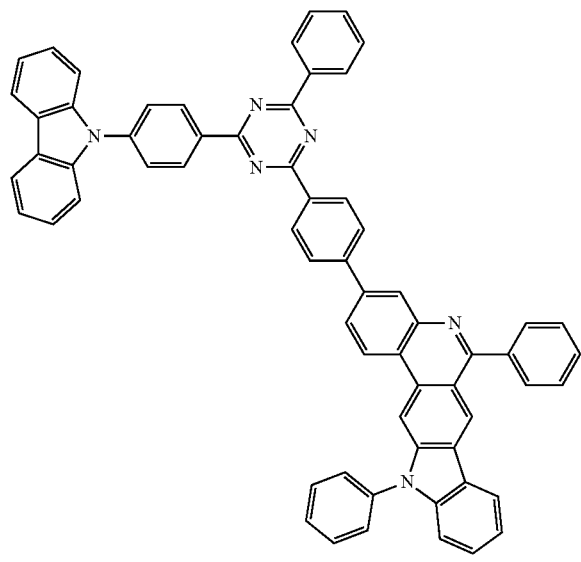
4-6
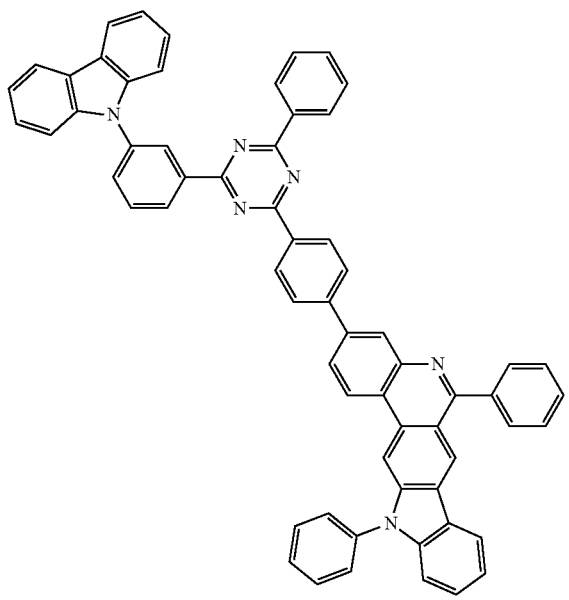
4-7
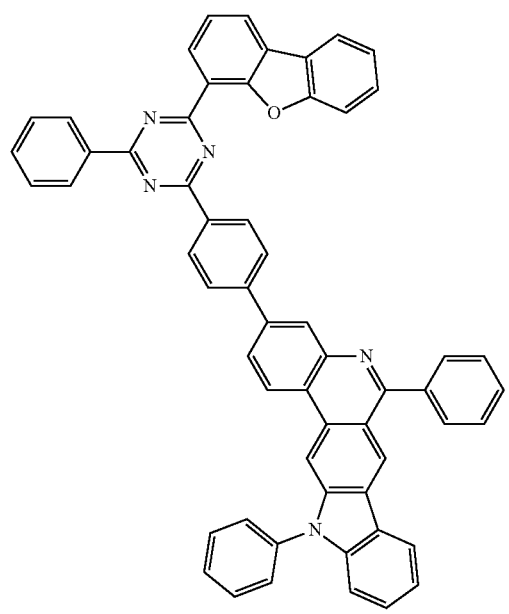
4-8
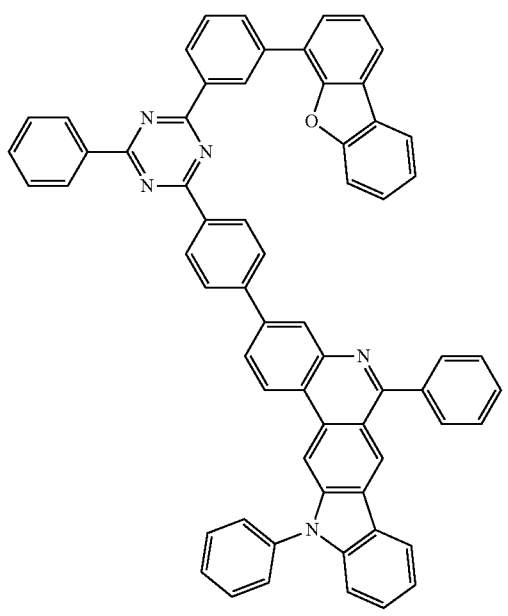

-continued
4-9
627
4-10
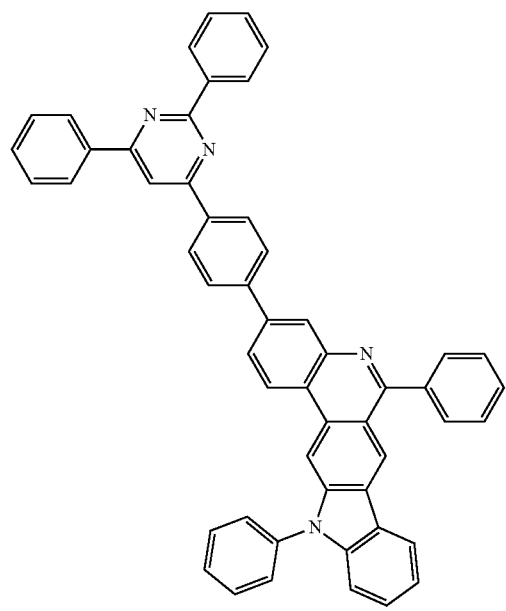
628
4-11
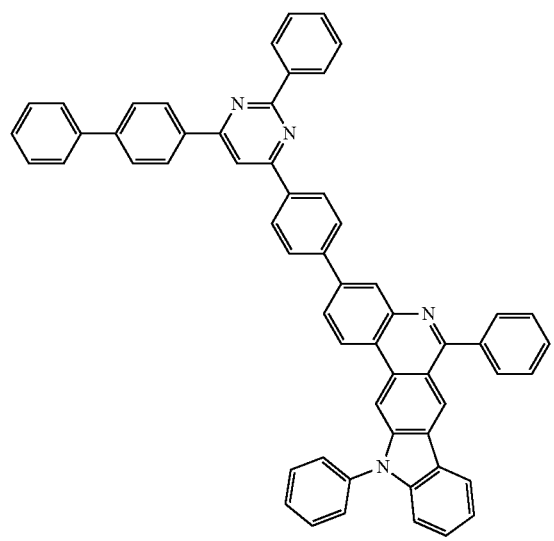
4-12
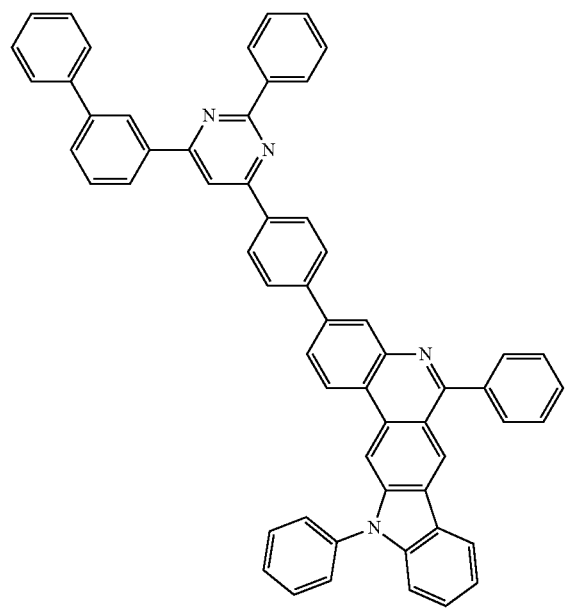

-continued
4-13
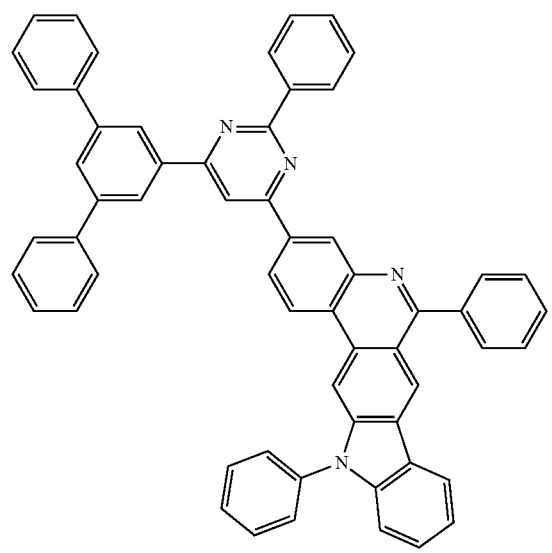
4-14
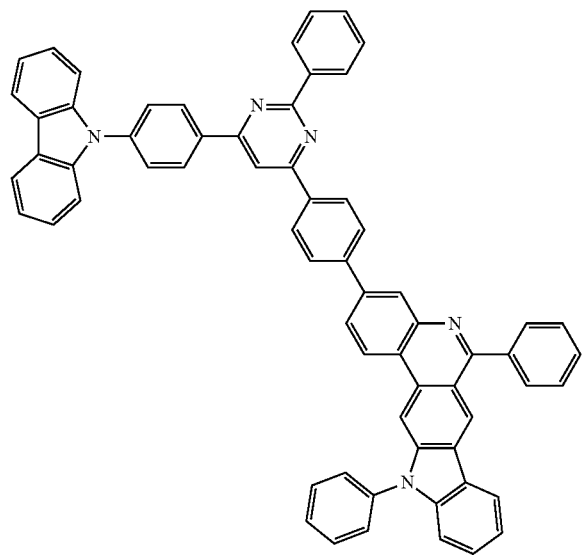
4-15
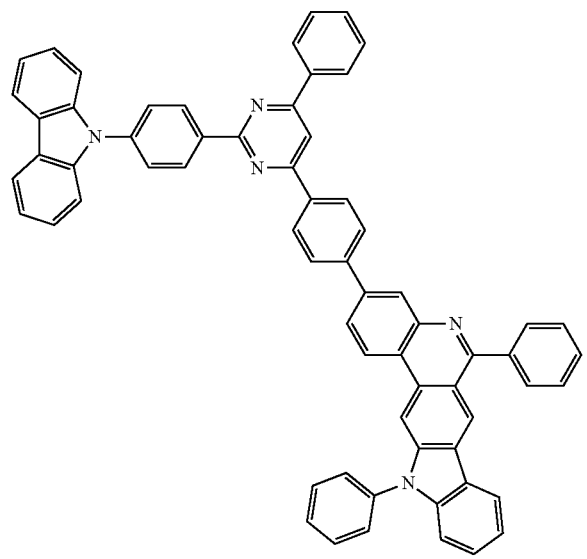
4-16
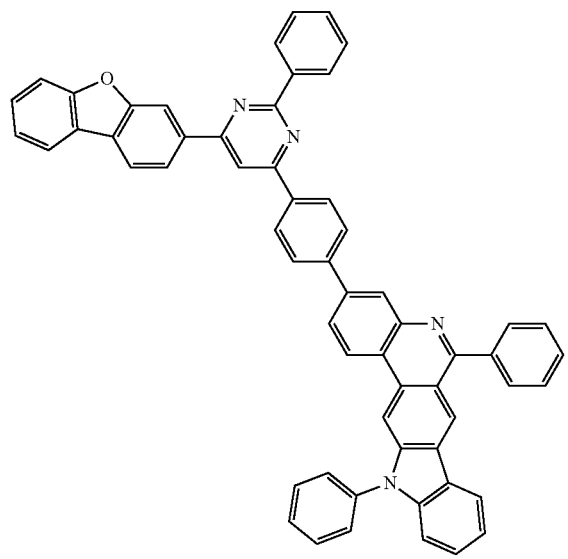

-continued
4-17
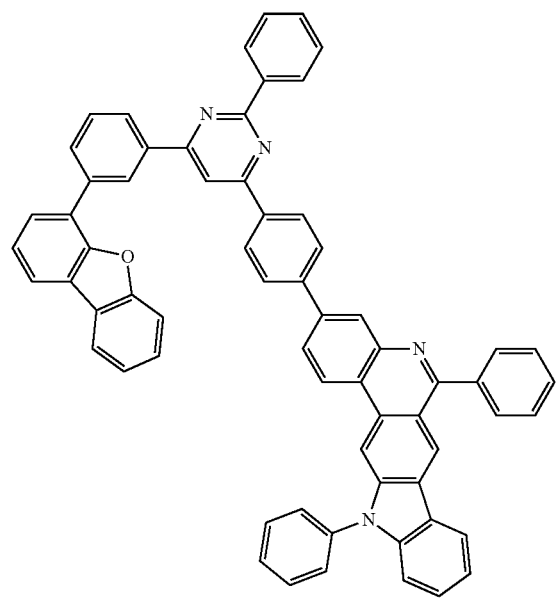
4-18
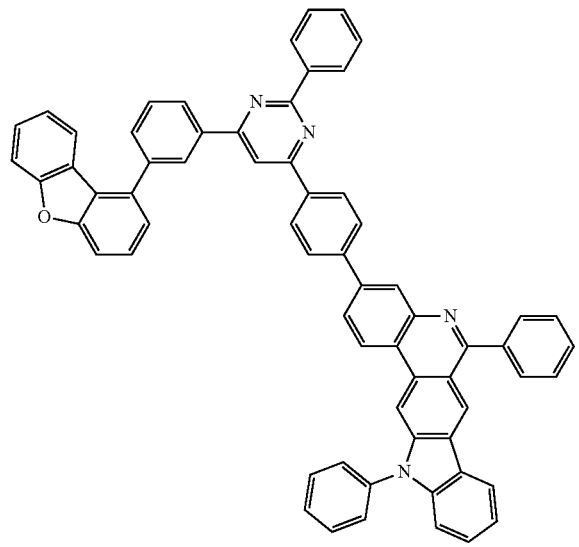
4-19
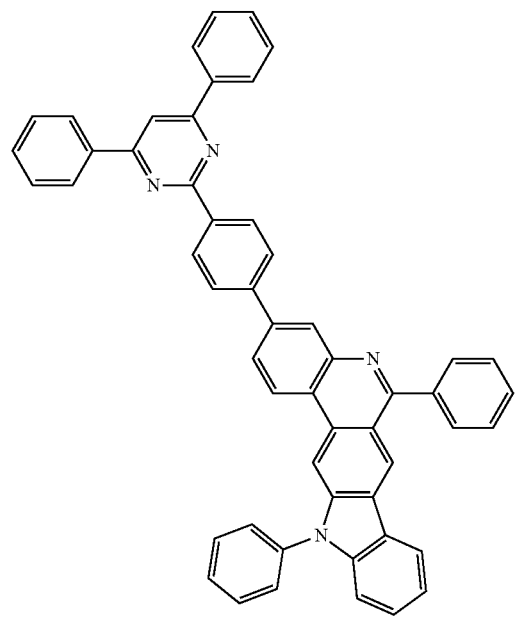
4-20
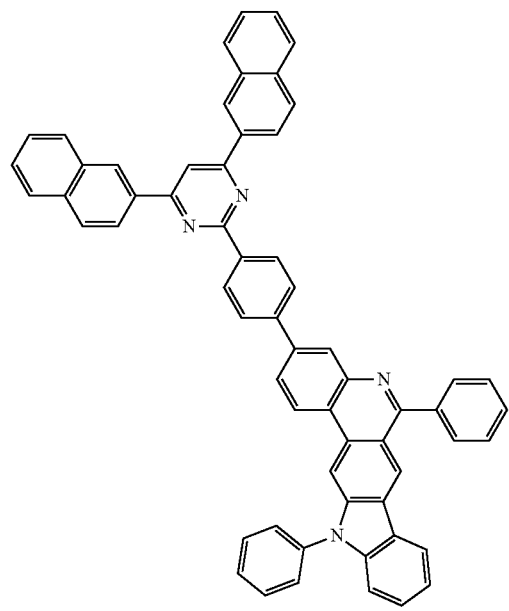

-continued
4-21
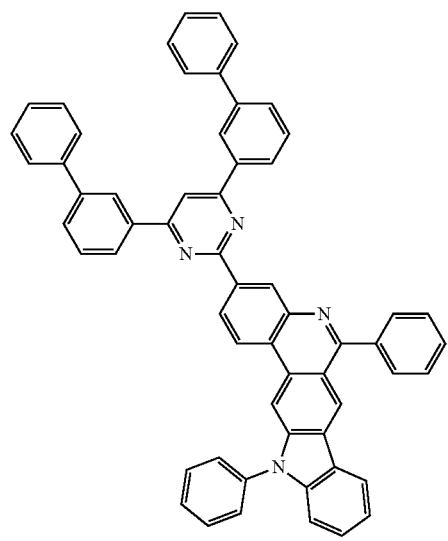
633
4-22
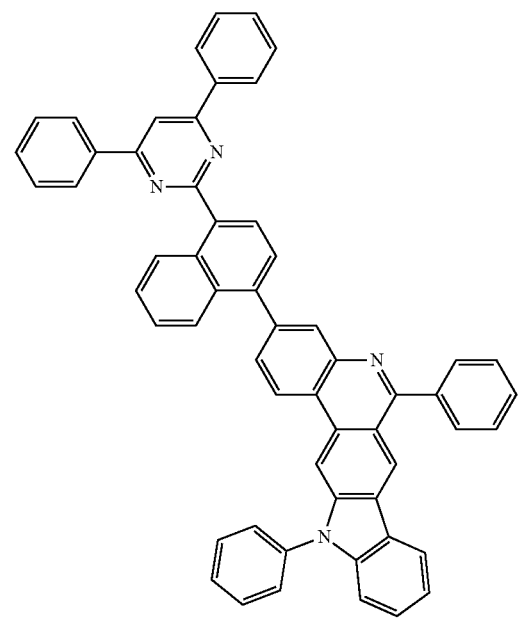
634
4-23
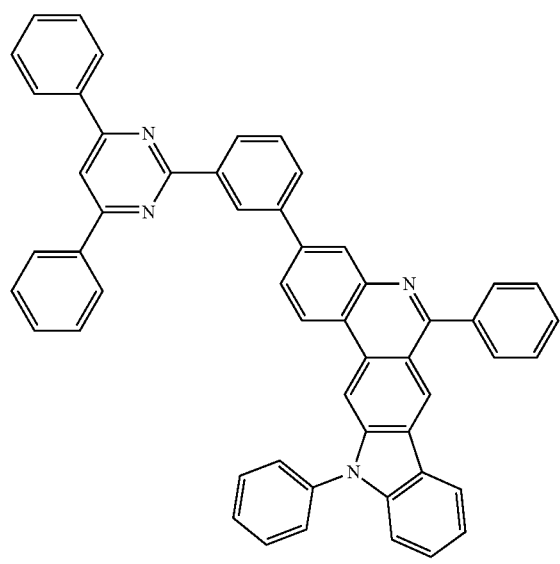
4-24
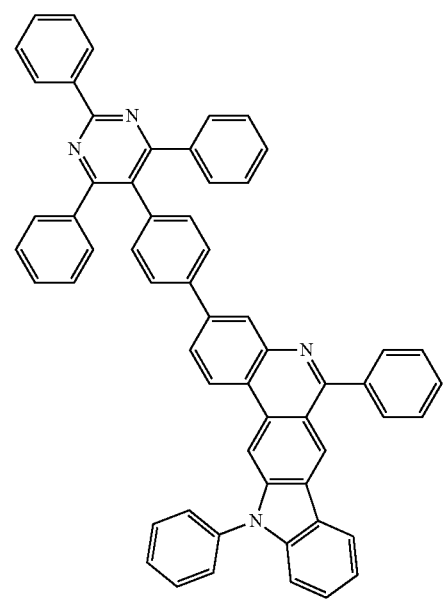

-continued
4-25
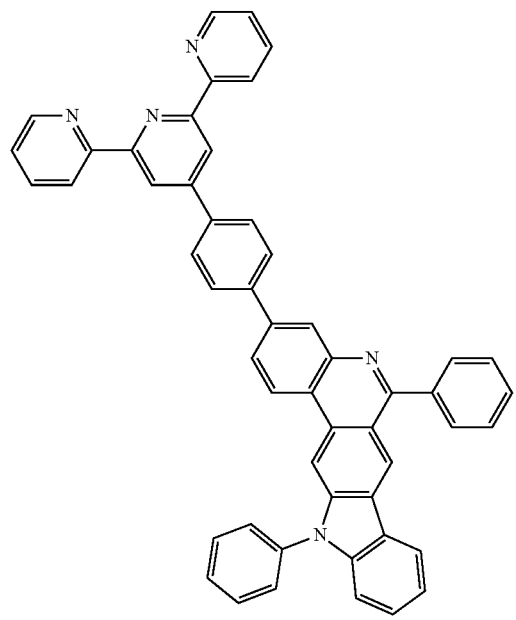
4-26
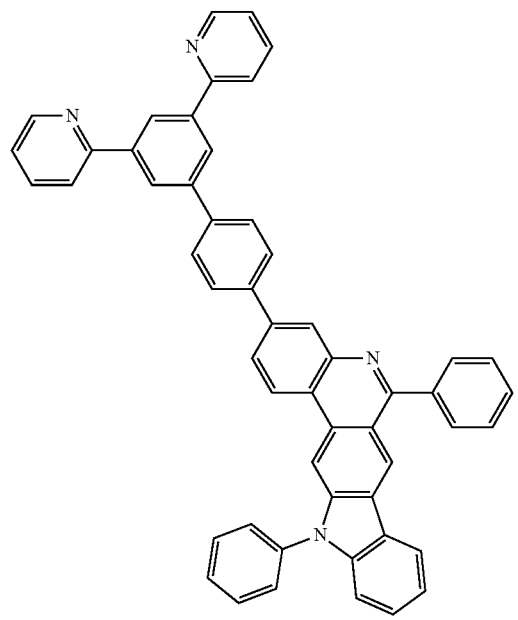
4-27
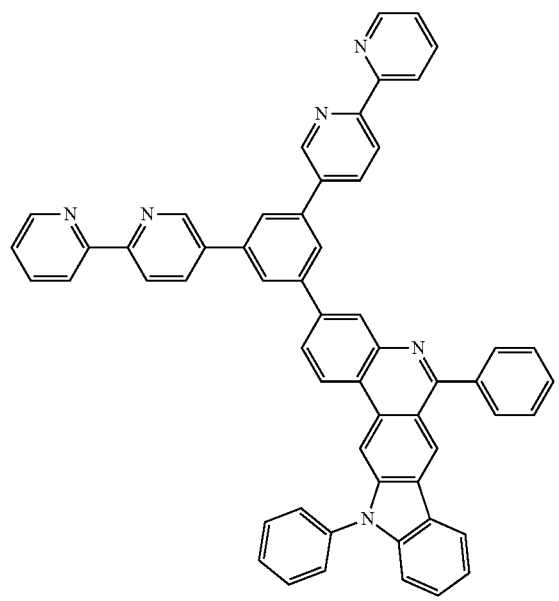
4-28
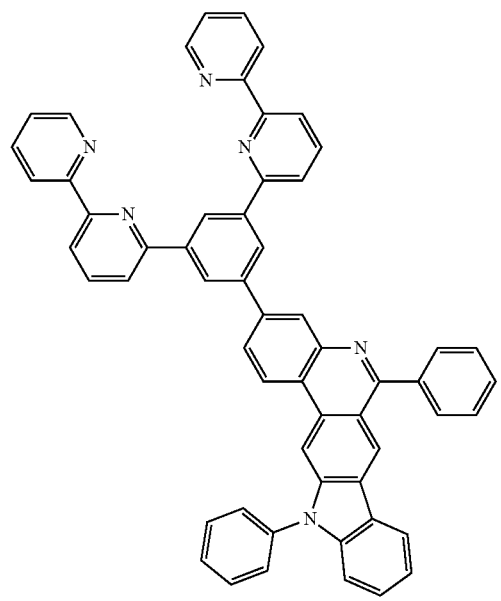

-continued
4-29
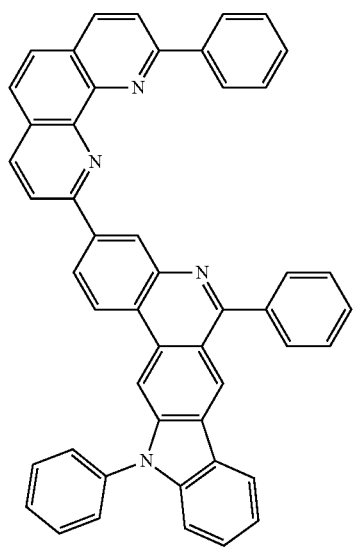
4-30
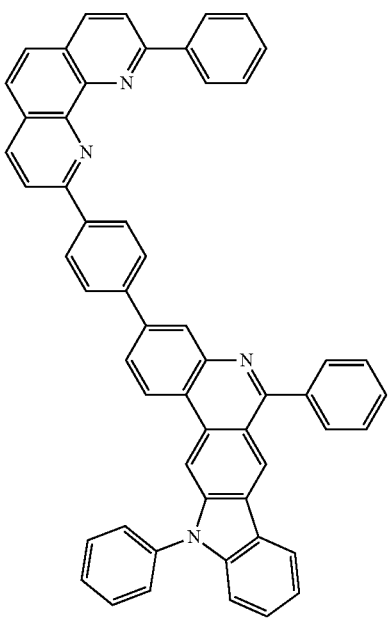
4-31
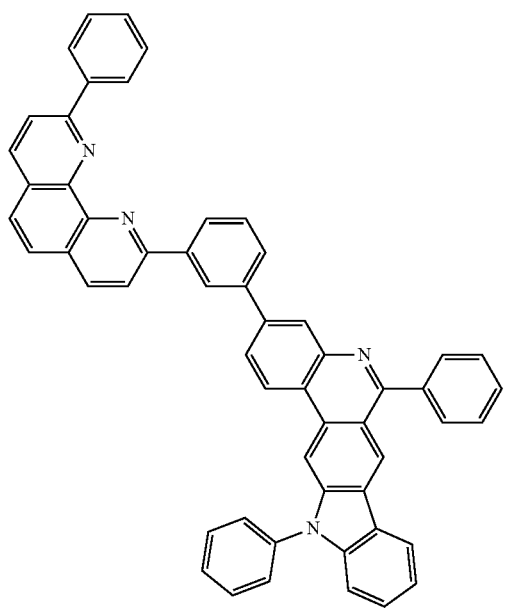
4-32
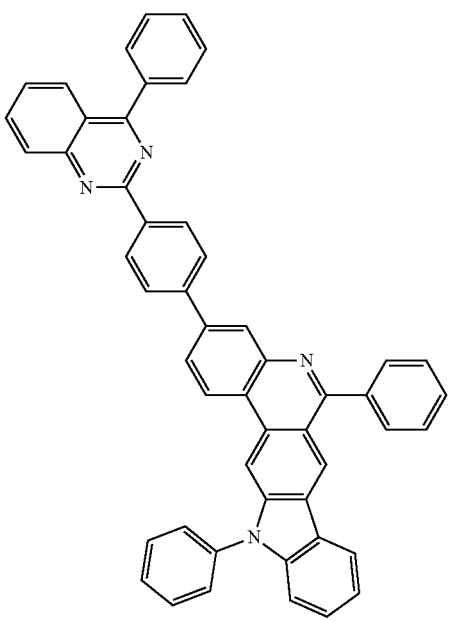

-continued
4-33
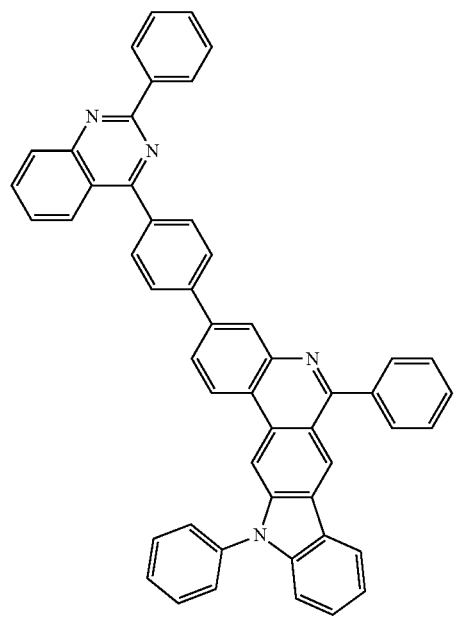
4-34
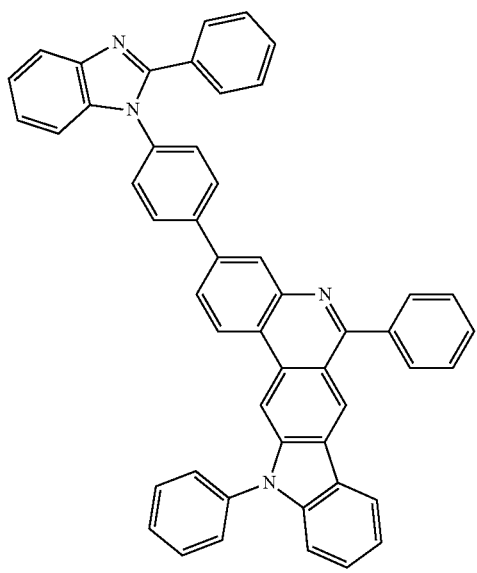
4-35
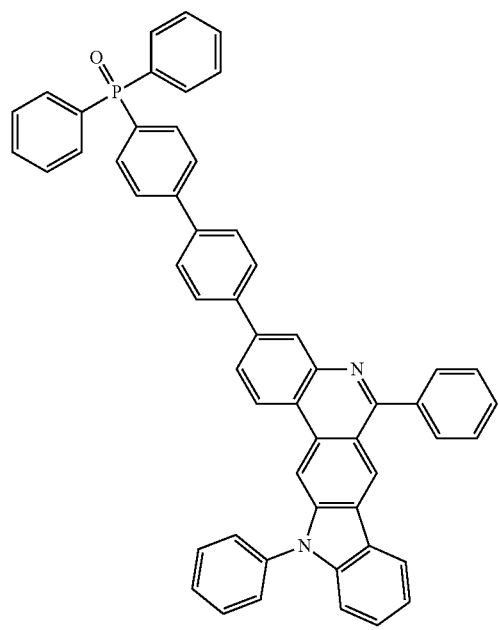
4-36
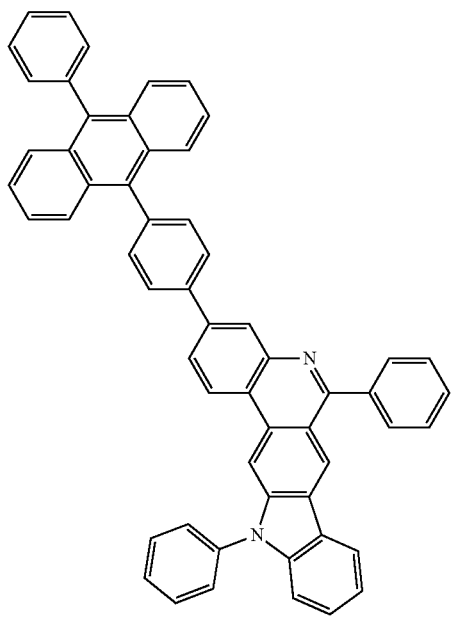

-continued
4-37
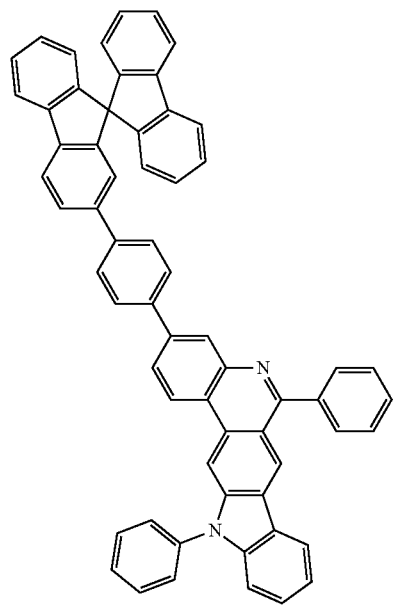
4-38
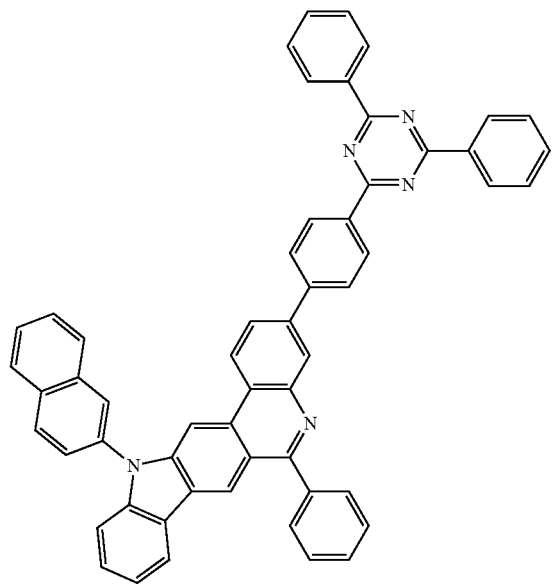
4-39
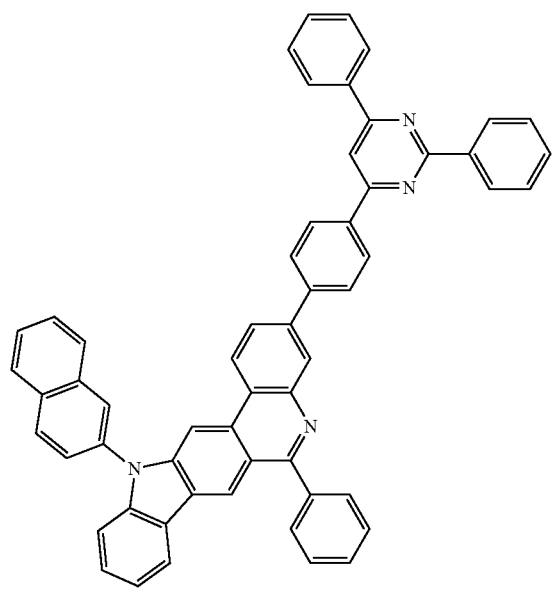
4-40
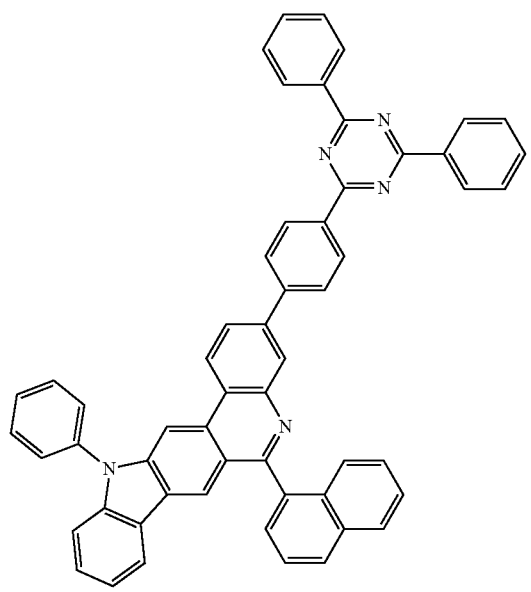

-continued
4-41
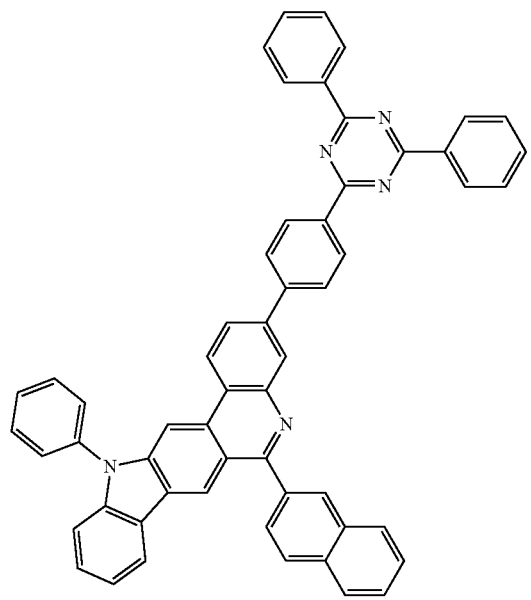
5
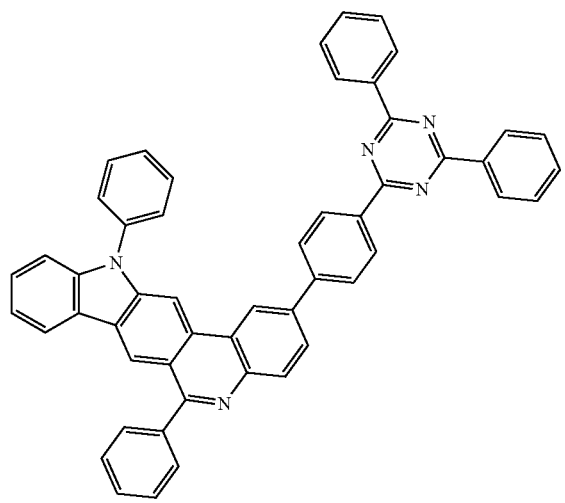
5-1
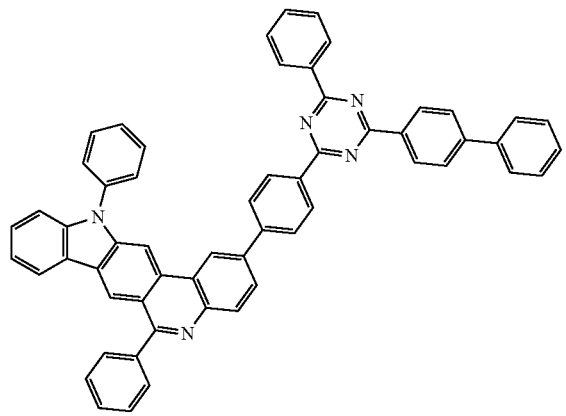
5-2
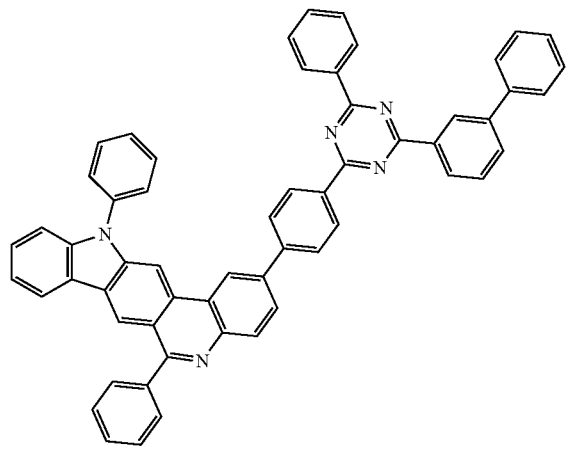
5-3
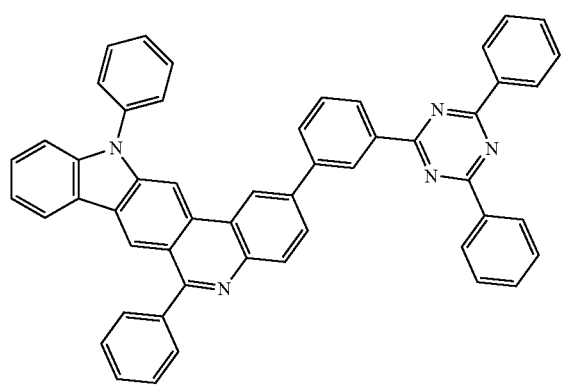
5-4
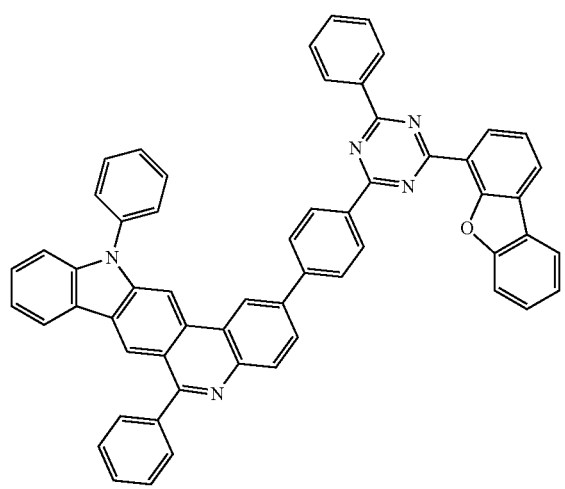

-continued
5-5
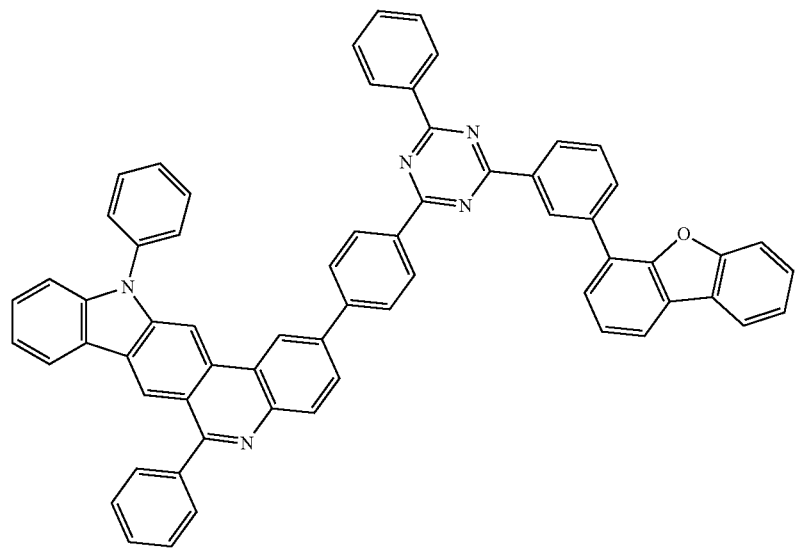
5-6
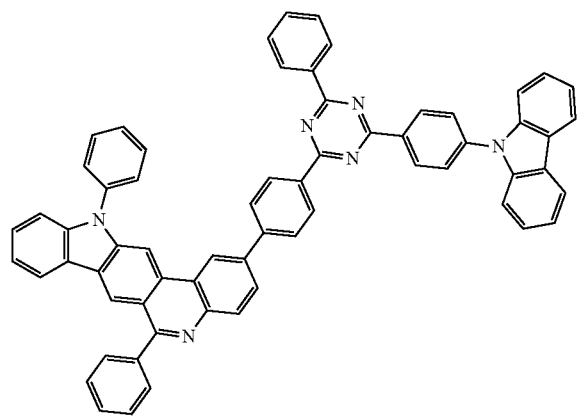
5-7
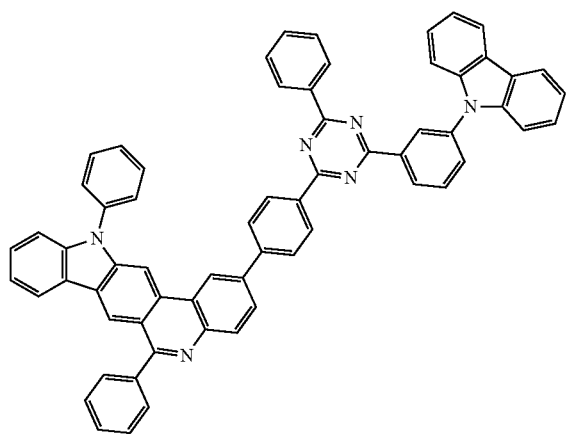
5-8
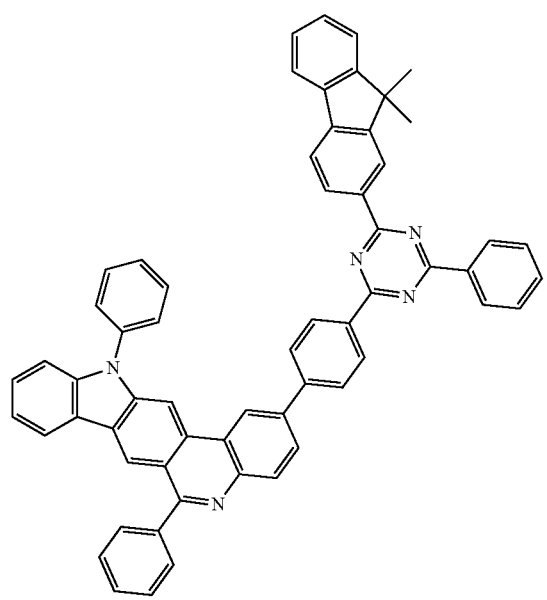
5-9

5-10
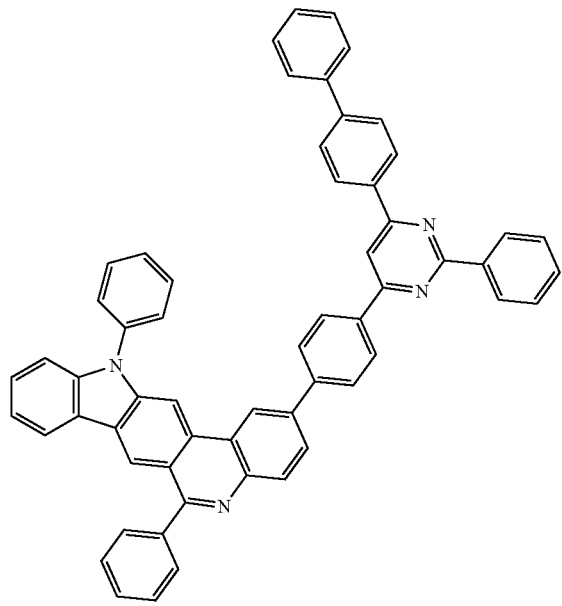
5-11
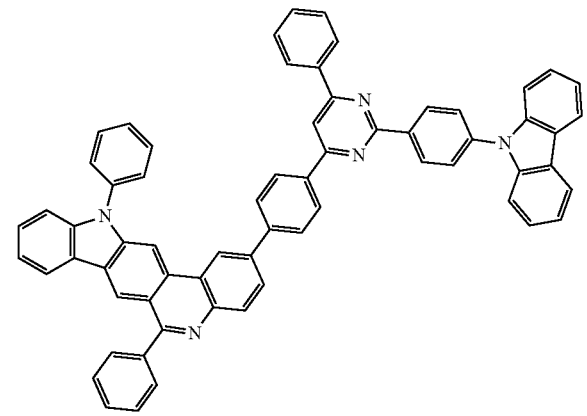
5-12
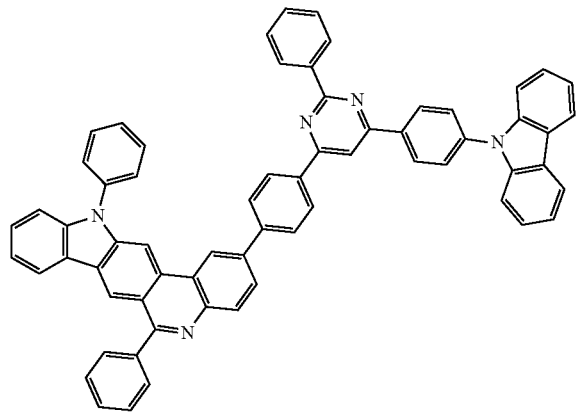
5-13
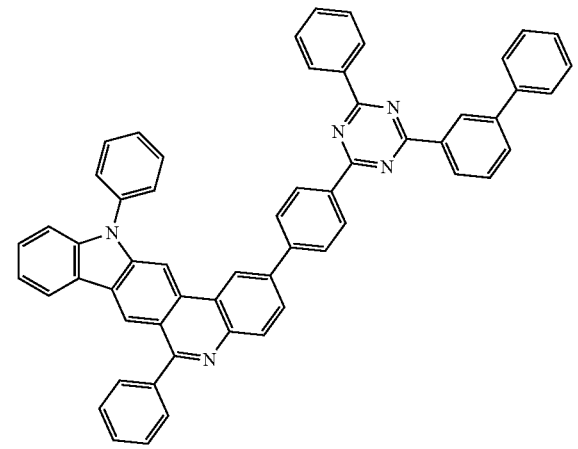
5-14
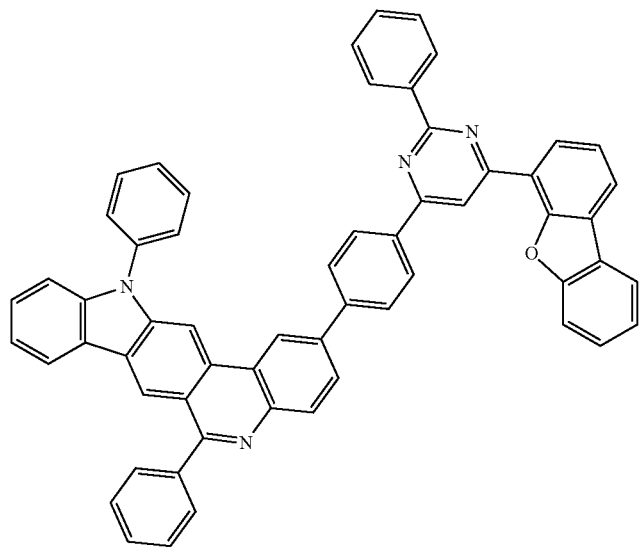

5-15
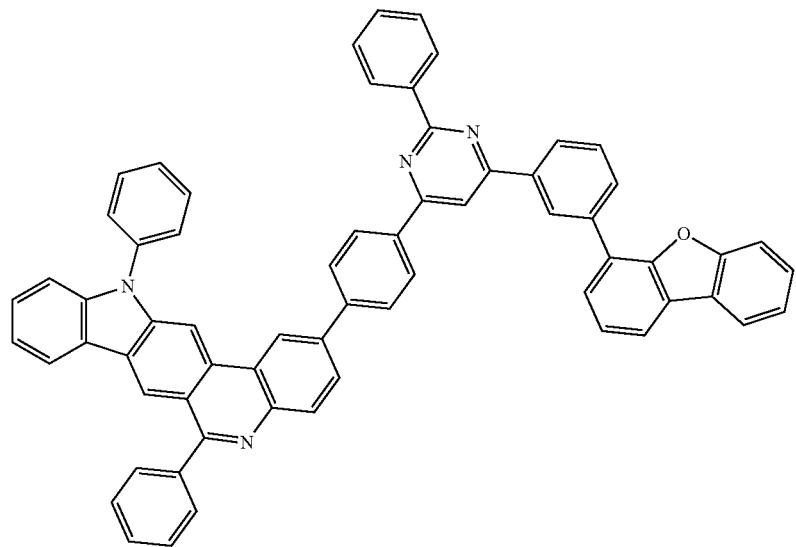
5-16
5-17
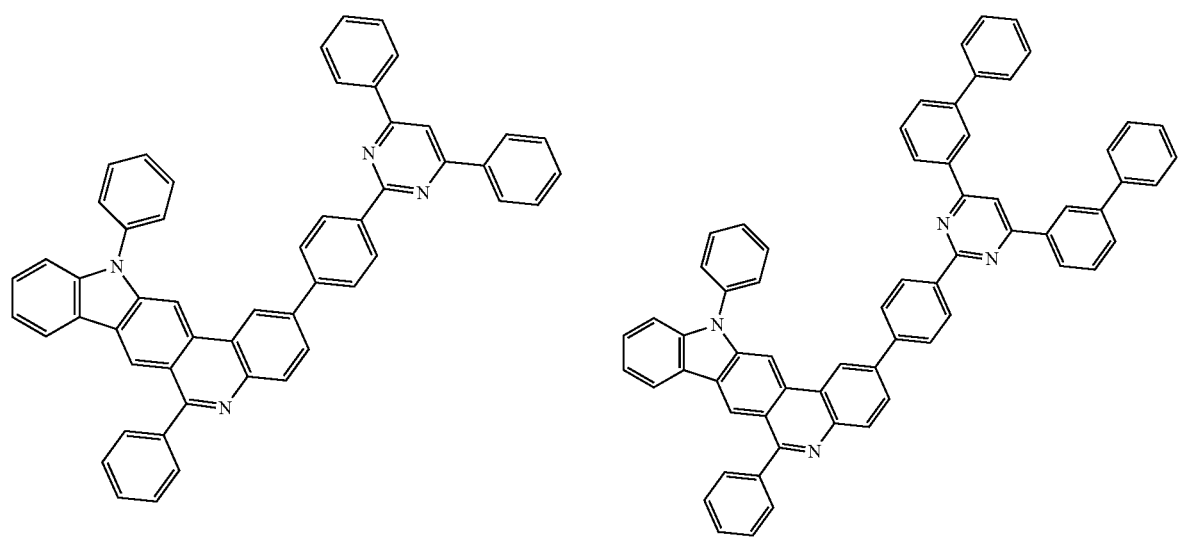

-continued
5-18
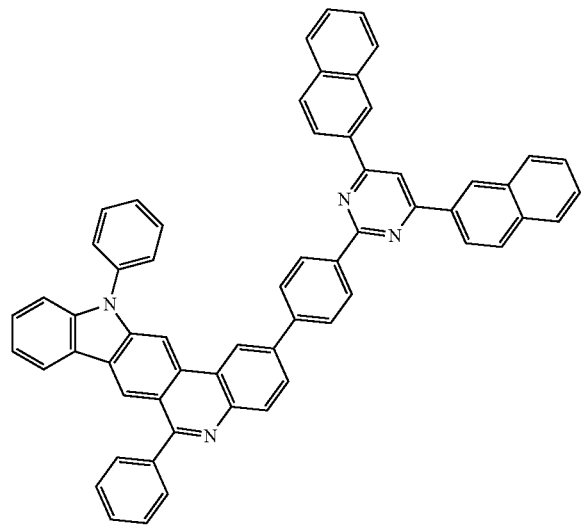
5-19
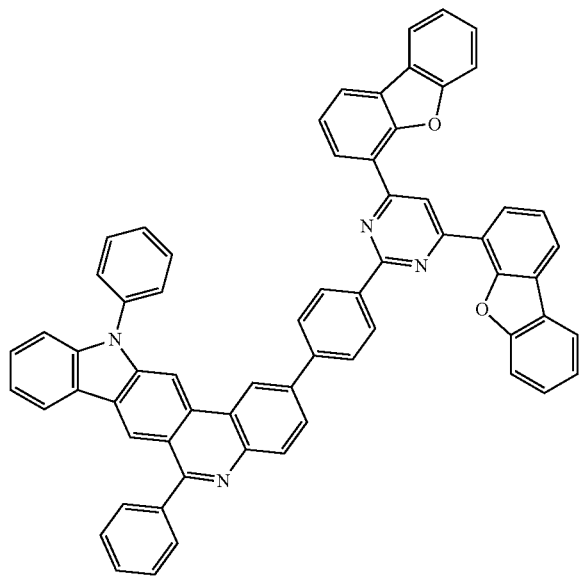
5-20
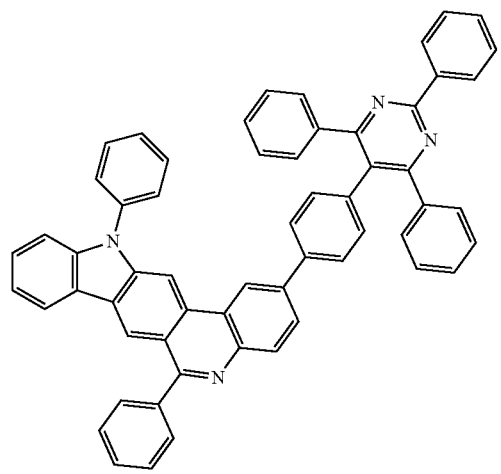
5-21
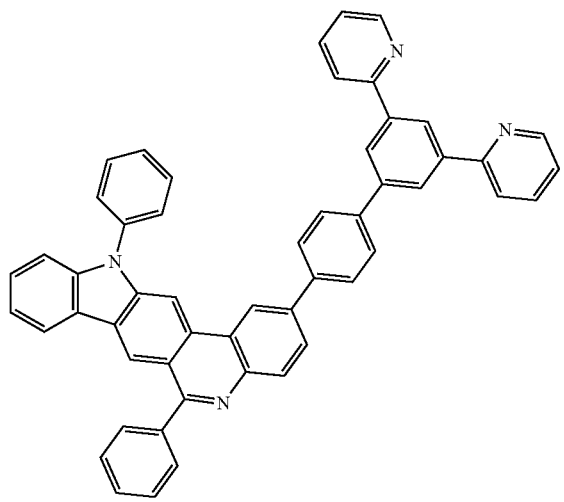
5-22
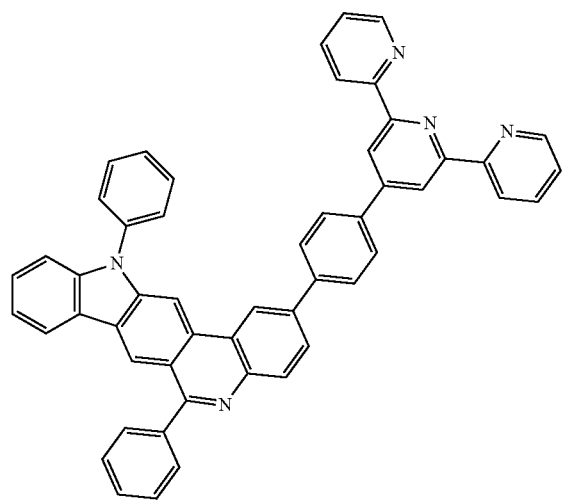
5-23
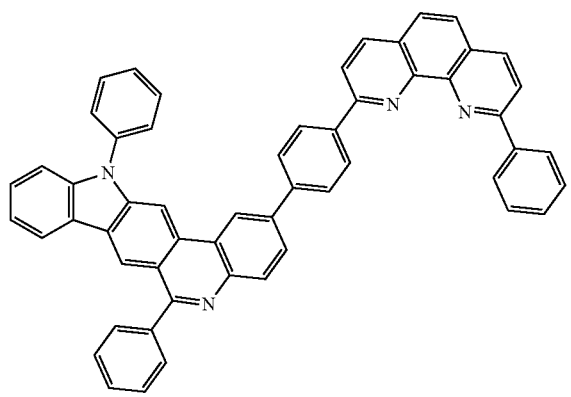

-continued
5-24
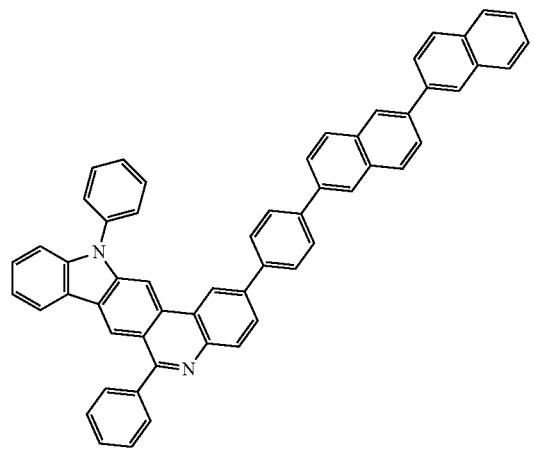
5-25
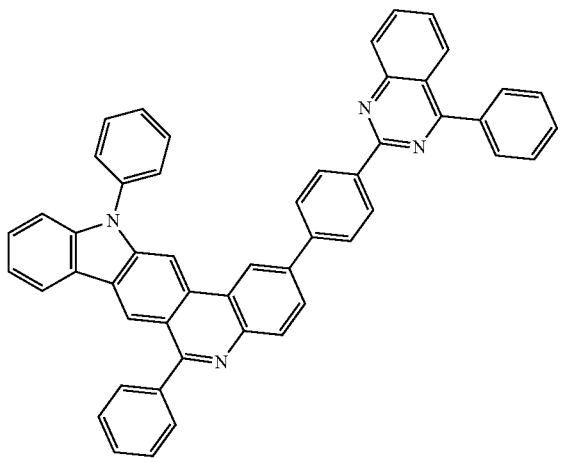
5-26
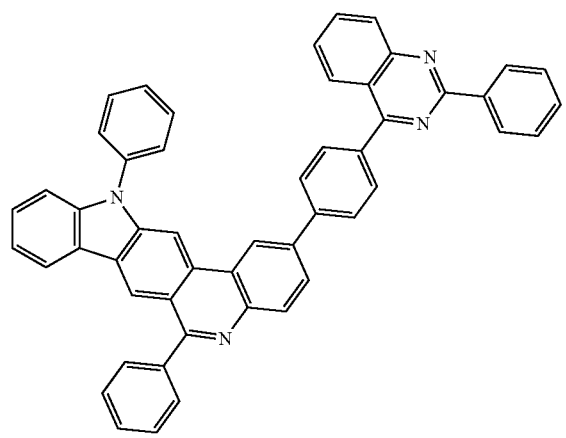
5-27
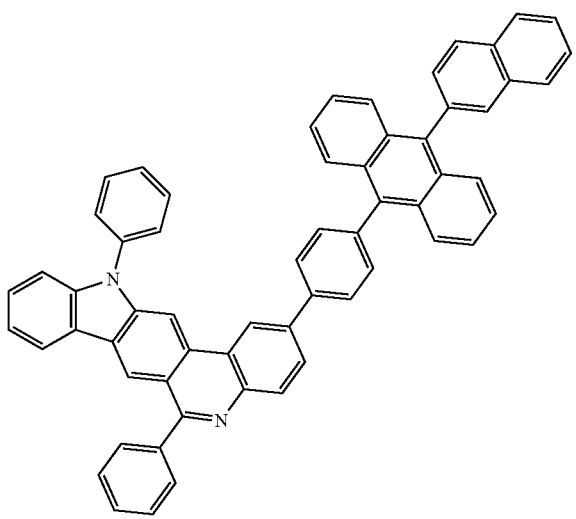
5-28
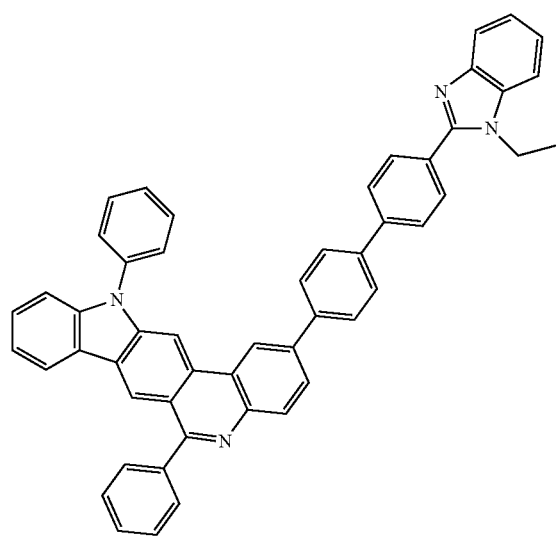
5-29
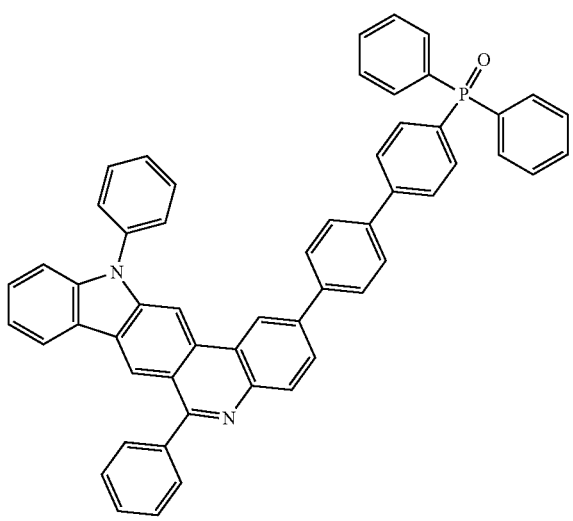

5-30
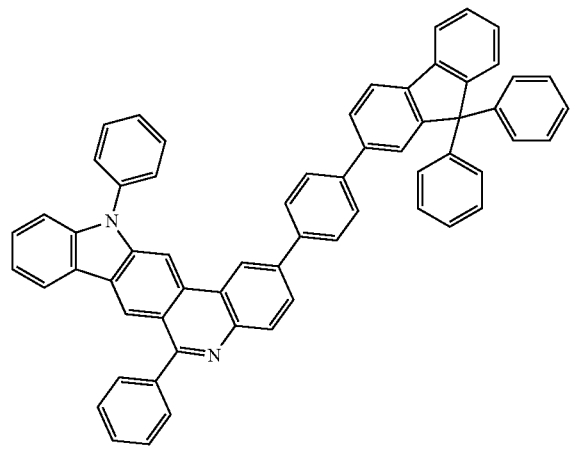
5-31
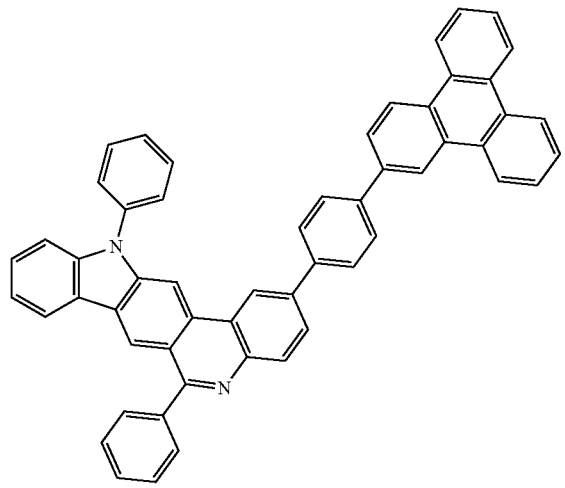
5-32
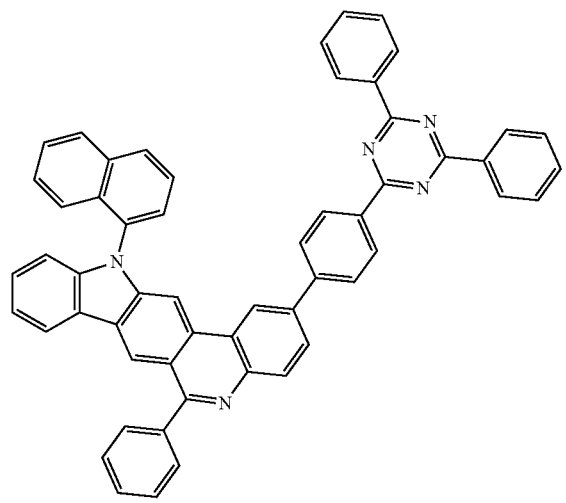
5-33
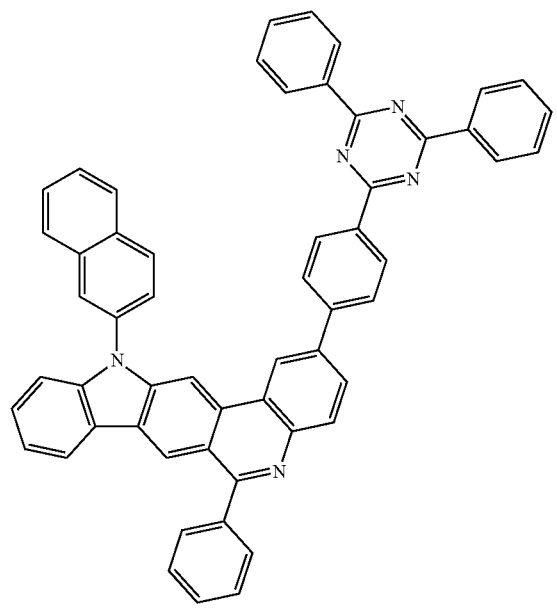

5-34
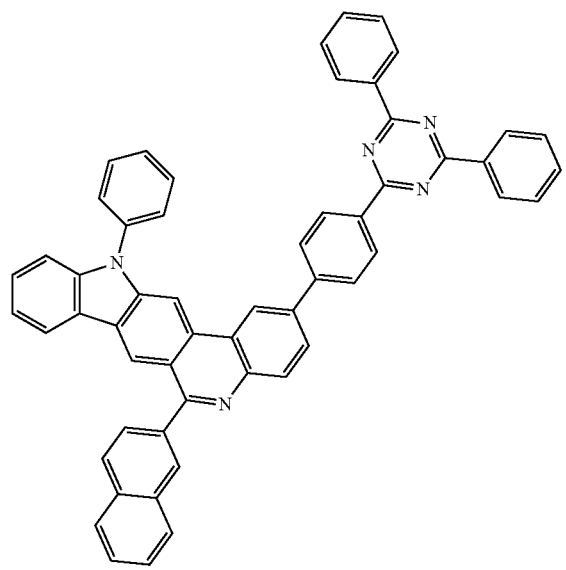
5-35
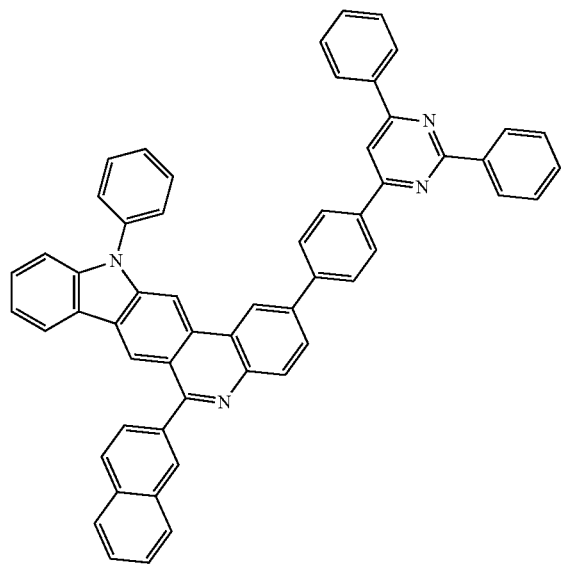
6
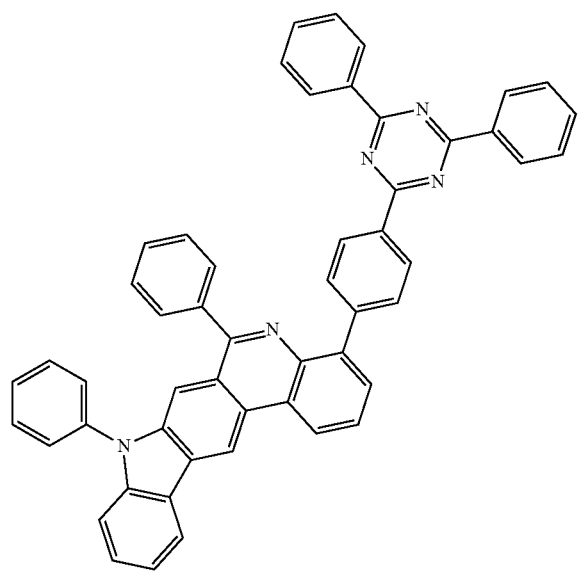
6-1
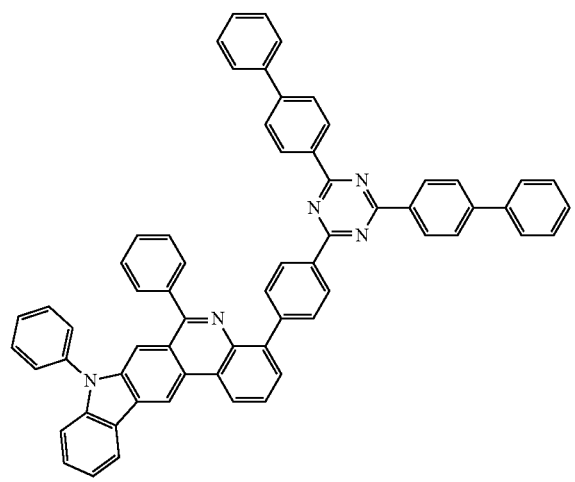

-continued
6-2
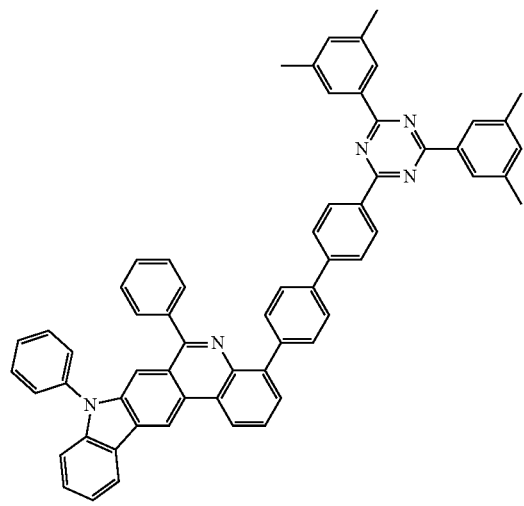
6-3
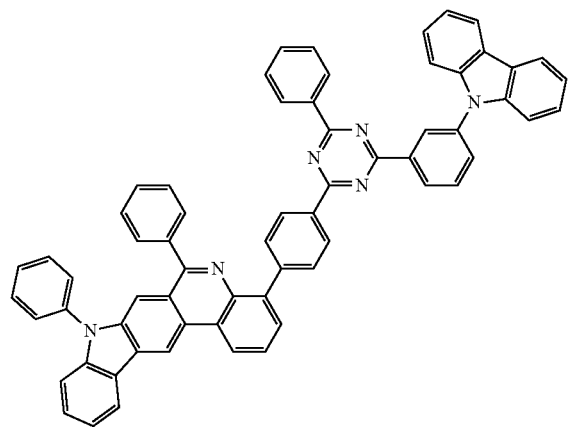
6-4
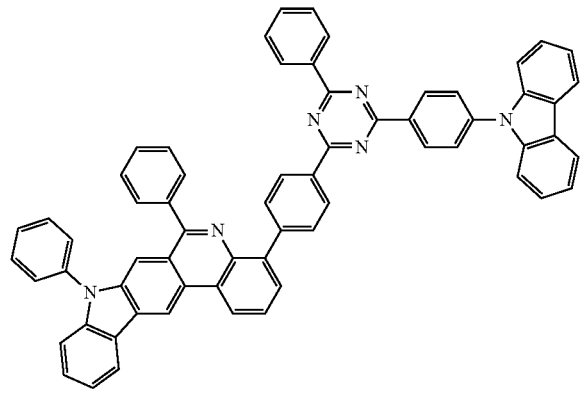
6-5
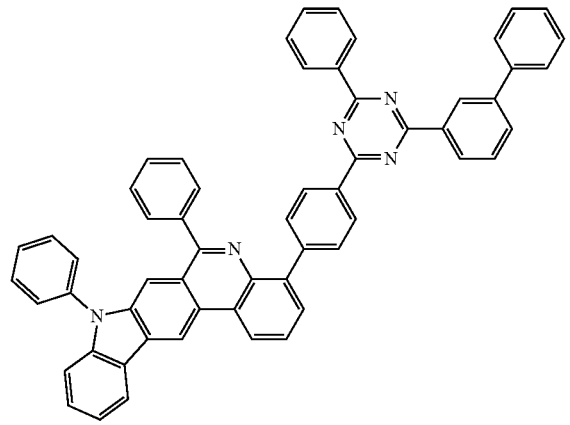
6-6
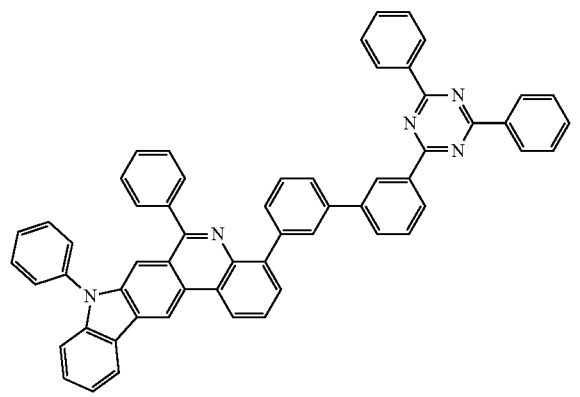
6-7
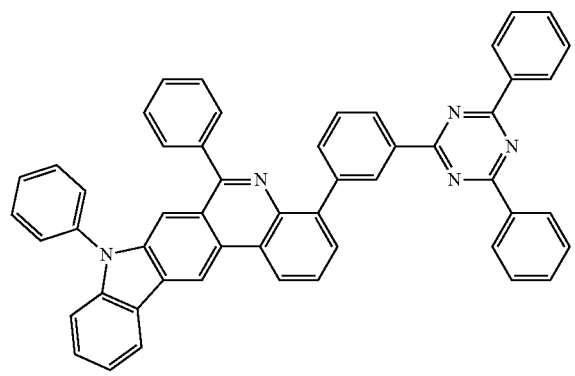

6-8
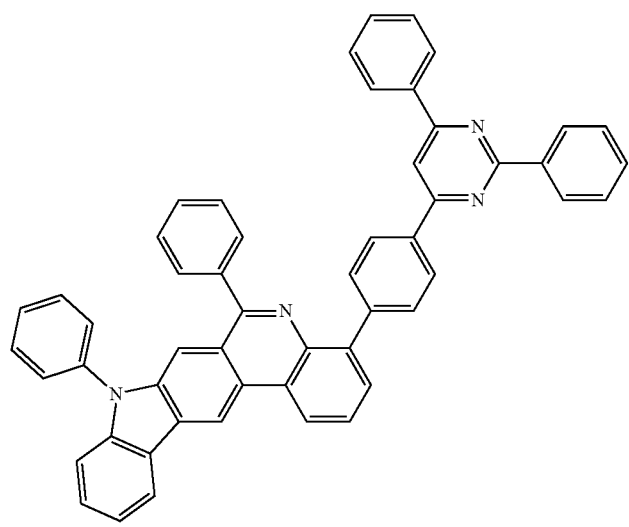
6-9
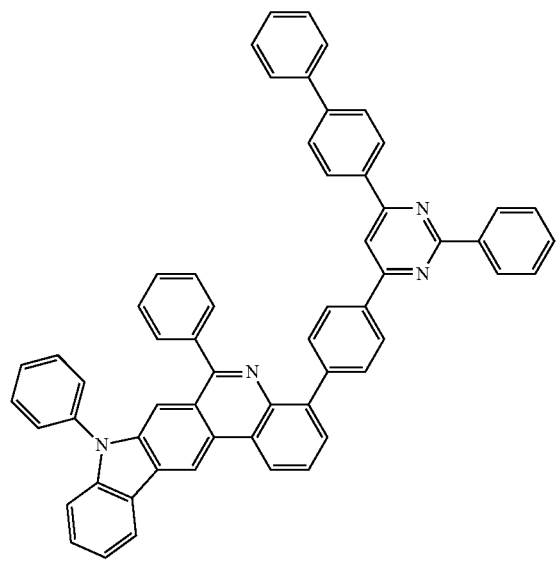
6-10
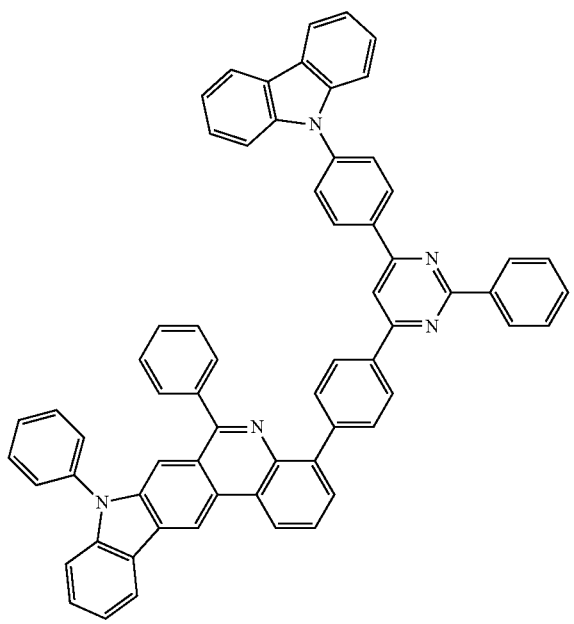

-continued
6-11
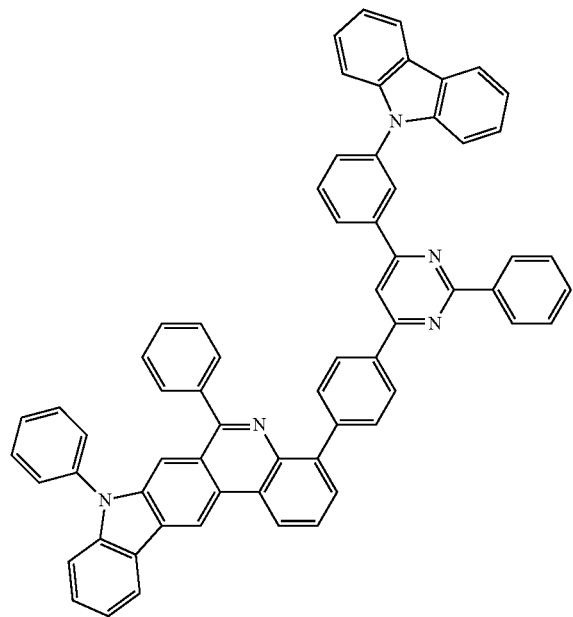
6-12
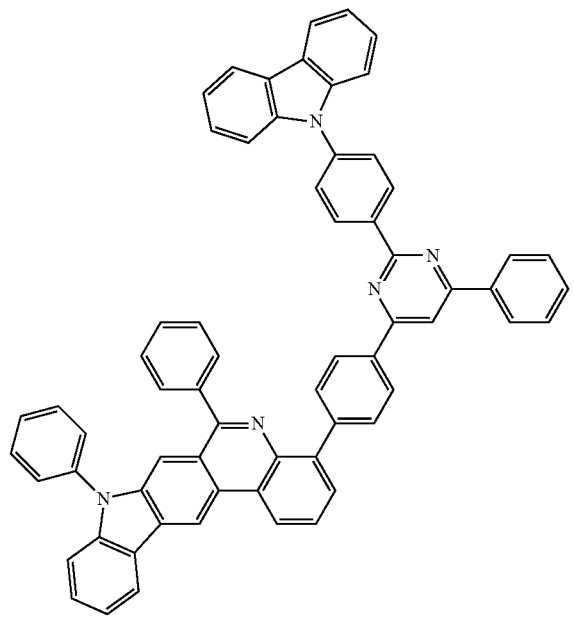
6-13
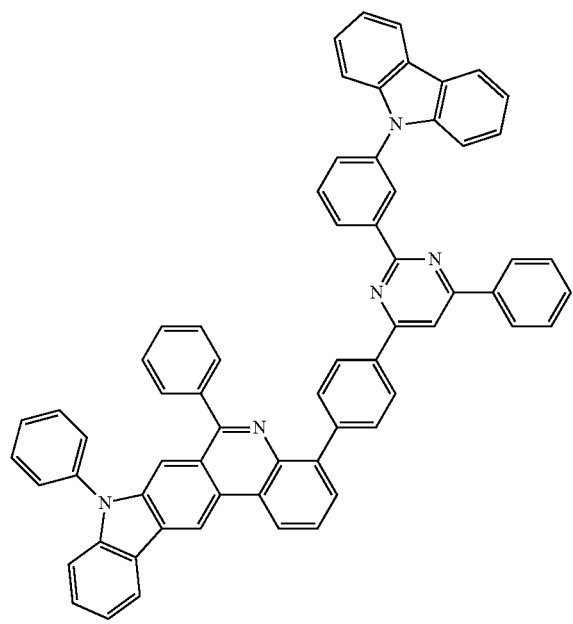
6-14
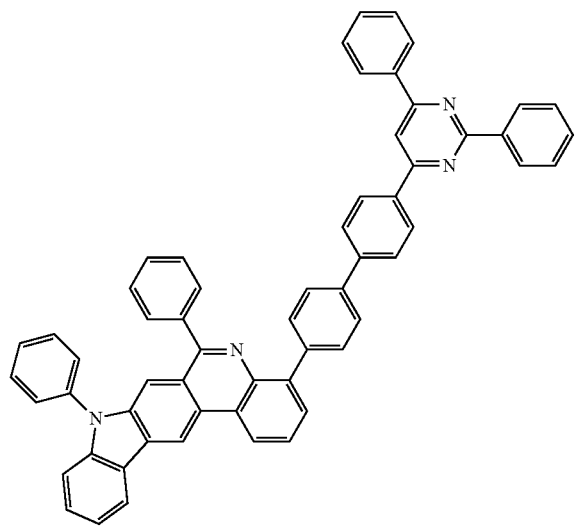

6-15
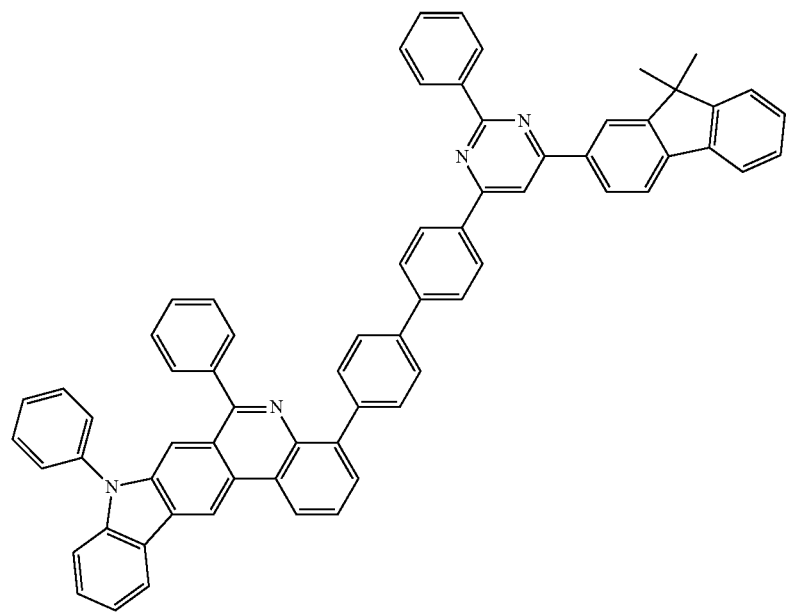
6-16
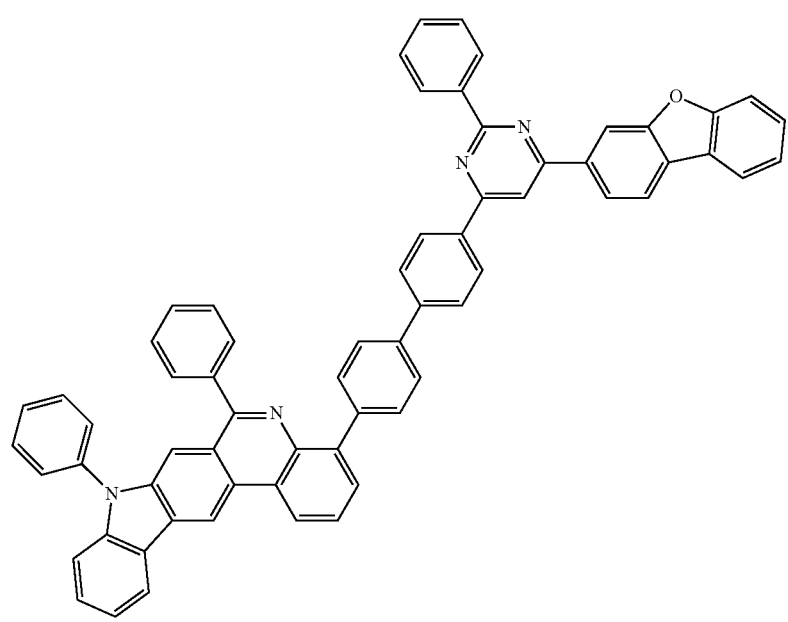

-continued
6-17
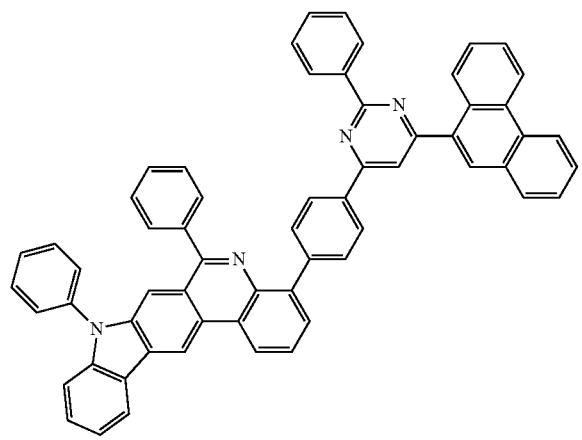
6-18
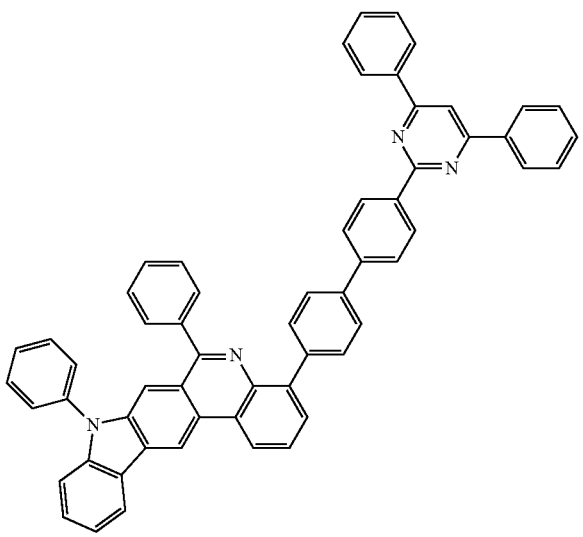
6-19
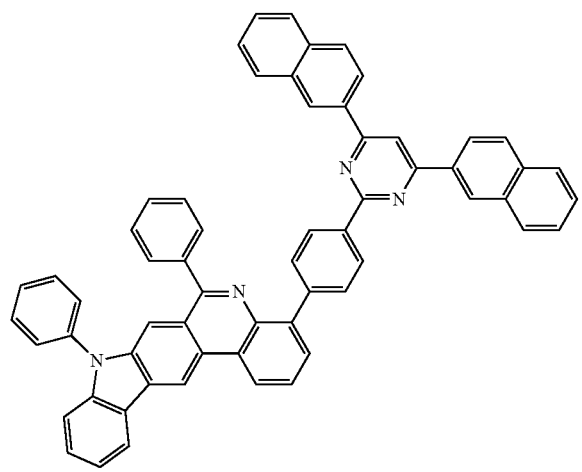
6-20
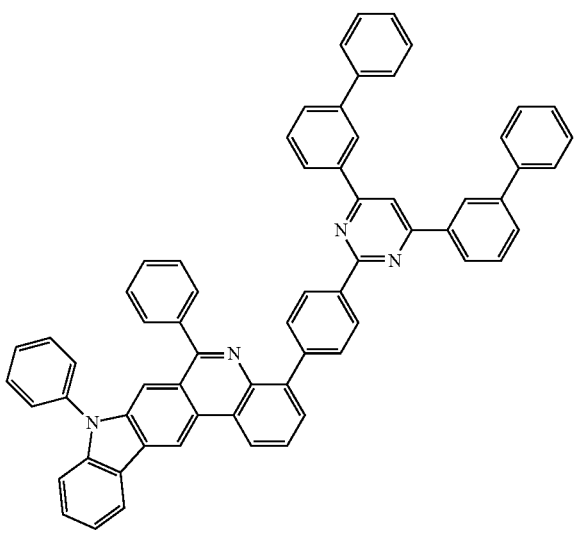
6-21
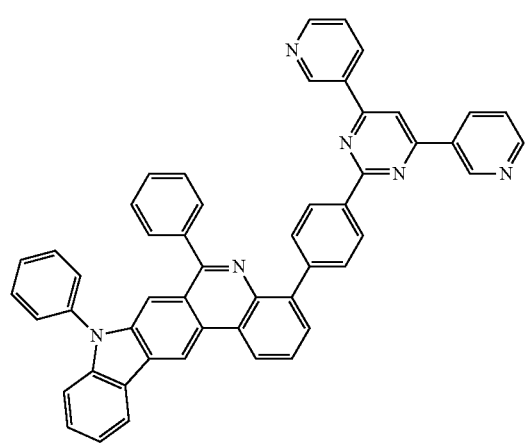
6-22
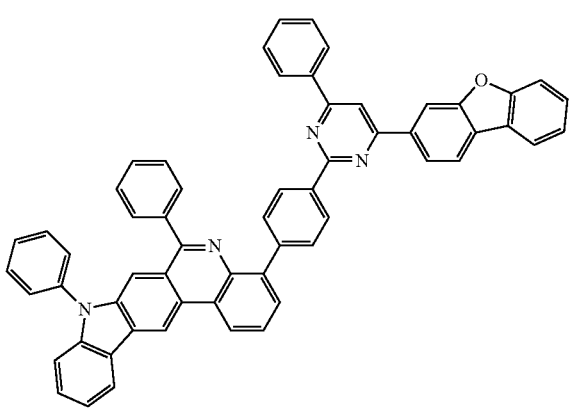

-continued
6-23
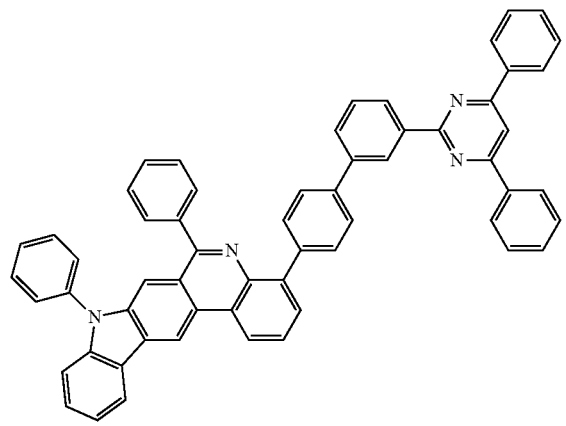
6-24
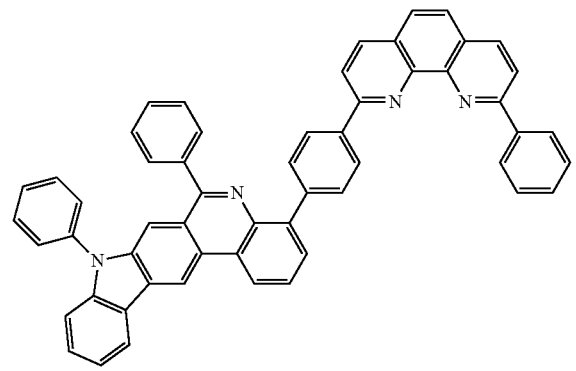
6-25
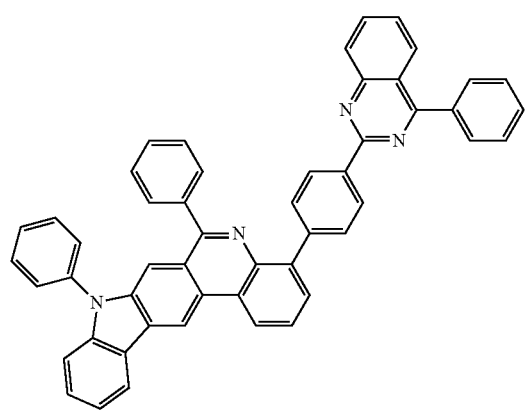
6-26
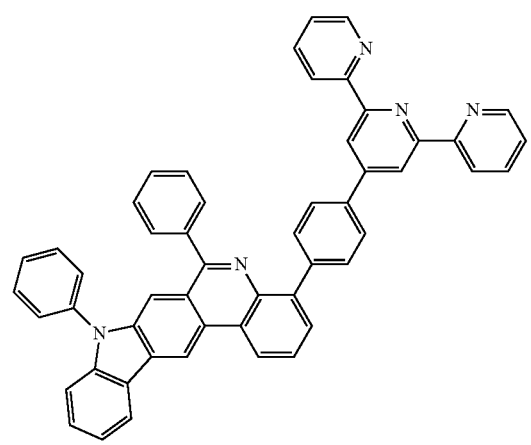
6-27
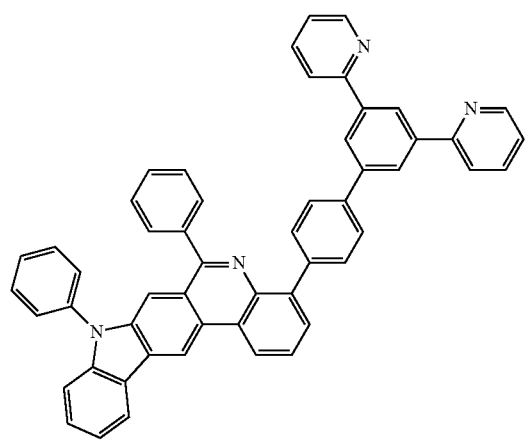
6-28
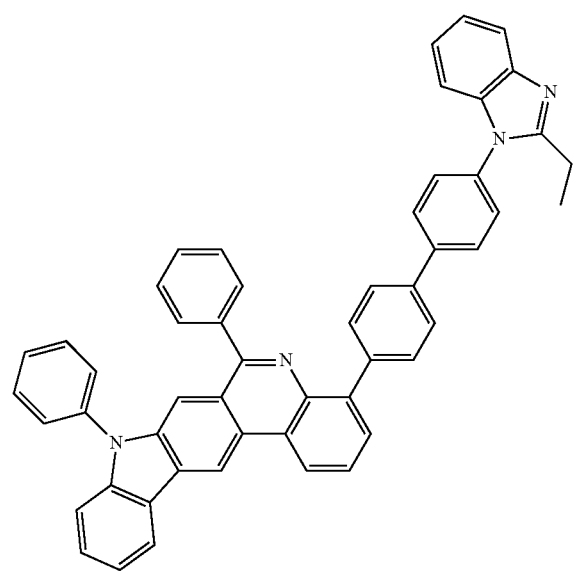

6-29
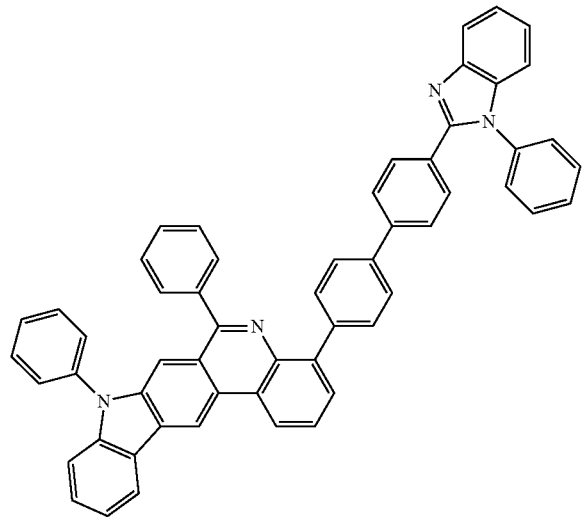
6-30
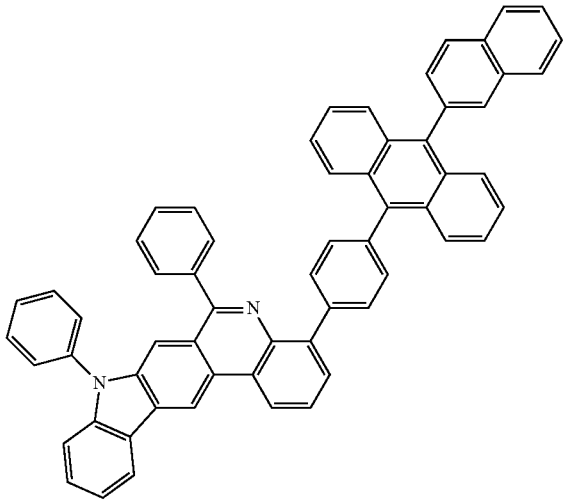
6-31
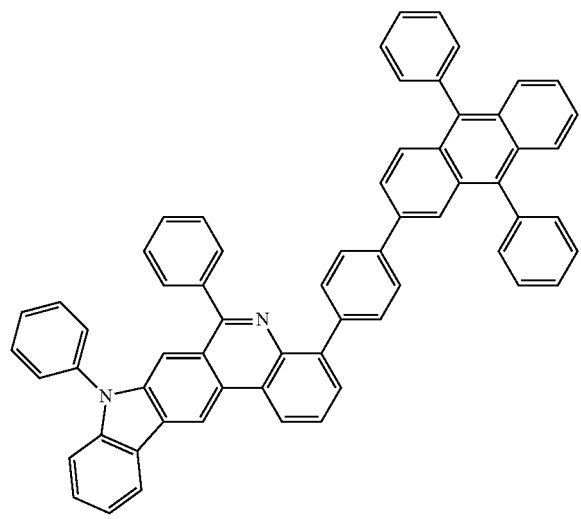
6-32
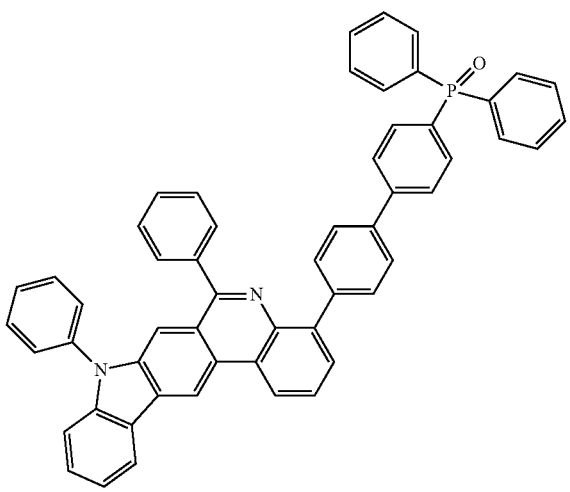

-continued
673
6-33
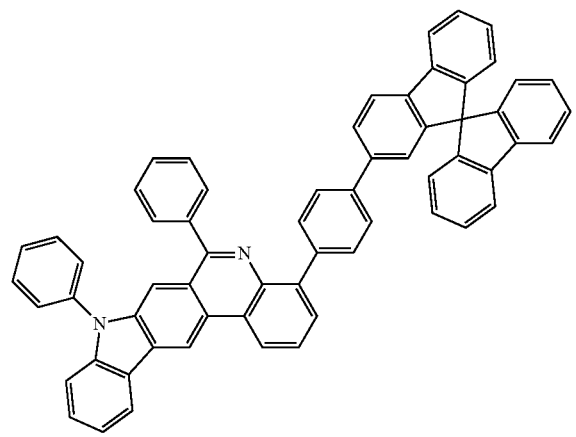
674
7
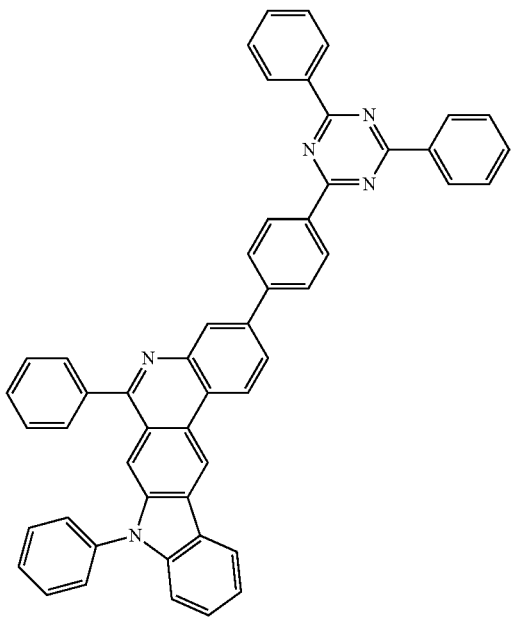
7-1
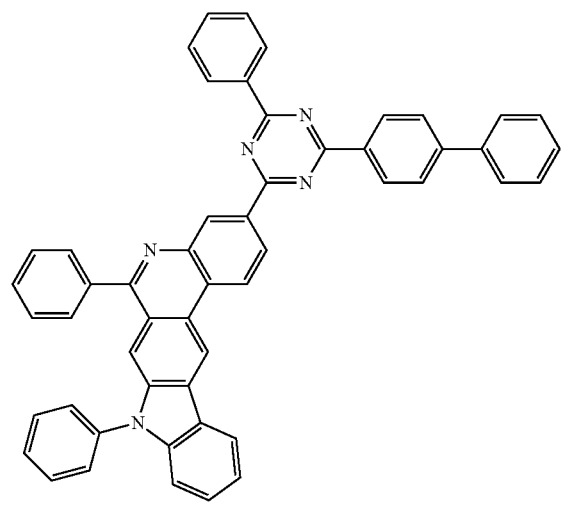
7-2
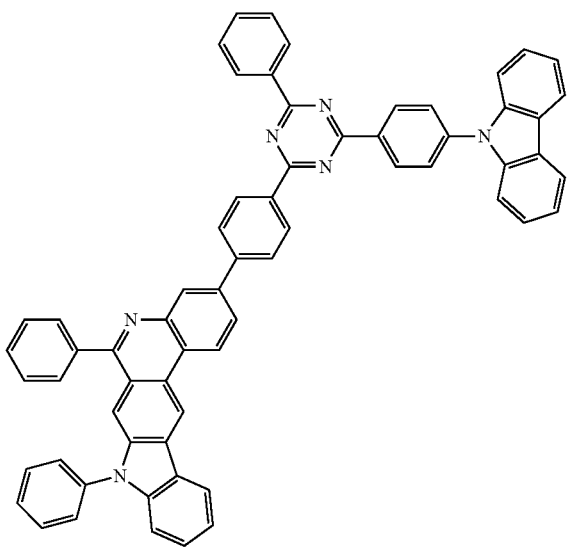

-continued
675
7-3
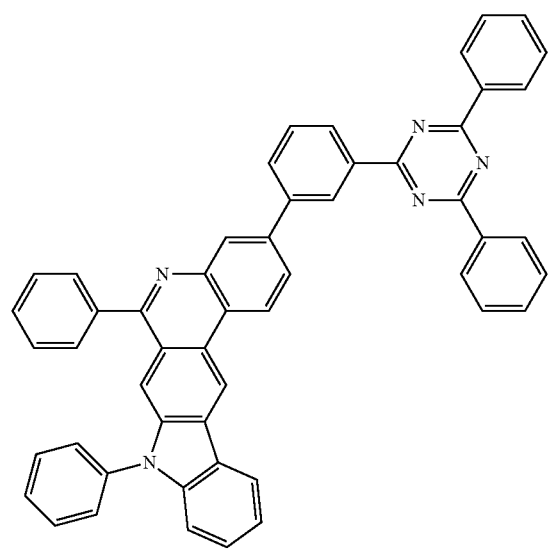
676
7-4
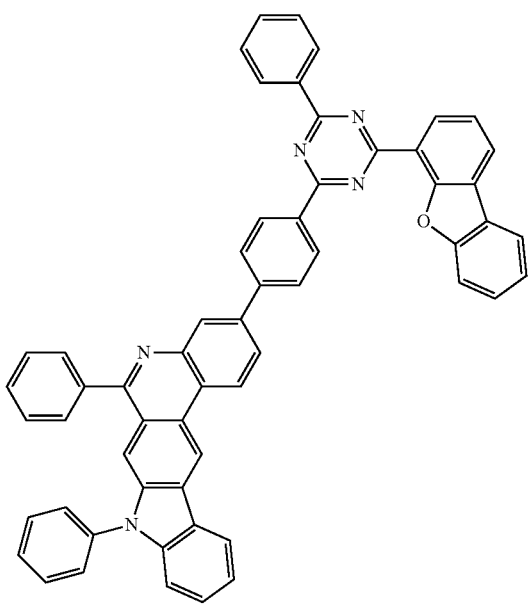
7-5
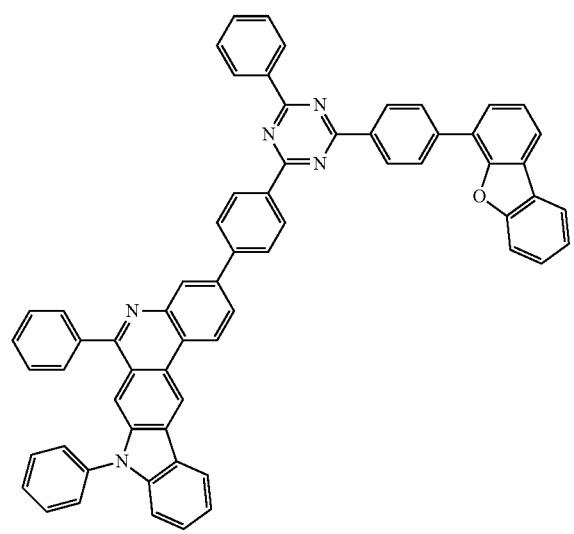
7-6
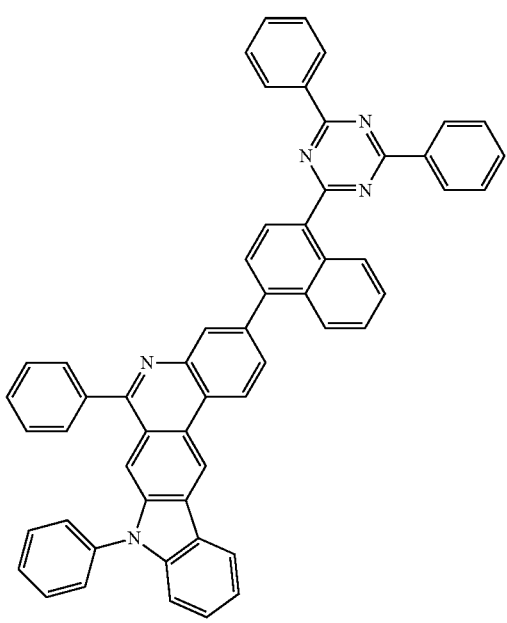

677 678
-continued
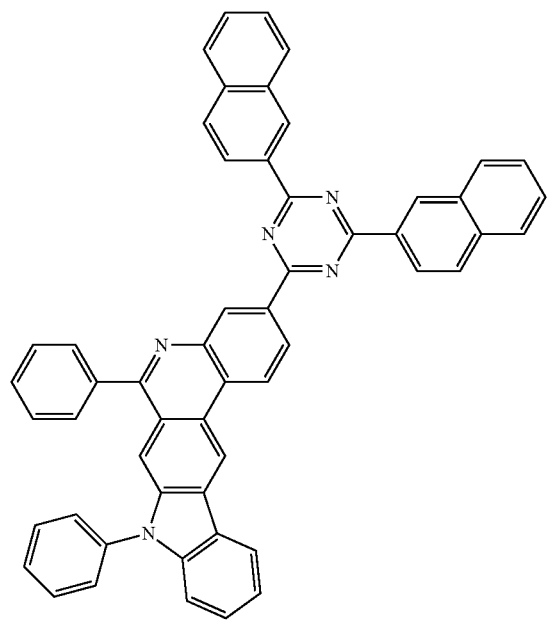
7-7
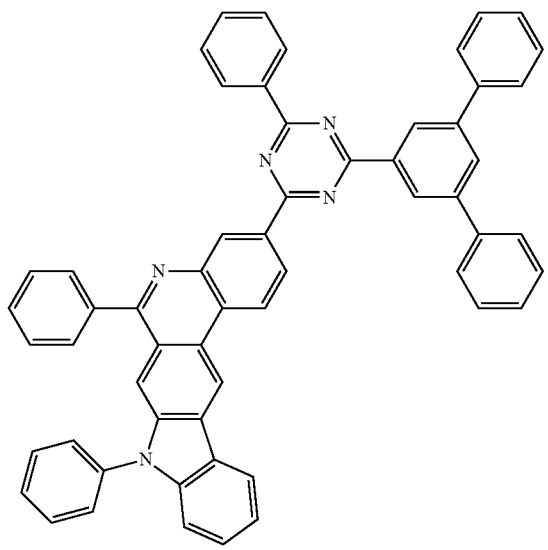
7-8
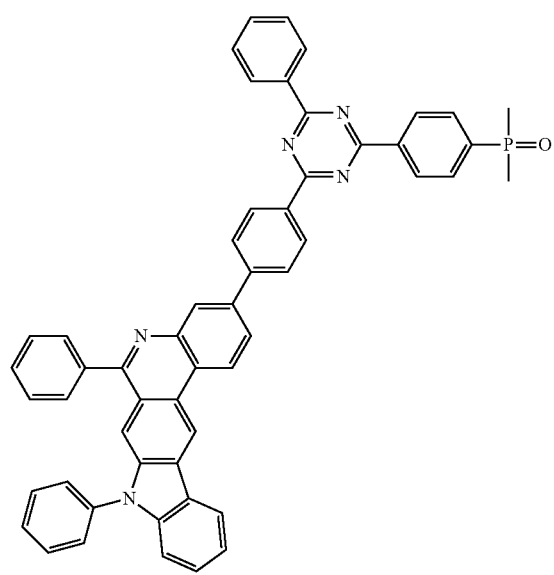
7-9
7-10

-continued
7-11
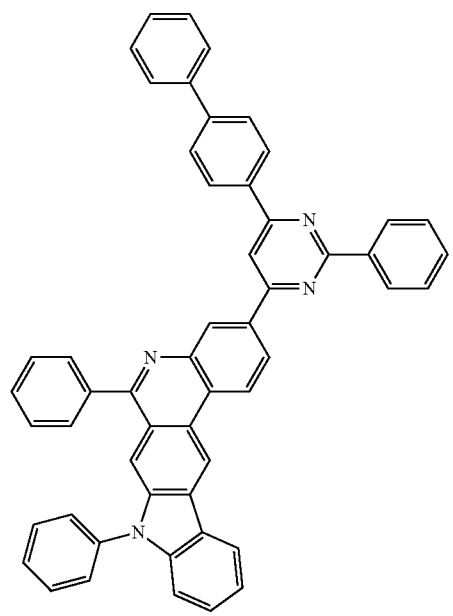
7-12
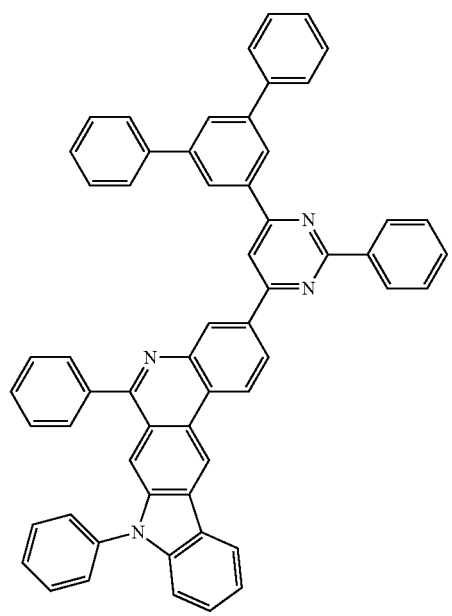
7-13
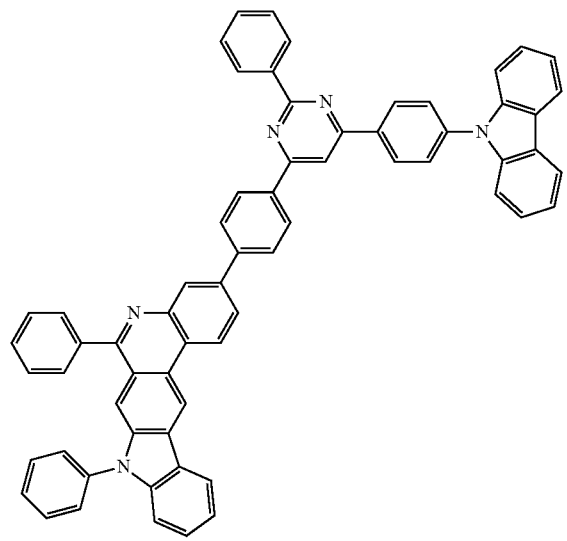
7-14
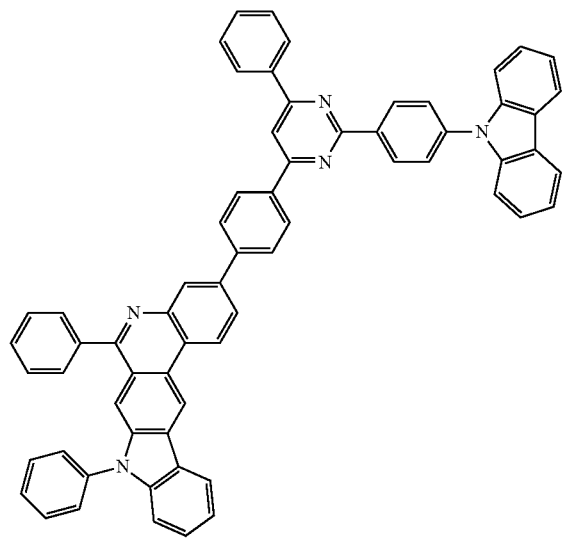

-continued
7-15
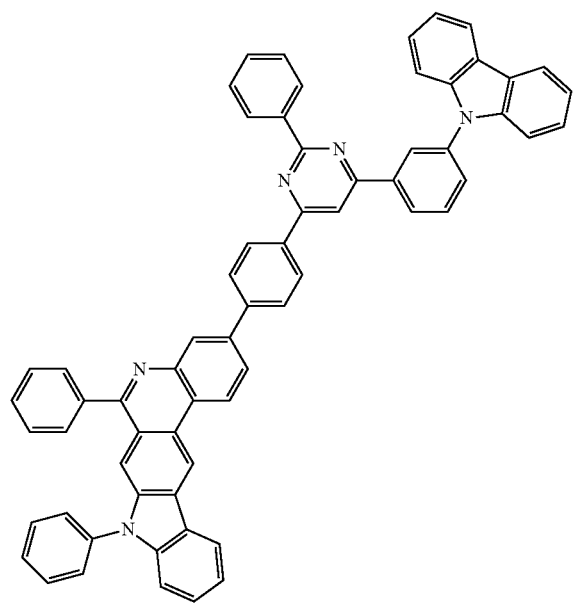
7-16
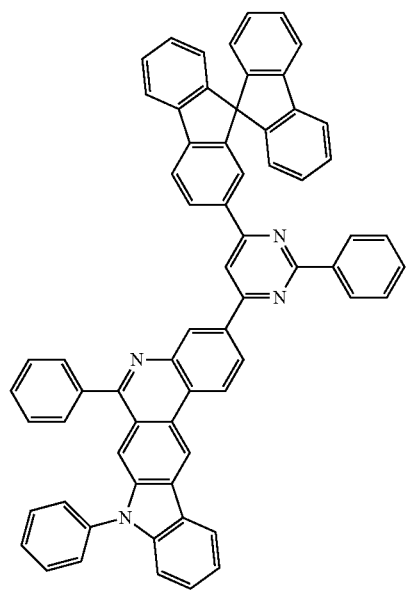
7-17
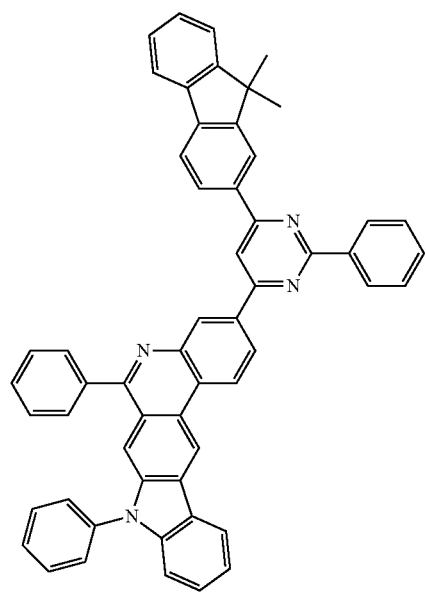
7-18
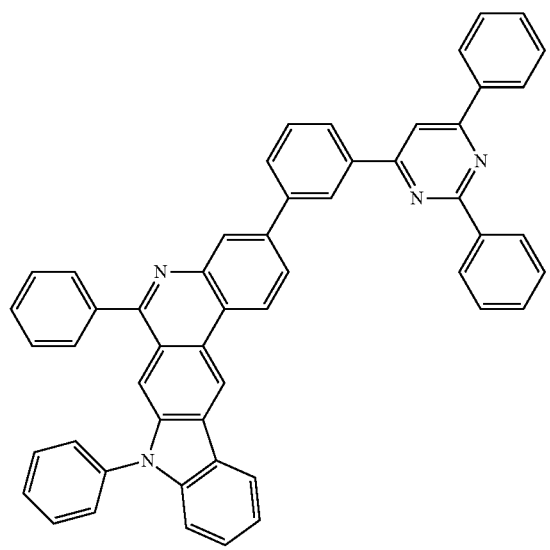

-continued
7-19
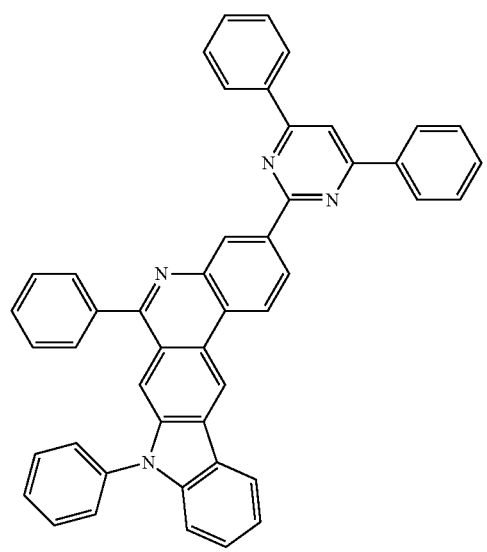
7-20
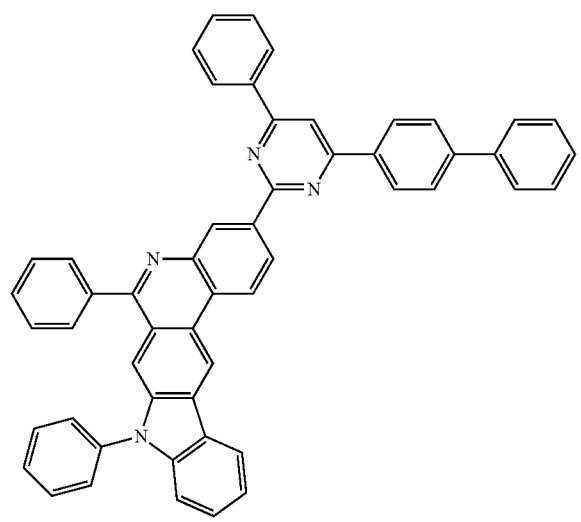
7-21
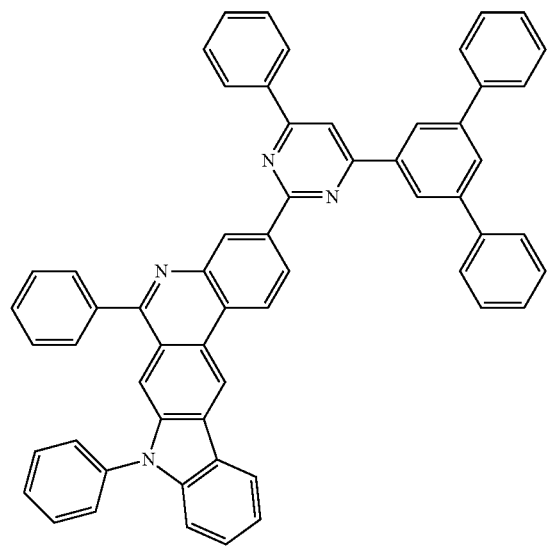
7-22
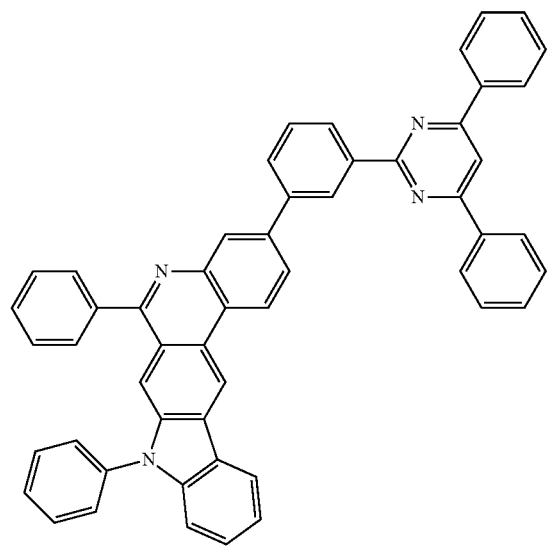

685
686
7-23
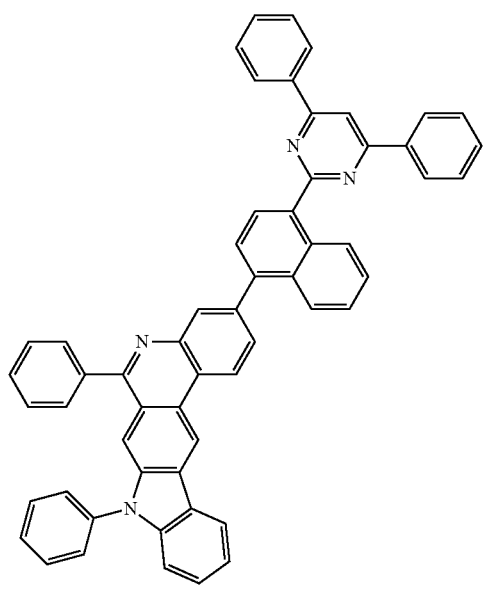
7-24
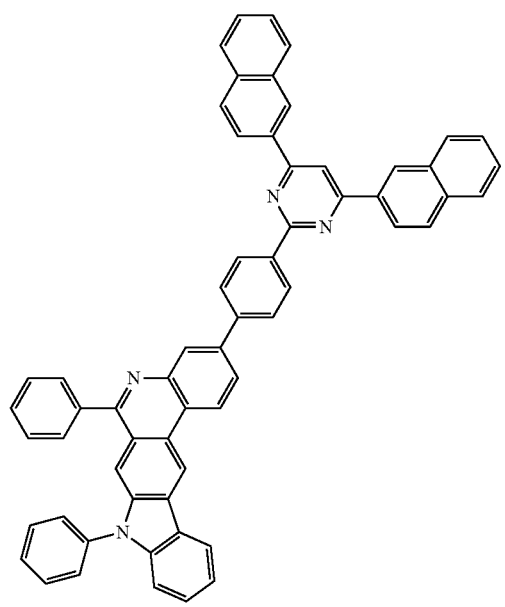
7-25
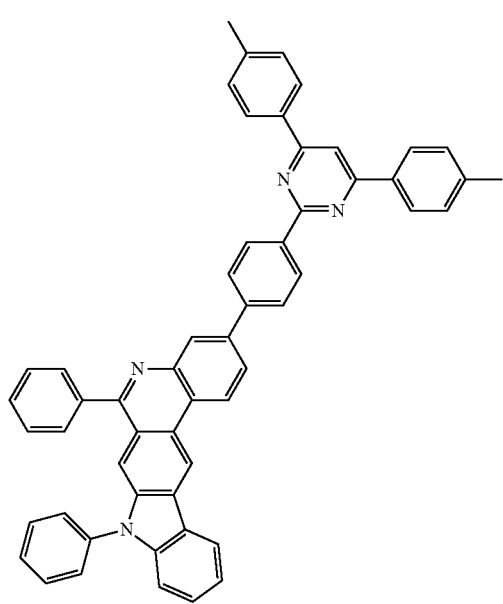
7-26
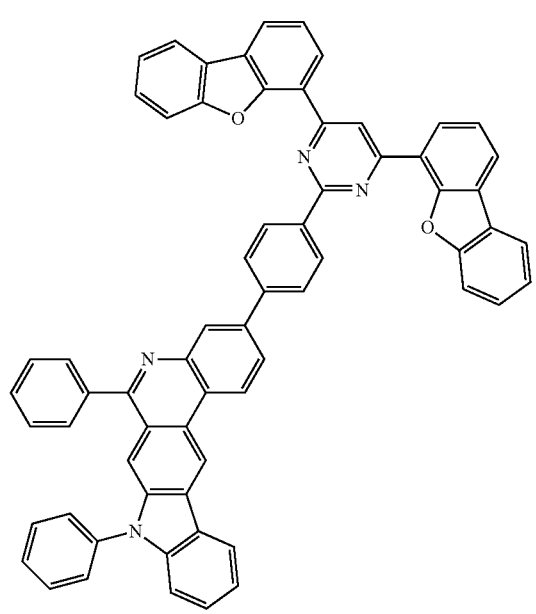

-continued
7-27
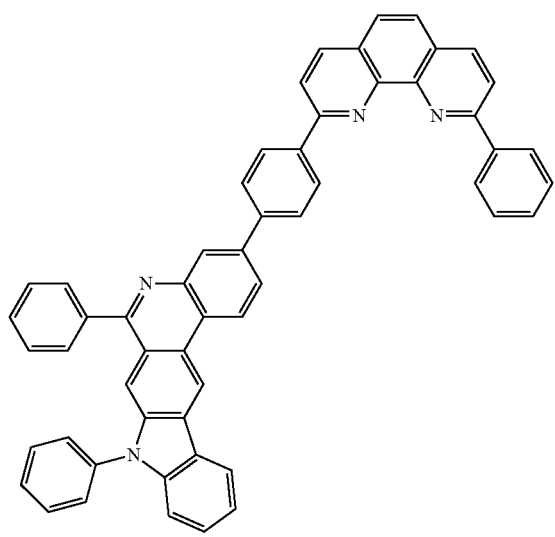
7-28
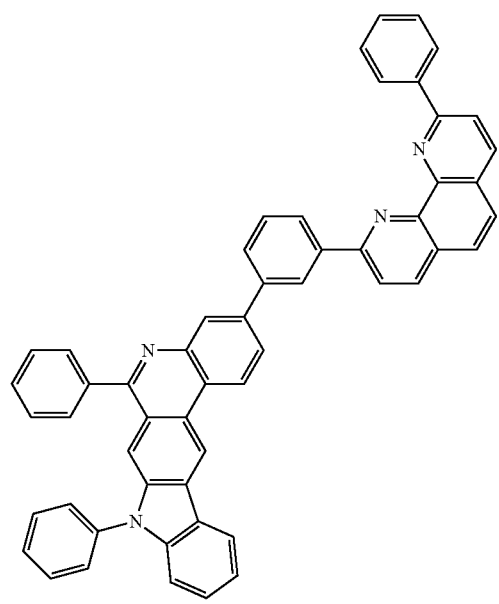
7-29
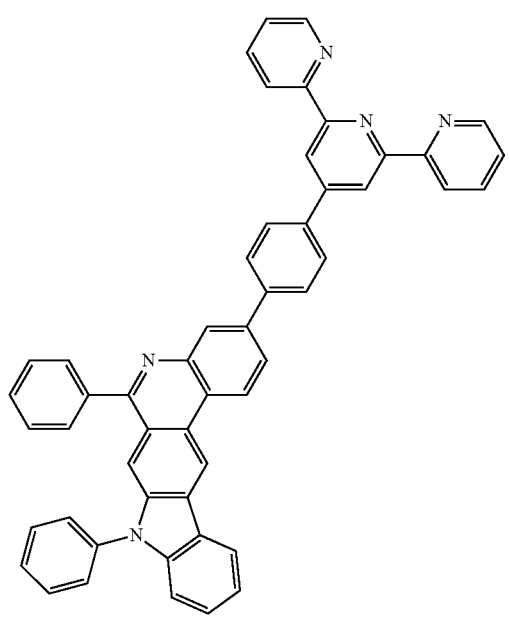
7-30
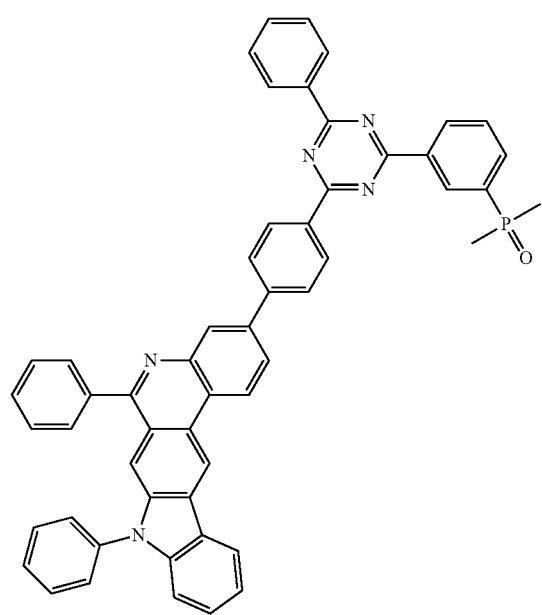

-continued
689
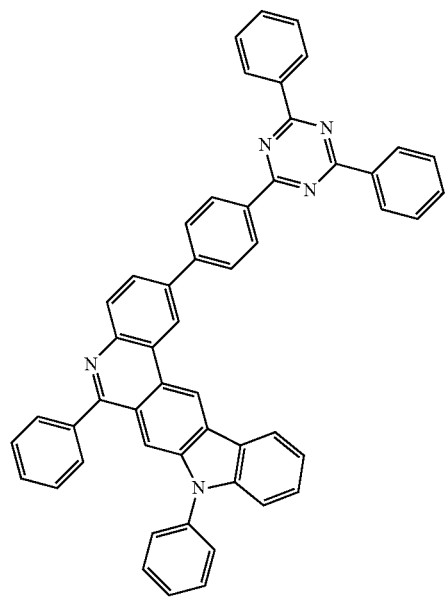
690
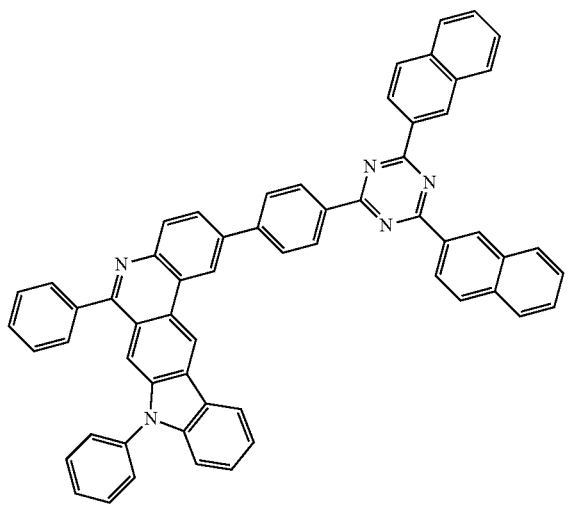
8
8-1
8-2
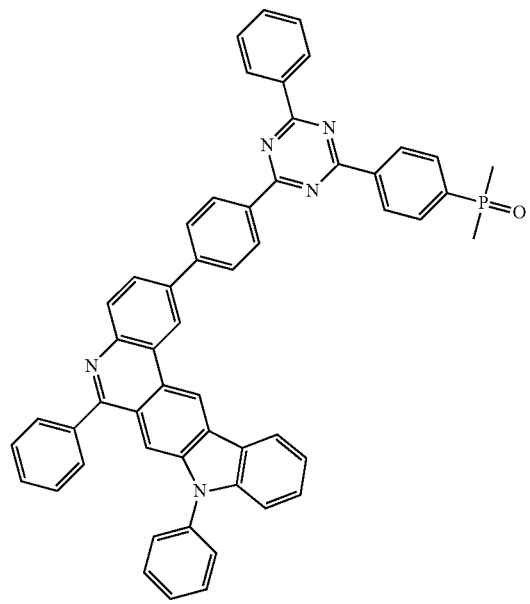
8-3
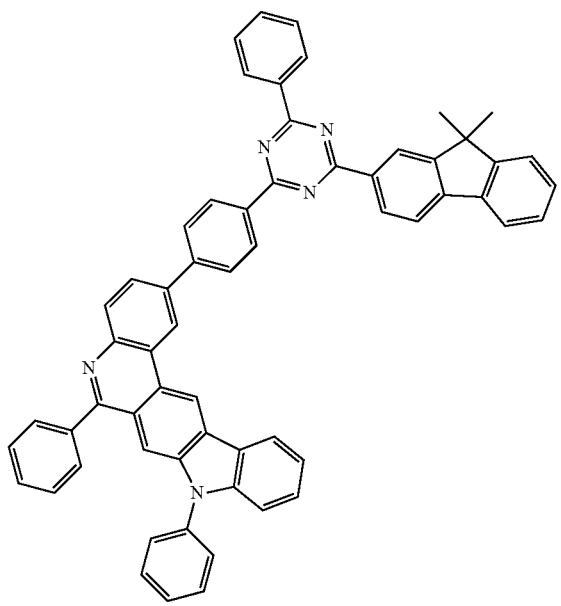

-continued
691
8-4
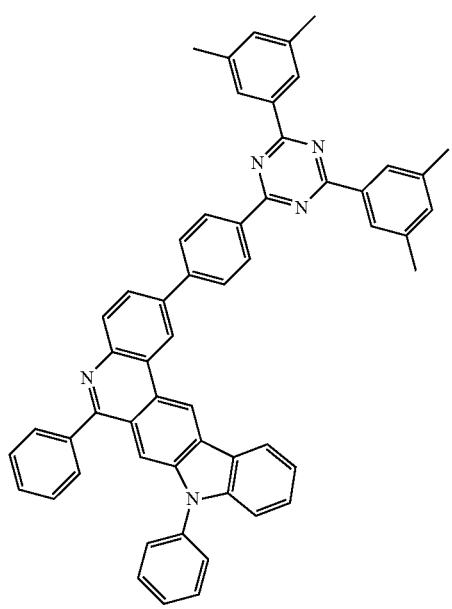
692
8-5
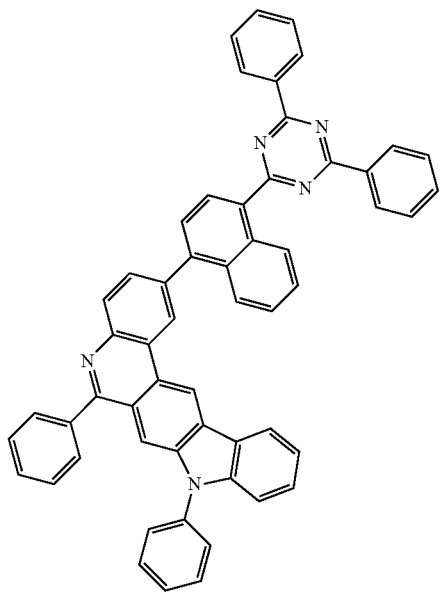
8-6
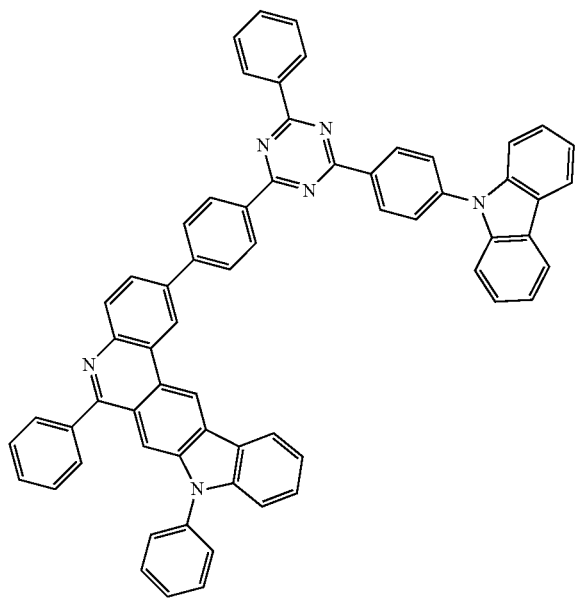
8-7
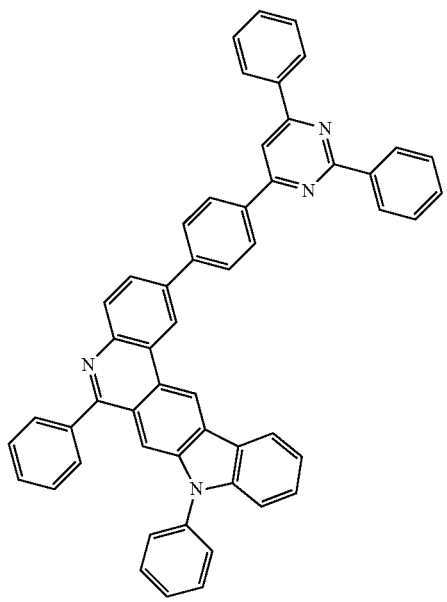

8-8
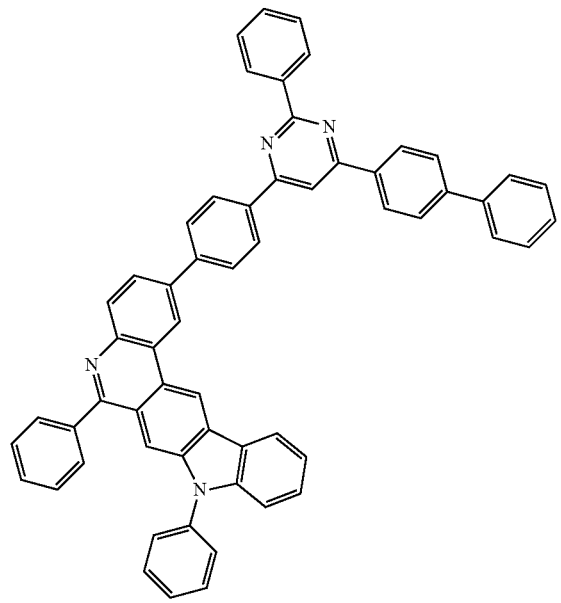
8-9
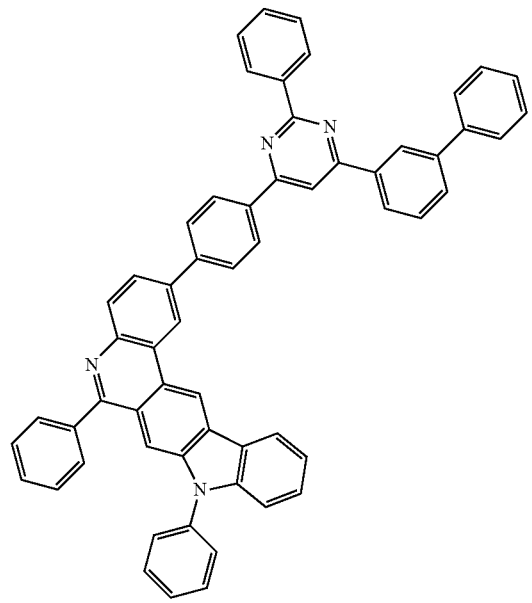
8-10
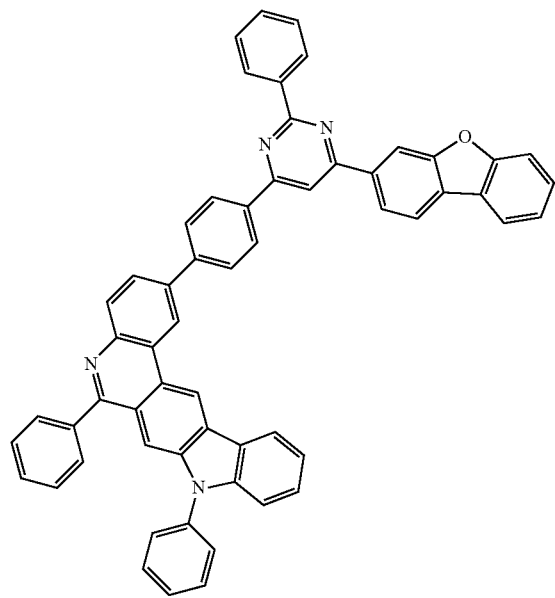
8-11
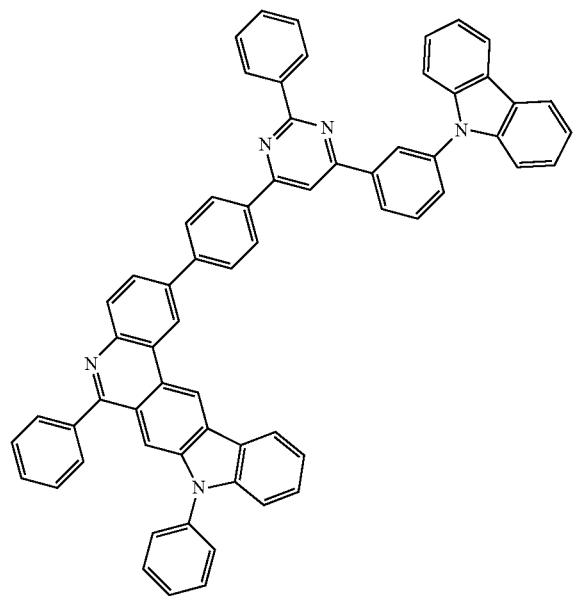

8-12
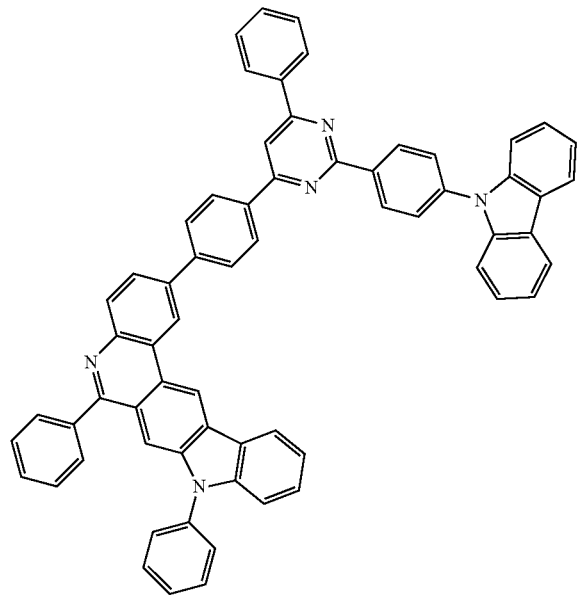
8-13
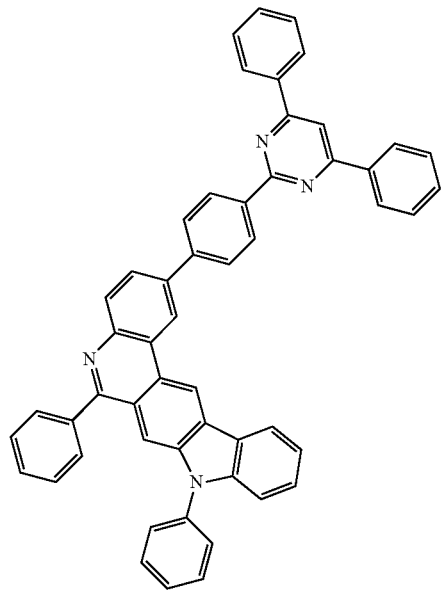
8-14
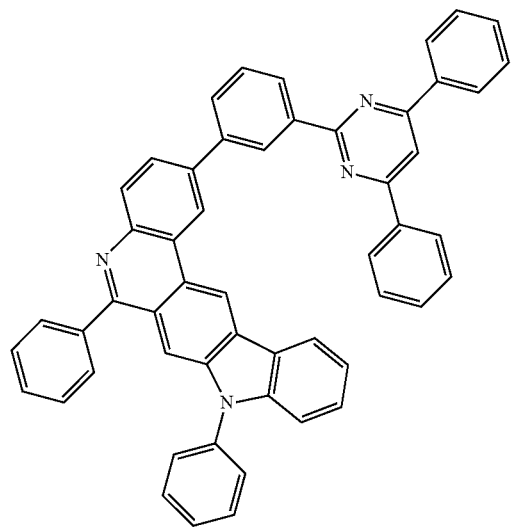
8-15
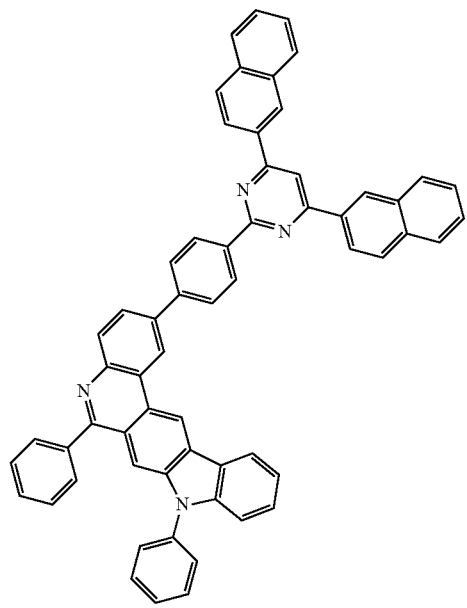

-continued
697
8-16
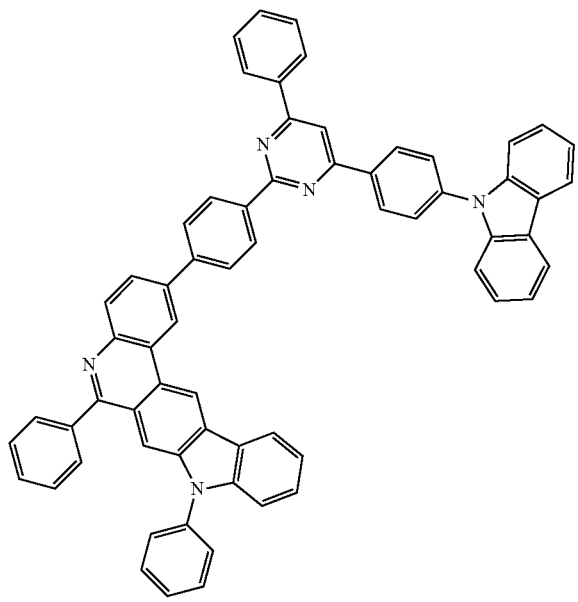
698
8-17
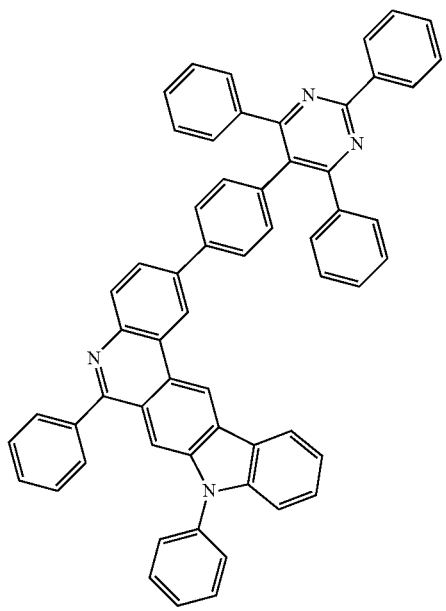
8-18
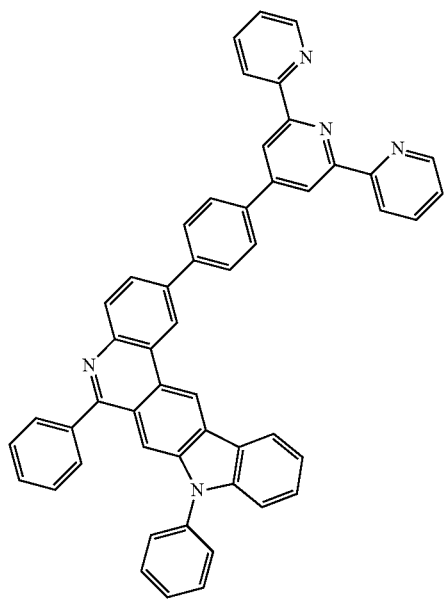
8-19
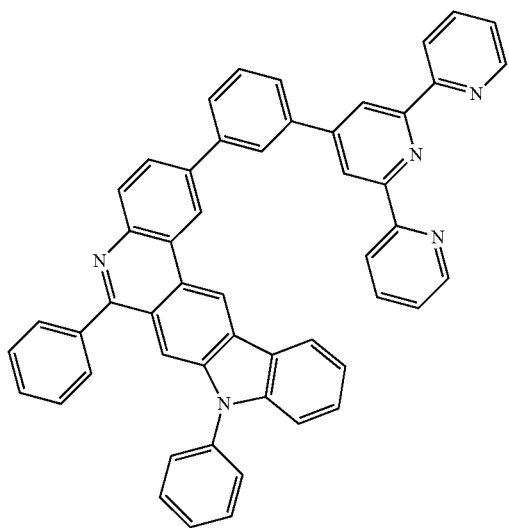

-continued
699
8-20
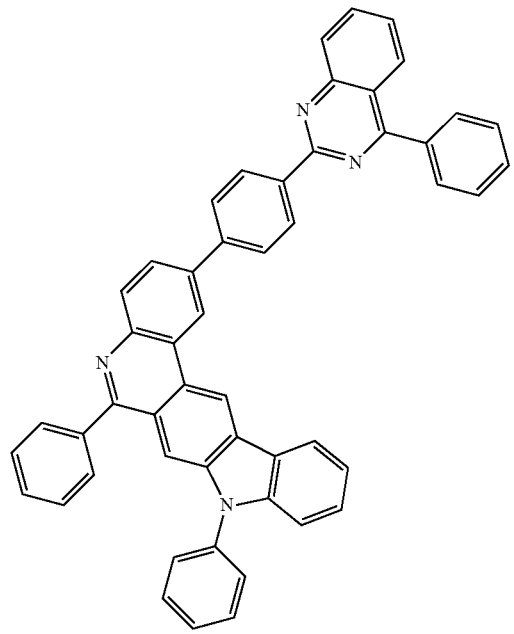
700
8-21
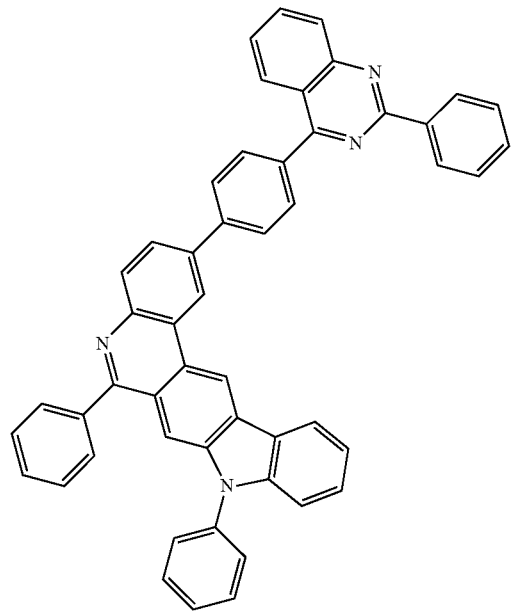
8-22
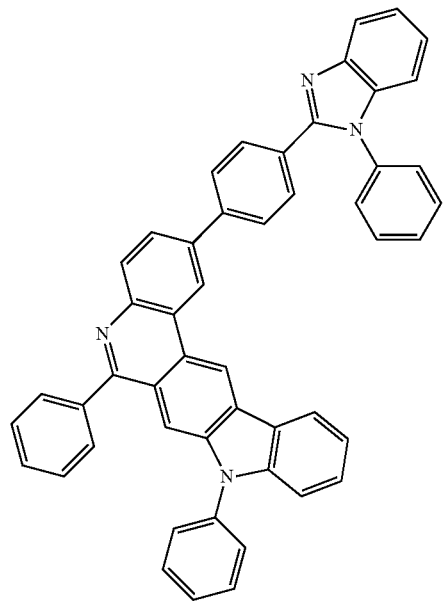
8-23
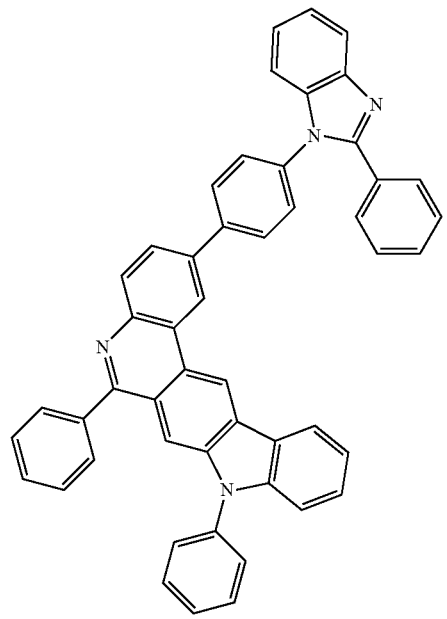

-continued
701
8-24
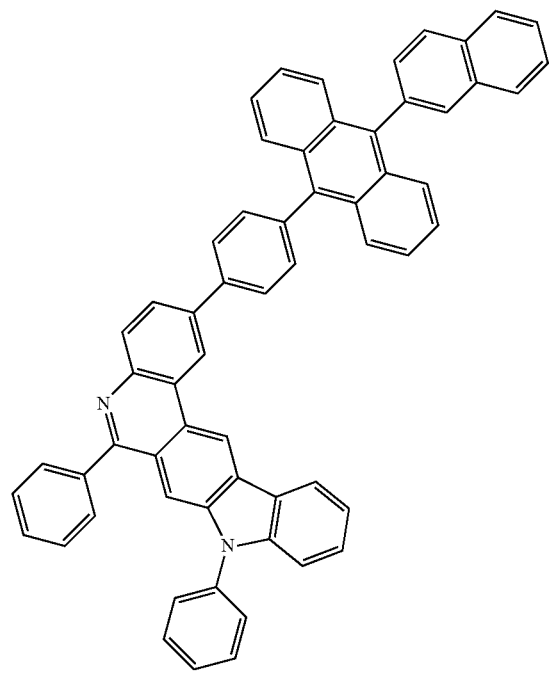
702
8-25
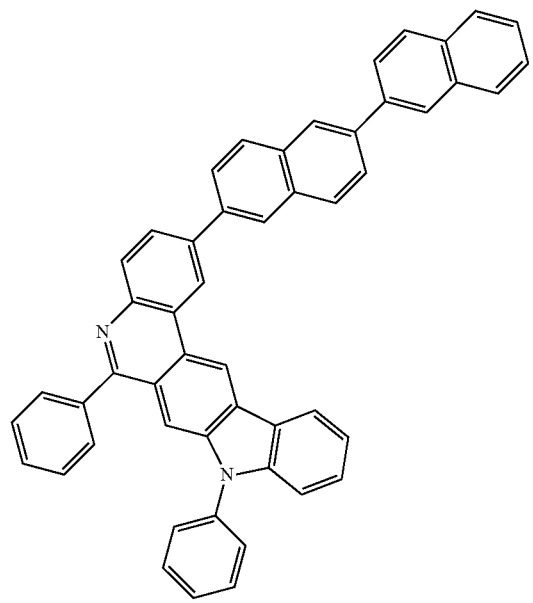
8-26
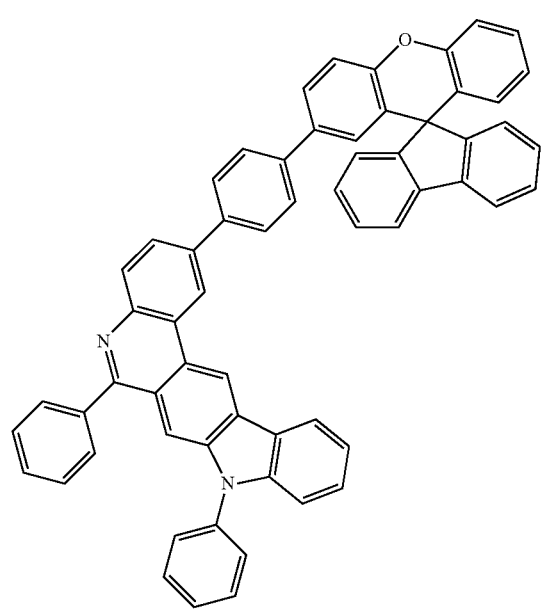
8-27
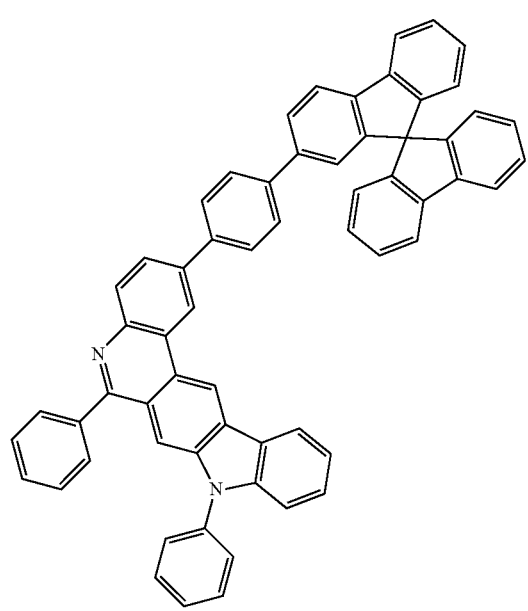

703
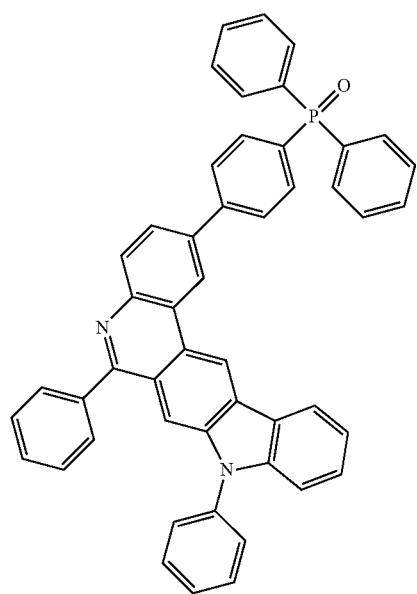
8-28
704
-continued
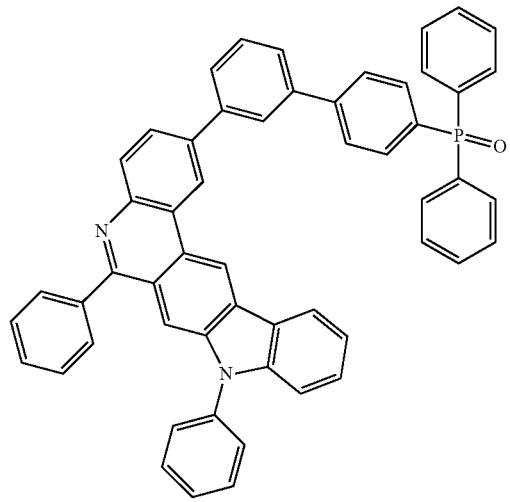
8-29
8-30
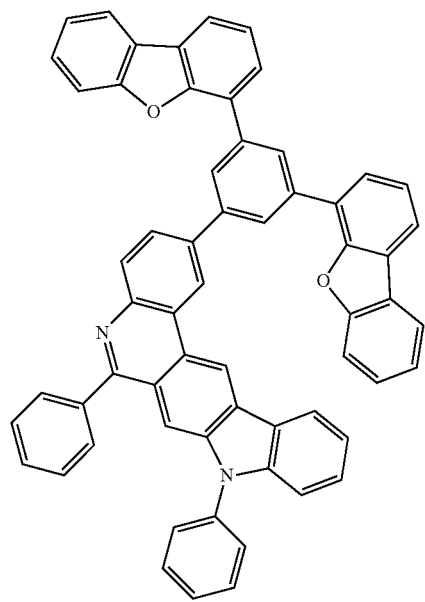
8-31
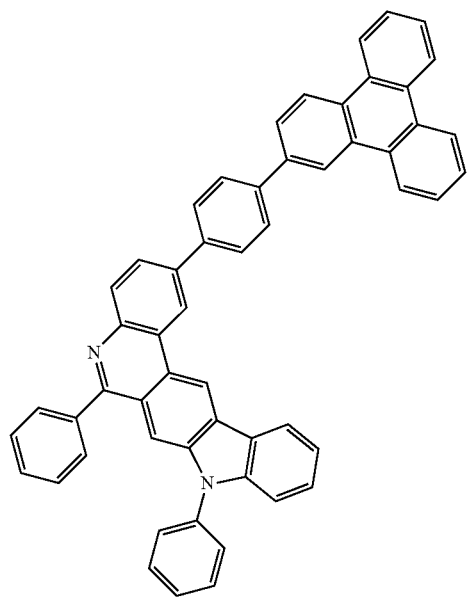

705
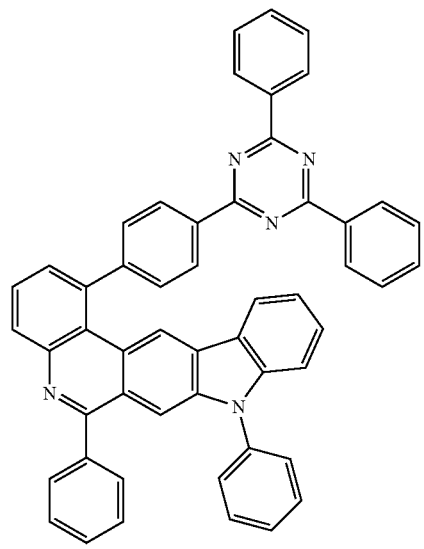
706
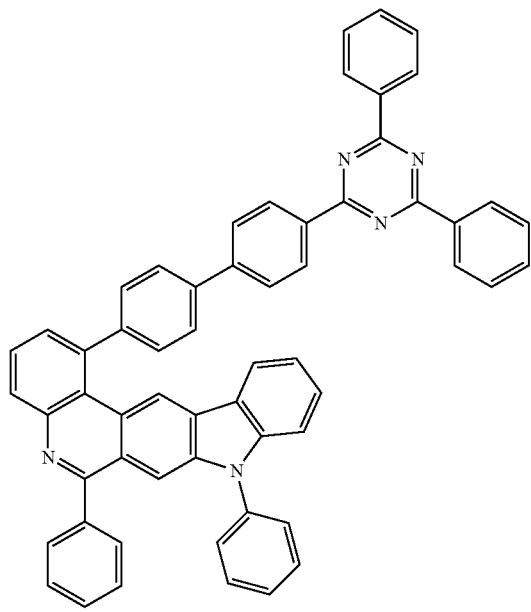
-continued
9
9-1
9-2
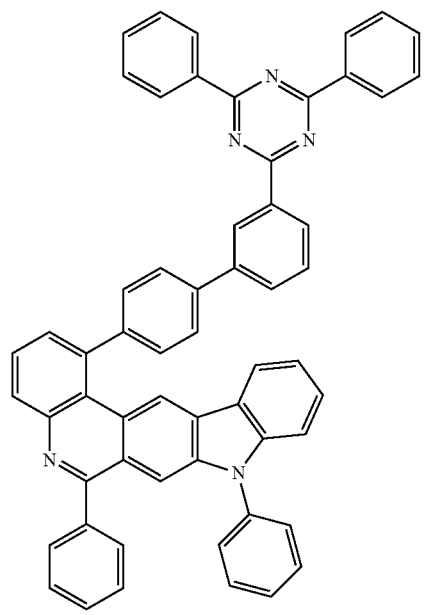
9-3
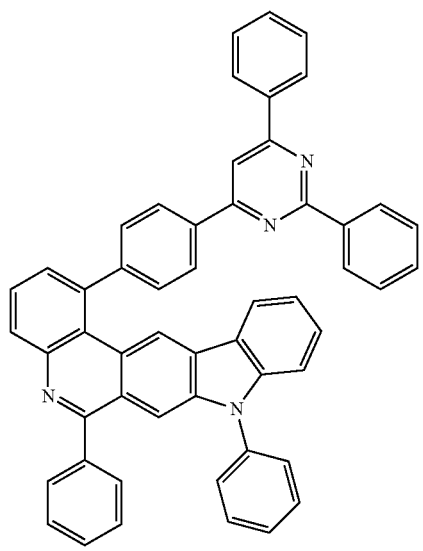

707 708
-continued
9-4 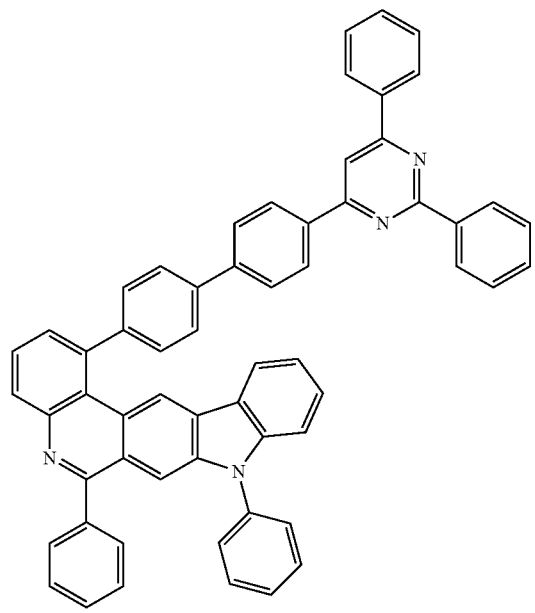 9-5 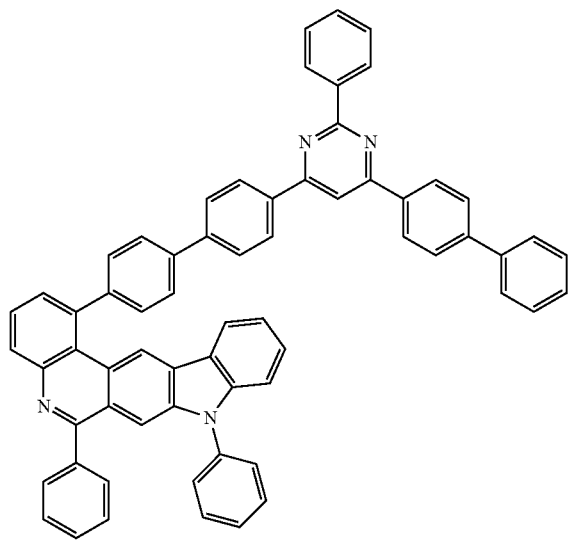
9-6 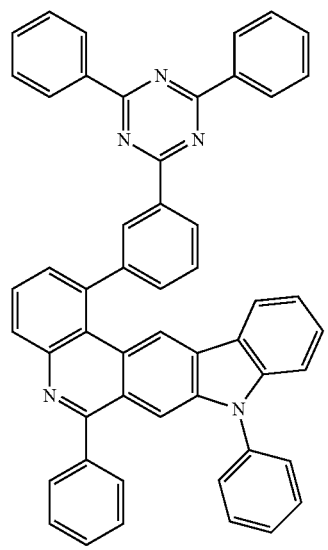 9-7 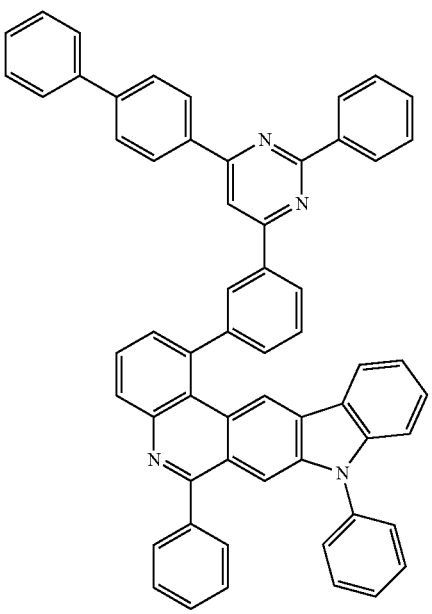

-continued
9-8
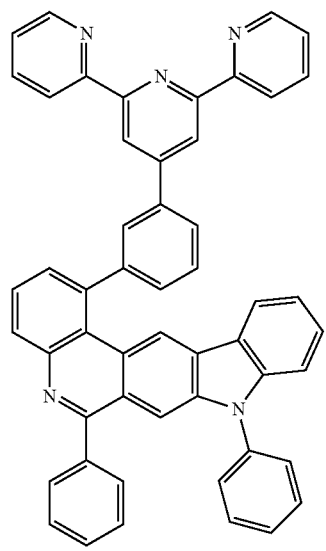
9-9
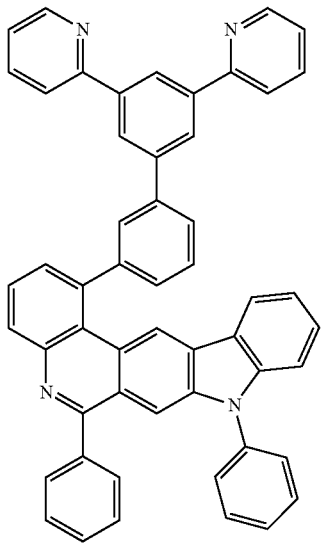
9-10
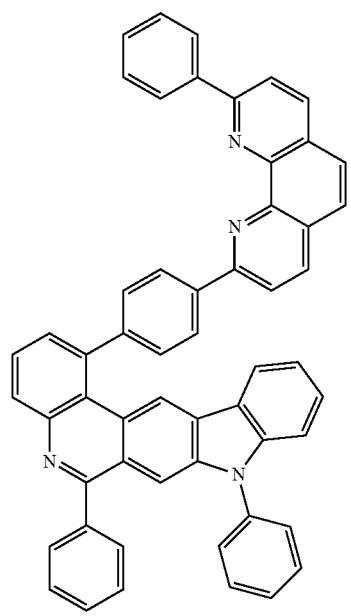
9-11
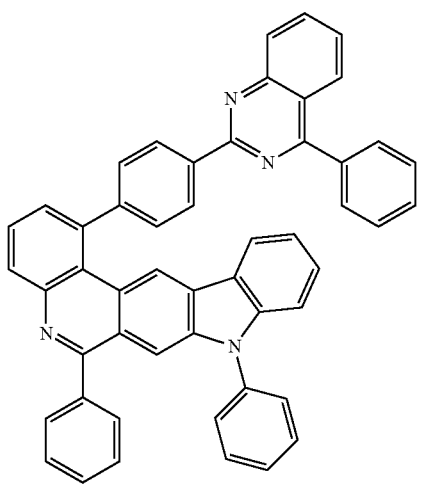

-continued
9-12
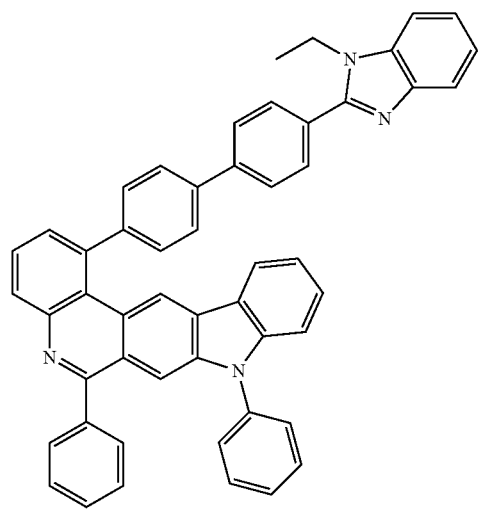
9-13
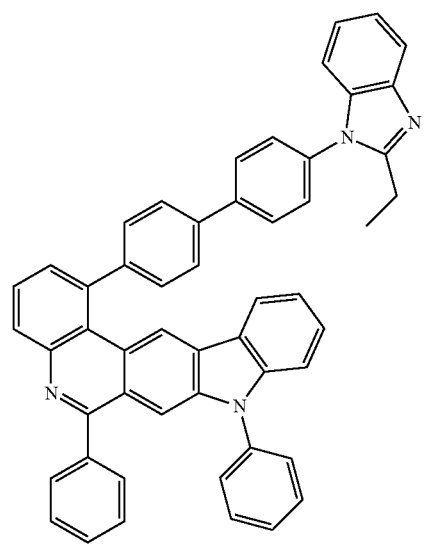
9-14
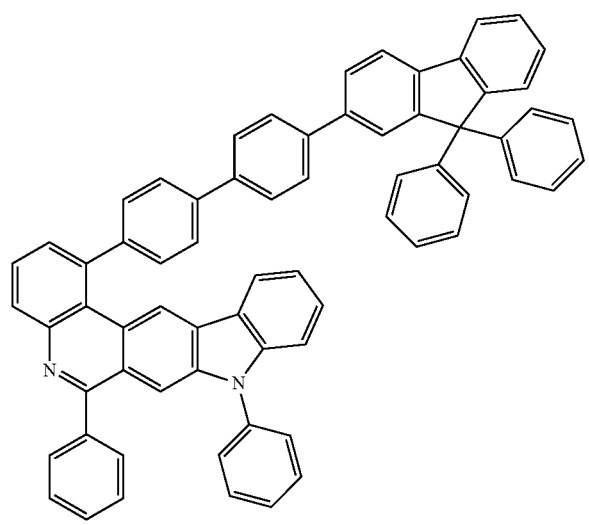
9-15
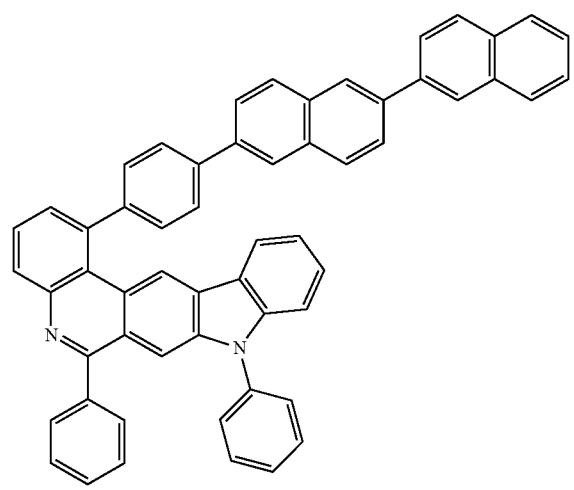
9-16
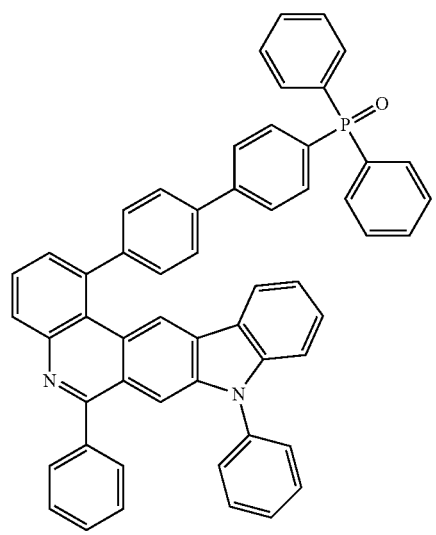
9-17
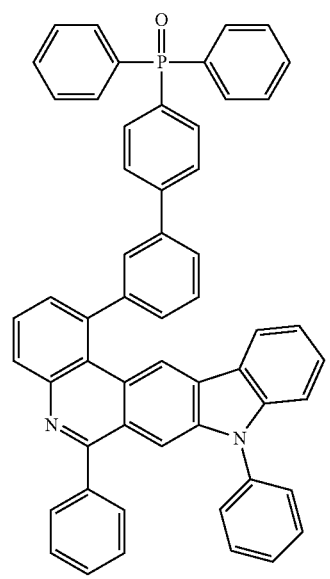

713 714
-continued
10 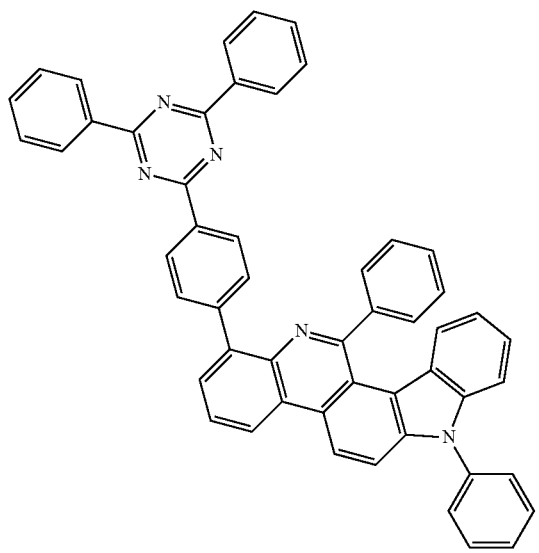 [SMILES: c1ccc(-c2nc(-c3ccccc3)nc(-c3ccc(-c4cccc5c4nc(-c4ccccc4)c4c5ccc5c4c4ccccc4n5-c4ccccc4)cc3)n2)cc1] 10-1 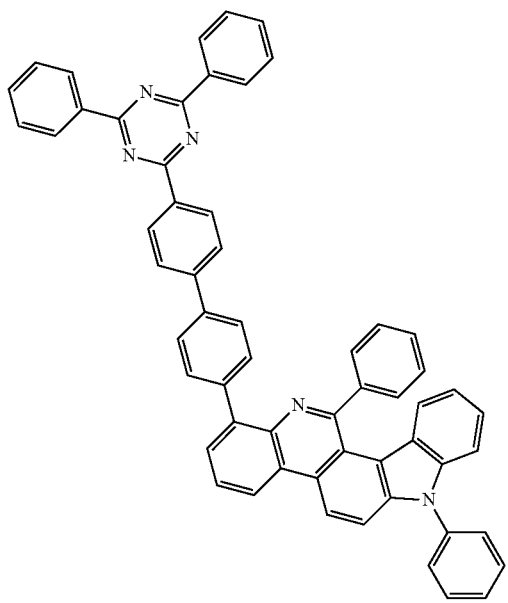
10-2 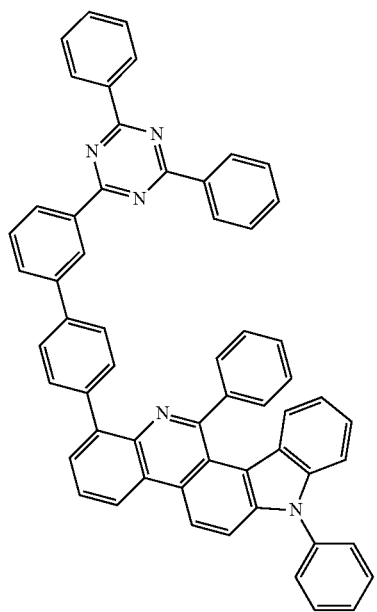 10-3 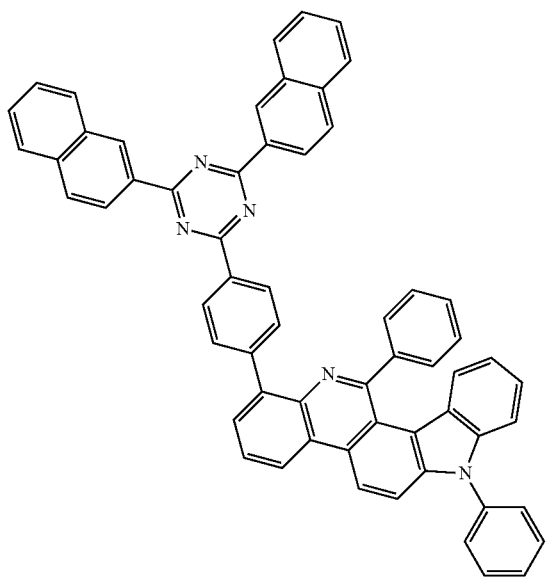

-continued
715 10-4
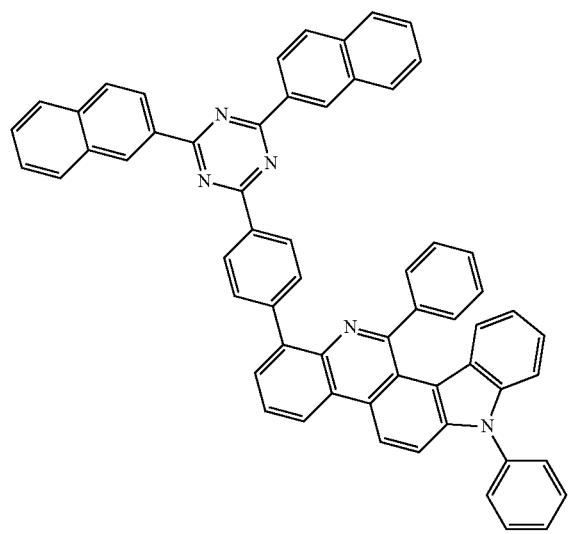 [SMILES: c1ccc(-c2nc3c(-c4ccc(-c5nc(-c6ccc7ccccc7c6)nc(-c6ccc7ccccc7c6)n5)cc4)cccc3c3ccc4c(c5ccccc5n4-c4ccccc4)c23)cc1]
716 10-5
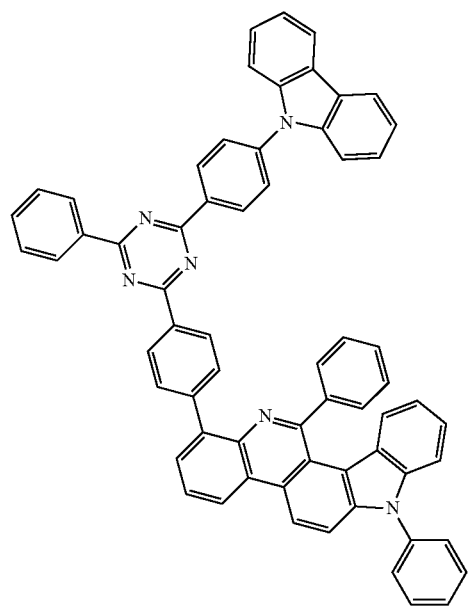
10-6
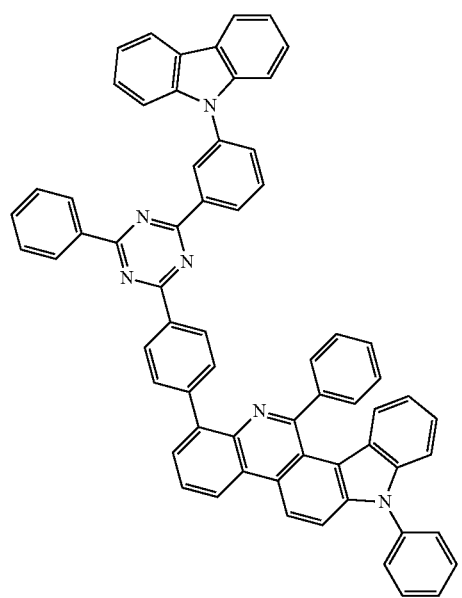
10-7
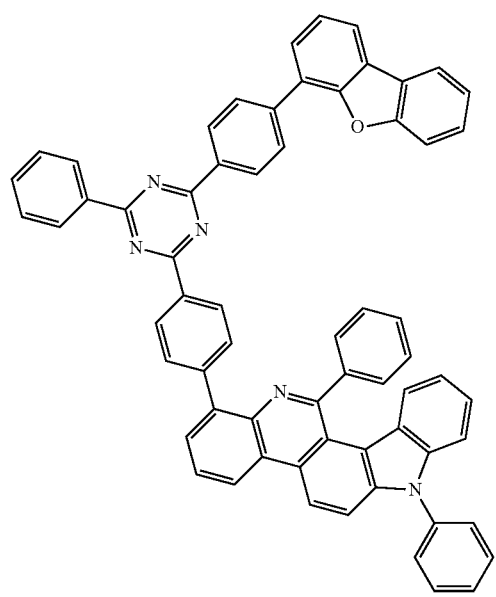

-continued
10-8
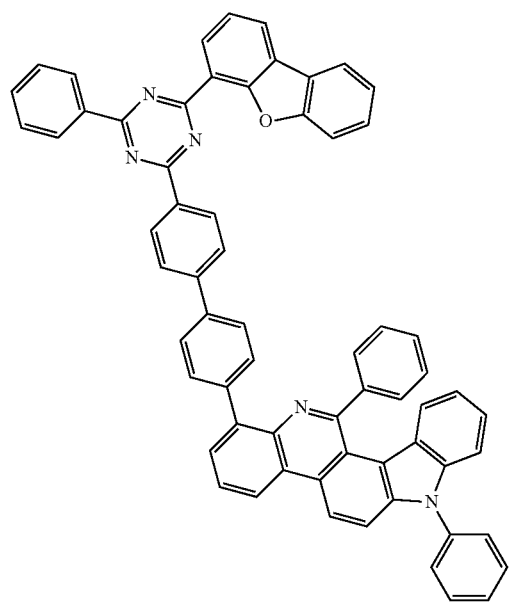
10-9
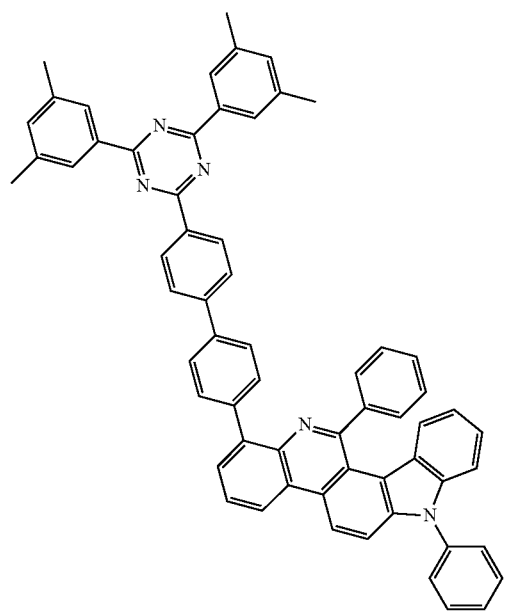
10-10
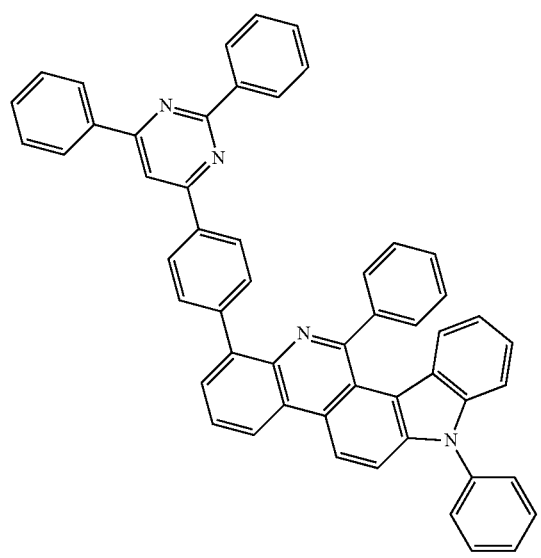
10-11
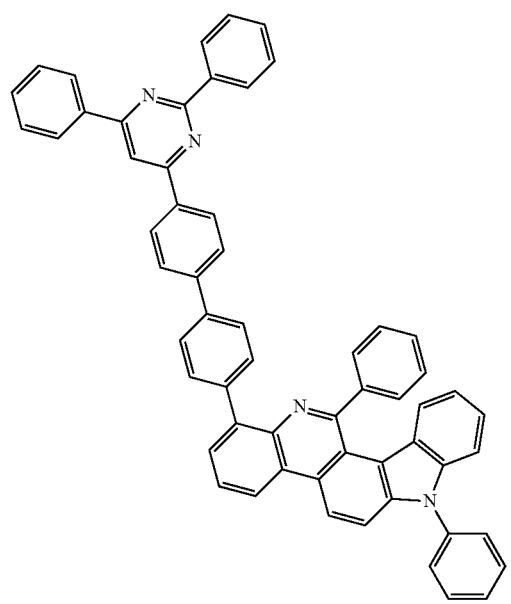

-continued
10-12
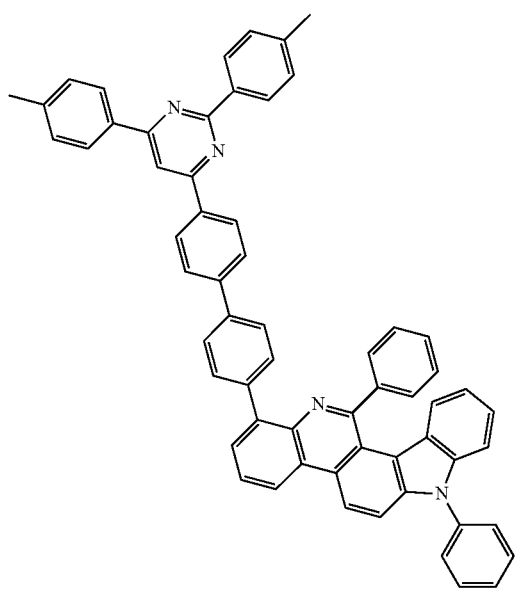
10-13
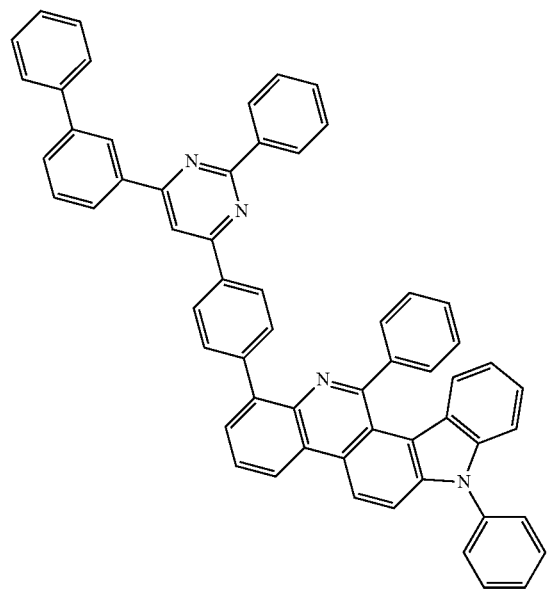
10-14
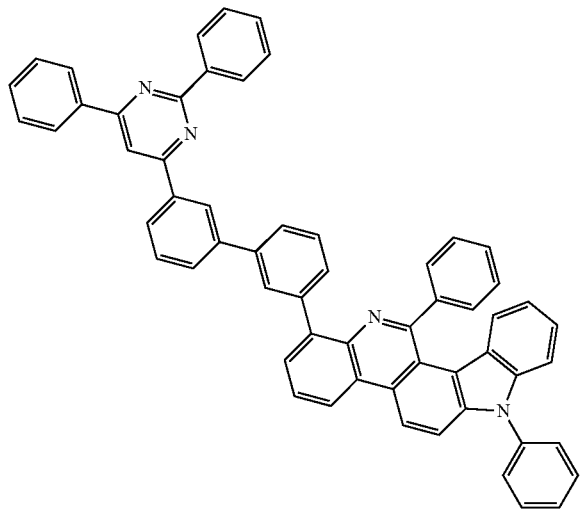
10-15
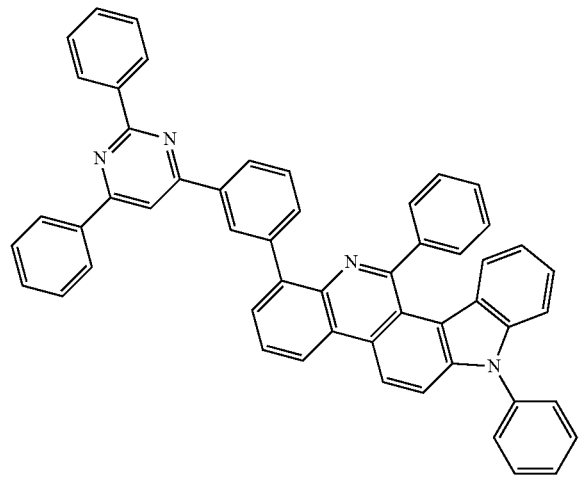

-continued
10-16
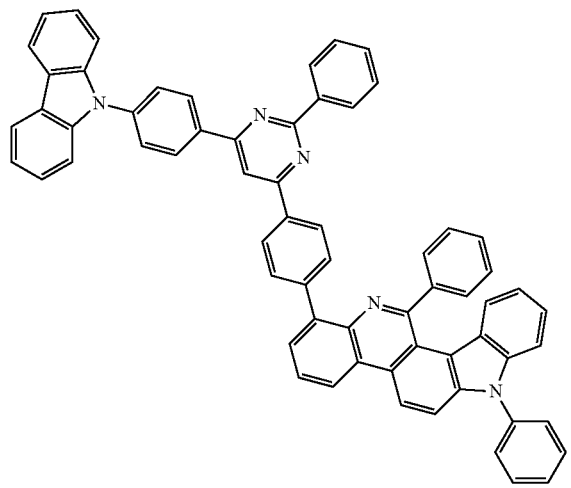
10-17
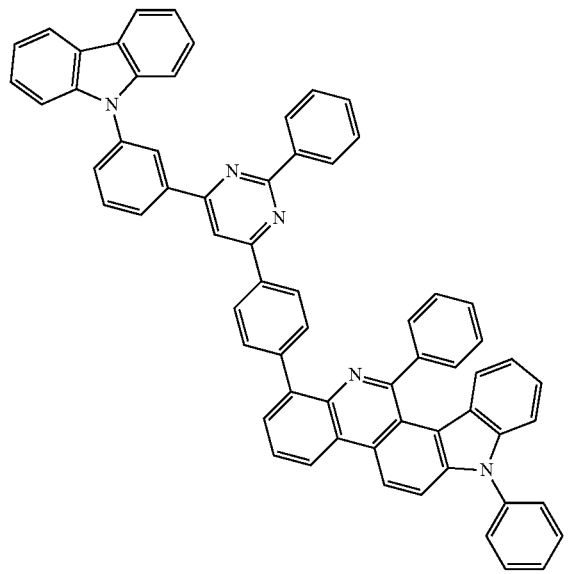
10-18
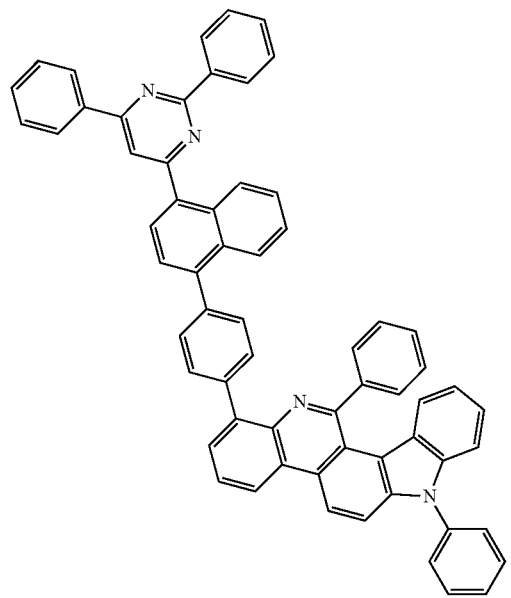 [SMILES: c1ccc(-c2cc(-c3ccc(-c4ccc(-c5cccc6c5nc(-c5ccccc5)c5c6ccc6c5c5ccccc5n6-c5ccccc5)cc4)c4ccccc34)nc(-c3ccccc3)n2)cc1]
10-19
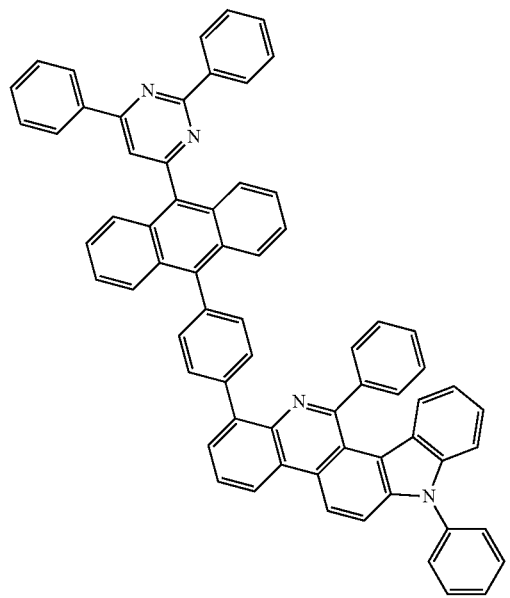

-continued
10-20
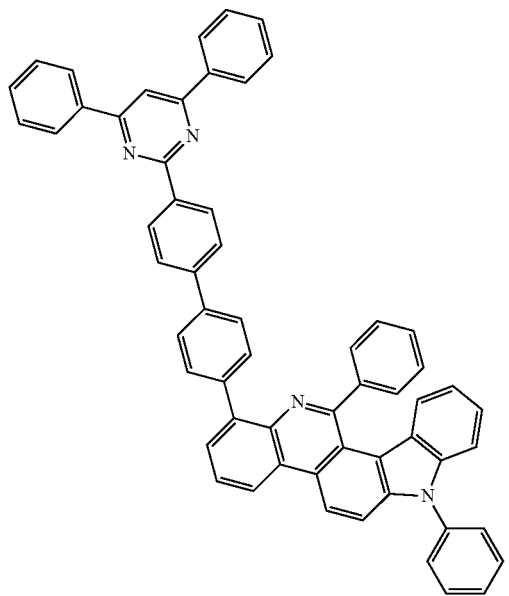
10-21
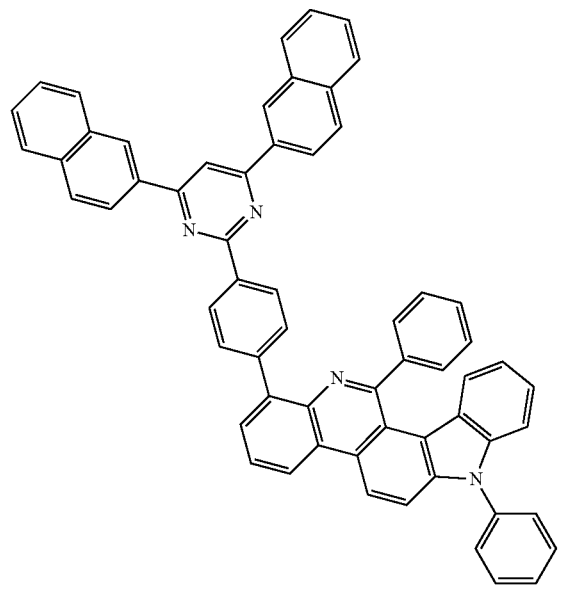
10-22
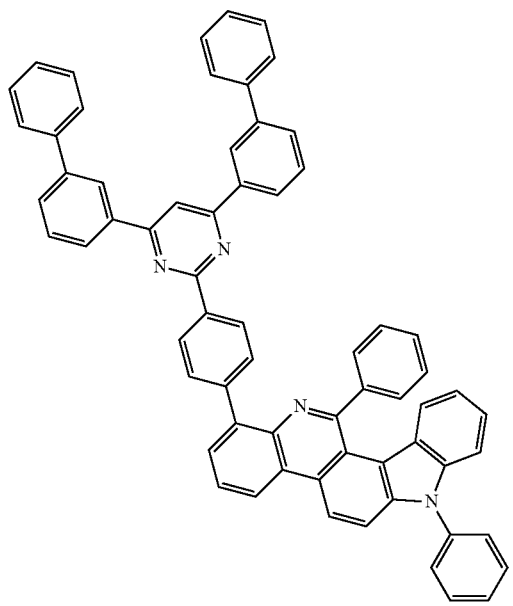 [SMILES: c1ccc(-c2cccc(-c3cc(-c4cccc(-c5ccccc5)c4)nc(-c4ccc(-c5cccc6c5nc(-c5ccccc5)c5c6ccc6c5c5ccccc5n6-c5ccccc5)cc4)n3)c2)cc1]
10-23
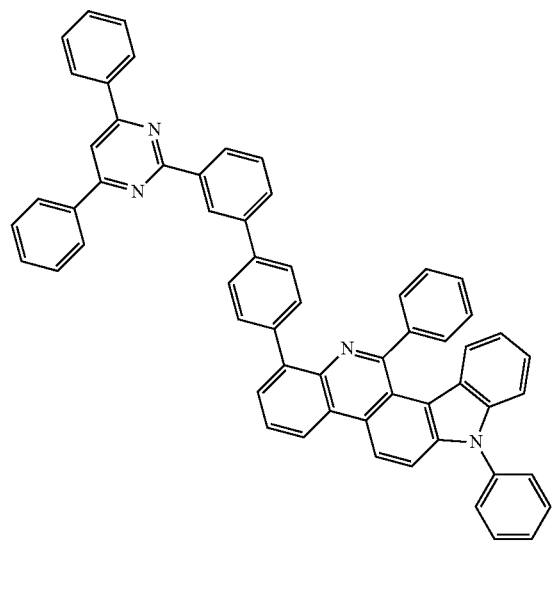

725
726
-continued
10-24 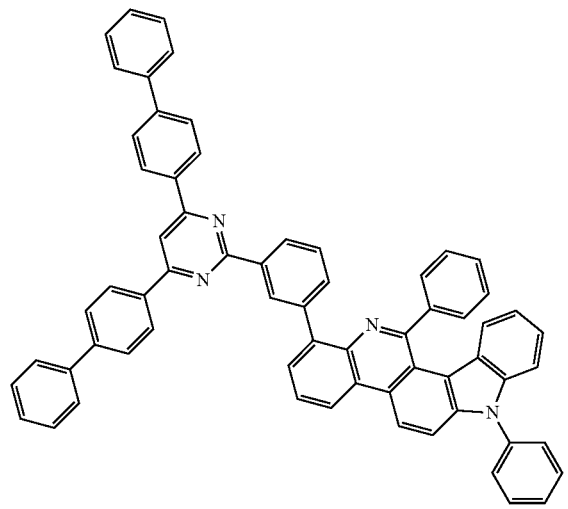
10-25 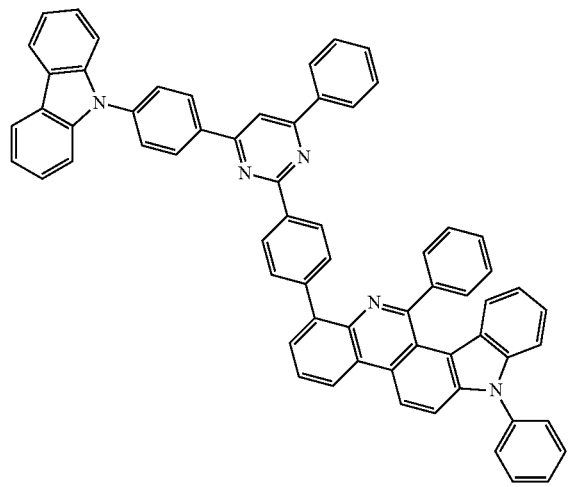
10-26 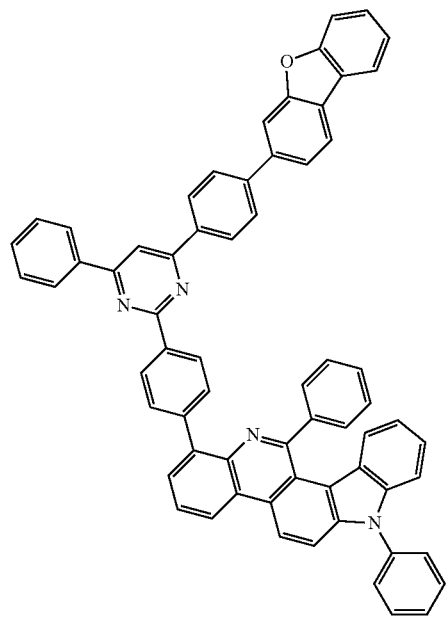
10-27 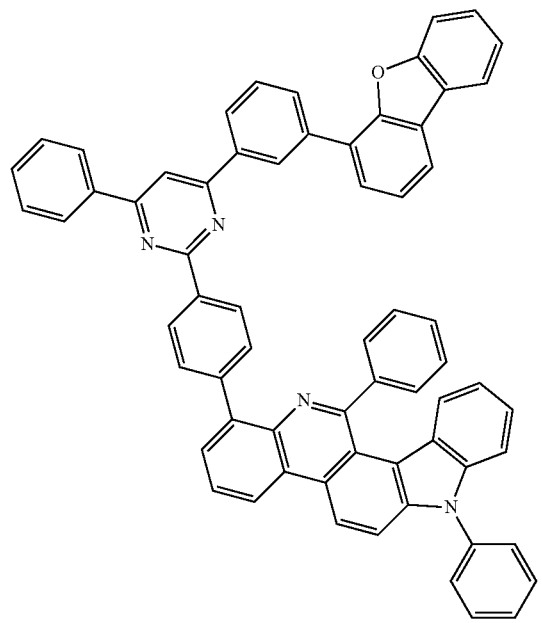

-continued
10-28
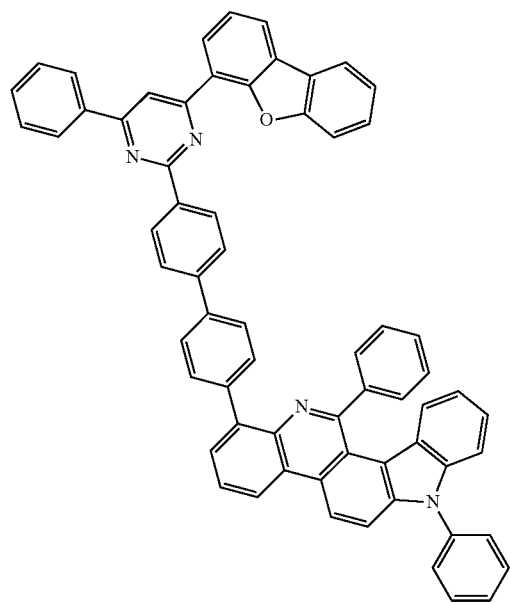
10-29
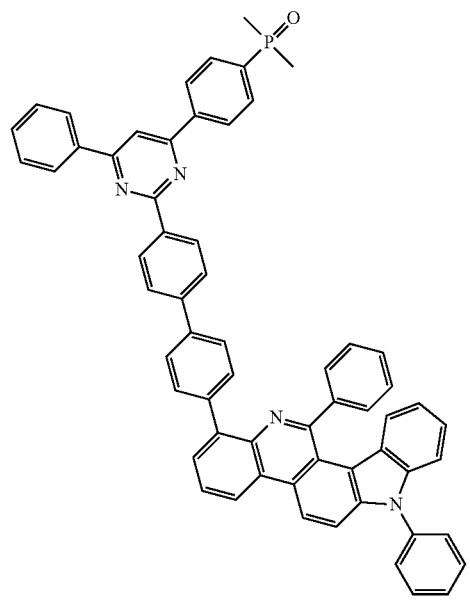
10-30
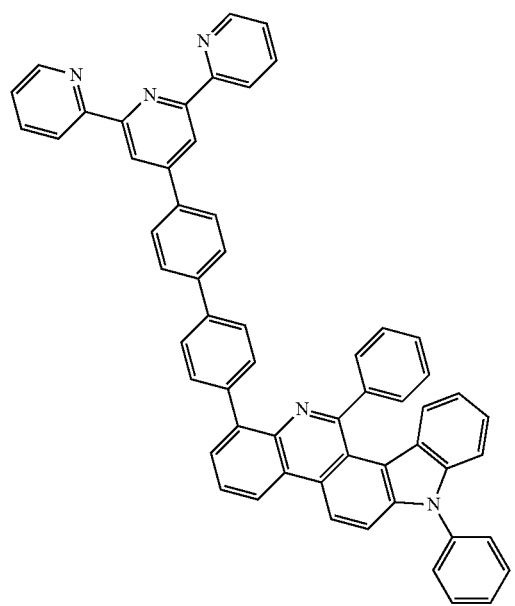
10-31
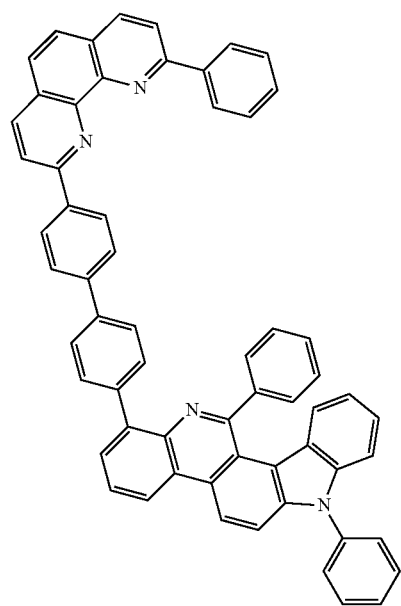

-continued
10-32
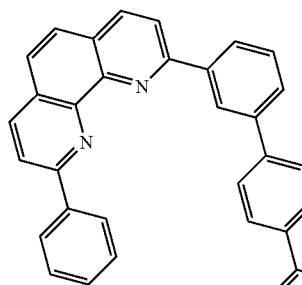
10-33
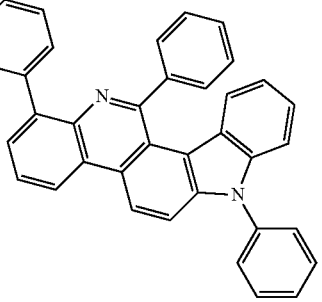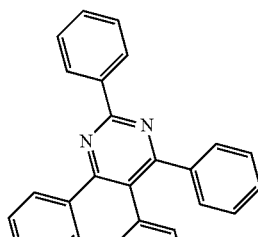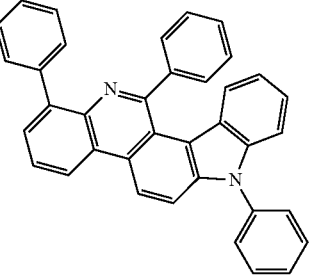
10-34
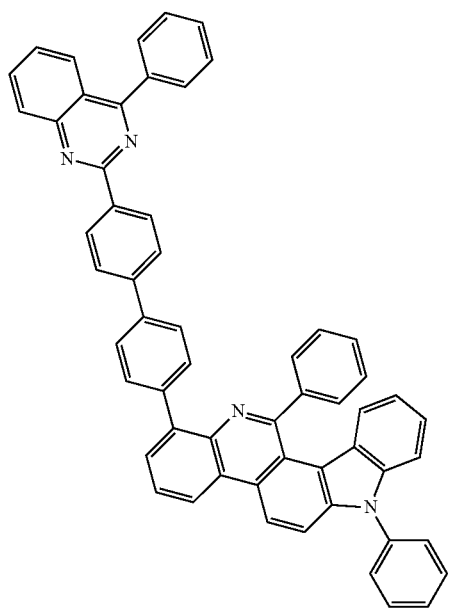
10-35
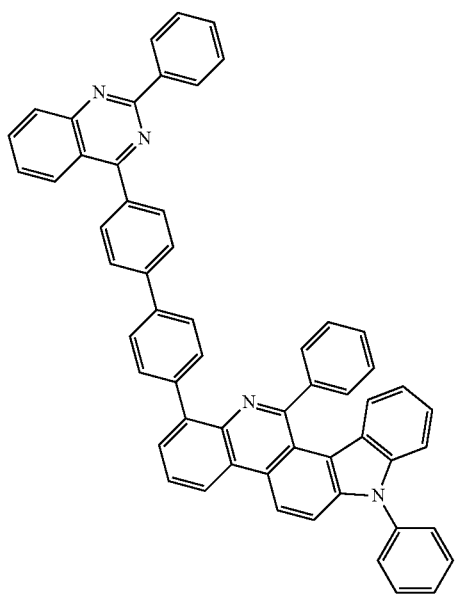

-continued
10-36
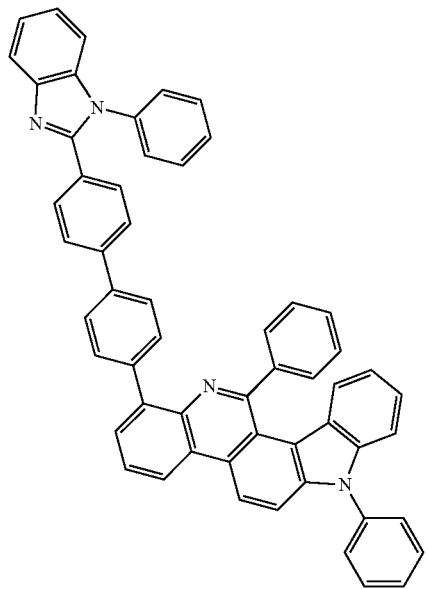 [SMILES: c1ccc(-c2nc3c(-c4ccc(-c5ccc(-c6nc7ccccc7n6-c6ccccc6)cc5)cc4)cccc3c3ccc4c(c5ccccc5n4-c4ccccc4)c23)cc1]
10-37
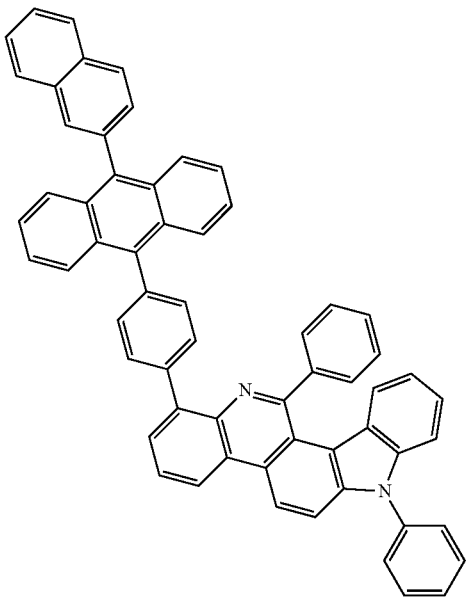
10-38
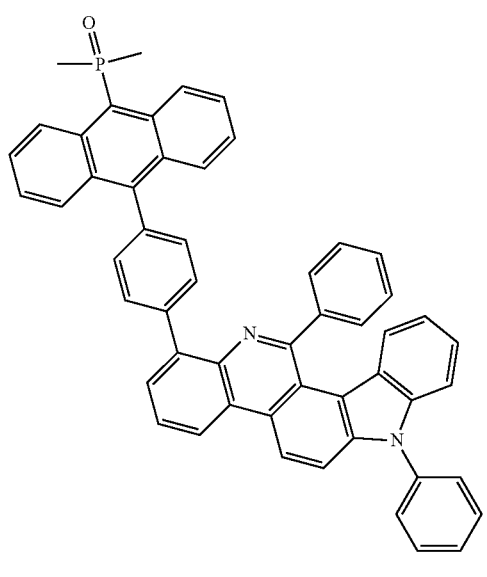
10-39
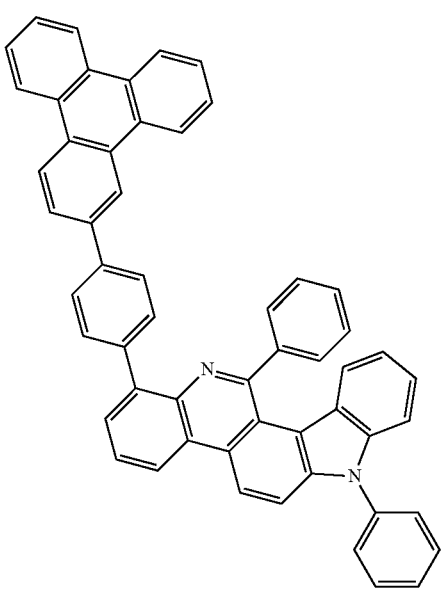

-continued
10-40
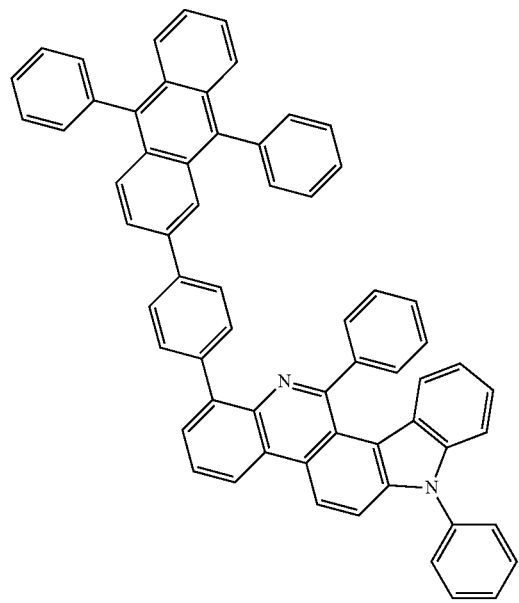 [SMILES: c1ccc(-c2c3ccccc3c(-c3ccccc3)c3cc(-c4ccc(-c5cccc6c5nc(-c5ccccc5)c5c6ccc6c5c5ccccc5n6-c5ccccc5)cc4)ccc23)cc1]
10-41
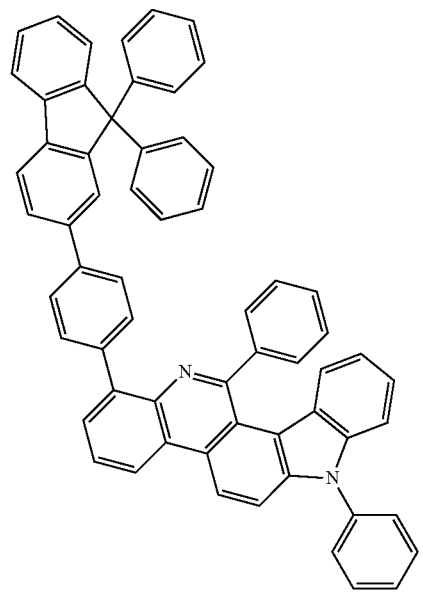
10-42
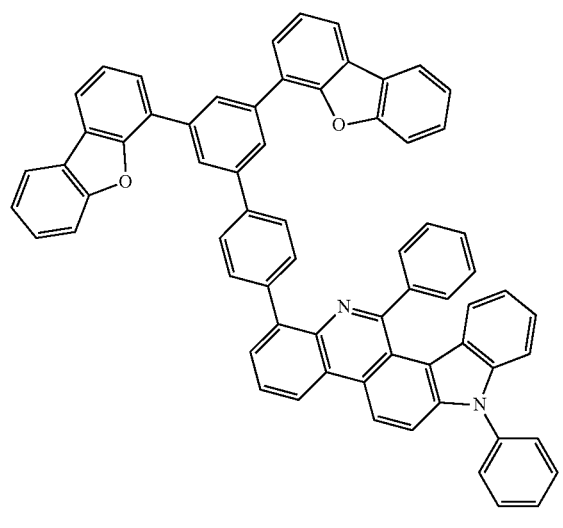
11
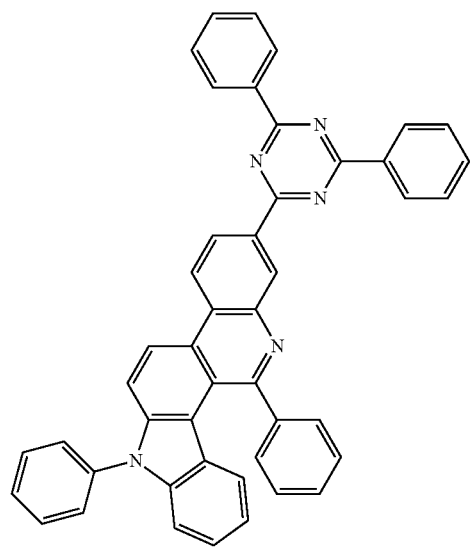

-continued
11-1
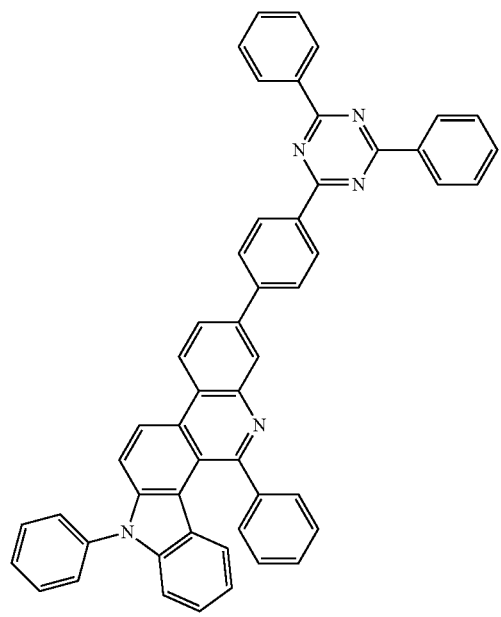
11-2
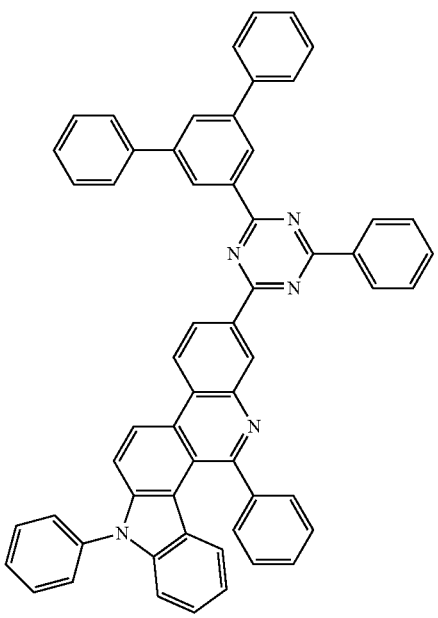
11-3
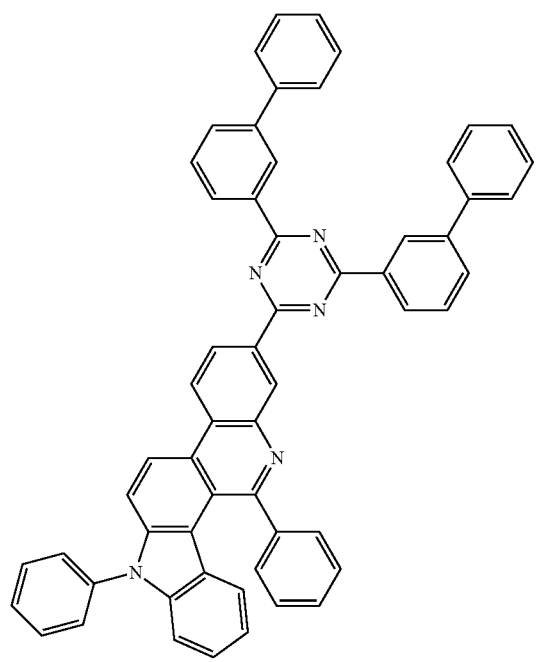
11-4
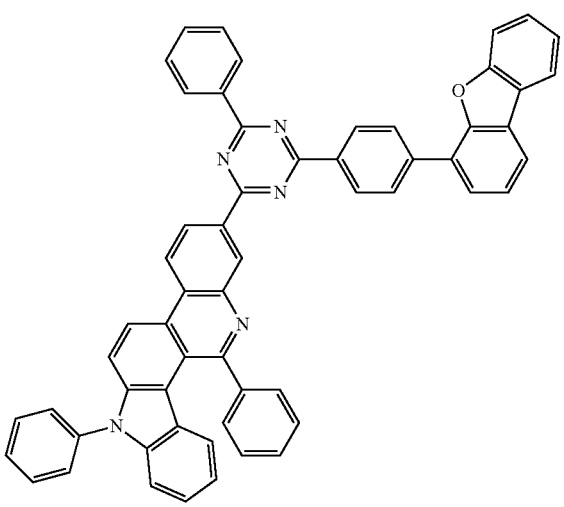

737 738
-continued
11-5
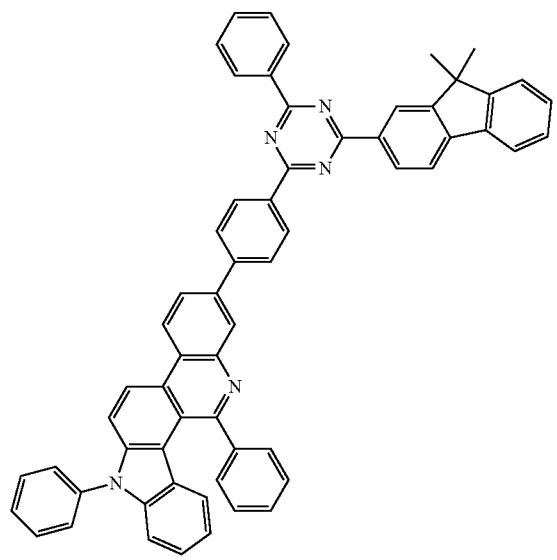
11-6
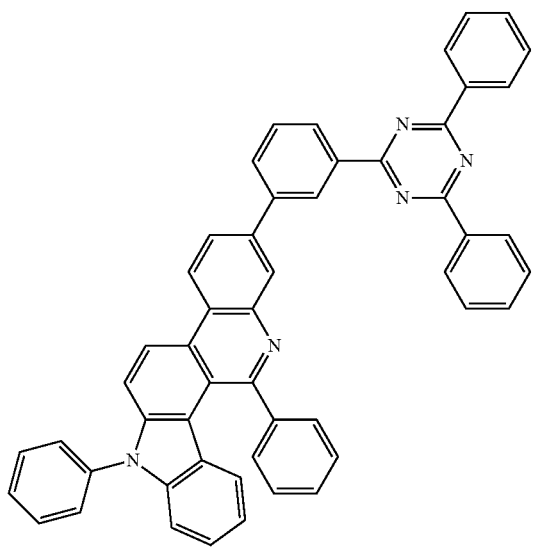
11-7
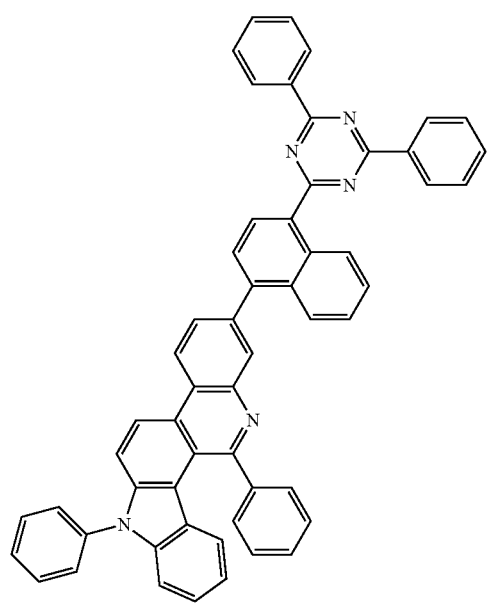
11-8
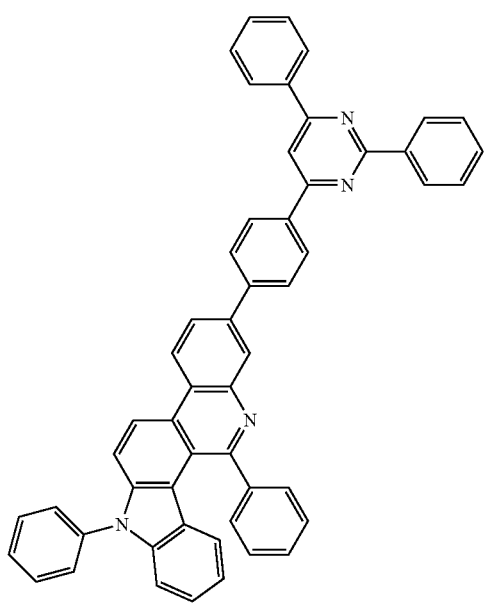

739
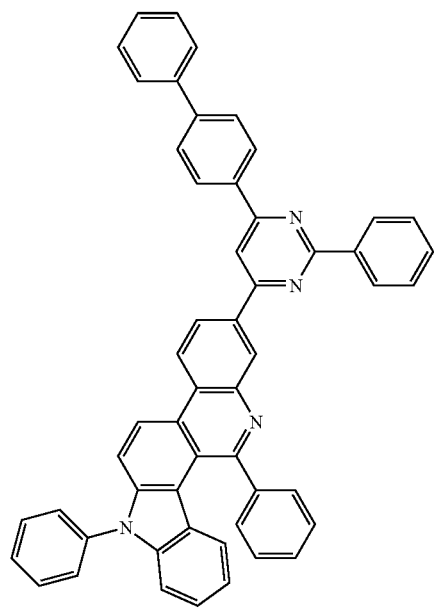
11-9
740
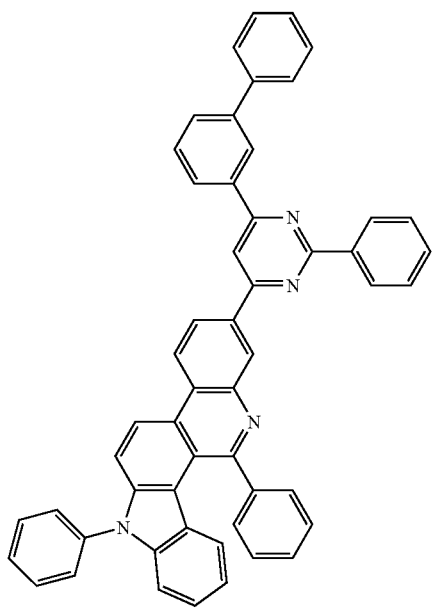
11-10
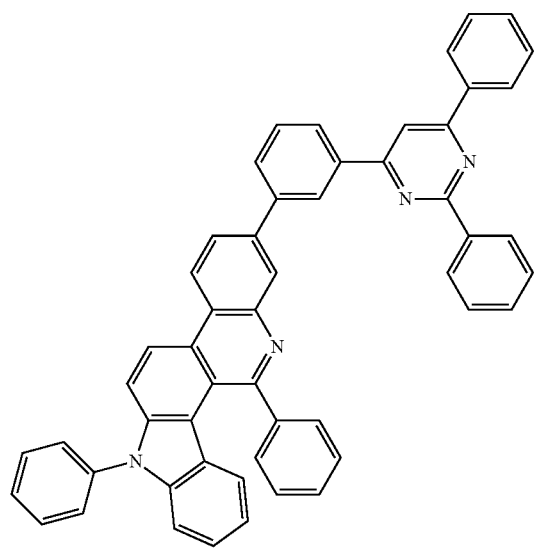
11-11
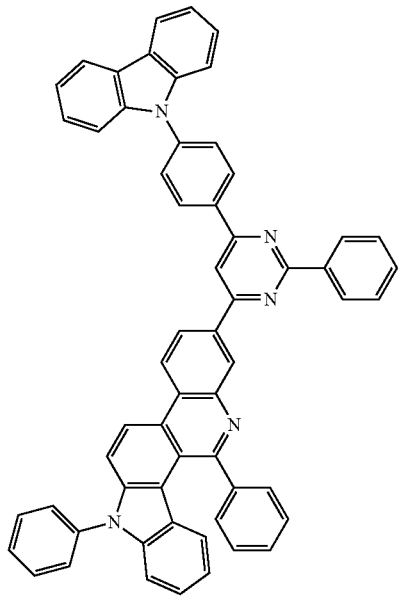
11-12

741
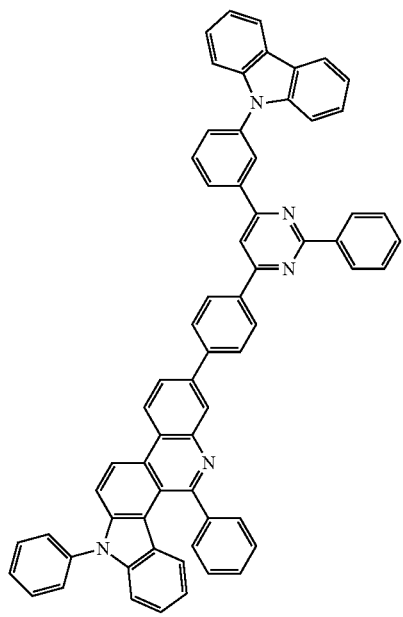
742
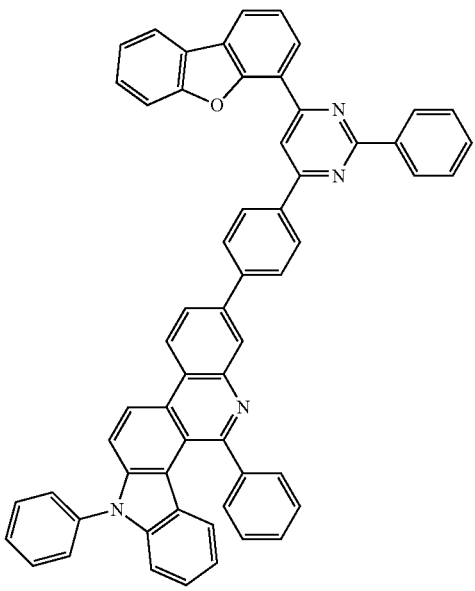
-continued
11-13
11-14
11-15
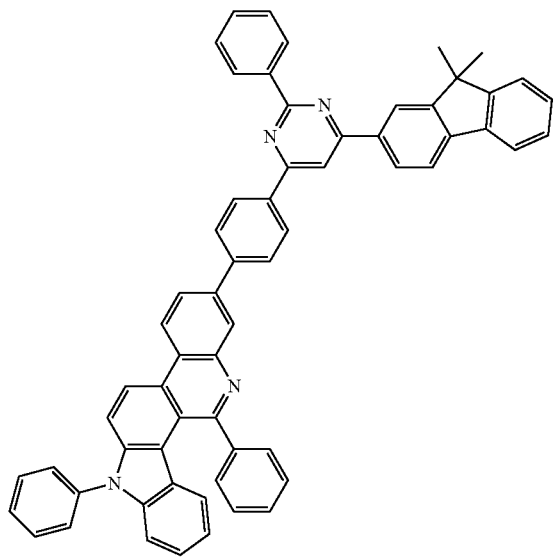
11-16
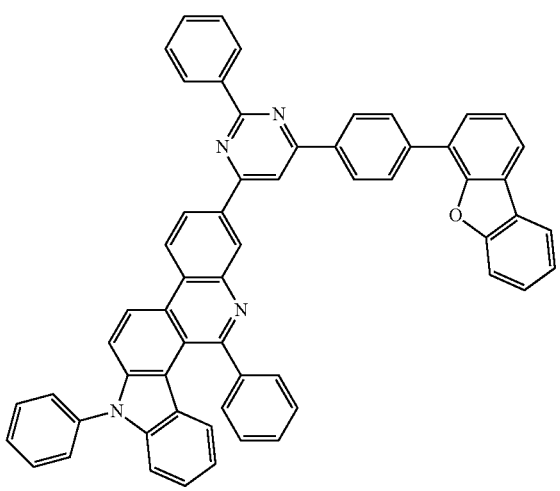

743
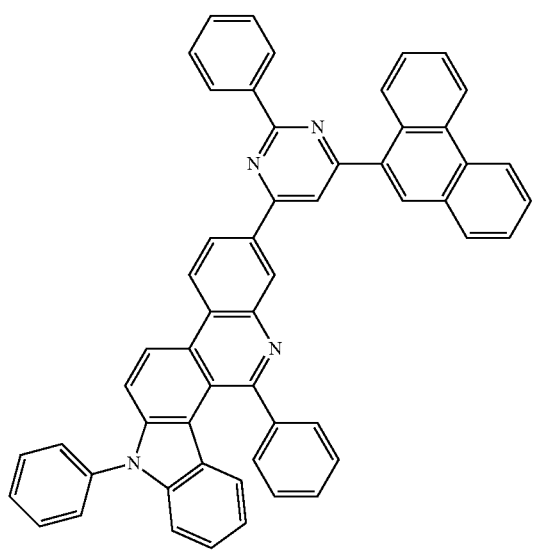
11-17
744
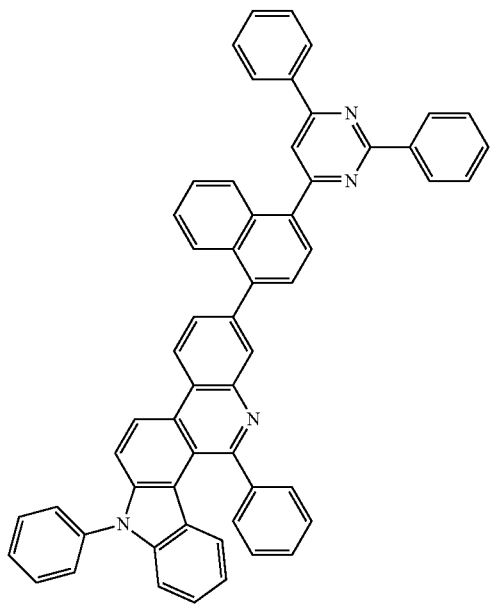
11-18
11-19
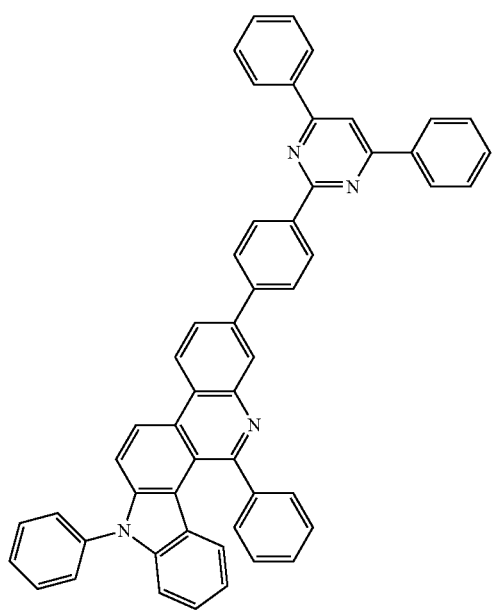
11-20
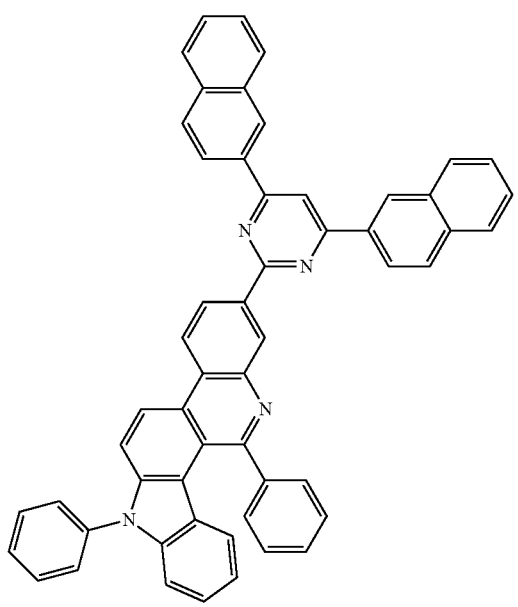

-continued
11-21
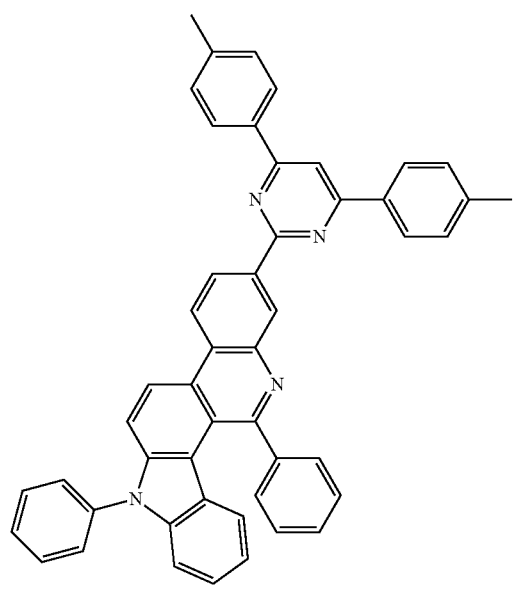
11-22
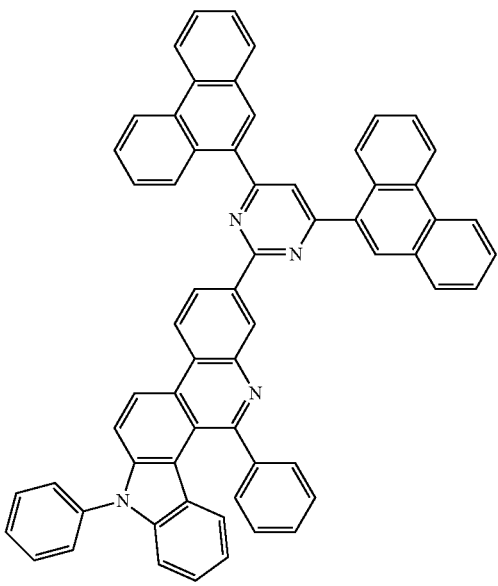
11-23
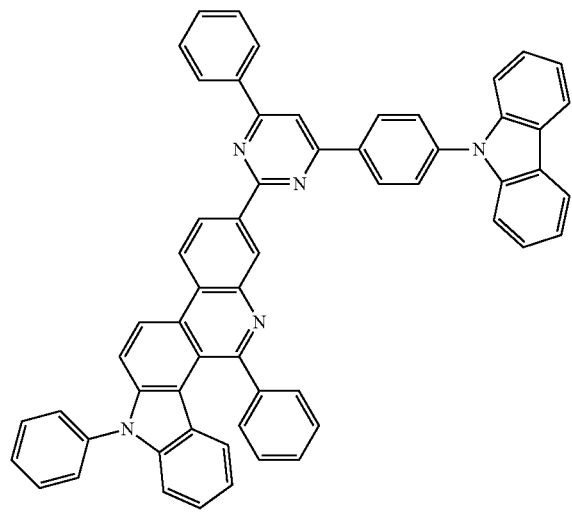
11-24
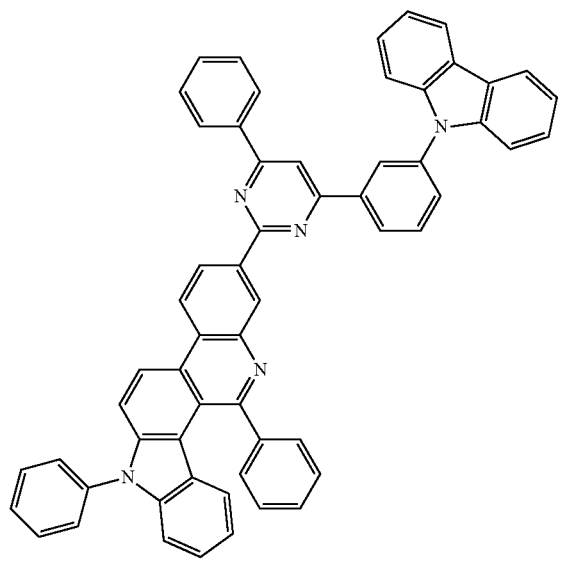

-continued
747
11-25
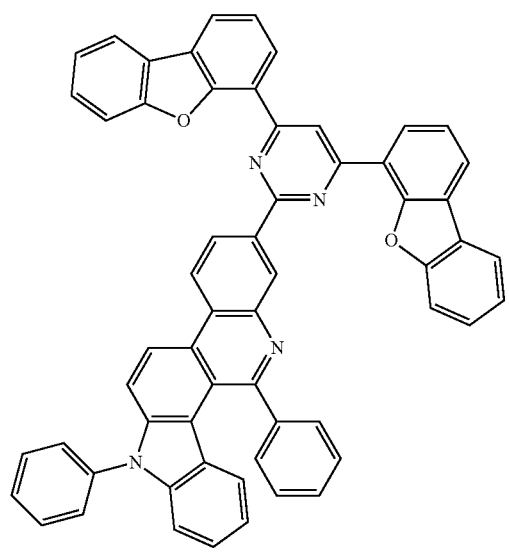
748
11-26
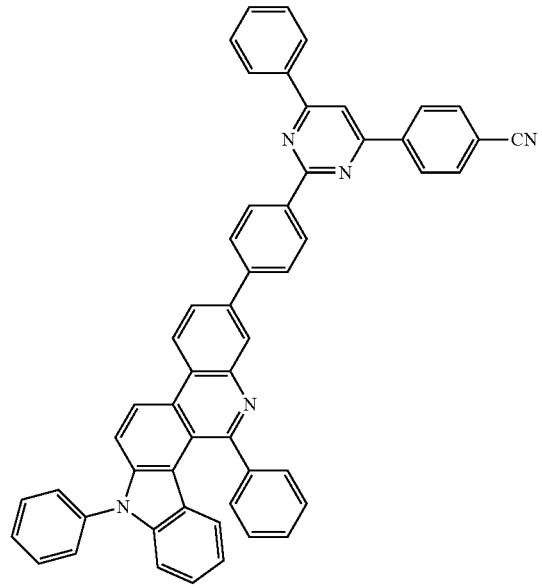
11-27
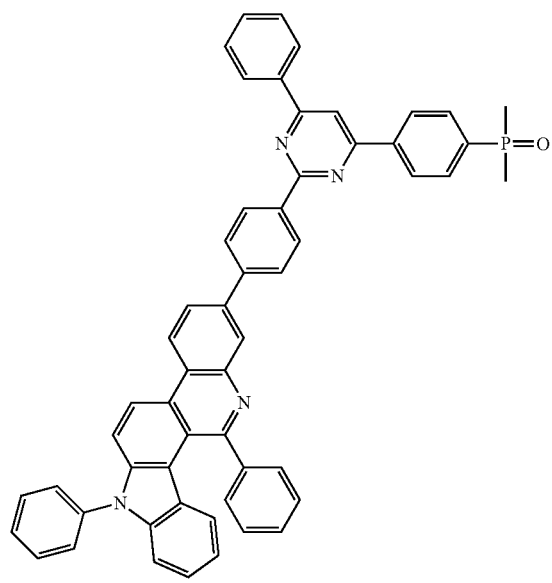
11-28
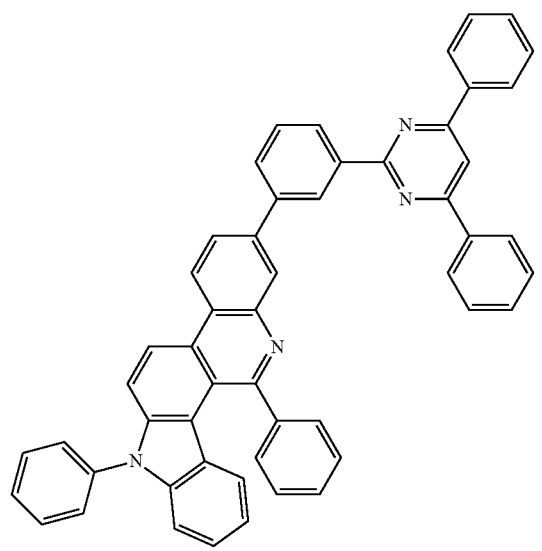

-continued
749
11-29
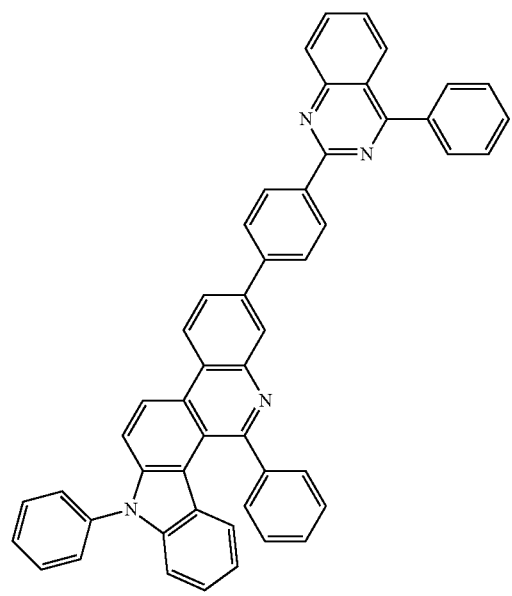
750
11-30
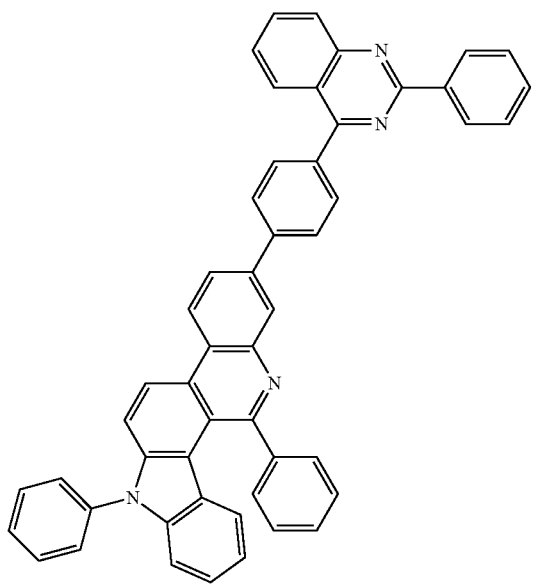
11-31
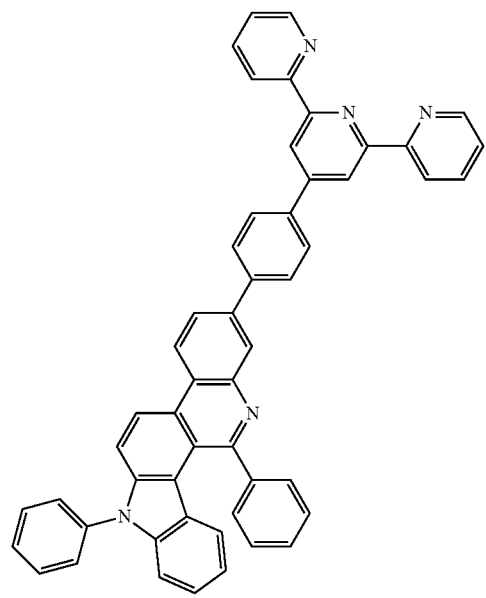
11-32
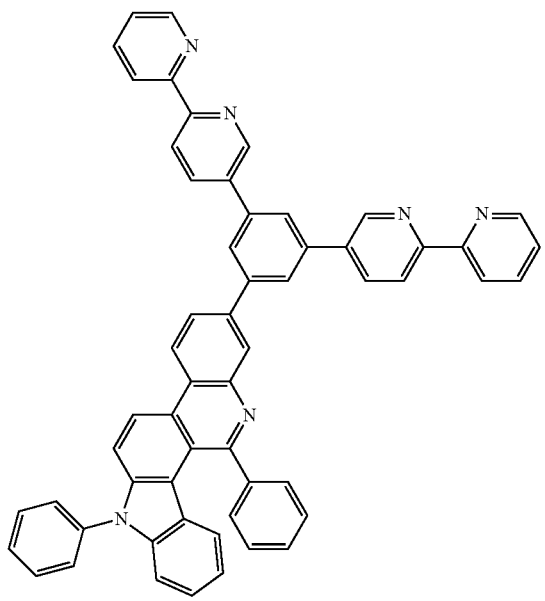

-continued
11-33
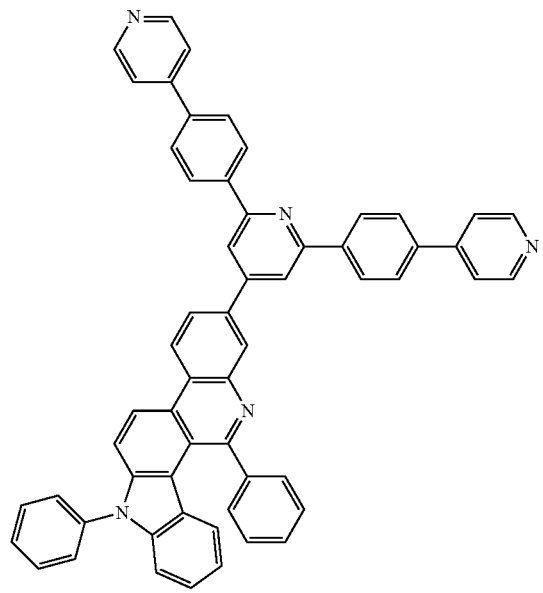
11-34
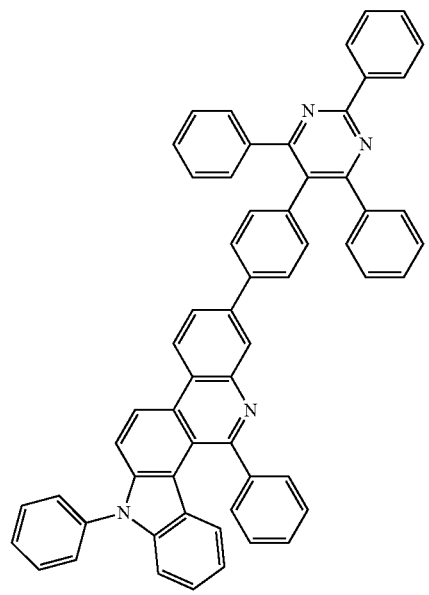
11-35
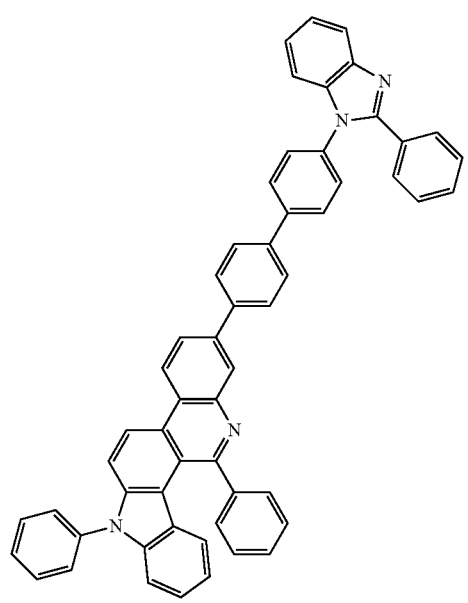
11-36
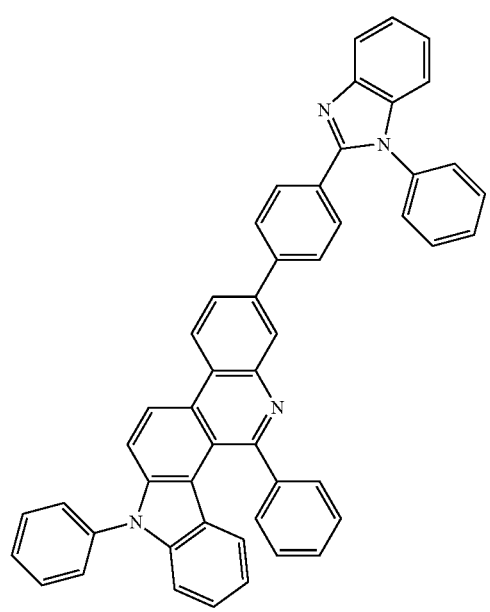

-continued
11-37
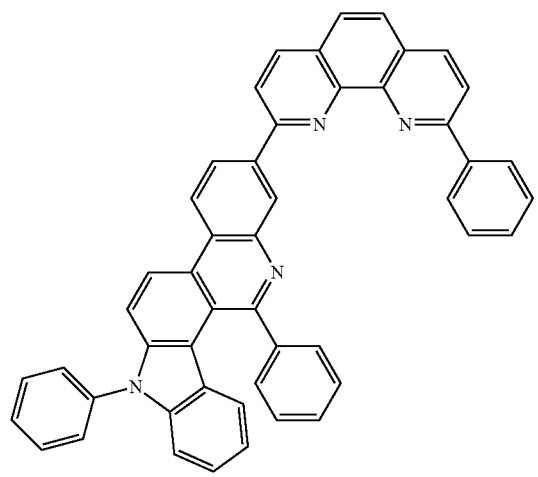
11-38
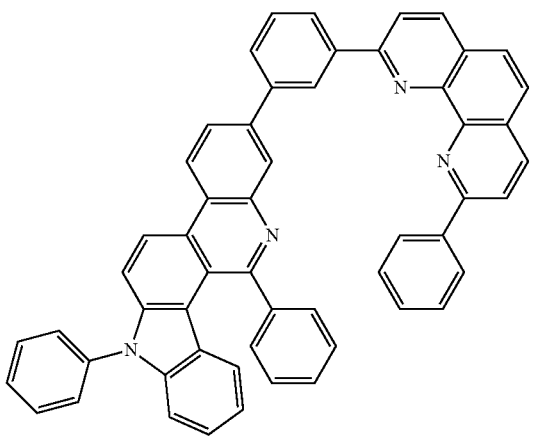
11-39
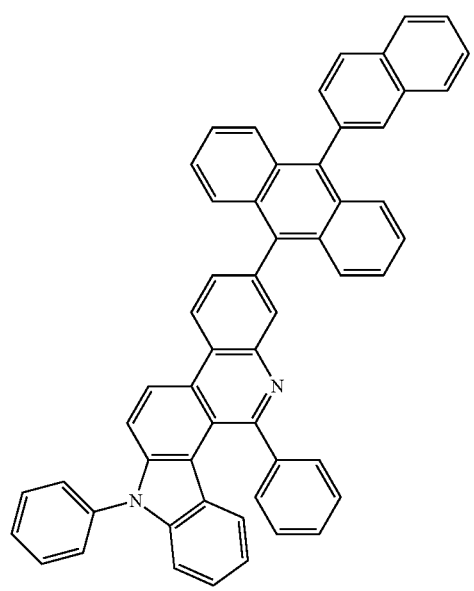
11-40
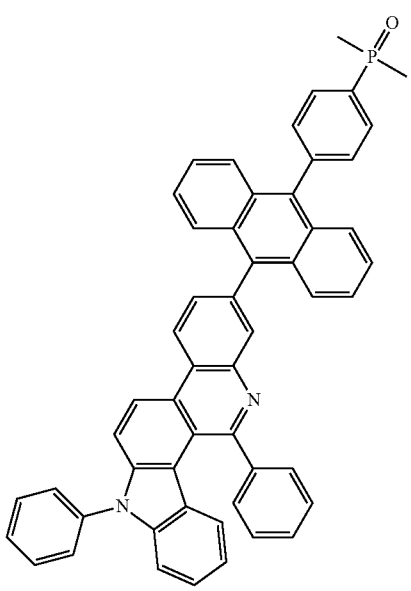
11-41
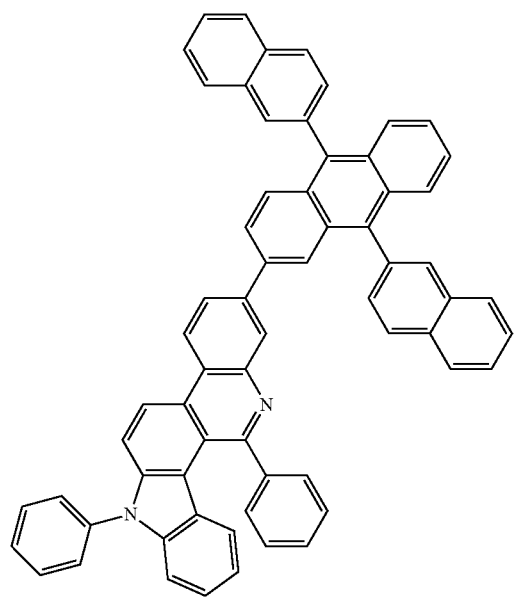
11-42
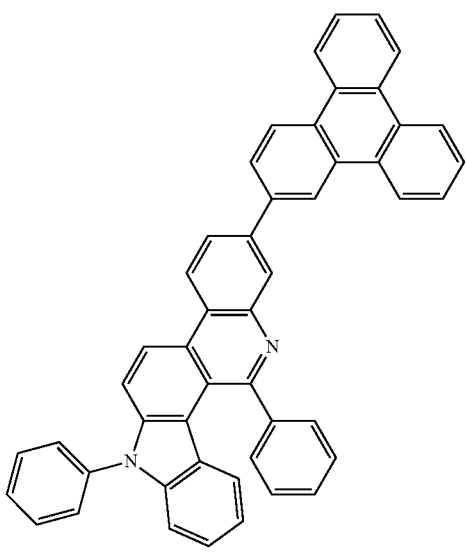

-continued
11-43
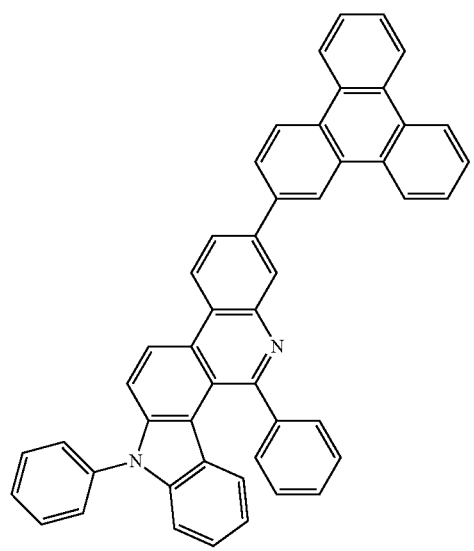
11-44
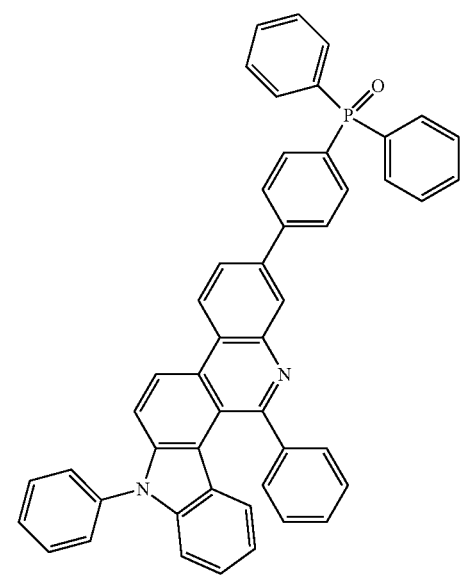
11-45
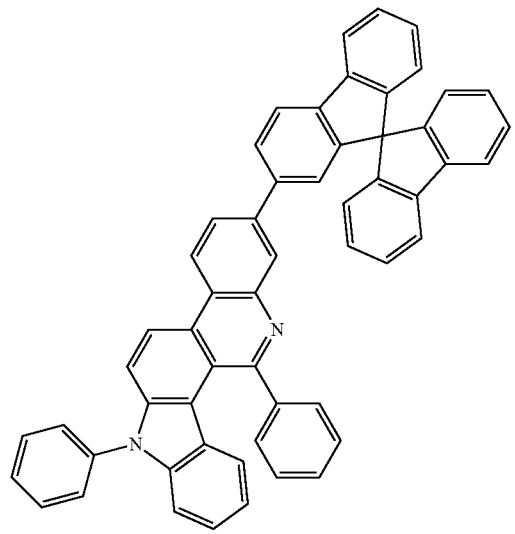
11-46
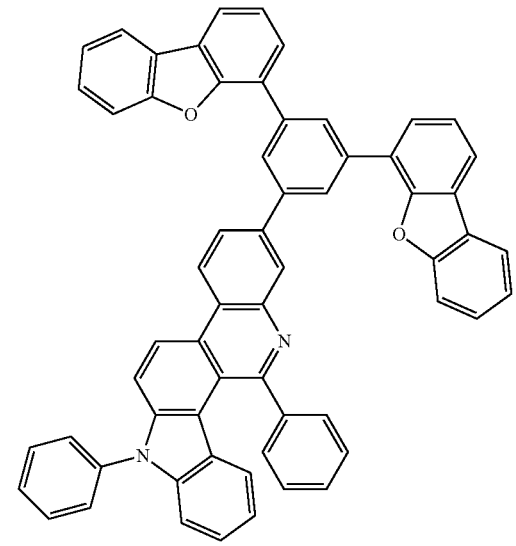

-continued
12
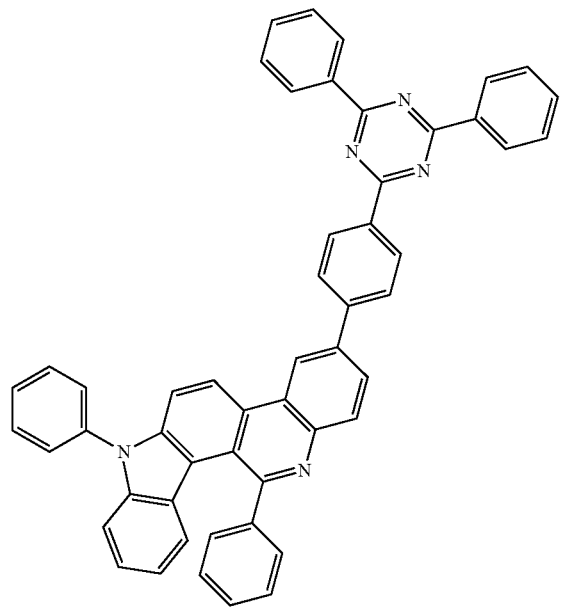
12-1
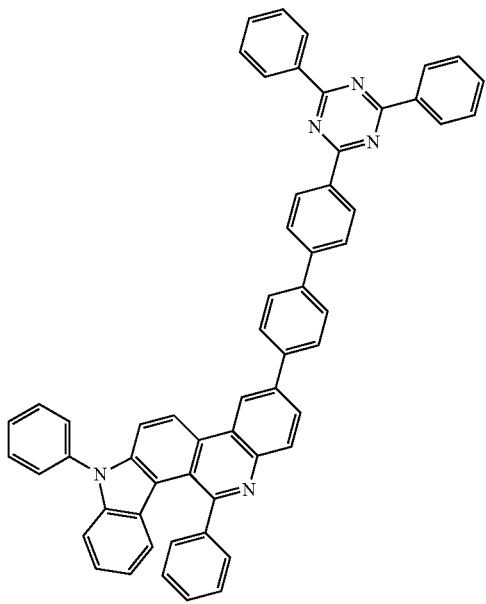 [SMILES: c1ccc(-c2nc(-c3ccccc3)nc(-c3ccc(-c4ccc(-c5ccc6nc(-c7ccccc7)c7c(ccc8c7c7ccccc7n8-c7ccccc7)c6c5)cc4)cc3)n2)cc1]
12-2
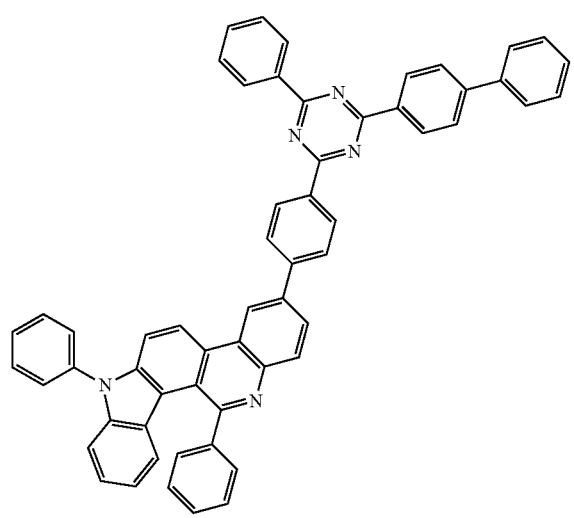
12-3
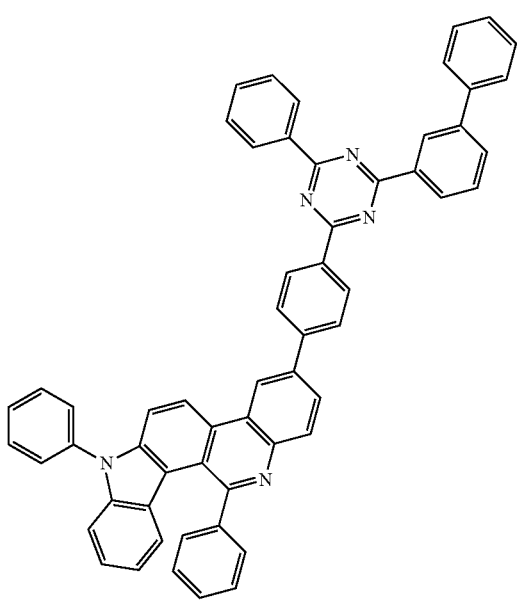

759
-continued
12-4
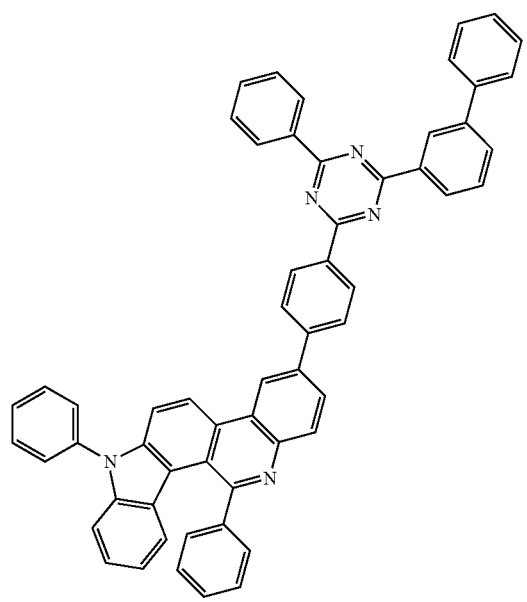
760
12-5
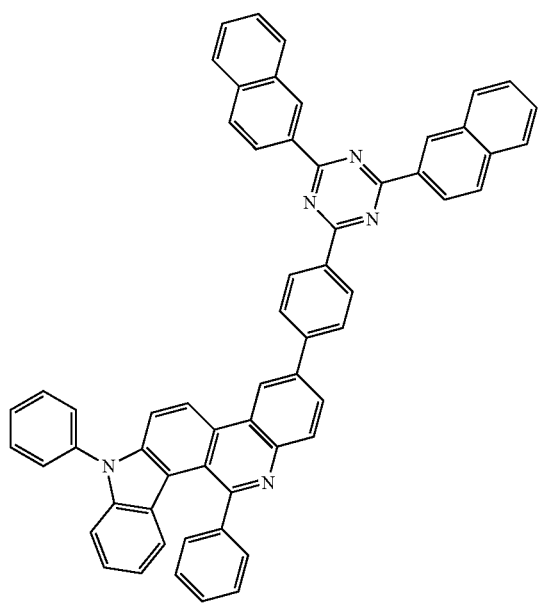
12-6
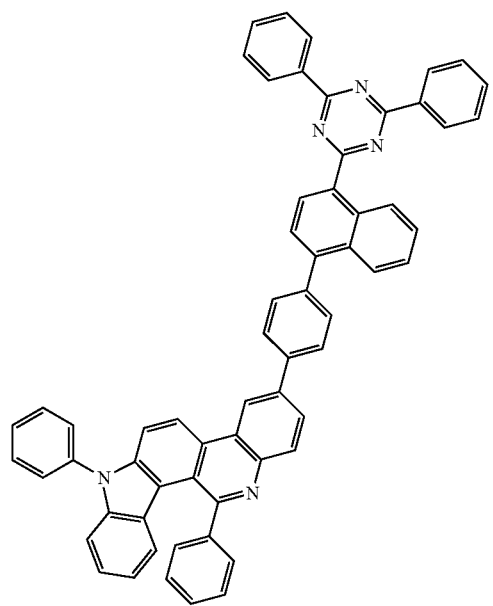
12-7
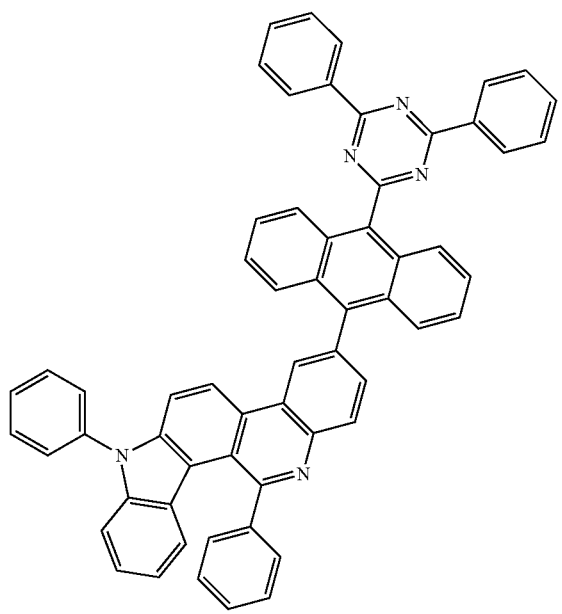

-continued
12-8
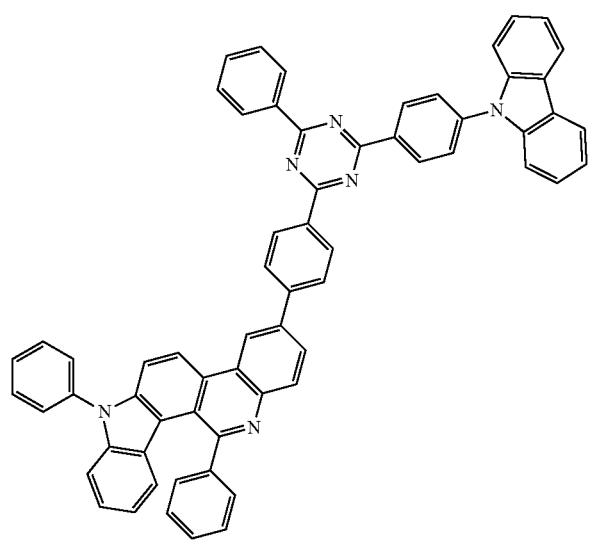
12-9
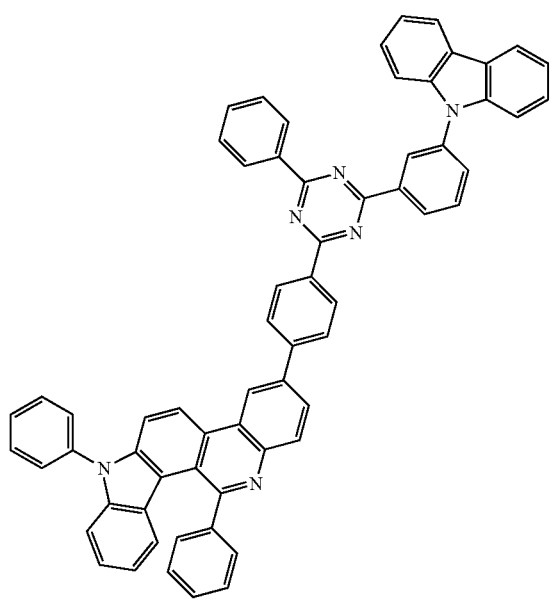
12-10
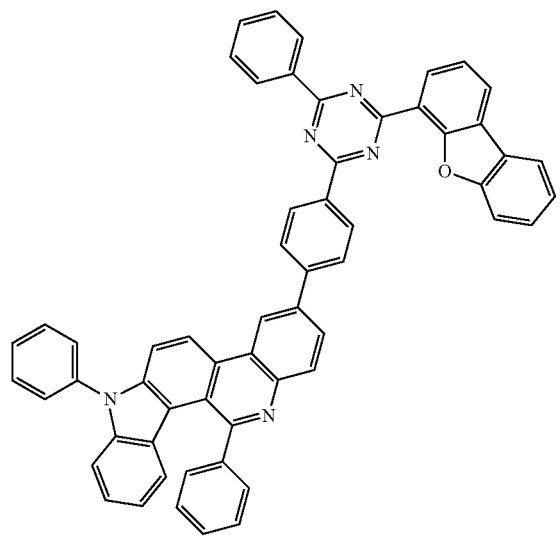
12-11
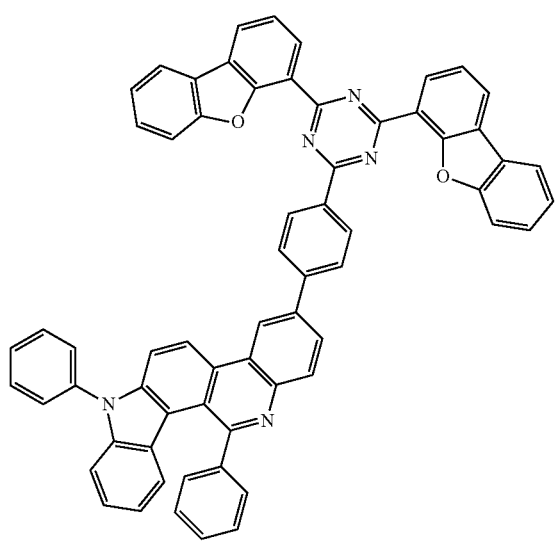

-continued
12-12
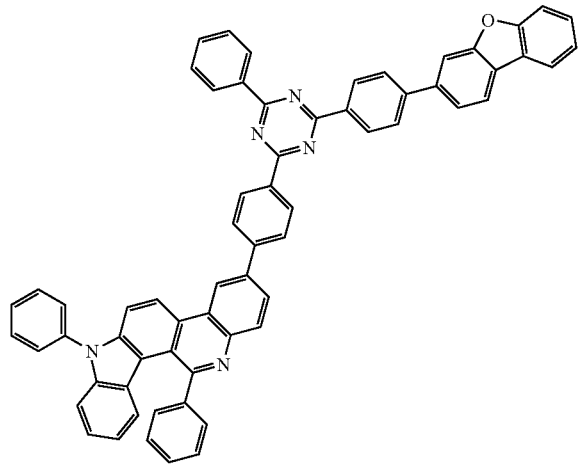
12-13
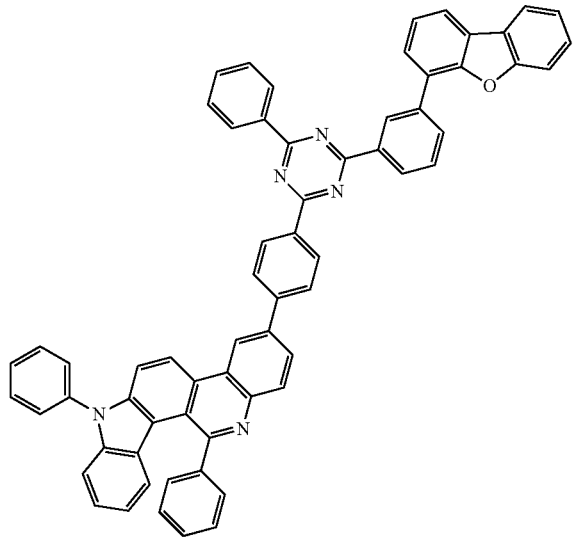
12-14
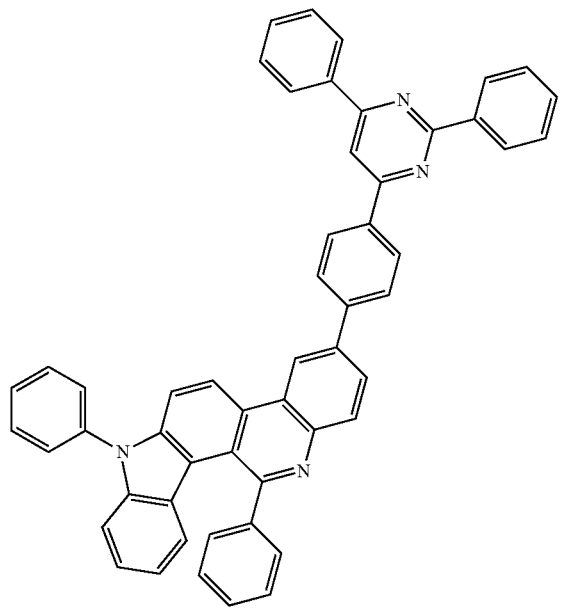
12-15
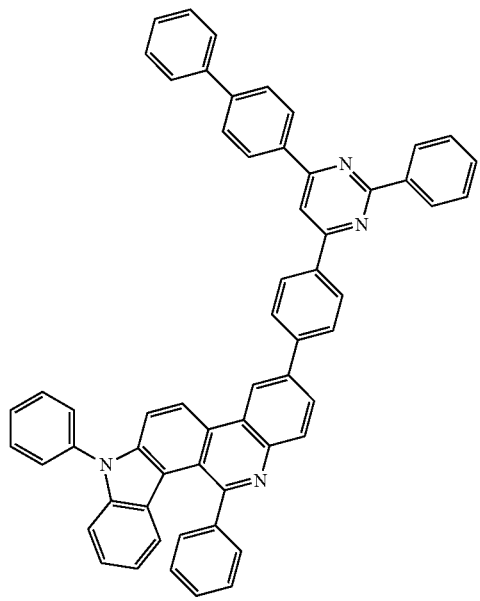

765
12-16
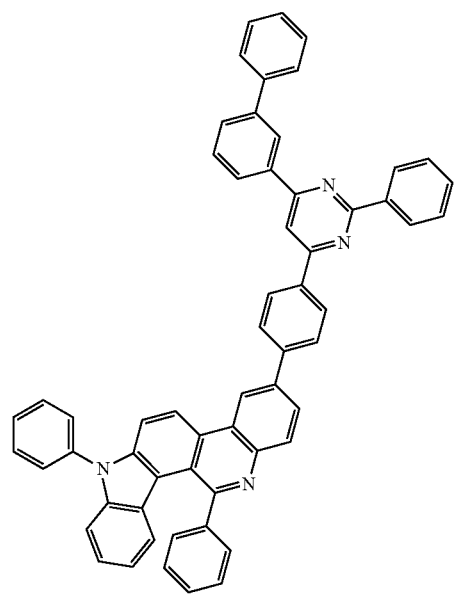
12-17
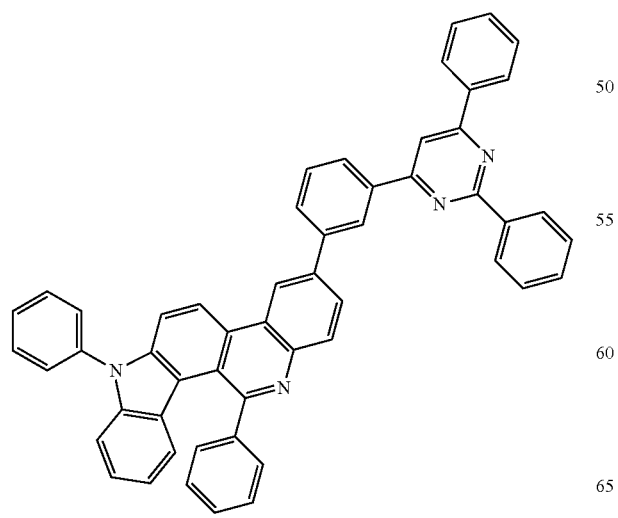
766
-continued
12-18
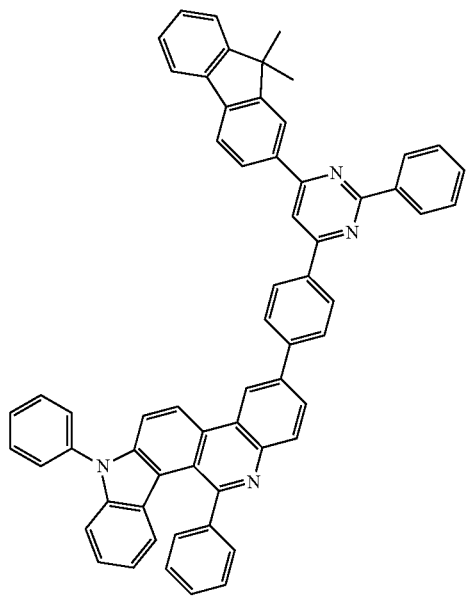
12-19
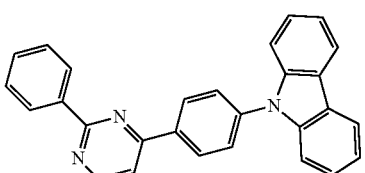

767
-continued
12-20
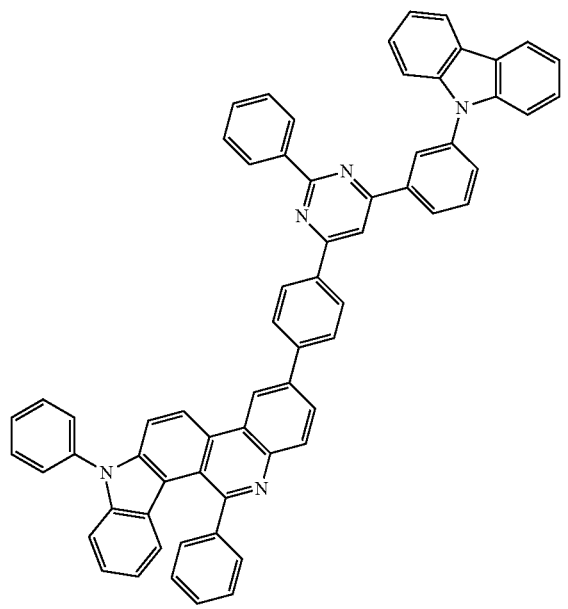
12-21
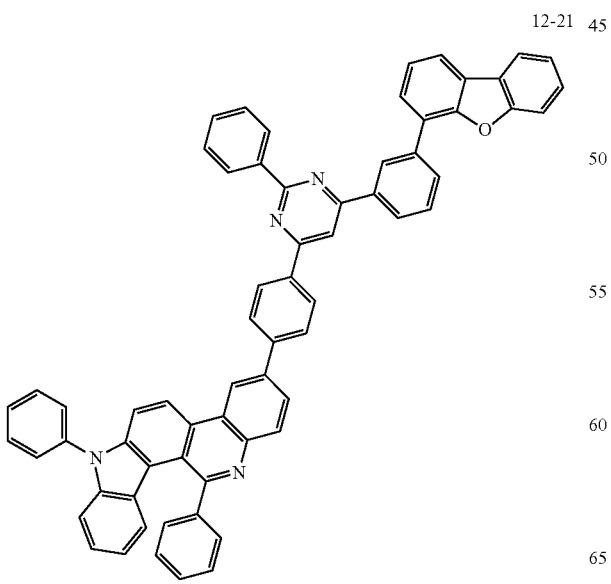
768
-continued
12-22
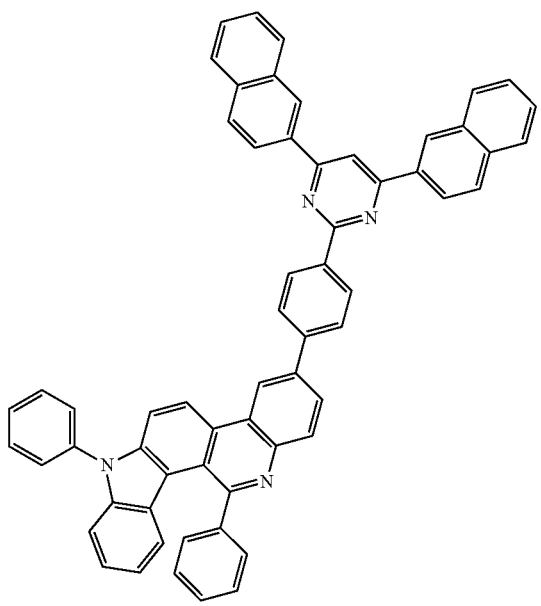
12-23
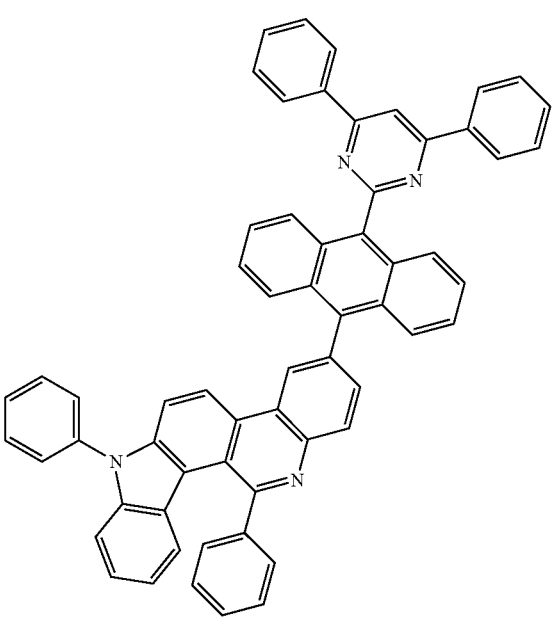

-continued
12-24
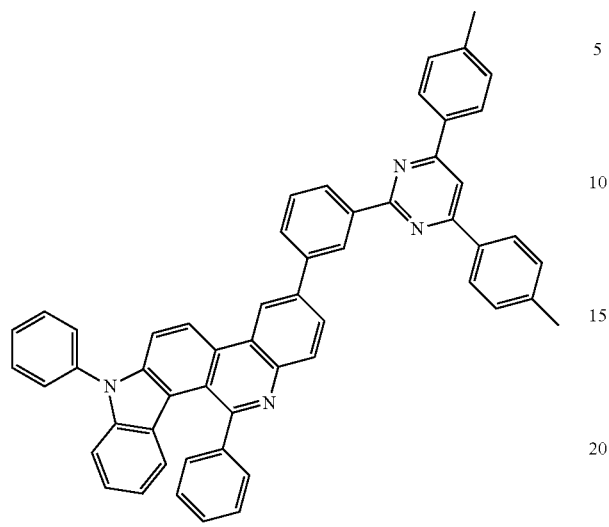
12-25
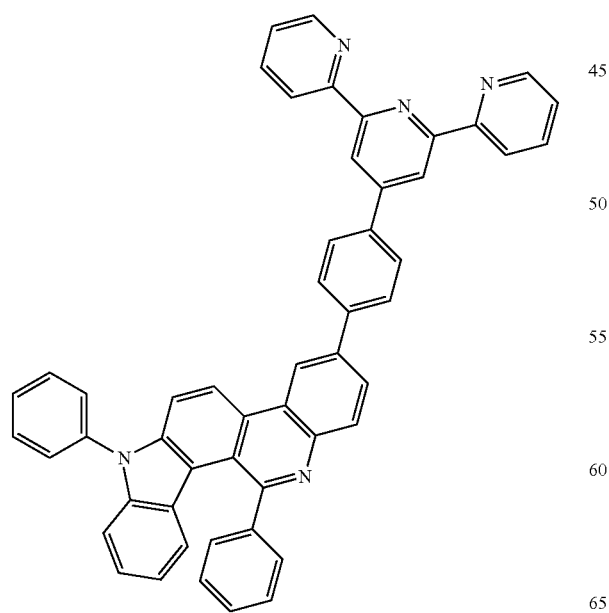
-continued
12-26
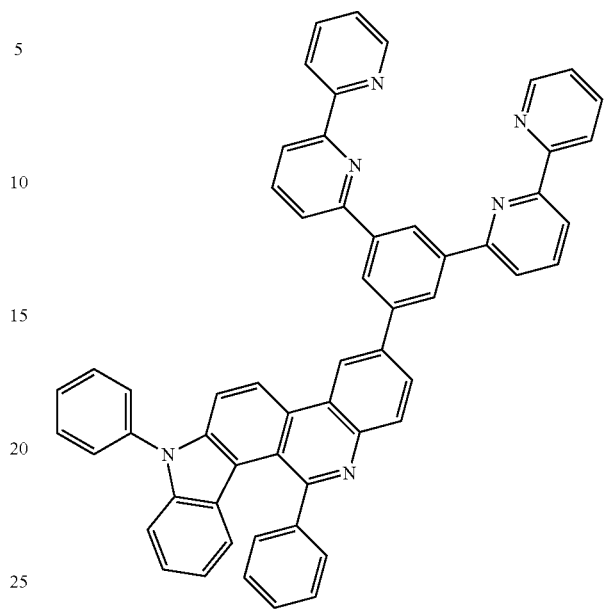
12-27
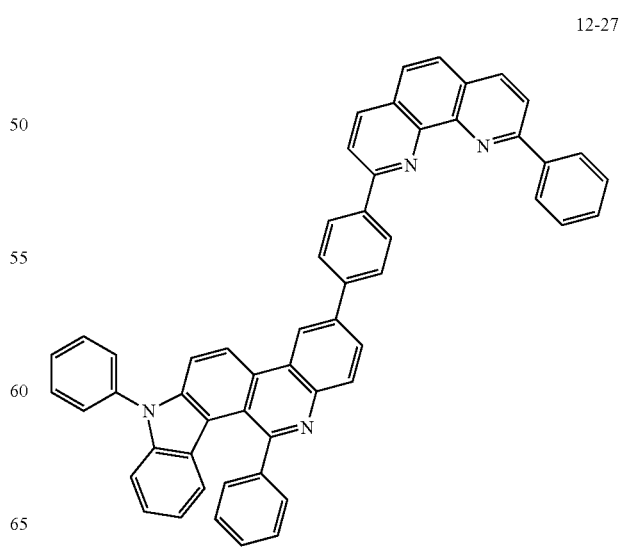

-continued
12-28
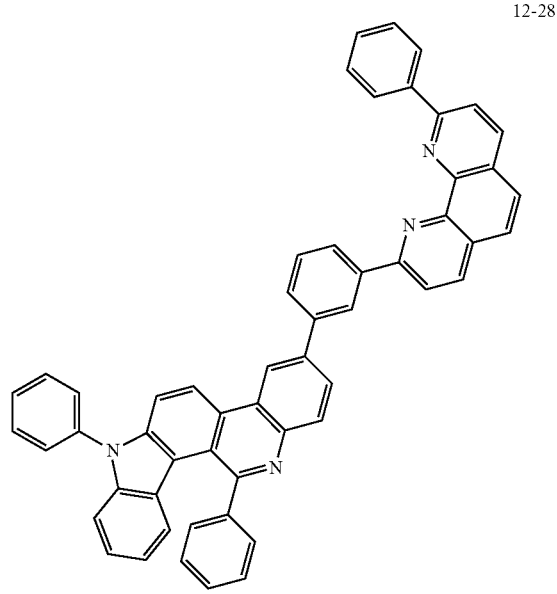
12-29
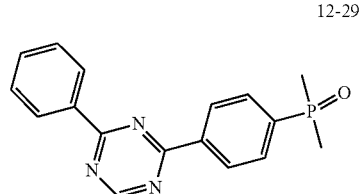
12-30
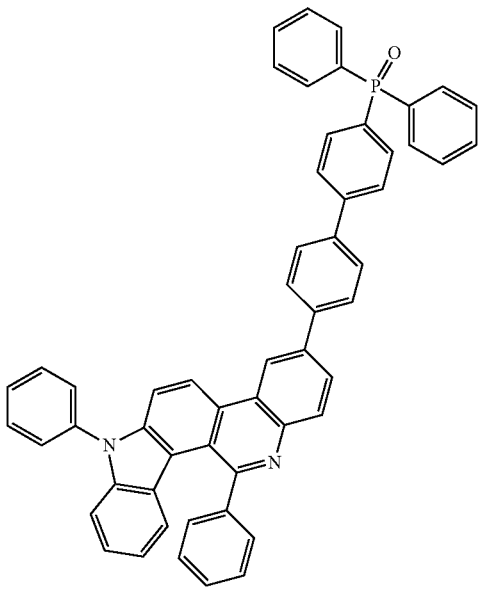
12-31
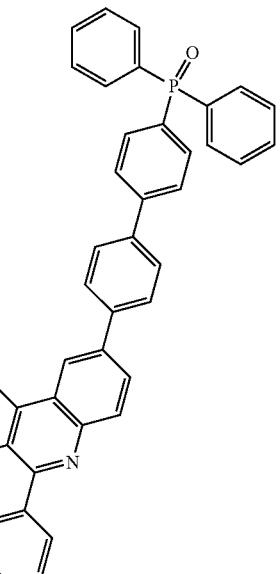

773
-continued
12-32
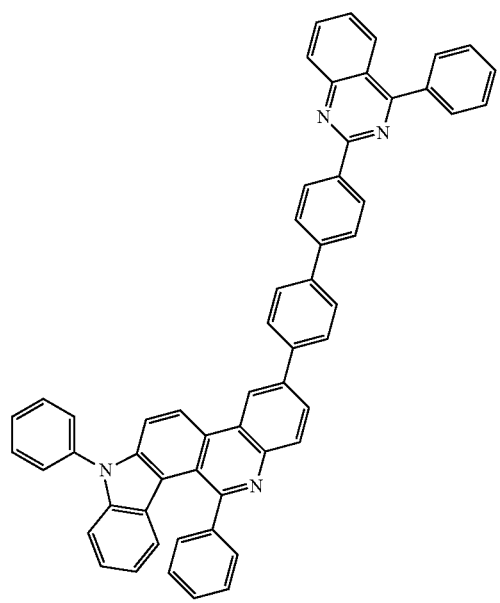
12-33
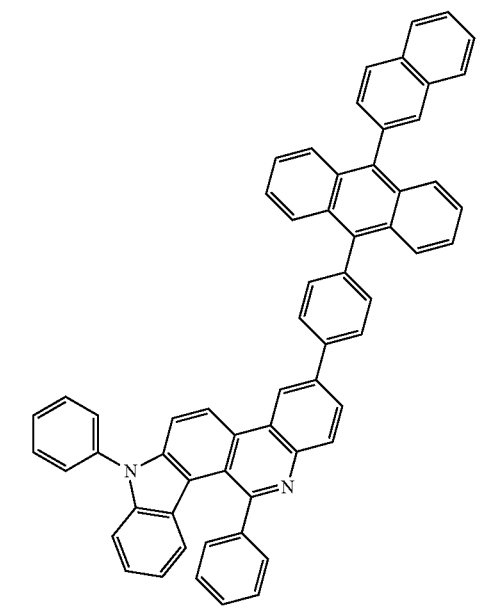
13
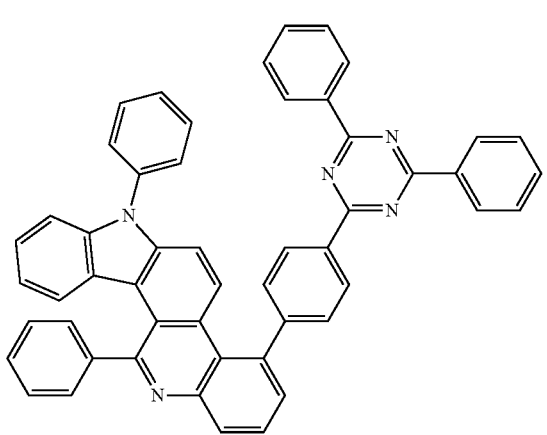
774
-continued
13-1
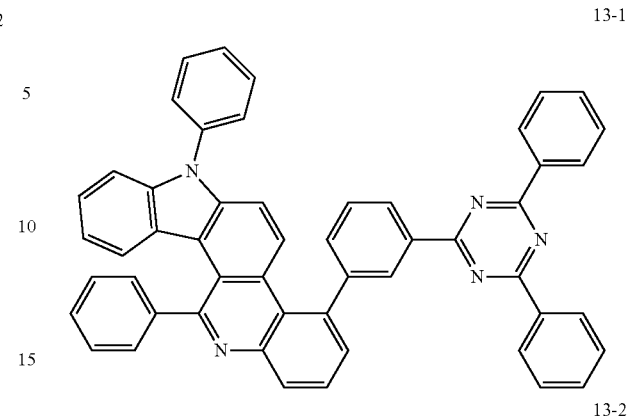
13-2
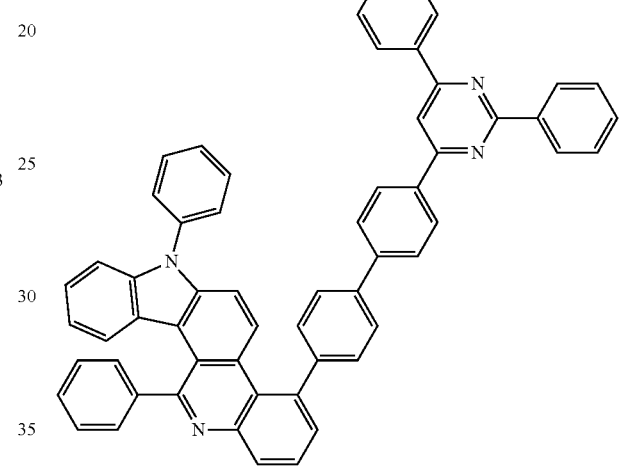
13-3
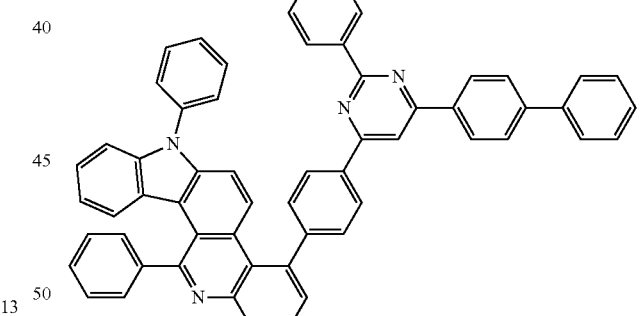
13-4
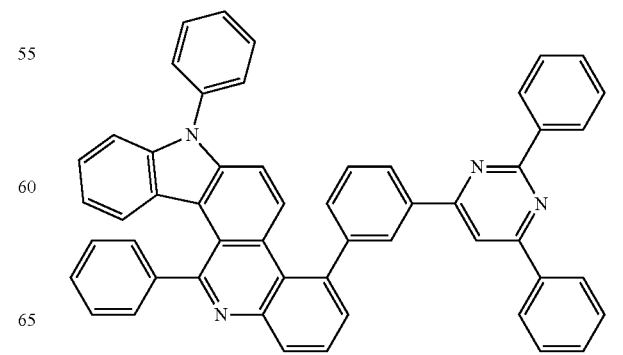

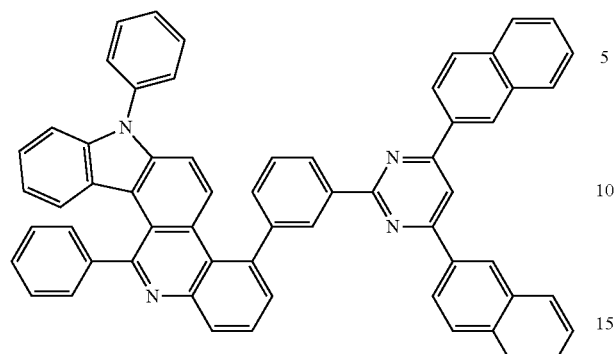
13-5
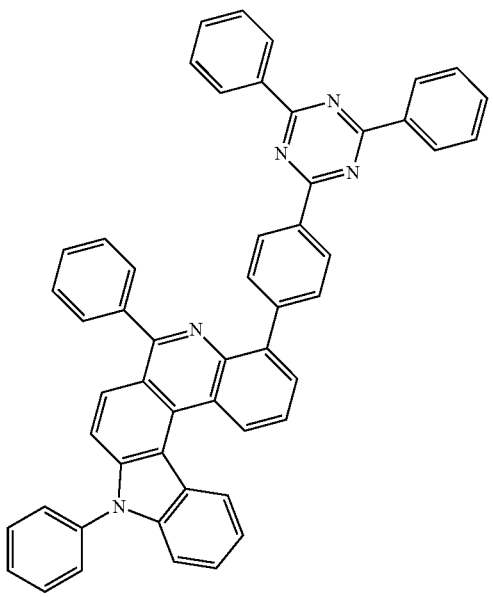
14
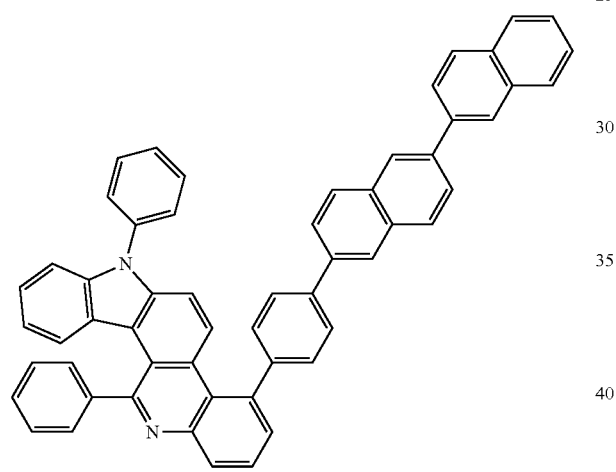
13-6
13-7
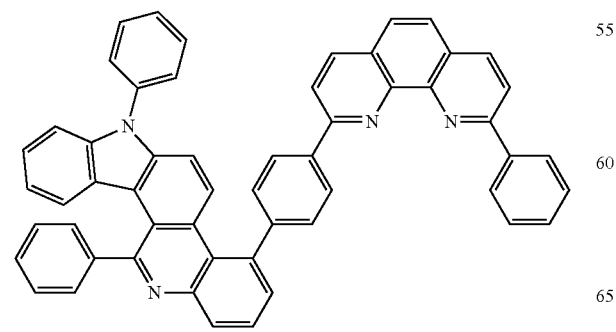
14-1

777
-continued
14-2
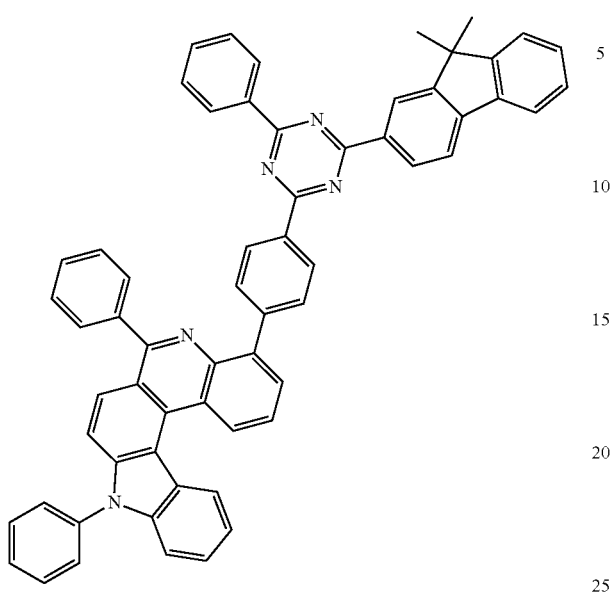
778
-continued
14-4
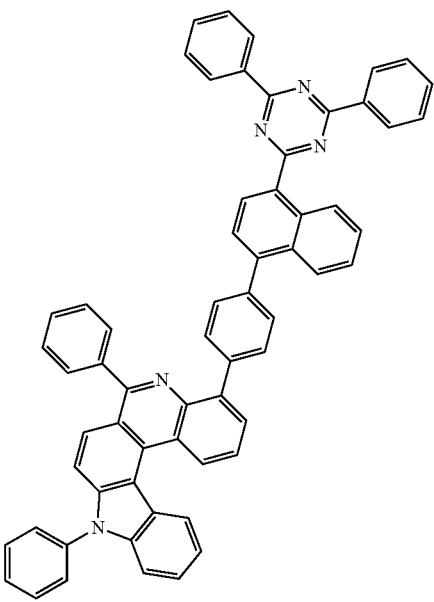
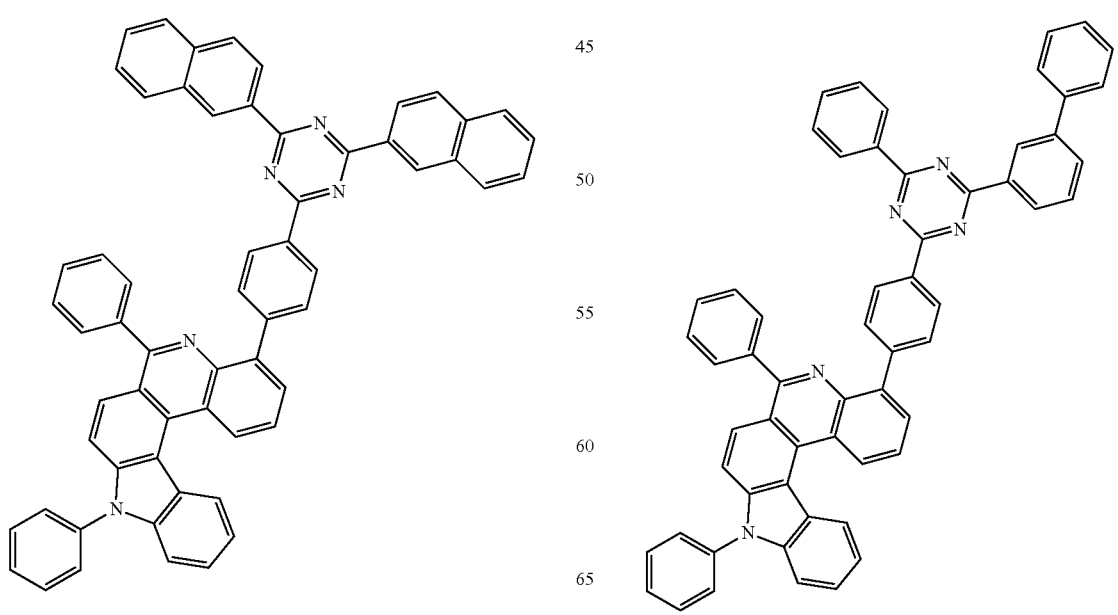
14-3
14-5

14-6
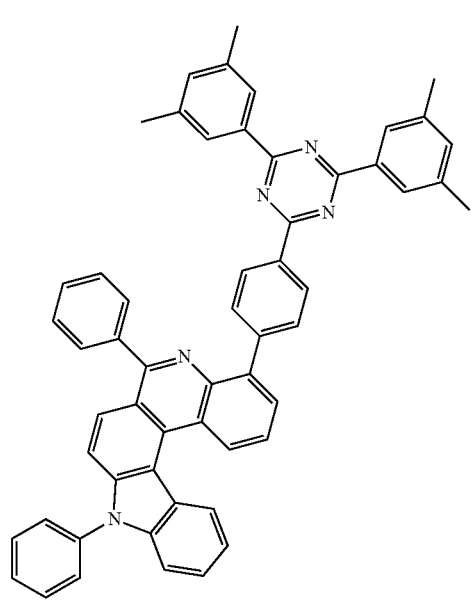
14-8
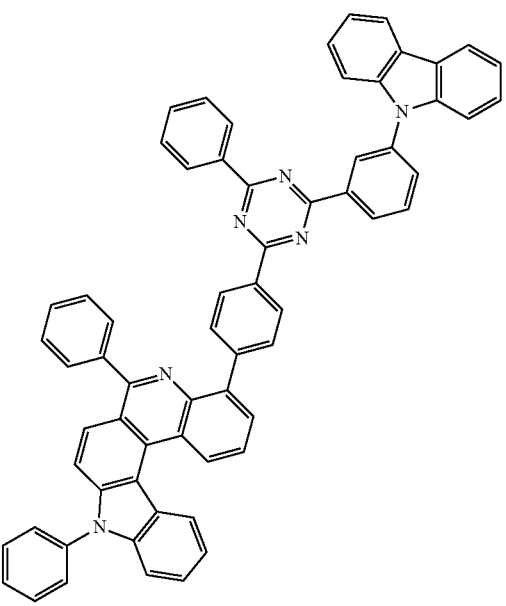
14-7
14-9

14-10
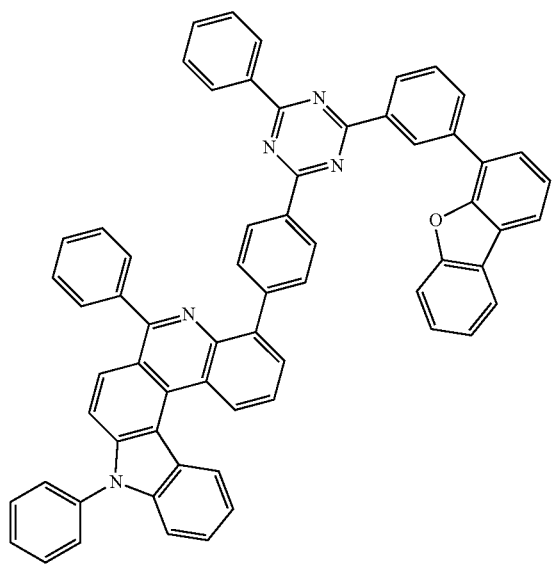
14-12
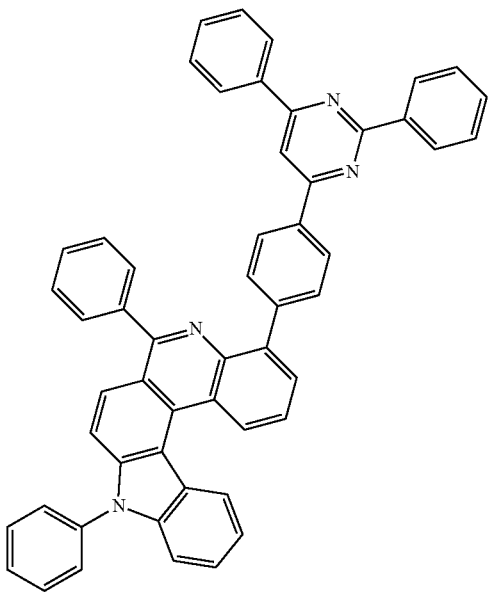
14-11
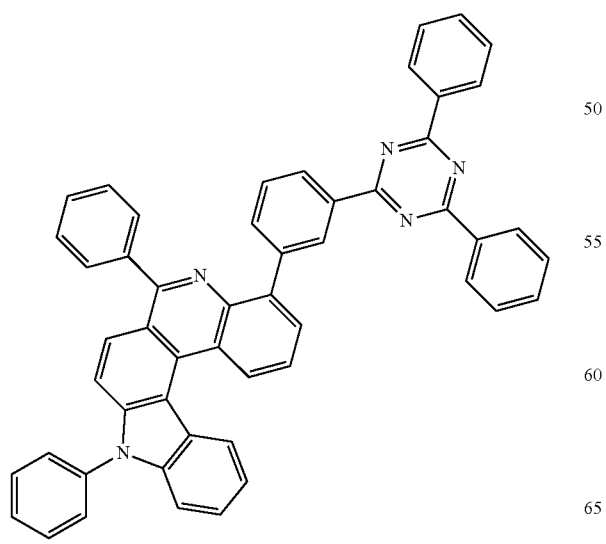
14-13
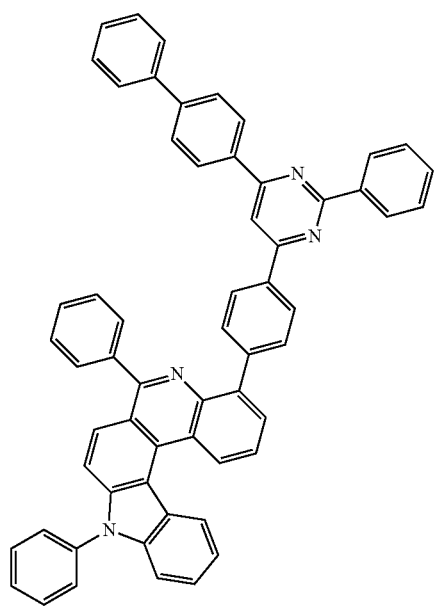

14-14
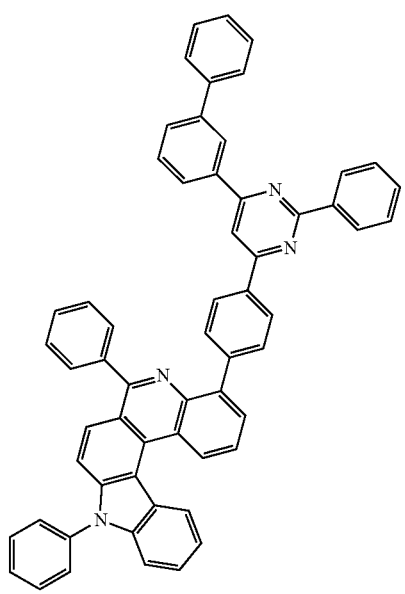
14-16
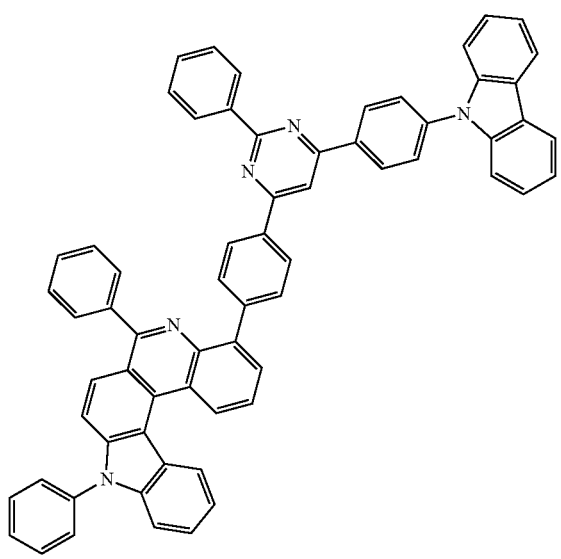
14-15
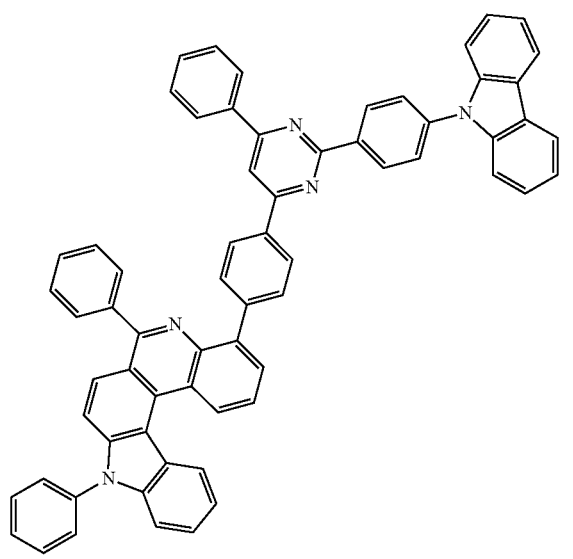
14-17
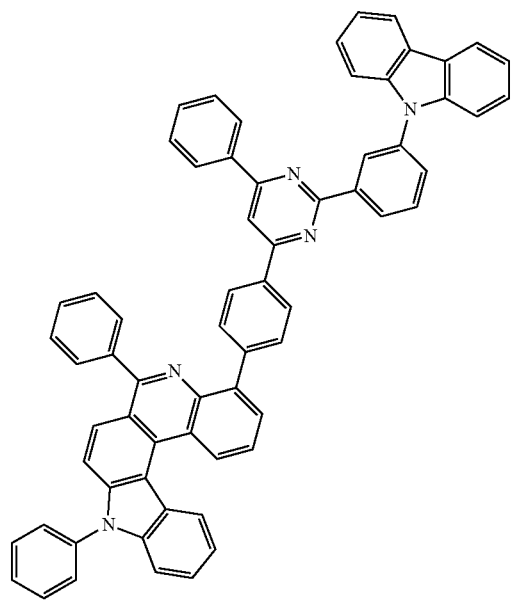

14-18
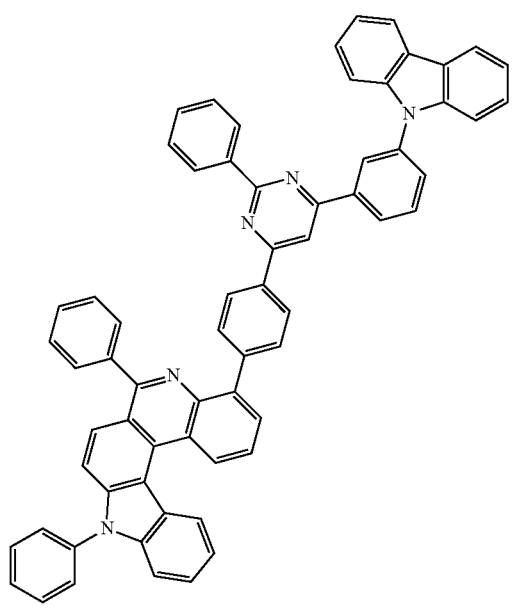
14-19
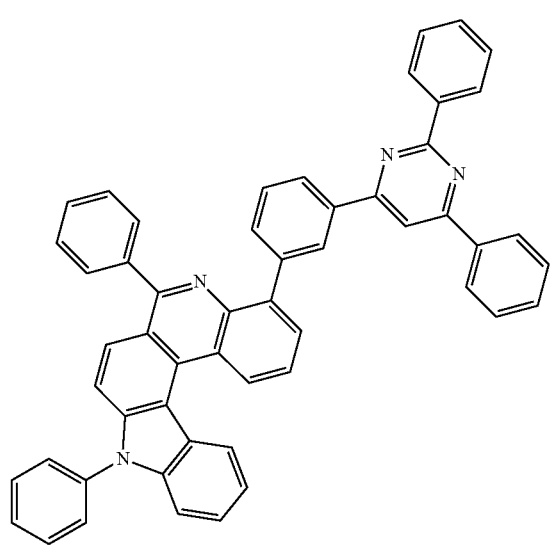
14-20
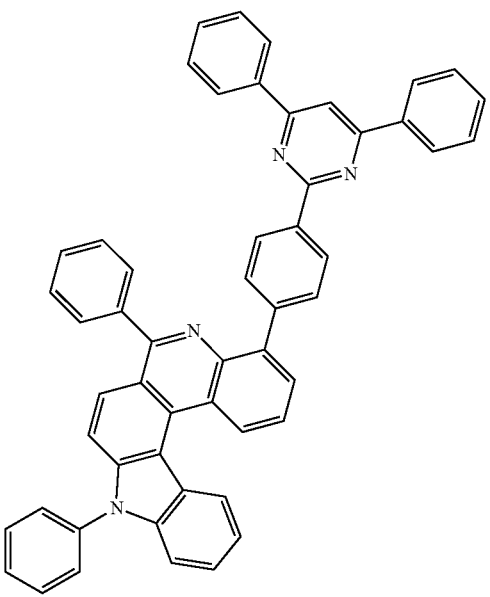
14-21
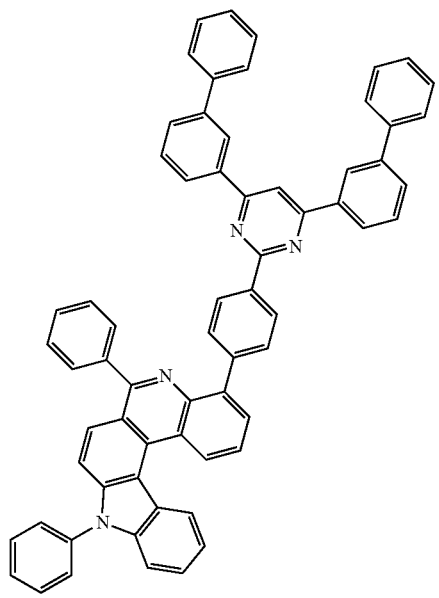

787
-continued
14-22
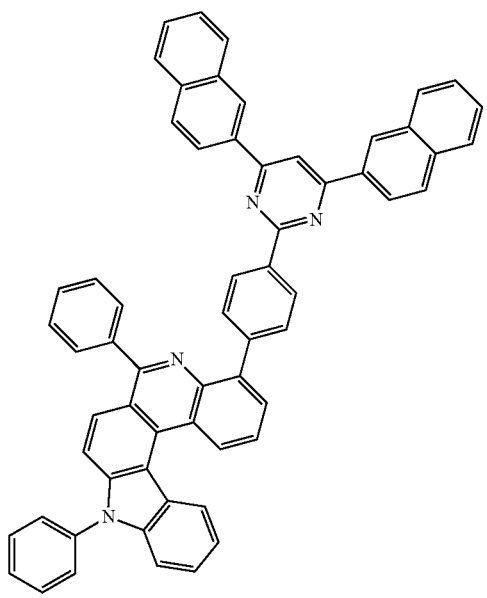
14-23
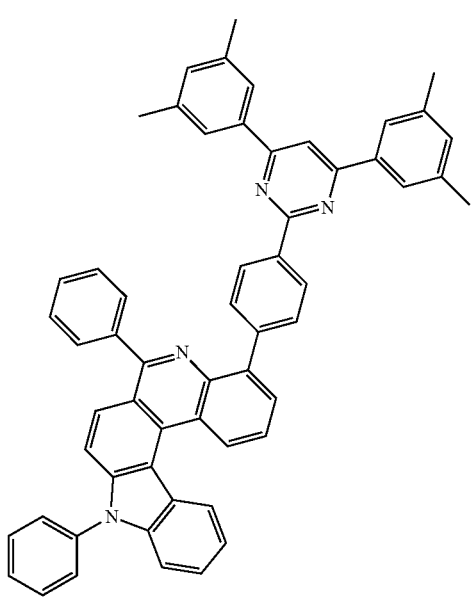
788
-continued
14-24
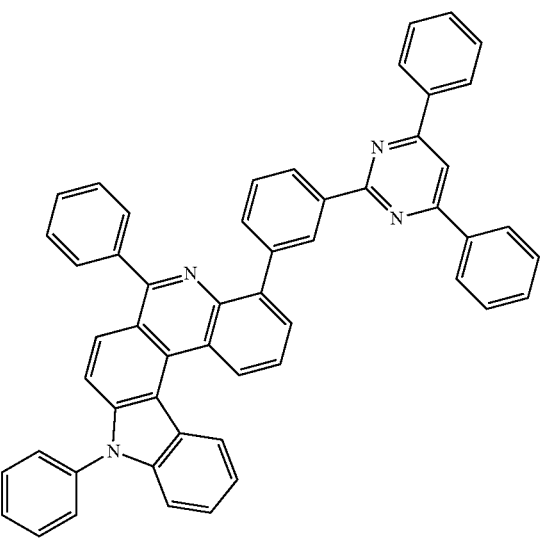
14-25
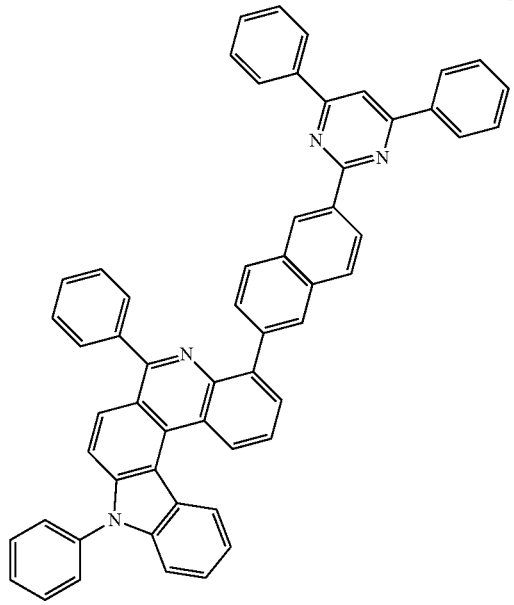

789
-continued
14-26
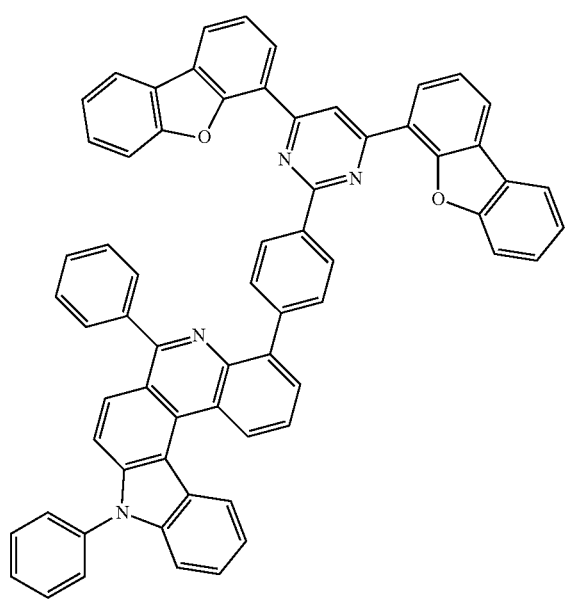
14-27
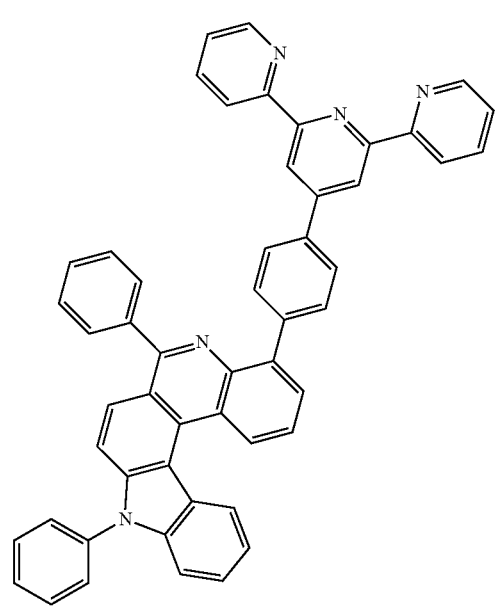
790
-continued
14-28
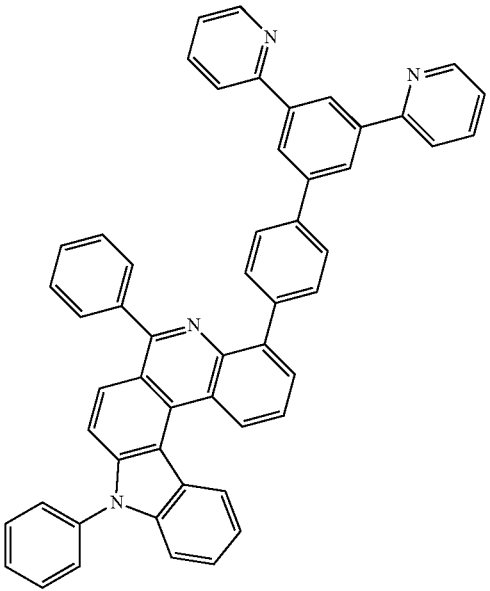
14-29
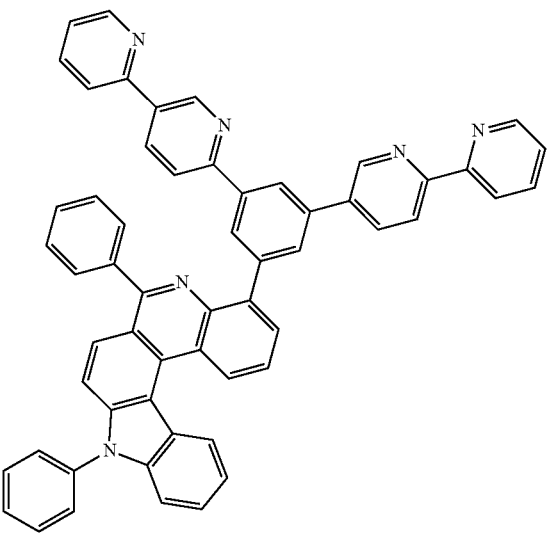

14-30
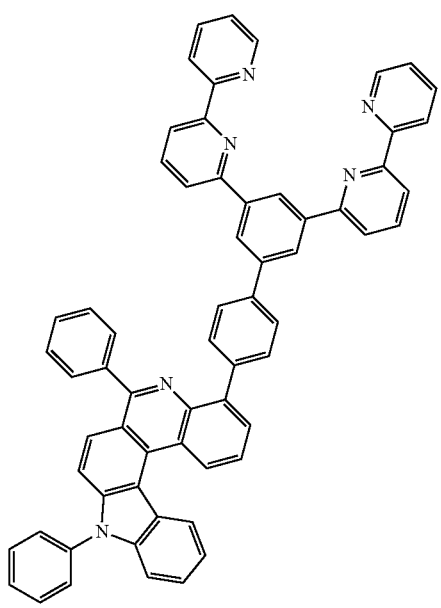
14-32
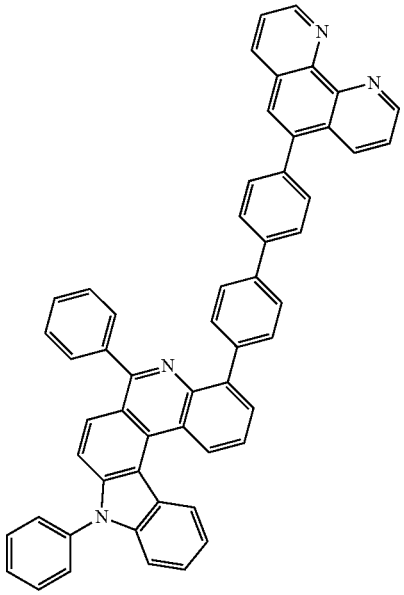 [SMILES: c1ccc(-c2nc3c(-c4ccc(-c5ccc(-c6cc7cccnc7c7ncccc67)c6ccccc56)cc4)cccc3c3c2ccc2c3c3ccccc3n2-c2ccccc2)cc1]
14-31
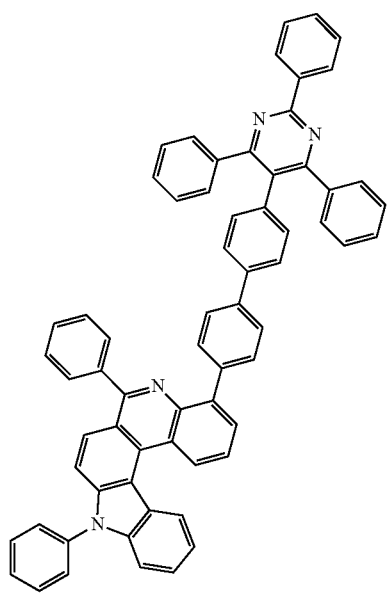
14-33

793
-continued
14-34
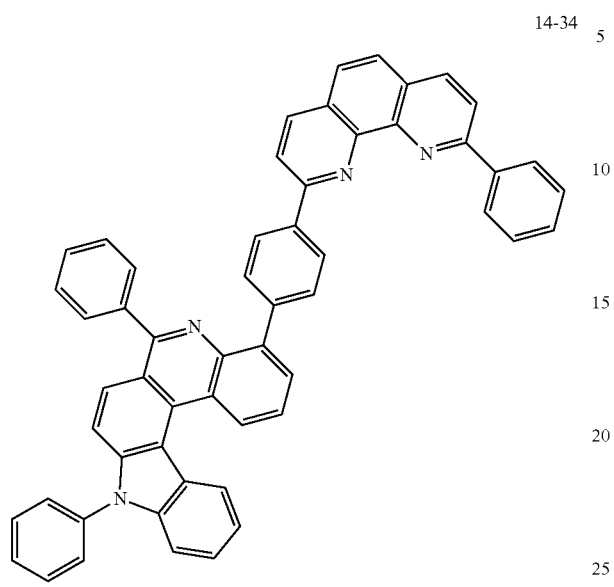
794
-continued
14-36
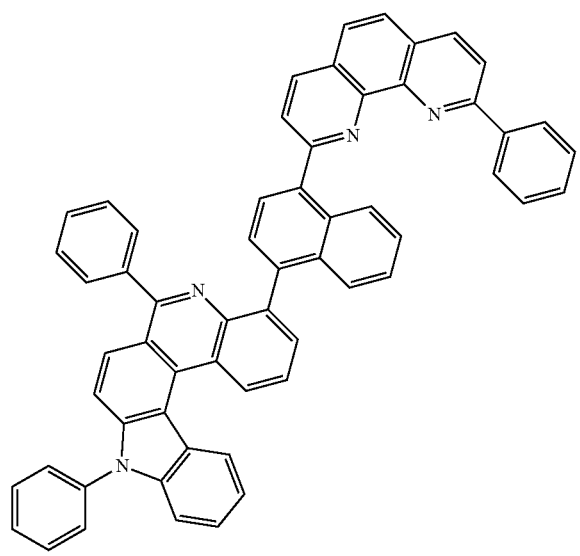
14-35
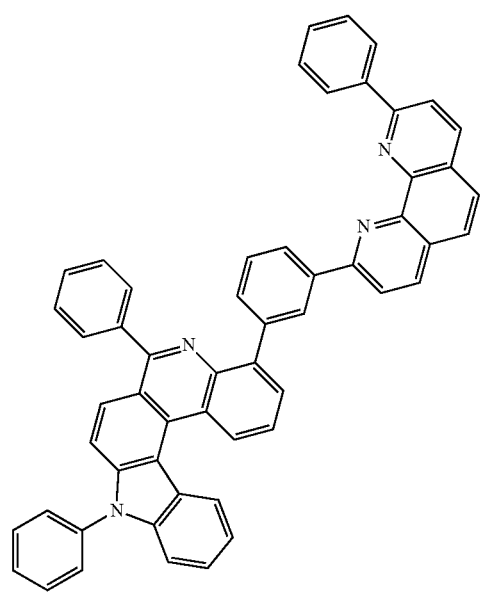
14-37
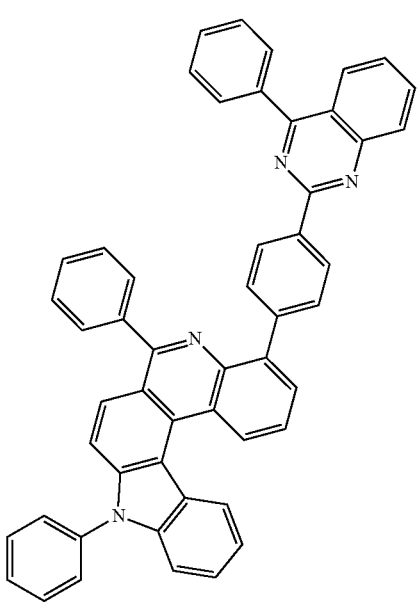

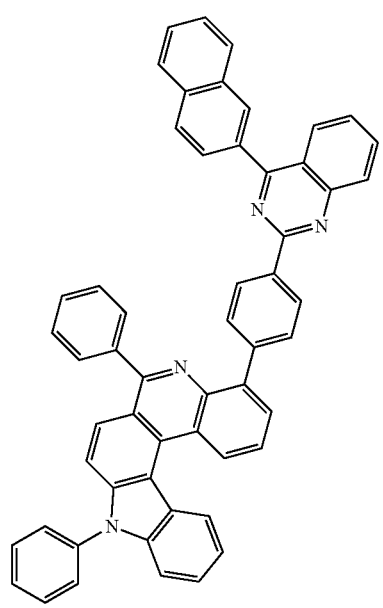
14-38
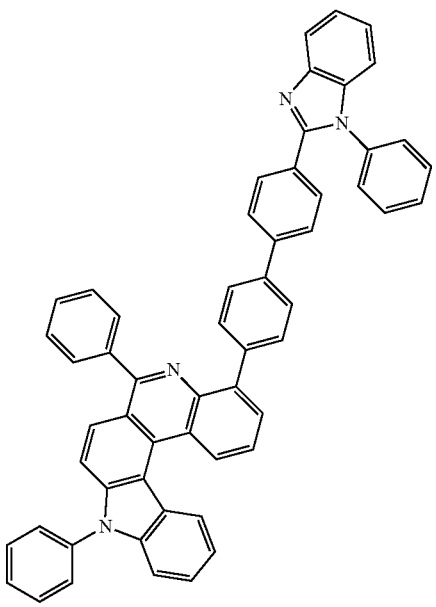
14-40
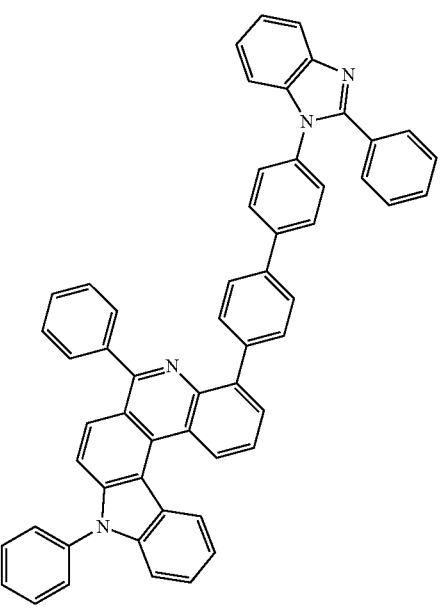
14-41
14-39

14-42
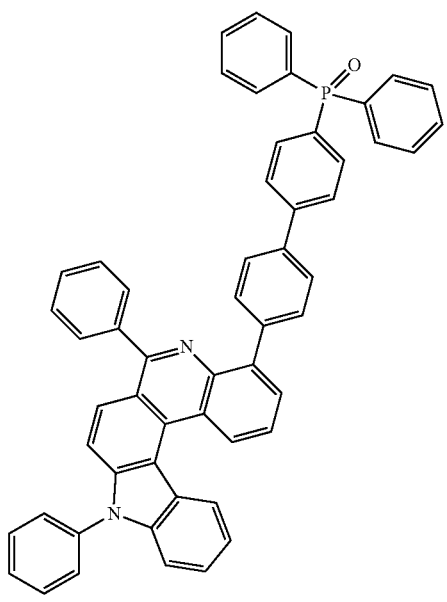
14-44
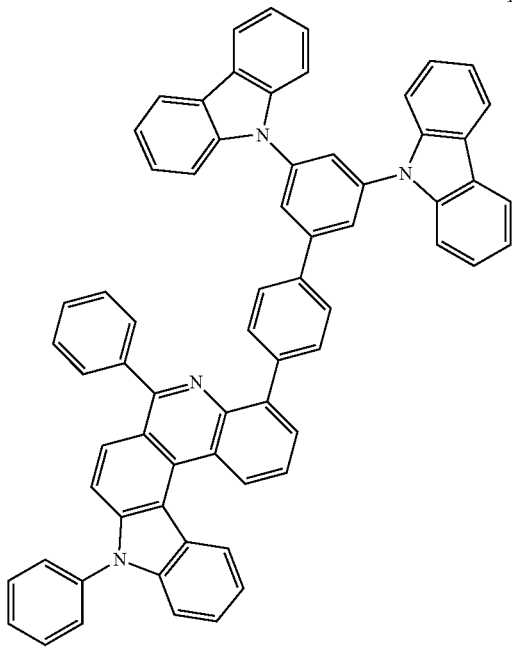
14-43
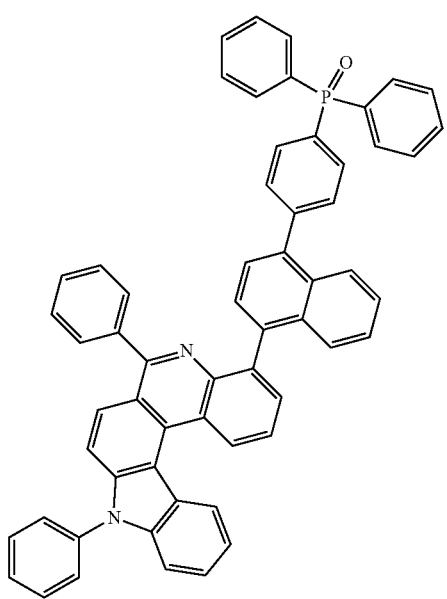 [SMILES: O=P(c1ccccc1)(c1ccccc1)c1ccc(-c2ccc(-c3cccc4c3nc(-c3ccccc3)c3ccc5c(c6ccccc6n5-c5ccccc5)c34)c3ccccc23)cc1]
14-45
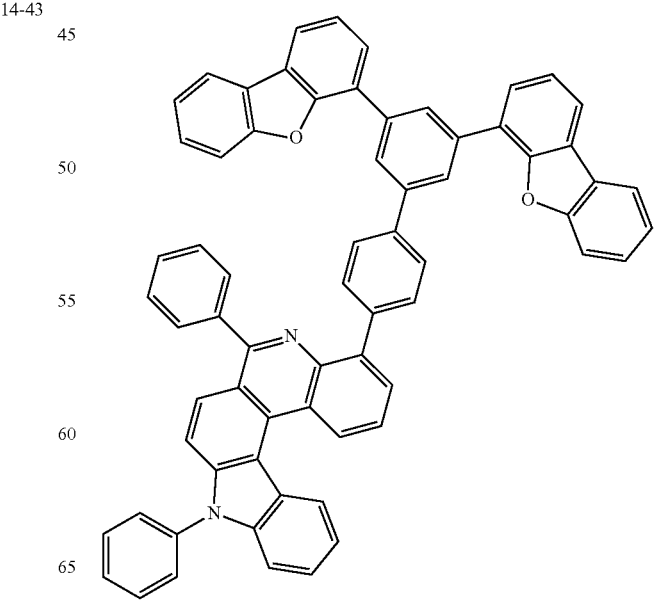

799
-continued
14-46
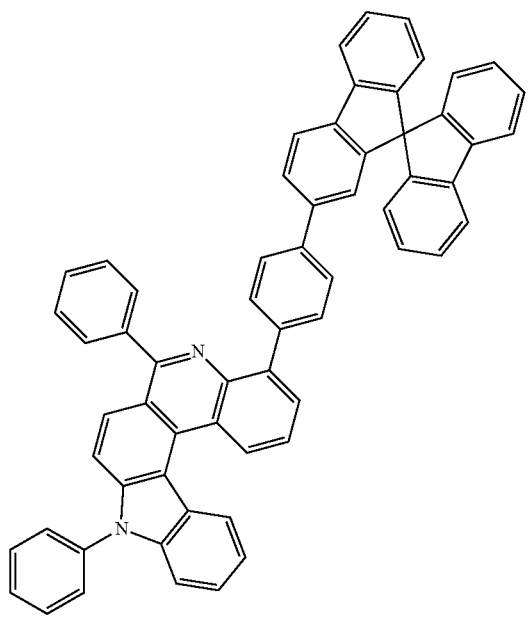
14-47
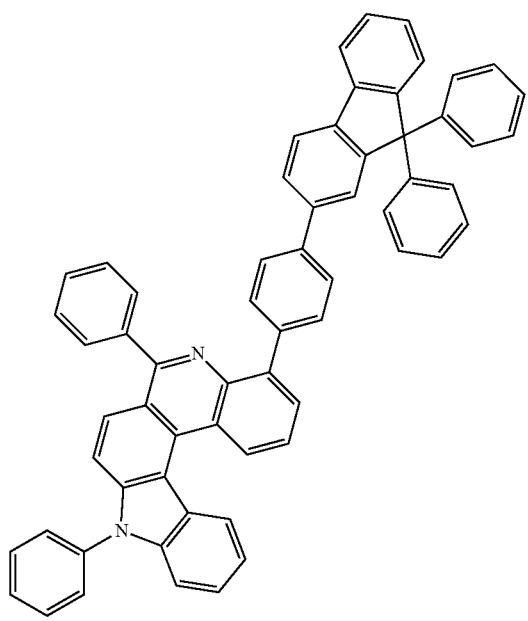
800
-continued
14-48
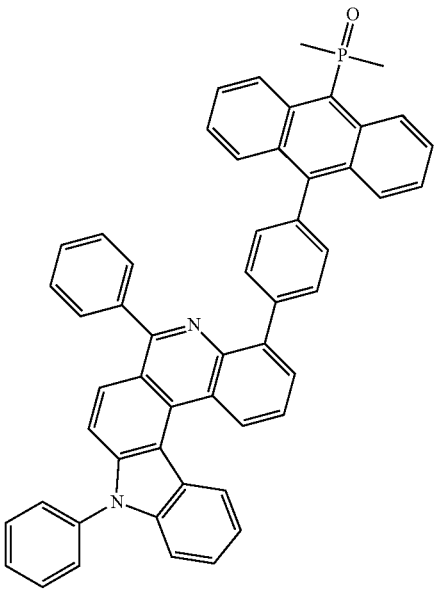
14-49
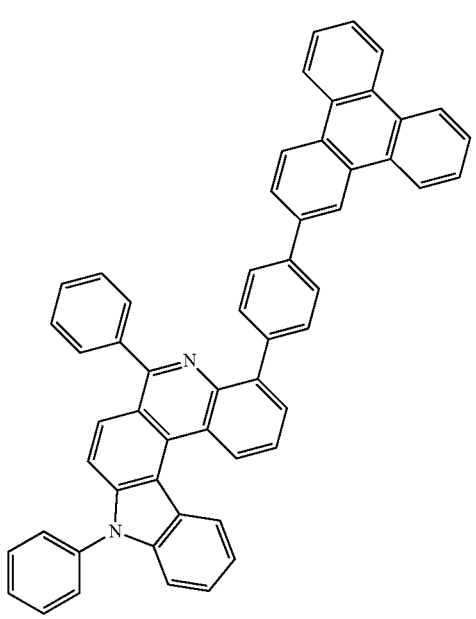

801
-continued
14-50
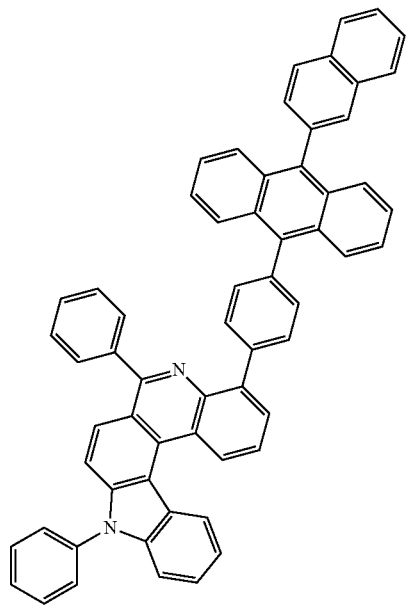
14-51
802
-continued
14-52
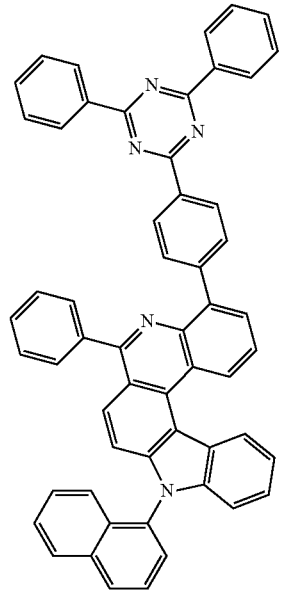
14-53
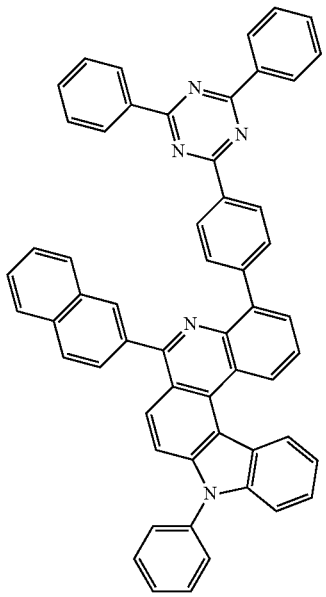

803
-continued
14-54
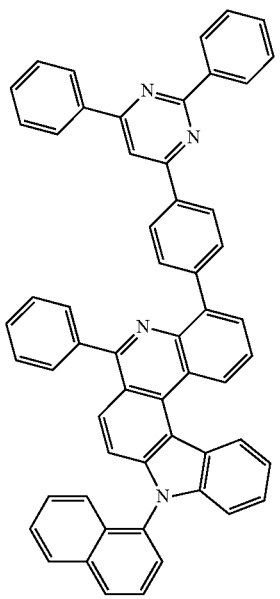
14-55
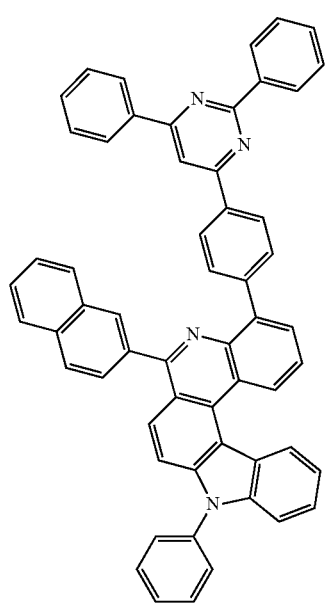
804
-continued
15
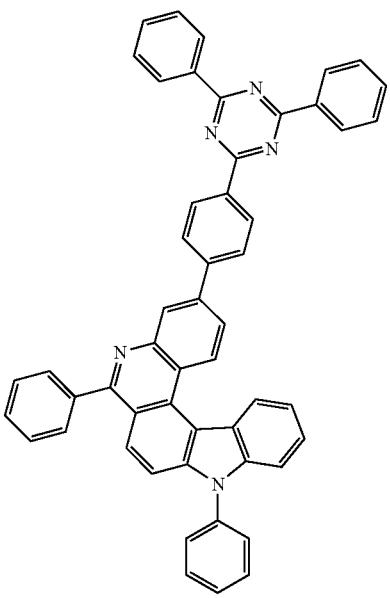
15-1
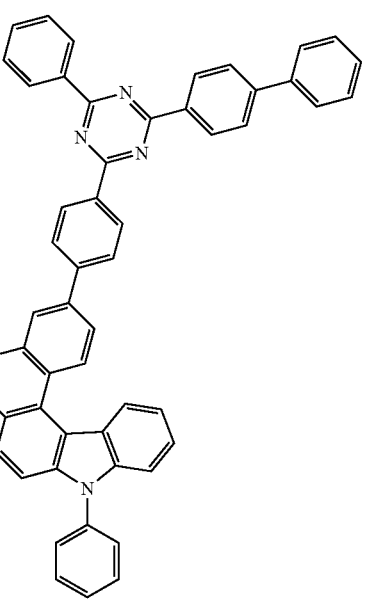

805
-continued
15-2
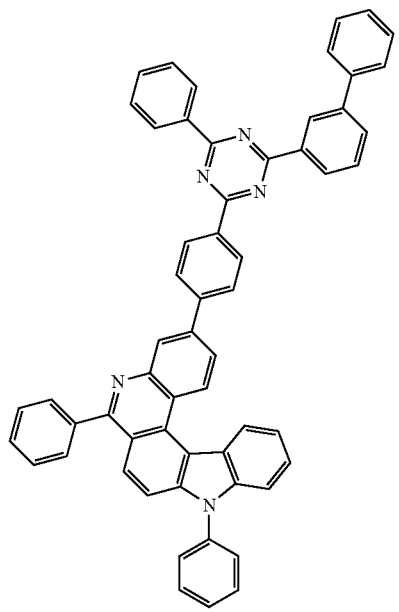 [SMILES: c1ccc(-c2cccc(-c3nc(-c4ccccc4)nc(-c4ccc(-c5ccc6c(c5)nc(-c5ccccc5)c5ccc7c(c8ccccc8n7-c7ccccc7)c56)cc4)n3)c2)cc1]
15-3
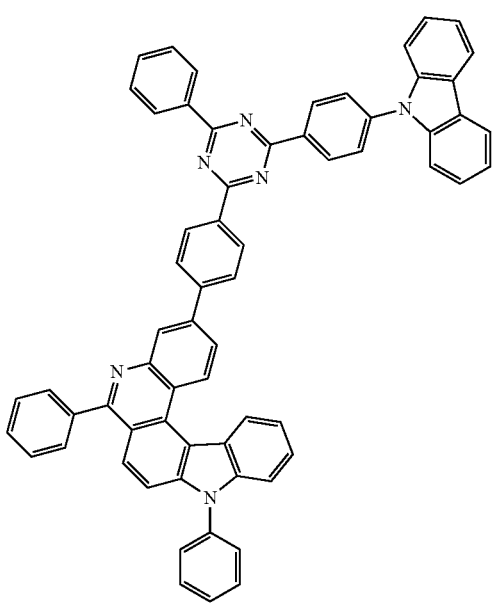
806
-continued
15-4
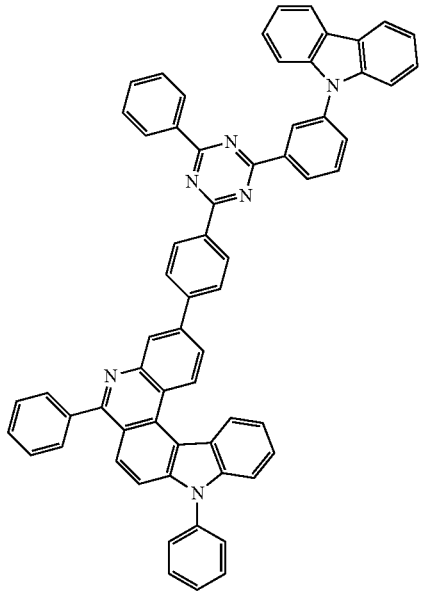 [SMILES: c1ccc(-c2nc(-c3ccc(-c4ccc5c(c4)nc(-c4ccccc4)c4ccc6c(c7ccccc7n6-c6ccccc6)c45)cc3)nc(-c3cccc(-n4c5ccccc5c5ccccc54)c3)n2)cc1]
15-5
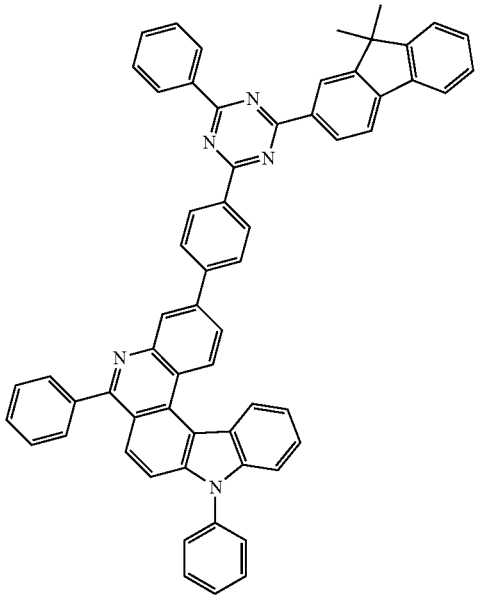

807
-continued
15-6
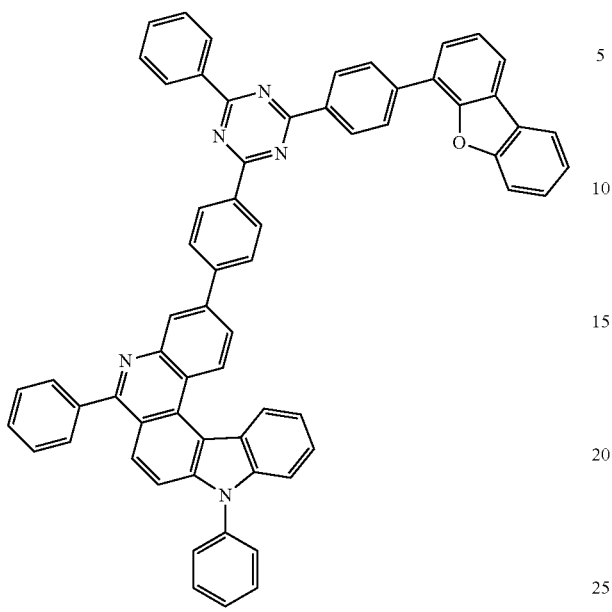
15-7
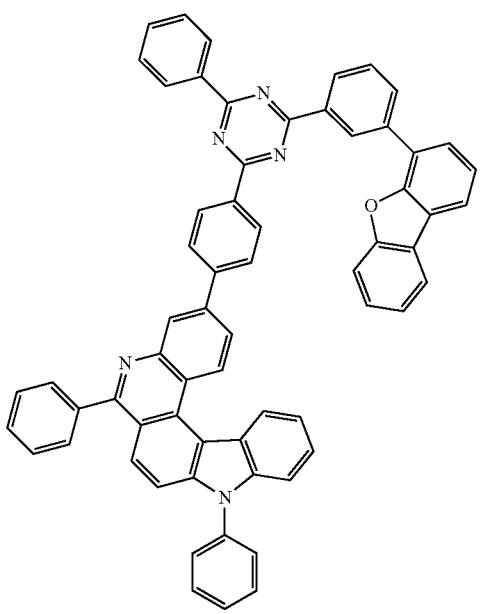
808
-continued
15-8
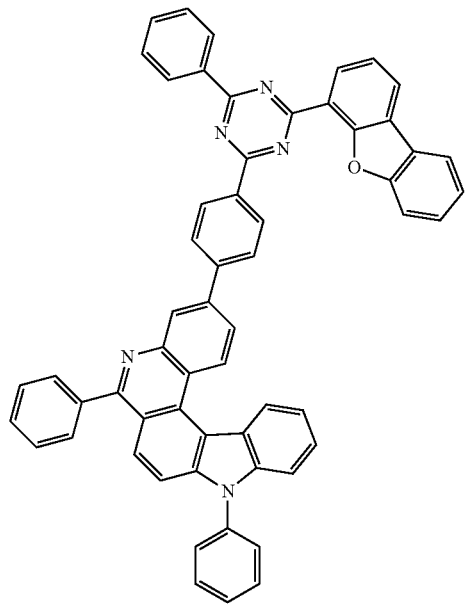 [SMILES: c1ccc(-c2nc(-c3ccc(-c4ccc5c(c4)nc(-c4ccccc4)c4ccc6c(c7ccccc7n6-c6ccccc6)c45)cc3)nc(-c3cccc4c3oc3ccccc34)n2)cc1]
15-9
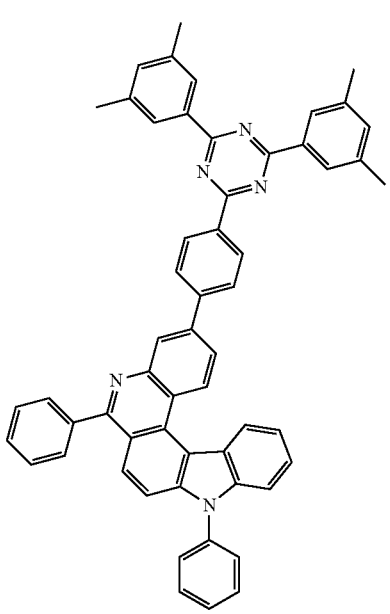

809
-continued
15-10
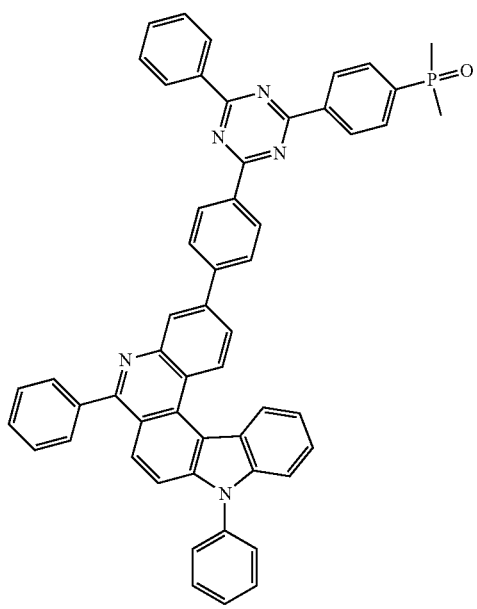
15-11
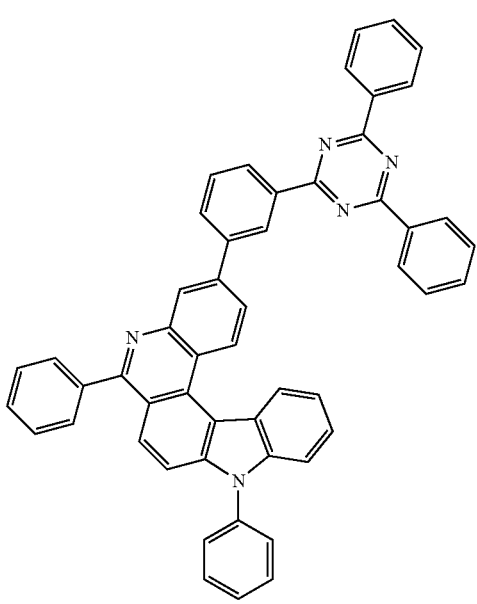 [SMILES: c1ccc(-c2nc(-c3ccccc3)nc(-c3cccc(-c4ccc5c(c4)nc(-c4ccccc4)c4ccc6c(c7ccccc7n6-c6ccccc6)c45)c3)n2)cc1]
810
-continued
15-12
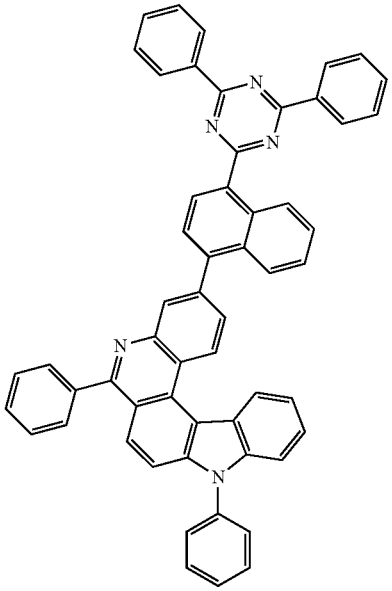
15-13
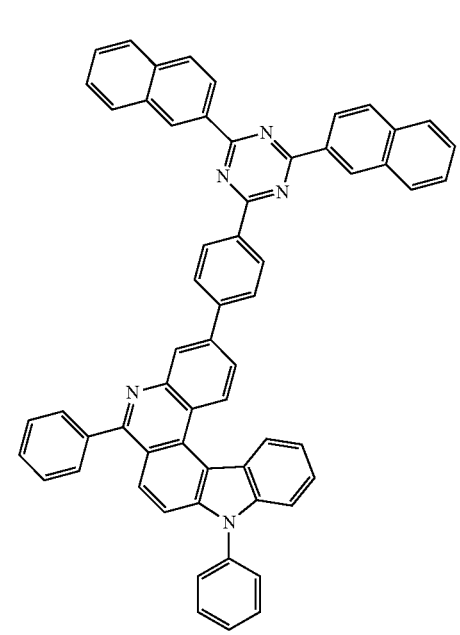

-continued
15-14
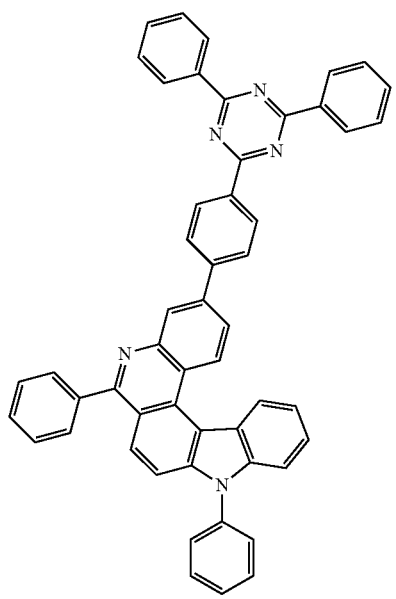
15-15
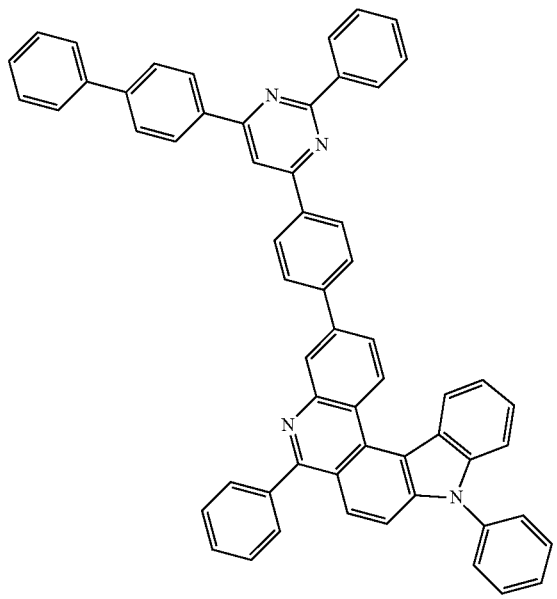
-continued
15-16
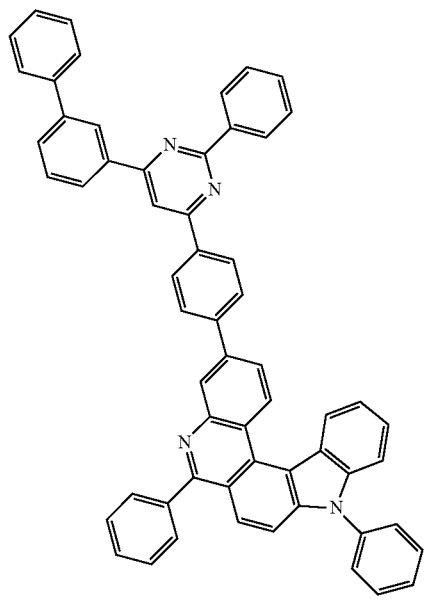
15-17
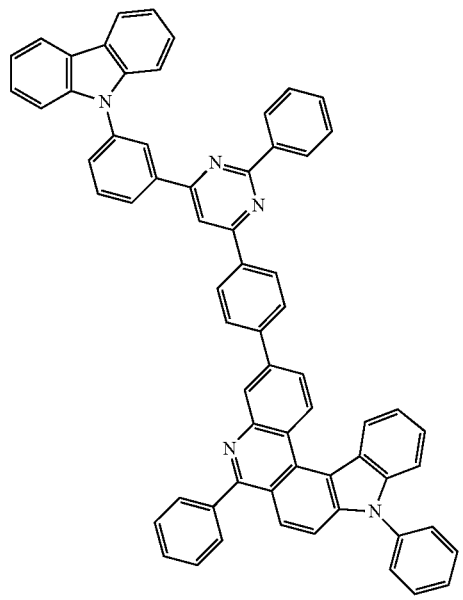

-continued
15-18
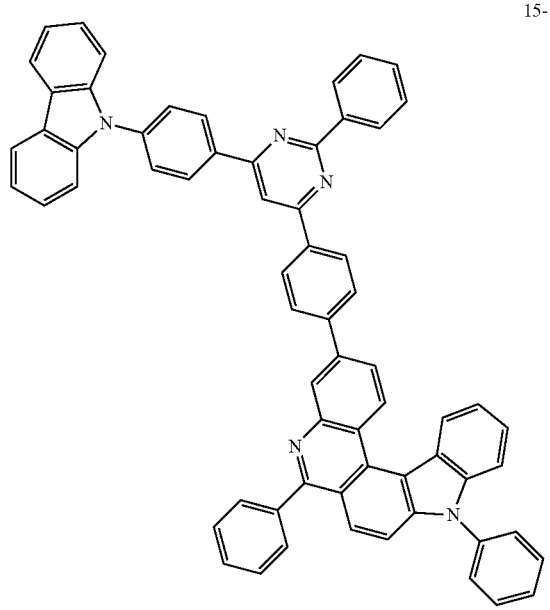
15-19
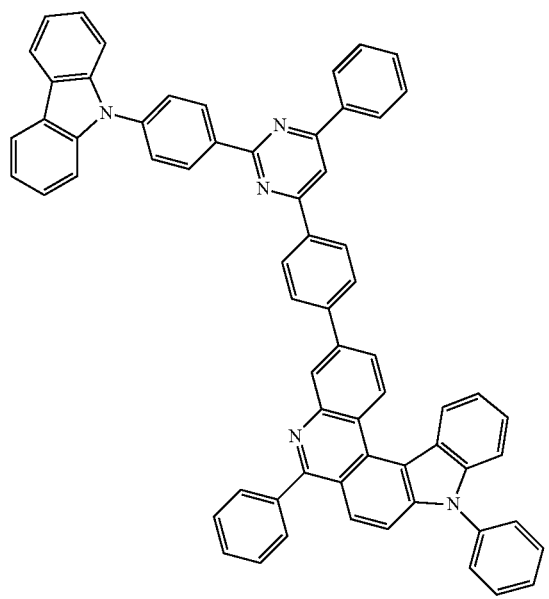
-continued
15-20
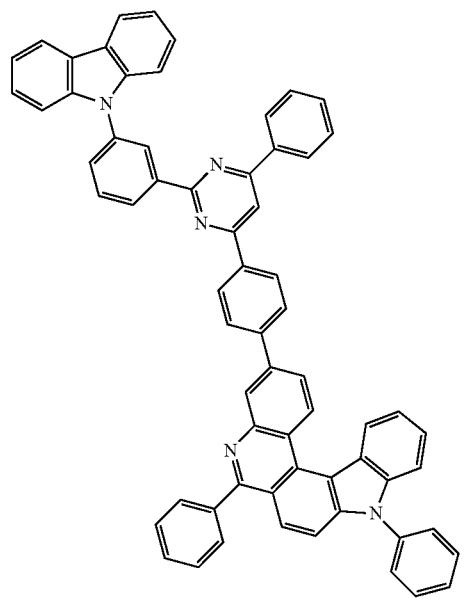
15-21
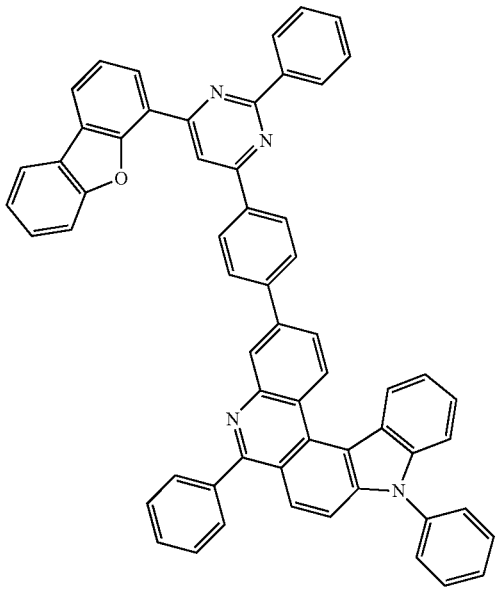

815
-continued
15-22
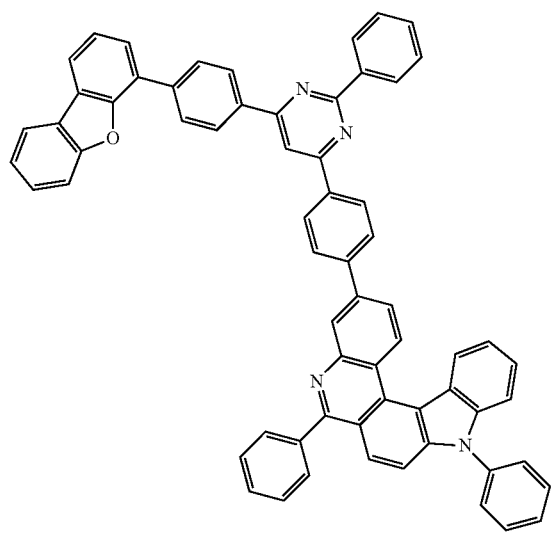
15-23
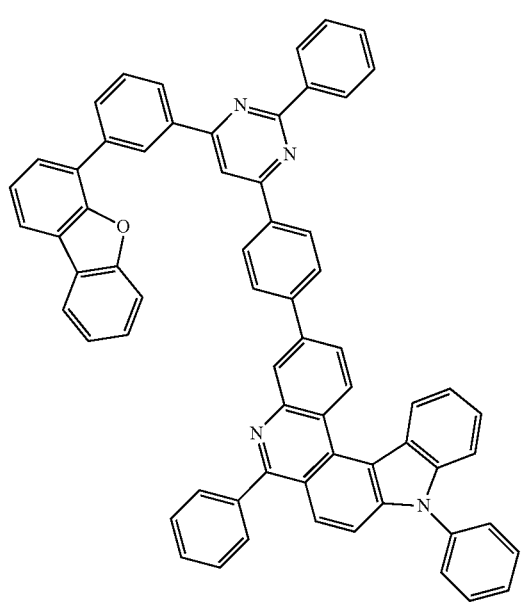
816
-continued
15-24
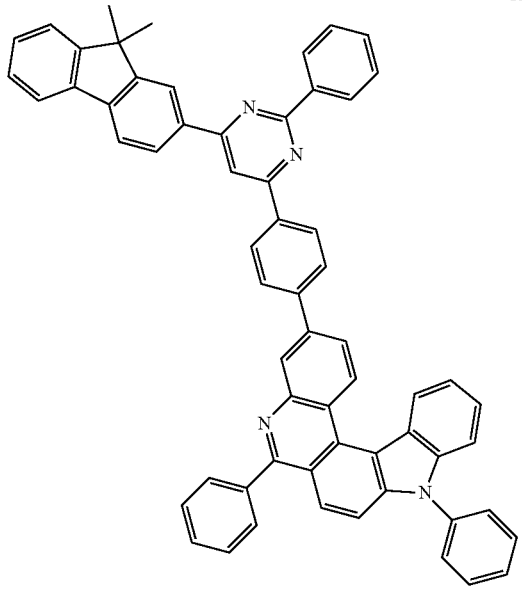
15-25
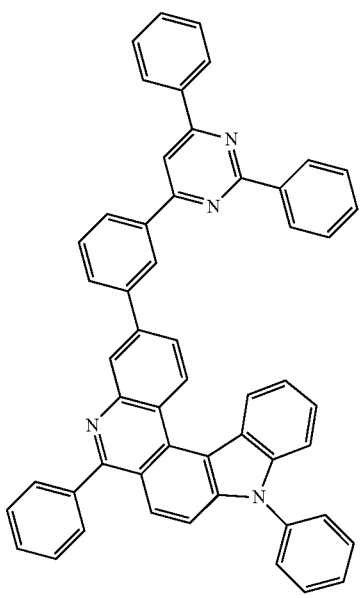

817
-continued
15-26
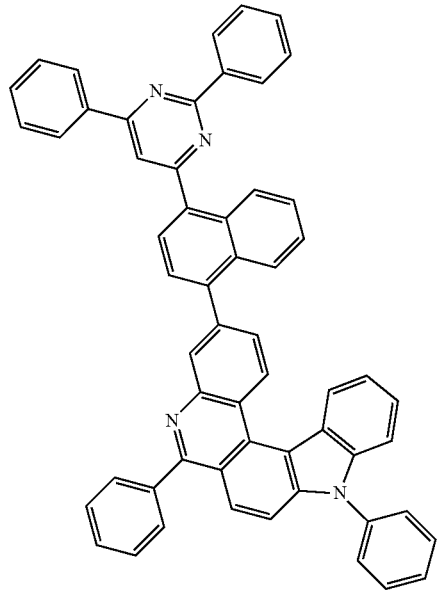
818
-continued
15-28
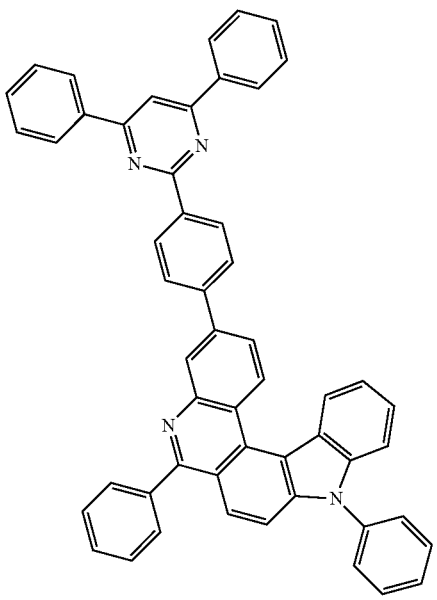
15-27
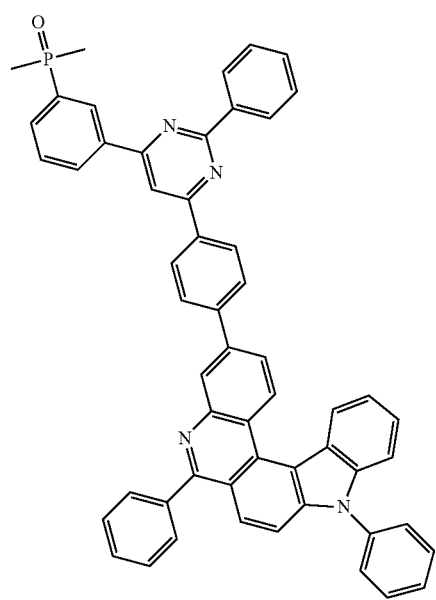
15-29
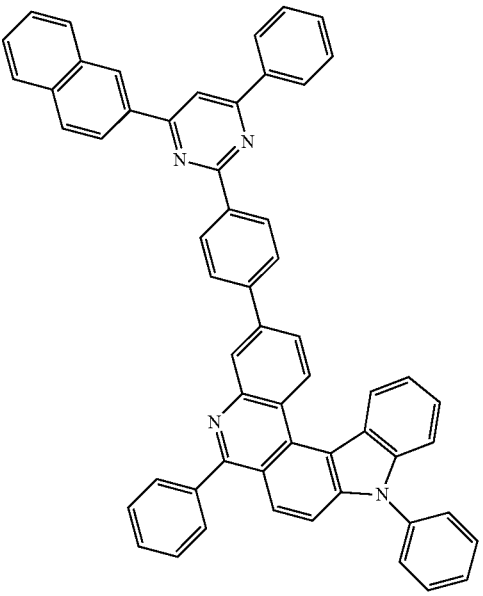

819
-continued
15-30
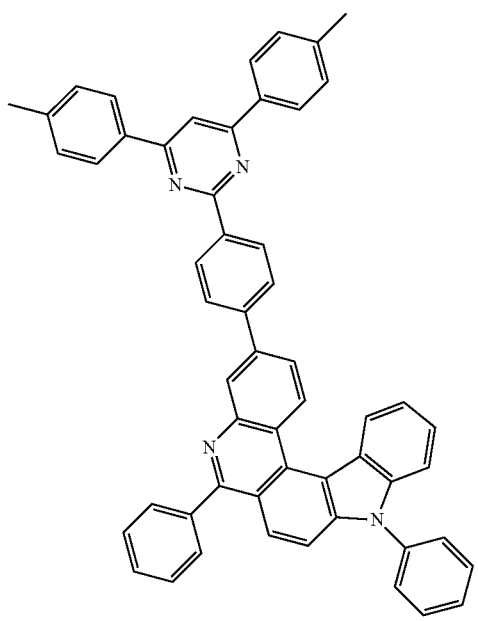 [SMILES: Cc1ccc(-c2cc(-c3ccc(C)cc3)nc(-c3ccc(-c4ccc5c(c4)nc(-c4ccccc4)c4ccc6c(c7ccccc7n6-c6ccccc6)c45)cc3)n2)cc1]
15-31
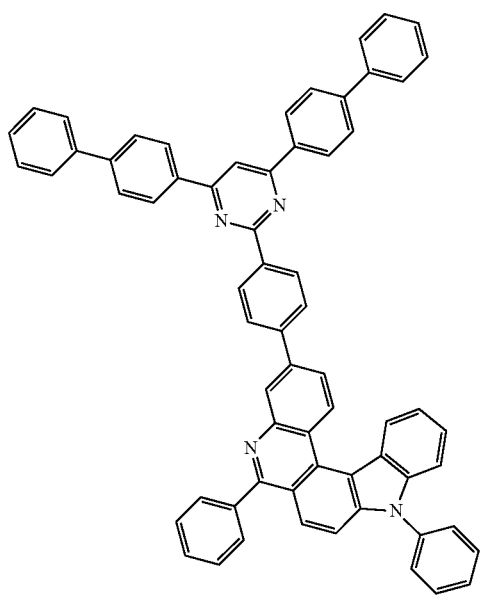
820
-continued
15-32
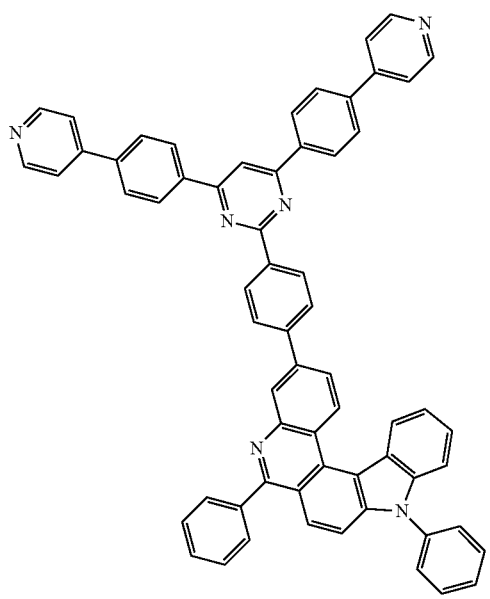
15-33
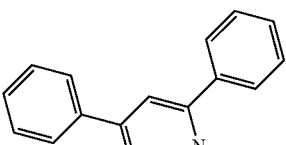
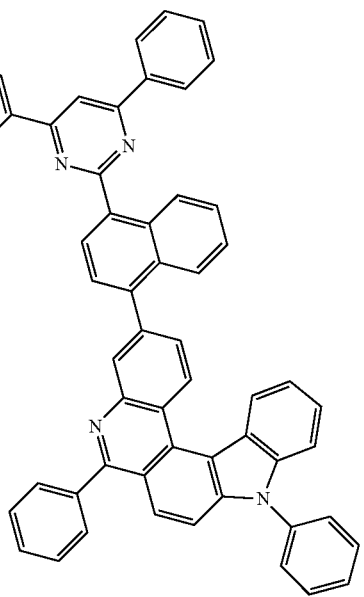

821
-continued
15-38
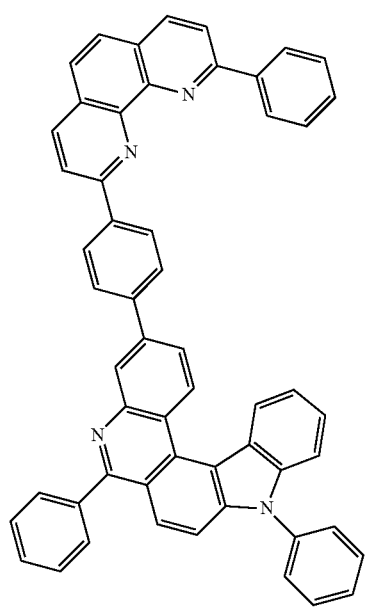
822
-continued
15-40
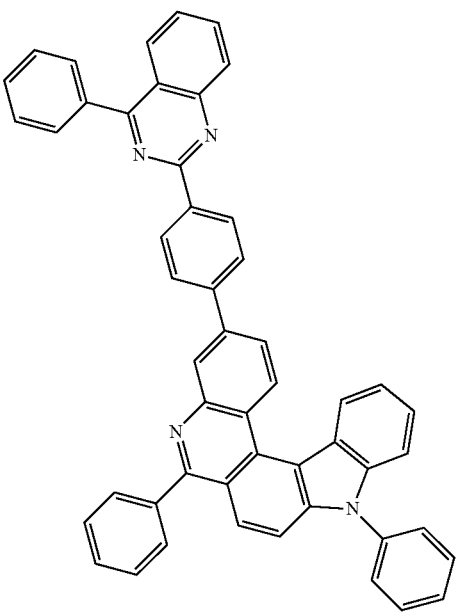
15-39
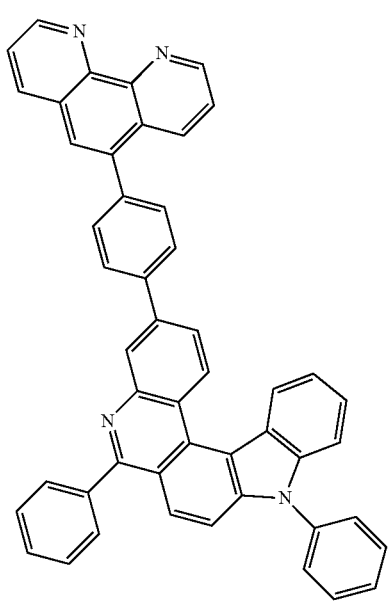
15-41
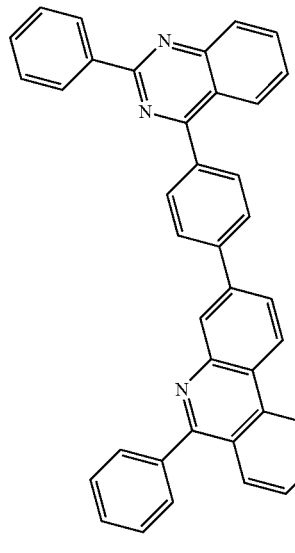

823
-continued
15-42
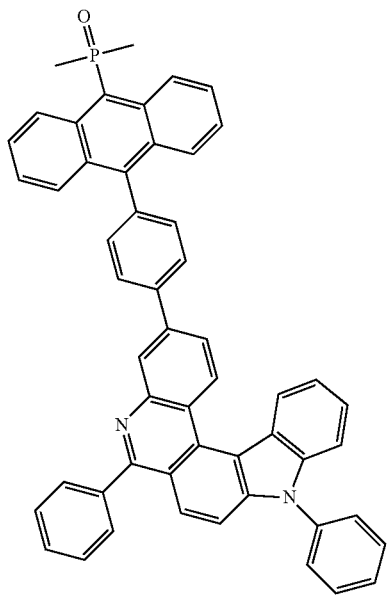 [SMILES: CP(C)(=O)c1c2ccccc2c(-c2ccc(-c3ccc4c(c3)nc(-c3ccccc3)c3ccc5c(c6ccccc6n5-c5ccccc5)c34)cc2)c2ccccc12]
15-43
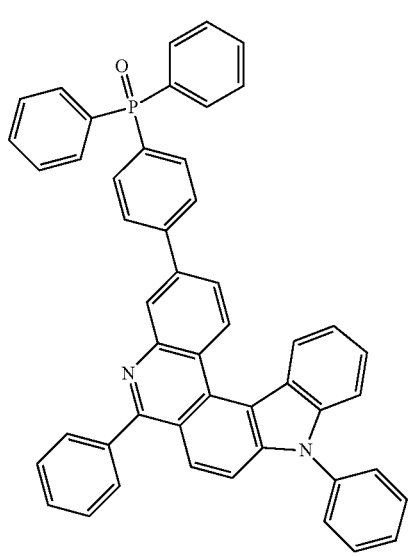
824
-continued
15-44
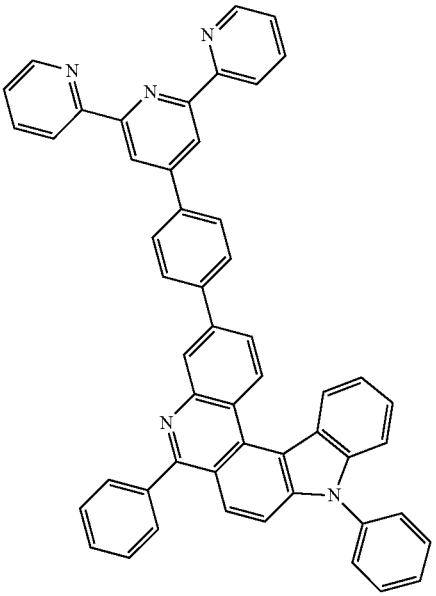
15-45
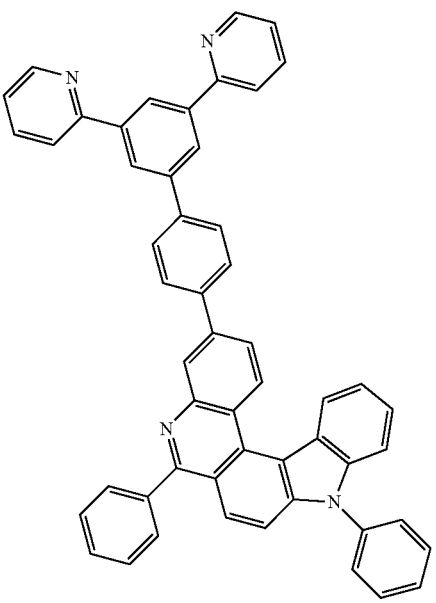

15-46
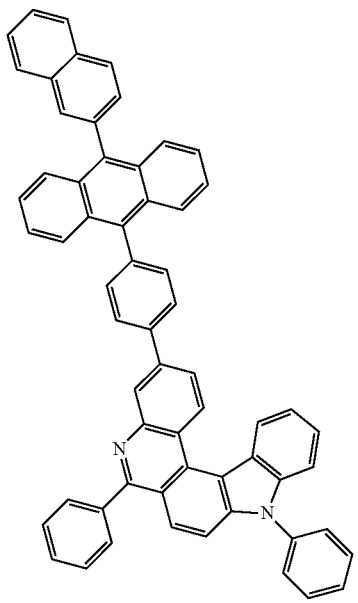
15-48
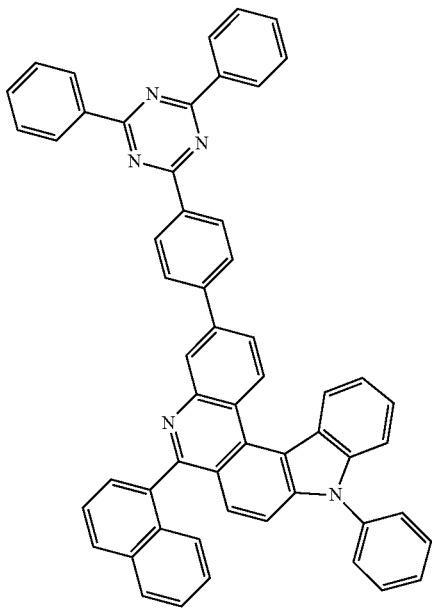
15-47
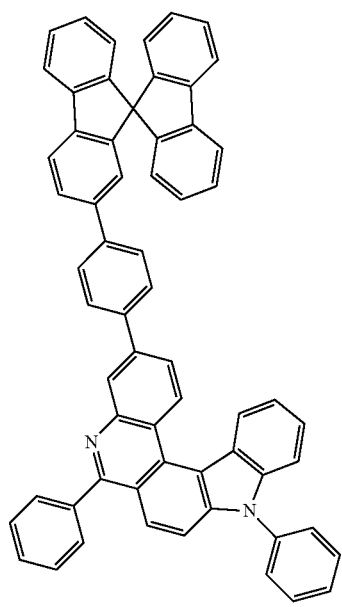
15-49
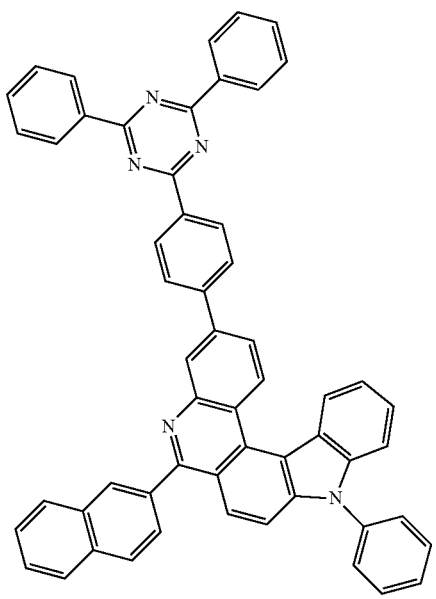

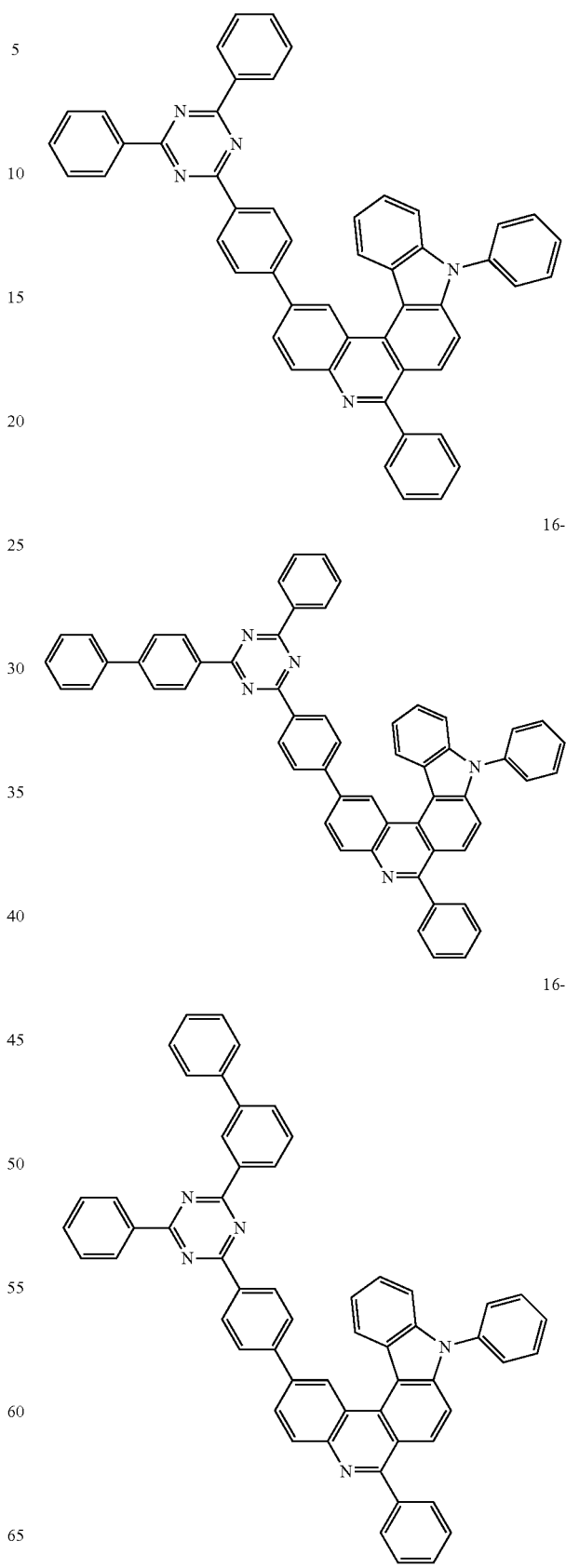

16-3
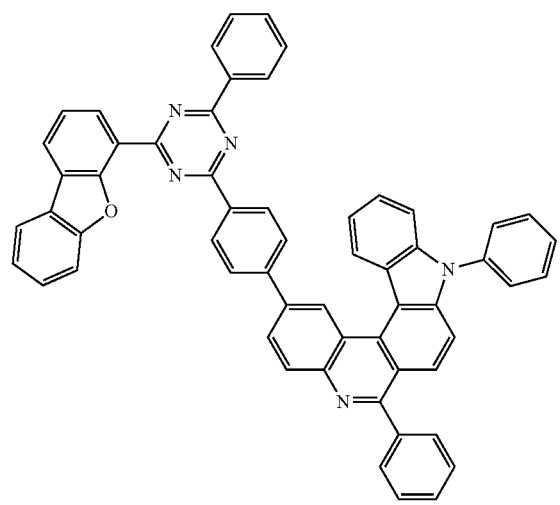
16-4
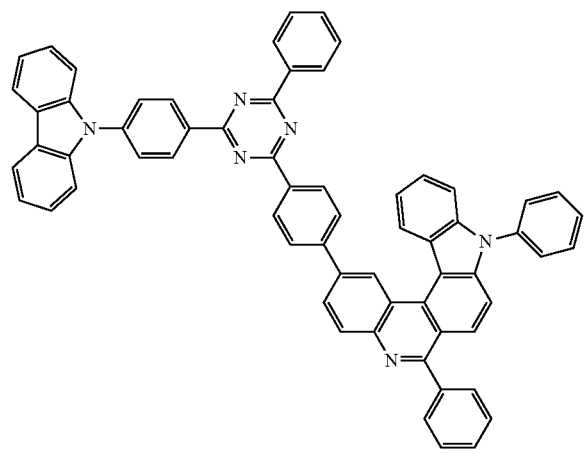
16-5
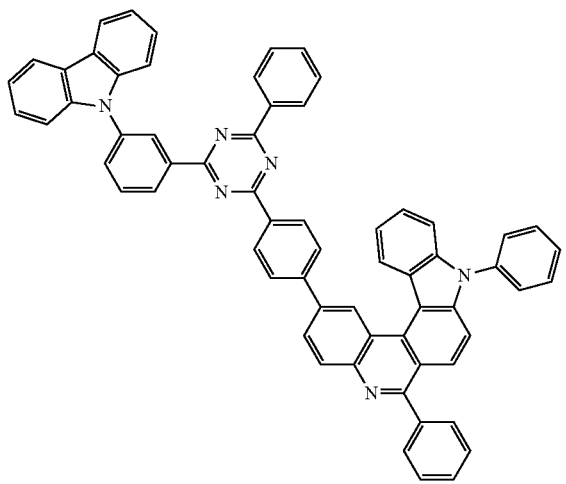
16-6
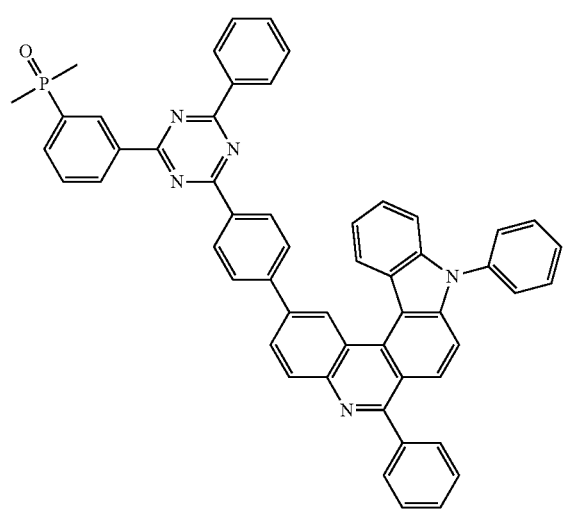
16-7
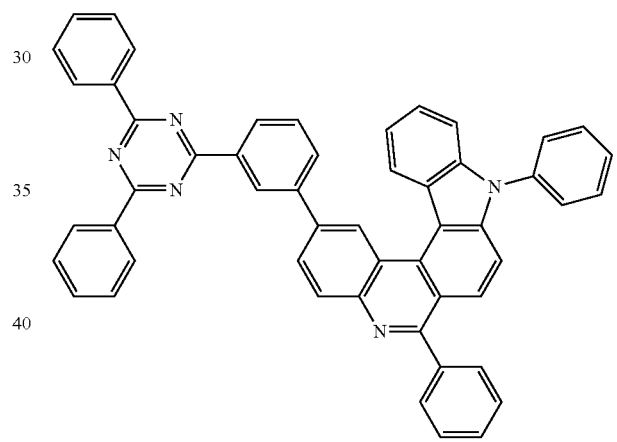
16-8
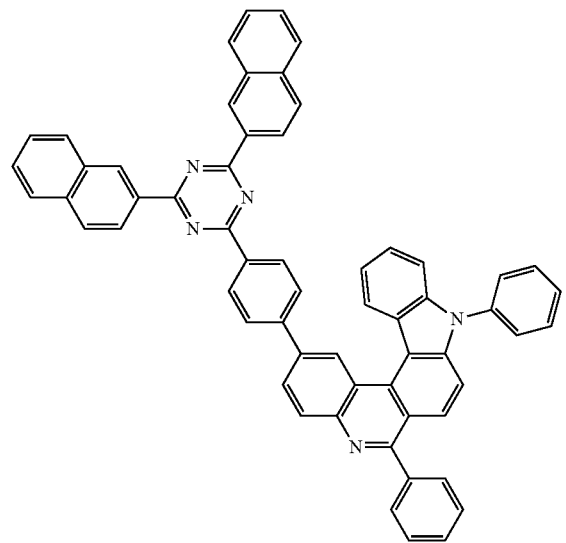

16-9
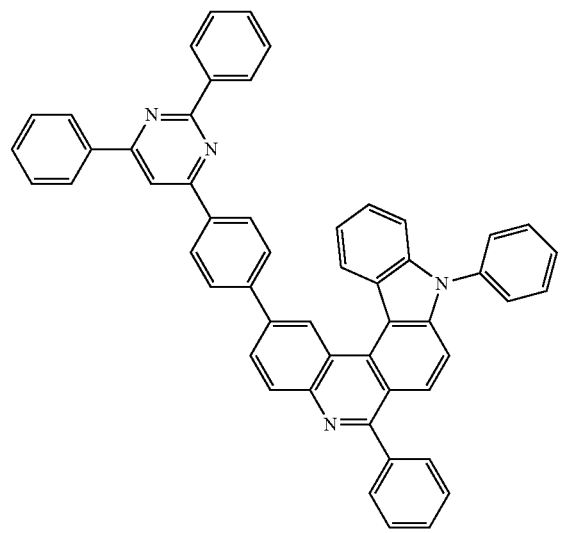
16-10
16-11
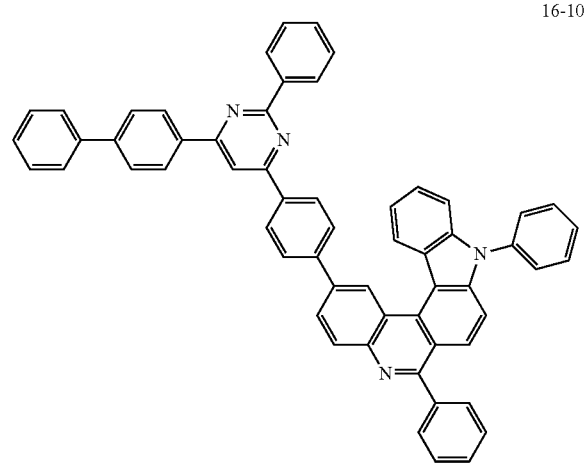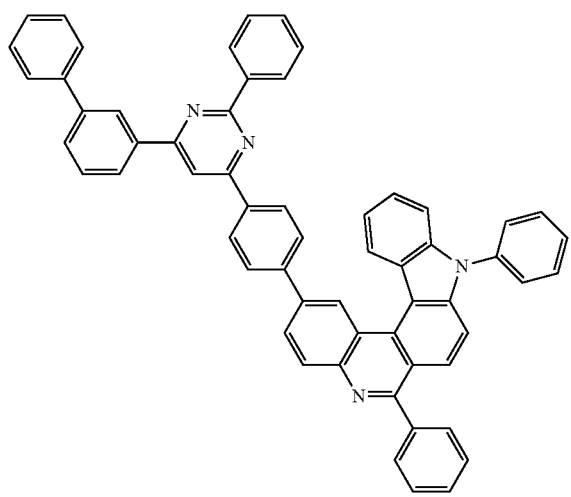
16-12
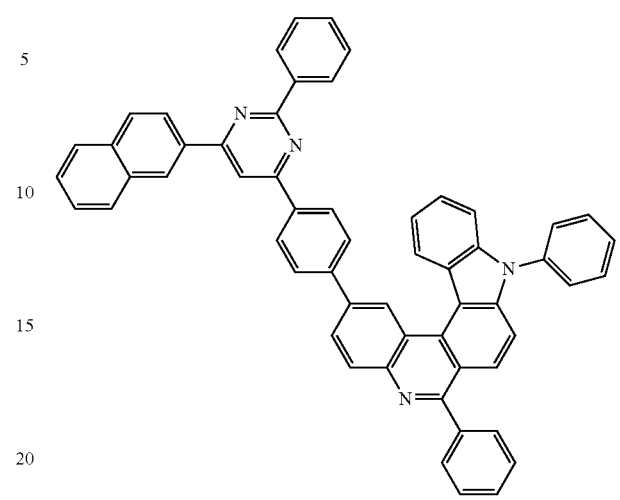
16-13
16-14

16-15
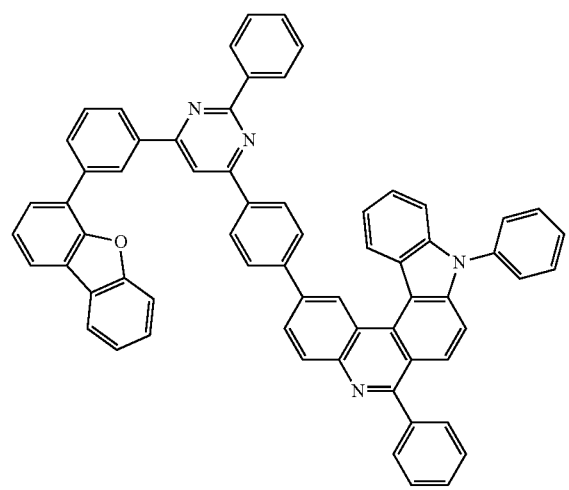
16-16
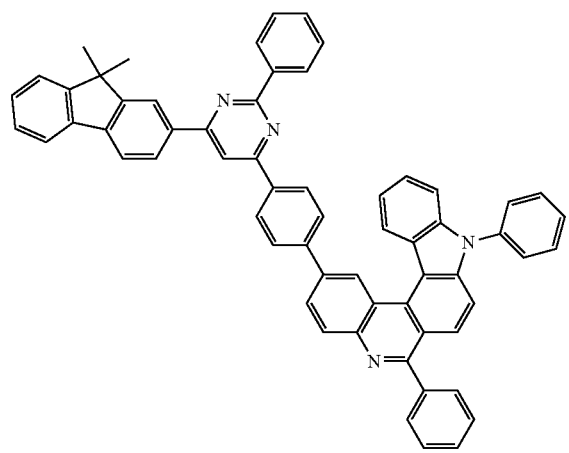
16-17
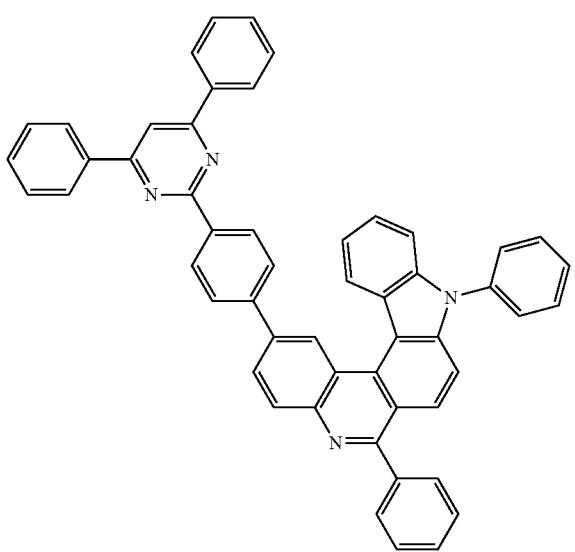
16-18
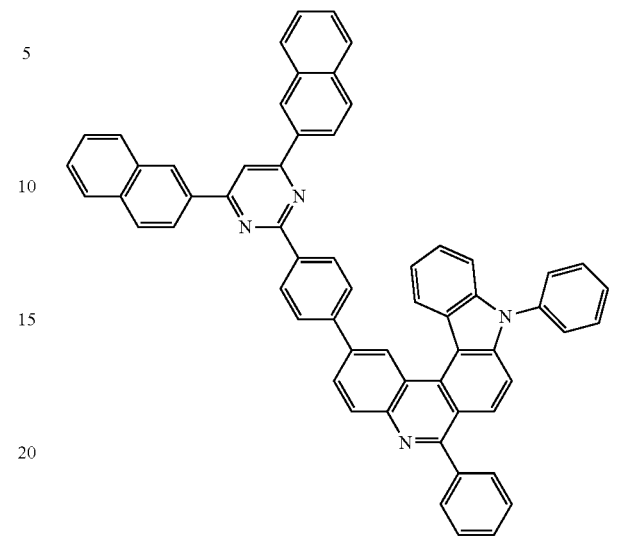
16-19
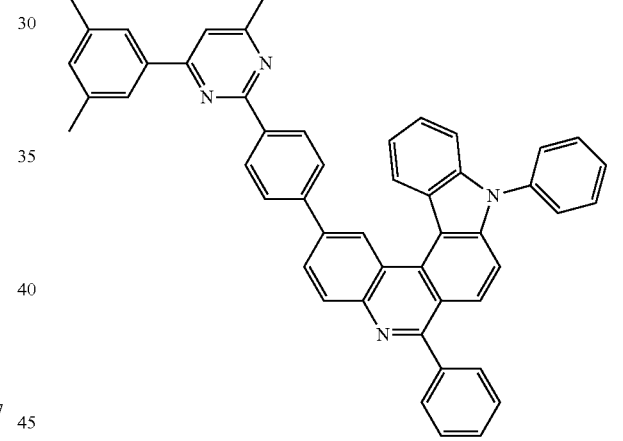
16-20
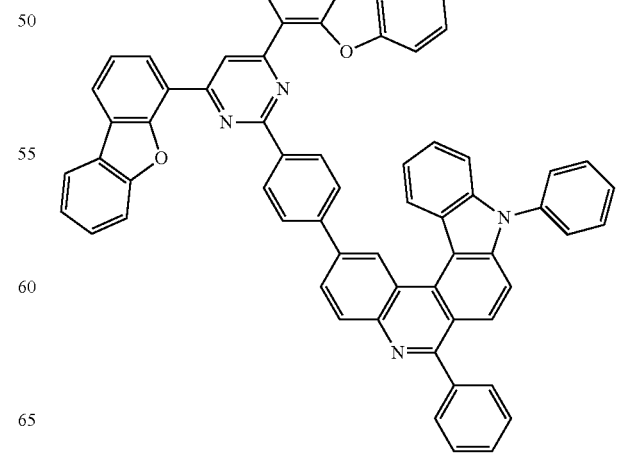

16-21
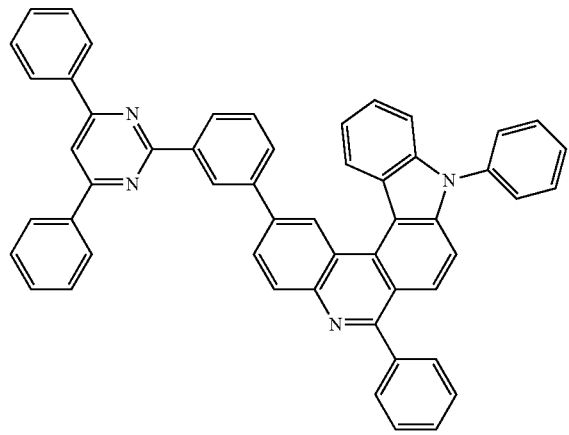
16-22
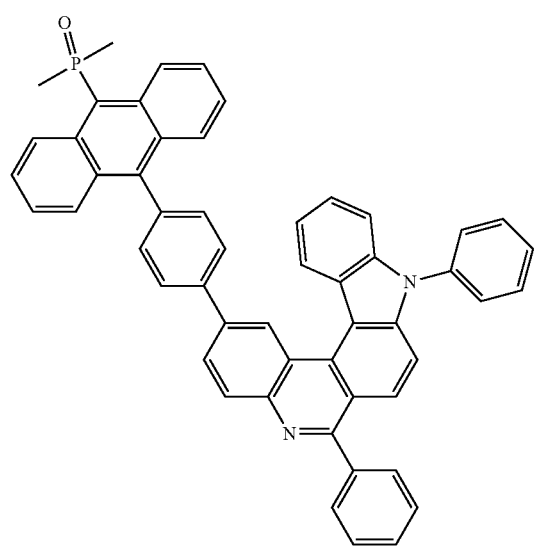
16-23
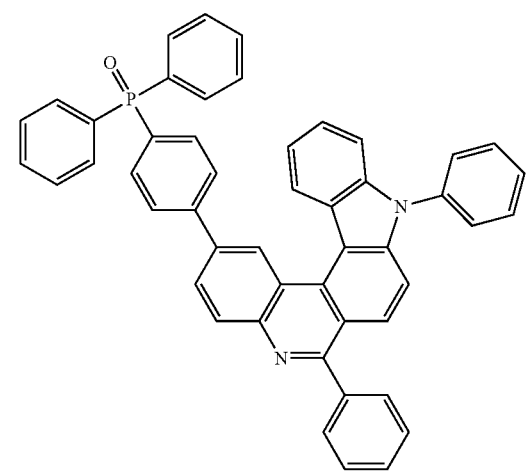
16-24
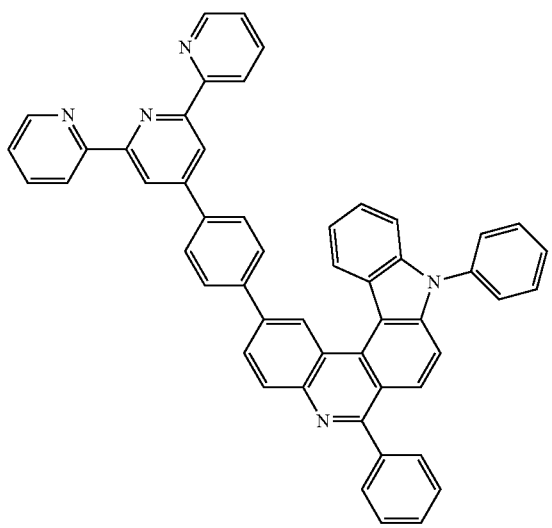
16-25
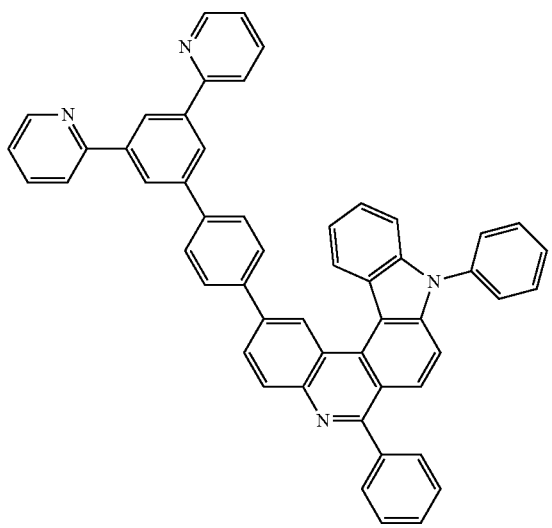
16-26
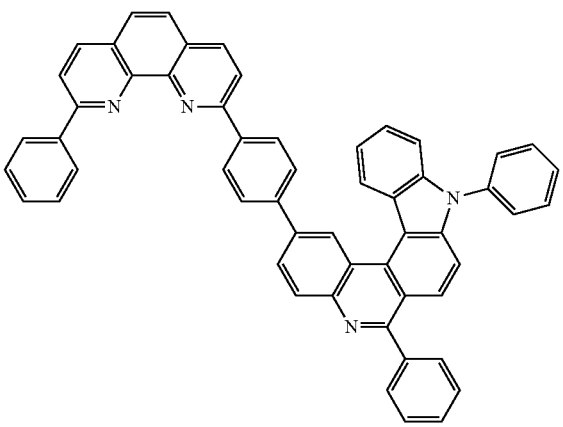

16-27
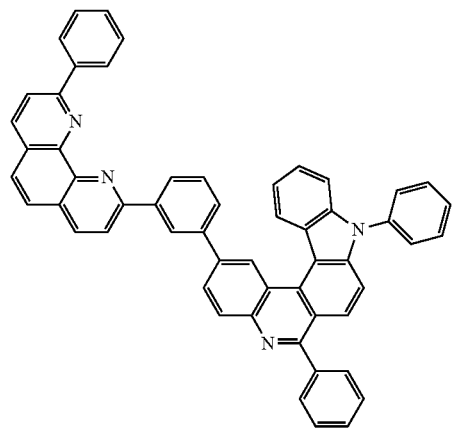
16-28
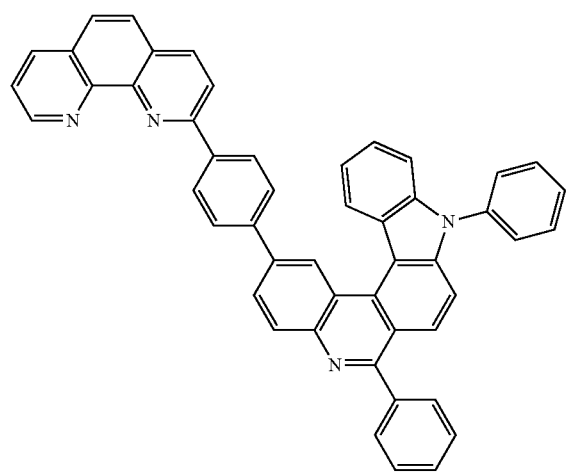
16-29
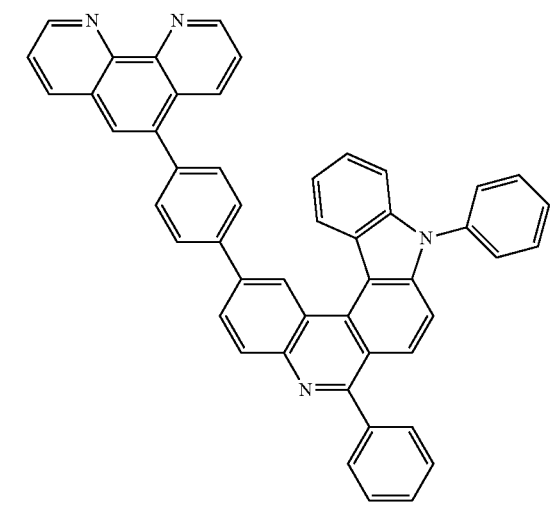
16-30
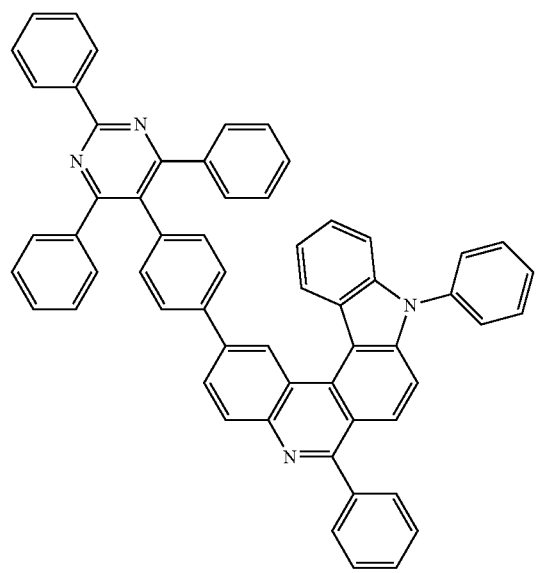
16-31
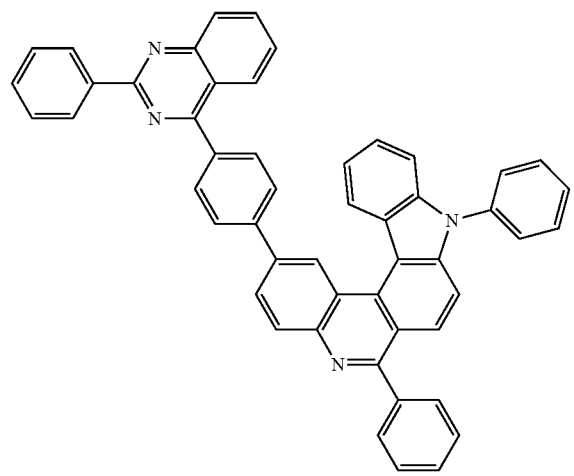
16-32
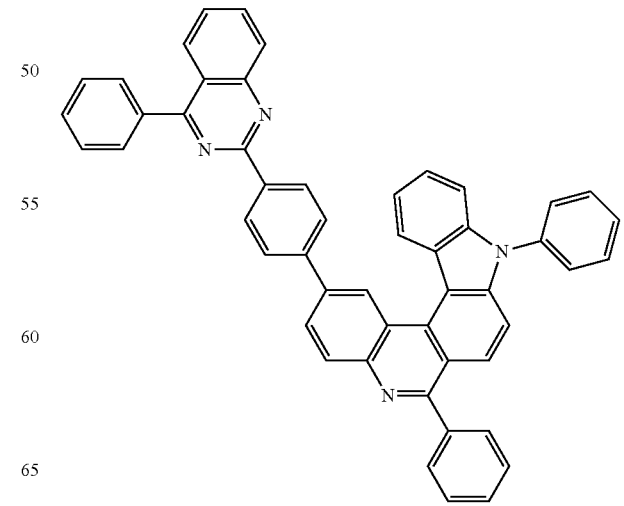

839
-continued
16-33
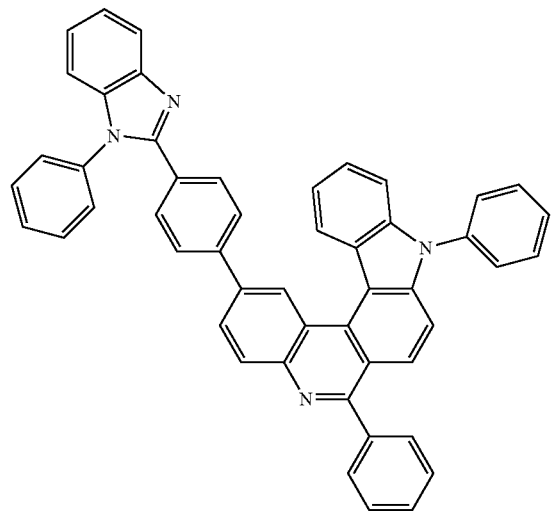
16-34
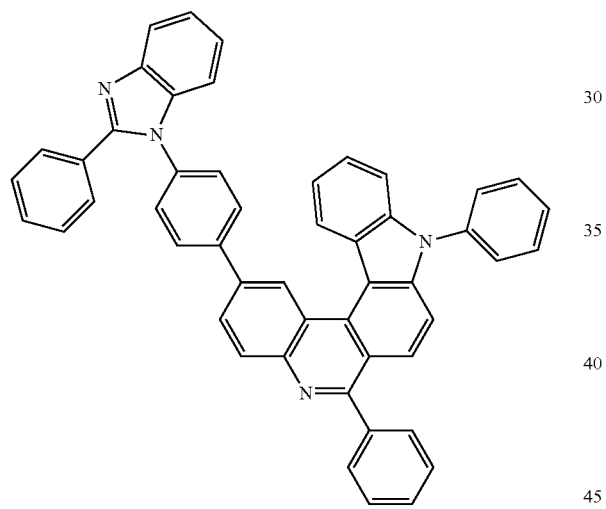
16-35
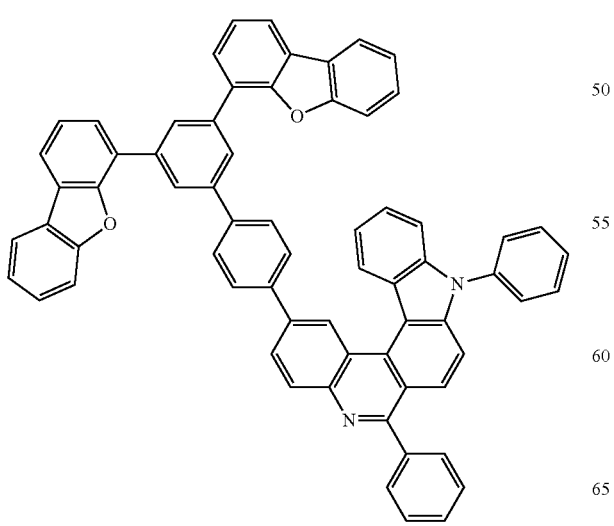
840
-continued
16-36
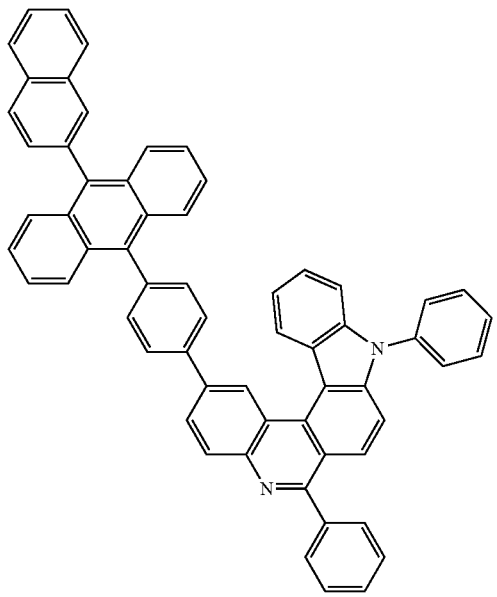
16-37
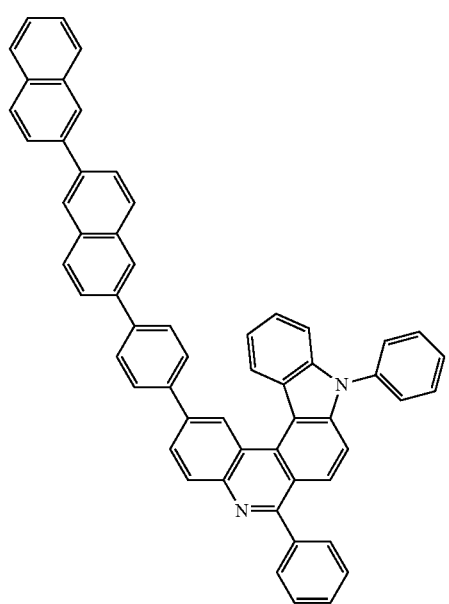

16-38
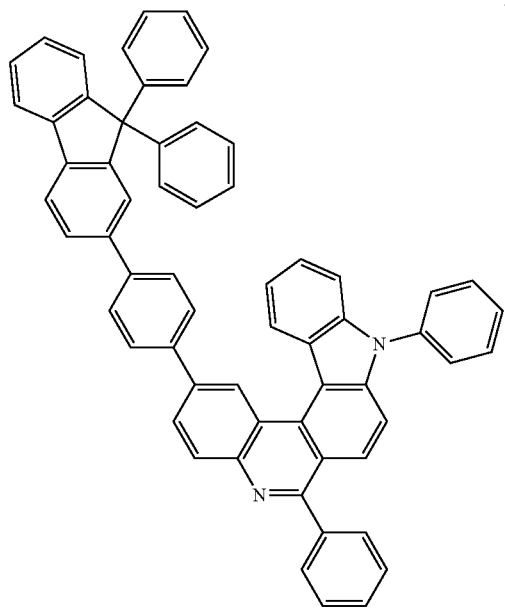
16-40
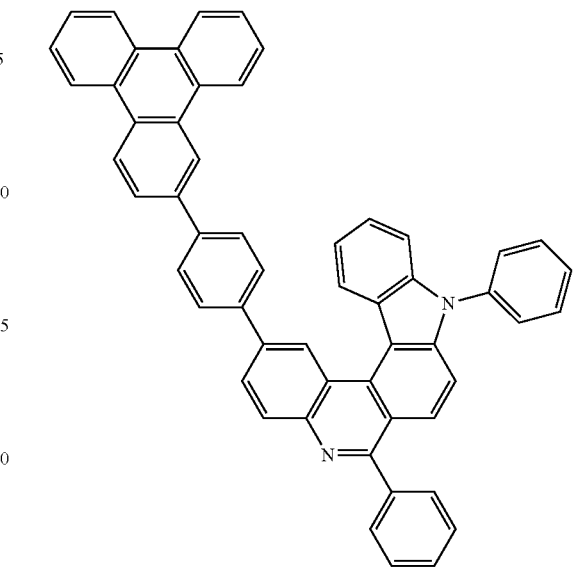
16-39
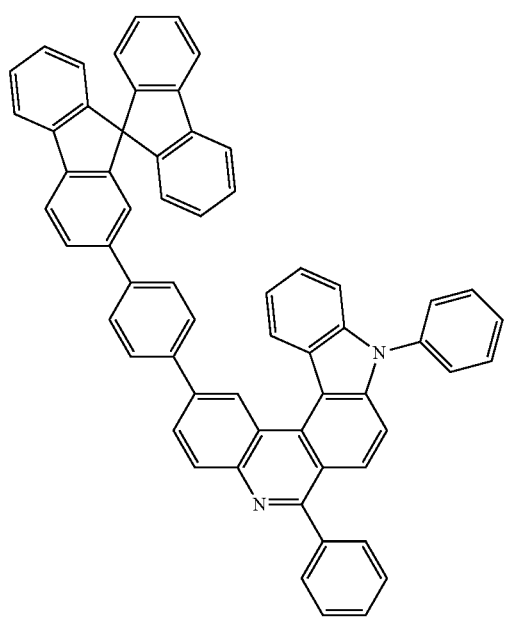
16-41
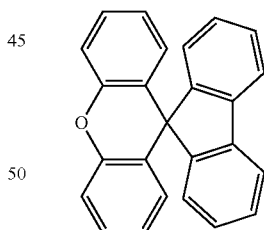

843
-continued 16-42
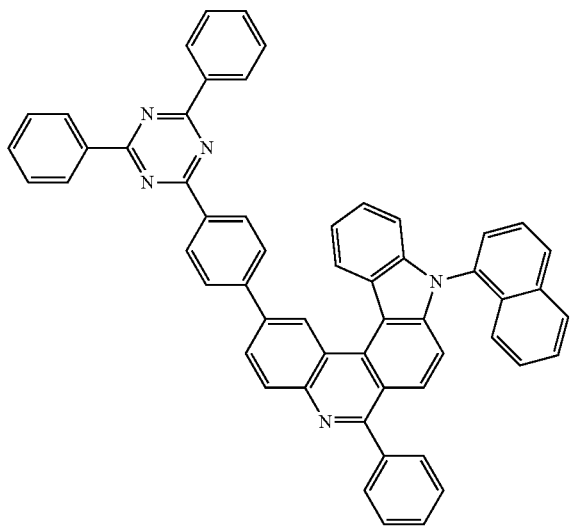

16-43
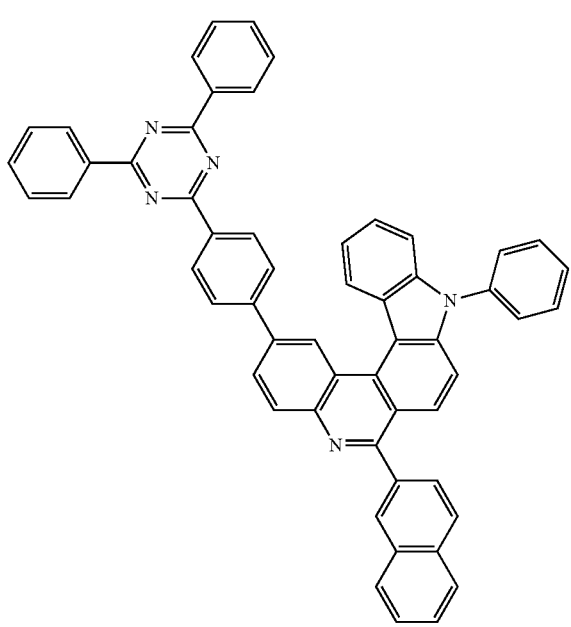

844
-continued 16-44
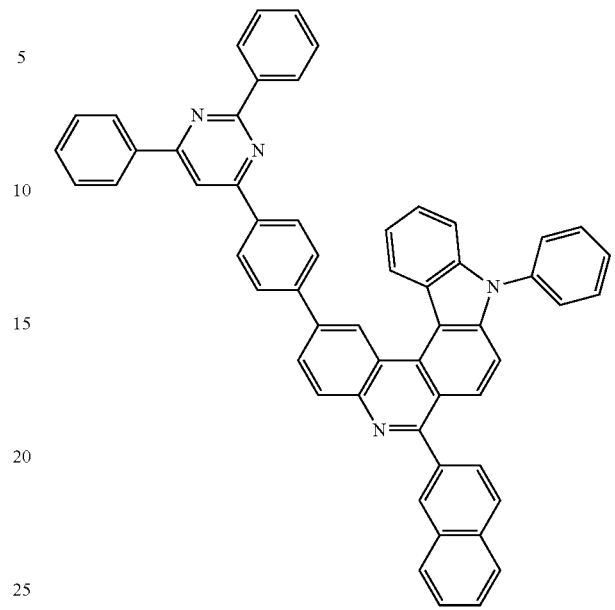

16-45
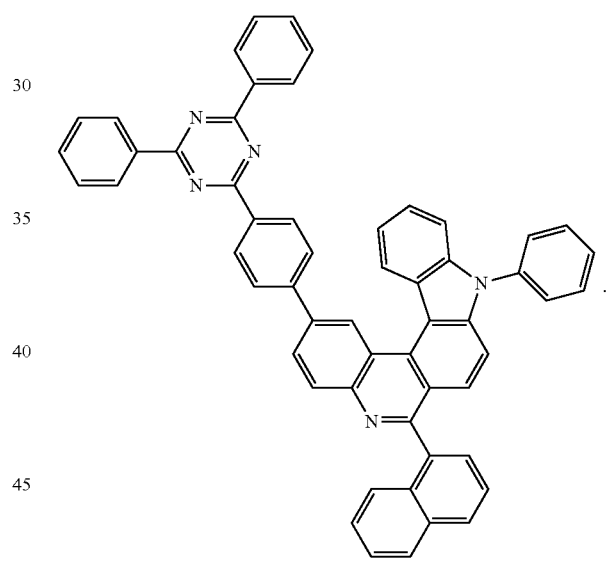

7. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

8. The organic light emitting device of claim 7, wherein the organic material layer comprises a light emitting layer, and the light emitting layer comprises the heterocyclic compound.

9. The organic light emitting device of claim 7, wherein the organic material layer comprises an electron injection layer or an electron transfer layer, and the electron injection layer or the electron transfer layer comprises the heterocyclic compound.

10. The organic light emitting device of claim 7, wherein the organic material layer comprises an electron blocking layer or a hole blocking layer, and the electron blocking layer or the hole blocking layer comprises the heterocyclic compound.

11. The organic light emitting device of claim 7, further comprising one, two or more layers selected from the group consisting of a light emitting layer, a hole injection layer, a hole transfer layer, an electron injection layer, an electron transfer layer, an electron blocking layer and a hole blocking layer.

12. The organic light emitting device of claim 7, comprising:
 a first electrode;
 a first stack provided on the first electrode and comprising a first light emitting layer;
 a charge generation layer provided on the first stack;
 a second stack provided on the charge generation layer and comprising a second light emitting layer; and
 a second electrode provided on the second stack.

13. The organic light emitting device of claim 12, wherein the charge generation layer comprises the heterocyclic compound.

14. The organic light emitting device of claim 13, wherein the charge generation layer is an N-type charge generation layer, and the charge generation layer comprises the heterocyclic compound.

* * * * *